(12) United States Patent
Bezman et al.

(10) Patent No.: US 12,077,584 B2
(45) Date of Patent: Sep. 3, 2024

(54) METHODS OF TREATING HLA-E-EXPRESSING CANCERS BY ADMINISTERING ANTIBODIES WHICH BIND HUMAN NATURAL KILLER CELL INHIBITORY RECEPTOR GROUP 2A (NKG2A)

(71) Applicant: BRISTOL-MYERS SQUIBB COMPANY, Princeton, NJ (US)

(72) Inventors: Natalie Bezman, Foster City, CA (US); Alan J. Korman, Piedmont, CA (US); Shrikant Deshpande, Fremont, CA (US); Amy D. Jhatakia, Fremont, CA (US); Richard Y. Huang, Bridgewater, NJ (US); Guodong Chen, East Brunswick, NJ (US); Ginger C. Rakestraw, Somerville, MA (US); Karla Ann Henning, Milpitas, CA (US); Vangipuram S. Rangan, Pleasant Hill, CA (US); Christine Bee, San Francisco, CA (US); Xiang Shao, Los Altos, CA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 70 days.

(21) Appl. No.: 17/670,398

(22) Filed: Feb. 11, 2022

(65) Prior Publication Data

US 2022/0204618 A1 Jun. 30, 2022

Related U.S. Application Data

(62) Division of application No. 16/683,927, filed on Nov. 14, 2019, now Pat. No. 11,274,150.

(60) Provisional application No. 62/927,211, filed on Oct. 29, 2019, provisional application No. 62/768,471, filed on Nov. 16, 2018.

(51) Int. Cl.
| | |
|---|---|
| *C07K 16/28* | (2006.01) |
| *A61K 39/00* | (2006.01) |
| *A61K 39/395* | (2006.01) |
| *A61K 47/68* | (2017.01) |
| *A61P 35/00* | (2006.01) |
| *C07K 1/22* | (2006.01) |
| *C12N 5/071* | (2010.01) |
| *C12N 15/85* | (2006.01) |
| *C12P 21/00* | (2006.01) |
| *G01N 33/68* | (2006.01) |

(52) U.S. Cl.
CPC ...... *C07K 16/2803* (2013.01); *A61K 39/3955* (2013.01); *A61K 47/6849* (2017.08); *A61P 35/00* (2018.01); *C07K 1/22* (2013.01); *C12N 5/0682* (2013.01); *C12N 15/85* (2013.01); *C12P 21/005* (2013.01); *G01N 33/68* (2013.01); *A61K 2039/505* (2013.01); *A61K 2039/507* (2013.01); *C07K 2317/21* (2013.01); *C07K 2317/24* (2013.01); *C07K 2317/31* (2013.01); *C07K 2317/33* (2013.01); *C07K 2317/56* (2013.01); *C07K 2317/565* (2013.01); *C07K 2317/76* (2013.01); *C07K 2317/77* (2013.01); *C07K 2317/92* (2013.01); *C07K 2317/94* (2013.01); *C12N 2510/02* (2013.01); *C12N 2800/107* (2013.01)

(58) Field of Classification Search
CPC ............ C07K 16/2803; A61K 39/3955; A61K 2039/505; A61K 2039/507; A61P 35/00
See application file for complete search history.

(56) References Cited

U.S. PATENT DOCUMENTS

| | | | |
|---|---|---|---|
| 6,262,244 B1 | 7/2001 | Houchins et al. | |
| 7,410,767 B1 | 8/2008 | Braud et al. | |
| 7,803,376 B2 | 9/2010 | Velardi et al. | |
| 8,206,709 B2 | 6/2012 | Spee et al. | |
| 8,796,427 B2 | 8/2014 | Spee et al. | |

(Continued)

FOREIGN PATENT DOCUMENTS

| | | |
|---|---|---|
| EP | 1831258 B1 | 10/2015 |
| EP | 3193929 B1 | 6/2019 |

(Continued)

OTHER PUBLICATIONS

Paul, WE (1993) Fundamental Immunology, 3rd ed. Raven Press, NY, Chap. 9, pp. 292-295.*

(Continued)

*Primary Examiner* — Robert S Landsman
(74) *Attorney, Agent, or Firm* — Melissa Wenk

(57) ABSTRACT

The present disclosure provides isolated monoclonal antibodies (e.g., humanized and human monoclonal antibodies), or antigen-binding fragments thereof, that specifically bind to human natural killer cell inhibitory receptor group 2A (NKG2A) protein with high affinity and exhibit therapeutically desirable functional properties, such as for the treatment of, for example, cancer. Immunoconjugates, bispecific molecules, and pharmaceutical compositions comprising the anti-NKG2A antibodies of the invention are also provided. Nucleic acid molecules encoding the antibodies, expression vectors, host cells, and methods of treatment of, for example, cancer using the antibodies are further provided. Combination therapy, in which an anti-NKG2A antibody in the present disclosure is co-administered with at least one additional agent such as another antibody (e.g., anti-PD-1, anti-PD-L1, and/or anti-CTLA-4 antibodies), is also provided.

76 Claims, 86 Drawing Sheets

Specification includes a Sequence Listing.

(56) References Cited

U.S. PATENT DOCUMENTS

| | | |
|---|---|---|
| 8,993,319 B2 | 3/2015 | Moretta et al. |
| 9,090,876 B2 | 7/2015 | Velardi et al. |
| 9,422,368 B2 | 8/2016 | Spee et al. |
| 9,447,185 B2 | 9/2016 | Romagne et al. |
| 9,683,041 B2 | 6/2017 | Spee et al. |
| 10,160,810 B2 | 12/2018 | Moretta et al. |
| 10,329,348 B2 | 6/2019 | Andre et al. |
| 10,435,469 B2 | 10/2019 | Goldberg et al. |
| 2005/0037002 A1 | 2/2005 | Velardi et al. |
| 2011/0229486 A1 | 9/2011 | Moretta et al. |
| 2015/0125464 A1 | 5/2015 | Moretta et al. |
| 2015/0132316 A1 | 5/2015 | Moretta et al. |
| 2017/0253658 A1 | 9/2017 | Van Der Burg et al. |
| 2017/0291947 A1 | 10/2017 | Andre et al. |
| 2017/0298131 A1 | 10/2017 | Andre et al. |
| 2019/0031755 A1 | 1/2019 | Andre et al. |
| 2019/0135938 A1 | 5/2019 | Moretta et al. |
| 2019/0248896 A1 | 8/2019 | Spee et al. |
| 2019/0322744 A1 | 10/2019 | Andre et al. |
| 2022/0259306 A1 | 8/2022 | Duan et al. |

FOREIGN PATENT DOCUMENTS

| | | |
|---|---|---|
| EP | 3693009 A1 | 8/2020 |
| WO | 2005009465 A1 | 2/2005 |
| WO | 2008009545 A1 | 1/2008 |
| WO | 2016032334 A1 | 3/2016 |
| WO | 2016041945 A1 | 3/2016 |
| WO | 2016041947 A1 | 3/2016 |
| WO | 2016062851 A1 | 4/2016 |
| WO | 2017125532 A1 | 7/2017 |
| WO | 2019175182 A1 | 9/2019 |

OTHER PUBLICATIONS

Rudikoff, S et al. (1982) Proc. Natl. Acad. Sci. USA, 79:1979-1983 (doi: 10.1073/pnas.79.6.1979).*

Colman, PM (1994) Research in Immunology, Elsevier, NY, 145(1):33-36.*

Bendig M. M. (1995) Methods: A Companion to Methods in Enzymology, 8:83-93.*

MacCallum et al. (Oct. 11, 1996) J. Mol. Biol., 262(5):732-745. (doi: 10.1006/jmbi. 1996.0548).*

Casset et al (2003) Biochemical and Biophysical Research Communications, 307:198-205. (doi: 10.1016/S0006-291X(03)01131-8).*

Chen et al. (1995) EMBO J., 14(12):2784-2794. (doi: 10.1002/j.1460-2075.1995.tb07278.x).*

Andre et al., 2018, "Anti-NKG2A mAb is a checkpoint inhibitor that promotes anti-tumor immunity by unleashing both T and NK cells" Cell 175(7):1731.

Araya et al., Trends in Biotechnology 29: 435-442 (2001).

Bottino et al., 2005, "Cellular ligands of activating NK receptors." Trends Immunol 26:221-6.

Creelan et al., 2019, "The NKG2A Immune Checkpoint—a new direction in cancer immunotherapy" Nature Reviews Clinical Oncology 16(5):277-278.

Ferris et al., 2018, Cancer Treatment Reviewes 63:48-60.

Haanen & Cerundolo, (2018) "NKG2A, a new kid on the immune checkpoint block" Cell 175:1720-2.

Hsu et al., (2018) "Contribution of NK cells to immunotherapy mediated by PD1/PD-L1 blockade" Journal of Clinical Investigation 128(10):4654-4668.

Johnston RJ et al., "The immunoreceptor TIGIT regulates antitumor and antiviral CD8 (+) T cell effector function." Cancer Cell 26:923-937 (2014).

Montfoort et al., (2018) "NKG2A Blockade Potentiates CD8 T Cell Immunity Induced by Cancer Vaccines" Cell 175:1744-55.

NCT02643550; "Study of Monalizumab and Cetuximab in Patients With Recurrent or Metastatic Squamous Cell Carcinoma of the Head and Neck"; NCT02643550 on Dec. 31, 2015 available at: https://clinicaltrials.gov/ct2/show/NCT02643550?term=monalizumab&draw=2&rank=5.

NCT02671435; "A Study of Durvalumab (MEDI4736) and Monalizumab in Solid Tumors"; NCT02671435 on Feb. 2, 2016 available at: https://clinicaltrials.gov/ct2/show/NCT02671435?term=monalizumab&draw=2&rank=3.

Platonova et al., 2011, "Profound coordinated alterations of intratumoral NK cell phenotype and function in lung carcinoma" Cancer Research 71(16):5412-22.

Woo et al., Cancer Res 72:917-27 (2012).

Wrenbeck et al. (2017) Curr. Opin. Struct. Biol. 45:36.

Brown, "Tolerance of single, but not multiple, amino acid replacements in antibody VH CDR 2: a means of minimizing B cell wastage from somatic hypermutation," vol. 156 (9), pp. 3285-3291 (1996).

* cited by examiner

13F3 I107T Anti-NKG2A Antibody Mutational Scan -
CDR Positions Analyzed

| | | | | | | | | | | | | | | | | | |
|---|---|---|---|---|---|---|---|---|---|---|---|---|---|---|---|---|---|
| Light Chain | | | | | | | | | | | | | | | | | |
| LCDR1 | 24<br>R | 25<br>A | 26<br>S | 27<br>Q | 28<br>G | 29<br>I | 30<br>N | 31<br>S | 32<br>A | 33<br>L | 34<br>A | | | | | | |
| LCDR2 | None | | | | | | | | | | | | | | | | |
| LCDR3 | 89<br>Q | 90<br>Q | 91<br>F | 92<br>N | 93<br>S | 94<br>Y | 95<br>P | 96<br>L | 97<br>T | | | | | | | | |
| | | | | | | | | | | | | | | | | | |
| Heavy Chain | | | | | | | | | | | | | | | | | |
| HCDR1* | 26<br>G | 27<br>F | 28<br>T | 29<br>F | 30<br>S | 31<br>S | 32<br>H | 33<br>S | 34<br>M | 35<br>N | | | | | | | |
| HCDR2 | 50<br>A | 51<br>I | 52<br>S | 52a<br>S | 53<br>S | 54<br>S | 55<br>S | 56<br>Y | 57<br>I | 58<br>Y | 59<br>Y | 60<br>A | 61<br>D | 62<br>S | 63<br>V | 64<br>K | 65<br>G |
| HCDR3 | 95<br>E | 96<br>E | 97<br>W | 98<br>G | 99<br>L | 100<br>P | 100a<br>F | 101<br>D | | | | | | | | | |

*Kabat definition was used for all CDRs except HCDR1, where the AbM definition was used

Alignment of Full Length Human NKG2C and Human NKG2C Amino Acid Sequences

```
hNKG2C  MSKQRGTFSE VSLAQDPKRQ QRKPKGNKSS ISGTEQEIFQ VELNLDNPSL  50
hNKG2A  MDNQGVIYSD LNLPPNPKRQ QRKPKGNKSS ILATEQEITY AELNLQKASQ  50 hNKG2C  NHQGIDKIYD CQGLLPPPEK LTAEVIGITC  IVLMATVLKT IVLIPFLEQ-  100
hNKG2A  DFQGNDKTYH CKDLPSAPEK LIVGILGIIC  LILMASVTI  VMIPSTLIQR  100 hNKG2C  -NNSSPNTRT QKARHCGHCP EEWITYSNSC YYIGKERRTW EESLLACTSK  150
hNKG2A  HNNSSLNTRT QKARHCGHCP EEWITYSNSC YYIGKERRTW EESLLACTSK  150 hNKG2C  NSSLLSIDNE EEMKFLASIL PSSWIGVFRN SSHPWVTIN GLAFKHKIKD   200
hNKG2A  NSSLLSIDNE EEMKFLSITS PSSWIGVFRN SSHPWVTMI GLAFKHEIKD   200 hNKG2C  SDNAELNCAV LQVNRLKSAQ CGSSMIYHCK HKL  233
hNKG2A  SDNAELNCAV LQVNRLKSAQ CGSSITYHCK HKL  233
```

Conserved (identical) amino acid residues: 177 of 233 (76%)
Similar amino acid residues: 14 of 233 (6%)
Different amino acid residues: 42 of 233 (18%)

FIG.6

Anti-NKG2A Antibody 13F3.A4 Heavy Chain Variable Region

```
       E   V   Q   L   V   E   S   G   G   G   L   V   K   P   G   G   S
  1   GAG GTG CAG CTG GTG GAG TCT GGG GGA GGC CTG GTC AAG CCG GGG GGG TCC

L   R   L   S   C   A   A   S   G   F   T   F   S  [CDR1]
                                                            S   H   S   M
 52   CTG AGA CTC TCC TGT GCA GCA TCT GGA TTC ACC TTC AGT  TCC CAT AGT ATG
      [CDR1, cont'd]
       N   W   V   R   Q   A   P   G   K   G   L   E   W   V   S  [CDR2]
                                                                    A   I
103   AAC TGG GTC CGC CAG GCT CCA GGG AAG GGG CTG GAG TGG GTC TCA  GCC ATA
      [CDR2, cont'd]
       S   S   S   Y   I   Y   Y   A   D   S   V   K   G   R   F
154   AGT AGT AGT TAC ATA TAC TAC GCA GAC TCA GTG AAG GGC CGA TTC T   I   S   R   D   N   A   K   N   S   L   Y   L   Q   M   N   S
205   ACC ATC TCC AGA GAC AAC GCC AAG AAC TCA CTG TAT CTG CAA ATG AAC AGC L   R   A   E   D   T   A   V   Y   Y   C   A   R  [CDR3]
                                                            E   E   W   G
256   CTG AGA GCC GAG GAC ACG GCT GTG TAT TAC TGT GCG AGA  GAA GAG TGG GGG
      [CDR3, cont'd]
       L   P   F   D   Y   W   G   Q   G   I   L   V   T   V   S   S
307   CTA CCC TTT GAC TAC TGG GGC CAG GGA ATC CTG GTC ACC GTC TCC TCA
```

FIG. 7A

Anti-NKG2A Antibody 13F3.A4 Light Chain Variable Region

```
      A   I   Q   L   T   Q   S   P   S   S   L   S   A   S   V   G   D
  1   GCC ATC CAG TTG ACC CAG TCT CCA TCC TCC CTG TCT GCA TCT GTA GGA GAC

R   V   T   I   T   C   [CDR1                              ]
                              R   A   S   Q   G   I   N   S   A   L   A
 52   AGA GTC ACC ATC ACT TGC CGG GCA AGT CAG GGC ATT AAC AGT GCT TTA GCC

W   Y   Q   Q   K   P   G   K   A   P   K   L   L   I   Y   [CDR2 ]
                                                                   D   A
103   TGG TAT CAG CAG AAA CCA GGG AAA GCT CCT AAG CTC CTG ATC TAT GAT GCC

[CDR2, cont'd        ]  G   V   P   S   R   F   S   G   S   G   S   G
      S   S   L   K   S
154   TCC AGT TTG AAA AGT    GGG GTC CCA TCA AGG TTC AGC GGC AGT GGA TCT GGG T   D   F   T   L   T   I   S   S   L   Q   P   E   D   F   A   T
205   ACA GAT TTC ACT CTC ACC ATC AGC AGC CTG CAG CCT GAA GAT TTT GCA ACT Y   Y   C   [CDR3                                          ]  F   G   Q   G   T
                  Q   Q   F   N   S   Y   P   L   T
256   TAT TAC TGT CAA CAG TTT AAT AGT TAC CCT CTC ACC TTC GGC CAA GGG ACA

R   L   E   I   K
307   CGA CTG GAG ATT AAA
```

FIG. 7B

Anti-NKG2A Antibody 2G6.C2 Heavy Chain Variable Region

```
      -1---2---3---4---5---6---7---8---9---10--11--12--13--14--15--16--17-
       E   V   Q   L   V   E   S   G   G   G   L   V   Q   R   G   G   S
  1   GAG GTG CAA CTG GTG GAG TCT GGG GGA GGC TTG GTA CAG CGG GGG GGG TCC

-18--19--20--21--22--23--24--25--26--27--28--29--30--31--32--33--34-
                                                                  CDR1
       L   R   L   S   C   A   A   S   G   F   T   F   S   S   N   S   M
 52   CTG AGA CTC TCC TGT GCA GCC TCT GGA TTC ACC TTC AGT AGC AAT AGC ATG

-35--36--37--38--39--40--41--42--43--44--45--46--47--48--49--50--51-
      CDR1, cont'd                                                  CDR2
       N   W   I   R   Q   A   P   G   K   G   L   E   W   V   A   H   I
103   AAC TGG ATC CGC CAG GCT CCA GGG AAG GGG CTG GAG TGG GTT GCA CAC ATT -52-52A--53--54--55--56--57--58--59--60--61--62--63--64--65--66--67-
      CDR2, cont'd
       S   S   G   S   S   F   I   Y   Y   A   D   S   V   K   G   R   F
154   AGT AGT GGT AGC AGT TTC ATA TAC TAC GCA GAC TCT GTG AAG GGC CGA TTC -68--69--70--71--72--73--74--75--76--77--78--79--80--81--82-82A-82B-
       T   I   S   R   D   N   A   K   N   S   L   S   L   Q   M   N   S
205   ACC ATC TCC AGA GAC AAT GCC AAG AAC TCT CTG TCT CTG CAA ATG AAC AGC -82C-83--84--85--86--87--88--89--90--91--92--93--94--95--96--97--98-
                                                                  CDR3
       L   R   D   E   D   T   A   V   Y   Y   C   A   R   D   D   W   G
256   CTG AGA GAC GAA GAC ACG GCT GTG TAT TAC TGT GCG AGA GAT GAC TGG GGA -99-100-100A-100B-101-102-103-104-105-106-107-108-109-110-111-112-113-
      CDR3, cont'd
       I   D   A   F   N   I   W   G   Q   G   T   M   V   T   V   S   S
307   ATT GAT GCT TTT AAT ATC TGG GGC CAA GGG ACA ATG GTC ACC GTC TCT TCA
```

FIG.8A

Anti-NKG2A Antibody 2G6.C2 Light Chain Variable Region

```
     -1---2---3---4---5---6---7---8---9--10--11--12--13--14--15--16--17-
      E   I   V   L   T   Q   S   P   A   T   L   S   L   S   P   G   E
  1  GAA ATT GTG TTG ACA CAG TCT CCA GCC ACC CTG TCT TTG TCT CCA GGG GAA

-18--19--20--21--22--23--24--25--26--27--28--29--30--31--32--33--34-
                                     |CDR1
      R   A   T   L   S   C   | R   A   S   Q   S   V   S   S   L   A
 52  AGA GCC ACC CTC TCC TGC  |AGG GCC AGT CAG AGT GTT AGC AGC TCC TTA GCC

-35--36--37--38--39--40--41--42--43--44--45--46--47--48--49--50--51-
                                                               |CDR2
      W   Y   Q   Q   K   P   G   Q   A   P   R   L   L   I   Y | D   A
103  TGG TAC CAA CAG AAA CCT GGC CAG GCT CCC AGG CTC CTC ATC TAT|GAT GCA

-52--53--54--55--56--57--58--59--60--61--62--63--64--65--66--67--68-
     |CDR2, cont'd
     | S   N   R   A   T | G   I   P   A   R   F   S   G   S   G   S   G
154  |TCC AAC AGG GCC ACT|GGC ATC CCA GCC AGG TTC AGT GGC AGT GGG TCT GGG -69--70--71--72--73--74--75--76--77--78--79--80--81--82--83--84--85-
      T   D   F   T   L   T   I   S   S   L   E   P   E   D   F   A   V
205  ACA GAC TTC ACT CTC ACC ATC AGC AGC CTA GAG CCT GAA GAT TTT GCA GTT -86--87--88--89--90--91--92--93--94--95--96--97--98--99-100-101-102-
                         |CDR3
      Y   Y   C   | Q   Q   R   S   N   W   I   F   T | F   G   P   G   T
256  TAT TAC TGT |CAG CAG CGT AGC AAC TGG ATA TTC ACT|TTC GGC CCT GGG ACC 103-104-105-106-107-

K   V   D   I   K
307  AAA GTG GAT ATC AAA
```

FIG.8B

Anti-NKG2A Antibody 11H9.A1 Heavy Chain Variable Region

```
1    E   V   Q   L   V   E   S   G   G   G   L   V   K   P   G   G   S
     GAG GTG CAG CTG GTG GAG TCT GGG GGA GGC CTG GTC AAG CCT GGG GGG TCC

CDR1
52   L   R   L   S   C   A   A   S   G   F   T   F   S   S   Y   S   M
     CTG AGA CTC TCC TGT GCA GCC TCT GGA TTC ACC TTC AGT AGC TAT AGC ATG
     ┌CDR1, cont'd┐                                        
     │ N   W   V │ R   Q   A   P   G   K   G   L   E   W   V   S
103  │ AAC│TGG GTC│CGC CAG GCT CCA GGG AAG GGG CTG GAG TGG GTC TCA
     └────┘                                                  ┌CDR2┐
                                                             │ S   I │
                                                             │ TCC ATT│
     ┌CDR2, cont'd                                                    ┐
     │ S   S   S   S   Y   I   Y   Y   A   D   S   V   K   G   R   F │
154  │ AGT AGT AGT AGT TAC ATA TAC TAC GCA GAC TCA GTG AAG GGC CGA TTC│
     └──────────────────────────────────────────────────────────────────┘

205  T   I   S   R   D   N   A   K   N   S   L   Y   L   Q   M   N   S
     ACC ATC TCC AGA GAC AAC GCC AAG AAC TCA CTG TAT CTG CAA ATG AAC AGC

CDR3
256  L   R   A   E   D   T   A   V   Y   Y   C   A   R   L   L   W   F
     CTG AGA GCC GAG GAC ACG GCT GTG TAT TAC TGT GCG AGA CTA CTA TGG TTC
     ┌CDR3, cont'd┐
     │ G   E   I   F   D   Y │ W   G   Q   G   T   L   V   T   V   S   S
307  │ GGG GAG ATT TTT GAC TAC│TGG GGC CAG GGA ACC CTG GTC ACC GTC TCC TCA
     └──────────────────────┘
```

FIG.9A

Anti-NKG2A Antibody 11H9.A1 Light Chain Variable Region

```
     A   I   Q   L   T   Q   S   P   S   S   L   S   A   S   V   G   D
 1   GCC ATC CAG TTG ACC CAG TCT CCA TCC TCC CTG TCT GCA TCT GTA GGA GAC
                                    ┌─CDR1──────────────────────────────────
     R   V   T   I   T   C   R   A   S   Q   G   I   S   S   A   L   A
52   AGA GTC ACC ATC ACT TGC CGG GCA AGT CAG GGC ATT AGC AGT GCT TTA GCC
     ─────────────────────┘                                        ┌─CDR2─
     W   Y   Q   Q   K   P   G   K   A   P   K   L   L   I   Y   D   A
103  TGG TAT CAG CAG AAA CCA GGG AAA GCT CCT AAG CTC CTG ATC TAT GAT GCC
     ────┘          ┌─CDR2, cont'd──┐
     S   S   L   K   S   G   V   P   S   R   F   S   G   S   G   S   G
154  TCC AGT TTG AAA AGT GGG GTC CCA TCA AGG TTC AGC GGC AGT GGA TCT GGG
     ────────────────┘

T   D   F   T   L   T   I   S   S   L   Q   P   E   D   F   A   T
205  ACA GAT TTC ACT CTC ACC ATC AGC AGC CTG CAG CCT GAA GAT TTT GCA ACT
                                             ┌─CDR3──────────────────────
     Y   Y   C   Q   Q   F   N   S   Y   P   I   T   F   G   Q   G   T
256  TAT TAC TGT CAA CAG TTT AAT AGT TAC CCG ATC ACC TTC GGC CAA GGG ACA
                ─────────────────────────────────────┘

R   L   E   I   K
307  CGA CTG GAG ATT AAA
```

FIG. 9B

Anti-NKG2A Antibody 4G5.D1 Heavy Chain Variable Region

```
      Q   M   Q   L   Q   E   S   G   P   G   L   V   K   P   S   E   T
  1   CAG ATG CAG CTG GAG GAG TCG GGC CCA GGA CTG GTG AAG CCT TCG GAG ACC
                                                      ┌─CDR1─────────────
      L   S   L   T   C   T   V   S   G   G   S   V   │ S   S   G   R   Y
 52   CTG TCC CTC ACC TGC ACT GTC TCT GGT GGC TCC GTC │AGC AGT GGT CGT TAC
      ─CDR1, cont'd─┐                                 
      Y   W   S     │W   I   R   Q   P   P   G   K   G   L   E   W   I   G
103   TAC TGG AGT   │TGG ATC CGG CAG CCC CCC GGG AAG GGA CTG GAG TGG ATT GGG
      ─CDR2─────────────────────────────────────────────────────────────
      Y   I   Y   Y   S   G   S   T   N   Y   N   P   S   L   K   S   R
154   TAT ATC TAT TAC AGT GGG AGC ACC AAC TAC AAC CCC TCC CTC AAG AGT CGA V   T   I   S   V   D   T   S   K   N   Q   F   S   L   K   L   T
205   GTC ACC ATA TCA GTA GAC ACG TCC AAG AAC CAG TTC TCC CTG AAG CTG ACC S   V   T   A   A   D   T   A   V   Y   Y   C   A   R   ┌─CDR3────
256   TCT GTG ACC GCT GCG GAC ACG GCC GTG TAT TAC TGT GCG AGA │ E   G   G
                                                              │GAG GGT GGA
      ─CDR3, cont'd─────────────────────────────────────┐
      D   Y   Y   Y   N   M   D   V                     │W   G   P   G   T   T   V   T
307   GAC TAC TAC TAC AAT ATG GAC GTC                   │TGG GGC CCA GGG ACC ACG GTC ACC

V   S   S
358   GTC TCC TCA
```

FIG.10A

Anti-NKG2A Antibody 4G5.D1 Light Chain Variable Region

| Pos | | | | | | | | | | | | | | | | | |
|---|---|---|---|---|---|---|---|---|---|---|---|---|---|---|---|---|---|
| | E | I | V | L | T | Q | S | P | G | T | L | S | L | S | P | G | E |
| 1 | GAA | ATT | GTG | TTG | ACG | CAG | TCT | CCA | GGC | ACC | CTG | TCT | TTG | TCT | CCA | GGG | GAA |
| | R | A | T | L | S | C | | | | | | | | | | | |
| 52 | AGA | GCC | ACC | CTC | TCC | TGC | | | | | | | | | | | |

CDR1: R A S Q S V S S Y L
AGG GCC AGT CAG AGT GTT AGC AGC TAC TTA

| | | | | | | | | | | | | | | | | | |
|---|---|---|---|---|---|---|---|---|---|---|---|---|---|---|---|---|---|
| | CDR1, cont'd | | | | | | | | | | | | | | | | |
| | A | W | Y | Q | Q | K | P | G | Q | A | P | R | L | L | I | Y | |
| 103 | GCC | TGG | TAC | CAG | CAG | AAA | CCT | GGC | CAG | GCT | CCA | AGG | CTC | CTC | ATC | TAT | |

CDR2: G (GGT)

| | CDR2, cont'd | | | | | | | | | | | | | | | |
|---|---|---|---|---|---|---|---|---|---|---|---|---|---|---|---|---|
| | A | S | R | A | T | G | I | P | D | R | F | S | G | S | G | S |
| 154 | GCA | TCC | AGG | GCC | ACT | GGC | ATC | CCA | GAC | AGG | TTC | AGT | GGC | AGT | GGG | TCT |

| | | | | | | | | | | | | | | | | |
|---|---|---|---|---|---|---|---|---|---|---|---|---|---|---|---|---|
| | G | T | D | F | T | L | T | I | S | R | L | E | P | E | D | F | A |
| 205 | GGG | ACA | GAC | TTC | ACT | CTC | ACC | ATC | AGC | AGA | CTG | GAG | CCT | GAA | GAT | TTT | GCA |

| | V | Y | Y | C | |
|---|---|---|---|---|---|
| 256 | GTG | TAT | TAC | TGT | |

CDR3: Q Q Y G S S P Y T
CAG CAG TAT GGT AGC TCA CCG TAC ACT

| | | | | | | | | |
|---|---|---|---|---|---|---|---|---|
| | F | G | Q | G | T | K | L | E | I | K |
| 307 | TTT | GGC | CAG | GGG | ACC | AAG | CTG | GAC | ATC | AAA |

FIG. 10B

Anti-NKG2A Antibody 1G5.B2 Heavy Chain Variable Region

```
      Q   V   Q   L   V   E   S   G   G   G   V   V   Q   P   G   R   S
  1   CAG GTC CAG CTG GTG GAG TCT GGG GGA GGC GTG GTC CAG CCT GGG AGG TCC

L   R   L   S   C   A   A   S   G   F   T   F   S        CDR1
                                                                D   Y   A   M
 52   CTG AGA CTC TCC TGT GCA GCC TCT GGA TTC ACC TTC AGT       GAC TAT GCT ATG

CDR1,cont'd                                                       CDR2
      H   W   V   R   Q   T   P   G   R   G   L   E   W   L   T        F   I
103   CAC TGG GTC CGC CAG ACT CCA GGC AGG GGG CTG GAG TGG CTG ACA      TTT ATA CDR2, cont'd
      S   Y   D   G   S   N   K   Y   H   A   D   S   V   K   G   R   F
154   TCA TAT GAT GGA AGC AAT AAA TAC CAC GCA GAC TCC GTG AAG GGC CGA TTC T   I   S   R   D   N   S   K   N   T   L   F   L   Q   M   N   S
205   ACC ATC TCC AGA GAC AAT TCC AAG AAC ACG CTG TTT CTG CAA ATG AAC AGT L   R   A   E   D   T   A   V   Y   Y   C   A   R        CDR3
                                                                D   S   W   D
256   CTG AGA GCT GAG GAC ACG GCT GTT TAT TAC TGT GCG AGA      GAT TCC TGG GAT CDR3, cont'd
      R   G   Y   F   D   L   W   G   R   G   T   L   V   T   V   S   S
307   CGG GGG TAC TTC GAT CTC TGG GGC CGT GGC ACC CTG GTC ACT GTC TCC TCA
```

FIG.11A

Anti-NKG2A Antibody 1G5.B2 Light Chain Variable Region

```
  1  E   I   V   L   T   Q   S   P   A   T   L   S   L   S   P   G   E
     GAA ATT GTG TTG ACA CAG TCT CCA GCC ACC CTG TCT TTG TCT CCA GGG GAA

┌─CDR1─────────────────────────────────────────┐
 52  R   A   T   L   S │ C   R   A   S   Q   S   V   S   S   Y   L   A │
     AGA GCC ACC CTC TCC│TGC AGG GCC AGT CAG AGT GTT AGC AGC TAC TTA GCC│
                      └───────────────────────────────────────────────┘

┌─CDR2──┐
103  W   Y   Q   Q   K   P   G   Q   A   P │ R   L │ L   I   Y   D   A
     TGG TAC CAA CAG AAA CCT GGC CAG GCT CCT│AGG CTC│CTC ATC TAT GAT GCA

┌─CDR2, cont'd──────┐
154  │ S   N   R   A   T │ G   I   P   A   R   F   S   G   S   G   S   G
     │TCC AAC AGG GCC ACT│GGC ATC CCA GCC AGG TTC AGT GGC AGT GGG TCT GGG
     └───────────────────┘

205  T   D   F   T   L   T   I   S   S   L   E   P   E   D   F   A   V
     ACA GAC TTC ACT CTC ACC ATC AGC AGC CTA GAG CCT GAA GAT TTT GCA GTT

┌─CDR3─────────────────────────────────┐
256  Y   Y   C │ Q   Q   R   S   N   W   T │ F   G   Q   G   T   K
     TAT TAC TGT│CAG CAG CGT AGC AAC TGG ACG│TTC GGC CAA GGG ACC AAG
                └──────────────────────────┘

307  V   E   I   K
     GTG GAA ATC AAA
```

NKG2A.9 Antibody Amino Acid Sequence

Light Chain Sequence

|     | CDR1 | CDR2 | CDR3 |     |
| --- | --- | --- | --- | --- |
|     | | | | VL |

AIQLTQSPSSLSASVGDRVTITCRASQG(I)SSALAWYQQKPGKAPKLLIYDASSLKSGVPSRFSGSGSGTDFTLTISSLQPEDFATYCQQFNSYPLTFGQGTRLEIK

|     | | | | CL |
| --- | --- | --- | --- | --- |

RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC

Heavy Chain Sequence

|     | CDR1 | CDR2 | CDR3 |     |
| --- | --- | --- | --- | --- |
|     | | | | VH |

EVQLVESGGGLVKPGGSLRLSCAASGFTFSSHSMNWVRQAPGKGLEWVSAISSSSSYIYYADSVKGRFTISRDNAKNSLYLQMNSLRAEDTAVYYCAREEWGLPFDY
WGQG(T)LVTVSS

|     | | | | CH |
| --- | --- | --- | --- | --- |

ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKRVEPKSCDKTHTCPPC
PAPEAEGAPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKA
KGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPG(K)

Legend

| Bold underline | CDR regions |
| --- | --- |
| ( ) | Two mutations made to 13F3 hybridoma VL sequence (N30S) and VH sequence (I107T) |
| (NST) | N-glycosylation motif |
| (K) | K was removed from the mature sequence |
| *Bold italics* | Three G1.3f mutations (L234A, L235E and G237A) made to g1f Fc region |

FIG. 13

NKG2A.9 Antibody Amino Acid Sequence

Light Chain
AIQLTQSPSS LSASVGDRVT ITCRASQGIS SALAWYQQKP GKAPKLLIYD ASSLKSGVPS
RFSGSGSGTD FTLTISSLQP EDFATYYCQQ FNSYPLTFGQ GTRLEIKRTV AAPSVFIFPP
SDEQLKSGTA SVVCLLNNFY PREAKVQWKV DNALQSGNSQ ESVTEQDSKD STYSLSSTLT
LSKADYEKHK VYACEVTHQG LSSPVTKSFN RGEC Heavy Chain
EVQLVESGGG LVKPGGSLRL SCAASGFTFS SHSMNWVRQA PGKGLEWVSA ISSSSSYIYY
ADSVKGRFTI SRDNAKNSLY LQMNSLRAED TAVYYCAREE WGLPFDYWGQ GTLVTVSSAS
TKGPSVFPLA PSSKSTSGGT AALGCLVKDY FPEPVTVSWN SGALTSGVHT FPAVLQSSGL
YSLSSVVTVP SSSLGTQTYI CNVNHKPSNT KVDKRVEPKS CDKTHTCPPC PAPEAEGAPS
VFLFPPKPKD TLMISRTPEV TCVVVDVSHE DPEVKFNWYV DGVEVHNAKT KPREEQYNST
YRVVSVLTVL HQDWLNGKEY KCKVSNKALP APIEKTISKA KGQPREPQVY TLPPSREEMT
KNQVSLTCLV KGFYPSDIAV EWESNGQPEN NYKTTPPVLD SDGSFFLYSK LTVDKSRWQQ
GNVFSCSVMH EALHNHYTQK SLSLSPG

FIG. 14

NKG2A.11 Antibody Amino Acid Sequence

Light Chain
AIQLTQSPSS LSASVGDRVT ITCRASQGIP SALAWYQQKP GKAPKLLIYD ASSLKSGVPS
RFSGSGSGTD FTLTISSLQP EDFATYYCQQ FNSYPLTFGQ GTRLEIKRTV AAPSVFIFPP
SDEQLKSGTA SVVCLLNNFY PREAKVQWKV DNALQSGNSQ ESVTEQDSKD STYSLSSTLT
LSKADYEKHK VYACEVTHQG LSSPVTKSFN RGEC Heavy Chain
EVQLVESGGG LVKPGGSLRL SCAASGFTFS SHSMNWVRQA PGKGLEWVSA ISSSSSYIYY
ADSVKGRFTI SRDNAKNSLY LQMNSLRAED TAVYYCAREE WGLPFDYWGQ GTLVTVSSAS
TKGPSVFPLA PSSKSTSGGT AALGCLVKDY FPEPVTVSWN SGALTSGVHT FPAVLQSSGL
YSLSSVVTVP SSSLGTQTYI CNVNHKPSNT KVDKRVEPKS CDKTHTCPPC PAPEAEGAPS
VFLFPPKPKD TLMISRTPEV TCVVVDVSHE DPEVKFNWYV DGVEVHNAKT KPREEQYNST
YRVVSVLTVL HQDWLNGKEY KCKVSNKALP APIEKTISKA KGQPREPQVY TLPPSREEMT
KNQVSLTCLV KGFYPSDIAV EWESNGQPEN NYKTTPPVLD SDGSFFLYSK LTVDKSRWQQ
GNVFSCSVMH EALHNHYTQK SLSLSPG

FIG. 15

Anti-NKG2A Antibodies: Binding and Blocking Human CHO Transfectants

Ability of Anti-NKG2A Antibodies to Block NKG2A/HLA-E Interaction in hNKG2A-expressing CHO Cells Ability of Anti-NKG2A Antibodies to Block NKG2A/HLA-E Interaction in hNKG2A-expressing CHO Cells Anti-NKG2A Antibodies Binding to hNKG2A-expressing CHO Cells Anti-NKG2A Antibodies Binding to hNKG2A-expressing CHO Cells Anti-NKG2A Antibodies Binding to Cynomolgus NKG2A-expressing CHO Cells Anti-NKG2A Antibodies Binding to Cynomolgus NKG2A-expressing CHO Cells Ability of 2G6.C2 Antibody to Bind Human NKG2A expressing CHO Cells and Block NKG2A/HLA-E Interaction Ability of 2G6.C2 Antibody to Bind Human NKG2A expressing CHO Cells and Block NKG2A/HLA-E Interaction Anti-NKG2A Antibodies Bound to Cynomolgus Monkey NK cells

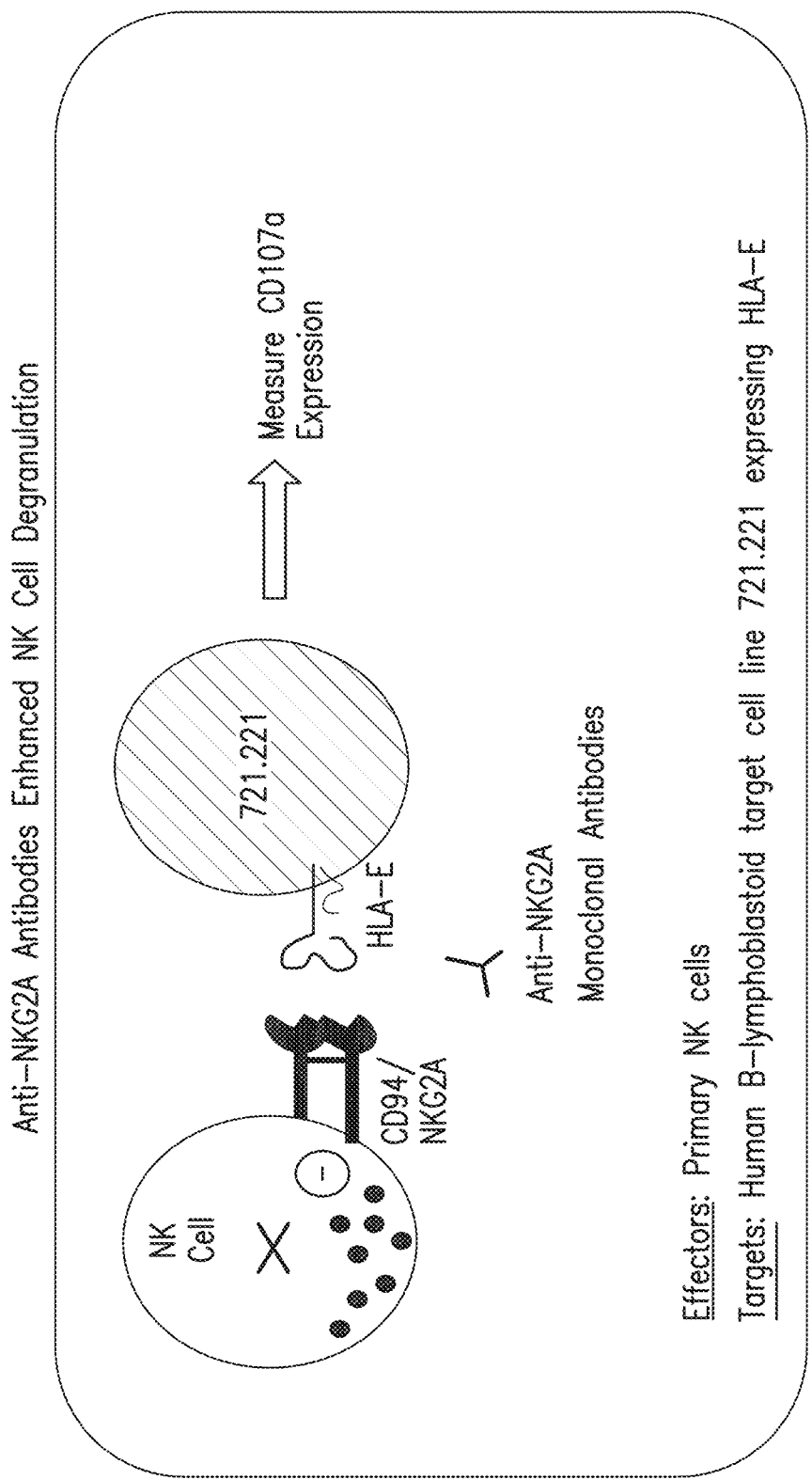

Anti-NKG2A Antibodies Enhanced NK Cell Responses of Interferon-gamma (IFNγ) Production IFNγ production Effectors: NKL Targets: CHO/MICA/HLA-E Anti-NKG2A Antibodies Enhanced CD8+ T Cell Response of Increased IFNγ Production Anti-NKG2A Antibodies Enhanced CD8+ T Cell Response of Increased IFNγ Production

| Epitope of 13F3.A4 and NKG2A.9 | HDX | FPOP |
|---|---|---|
| | BOLD | ⊘ |

Linker amino acid sequence mFc
VPRDSGSKPSISTVPEVSSVFIFPPKPKDVLTITLTPKVTCVVVDISKDDPEVQFSW
FVDDVEVHTAQTQPREEQFNSTFRSVSELPIMHQDWLNGKEFKCRVNSAAFPAPI
EKTISKTKGRPKAPQVYTIPPPKEQMAKDKVSLTCMITDFFPEDITVEWQWNGQ
PAENYKNTQPIMDTDGSYFVYSKLNVQKSNWEAGNTFTCSVLHEGLHNHHTEK
SLSHSPGK ASTEGRGGHCPEEWITYSNSCYYIGKERTWEESLLACTSKNSSLLSI
DNEEEMKFLSIISPSSWIGV RNSSHIPWVTMNGLAFKHEIKDSDNAEMNCAVLQ hNKG2A hCD94
VNRLKSAQCGSSIIYHCKHKLGGSGGGSCCSQEKWVGYRCNCYFISSEQKTWNE
SRHLCASQKSSLLQLNTDELDFMSSSQQFYWIGLSYSEEHTAWLWENGSALSQ
YLFPSFETFNTKNCIAYNPNGNALDESCEDKNRYICKQQLI

FIG. 30

Heavy Chain Variable Region Clustal 2.1 Alignment of Anti-NKG2A Antibodies

```
                FR1                          CDR1  FR2                    CDR2                       
13F3      EVQLVESGGGLVKPGGSLRLSCAASGFTFSSHSMN WVRQAPGKGLEWVS AISSSSSYIYYADSVKG  66
NKG2a.9   EVQLVESGGGLVKPGGSLRLSCAASGFTFSSHSMN WVRQAPGKGLEWVS AISSSSSYIYYADSVKG  66
NKG2a.11  EVQLVESGGGLVKPGGSLRLSCAASGFTFSSHSMN WVRQAPGKGLEWVS AISSSSSYIYYADSVKG  66
          ************************************************** *****************

FR3                           CDR3              FR4
13F3      RFTISRDNAKNSLYLQMNSLRAEDTAVYYCAR EEWGLPFDYW GQGTLVTVSS  118
NKG2a.9   RFTISRDNAKNSLYLQMNSLRAEDTAVYYCAR EEWGLPFDYW GQGTLVTVSS  118
NKG2a.11  RFTISRDNAKNSLYLQMNSLRAEDTAVYYCAR EEWGLPFDYW GQGTLVTVSS  118
          ******************************** ********** **********
```

FIG.32A

Light Chain Variable Region Clustal 2.1 Alignment of Anti-NKG2A Antibodies

```
                   FR1                         CDR1              FR2                    CDR2
13F3       AIQLTQSPSSLSASVGDRVTITCRASQGINSALAWYQQKPGKAPKLLIYDASSLKSGVPS 60
NKG2A.9    AIQLTQSPSSLSASVGDRVTITCRASQGISSALAWYQQKPGKAPKLLIYDASSLKSGVPS 60
NKG2A.11   AIQLTQSPSSLSASVGDRVTITCRASQGIPSALAWYQQKPGKAPKLLIYDASSLKSGVPS 60
           **********************************:***********************

FR3                              CDR3           FR4
13F3       RFSGSGSGTDFTLTISSLQPEDFATYYCQQFNSYPLTFGQGTRLEIK 107
NKG2A.9    RFSGSGSGTDFTLTISSLQPEDFATYYCQQFNSYPLTFGQGTRLEIK 107
NKG2A.11   RFSGSGSGTDFTLTISSLQPEDFATYYCQQFNSYPLTFGQGTRLEIK 107
           ***********************************************
```

FIG. 32B

NKG2A.9 and Anti-PD-L1 Antibodies Enhanced IFN-γ Induction by NKG2A+ CD8 T Cells Co-cultured with CHO/scOKT3/HLA-E/PD-L1

NKG2A.9 and Anti-PD-L1 Antibodies Enhanced IFN-γ Induction by NKG2A+ CD8 T Cells Co-cultured with CHO/scOKT3/HLA-E/PD-L1

NKG2A.9 and anti-PD-L1 Antibodies Enhanced IFN-γ
Production by Tumor Infiltrating NKG2A⁺ CD8+ T Cells
Co-cultured with CHO/scOKT3/HLA-E/PD-L1

Paired t test **p<0.0001, *p<0.0005, **p<0.005, *p<0.05
⊢──⊣ Represents comparison of groups NKG2A.9 Antibody Was Internalized After Binding to NKG2A-expressing Cells NKG2A.9 Antibody Was Internalized After Binding to NKG2A-expressing Cells NKG2A.9 Antibody Enhanced NK Cell Degranulation and Lysis of HLA-E Expressing Head and Neck Tumor Cells NKG2A.9 Antibody Enhanced NK Cell Degranulation and Lysis of HLA-E Expressing Head and Neck Tumor Cells NKG2A.9 Antibody Enhanced NK Cell Degranulation and Lysis
of HLA-E Expressing Head and Neck Tumor Cells NKG2A.9 Antibody Enhanced NK Cell Degranulation and Lysis
of HLA-E Expressing Head and Neck Tumor Cells 13F3.A4 Antibody Enhanced the Functional Activity of Natural Killer Cells 13F3.A4 Antibody Enhanced the Functional Activity of Natural Killer Cells Combination of Anti-mNKG2A and Anti-mPD-1 Antibodies
Reduced Tumor Growth in the CT26 Mouse Model Combination of Anti-mNKG2A and Anti-mPD-1 Antibodies
Reduced Tumor Growth in the CT26 Mouse Model Anti-mNKG2A and Anti-mPD-1 Antibodies Increased NK and Tumor-specific CD8 T cell Cytotoxicity and IFN-γ in the CT26 Murine Colon Carcinoma Anti-mNKG2A and Anti-mPD-1 Antibodies Increased NK and Tumor-specific CD8 T cell Cytotoxicity and IFN-γ in the CT26 Murine Colon Carcinoma

METHODS OF TREATING HLA-E-EXPRESSING CANCERS BY ADMINISTERING ANTIBODIES WHICH BIND HUMAN NATURAL KILLER CELL INHIBITORY RECEPTOR GROUP 2A (NKG2A)

CROSS REFERENCE TO RELATED APPLICATIONS

This application is a divisional of U.S. patent application Ser. No. 16/683,927 now U.S. Pat. No. 11,274,150, filed Nov. 14, 2019, and claims the benefit of priority of U.S. Provisional Application No. 62/768,471, filed Nov. 16, 2018, and U.S. Provisional Application No. 62/927,211, filed Oct. 29, 2019, each of which are incorporated herein by reference in their entireties.

TECHNICAL FIELD

This invention relates to anti-NKG2A (natural killer cell inhibitory receptor group 2A) antibodies and pharmaceutical compositions thereof. The invention also relates to methods for using such antibodies, including methods for treating diseases such as cancer by administering the anti-NKG2A antibodies and pharmaceutical compositions thereof.

REFERENCE TO SEQUENCE LISTING SUBMITTED ELECTRONICALLY VIA EFS-WEB

The instant application contains a Sequence Listing which has been submitted electronically in ASCII format and is hereby incorporated by reference in its entirety. Said ASCII copy, created on Feb. 10, 2022, is named 20220210_SEQ_13119USDIV2.txt and is 263 KB in size.

BACKGROUND

Cancer is a global epidemic. According to the Global Health Data Exchange, cancer is one of the leading causes of disease and the second leading cause of death, causing about 17% of deaths worldwide. ("Hannah Ritchie and Max Roser, "Causes of Death—Share of deaths by cause, World, 2017", OurWorldInData.org, 2018. According to the World Health Organization, even in 2010, the economic impact of cancer was $1.16 trillion; in 2018, cancer accounted for an estimated 9.6 million deaths worldwide. ("Cancer." *World Health Organization*. World Health Organization, 2018. According to the National Cancer Institute estimates, in 2019, over 1.7 million new patients will be diagnosed with cancer, and over 600,000 patients will die from cancer in the United States. ("*Cancer Stat Facts: Cancer of Any Site*." SEER Training Modules, U. S. National Institutes of Health, National Cancer Institute, 2019.

Traditional cancer treatments include surgery, radiation therapy, and chemotherapy, amongst other therapies. In recent years, immuno-oncology or immunotherapy has emerged as a new option to treat cancer using the body's immune system. Immuno-oncology is different from traditional cancer treatments, which, for example, have tried to target tumors directly and/or to disrupt the tumor blood supply. Instead, immuno-oncology is designed to harness the patient's own immune system to help restore or to enhance the patient's anti-tumor immune response. Without an immuno-oncology approach, a patient's own immune responses frequently fail to prevent tumor growth for various reasons. For example, many tumors have developed specialized mechanisms to evade the patient's immune responses. Tumor cells may also lose the expression of antigens that may be recognized by the patient's immune system. In other cases, a tumor's rapid growth may even overwhelm the immune system's capacity to effectively control the tumor. (Abbas et al., "Chap. 18: Immunity to Tumors", in Cellular and Molecular Immunology, $9^{th}$ ed. Elsevier, Inc., (2018)). Understanding how the immune system affects cancer development and how the immune system can be used to treat cancer has presented challenging, multi-faceted problems. For example, many patients do not respond to existing immuno-oncology treatments, and some develop resistance mechanisms, such as T cell exhaustion, which is when a T cell, a specific type of white blood cell, no longer functions properly. (Dempke et al., *Eur. J. of Cancer*, 74: 55-72 (2017)).

Patients need improved treatments for diseases such as cancer to improve upon traditional therapies, including currently available cancer immunotherapies. There is a great need for novel immuno-oncology agents used either alone or in combination with existing agents to improve patients' response rates and to overcome drug resistance.

SUMMARY OF THE INVENTION

The present invention provides, in some aspects, isolated monoclonal antibodies (e.g., humanized and human monoclonal antibodies) that bind to human NKG2A protein (SEQ ID NO: 1), i.e., anti-NKG2A antibodies, including anti-hNKG2A antibodies that exhibit desirable functional properties. In one aspect, the desirable functional properties of the anti-NKG2A antibodies disclosed herein include to stimulate immune responses, for example, to treat cancer. In another aspect, the desirable functional properties of the anti-NKG2A antibodies disclosed herein include to treat virus-infected subjects, including human patients. In some embodiments, the anti-NKG2A antibodies disclosed herein treat infectious diseases. In another aspect, the anti-NKG2A antibodies disclosed herein treat autoimmune conditions. In other embodiments, the anti-NKG2A antibodies of the invention are used as antagonistic anti-NKG2A antibodies to stimulate and/or enhance an immune response in a subject, e.g., to stimulate and/or enhance the anti-tumor responses of the immune system, including natural killer cells and/or T cells. In other embodiments, the anti-NKG2A antibodies of the invention are used in combination with other antibodies to treat various conditions, including cancer, infectious diseases, including viral infections, and autoimmune diseases. Accordingly, in some embodiments, the anti-NKG2A antibodies disclosed herein, either alone or in combination with other treatments, such as other immuno-oncology treatments and/or chemotherapy and/or surgery, are used to treat various conditions or diseases, including cancer and viral infections. In other embodiments, the anti-NKG2A antibodies disclosed herein are used in methods to detect NKG2A protein in a sample.

In one aspect, the present invention provides an isolated monoclonal antibody, or an antigen-binding fragment thereof, wherein the antibody, or an antigen-binding fragment thereof, specifically binds human NKG2A and exhibits at least one of the following properties:
  (a) reduces (e.g., blocks) binding and/or interaction of an NKG2A ligand (e.g., HLA-E in humans) to human NKG2A protein;
  (b) reverses NKG2A-mediated inhibitory signaling;

(c) does not bind, or binds with low affinity to, human NKG2C protein;
(d) binds to human and/or cynomolgus NKG2A;
(e) enhances natural killer cell response;
(f) enhances the functional activity of T cells;
(g) has reduced binding to human Fc gamma receptor (FcγR);
(h) induces and/or enhances an anti-tumor immune response;
(i) induces and/or enhances an anti-viral immune response;
and/or
(j) has low immunogenicity in subjects, including human subjects.

In one embodiment, the isolated monoclonal antibody, or an antigen-binding fragment thereof, has one or more of the following properties:
(a) has an $EC_{50}$ value of about 0.6 nM or lower for binding to human NKG2A protein as measured by cell binding assay;
(b) has an $EC_{50}$ value of about 9.0 nM or higher for binding to human NKG2C protein as measured by cell binding assay;
(c) has an $EC_{50}$ value for the binding to human NKG2A protein that is about 15-fold less than a second $EC_{50}$ value for binding to human NKG2C protein;
(d) has an $IC_{50}$ value of about 1.0 nM or lower for reducing the binding and/or interaction of HLA-E to human NKG2A protein as measured by cell blocking assay;
(e) binds to human NKG2A protein with a $K_D$ of about 0.4 nM or lower as measured by Scatchard analysis;
(f) binds to human NKG2A with a $K_D$ of about 61 nM or lower as measured by surface plasmon resonance;
(g) binds to cynomolgus NKG2A with a $K_D$ of about 1.0 nM or lower as measured by Scatchard analysis;
(h) is internalized upon binding to NKG2A-expressing cells;
(i) increases interferon-gamma (IFNγ) production;
(j) exhibits internationalization with an $EC_{50}$ value of about 0.5 nM or lower; and/or
(k) wherein the half-life of the anti-NKG2A antibody: NKG2A complex is about 40 seconds or longer. In some embodiments, the half-life of the anti-NKG2A antibody:NKG2A complex is measured using surface plasmon resonance analysis.

In one embodiment, the anti-NKG2A antibodies, or antigen binding fragment thereof, disclosed herein reduce (e.g., block) the interaction of human NKG2A protein and human NKG2A ligand (i.e., HLA-E).

In another aspect, the present invention provides an isolated monoclonal antibody, or antigen-binding fragment thereof, that specifically binds to human NKG2A protein, wherein the antibody comprises:
(a) a heavy chain variable domain comprising amino acid sequences of SEQ ID NOs: 10, 11, 12, and a light chain variable domain comprising amino acid sequences of SEQ ID NOs: 13, 14, and 15;
(b) a heavy chain variable domain comprising amino acid sequences of SEQ ID NOs: 10, 11, and 12, and a light chain variable domain comprising amino acid sequences of SEQ ID NOs: 154, 14, and 15; or
(c) a heavy chain variable domain comprising amino acid sequences of SEQ ID NOs: 10, 11, and 12, and a light chain variable domain comprising amino acid sequences of SEQ ID NOs: 155, 14, and 15.

In another aspect, the invention provides an isolated monoclonal antibody, or antigen-binding fragment thereof, that specifically binds to human NKG2A protein, and comprises heavy and light chain variable regions, wherein
(a) the heavy chain variable region comprises an amino acid sequence that is at least about 80%, at least about 85% at least about 90%, at least about 95%, at least about 96%, at least about 97%, at least about 98%, at least about 99%, about 100%, or 100% identical to the amino acid sequence of SEQ ID NO: 8 or SEQ ID NO: 167; and/or
(b) the light chain variable region comprises an amino acid sequence that is at least about 80%, at least about 85% at least about 90%, at least about 95%, at least about 96%, at least about 97%, at least about 98%, at least about 99%, about 100%, or 100% identical to the amino acid sequence of SEQ ID NO: 9, SEQ ID NO: 164, or SEQ ID NO: 169, respectively.

In some embodiments, the isolated monoclonal antibody, or antigen-binding fragment thereof, that specifically binds to human NKG2A protein, comprises a heavy chain variable region that comprises the amino acid sequence of SEQ ID NO: 8, and a light chain variable region that comprises the amino acid sequence of SEQ ID NO: 9.

In some embodiments, the isolated monoclonal antibody, or antigen-binding fragment thereof, that specifically binds to human NKG2A protein, comprises a heavy chain variable region that comprises the amino acid sequence of SEQ ID NO: 8, and a light chain variable region that comprises the amino acid sequence of SEQ ID NO: 164.

In some embodiments, the isolated monoclonal antibody, or antigen-binding fragment thereof, that specifically binds to human NKG2A protein, comprises a heavy chain variable region that comprises the amino acid sequence of SEQ ID NO: 167, and a light chain variable region that comprises the amino acid sequence of SEQ ID NO: 169.

In another aspect, the invention provides an isolated monoclonal antibody, or antigen-binding fragment thereof, that specifically binds to human NKG2A protein, wherein the heavy and light chains consist essentially of:
(a) the amino acid sequences of SEQ ID NOs: 7 and 5, respectively;
(b) the amino acid sequences of SEQ ID NOs: 7 and 19, respectively; or
(c) the amino acid sequences of SEQ ID NOs: 35 and 36, respectively.

In some embodiments, the isolated monoclonal antibody, or antigen-binding fragment thereof, competes for binding to NKG2A protein with or binds to the same epitope as the anti-NKG2A antibodies disclosed herein.

In another aspect, the invention provides an isolated monoclonal antibody, or antigen-binding fragment thereof, that, when bound to human NKG2A protein, the antibody, or an antigen-binding fragment thereof, specifically binds to the following amino acid residues as determined by hydrogen-deuterium exchange mass spectrometry (HDX-MS):

(a) LSIDNEEMKF; (SEQ ID NO: 156)

(b) PSSWIGVFRNSSHHPW; (SEQ ID NO: 157)

-continued (c) LAFKHEIKDSDN; (SEQ ID NO: 158)
and (d) QVNRLKSAQQCGSSIIYHC. (SEQ ID NO: 159)

In some embodiments, the monoclonal antibody blocks the binding of an NKG2A ligand (e.g., HLA-E in humans) to human NKG2A protein.

In another aspect, the invention provides an isolated monoclonal antibody, or antigen-binding fragment thereof, that, when bound to human NKG2A, specifically binds to the following amino acid residues as determined by HDX-MS and/or fast photochemical oxidation of proteins (FPOP) epitope mapping:

(a) LSIDNEEMKF (SEQ ID NO: 156)

(b) PSSWIGVFRNSSHHPW (SEQ ID NO: 157)

(c) LAFKHEIKDSDN (SEQ ID NO: 158)

(d) L;
and (e) QVNRLKSAQQCGSSIIYHC. (SEQ ID NO: 159)

In some embodiments, the antibody blocks the binding of an NKG2A ligand (e.g., HLA-E in humans) to human NKG2A protein.

In some embodiments, the isolated monoclonal antibody is a full-length antibody. In other embodiments, the isolated monoclonal antibody is a full-length IgG1 antibody. In some other embodiments, the isolated monoclonal antibody is an antibody fragment. In other embodiments, the antibody fragment is a Fab, Fab', (Fab')2, Fv, or scFv fragment. In other embodiments, the isolated monoclonal antibody is a human, humanized, or chimeric antibody.

In one aspect, the invention provides an isolated, full-length monoclonal antibody that binds specifically to human NKG2A protein, wherein
  (a) the heavy chain comprises an amino acid sequence that is at least about 80%, at least about 85%, at least about 90%, at least about 95%, at least about 96%, at least about 97%, at least about 98%, at least about 99%, about 100%, or 100% identical to the amino acid sequence of SEQ ID NO: 7, and/or
  (b) the light chain comprises an amino acid sequence that is at least about 80%, at least about 85%, at least about 90%, at least about 95%, at least about 96%, at least about 97%, at least about 98%, at least about 99%, about 100%, or 100% identical to the amino acid sequence of SEQ ID NO: 5.

In some embodiments, the heavy chain of the isolated, full-length monoclonal antibody comprises the amino acid sequence set forth in SEQ ID NO: 7, and the light chain comprises the amino acid sequence set forth in SEQ ID NO: 5.

In another aspect, the isolated, full-length monoclonal antibody specifically binds to human NKG2A protein, wherein the heavy chain consists essentially of the amino acid sequence set forth in SEQ ID NO: 7, and the light chain consists essentially of the amino acid sequence set forth in SEQ ID NO: 5.

In another aspect, the invention provides an isolated nucleic acid molecule that encodes the heavy chain variable region and/or light chain variable region of the antibodies or antigen binding fragments thereof described herein. In some embodiments, the nucleic acid molecule is complementary DNA (cDNA).

In another aspect, the invention provides an expression vector comprising the nucleic acid molecules described herein. In another aspect, the invention provides a host cell transformed with the expression vector described herein.

In another aspect, the invention provides an immunoconjugate that comprises the antibodies described herein linked to an agent.

In another aspect, the invention provides methods of producing the antibody comprising culturing the host cell described herein. In some embodiments, the methods further comprise recovering the antibody from the host cell.

In another aspect, the invention provides a bispecific molecule comprising the anti-NKG2A antibodies described herein linked to a second functional moiety.

In another aspect, the invention provides a composition comprising the anti-NKG2A antibodies described herein, or the bispecific molecules described herein, and a pharmaceutically acceptable carrier and/or a soluble neutral-active hyaluronidase glycoprotein. In some embodiments, the composition further comprises an additional therapeutic agent. In other embodiments, the additional therapeutic agent is an anti-PD-1 antibody, anti-PD-L1 antibody, and/or an anti-CTLA-4 antibody. In other embodiments, the anti-PD-1 antibody is nivolumab, and the anti-CTLA antibody is ipilimumab. In other embodiments, the antibodies described herein are for use as a medicament for treating cancer.

In some embodiments, the cancer that is treated using the anti-NKG2A antibodies, immunoconjugates, bispecific molecules, and compositions described herein is bladder cancer, breast cancer, uterine/cervical cancer, ovarian cancer, prostate cancer, testicular cancer, esophageal cancer, gastrointestinal cancer, pancreatic cancer, colorectal cancer, kidney cancer, head and neck cancer, lung cancer, stomach cancer, germ cell cancer, bone cancer, liver cancer, thyroid cancer, skin cancer, neoplasm of the central nervous system, lymphoma, leukemia, myeloma, sarcoma, endometrial, cervical, gastric, melanoma, renal, urothelial, glioblastoma multiform, or virus-related cancer. In other embodiments, the cancer is cervical, head and neck squamous cell carcinoma (HNSCC), pancreatic, non-small cell lung cancer-adenocarcinoma type (NSCLC-AD), non-small cell lung cancer-squamous cell type (NSCLC-SQC), gastric, melanoma, colorectal (CRC), endometrial, ovarian, renal cell carcinoma (RCC), urothelial carcinoma (UCC), breast, small cell lung, glioblastoma mulitforme, prostate cancer (also known as adenocarcinoma of the prostate or PRC), or non-Hodgkin lymphoma.

In some embodiments, the anti-NKG2A antibodies are for use in enhancing an immune response. In other embodiments, the invention provides use of the anti-NKG2A antibodies described herein in the manufacture of a medicament for treatment of cancer.

In one aspect, the invention provides methods for treating or delaying progression of cancer in a human subject comprising administering to the human subject an effective amount of the anti-NKG2A antibodies, immunoconjugates, bispecific molecules, or compositions described herein. In some embodiments, the cancer is bladder cancer, breast cancer, uterine/cervical cancer, ovarian cancer, prostate cancer, testicular cancer, esophageal cancer, gastrointestinal cancer, pancreatic cancer, colorectal cancer, kidney cancer, head and neck cancer, lung cancer, stomach cancer, germ cell cancer, bone cancer, liver cancer, thyroid cancer, skin cancer, neoplasm of the central nervous system, lymphoma, leukemia, myeloma, sarcoma, endometrial, cervical, gastric, melanoma, renal, urothelial, glioblastoma multiform, or virus-related cancer. In other embodiments, the cancer is cervical, head and neck squamous cell carcinoma (HNSCC), pancreatic, non-small cell lung cancer-adenocarcinoma type (NSCLC-AD), non-small cell lung cancer-squamous cell type (NSCLC-SQC), gastric, melanoma, colorectal (CRC), endometrial, ovarian, renal cell carcinoma (RCC), urothelial carcinoma (UCC), breast, small cell lung, glioblastoma mulitforme, prostate cancer (also known as adenocarcinoma of the prostate or PRC), or non-Hodgkin lymphoma.

In other embodiments, the methods further comprise administering one or more additional therapeutic agent(s) to the human subject. In some embodiments, the one or more additional therapeutic agent(s) is a chemotherapeutic agent, a radiotherapeutic agent, and/or an immunotherapeutic agent. In other embodiments, the one or more additional therapeutic agent(s) is an anti-PD-1 antibody, an anti-PD-L1 antibody, and/or an anti-CTLA-4 antibody. In some embodiments, the anti-PD-1 antibody is nivolumab, and the anti-CTLA-4 antibody is ipililumab.

In another aspect, the invention provides methods of stimulating an immune response in a human subject comprising administering to the human subject an effective amount of the anti-NKG2A antibodies, bispecific molecules, or compositions described herein. In some embodiments, the human subject has a tumor and an anti-tumor immune response is stimulated. In other embodiments, the human subject has a chronic viral infection and an anti-viral immune response is stimulated.

In another aspect, the invention provides methods of detecting presence of NKG2A protein in a sample comprising contacting the sample with the antibody, or antigen-binding fragment thereof, disclosed herein, under conditions that allow for formation of a complex between the antibody, or antigen-binding fragment thereof, and NKG2A protein, and detecting the formation of the complex. In some embodiments of the method, the antibody, or antigen-binding fragment thereof, forms a complex 15 times more quickly with NKG2A protein than with NKG2C protein.

Other features and advantages of the instant disclosure will be apparent from the following detailed description and examples, which should not be construed as limiting. The contents of all references, GenBank and other sequence entries, patents and published patent applications cited throughout this application are expressly incorporated herein by reference.

BRIEF DESCRIPTION OF THE DRAWINGS

FIG. 1A illustrates the hybridoma method and anti-NKG2A antibody discovery and development steps at a high level. FIG. 1B illustrates the antibody library generation method used for antibody discovery. FIG. 1C illustrates the single B cell cloning (SBCC) method.

FIG. 2 shows the steps for generating variants of the 13F3.A4 I107T antibody and to characterize its binding to NKG2A protein. This analysis allowed the inventors to generate variants of the 13F3.A4 I107T antibody with improved properties, and provided a rich set of information about the effect of single amino acid substitutions on the binding of the 13F3.A4 I107T antibody to NKG2A protein. FIG. 2 discloses SEQ ID NOs: 183-190, respectively, in order of appearance from top to bottom.

FIG. 3 discloses SEQ ID NOs: 191 (germline) and SEQ ID NO: 192 (parental).

FIG. 4 shows the CDR positions that were analyzed for the 13F3.A4 I107T anti-NKG2A antibody using mutational scan analysis. FIG. 4 discloses SEQ ID NOs: 30, 15, 192, 11, and 193, respectively, in order of appearance.

FIG. 6 shows the alignment of the canonical sequence of full length human NKG2A (SEQ ID NO: 182) and human NKG2C (SEQ ID NO: 3) amino acid sequences. About 76% of amino acid residues (177 out of 233 amino acid residues) are conserved, about 6% of amino acid residues (14 of 233 amino acid residues) are similar, and only about 18% of amino acid residues (42 of 233 amino acid residues) are different between the human NKG2A and human NKG2C proteins.

FIG. 7A shows the nucleotide sequence (SEQ ID NO: 166) and the amino acid sequence (SEQ ID NO: 167 without signal sequence) of the mature heavy chain variable (VH) region of the anti-NKG2A antibody 13F3.A4. The amino acid sequences of the VH CDR1 (SEQ ID NO: 27), VH CDR2 (SEQ ID NO: 28), and VH CDR3 (SEQ ID NO: 29) sequences are shown in gray boxes.

FIG. 7B shows the nucleotide sequences (SEQ ID NO: 168) and amino acid sequences (SEQ ID NO: 169) of the light chain variable region of the 13F3.A4 antibody. The amino acid sequences of the VL CDR1 (SEQ ID NO: 30), VL CDR2 (SEQ ID NO: 31), and VL CDR3 (SEQ ID NO: 32) sequences are shown in gray boxes.

FIG. 8A shows the nucleotide sequence (SEQ ID NO: 51) and the amino acid sequence (SEQ ID NO: 52) of the mature VH region of the anti-NKG2A antibody 2G6.C2. The amino acid sequences of the VH CDR1 (SEQ ID NO: 55), VH CDR2 (SEQ ID NO: 56), and VH CDR3 (SEQ ID NO: 57) sequences are shown in gray boxes.

FIG. 8B shows the nucleotide sequences (SEQ ID NO: 53) and amino acid sequences (SEQ ID NO: 54) of the mature VL region of the anti-NKG2A antibody 2G6.C2. The amino acid sequences of the VL CDR1 (SEQ ID NO: 58), VL CDR2 (SEQ ID NO: 59), and VL CDR3 (SEQ ID NO: 60) sequences are shown in gray boxes.

FIG. 9A shows the nucleotide sequence (SEQ ID NO: 170) and the amino acid sequence (SEQ ID NO: 171) of the mature heavy chain variable (VH) region of the anti-NKG2A antibody 11H9.A1. The amino acid sequences of the VH CDR1 (SEQ ID NO: 41), VH CDR2 (SEQ ID NO: 42), and VH CDR3 (SEQ ID NO: 43) sequences are shown in gray boxes.

FIG. 9B shows the nucleotide sequences (SEQ ID NO: 172) and amino acid sequences (SEQ ID NO: 173) of the light chain variable region of the mature anti-NKG2A antibody 11H9.A1. The amino acid sequences of the VL CDR1 (SEQ ID NO: 44), VL CDR2 (SEQ ID NO: 45), and VL CDR3 (SEQ ID NO: 46) sequences are shown in gray boxes.

FIG. 10A shows the nucleotide sequence (SEQ ID NO: 174) and the amino acid sequence (SEQ ID NO: 175) of the mature VH region of the anti-NKG2A antibody 4G5.D1. The amino acid sequences of the VH CDR1 (SEQ ID NO: 69), VH CDR2 (SEQ ID NO: 70), and VH CDR3 (SEQ ID NO: 71) sequences are shown in gray boxes.

FIG. 10B shows the nucleotide sequence (SEQ ID NO: 176) and amino acid sequences (SEQ ID NO: 177) of the VL of the 4G5.D1 antibody. The amino acid sequences of the VL CDR1 (SEQ ID NO: 72), VL CDR2 (SEQ ID NO: 73), and VL CDR3 (SEQ ID NO: 74) sequences are shown in gray boxes.

FIG. 11A shows the nucleotide sequence (SEQ ID NO: 178) and the amino acid sequence (SEQ ID NO: 179) of the mature VH region of the anti-NKG2A antibody 1G5.B2. The amino acid sequences of the VH CDR1 (SEQ ID NO: 83), VH CDR2 (SEQ ID NO: 84), and VH CDR3 (SEQ ID NO: 85) sequences are shown in gray boxes.

FIG. 11B shows the nucleotide sequence (SEQ ID NO: 180) and the amino acid sequence (SEQ ID NO: 181) of the VL region of the 1G5.B2 antibody. The amino acid sequences of the VL CDR1 (SEQ ID NO: 86), VL CDR2 (SEQ ID NO: 87), and VL CDR3 (SEQ ID NO: 88) sequences are shown in gray boxes.

FIG. 12 shows the amino acid sequence liabilities that were assessed in the 13F3.A4 antibody. The V, D, and J germline derivations are indicated. The amino acid sequences of the heavy chain variable region of the 13F3.A4 antibody (SEQ ID NO: 167) are shown on the left, and the amino acid sequences of the light chain variable region of the 13F3.A4 antibody (SEQ ID NO: 169) are shown on the right. The amino acid sequences of the VL CDR1 (SEQ ID NO: 30), VL CDR2 (SEQ ID NO: 31), and VL CDR3 (SEQ ID NO: 32) sequences are underlined. The amino acid sequences of the VH CDR1 (SEQ ID NO: 27), VH CDR2 (SEQ ID NO: 28), and VH CDR3 (SEQ ID NO: 29) sequences are underlined. The sequence liabilities that were assessed are circled and labeled.

FIG. 13 shows the full length amino acid sequence of anti-NKG2A antibody NKG2A.9. The light chain amino acid sequence is set forth in SEQ ID NO: 5, and the heavy chain amino acid sequence is set forth in SEQ ID NO: 163 (shown with the terminal lysine, which in another embodiment is absent). FIG. 13 identifies with an oval two mutations made to the 13F3.A4 VL sequence (N30S) and VH sequence (I107T) to result in the NKG2A.9 sequence. The N-glycosylation motif is shown with a dashed oval. Three mutations (L234A, L235E, and G273A) that were made to the Fc region are shown in bold italics. The terminal amino acid lysine in the heavy chain sequence was removed from the mature sequence. The amino acid sequences of the VL CDR1 (SEQ ID NO: 13), VL CDR2 (SEQ ID NO: 14), and VL CDR3 (SEQ ID NO: 15) sequences are in bold and underlined. The amino acid sequences of the VH CDR1 (SEQ ID NO: 10), VH CDR2 (SEQ ID NO: 11), and VH CDR3 (SEQ ID NO: 12) sequences are in bold and underlined.

FIG. 14 shows the full length amino acid sequence of anti-NKG2A antibody NKG2A.9. The light chain amino acid sequence is set forth in SEQ ID NO: 5, and the heavy chain amino acid sequence is set forth in SEQ ID NO: 7.

FIG. 15 shows the full length amino acid sequence of anti-NKG2A antibody NKG2A.11. The light chain amino acid sequence is set forth in SEQ ID NO: 19, and the heavy chain amino acid sequence is set forth in SEQ ID NO: 7.

As shown in FIG. 18B, the 13F3.A4, 11H9.A1, and 2EB.B1 antibodies showed specific binding to the human NKG2A-expressing CHO cells.

As shown in FIG. 24B, the 11H9.A1 and 4G5.D1 antibodies did not bind to cynomolgus NKG2A+ NK cells, while the 13F3.A4 antibody desirably bound to cynomolgus monkey NKG2A+ NK cells, as indicated by the $EC_{50}$ value of 0.2 nM.

FIG. 25A illustrates the in vitro method used to assess whether anti-NKGA antibodies increased NK cell degranulation.

FIG. 30 shows the epitopes of NKG2A.9 and 13F3.A4 antibodies as determined by HDX-MS and by FPOP mapped to the mFc-hNKG2A-hCD94 sequence (SEQ ID NO: 125). The bold, underlined epitopes were determined by HDX-MS, and the circled epitopes were determined by FPOP analysis.

FIG. 32A-B show the alignment of VH region (SEQ ID NOS: 167, 8, and 8, respectively, in order of appearance from top to bottom) (FIG. 32A) and VL regions (SEQ ID NOS: 169, 9, and 164, respectively, in order of appearance from top of bottom) (FIG. 32B) of certain portions of the anti-NKG2A antibodies (13F3.A4, NKG2A.9, and NKG2A.11). This alignment resulted in the discovery of anti-NKG2A antibodies with consensus CDR sequences shown in boxes.

FIG. 40A-D show the tumor volume at various time points after tumor implantation in mice (n=10/group) treated with isotype (FIG. 40A), anti-mNKG2A antibody alone (FIG. 40B), anti-mPD-1 antibody alone (FIG. 40C), or a combination of anti-mNKG2A and anti-mPD1 antibodies (FIG. 40D). FIG. 40E shows the average tumor volume as a function of time (days after tumor implantation) in mice treated with isotype, anti-mNKG2A antibody alone, anti-mPD-1 antibody alone, or a combination of anti-mNKG2A and anti-mPD-1 antibodies.

FIG. 42A-D show the tumor volume at various time points after tumor implantation in mice treated with isotype (FIG. 42A), anti-mCTLA-4 antibody (FIG. 42B, CTLA-4 IgG2a, 0.1 mg/kg), anti-mNKG2A antibody (FIG. 42C, 10 mg/kg), or a combination of anti-mNKG2A and anti-mCTLA-4 (FIG. 42D). FIG. 42E shows the average tumor volume as a function of time (days after tumor implantation) in mice treated with isotype, anti-mCTLA-4 alone, anti-mNKG2A alone, or combination of anti-mNKG2A and anti-mCTLA-4.

FIG. 54A-C show the results of using an in silico HLA binding tool to analyze the 13F3.A4 antibody for undesirable binding clusters. FIGS. 54A-C disclose SEQ ID NOS: 197-204, respectively, in order of appearance from top to bottom.

DETAILED DESCRIPTION

Figure 1A:
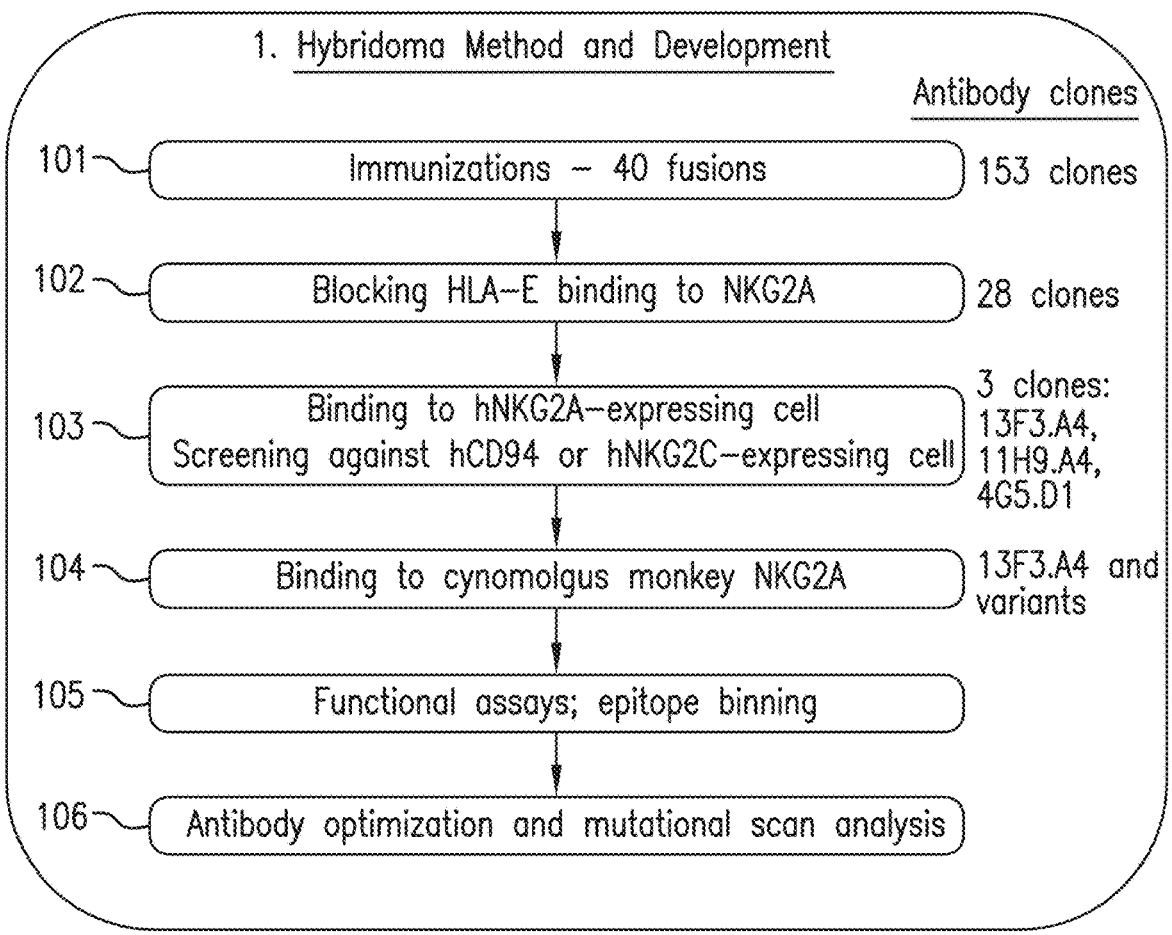
FIG. 1A-C illustrate three methods that were used to discover and test the anti-NKG2A antibodies disclosed herein.

In some aspects, the present invention provides isolated antibodies, such as monoclonal antibodies, e.g., humanized, human, and chimeric monoclonal antibodies, that specifically bind to human NKG2A ("hNKG2A") and have antagonistic activity to stimulate an anti-tumor immune response. In some embodiments, the anti-NKG2A antibodies described herein comprise particular structural features such as CDR regions comprising particular amino acid sequences. In other embodiments, the anti-NKG2A antibodies compete for binding to human NKG2A protein with, or bind to the same or similar epitope as, the anti-NKG2A antibodies of the present invention.

In some aspects, the present invention provides methods of making such anti-NKG2A antibodies, immunoconjugates, and bispecific molecules comprising such anti-NKG2A antibodies or antigen-binding fragments thereof, and pharmaceutical compositions formulated to contain the anti-NKG2A antibodies or antigen-binding fragments thereof. In some aspects, the present invention provides methods of using the anti-NKG2A antibodies, either alone or in combination with other agents, e.g., other immuno-oncology agents (e.g., antibodies), chemotherapy, radiation therapy, and/or surgery, to enhance the immune response. Accordingly, in some embodiments, the anti-NKG2A antibodies described herein are used to treat a variety of conditions, including, for example, to safely and effectively treat cancer and/or infections.

An important role of the immune system is its ability to differentiate between normal cells and "foreign" cells. The immune system can thus attack the foreign cells and leave normal cells alone. Tumors express antigens that are recognized as foreign by the host. The immune system uses "checkpoints," which are molecules on certain immune cells that need to be activated or inactivated to begin an immune response. Tumor cells can sometimes use these checkpoints to avoid being attacked by the immune system. Some immuno-oncology drugs target these checkpoints by acting as checkpoint inhibitors. Programmed death protein 1 (PD-1) is a checkpoint inhibitor that acts as a brake to prevent T cells from attacking other cells in the body. PD-1 does this when it binds to programmed death ligand 1 (PD-L1), a protein on some normal (and cancer) cells. When PD-1 binds to PD-L1, this interaction signals the T cell to not attack other cells. Some cancer cells have large amounts of PD-L1, which helps them evade immune attack. Therapeutic agents such as monoclonal antibodies that target this PD-1/PD-L1 interaction, such as nivolumab (Opdivo®), can block the PD-1/PD-L1 binding to increase the body's immune response against tumor cells.

Natural killer cell inhibitory receptor Group 2A (NKG2A) is a member of the NKG2 lectin receptor family that also includes NKG2C, NKG2D, and NKG2E. (Iwaszko and Bogunia-Kubik, *Arch Immunol Ther Exp*, 59:353-67 (2011)). NKG2A, NKG2C, and NKG2E have high homology in their amino acid sequence of the extracellular domains, whereas NKG2D is a functionally distinct type of receptor. NKG2A forms a heterodimer with CD94. Among NKG2/CD94 heterodimers, NKG2A/CD94 is the only receptor that has inhibitory function, whereas NKG2C/CD94 and NKG2E/CD94 are activating receptors. NKG2D is also an activating receptor, but it does not form a heterodimer with CD94, nor does NKG2D bind HLA-E. The NKG2/CD94 receptors recognize non-classical major histocompatibility (MHC) class I molecules, which is Human Leukocyte Antigen-E (HLA-E) in humans and Qa-1 in mice. (Braud et al, Nature, 391:795-99 (1998), Vance et al., J. Exp. Med. 188:1841-48 (1998). NKG2A/CD94 binds to HLA-E with about a six-fold stronger affinity than NKG2C/CD94.

Id. NKG2A is expressed on natural killer (NK), effector/memory CD8+ T, NKT, and gamma delta (γδ) T cells. NKG2A expression is induced by T cell receptor (TCR) engagement and after stimulation with certain cytokines, including IL-2, IL-10, IL-15, IL-18, IL-21, although the capacity of cytokines to induce NKG2A expression depends on TCR engagement (Cho, Blood, 118:116-28 (2011). NKG2A has two immunoreceptor tyrosine-based inhibitory motifs (ITIMS) that transmit intracellular inhibitory signals. (Kabat et al, J. Immunol, 169:1948-58 (2002); Le Dréan El, Eur. J. Immunol 28:264076 (1998). The anti-NKG2A antibodies described herein inhibit the NKG2A protein and thus act as checkpoint inhibitors.

Definitions

In order that the present description may be more readily understood, certain terms are first defined. Unless defined otherwise, all technical and scientific terms used herein have the same meaning as commonly understood by one of ordinary skill in the art to which this disclosure is related. Additional definitions are set forth throughout the detailed description. The headings provided herein are not limitations of the various aspects of the disclosure, which can be understood by reference to the specification as a whole. Accordingly, the terms defined immediately below are more fully defined by reference to the specification in its entirety.

As used herein, "NKG2A" refers to the natural killer cell inhibitory receptor Group 2 protein that in humans is encoded by the NKG2A gene. NKG2A is also known as, for example, CD159 antigen-like family member A, NK cell receptor A, NKG2A-activating NK receptor, NKG2-A/B-activating NK receptor, killer cell lectin like receptor C1 (CD159a), and NKG2-A/NKG2-B type II integral membrane protein.

Three isoforms of human NKG2A protein that correspond to five variants of the mRNA transcript have been identified.

Isoform 1 that corresponds to variant 1 (nucleotide sequence set forth at SEQ ID NO: 1 or 209, and amino acid sequence set forth at SEQ ID NO: 2) and variant 3 (nucleotide sequence set forth at SEQ ID NO: 212, and amino acid sequence set forth at SEQ ID NO: 182) consists of 233 amino acids and represents the canonical NGK2A sequence. Isoform 1 variant 3 is also a naturally occurring variant that is a Single Nucleotide Polymorphism (SNP) at residue 29 in which asparagine (N) is changed to a serine (S), i.e., N29S (SEQ ID NO: 182).

Isoform 2 that corresponds to variant 2 (nucleotide sequence set forth at SEQ ID NO: 210, and amino acid sequence set forth at SEQ ID NO: 206) and variant 4 (nucleotide sequence set forth at SEQ ID NO: 211, and amino acid sequence set forth at SEQ ID NO: 207) lacks an in-frame coding exon resulting in the absence of residues 96-113 compared to variant 1 and variant 3, respectively, and is also referred to as NKG2A isoform NKG2-B. Variant 4 has the N29S SNP.

Isoform 3 that correspond to variant 5 (nucleotide sequence set forth at SEQ ID NO: 208, and amino acid sequence set forth at SEQ ID NO: 205) consists of 228 amino acids, and lacks residues 229-233 that encode five C-terminal amino acids. This variant also has the N29S SNP.

Below are the amino acid sequences of the known human NGK2A variants.

(1) Variant 1: Human NGK2A isoform 1 (nucleotide sequence set forth at SEQ ID NO: 1 or 209 (Accession No. NM 002259.5), and amino acid sequence set forth at SEQ ID NO: 2 (Accession No. NP 002250.2; UniProt ID P26715-1)):

```
                                                         (SEQ ID NO: 2)
MDNQGVIYSD LNLPPNPKRQ QRKPKGNKNS ILATEQEITY AELNLQKASQ    50

DFQGNDKTYH CKDLPSAPEK LIVGILGIIC LILMASVVTI VVIPSTLIQR   100

HNNSSLNTRT QKARHCGHCP EEWITYSNSC YYIGKERRTW EESLLACTSK   150

NSSLLSIDNE EEMKFLSIIS PSSWIGVFRN SSHHPWVTMN GLAFKHEIKD   200

SDNAELNCAV LQVNRLKSAQ CGSSIIYHCK HKL                     233
```

(2) Variant 2: Human NGK2A isoform 2 is also referred to as NKG2A isoform NKG2B (nucleotide sequence set forth at SEQ ID NO: 210 (Accession No. NM 007328.4), and amino acid sequence set forth at SEQ ID NO: 206 (Accession No. NP 015567.2; UniProt ID P26715-2)):

```
                                                       (SEQ ID NO: 206)
MDNQGVIYSD LNLPPNPKRQ QRKPKGNKNS ILATEQEITY AELNLQKASQ    50

DFQGNDKTYH CKDLPSAPEK LIVGILGIIC LILMASVVTI VVIPSRHCGH   100

CPEEWITYSN SCYYIGKERR TWEESLLACT SKNSSLLSID NEEEMKFLSI   150

ISPSSWIGVF RNSSHHPWVT MNGLAFKHEI KDSDNAELNC AVLQVNRLKS   200

AQCGSSIIYH CKHKL                                         215
```

(3) Variant 3: Human NGK2A isoform 1 with the N29S SNP bolded and highlighted (nucleotide sequence set forth at SEQ ID NO: 212 (Accession No. NM 213658.2), and amino acid sequence set forth at SEQ ID NO: 182 (Accession No. NP 998823.1 or AAL65234.1):

```
                                                             (SEQ ID NO: 182)
MDNQGVIYSD  LNLPPNPKRQ  QRKPKGNKSS  ILATEQEITY  AELNLQKASQ        50

DFQGNDKTYH  CKDLPSAPEK  LIVGILGIIC  LILMASVVTI  VVIPSTLIQR       100

HNNSSLNTRT  QKARHCGHCP  EEWITYSNSC  YYIGKERRTW  EESLLACTSK       150

NSSLLSIDNE  EEMKFLSIIS  PSSWIGVFRN  SSHHPWVTMN  GLAFKHEIKD       200

SDNAELNCAV  LQVNRLKSAQ  CGSSIIYHCK  HKL                          233
```

(4) Variant 4: Human NKG2A isoform 2 also corresponds to variant 4 (nucleotide sequence set forth at SEQ ID NO: 211 (Accession No. NM 213657.2), and amino acid sequence set forth at SEO ID NO: 207 (Accession No. NP 998822.11)):

```
                                                             (SEQ ID NO: 207)
MDNQGVIYSD  LNLPPNPKRQ  QRKPKGNKSS  ILATEQEITY  AELNLQKASQ        50

DFQGNDKTYH  CKDLPSAPEK  LIVGILGIIC  LILMASVVTI  VVIPSRHCGH       100

CPEEWITYSN  SCYYIGKERR  TWEESLLACT  SKNSSLLSID  NEEEMKFLSI       150

ISPSSWIGVF  RNSSHHPWVT  MNGLAFKHEI  KDSDNAELNC  AVLQVNRLKS       200

AQCGSSIIYH  CKHKL                                                215
```

(5) Variant 5: Human NGK2A isoform 3 is also referred to as NKG2A isoform C (nucleotide sequence set forth at SEQ ID NO: 208 (Accession No. NM 001304448.1), and amino acid sequence set forth at SEQ ID NO: 205 (Accession No. NM 001291377.1)):

```
                                                             (SEQ ID NO: 205)
MDNQGVIYSD  LNLPPNPKRQ  QRKPKGNKSS  ILATEQEITY  AELNLQKASQ        50

DFQGNDKTYH  CKDLPSAPEK  LIVGILGIIC  LILMASVVTI  VVIPSTLIQR       100

HNNSSLNTRT  QKARHCGHCP  EEWITYSNSC  YYIGKERRTW  EESLLACTSK       150

NSSLLSIDNE  EEMKFLSIIS  PSSWIGVFRN  SSHHPWVTMN  GLAFKHEIKD       200

SDNAELNCAV  LQVNRLKSAQ  CGSSIIYH                                 228
```

The Table below provides a summary of the DNA and protein accession numbers and corresponding SEQ ID NOs described above.

| NKG2A Variant | SEQ ID NO | DNA Accession No. (GenBank unless otherwise specified) | Corresponding Protein SEQ ID NO | Protein Accession No. (GenBank unless otherwise specified) |
|---|---|---|---|---|
| 1 | 1 or 209 | NM 002259.5 | 2 | NP 002250.2; UniProt ID P26715-1 |
| 2 | 210 | NM 007328.4 | 206 | NP 015567.2; UnitProt ID P26715-2 |
| 3 | 212 | NM 213658.2 | 182 | NP 998823.1; AAL65234.1 |
| 4 | 211 | NM 213657.2 | 207 | NP 998822.1 |
| 5 | 208 | NM 001304448.1 | 205 | NP 001291377.1 |

The term "antibody" or "immunoglobulin," which is used interchangeably herein, refers to a protein comprising at least two heavy (H) chains and two light (L) chains interconnected by disulfide bonds. Each heavy chain is comprised of a heavy chain variable region (abbreviated herein as VH) and a heavy chain constant region (abbreviated herein as CH). In certain antibodies, e.g., naturally occurring IgG antibodies, the heavy chain constant region is comprised of a hinge and three domains, CH1, CH2 and CH3. In certain antibodies, e.g., naturally occurring IgG antibodies, each light chain is comprised of a light chain variable region (abbreviated herein as VL) and a light chain constant region. The light chain constant region is comprised of one domain (abbreviated herein as CL). The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies can mediate the binding of the immunoglobulin to host tissues or factors, including various cells of the immune system (e.g., effector cells) and the first component (C1q) of the classical complement system. A heavy chain may or may not have the C-terminal lysine. Unless specified otherwise herein, the amino acids in the variable regions are numbered using the Kabat numbering system and those in the constant regions are numbered using the EU system. An immunoglobulin can be from any of the known isotypes, including IgA, secretory IgA, IgD, IgE, IgG, and IgM. The IgG isotype is divided in subclasses in certain species: IgG1, IgG2, IgG3, and IgG4 in humans, and IgG1, IgG2a, IgG2b, and IgG3 in mice. In certain embodiments, the anti-NKG2A antibodies described herein are of the IgG1 subtype. Immunoglobulins, e.g., IgG1, exist in several allotypes, which differ from each other in at most a few amino acids. "Antibody" includes, by way of example, both naturally occurring and non-naturally occurring antibodies; monoclonal and polyclonal antibodies; chimeric and humanized antibodies; human and non-human antibodies and wholly synthetic antibodies.

As used herein, an "IgG antibody" has the structure of a naturally occurring IgG antibody, i.e., it has the same number of heavy and light chains and disulfide bonds as a naturally occurring IgG antibody of the same subclass. For example, an anti-NKG2A IgG1, IgG2, IgG3, or IgG4 antibody consists of two heavy chains (HCs) and two light chains (LCs), wherein the two heavy chains and light chains are linked by the same number and location of disulfide bridges that occur in naturally occurring IgG1, IgG2, IgG3, and IgG4 antibodies, respectively (unless the antibody has been mutated to modify the disulfide bonds).

An "antigen" is a molecule or substance that triggers an immune response and to which an antibody binds. Antibodies typically bind specifically to their cognate antigen with high affinity, reflected by a dissociation constant ($K_D$) of $10^{-5}$ to $10^{-11}$ M or less, but does not bind with high affinity to unrelated antigens. Any $K_D$ greater than about $10^{-4}$ M is generally considered to indicate nonspecific binding. As used herein, an antibody that "binds specifically" to an antigen refers to an antibody that binds to the antigen and, in some cases, substantially identical antigens, with high affinity, which means having a $K_D$ of $10^{-6}$ M or lower, $K_D$ of $10^{-7}$ M or lower, $10^{-8}$ M or lower, $10^{-9}$ M or lower, or between $10^{-8}$ M and $10^{-10}$ M or lower, but does not bind with high affinity to unrelated antigens. An antigen is "substantially identical" to a given antigen if it exhibits a high degree of sequence identity to the given antigen, for example, if it exhibits at least 80%, at least 85%, at least 90%, at least 95%, at least 96%, at least 97%, at least 98%, or at least 99% sequence identity to the sequence of the given antigen. By way of example, an antibody that binds specifically to human NKG2A, in some embodiments, also cross-reacts with NKG2A antigens from certain non-human primate species (e.g., cynomolgus monkey NKG2A), but does not cross-react with NKG2A antigens from other species or with an antigen other than NKG2A.

As used herein, the term "antigen-binding portion" or "antigen-binding fragment" of an antibody are used interchangeably herein, and refers to one or more parts of an antibody that retain the ability to specifically bind to an antigen (e.g., human NKG2A). It has been shown that the antigen-binding function of an antibody can be performed by fragments or portions of a full-length antibody. Examples of binding fragments encompassed within the term "antigen-binding portion" or "antigen-binding fragment" of an antibody, e.g., an anti-NKG2A antibody described herein, include:

(1) a Fab fragment (fragment from papain cleavage) or a similar monovalent fragment consisting of the VL, VH, LC and CH1 domains;
(2) a F(ab')2 fragment (fragment from pepsin cleavage) or a similar bivalent fragment comprising two Fab fragments linked by a disulfide bridge at the hinge region;
(3) a Fd fragment consisting of the $V_H$ and CH1 domains;
(4) a Fv fragment consisting of the $V_L$ and $V_H$ domains of a single arm of an antibody,
(5) a single domain antibody (dAb) fragment (Ward et al., (1989) *Nature* 341:544-46), which consists of a VH domain;
(6) an isolated complementarity determining region (CDR); and
(7) a combination of two or more isolated CDRs, which can optionally be joined by a synthetic linker.

Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) *Science* 242:423-426; and Huston et al. (1988) *Proc. Natl. Acad. Sci. USA* 85:5879-5883). Such single chain antibodies are also encompassed within the term "antigen-binding portion" or "antigen-binding fragment" of an antibody. These antibody fragments are obtained using conventional techniques known to those with skill in the art, and the fragments are screened for utility in the same manner as are intact antibodies. Antigen-binding portions can be produced by recombinant DNA techniques, or by enzymatic or chemical cleavage of intact immunoglobulins.

A "bispecific" or "bifunctional antibody" is an artificial hybrid antibody having two different binding specificities, e.g., two different heavy/light chain pairs, giving rise to two antigen binding sites with specificity for different antigens. Bispecific antibodies can be produced by a variety of methods including fusion of hybridomas or linking of Fab' fragments. See, e.g., Songsivilai & Lachmann, *Clin. Exp. Immunol.* 79:315-321 (1990); Kostelny et al., *J. Immunol.* 148, 1547-1553 (1992).

As used herein, the term "monoclonal antibody" refers to an antibody obtained from a population of substantially homogeneous antibodies, i.e., the individual antibodies in the population are substantially similar and bind the same epitope(s) (e.g., the antibodies display a single binding specificity and affinity), except for possible variants that may arise during production of the monoclonal antibody, such variants generally being present in minor amounts. The modifier "monoclonal" indicates the character of the antibody as having been obtained from a substantially homogenous population of antibodies, and does not require production of the antibody by any particular method. The term "human monoclonal antibody" refers to an antibody from a population of substantially homogeneous antibodies that displays a single binding specificity and that has variable and optional constant regions derived from human germline immunoglobulin sequences. In one embodiment, human monoclonal antibodies are produced by using a hybridoma method. Using the hybridoma method, a transgenic non-human animal, e.g., a transgenic mouse, is exposed to an antigen and a white blood cell known as a B cell produces antibodies that bind to the antigen, which is harvested from the transgenic non-human animal. The isolated B cells are fused with an immortalized cell to produce a hybrid cell line called a hybridoma. In one embodiment, the hybridoma has a genome comprising a human heavy chain transgene and a light chain transgene fused to an immortalized cell.

As used herein, the term "recombinant human antibody" includes all human antibodies that are prepared, expressed, created or isolated by recombinant means, such as (1) antibodies isolated from an animal (e.g., a mouse) that is transgenic or transchromosomal for human immunoglobulin genes or a hybridoma prepared therefrom; (2) antibodies isolated from a host cell transformed to express the antibody, e.g., from a transfectoma; (3) antibodies isolated from a recombinant, combinatorial human antibody library; and (4) antibodies prepared, expressed, created, or isolated by any other means that involve splicing of human immunoglobulin gene sequences to other DNA sequences. Such recombinant human antibodies comprise variable and constant regions that use particular human germline immunoglobulin sequences are encoded by the germline genes, but include subsequent rearrangements and mutations that occur, for example, during antibody maturation. As known in the art (see, e.g., Lonberg (2005) *Nature Biotech.* 23(9): 1117-1125), the variable region contains the antigen binding domain, which is encoded by various genes that rearrange to form an antibody specific for a foreign antigen. In addition to rearrangement, the variable region can be further modified by multiple single amino acid changes (referred to as somatic mutation or hypermutation) to increase antibody affinity to the foreign antigen. The constant region will change in further response to an antigen (i.e., isotype switch). Thus, the rearranged and somatically mutated nucleic acid molecules that encode the light chain and heavy chain immunoglobulin polypeptides in response to an antigen cannot have sequence identity with the original nucleic acid molecules, but instead will be substantially identical or similar (e.g., have at least 80% identity).

As used herein, a "human antibody" refers to an antibody having variable regions in which both the framework and CDR regions are derived from human germline immunoglobulin sequences. Furthermore, if the antibody contains a constant region, the constant region is also derived from human germline immunoglobulin sequences. The anti-NKG2A antibodies described herein may include amino acid residues not encoded by human germline immunoglobulin sequences (e.g., because of mutations introduced by random or site-specific mutagenesis in vitro or by somatic mutation in vivo). However, the term "human antibody" is not intended to include antibodies in which CDR sequences derived from the germline of another non-human mammalian species, such as a mouse, have been grafted onto human framework sequences. As used herein, the terms "human" and "fully human" antibodies are used interchangeably.

A "humanized antibody" refers to an antibody in which some, most, or all of the amino acids outside the CDR domains of a non-human antibody are replaced with corresponding amino acids derived from human antibodies. In one embodiment of a humanized form of an antibody, some, most, or all of the amino acids outside the CDR domains have been replaced with amino acids from human antibodies, whereas some, most, or all amino acids within one or more CDR regions are unchanged. Small additions, deletions, insertions, substitutions, or modifications of amino acids are permissible as long as they do not prevent the antibody from binding to a particular antigen. A "humanized antibody" retains an antigenic specificity similar to that of the original antibody.

A "chimeric antibody" refers to an antibody in which the variable regions are derived from one species and the constant regions are derived from another species, such as an antibody in which the variable regions are derived from a mouse antibody and the constant regions are derived from a human antibody.

As used herein, "isotype" refers to the antibody class (e.g., IgG (including IgG1, IgG2, IgG3, and IgG4), IgM, IgA (including IgA1 and IgA2), IgD, and IgE antibody) that is encoded by the heavy chain constant region genes of the antibody.

"Allotype" refers to naturally occurring variants within a specific isotype group, where variants differ in a few amino acids. (See, e.g., Jefferis et al. (2009) mAbs 1:1). Anti-NKG2A antibodies described herein can be of any allotype. As used herein, antibodies referred to as "IgG1f," "IgG1.1f," or "IgG1.3f" isotype are IgG1, effectorless IgG1.1, or effectorless IgG1.3 antibodies of the allotype "f," respectively.

The phrases "an antibody recognizing an antigen" and "an antibody specific for an antigen" are used interchangeably herein with the phrase "an antibody that binds specifically to an antigen."

As used herein, an "isolated antibody" refers to an antibody that is substantially free of other proteins and cellular materials.

As used herein, an "effector function" refers to the interaction of an antibody Fc region with an Fc receptor or ligand, or a biochemical event that results therefrom. Exemplary "effector functions" include C1q binding, complement dependent cytotoxicity (CDC), Fc receptor binding, FcγR-mediated effector functions such as ADCC and antibody dependent cell-mediated phagocytosis (ADCP), and down-regulation of a cell surface receptor (e.g., the B cell receptor; BCR). Such effector functions generally require the Fc region to be combined with a binding domain (e.g., an antibody variable domain).

An "Fc receptor" or "FcR" is a receptor that binds to the Fc region of an immunoglobulin. FcRs that bind to an IgG antibody comprise receptors of the FcγR family, including allelic variants and alternatively spliced forms of these receptors. The FcγR family consists of three activating (FcγRI, FcγRIII, and FcγRIV in mice; FcγRIA, FcγRIIA, and FcγRIIIA in humans) and one inhibitory (FcγRIIb, or equivalently FcγRIIB) receptor. Various exemplary properties of human FcγRs are known in the art. The majority of innate effector cell types co-express one or more activating FcγR and the inhibitory FcγRIIb, whereas natural killer (NK) cells selectively express one activating Fc receptor (FcγRIII in mice and FcγRIIIA in humans) but not the inhibitory FcγRIIb in mice and humans. Human IgG1 binds to most human Fc receptors and is considered equivalent to murine IgG2a with respect to the types of activating Fc receptors that it binds to.

As used herein, an "Fc region" (fragment crystallizable region) or "Fc domain" or "Fc" refers to the C-terminal region of the heavy chain of an antibody that mediates the binding of the immunoglobulin to host tissues or factors, including binding to Fc receptors located on various cells of the immune system (e.g., effector cells) or to the first component (C1q) of the classical complement system. Thus, an Fc region comprises the constant region of an antibody excluding the first constant region immunoglobulin domain (e.g., CH1 or CL). In IgG, IgA, and IgD antibody isotypes, the Fc region comprises two identical protein fragments, derived from the second (CH2) and third (CH3) constant domains of the antibody's two heavy chains. In IgM and IgE antibody isotopes, the Fc regions comprise three heavy chain constant domains (CH domains 2-4) in each polypeptide chain. For IgG, the Fc region comprises immunoglobulin domains CH2 and CH3 and the hinge between CH1 and CH2 domains. Although the definition of the boundaries of the Fc region of an immunoglobulin heavy chain might vary, as defined herein, the human IgG heavy chain Fc region is defined to stretch from an amino acid residue D221 for IgG1, V222 for IgG2, L221 for IgG3, and P224 for IgG4 to the carboxy-terminus of the heavy chain, wherein the numbering is according to the EU index as in Kabat (Kabat, et al., 1991). The CH2 domain of a human IgG Fc region extends from amino acid 237 to amino acid 340, and the CH3 domain is positioned on C-terminal side of a CH2 domain in an Fc region, i.e., it extends from amino acid 341 to amino acid 447 or 446 (if the C-terminal lysine residue is absent) or 445 (if the C-terminal glycine and lysine residues are absent) of an IgG. As used herein, the Fc region can be a native sequence Fc, including any allotypic variant, or a variant Fc (e.g., a non-naturally occurring Fc). Fc can also refer to this region in isolation or in the context of an Fc-comprising protein polypeptide such as a "binding protein comprising an Fc region," also referred to as an "Fc fusion protein" (e.g., an antibody or immunoadhesin).

A "native sequence Fc region" or "native sequence Fc" has an amino acid sequence that is identical to the amino acid sequence of an Fc region found in nature. Native sequence human Fc regions include a native sequence human IgG1 Fch region; native sequence human IgG2 Fc region; native sequence human IgG3 Fc region; and native sequence human IgG4 Fc region as well as naturally occurring variants thereof. Native sequence Fc include the various allotypes of Fcs. (See, e.g., Jefferis et al. (2009) mAbs 1:1).

The term "epitope" or "antigenic determinant" refers to a site on an antigen (e.g., hNKG2A protein) to which an immunoglobulin or antibody specifically binds, e.g., as defined by the specific method used to identify it. Epitopes can be formed both from (1) contiguous amino acids (usually a linear epitope) or (2) non-contiguous amino acids juxtaposed by tertiary folding of the protein (usually a conformational epitope). Epitopes formed from contiguous amino acids are typically, but not always, retained on exposure to denaturing solvents, whereas epitopes formed by tertiary folding are typically lost on treatment with denaturing solvents. An epitope typically includes at least 3, 4, 5, 6, 7, 8, 9, 10, 11, 12, 13, 14, 15, 16, 17, 18, 19, 20, 21, or 22 amino acids in a unique spatial conformation.

The term "epitope mapping" refers to the process of identification of the molecular determinants for antibody-antigen recognition. Methods for determining what epitopes are bound by a given antibody (i.e., epitope mapping) are well known in the art and include, for example, immunoblotting and immunoprecipitation assays, wherein overlapping or contiguous peptides from the protein (e.g., from NKG2A) are tested for reactivity with a given antibody (e.g., anti-NKG2A antibody). Methods for determining spatial conformation of epitopes include techniques known in the art and those described herein, for example, x-ray crystallography; antigen mutational analysis, two-dimensional nuclear magnetic resonance; yeast display; and hydrogen/deuterium exchange-mass spectrometry (HDX-MS) (see, e.g., *Epitope Mapping Protocols in Methods in Molecular Biology*, Vol. 66, G. E. Morris, Ed. (1996)).

The term "binds to the same epitope" with reference to two or more antibodies means that the antibodies bind to the same segment of amino acid residues, as determined by a given method. Techniques for determining whether antibodies bind to the "same epitope on NKG2A" with the antibodies described herein include, for example, epitope mapping methods, such as x-ray analyses of crystals of antigen: antibody complexes, which provides atomic resolution of the epitope, HDX-MS, and fast photochemical oxidation of proteins (FPOP). Other methods monitor the binding of the antibody to antigen fragments (e.g. proteolytic fragments) or to mutated variations of the antigen, where loss of binding due to a modification of an amino acid residue within the antigen sequence is often considered an indication of an epitope component, such as alanine scanning mutagenesis (Cunningham & Wells (1985) *Science* 244:1081) or yeast display of mutant target sequence variants. In addition, computational combinatorial methods for epitope mapping can also be used. These methods rely on the ability of the antibody of interest to affinity isolate specific short peptides from combinatorial phage display peptide libraries. Antibodies having the same VH and VL or the same CDR1, CDR2, and CDR3 sequences are expected to bind to the same epitope.

Antibodies that "compete with another antibody for binding to a target" refer to antibodies that inhibit (partially or completely) the binding of the other antibody to the target. Whether two antibodies compete with each other for binding to a target, i.e., whether and to what extent one antibody inhibits the binding of the other antibody to a target, may be determined using known binding competition experiments, e.g., Biacore® surface plasmon resonance (SPR) analysis. In certain embodiments, an antibody competes with, and inhibits binding of another antibody to a target by at least 50%, 60%, 70%, 80%, 90% or 100%. The level of inhibition or competition may be different depending on which antibody is the "blocking antibody" (i.e., the cold antibody that is incubated first with the target). Competition assays can be conducted as described, for example, in Ed Harlow and David Lane, Cold Spring Harb. Protoc. 2006; doi:10.1101/pdb.prot4277 or in Chapter 11 of "Using Antibodies" by Ed Harlow and David Lane, Cold Spring Harbor Laboratory Press, Cold Spring Harbor, N.Y., USA 1999. Two antibodies "cross-compete" if antibodies block each other both ways by at least 50%, i.e., regardless of whether one or the other antibody is contacted first with the antigen in the competition experiment.

Competitive binding assays for determining whether two antibodies compete or cross-compete for binding include competition for binding to T cells expressing NKG2A, e.g., by flow cytometry. Other methods include: SPR (e.g., Biacore®); solid phase direct or indirect radioimmunoassay (RIA); solid phase direct or indirect enzyme immunoassay (EIA); sandwich competition assay (see Stahli et al., *Methods in Enzymology* 9:242 (1983)); solid phase direct biotin-avidin EIA (see Kirkland et al., *J. Immunol.* 137:3614 (1986)); solid phase direct labeled assay; solid phase direct labeled sandwich assay (see Harlow and Lane, Antibodies: A Laboratory Manual, Cold Spring Harbor Press (1988)); solid phase direct label RIA using 1-125 label (see Morel et al., *Mol. Immunol.* 25(1):7 (1988)); solid phase direct biotin-avidin EIA (Cheung et al., *Virology* 176:546 (1990)); and direct labeled RIA. (Moldenhauer et al., *Scand. J. Immunol.* 32:77 (1990)).

As used herein, the terms "specific binding," "selective binding," "selectively binds," and "specifically binds," refer to antibody binding to an epitope on a predetermined antigen. In some embodiments, the antibody: (1) binds with an equilibrium dissociation constant ($K_D$) of approximately less than $10^{-6}$ M, such as approximately less than $10^{-7}$ M, $10^{-6}$ M, $10^{-9}$ M or $10^{-10}$ M or even lower when determined by, e.g., SPR technology in a Biacore® SPR instrument using the predetermined antigen, e.g., recombinant human NKG2A as the analyte and the antibody as the ligand, or Scatchard analysis of binding of the antibody to antigen positive cells; and (2) binds to the predetermined antigen with an affinity that is at least two-fold greater than its affinity for binding to a non-specific antigen (e.g., BSA, casein) other than the predetermined antigen or a closely-related antigen. Accordingly, an antibody that "specifically binds to human NKG2A" refers to an antibody that binds to soluble or cell bound human NKG2A with a $K_D$ of $10^{-6}$ M or less, such as approximately less than $10^{-7}$ M, $10^{-8}$ M, $10^{-9}$ M or $10^{-10}$ M or even lower. An antibody that "cross-reacts with cynomolgus NKG2A" refers to an antibody that binds to cynomolgus NKG2A with a $K_D$ of $10^{-6}$ M or less, such as approximately less than $10^{-7}$, $10^{-8}$ M, $10^{-9}$ M or $10^{-10}$ M or even lower.

The terms "$k_a$", "$k_{assoc}$", or "$k_{on}$" are used interchangeably herein to refer to the association rate constant of a particular antibody-antigen interaction. The terms "$k_d$," "$k_{dis}$", or "$k_{off}$" are used interchangeably herein to refer to the dissociation rate constant of a particular antibody-antigen interaction. The term "$K_D$", as used herein, refers to the equilibrium dissociation constant, which is obtained from the ratio of $k_d$ to $k_a$ (i.e., $k_d/k_a$) and is expressed as a molar concentration (M). $K_D$ values for antibodies can be determined using methods well established in the art. Available methods for determining the $K_D$ of an antibody include but are not limited to surface plasmon resonance (SPR), using, for example, a biosensor system such as a Biacore® system, and flow cytometry and Scatchard analysis.

The term "$IC_{50}$" means half maximal inhibitory concentration, and measures the potency of a substance, for example, an antibody, to inhibit a specific biological or biochemical response. In other words, $IC_{50}$ is used as a measure of potency; the smaller the $IC_{50}$, the more potent the substance is. In the context of an in vitro or in vivo assay using an antibody, or antigen binding fragment thereof, $IC_{50}$ refers to the concentration of the antibody, or antigen-binding fragment thereof, that reduces the maximal biological or biochemical response by 50%.

The term "$EC_{50}$" means half maximal effective concentration, and measures the potency of a substance, for example, an antibody, to induce a specific biological or biochemical response. As with $IC_{50}$, $EC_{50}$ is used as a measure of potency; the smaller the $EC_{50}$, the more potent the substance is. In the context of an in vitro or in vivo assay using an antibody or antigen binding fragment thereof, $EC_{50}$ refers to the concentration of the antibody or antigen-binding fragment thereof that induces a response that is 50% of the maximal biological or biochemical response.

"Receptor occupancy" or "occupancy of the receptor," as used herein, refers to the amount of antibody (e.g., the anti-NKG2A antibodies described herein) that is bound to the immunostimulatory receptor (e.g., human NKG2A). "Percent (%) receptor occupancy" or "percent (%) occupancy of the receptor" can be calculated using the following formula: ([ΔMFI of Test]/[ΔMFI of Total])×100. Change in mean fluorescence unit (ΔMFI) is calculated by subtracting the MFI of background staining with an isotype control antibody from the MFI from the bound antibody. The total receptor level is determined by adding a saturating amount of antibody to determine the maximum expression and, therefore, MFI of the particular immunostimulatory receptor. An alternative means to calculate total receptor expression is to use an antibody against the same immunostimulatory receptor that does not compete with the antibody for which receptor occupancy is being calculated.

As used herein, the term "naturally-occurring" as applied to a substance is a substance that is present in nature that has not been intentionally modified by people. For example, a polypeptide or polynucleotide sequence that is present in an organism (including viruses) that can be isolated from a source in nature and which has not been intentionally modified by people in the laboratory is naturally-occurring.

A "polypeptide" refers to a chain comprising at least two consecutively linked amino acid residues, with no upper limit on the length of the chain. One or more amino acid residues in the protein may contain a modification such as, but not limited to, glycosylation, phosphorylation or a disulfide bond. A "protein" comprises one or more polypeptides.

The term "nucleic acid molecule," as used herein, is intended to include DNA molecules and RNA molecules. A nucleic acid molecule is single-stranded or double-stranded, and may be complementary DNA (cDNA).

The term "cDNA" or "complementary DNA" refers to a non-naturally occurring nucleic acid molecule that has been created or derived from mRNA, i.e., the non-coding regions have been removed.

As used herein, the term "conservative sequence modifications" refers to amino acid modifications that do not significantly affect or alter the binding characteristics of the antibody containing the amino acid sequence. Such conservative modifications include amino acid substitutions, additions, and deletions. Modifications can be introduced into an antibody of the invention by standard techniques known in the art, such as site-directed mutagenesis and polymerase chain reaction (PCR)-mediated mutagenesis. "Conservative amino acid substitutions" refers to substitutions of an amino acid residue with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine), and aromatic side chains (e.g., tyrosine, phenylalanine, tryptophan, histidine). In certain embodiments, a predicted nonessential amino acid residue in an anti-NKG2A antibody is replaced with another amino acid residue from the same side chain family. Methods of identifying nucleotide and amino acid conservative substitutions that do not eliminate antigen binding are well-known in the art (see, e.g., Brummell et al., *Biochem.* 32: 1180-1187 (1993); Kobayashi et al. *Protein Eng.* 12(10):879-884 (1999); and Burks et al. *Proc. Natl. Acad. Sci. USA* 94:412-417 (1997)).

For nucleic acids, the term "substantial homology" indicates that two nucleic acids, or designated sequences thereof, when optimally aligned and compared, are identical, with appropriate nucleotide insertions or deletions, in at least about 80% of the nucleotides, at least about 90% to 95%, or at least about 98% to 99.5% of the nucleotides. Alternatively, substantial homology exists when the segments will hybridize under selective hybridization conditions to the complement of the nucleic acid strand.

For polypeptides, the term "substantial homology" indicates that two polypeptides, or designated sequences thereof, when optimally aligned and compared, are identical, with appropriate amino acid insertions or deletions, in at least about 80% of the amino acids, at least about 90% to 95%, or at least about 98% to 99.5% of the amino acids.

The percent identity between two sequences is a function of the number of identical positions shared by the sequences (i.e., percent homology=(number of identical positions)/(total number of positions)×100), taking into account the number of gaps and the length of each gap that need to be introduced for optimal alignment of the two sequences. The comparison of sequences and determination of percent identity between two sequences can be accomplished using a mathematical algorithm, as described in the non-limiting examples below.

The percent identity between two nucleotide sequences can be determined, e.g., using the GAP program in the GCG software package, using a nwsgapdna.cmp matrix and a gap weight of 40, 50, 60, 70, or 80 and a length weight of 1, 2, 3, 4, 5, or 6. The percent identity between two nucleotide or amino acid sequences can also be determined using the algorithm of E. Meyers and W. Miller (CABIOS, 4:11-17 (1989)), which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (*J. Mol. Biol.* (48):444-453 (1970)) algorithm, which has been incorporated into the GAP program in the GCG software package, using either a Blossum 62 matrix or a PAM250 matrix, and a gap weight of 16, 14, 12, 10, 8, 6, or 4 and a length weight of 1, 2, 3, 4, 5, or 6.

The nucleic acid and protein sequences described herein can further be used as a "query sequence" to perform a search against public databases to, for example, identify related sequences. Such searches can be performed using the NBLAST and XBLAST programs (version 2.0) of Altschul, et al. (1990) *J. Mol. Biol.* 215:403-10. BLAST nucleotide searches can be performed with the NBLAST program, score=100, wordlength=12 to obtain nucleotide sequences homologous to the nucleic acid molecules described herein. BLAST protein searches can be performed with the XBLAST program, score=50, wordlength=3 to obtain amino acid sequences homologous to the protein molecules described herein. To obtain gapped alignments for comparison purposes, Gapped BLAST can be used as described in Altschul et al., (1997) Nucleic Acids Res. 25(17):3389-3402. When utilizing BLAST and Gapped BLAST programs, the default parameters of the respective programs (e.g., XBLAST and NBLAST) can be used. (See, e.g., National Center for Biotechnology Information (NCBI).

The nucleic acids may be present in whole cells, e.g., a host cell, in a cell lysate, or in a partially purified or substantially pure form. A nucleic acid is "isolated" or "rendered substantially pure" when purified away from other cellular components or other contaminants, e.g., other cellular nucleic acids (e.g., the other parts of the chromosome) or proteins, by standard techniques, including alkaline/SDS treatment, CsC1 banding, column chromatography, agarose gel electrophoresis and others well known in the art. (See, F. Ausubel, et al., ed. Current Protocols in Molecular Biology, Greene Publishing and Wiley Interscience, New York (1987)).

The term "vector," as used herein, is intended to refer to a nucleic acid molecule capable of transporting another nucleic acid to which it has been linked. One type of vector is a "plasmid," which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). Expression vectors useful in recombinant DNA techniques include plasmids. As used herein, "plasmid" and "vector" may be used interchangeably, as the plasmid is the most commonly used form of vector. However, also included are other forms of expression vectors, such as viral vectors (e.g., replication defective retroviruses, adenoviruses and adeno-associated viruses), which serve equivalent functions.

The term "host cell" or "recombinant host cell", which are used interchangeably, refers to a cell that comprises a nucleic acid that is not naturally present in the cell, and may be a cell into which a recombinant expression vector has been introduced. It should be understood that such terms refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

An "immune response" is as understood in the art, and generally refers to a biological response in a vertebrate against foreign agents or abnormal, e.g., cancerous cells, where the response protects the vertebrate against these agents and diseases caused by them. An immune response is mediated by the action of one or more cells of the immune system (for example, a T lymphocyte, B lymphocyte, natural killer (NK) cell, macrophage, eosinophil, mast cell, dendritic cell or neutrophil) and soluble macromolecules produced by any of these cells or the liver (including antibodies, cytokines, and complement) that results in selective targeting, binding to, damage to, destruction of, and/or elimination from the vertebrate's body of invading pathogens, cells or tissues infected with pathogens, cancerous or other abnormal cells, or, in cases of autoimmunity or pathological inflammation, normal cells or tissues, including, for example, human cells or tissues. An immune reaction includes, e.g., activation or inhibition of a T cell, e.g., an effector T cell or a T helper (Th) cell, such as a CD4+ or CD8+ T cell, or the inhibition or depletion of a Treg cell.

"Effector T" ("Teff") cells are T cells (e.g., CD4+ and CD8+ T cells) with cytolytic activities as well as T helper (Th) cells. Th cells secrete cytokines and activate and direct other immune cells, but does not include regulatory T cells (Treg cells).

T regulatory ("Treg") cells are a subpopulation of T cells that modulate the immune system, maintain tolerance to self-antigens, and prevent autoimmune disease. Memory B cells are a B cell sub-type that are formed within germinal centers following primary infection and are important in generating an accelerated and more robust antibody-mediated immune response in the case of re-infection (also known as a secondary immune response).

"Natural killer" (NK) cells are important mediators of the immune response against pathogens and tumors, and are part of the innate immune system. NK cells also have a role in regulating the adaptive immune response, and have been shown in different contexts to stimulate or inhibit T cell responses. NK cells provide rapid responses to viral-infected cells and respond to tumor formation.

As used herein, the term "T cell-mediated response" refers to a response mediated by T cells, e.g., effector T cells (e.g., CD8+ cells) and helper T cells (e.g., CD4+ cells). T cell mediated responses include, for example, T cell cytotoxicity and proliferation.

As used herein, the term "cytotoxic T lymphocyte (CTL) response" refers to an immune response induced by cytotoxic T cells. CTL responses are mediated by, for example, CD8+ T cells.

An "immunomodulator" or "immunoregulator" refers to an agent, e.g., a component of a signaling pathway that may be involved in modulating, regulating, or modifying an immune response. "Modulating," "regulating," or "modifying" an immune response refers to any alteration in a cell of the immune system or in the activity of such cell (e.g., an effector T cell, such as a Th1 cell). Such modulation includes stimulation or suppression of the immune system, which may be manifested by an increase or decrease in the number of various cell types, an increase or decrease in the activity of these cells, and/or any other changes that can occur within the immune system. Both inhibitory and stimulatory immunomodulators have been identified, some of which may have enhanced function in a tumor microenvironment. In some embodiments, the immunomodulator is located on the surface of a T cell. An "immunomodulatory target" or "immunoregulatory target" is an immunomodulator that is targeted for binding by, and whose activity is altered by the binding of, a substance, agent, moiety, compound or molecule. Immunomodulatory targets include, for example, receptors on the surface of a cell ("immunomodulatory receptors") and receptor ligands ("immunomodulatory ligands").

"Immunotherapy" refers to the treatment of a subject, such as a human subject, afflicted with or at risk of contracting or suffering a recurrence of a disease by a method comprising inducing, enhancing, suppressing, or otherwise modifying an immune response.

"Immunostimulating therapy" or "immunostimulatory therapy" refers to a therapy that results in increasing (inducing or enhancing) an immune response in a subject for, e.g., treating cancer.

"Potentiating an endogenous immune response" means increasing the effectiveness or potency of an existing immune response in a subject, such as a human subject. This increase in effectiveness and potency may be achieved, for example, by overcoming mechanisms that suppress the endogenous host immune response or by stimulating mechanisms that enhance the endogenous host immune response.

As used herein, the term "linked" refers to the association of two or more molecules. The linkage can be covalent or non-covalent. The linkage also can be genetic (i.e., recombinantly fused). Such linkages can be achieved using a wide variety of art recognized techniques, such as chemical conjugation and recombinant protein production.

As used herein, "administering" refers to the physical introduction of a composition comprising a therapeutic agent, e.g., an anti-NKG2A antibody, to a subject, using any of the various methods and delivery systems known to those skilled in the art. "Administering" includes, for example, administration to a human patient by another, such as, for example, one or more healthcare providers, and self-administration by the human patient. Various routes of administration for antibodies described herein include intravenous, intraperitoneal, intramuscular, subcutaneous, spinal or other parenteral routes of administration, for example, by injection or infusion. The phrase "parenteral administration" as used herein means modes of administration other than enteral and topical administration, such as by injection, and includes, without limitation, intravenous, intraperitoneal, intramuscular, intraarterial, intrathecal, intralymphatic, intralesional, intracapsular, intraorbital, intracardiac, intradermal, transtracheal, subcutaneous, subcuticular, intraarticular, subcapsular, subarachnoid, intraspinal, epidural and intrasternal injection and infusion, as well as in vivo electroporation. Alternatively, an antibody described herein can be administered via a non-parenteral route, such as a topical, epidermal or mucosal route of administration, for example, intranasally, orally, vaginally, rectally, sublingually or topically. Administering can also be performed, for example, once, a plurality of times, and/or over one or more extended periods.

As used herein, "adjunctive" or "combined" administration (coadministration) includes simultaneous administration of the compounds in the same or different dosage form, or separate administration of the compounds (e.g., sequential administration). Thus, a first antibody, e.g., the anti-NKG2A antibody, and a second, third, or more antibodies can be simultaneously administered in a single formulation. Alternatively, the first and second (or more) antibodies can be formulated for separate administration and are administered concurrently or sequentially. "Combination" therapy, as used herein, means administration of two or more therapeutic agents in a coordinated fashion, and includes, but is not limited to, concurrent dosing. Specifically, combination therapy encompasses both co-administration (e.g. administration of a co-formulation or simultaneous administration of separate therapeutic compositions) and serial or sequential administration, provided that administration of one therapeutic agent is conditioned in some way on administration of another therapeutic agent. For example, one therapeutic agent may be administered only after a different therapeutic agent has been administered and allowed to act for a prescribed period of time. (See, e.g., Kohrt et al. (2011) *Blood* 117:2423).

For example, the anti-NKG2A antibody can be administered first followed by (e.g., immediately followed by) the administration of a second antibody, or vice versa. In one embodiment, the anti-NKG2A antibody is administered prior to administration of the second antibody. In another embodiment, the anti-NKG2A antibody is administered, for example, within about 30 minutes of the second antibody. Such concurrent or sequential administration preferably results in both antibodies being simultaneously present in treated patients.

As used herein, the terms "inhibits" or "blocks" are used interchangeably and encompass both partial and complete inhibition/blocking. In some embodiments, the anti-NKG2A antibody described herein inhibits binding of NKG2A to HLA-E by at least about 50%, for example, about 60%, 70%, 80%, 90%, 95%, 99%, or 100%, determined, e.g., as further described herein. In some embodiments, the anti-NKG2A antibody inhibits binding of NKG2A to HLA-E by no more than 50%, for example, by about 40%, 30%, 20%, 10%, 5% or 1%, determined, e.g., as further described herein.

As used herein, "cancer" refers a broad group of diseases characterized by the uncontrolled growth of abnormal cells in the body. Unregulated cell growth or division may result in the formation of malignant tumors or cells that invade neighboring tissues and may metastasize to distant parts of the body through the lymphatic system or bloodstream.

The terms "treat," "treating," and "treatment," as used herein, refer to any type of intervention or process performed on, or administering an active agent to, the subject with the objective of reversing, alleviating, ameliorating, inhibiting, or slowing down or preventing the progression, development, severity or recurrence of a symptom, complication, condition or biochemical indicia associated with a disease. In contrast, "prophylaxis" or "prevention" refers to administration to a subject who does not have a disease to prevent the disease from occurring. As used herein, "treat," "treating," and "treatment" does not encompass prophylaxis or prevention.

The term "effective dose" or "effective dosage" is defined as an amount sufficient to achieve or at least partially achieve a desired effect. A "therapeutically effective amount" or "therapeutically effective dosage" of a drug or therapeutic agent is any amount of the drug that, when used alone or in combination with another therapeutic agent, promotes disease regression evidenced by a decrease in severity of disease symptoms, an increase in frequency and duration of disease symptom-free periods, or a prevention of impairment or disability due to the disease affliction. A "prophylactically effective amount" or a "prophylactically effective dosage" of a drug is an amount of the drug that, when administered alone or in combination with another therapeutic agent to a subject at risk of developing a disease or of suffering a recurrence of disease, prevents the development or recurrence of the disease. The ability of a therapeutic agent to promote disease regression or of a prophylactic agent to prevent the development or recurrence of the disease can be evaluated using a variety of methods known to the skilled practitioner, such as in human subjects during clinical trials, in animal model systems predictive of efficacy in humans, or by assaying the activity of the agent in in vitro assays.

The administration of effective amounts of the anti-NKG2A antibody alone, or anti-NKG2A antibody combined with, for example, an anti-PD-1 antibody, combined with an anti-PD-L1 antibody, or combined with an anti-CTLA-4 antibody, according to any of the methods provided herein, can result in at least one therapeutic effect, including, for example, reduced tumor growth or size, reduced number of metastatic lesions appearing over time, complete remission, partial remission, or stable disease. For example, the methods of treatment produce a comparable clinical benefit rate (CBR=complete remission (CR)+partial remission (PR)+ stable disease (SD) lasting≥6 months) better than that achieved without administration of the anti-NKG2A antibody, or than that achieved with administration of any one of the combined antibodies alone, e.g., the improvement of clinical benefit rate is about 20%, 30%, 40%, 50%, 60%, 70%, 80% or more.

By way of example, an anti-cancer agent is a drug that slows cancer progression or promotes cancer regression in a subject, including a human subject. In some embodiments, a therapeutically effective amount of the drug promotes cancer regression to the point of eliminating the cancer. "Promoting cancer regression" means that administering an effective amount of the drug, alone or in combination with an anti-neoplastic agent, results in a reduction in tumor growth or size, necrosis of the tumor, a decrease in severity of at least one disease symptom, an increase in frequency and duration of disease symptom-free periods, a prevention of impairment or disability due to the disease affliction, or otherwise amelioration of disease symptoms in the patient. "Pharmacological effectiveness," "effectiveness," or "efficacy" refers to the ability of the drug to promote cancer regression in the patient. "Physiological safety" refers to an acceptably low level of toxicity or other adverse physiological effects at the cellular, organ and/or organism level (adverse effects) resulting from administration of the drug.

By way of example, for the treatment of tumors, a therapeutically effective amount or dosage of the drug inhibits tumor cell growth by at least about 20%, by at least about 30% by at least about 40%, by at least about 50%, by at least about 60%, by at least above 70%, by at least about 80% relative to untreated subjects, or by at least about 90%. In some embodiments, a therapeutically effective amount or dosage of the drug completely inhibits cell growth or tumor growth, i.e., inhibits cell growth or tumor growth by 100%. The ability of a compound, including an antibody, to inhibit tumor growth can be evaluated using the assays described herein. Alternatively, this property of a composition can be evaluated by examining the ability of the compound to inhibit cell growth; such inhibition can be measured in vitro by assays known to person of ordinary skill in the art. In some embodiments, inhibition of tumor growth may not be immediate after treatment, and may only occur after a period of time or after repeated administration. In other embodiments described herein, tumor regression is observed and continues for at least about 20 days, at least about 30 days, at least about 40 days, at least about 50 days, or at least about 60 days, or longer.

As used herein, the terms "fixed dose", "flat dose" and "flat-fixed dose" are used interchangeably and refer to a dose that is administered to a patient without regard for the weight or body surface area of the patient. The fixed or flat dose is therefore not provided as a mg/kg dose, but rather as an absolute amount of the therapeutic agent.

As used herein, the term "weight based" dose or dosing means that a dose administered to a patient is calculated based on the patient's weight. For example, when a 60 kg patient requires 3 mg/kg of an anti-NKG2A antibody, one can calculate and use the appropriate amount of the anti-NKG2A antibody (i.e., 180 mg) for administration.

The term "patient" includes human and other mammalian subjects that receive either therapeutic or prophylactic treatment.

The term "subject" includes any human or non-human animal. For example, the methods and compositions herein disclosed can be used to treat a subject having cancer. A non-human animal includes all vertebrates, e.g., mammals and non-mammals, including non-human primates, sheep, dogs, cows, chickens, amphibians, reptiles, etc. In one embodiment, the subject is a human subject.

As used herein, the term "a" or "an" entity refers to one or more of that entity unless otherwise specified; for example, "a nucleotide sequence" is understood to represent one or more nucleotide sequences. As such, the terms "a" or "an", "one or more," and "at least one" can be used interchangeably herein.

As used herein, "and/or" is to be taken as specific disclosure of each of the two specified features or components with or without the other. Thus, the term "and/or" as used in a phrase such as "A and/or B" includes "A and B," "A or B," "A" alone, and "B" alone. Likewise, the term "and/or" as used in a phrase such as "A, B, and/or C" encompasses each of the following: A, B, and C; A, B, or C; A or C; A or B; B or C; A and C; A and B; B and C; A alone; B alone; and C alone.

It is understood that wherever aspects are described herein with the language "comprising," otherwise analogous aspects described in terms of "consisting of" and/or "consisting essentially of" are also provided.

Units, prefixes, and symbols are denoted in their Systeme International de Unites (SI) accepted form unless otherwise indicated. Numeric ranges are inclusive of the numbers defining the range. Unless otherwise indicated, nucleotide sequences are written left to right in 5' to 3' orientation. Amino acid sequences are written left to right in amino to carboxy orientation.

As used herein, the term "about" or "approximately" means roughly, around, or in the region of. When the term "about" is used in conjunction with a numerical range, it modifies that range by extending the boundaries above and below the numerical values set forth. In general, the term "about" can modify a numerical value above and below the stated value by a variance of, e.g., 10 percent, up or down (higher or lower).

The headings provided herein are not limitations of the various aspects of the disclosure, and should be read by reference to the specification as a whole. Accordingly, the terms defined immediately below are more fully defined by reference to the specification in its entirety. Various aspects described herein are described in further detail in the following subsections.

I. Anti-NKG2A Antibodies

The present disclosure describes, in some embodiments, anti-NKG2A antibodies, such as fully human, humanized, and chimeric antibodies, with desirable functions or properties. For example, the antibodies specifically bind human NKG2A protein with high affinity. In certain embodiments, the antibodies are antagonistic antibodies that block or reverse NKG2A-mediated inhibition on immune cells such as T cells and NK cells. In some embodiments, the anti-human NKG2A (anti-huNKG2A) antibodies have desirable properties for use as therapeutic agents in treating diseases such as cancers or infections.

Specific anti-NKG2A antibodies described herein are antibodies having the CDR and/or variable region sequences of antibodies 13F3.A4, NKG2A.6, NKG2A.7, NKG2A.8, NKG2A.9, NKG2A.11, isolated and structurally characterized as described herein, as well as antibodies having at least 80% identity (for example, at least 85% identity, at least 90% identity, at least 95% identity, or at least 99% identity) to the amino acid sequences of the anti-NKG2A antibodies described herein. In some embodiments, the anti-NKG2A antibodies described herein have at least 80% identity (for example, at least 85% identity, at least 90% identity, at least 95% identity, or at least 99% identity) to the variable region or CDR sequences of the anti-NKG2A antibodies described herein.

In some aspects, the antibodies of the invention are characterized by particular functional features or properties. For example, the antibodies specifically bind to human NKG2A with high affinity. In some embodiments, the anti-NKG2A antibodies inhibits the binding of NKG2A to its ligand HLA-E, which restores NK and T cell responses against tumors that express HLA-E. In other words, the anti-NKG2A antibodies described herein stimulate T cell and NK cell anti-tumor responses by inhibiting or blocking the interaction between NKG2A protein and its ligand HLA-E.

In some embodiments, the Anti-NKG2A antibodies described herein exhibit one or more of the following properties:
(1) Binds specifically to human NKG2A protein;
(2) Blocks or reduces binding and/or interaction of an NKG2A ligand (e.g., HLA-E in humans) to human NKG2A protein; (In other embodiments, the anti-NKG2A antibodies described herein blocks or reduces binding and/or interaction of an NKG2A ligand to non-human NKG2A protein);
(3) Reverses NKG2A-mediated inhibitory signaling;
(4) Does not bind, or binds with low affinity to, human NKG2C protein;
(5) Binds with high affinity to human and cynomolgus monkey NKG2A
(6) Does not bind, or shows low affinity to, mouse or rat NKG2A;
(7) Does not interfere with activating signal from HLA-E binding to NKG2C protein;
(8) Has reduced binding to human Fc gamma receptor (FcγR);
(9) Induces and/or enhances an anti-tumor immune response;
(10) Enhances the functional activity of T cells; (In some embodiments, increases cytototoxic T cell function as measured by, for example, lysis of HLA-E-expressing tumor cells);
(11) Enhances the functional activity of natural killer (NK) cells by, for example, inducing NK cell activation;
(12) Increases cytokine, for example, IFNγ production; and/or
(13) Specifically binds to an epitope located within discontinuous regions comprising the following amino acid residues as determined by HDX-MS and/or FPOP epitope mapping:
Region 1: $^{155}$LSIDNEEEMKF$^{165}$ (amino acid residues 155 to 165 of SEQ ID NO: 2;
Region 2: $^{171}$PSSWIGVFRNSSHHPW$^{186}$ (amino acid residues 171 to 186 of SEQ ID NO: 2;
Region 3: $^{192}$LAFKHEIKDSDN$^{203}$ (amino acid residues 192 to 203 of SEQ ID NO: 2;
Region 4: L (amino acid residue 206 of SEQ ID NO: 2); and
Region 5: $^{212}$QVNRLKSAQCGSSIIYHC$^{229}$ (amino acid residues 212 to 229 of SEQ ID NO: 2).
(14) Specifically binds to an epitope located within discontinuous regions comprising the following amino acid residues as determined by HDX-MS:
Region 1: $^{155}$LSIDNEEEMKF$^{165}$ (amino acid residues 155 to 165 of SEQ ID NO: 2)
Region 2: $^{171}$PSSWIGVFRNSSHHPW$^{186}$ (amino acid residues 171 to 186 of SEQ ID NO: 2);
Region 3: $^{192}$LAFKHEIKDSDN$^{203}$ (amino acid residues 192 to 203 of SEQ ID NO: 2); and
Region 5: $^{212}$QVNRLKSAQCGSSIIYHC$^{229}$ (amino acid residues 212 to 229 of SEQ ID NO: 2).

In some embodiments, the anti-NKG2A antibodies described herein bind with high affinity to human and cynomolgus monkey NKG2A, and does not bind to, or binds with low affinity to non-primate NKG2A, such as mouse or rat NKG2A. Specifically, in some embodiments, the anti-NKG2A antibodies exhibit one or more of the following properties:
(a) has an $EC_{50}$ value of about 0.6 nM or lower for binding to human NKG2A protein as measured by cell binding assay;
(b) has an $EC_{50}$ value of about 9.0 nM or higher for binding to human NKG2C protein as measured by cell binding assay;
(c) has an $IC_{50}$ value of about 1.0 nM or lower for reducing the binding and/or interaction of HLA-E to human NKG2A protein as measured by cell blocking assay;
(d) binds to human NKG2A protein with a $K_D$ of about 0.4 nM or lower as measured by Scatchard analysis;
(e) binds to human NKG2A protein with a $K_D$ of about 61 nM or lower as measured by surface plasmon resonance;
(f) binds to cynomolgus NKG2A protein with a $K_D$ of about 1.0 nM or lower as measured by Scatchard analysis;
(g) is internalized upon binding to NKG2A-expressing cells;
(h) increases interferon-gamma (IFNγ) production; and/or
(i) wherein the half-life of the anti-NKG2A antibody: NKG2A protein complex is about 40 seconds or longer.

In some embodiments, the anti-NKG2A antibodies described herein block binding and/or interaction of an NKG2A ligand (HLA-E in humans) to human NKG2A protein. Specifically, in some embodiments, the anti-NKG2A antibodies exhibit one or more of the following properties:

a) Anti-NKG2A antibody blocks HLA-E pentamer from binding to cells expressing human NKG2A with an $IC_{50}$ of about 0.30 nM for NKL and an $IC_{50}$ of about 1.0 nM for CHO-hNKG2A cells;
b) Anti-NKG2A antibody complexed with either HNKG2A-CD94-mFC or cynomolgus NKG2A-CD94-mFc protein blocks human HLA-E binding.

In some embodiments, the anti-NKG2A antibodies described herein is specific to human NKG2A. Specifically, in some embodiments, the anti-NKG2A antibodies exhibit one or more of the following properties:
a) Has an $EC_{50}$ value for the anti-NKG2A antibody binding to human NKG2A that is about 15-fold less than a second $EC_{50}$ value for the anti-NKG2A antibody binding to human NKG2C protein. In some embodiments, the $EC_{50}$ value for the anti-NKG2A antibody binding to human NKG2A was about 0.6 nM, while the $EC_{50}$ value for the anti-NKG2A antibody binding to human NKG2C was about 9.0 nM.
b) No specific binding of the anti-NKG2A antibody to human NKG2C based on SPR analysis; and/or
c) Does not block human NKG2C and HLA-E interaction as measured by flow cytometry.

In some embodiments, the anti-NKG2A has an inert Fc (for example, the antibody is IgG1 isotype) to reduce or prevent FcγR binding. Although not bound by any theory, since NKG2A is an inhibitory receptor expressed on CD8+ T and NK cells, reducing agonism or depletion of NKG2A+ CD8+ T or NK cells is beneficial for anti-tumor function. Thus, blocking NKG2A and HLA-E interaction can be done with an anti-NKG2A antibody that does not interact with human FcγRs.

In some embodiments, the anti-NKG2A described herein enhances the anti-tumor functional activity of T cells. Specifically, in some embodiments, the anti-NKG2A antibodies exhibit one or more of the following properties:
a) Reverses the inhibition of NK-κB signaling in a NKG2A-expressing Jurkat T cell line stimulated by CHO/scOKT3/HLA-E, with an $EC_{50}$ value of about 0.2 nM or lower.
b) Induces interferon-gamma (IFN-γ) in NKG2A$^+$ CD8 T isolated from healthy donor PBMC co-cultured with CHO/scOKT3/HLA-E/PD-L1.
c) Induces IFN-γ in NKG2A$^+$ CD8 T cells isolated from human tumors co-cultured with CHO/scOKT3/HLA-E/PD-L1.

In some embodiments, the anti-NKG2A antibodies described herein enhances the anti-tumor functional activity of NK cells. Specifically, in some embodiments, the anti-NKG2A antibodies exhibit one or more of the following properties:
a) Increases IFN-γ production in NKL cells co-cultured with CHO/MICA/HLA-E.
b) Induces a dose-dependent increase in NK cell degranulation and lysis of HLA-E-expressing tumor cells.

In some embodiments, the anti-NKG2A antibodies described herein is internalized after binding to NKG2A-expressing cells. Specifically, in some embodiments, the anti-NKG2A antibodies exhibit internationalization with an $EC_{50}$ of about 0.5 nM lower or lower. In some embodiments, the anti-NKG2A antibodies exhibit dose-dependent internationalization with an $EC_{50}$ of about 0.5 nM lower or lower.

In some embodiments, the anti-NKG2A antibodies of the invention lack sequence liabilities that reduce the chemical stability of the antibodies. The anti-NKG2A antibodies of the invention have various important uses, e.g., for treatment and/or diagnosis of cancer and other disorders associated with NKG2A expression and/or activity.

In some embodiments, the anti-NKG2A antibodies disclosed herein by amino acid sequence bind to specific epitopes on human NKG2A, as described in Example 4.

Binding to human NKG2A can be assessed using one or more techniques well established in the art. For example, in some embodiments, the antibody is tested by a flow cytometry assay in which the antibody is reacted with a cell line that expresses human NKG2A, such as CHO cells that have been transfected to express human NKG2A on their cell surface. Additionally or alternatively, the binding of the antibody, including the binding kinetics (e.g., $K_D$ value) can be tested in Biacore binding assays. Still other suitable binding assays include ELISA assays using, for example, a recombinant human NKG2A protein.

In some embodiments, anti-NKG2A antibodies or antigen-binding fragments thereof described herein bind to human NKG2A protein with high affinity, for example, with nanomolar affinity, including with a $K_D$ of $1\times10^{-6}$ M or lower, $1\times10^{-7}$ M or lower, $1\times10^{-8}$ M or lower, $1\times10^{-9}$ M or lower, or $10^{-10}$ M or lower.

Some embodiments of the present invention relates to an anti-NKG2A monoclonal antibody or antigen-binding portion thereof that specifically binds to an epitope located within discontinuous regions comprising the following amino acid residues as determined by HDX-MS and/or FPOP epitope mapping:
Region 1: $^{155}$LSIDNEEEMKF$^{165}$ (amino acid residues 155 to 165 of SEQ ID NO: 2 (native hNKG2A amino acid sequence);
Region 2: $^{171}$PSSWIGVFRNSSHHPW$^{186}$ (amino acid residues 171 to 186 of SEQ ID NO: 2);
Region 3: $^{192}$LAFKHEIKDSDN$^{203}$ (amino acid residues 192 to 203 of SEQ ID NO: 2);
Region 4: L (amino acid residue 206 of SEQ ID NO: 2); and
Region 5: $^{212}$QVNRLKSAQCGSSIIYHC$^{229}$ (amino acid residues 212 to 229 of SEQ ID NO: 2).

In some embodiments, the invention is directed to an anti-NKG2A monoclonal antibody or antigen-binding portion thereof that specifically binds to an epitope located within discontinuous regions comprising the following amino acid residues as determined by HDX-MS:
Region 1: $^{155}$LSIDNEEEMKF$^{165}$ (amino acid residues 155 to 165 of SEQ ID NO: 2);
Region 2: $^{171}$PSSWIGVFRNSSHHPW$^{186}$ (amino acid residues 171 to 186 of SEQ ID NO: 2);
Region 3: $^{192}$LAFKHEIKDSDN$^{203}$ (amino acid residues 192 to 203 of SEQ ID NO: 2); and
Region 5: $^{212}$QVNRLKSAQCGSSIIYHC$^{229}$ (amino acid residues 212 to 229 of SEQ ID NO: 2.

In some embodiments, the anti-NKG2A antibodies described herein enhance NK cell function by blocking NKG2A/HLA-E-mediated inhibition. In another embodiment, the anti-NKG2A antibody binds to human NKG2A protein and stimulates an anti-tumor immune response, e.g., an antigen-specific T cell and/or NK cell response. The ability of the anti-NKG2A antibody to stimulate an immune response can be tested by measuring tumor growth, such as in an in vivo tumor graft model, as described in the Examples herein. In other embodiments, the anti-NKG2A antibodies or antigen binding portions thereof increase cytokine production (e.g., interferon-gamma (IFN-γ) in NKG2A-expressing T cells and/or increase T cell proliferation, including effector T cells and cytotoxic T cells (also known as CD8$^+$ T cells).

In another embodiment, the anti-NKG2A antibody, or antigen-binding fragment thereof, binds to human NKG2A and exhibits at least one of the following properties:
- a) binds to one or more of the following residues as determined by HDX-MS and/or FPOP epitope mapping:
  - Region 1: $^{155}$LSIDNEEEMKF$^{165}$ (amino acid residues 155 to 165 of SEQ ID NO: 2 (native hNKG2A amino acid sequence);
  - Region 2: $^{171}$PSSWIGVFRNSSHHPW$^{186}$ (amino acid residues 171 to 186 of SEQ ID NO: 2);
  - Region 3: $^{192}$LAFKHEIKDSDN$^{203}$ (amino acid residues 192 to 203 of SEQ ID NO: 2);
  - Region 4: L (amino acid residue 206 of SEQ ID NO: 2); and
  - Region 5: $^{212}$QVNRLKSAQCGSSIIYHC$^{229}$ (amino acid residues 212 to 229 of SEQ ID NO: 2);
- b) binds to the same epitope on human NKG2A as NKG2A.11 and 13F3.A4 antibodies;
- c) competes for binding to human NKG2A with NKG2A.11 and 13F3.A4 antibodies;
- d) binds to human NK cell with an $EC_{50}$ of about 0.4 nM as measured by Biacore;
- e) blocks binding of human NK cells to HLA-E with an $IC_{50}$ of about 0.3 nM as measured by Biacore;
- f) binds to cynomolgus monkey NKG2A-expressing CHO cells with an $EC_{50}$ of about 1 nM or lower;
- g) has low binding to human NKG2C with an $EC_{50}$ of about 9.0 nM or higher (in other words, the anti-NKG2A antibody does not block the interaction of human NKG2C to HLA-E); and/or
- h) enhances CD8+ T cell and NK cell anti-tumor responses. For example:
  - i. increases IFN-γ production in a primary T:CHO-OKT3-HLA-E-PDL1 assay;
  - ii. increases IFN-γ production in T cell tumor-infiltrating lymphocytes (TILs):CHO-OKT3-HLA-E-PDL1 assay; and/or
  - iii. increases cytoxocity and IFN-γ production in primary NK cell assays.

In some embodiments, the anti-NKG2A antibodies of the invention include humanized and fully human monoclonal antibodies. In other embodiments, the antibodies are, for example, chimeric monoclonal antibodies.

a. Anti NKG2A Monoclonal Antibodies

In some embodiments, the antibodies of the invention are monoclonal antibodies 13F3.A4, NKG2A.9, and NKG2A.11, which are isolated and structurally characterized as described in the following Examples. The VH and the VL amino acid sequences are set forth in the Sequence Table and Sequence Listing.

Given that each of these antibodies can bind to human NKG2A, the VH and VL sequences can be "mixed and matched" to create other anti-hNKG2A binding molecules of the invention. In some embodiments, when VH and VL chains are mixed and matched, a VH sequence from a particular VH/VL pairing is replaced with a structurally similar VH sequence. Likewise, in some embodiments, a VL sequence from a particular VH/VL pairing is replaced with a structurally similar VL sequence. Accordingly, in one aspect, this disclosure provides an isolated monoclonal antibody, or antigen-binding fragment thereof, that binds to human NKG2A protein, wherein the light and heavy chain variable regions comprise:
- (a) the amino acid sequences of SEQ ID NOs: 9 and 8, respectively;
- (b) the amino acid sequences of SEQ ID NOs: 164 and 8, respectively; or
- (c) the amino acid sequences of SEQ ID NOs: 169 and 167, respectively.

In another aspect, this disclosure provides antibodies that comprise the heavy chain and light chain CDR1s, CDR2s and CDR3s of NKG2A.9, NKG2A.11, and 13F3A.4 antibodies. Accordingly, in one aspect, this disclosure provides an isolated monoclonal antibody, or antigen binding fragment thereof, that binds to human NKG2A protein, wherein the antibody comprises:
- (a) a heavy chain variable domain comprising CDR1, CDR2, and CDR3 regions comprising the amino acid sequences of SEQ ID NOs: 10, 11, 12, respectively, and a light chain variable domain comprising CDR1, CDR2, and CDR3 regions comprising the amino acid sequences of SEQ ID NOs: 13, 14, and 15, respectively;
- (b) a heavy chain variable domain comprising CDR1, CDR2, and CDR3 regions comprising the amino acid sequences of SEQ ID NOs: 10, 11, and 12, respectively, and a light chain variable domain comprising CDR1, CDR2, and CDR3 regions comprising the amino acid sequences of SEQ ID NOs: 154, 14, and 15, respectively; or
- (c) a heavy chain variable domain comprising CDR1, CDR2, and CDR3 region comprising the amino acid sequences of SEQ ID NOs: 10, 11, and 12, respectively, and a light chain variable domain comprising CDR1, CDR2, and CDR3 regions comprising the amino acid sequences of SEQ ID NOs: 155, 14, and 15, respectively.

It is well known in the art that the CDR3 domain, independently from the CDR1 and/or CDR2 domain(s), alone can determine the binding specificity of an antibody for a cognate antigen and that multiple antibodies can predictably be generated having the same binding specificity based on a common CDR3 sequence. (See, e.g., Klimka et al., *British J. of Cancer* 83(2):252-260 (2000). Accordingly, the present disclosure provides monoclonal antibodies comprising one or more heavy and/or light chain CDR3 domains from an antibody derived from a human or non-human animal, wherein the monoclonal antibody is capable of specifically binding to human NKG2A. In certain aspects, the present disclosure provides monoclonal antibodies comprising one or more heavy and/or light chain CDR3 domain from a non-human antibody, wherein the monoclonal antibody is capable of specifically binding to human NKG2A. Within some embodiments, such inventive antibodies comprising one or more heavy and/or light chain CDR3 domain from a non-human antibody (a) are capable of competing for binding with; (b) retain the functional characteristics; (c) bind to the same epitope; and/or (d) have a similar binding affinity as the corresponding parental non-human antibody.

In other aspects, the present disclosure provides monoclonal antibodies comprising one or more heavy and/or light chain CDR3 domain from a human antibody, such as, e.g., a human antibody obtained from a non-human animal, wherein the human antibody is capable of specifically binding to human NKG2A. In other aspects, the present disclosure provides monoclonal antibodies comprising one or more heavy and/or light chain CDR3 domain from a first human antibody, such as, for example, a human antibody obtained from a non-human animal, wherein the first human antibody is capable of specifically binding to human NKG2A, and wherein the CDR3 domain from the first human antibody replaces a CDR3 domain in a human antibody that lacks binding specificity for NKG2A to generate a second human antibody that is capable of specifically binding to human NKG2A. In some embodiments, such inventive antibodies comprising one or more heavy and/or light chain CDR3 domain from the first human antibody (a) are capable of competing for binding with; (b) retain the functional characteristics; (c) bind to the same epitope; and/or (d) have a similar binding affinity as the corresponding parental non-human antibody.

In some embodiments, the present invention provides anti-hNKG2A antibodies with inert Fc human IgG1.3 as the isotype. In some embodiments, such anti-hNKG2A antibodies with an inert Fc exhibit superior efficacy in treating cancer compared to other isotypes.

b. Antibodies with Conservative Modifications

In certain embodiments, an anti-NKG2A antibody of the invention comprises a heavy chain variable region comprising CDR1, CDR2, and CDR3 sequences and a light chain variable region comprising CDR1, CDR2, and CDR3 sequences, wherein one or more of these CDR sequences comprise specified amino acid sequences based on the antibodies described herein (e.g., the 13F3.A4, NKG2A.9, and NKG2A.11 antibodies), or conservative modifications thereof, and wherein the antibodies retain the desired functional properties of the anti-hNKG2A antibodies of the invention. It is understood in the art that certain conservative sequence modifications can be made that do not remove antigen binding. (See, e.g., Brummell et al. (1993) Biochem 32:1180-8). Accordingly, this disclosure provides an isolated monoclonal antibody, or antigen binding fragment thereof, comprising a heavy chain variable region comprising CDR1, CDR2, and CDR3 sequences and a light chain variable region comprising CDR1, CDR2, and CDR3 sequences, wherein:
  (a) the heavy chain variable region comprising a CDR3 sequence comprising an amino acid sequence set forth in SEQ ID NO: 12, or conservative modifications thereof; and
  (b) the antibody, or antigen binding portion thereof, specifically binds human NKG2A.

In additional embodiments, the antibody has one or more of the functional properties described herein, such as high affinity binding to human NKG2A, and/or the ability to block the NKG2A/HLA-E interaction.

In some embodiments, the heavy chain variable region comprising a CDR2 sequence comprises an amino acid sequence set forth in SEQ ID NO: 11, or conservative modifications thereof and the light chain variable region comprising a CDR2 sequence comprises an amino acid sequence set forth in SEQ ID NO: 14, or conservative modifications thereof. In another embodiment, the heavy chain variable region comprises a CDR1 sequence comprising an amino acid sequence set forth in SEQ ID NO: 10, or conservative modifications thereof and the light chain variable region comprising a CDR1 sequence comprising an amino acid sequence set forth in SEQ ID NOs: 13, 154, or 155, or conservative modifications thereof.

In various embodiments, the anti-NKG2A antibody is, for example, human antibodies, humanized antibodies, or chimeric antibodies.

c. Antibodies that Bind to the Same Epitope as Anti-hNKG2A Antibodies

In another embodiment, this disclosure provides antibodies that bind to the same epitope on human NKG2A protein as any of the anti-hNKG2A monoclonal antibodies of the invention (i.e., antibodies that have the ability to cross-compete for binding to human NKG2A protein with any of the monoclonal antibodies of the invention). In some embodiments, the reference antibody for cross-competition studies are the monoclonal antibodies NKG2A.9, NKG2A.11, and 13F3.A4 in standard human NKG2A binding assays. For example, standard ELISA assays can be used in which a recombinant human NKG2A protein is immobilized on the plate, one of the antibodies is fluorescently labeled, and the ability of non-labeled antibodies to compete off the binding of the labeled antibody is evaluated. Additionally or alternatively, Biacore analysis can be used to assess the antibodies' ability to cross-compete. The ability of a test antibody to inhibit the binding of, for example, NKG2A.9, NKG2A.11, and/or 13F3.A4, to human NKG2A demonstrates that the test antibody can compete with NKG2A.9, NKG2A.11, and/or 13F3.A4 for binding to human NKG2A and thus binds to the same epitope on human NKG2A.9 as NKG2A.9, NKG2A.11, and/or 13F3.A4. In some embodiments, the antibody that binds to the same epitope on human NKG2A as NKG2A.9, NKG2A.11, and/or 13F3.A4 is a humanized or human monoclonal antibody.

As discussed further in Example 4, the binding of NKG2A.9 and 13F3.A4 has been mapped to specific residues. Accordingly, in one embodiment, the invention provides an isolated monoclonal antibody, or antigen-binding fragment thereof, that, when bound to human NKG2A protein, the antibody, or antigen-binding fragment thereof, specifically binds to the following amino acid residues as determined by hydrogen-deuterium exchange mass spectrometry (HDX-MS):

```
                                        (SEQ ID NO: 156)
    (e) LSIDNEEMKF;

(SEQ ID NO: 157)
    (f) PSSWIGVFRNSSHHPW;

(SEQ ID NO: 158)
    (g) LAFKHEIKDSDN;
    and (SEQ ID NO: 159)
    (h) QVNRLKSAQQCGSSIIYHC,
``` wherein the monoclonal antibody blocks the binding of an NKG2A ligand (e.g., HLA-E in humans) to human NKG2A protein.

In another embodiment, the invention provides an isolated monoclonal antibody, or antigen-binding fragment thereof, that, when bound to human NKG2A, the monoclonal antibody specifically binds to the following amino acid residues as determined by HDX-MS and/or fast photochemical oxidation of proteins (FPOP) epitope mapping:

```
                                        (SEQ ID NO: 156)
    (f) LSIDNEEMKF;

(SEQ ID NO: 157)
    (g) PSSWIGVFRNSSHHPW;

(SEQ ID NO: 158)
    (h) LAFKHEIKDSDN;

(i) L;
    and (SEQ ID NO: 159)
    (j) QVNRLKSAQQCGSSIIYHC,
``` wherein the monoclonal antibody blocks the binding of an NKG2A ligand (e.g., HLA-E in humans) to human NKG2A protein.

Such humanized or human monoclonal antibodies can be prepared and isolated as described herein. For example, anti-hNKG2A antibodies that bind to the same or similar epitopes to the antibodies disclosed herein may be raised using immunization protocols, e.g., those described herein. The resulting antibodies can be screened for high affinity binding to human NKG2A. Selected antibodies can then be studied, e.g., in yeast display assay in which sequence variants of hNKG2A are presented on the surface of yeast cells, or by hydrogen-deuterium exchange experiments and/or FPOP, to determine the precise epitope bound by the antibody.

Epitope determinations may be made by any method known in the art. In some embodiments, anti-hNKG2A antibodies are considered to bind to the same epitope as an anti-anti-hNKG2A mAb disclosed herein if they make contact with one or more of the same residues within at least one region of hNKG2A; if they make contacts with a majority of the residues within at least one region of hNKG2A; if they make contacts with a majority of the residues within each region of hNKG2A; if they make contact with a majority of contacts along the entire length of hNKG2A; if they make contacts within all of the same distinct regions of hNKG2A; if they make contact with all of the residues at any one region on hNKG2A; or if they make contact with all of the same residues at all of the same regions. Epitope "regions" are clusters of residues along, but not necessarily directly adjacent within, the primary sequence.

Techniques for determining antibodies that bind to the "same epitope on hNKG2A" with the antibodies described herein include x-ray analyses of crystals of antigen:antibody complexes, which provides atomic resolution of the epitope. Other methods monitor the binding of the antibody to antigen fragments or mutated variations of the antigen where loss of binding due to an amino acid modification within the antigen sequence indicates the epitope component. Methods may also rely on the ability of an antibody of interest to affinity isolate specific short peptides (either in native three dimensional form or in denatured form) from combinatorial phage display peptide libraries or from a protease digest of the target protein. The peptides are then regarded as leads for the definition of the epitope corresponding to the antibody used to screen the peptide library. For epitope mapping, computational algorithms have also been developed that have been shown to map conformational discontinuous epitopes.

The epitope or region comprising the epitope can also be identified by screening for binding to a series of overlapping peptides spanning NKG2A. Alternatively, the method of Jespers et al. (1994) *Biotechnology* 12:899 may be used to guide the selection of antibodies having the same epitope and therefore similar properties to the anti-NKG2A antibodies described herein. Using phage display, first, the heavy chain of the anti-NKG2A antibody is paired with a repertoire of (e.g., human) light chains to select an NKG2A-binding antibody, and then the new light chain is paired with a repertoire of (e.g., human) heavy chains to select a (e.g., human) NKG2A-binding antibody having the same epitope or epitope region as an anti-NKG2A antibody described herein. Alternatively, variants of an antibody described herein can be obtained by mutagenesis of cDNA sequences encoding the heavy and light chains of the antibody.

Alanine scanning mutagenesis, as described by Cunningham & Wells, *Science* 244: 1081 (1989), or some other form of point mutagenesis of amino acid residues in NKG2A may also be used to determine the functional epitope for an anti-NKG2A antibody.

The epitope or epitope region (an "epitope region" is a region comprising the epitope or overlapping with the epitope) bound by a specific antibody may also be determined by assessing binding of the antibody to peptides comprising NKG2A fragments. A series of overlapping peptides encompassing the NKG2A sequence (e.g., human NKG2A) may be synthesized and screened for binding, e.g. in a direct ELISA, a competitive ELISA (where the peptide is assessed for its ability to prevent binding of an antibody to NKG2A bound to a well of a microtiter plate), or on a chip. Such peptide screening methods may not be capable of detecting some discontinuous functional epitopes, i.e., functional epitopes that involve amino acid residues that are not contiguous along the primary sequence of the NKG2A polypeptide chain.

An epitope may also be identified by MS-based protein footprinting, such as HDX-MS and Fast Photochemical Oxidation of Proteins (FPOP). HDX-MS may be conducted, e.g., as further described at Wei et al. (2014) *Drug Discovery Today* 19:95, the methods of which are specifically incorporated by reference herein. FPOP may be conducted as described, e.g., in Hambley & Gross (2005) *J. American Soc. Mass Spectrometry* 16:2057, the methods of which are specifically incorporated by reference herein.

The epitope bound by anti-NKG2A antibodies may also be determined by structural methods, such as X-ray crystal structure determination (e.g., WO2005/044853), molecular modeling and nuclear magnetic resonance (NMR) spectroscopy, including NMR determination of the H-D exchange rates of labile amide hydrogens in NKG2A when free and when bound in a complex with an antibody of interest (Zinn-Justin et al. (1992) *Biochemistry* 31:11335; Zinn-Justin et al. (1993) *Biochemistry* 32:6884).

Unless otherwise indicated, and with reference to the claims, the epitope bound by an antibody is the epitope as determined by HDX-MS methods.

Anti-NKG2A Antibodies that Bind with High Affinity

In some embodiments, the anti-hNKG2A antibodies of the present invention bind to hNKG2A with high affinity, making them effective therapeutic agents. In various embodiments, anti-hNKG2A antibodies of the present invention bind to hNKG2A with a $K_D$ of less than 10 nM, 5 nM, 2 nM, 1 nM, 300 pM or 100 pM. Standard assays to evaluate the binding ability of the antibodies toward hNKG2A include ELISAs, RIAs, Western blots, biolayer interferometry (BLI) and Biacore™ SPR analysis (see Example 10).

d. Anti NKG2A Antibody Sequence Variants

Anti-NKG2A antibody sequence variants disclosed herein maintain the desirable functional properties disclosed herein. The CDR regions are delineated using the Kabat system (Kabat, et al., 1991) unless otherwise specified. In some embodiments, the present invention further provides human or humanized anti-hNKG2A antibodies comprising CDR sequences that are at least 70%, 75%, 80%, 85%, 90%, or 95%, 96%, 97%, 98%, 99%, or 99.5% identical to the CDR sequences of the antibodies disclosed herein. The present invention also provides anti-anti-hNKG2A antibodies comprising heavy and/or light chain variable domain sequences that are at least 70%, 75%, 80%, 85%, 90%, 95%, 96%, 97%, 98%, 99%, or 99.5% identical to the heavy and/or light chain variable domain sequences of the antibodies disclosed herein, as well as anti-hNKG2A antibodies comprising full-length heavy and/or light chain sequences that are at least 70%, 75%, 80%, 85%, 90%, 95%, 96%, 97%, 98%, 99%, or 99.5% identical to the heavy and/or light chain sequences of the antibodies disclosed herein.

II. Engineered and Modified Antibodies a. $V_H$ and $V_L$ Regions

Also provided are engineered and modified antibodies that can be prepared using an antibody having one or more of the $V_H$ and/or $V_L$ sequences disclosed herein as starting material to engineer a modified antibody, which modified antibody may have altered properties from the starting antibody. In some embodiments, an antibody as described herein was engineered by modifying one or more residues within one or both variable regions (i.e., $V_H$ and/or $V_L$), for example, within one or more CDR regions and/or within one or more framework regions. Additionally or alternatively, an antibody as described herein was engineered by modifying residues within the constant region(s), for example, to alter the effector function(s) of the antibody.

In one embodiment, the variable region engineering includes CDR grafting. Such grafting is of particular use in humanizing non-human anti-NKG2A antibodies, e.g., anti-HNKG2A antibodies that compete for binding with the anti-hNKG2A antibodies disclosed herein and/or bind to the same epitope as the select anti-hNKG2A antibodies disclosed herein. Antibodies interact with target antigens predominantly through amino acid residues that are located in the heavy and light chain CDRs. The CDRs are hypervariable in sequence and/or form structurally defined loops ("hypervariable loops"). Expression vectors can be constructed such that they include CDR sequences from a specific reference (also called "parental") antibody grafted onto framework sequences from a different antibody (see, e.g., Riechmann, L. et al. (1998) Nature 332:323-327; Jones, P. et al. (1986) Nature 321:522-525; Queen, C. et al. (1989) Proc. Natl. Acad. See. U.S.A. 86:10029-10033; U.S. Pat. No. 5,225,539 to Winter, and U.S. Pat. Nos. 5,530,101; 5,585,089; 5,693,762 and 6,180,370 to Queen et al.). In some instances, the resulting recombinant antibody has properties that are similar to the parental antibody. The engineered antibody can then be further modified to acquire properties that are distinct from the parental antibody. In other instances, grafting the parental CDR sequences onto a framework abrogates certain characteristics of the parental antibody such that the recombinant antibody no longer has these characteristics. One exemplary characteristic is binding affinity with respect to an antigen. In such instances, it might be advantageous to modify the engineered antibody further to regain the desired characteristics of the parental antibody.

Such framework sequences can be obtained from public DNA databases or published references that include germline antibody gene sequences. For example, germline DNA sequences for human heavy and light chain variable region genes can be found in the "VBase" human germline sequence database, as well as in Kabat, E. A., et al., 1991); Tomlinson, I. M., et al. (1992) "The Repertoire of Human Germline $V_H$ Sequences Reveals about Fifty Groups of $V_H$ Segments with Different Hypervariable Loops" J. Mol. Biol. 227:776-798; and Cox, J. P. L. et al. (1994) "A Directory of Human Germ-line $V_H$ Segments Reveals a Strong Bias in their Usage," Eur. J. Immunol. 24:827-836; the contents of each of which are expressly incorporated herein by reference.

In some embodiments, framework sequences for use in the antibodies described herein are those that are structurally similar to the framework sequences used by antibodies described herein. The $V_H$ CDR1, 2, and 3 sequences and the $V_L$ CDR1, 2, and 3 sequences can be grafted onto framework regions that have the identical sequence as that found in the germline immunoglobulin gene from which the framework sequence derive, or the CDR sequences can be grafted onto framework regions that contain up to 20 amino acid substitutions, including conservative amino acid substitutions, as compared to the germline sequences. For example, it has been found that in certain instances, it is beneficial to mutate residues within the framework regions to maintain or enhance the antigen binding ability of the antibody (see e.g., U.S. Pat. Nos. 5,530,101; 5,585,089; 5,693,762 and 6,180, 370 to Queen et al).

Engineered antibodies described herein include those in which modifications have been made to framework residues within $V_H$ and/or $V_L$, e.g., to improve the properties of the antibody, such as to decrease the immunogenicity of the antibody. For example, one approach is to "back-mutate" one or more framework residues to the corresponding germline sequence. More specifically, an antibody that has undergone somatic mutation may contain framework residues that differ from the germline sequence from which the antibody is derived. Such residues can be identified by comparing the antibody framework sequences to the germline sequences from which the antibody is derived. To return the framework region sequences to their germline configuration, the somatic mutations can be "back-mutated" to the germline sequence by, for example, site-directed mutagenesis or PCR-mediated mutagenesis. Such "back-mutated" antibodies are also encompassed in this disclosure.

Another type of framework modification involves mutating one or more residues within the framework region, or even within one or more CDR regions, to remove T cell epitopes to thereby reduce the potential immunogenicity of the antibody. This approach is also referred to as "de-immunization" and is described in further detail in U.S. Patent Publication No. 20030153043 by Carr et al.

Another type of variable region modification is to mutate amino acid residues within the CDR regions to improve one or more binding properties (e.g., affinity) of the antibody of interest. Site-directed mutagenesis or PCR-mediated mutagenesis can be performed to introduce the mutation(s) and the effect on antibody binding, or other functional property of interest. Preferably, conservative modifications are introduced. The mutations may be amino acid additions, deletions, or substitutions. In some embodiments, no more than one, two, three, four or five residues within a CDR region are altered.

Methionine residues in CDRs of antibodies can be oxidized, resulting in potential chemical degradation and consequent reduction in antibody potency. Accordingly, also provided herein are anti-NKG2A antibodies that have one or more methionine residues in the heavy and/or light chain CDRs replaced with amino acid residues that do not undergo oxidative degradation. Similarly, deamidation sites may be removed from anti-NKG2A antibodies, particularly in the CDRs. Also provided herein are antibodies in which potential glycosylation sites within the antigen binding domain were eliminated to prevent glycosylation that may interfere with antigen binding. See, e.g., U.S. Pat. No. 5,714,350.

b. Antibody Masking

In some embodiments, the antibodies disclosed herein are modified to limit their binding to specific cells and/or tissue. In one embodiment, such antibodies comprise a blocking peptide "mask" that specifically binds to the antigen binding surface of the antibody and interferes with antigen binding. In some embodiments, the mask is linked to each of the binding arms of the antibody by a protease cleavable linker.

See, e.g., U.S. Pat. No. 8,518,404 to CytomX. Antibodies with protease cleavable linkers are useful for treatment of cancers in which protease levels are greatly increased in the tumor microenvironment compared with non-tumor tissues. Selective cleavage of the cleavable linker in the tumor microenvironment allows disassociation of the masking/blocking peptide, enabling antigen binding selectively in the tumor, rather than in peripheral tissues in which antigen binding might cause unwanted side effects.

In another embodiment, a bivalent binding compound ("masking ligand") comprising two antigen binding domains is developed that binds to both antigen binding surfaces of the (bivalent) antibody and interferes with antigen binding. In one embodiment, the two binding domain masks are linked to each other (but not the antibody) by a cleavable linker, for example, cleavable by a peptidase. (See, e.g., WO 2010/077643 to Tegopharm Corp). Masking ligands may comprise, or be derived from, the antigen to which the antibody is intended to bind, or may be independently generated (e.g., anti-idiotype binding fragments). Such masking ligands are useful for treatment of cancers in which protease levels are greatly increased in the tumor microenvironment compared with non-tumor tissues. Selective cleavage of the cleavable linker in the tumor microenvironment allows disassociation of the two binding domains from each other, reducing the avidity for the antigen-binding surfaces of the antibody. The resulting dissociation of the masking ligand from the antibody enables antigen binding selectively in the tumor, rather than in peripheral tissues in which antigen binding might cause unwanted side effects.

c. Fcs and Modified Fc Regions

In one embodiment, the antibodies described herein may comprise Fc regions selected based on the biological activities of the antibody. Salfeld, *Nat. Biotechnol.* 25:1369 (2007). Human IgGs, for example, can be classified into four subclasses, IgG1, IgG2, IgG3, and IgG4. Each of these subclasses comprise an Fc region having a unique profile for binding to one or more of Fcγ receptors (activating receptors FcγRI (CD64), FcγRIIA, FcγRIIC (CD32a,c); FcγRIIIA and FcγRIIIB (CD16a,b) and inhibiting receptor FcγRIIB (CD32b), and for the first component of complement (C1q). Human IgG1 and IgG3 bind to all Fcγ receptors; IgG2 binds to FcγRIIA$_{H131}$, and with lower affinity to FcγRIIA$_{R131}$ FcγRIIIA$_{V158}$; IgG4 binds to FcγRI, FcγRIIA, FcγRIIB, FcγRIIC, and FcγRIIIA$_{V158}$; and the inhibitory receptor FcγRIIB has a lower affinity for IgG1, IgG2 and IgG3 than all other Fcγ receptors. (Bruhns et al. (2009) *Blood* 113: 3716). Studies have shown that FcγRT does not bind to IgG2, and FcγRIIIB does not bind to IgG2 or IgG4. Id. In general, with regard to ADCC activity, human IgG1≥IgG3>>IgG4≥IgG2. In some embodiments, an IgG1 constant domain, rather than an IgG2 or IgG4, is chosen, e.g., for use in a therapeutic composition because ADCC is desired.

Anti-hNKG2A antibody variable regions described herein may be linked (e.g., covalently linked or fused) to an Fc, e.g., an IgG1, IgG2, IgG3 or IgG4 Fc, which may be of any allotype or isoallotype, e.g., for IgG1: G1m, G1m1(a), G1m2(x), G1m3(f), G1m17(z); for IgG2: G2m, G2m23(n); for IgG3: G3m, G3m21(g1), G3m28(g5), G3m11(b0), G3m5(b1), G3m13(b3), G3m14(b4), G3m10(b5), G3m15(s), G3m16(t), G3m6(c3), G3m24(c5), G3m26(u), G3m27(v). (See, e.g., Jefferis et al. (2009) mAbs 1:1). Selection of allotype may be influenced by the potential immunogenicity concerns, e.g. to minimize the formation of anti-drug antibodies.

In some embodiments, anti-NKG2A antibodies of the present invention is unable to interact with human FcγRs. Since NKG2A is an inhibitory receptor expressed on CD8+ T and NK cells, avoiding or reducing agonism or depletion of NKG2A+ CD8+ T or NK cells enhances anti-tumor immunity. Thus, blockade of the NKG2A/HLA-E interaction was desired with an anti-NKG2A antibody unable to interact with human FcγRs.

d. Half-Life Extension

In some embodiments, the anti-NKG2A antibody is modified to increase its biological half-life, e.g., the antibody's half-life in serum. Various approaches are known in the art. In one embodiment, the antibody is altered within the CH1 or CL region to contain a salvage receptor binding epitope taken from two loops of a CH2 domain of an Fc region of an IgG, as described in U.S. Pat. Nos. 5,869,046 and 6,121,022 by Presta et al. For example, a combination Fc variant comprising M252Y, S254T and T256E, increases half-life-nearly four-fold. (Dall'Acqua et al. (2006) *J. Biol. Chem.* 281:23514). Other modifications for increasing FcRn binding are described in Yeung et al. (2010) *J. Immunol.* 182:7663-7671; U.S. Pat. Nos. 6,277,375; 6,821,505; WO 97/34631; WO 2002/060919.

The serum half-life of the antibodies described herein can also be increased by pegylation. An antibody can be pegylated, for example, to increase the biological (e.g., serum) half-life of the antibody. To pegylate an antibody, the antibody, or fragment thereof, typically is reacted with a polyethylene glycol (PEG) reagent, such as a reactive ester or aldehyde derivative of PEG, under conditions in which one or more PEG groups become attached to the antibody or antibody fragment. Preferably, the pegylation is carried out via an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono (C1-C10) alkoxy- or aryloxy-polyethylene glycol or polyethylene glycol-maleimide. In certain embodiments, the antibody to be pegylated is an aglycosylated antibody. Methods for pegylating proteins are known in the art and can be applied to the antibodies described herein. (See, e.g., EP 0154316 by Nishimura et al. and EP 0401384 by Ishikawa et al.

In some instances, it may be desirable to decrease the half-life of an antibody, rather than to increase it. In some embodiments, the antibodies described herein include modifications to decrease their half-life. Modifications such as I253A (Hornick et al. (2000) *J. Nucl. Med.* 41:355) and H435A/R, I253A or H310A (Kim et al. (2000) *Eur. J. Immunol.* 29:2819) in Fc of human IgG1 can decrease FcRn binding, thus decreasing half-life (increasing clearance) for use in situations where rapid clearance is preferred, such as for medical imaging. (See also Kenanova et al. (2005) *Cancer Res.* 65:622). Other means to enhance clearance include formatting the antigen binding domains of the present invention as antibody fragments lacking the ability to bind FcRn, such as Fab fragments. Such modification can, for example, reduce the circulating half-life of an antibody from a couple of weeks to hours. Selective PEGylation of antibody fragments can then be used to increase the half-life of the antibody fragments when desired. (Chapman et al. (1999) *Nat. Biotechnol.* 17:780). Antibody fragments may also be fused to human serum albumin, e.g. in a fusion protein construct, to increase half-life. (Yeh et al. (1992) *Proc. Nat'l Acad. Sci.* 89:1904). Alternatively, a bispecific antibody may be constructed with a first antigen binding domain of the present invention and a second antigen binding domain that binds to human serum albumin (HSA). (See WO 2009/127691 and patent references cited therein). Alternatively, specialized polypeptide sequences can be added to antibody fragments to increase half-life, e.g. "XTEN" polypeptide sequences. (Schellenberger et al. (2009) *Nat. Biotechnol.* 27:1186; Int'l Pat. Appl. Pub. WO 2010/091122).

e. Additional Fc Variants

In some embodiments, when using an IgG1 constant domain, a potential protease cleavage site in the hinge of IgG1 constructs can be eliminated by D221G and K222S modifications, increasing the stability of the antibody. (WO 2014/043344).

The affinities and binding properties of an Fc variant for its ligands (Fc receptors) may be determined by a variety of in vitro assay methods (e.g., biochemical or immunological based assays) known in the art including but not limited to, equilibrium methods (e.g., enzyme-linked immunosorbent assay (ELISA), or radioimmunoassay (RIA)), or kinetics (e.g., BIACORE® SPR analysis), and other methods such as indirect binding assays, competitive inhibition assays, fluorescence resonance energy transfer (FRET), gel electrophoresis, and chromatography (e.g., gel filtration). These and other methods may use a label on one or more of the components being examined and/or employ various detection methods including but not limited to chromogenic, fluorescent, luminescent, or isotopic labels. A detailed description of binding affinities and kinetics can be found in Paul, W. E., ed., Fundamental Immunology, 4th Ed., Lippincott-Raven, Philadelphia (1999), which focuses on antibody-immunogen interactions.

In still other embodiments, the glycosylation of an antibody is modified to increase or decrease effector function. For example, an aglycoslated antibody can be made that lacks all effector function by mutating the conserved asparagine residue at position 297 (e.g. N297A), thus abolishing complement and FcγRI binding. (Bolt et al. (1993) *Eur. J. Immunol.* 23:403; see also Tao & Morrison (1989) *J. Immunol.* 143:2595 (using N297Q in IgG1 to eliminate glycosylation at position 297)).

Although aglycosylated antibodies generally lack effector function, mutations can be introduced to restore that function. Aglycosylated antibodies, e.g. those resulting from N297A/C/D/or H mutations or produced in systems (e.g. *E. coli*) that do not glycosylate proteins, can be further mutated to restore FcγR binding, e.g. S298G and/or T299A/G/or H (WO 2009/079242), or E382V and M428I (Jung et al. (2010) *Proc. Nat'l Acad. Sci. (USA)* 107:604).

Glycoengineering can also be used to modify the antiinflammatory properties of an IgG construct by changing the α2,6 sialyl content of the carbohydrate chains attached at Asn297 of the Fc regions, wherein an increased proportion of α2,6 sialylated forms results in enhanced anti-inflammatory effects. (See Nimmerjahn et al. (2008) *Ann. Rev. Immunol.* 26:513). Conversely, reduction in the proportion of antibodies having α2,6 sialylated carbohydrates may be useful in cases where anti-inflammatory properties are not wanted. Methods of modifying α2,6 sialylation content of antibodies, for example, by selective purification of α2,6 sialylated forms or by enzymatic modification, are provided at U.S. Pat. Appl. Pub. No. 2008/0206246. In other embodiments, the amino acid sequence of the Fc region may be modified to mimic the effect of α2,6 sialylation, for example, by inclusion of an F241A modification. (WO 2013/095966).

III. Antibody Physical Properties

In certain embodiments, the antibodies described herein contain one or more glycosylation sites in either the light or heavy chain variable region. Such glycosylation sites may result in increased immunogenicity of the antibody or an altered antibody pharmacokinetics due to altered antigen binding (Marshall et al (1972) *Ann. Rev. Biochem.* 41:673-702; Gala and Morrison (2004) *J. Immunol.* 172:5489-94; Wallick et al (1988) *J. Exp. Med.* 168:1099-109; Spiro (2002) *Glycobiology* 12:43R-56R; Parekh et al (1985) *Nature* 316:452-7; Mimura et al. (2000) *Mol Immunol* 37:697-706). Glycosylation has been known to occur at motifs containing an N-X-S/T sequence. In some embodiments, the anti-hNKG2A antibody does not contain variable region glycosylation. Such antibodies can be obtained by selecting antibodies that do not contain the glycosylation motif in the variable region or by mutating residues within the glycosylation region.

In certain embodiments, the antibodies described herein do not contain asparagine isomerism sites. The deamidation of asparagine may occur on N-G or D-G sequences and result in the creation of an isoaspartic acid residue that introduces a kink into the polypeptide chain and decreases its stability (known as the isoaspartic acid effect).

In some embodiments, the antibodies described herein have an isoelectric point (pI) in the pH range between 6 and 9.5. In some embodiments, the antibodies described herein have a pI in the pH range of 7-9.5 or 6-8. Antibodies having a pI within a desired pI range can be obtained either by selecting antibodies with a pI in the pH range from a group of candidates or by mutating charged surface residues of a particular antibody.

In some embodiments, the antibodies described herein are selected and/or engineered have a temperature of initial unfolding ($T_{M1}$) greater than 60° C., greater than 65° C., or greater than 70° C. The melting point of an antibody may be measured using differential scanning calorimetry (Chen et al (2003) *Pharm Res* 20:1952-60; Ghirlando et al (1999) *Immunol Lett.* 68:47-52) or circular dichroism (Murray et al. (2002) *J. Chromatogr. Sci.* 40:343-9).

In some embodiments, the antibodies described herein are selected and/or engineered to have advantageous degradation properties, e.g., slow degradation in vitro and/or in vivo. Antibody degradation can be measured using capillary electrophoresis (CE) and MALDI-MS (Alexander A J and Hughes D E (1995) *Anal Chem.* 67:3626-32). In some embodiments, the antibodies described herein are selected and/or engineered to have favorable aggregation properties, e.g., antibodies that show minimal aggregation in vitro and/or in vivo, which may elicit an unwanted immune response and/or altered or unfavorable pharmacokinetic properties. In some embodiments, the antibodies described herein show aggregation of 25% or less, 20% or less, 15% or less, 10% or less, or 5% or less compared to aggregation of the parent antibody. Aggregation can be measured by several techniques, including size-exclusion column (SEC), high performance liquid chromatography (HPLC), and light scattering.

IV. Nucleic Acid Molecules and Recombinant Methods

Another aspect described herein pertains to nucleic acid molecules that encode the anti-hNKG2A antibodies described herein. The nucleic acids may be present in whole cells e.g., a host cell, in a cell lysate, or in a partially purified or substantially pure form. A nucleic acid is "isolated" or "rendered substantially pure" when purified away from other cellular components or other contaminants, e.g., other cellular nucleic acids (e.g., other chromosomal DNA, e.g., the chromosomal DNA that is linked to the isolated DNA in nature) or proteins, by standard techniques, including alkaline/SDS treatment, CsC1 banding, column chromatography, restriction enzymes, agarose gel electrophoresis, and others well known in the art. (See, F. Ausubel, et al., ed. (1987) Current Protocols in Molecular Biology, Greene Publishing and Wiley Interscience, New York). A nucleic acid described herein can be, for example, DNA or RNA and may or may not contain introns. In a certain embodiments, the nucleic acid is a cDNA molecule.

Nucleic acids described herein can be obtained using standard molecular biology techniques. For antibodies expressed by hybridomas (e.g., hybridomas prepared from transgenic mice carrying human immunoglobulin genes as described further below), cDNAs encoding the light and/or heavy chains of the antibody made by the hybridoma can be obtained by standard PCR amplification or cDNA cloning techniques. For antibodies obtained from an immunoglobulin gene library (e.g., using phage display techniques), nucleic acid encoding the antibody can be recovered from the library.

Once DNA fragments encoding $V_H$ and $V_L$ segments are obtained, these DNA fragments can be further manipulated by standard recombinant DNA techniques, for example, to convert the variable region genes to full-length antibody chain genes, to Fab fragment genes or to a scFv gene. In these manipulations, a $V_L$- or $V_H$-encoding DNA fragment is operatively linked to another DNA fragment encoding another protein, such as an antibody constant region or a flexible linker. The term "operatively linked," as used in this context, means that the two DNA fragments are joined such that the amino acid sequences encoded by the two DNA fragments remain in-frame.

Isolated DNA encoding the VH region can be converted to a full-length heavy chain gene by operatively linking the VH-encoding DNA to another DNA molecule encoding heavy chain constant regions (hinge, CH1, CH2 and/or CH3). The sequences of human heavy chain constant region genes are known in the art (see e.g., Kabat, et al., 1991), and DNA fragments encompassing these regions can be obtained by standard PCR amplification. The heavy chain constant region can be an IgG (IgG1, IgG2, IgG3, or IgG4), IgA, IgE, IgM or IgD constant region, for example, an IgG1 region. For a Fab fragment heavy chain gene, the VH-encoding DNA can be operatively linked to another DNA molecule encoding only the heavy chain CH1 constant region.

The isolated DNA encoding the VL region can be converted to a full-length light chain gene (as well as a Fab light chain gene) by operatively linking the VL-encoding DNA to another DNA molecule encoding the light chain constant region, CL. The sequences of human light chain constant region genes are known in the art (see e.g., Kabat, et al., 1991) Sequences of Proteins of Immunological Interest, Fifth Edition, U.S. Department of Health and Human Services, NIH Publication No. 91-3242), and DNA fragments encompassing these regions can be obtained by standard PCR amplification. The light chain constant region can be a kappa or lambda constant region.

To create a scFv gene, the $V_H$- and $V_L$-encoding DNA fragments are operatively linked to another fragment encoding a flexible linker, e.g., encoding the amino acid sequence (Gly$_4$-Ser)$_3$ (SEQ ID NO: 160), such that the $V_H$ and $V_L$ sequences can be expressed as a contiguous single-chain protein, with the $V_L$ and $V_H$ regions joined by the flexible linker (see e.g., Bird et al. (1988) *Science* 242:423-426; Huston et al. (1988) *Proc. Natl. Acad. Sci. USA* 85:5879-5883; McCafferty et al., (1990) *Nature* 348:552-554).

V. Antibody Generation

Various antibodies of the present invention, e.g. those that bind to the same epitope as selected anti-hNKG2A antibodies disclosed herein, can be produced using a variety of known techniques, such as the standard somatic cell hybridization technique described by Kohler and Milstein, *Nature* 256: 495 (1975). Other techniques for producing monoclonal antibodies also can be employed, e.g., viral or oncogenic transformation of B lymphocytes, phage display technique using libraries of human antibody genes.

An exemplary animal system for preparing hybridomas is the murine system. Hybridoma production in the mouse is a well-established procedure. Immunization protocols and techniques for isolation of immunized splenocytes for fusion are known in the art. Fusion partners (e.g., murine myeloma cells) and fusion procedures are also known.

Chimeric or humanized antibodies described herein can be prepared based on the sequence of a murine monoclonal antibody prepared as described above. DNA encoding the heavy and light chain immunoglobulins can be obtained from the murine hybridoma of interest and engineered to contain non-murine (e.g., human) immunoglobulin sequences using standard molecular biology techniques. For example, to create a chimeric antibody, the murine variable regions can be linked to human constant regions using methods known in the art (see e.g., U.S. Pat. No. 4,816,567 to Cabilly et al.). To create a humanized antibody, the murine CDR regions can be inserted into a human framework using methods known in the art (see e.g., U.S. Pat. No. 5,225,539 to Winter, and U.S. Pat. Nos. 5,530,101; 5,585,089; 5,693,762 and 6,180,370 to Queen et al.).

In one embodiment, the antibodies described herein are human monoclonal antibodies. Such human monoclonal antibodies directed against human NKG2A can be generated using transgenic or transchromosomic mice carrying parts of the human immune system rather than the mouse system. These transgenic and transchromosomic mice include mice referred to herein as HuMAb mice and KM mice, respectively, and are collectively referred to herein as "human Ig mice."

The HuMAb Mouse® (Medarex, Inc.) contains human immunoglobulin gene miniloci that encode un-rearranged human heavy (μ and γ) and κ light chain immunoglobulin sequences, together with targeted mutations that inactivate the endogenous μ and κ chain loci (see e.g., Lonberg, et al. (1994) Nature 368(6474): 856-859). Accordingly, the mice exhibit reduced expression of mouse IgM or κ, and in response to immunization, the introduced human heavy and light chain transgenes undergo class switching and somatic mutation to generate high affinity human IgGκ monoclonal antibodies (Lonberg, N. et al. (1994), supra; reviewed in Lonberg, N. (1994) *Handbook of Experimental Pharmacology* 113:49-101; Lonberg, N. and Huszar, D. (1995) *Intern. Rev. Immunol.* 13: 65-93, and Harding, F. and Lonberg, N. (1995) *Ann. N.Y. Acad. Sci.* 764:536-546). The preparation and use of HuMab mice, and the genomic modifications carried by such mice, is further described in Taylor, L. et al. (1992) *Nucleic Acids Research* 20:6287-6295; Chen, J. et al. (1993) *International Immunology* 5: 647-656; Tuaillon et al. (1993) *Proc. Natl. Acad. Sci. USA* 90:3720-3724; Choi et al. (1993) *Nature Genetics* 4:117-123; Chen, J. et al. (1993) *EMBO J.* 12: 821-830; Tuaillon et al. (1994) *J. Immunol.* 152:2912-2920; Taylor, L. et al. (1994) *International Immunology* 6: 579-591; and Fishwild, D. et al. (1996) *Nature Biotechnology* 14: 845-851, the contents of all of which are hereby specifically incorporated by reference in their entirety. (See, also, U.S. Pat. Nos. 5,545,806; 5,569,825; 5,625,126; 5,633,425; 5,789,650; 5,877,397; 5,661,016;

5,814,318; 5,874,299; and 5,770,429; all to Lonberg and Kay; U.S. Pat. No. 5,545,807 to Surani et al.; PCT Publication Nos. WO 92/03918, WO 93/12227, WO 94/25585, WO 97/13852, WO 98/24884 and WO 99/45962, all to Lonberg and Kay; and PCT Publication No. WO 01/14424 to Korman et al.)

In certain embodiments, antibodies described herein are raised using a mouse that carries human immunoglobulin sequences on transgenes and transchromosomes, such as a mouse that carries a human heavy chain transgene and a human light chain transchromosome. Such mice, referred to herein as "KM mice", are described in detail in PCT Publication WO 02/43478 to Ishida et al.

Still further, alternative transgenic animal systems expressing human immunoglobulin genes are available in the art and can be used to raise anti-hNKG2A antibodies described herein. For example, an alternative transgenic system referred to as the Xenomouse (Abgenix, Inc.) can be used; such mice are described in, for example, U.S. Pat. Nos. 5,939,598; 6,075,181; 6,114,598; 6, 150,584 and 6,162,963 to Kucherlapati et al.

Moreover, alternative transchromosomic animal systems expressing human immunoglobulin genes are available in the art and can be used to raise anti-nkg2a antibodies described herein. For example, mice carrying both a human heavy chain transchromosome and a human light chain transchromosome, referred to as "TC mice" can be used; such mice are described in Tomizuka et al. (2000) *Proc. Natl. Acad. Sci. USA* 97:722-727. Furthermore, cows carrying human heavy and light chain transchromosomes have been described in the art (Kuroiwa et al. (2002) *Nature Biotechnology* 20:889-894) and can be used to raise anti-hNKG2A antibodies described herein.

Additional mouse systems described in the art for raising human antibodies, e.g., human anti-hNKG2Aantibodies, include (i) the VELOCIMMUNE® mouse (Regeneron Pharmaceuticals, Inc.), in which the endogenous mouse heavy and light chain variable regions have been replaced, via homologous recombination, with human heavy and light chain variable regions, operatively linked to the endogenous mouse constant regions, such that chimeric antibodies (human V/mouse C) are raised in the mice, and then subsequently converted to fully human antibodies using standard recombinant DNA techniques; and (ii) the MeMo® mouse (Merus Biopharmaceuticals, Inc.), in which the mouse contains un-rearranged human heavy chain variable regions but a single rearranged human common light chain variable region. Such mice, and use thereof to raise antibodies, are described in, for example, WO 2009/15777, US 2010/0069614, WO 2011/072204, WO 2011/097603, WO 2011/163311, WO 2011/163314, WO 2012/148873, US 2012/0070861 and US 2012/0073004.

Human monoclonal antibodies described herein can also be prepared using phage display methods for screening libraries of human immunoglobulin genes. Such phage display methods for isolating human antibodies are established in the art. (See, e.g., U.S. Pat. Nos. 5,223,409; 5,403,484; and 5,571,698 to Ladner et al.; U.S. Pat. Nos. 5,427,908 and 5,580,717 to Dower et al.; U.S. Pat. Nos. 5,969,108 and 6,172,197 to McCafferty et al.; and U.S. Pat. Nos. 5,885,793; 6,521,404; 6,544,731; 6,555,313; 6,582,915 and 6,593,081 to Griffiths et al.).

Human monoclonal antibodies described herein can also be prepared using mice with severe combined immunodeficiency (SCID) into which human immune cells have been reconstituted such that a human antibody response can be generated upon immunization. Such mice are described in, for example, U.S. Pat. Nos. 5,476,996 and 5,698,767 to Wilson et al.

Immunizations

To generate fully human antibodies to human NKG2A, mice or transgenic or transchromosomal mice containing human immunoglobulin genes (e.g., HCo12, HCo7 or KM mice) can be immunized with a purified or enriched preparation of the NKG2A antigen and/or cells expressing NKG2A, as described for other antigens, for example, by Lonberg et al. (1994) *Nature* 368(6474): 856-859; Fishwild et al. (1996) *Nature Biotechnology* 14: 845-851 and WO 98/24884. Alternatively, mice can be immunized with DNA encoding human NKG2A. Preferably, the mice will be 6-16 weeks of age upon the first infusion. For example, a purified or enriched preparation (e.g, 5 µg-50 µg) of the recombinant human NKG2A antigen can be used to immunize the mice intraperitoneally. If the immunizations using a purified or enriched preparation of the NKG2A antigen do not result in antibodies, mice can also be immunized with cells expressing NKG2A, e.g., a cell line, to promote immune responses.

The HuMAb transgenic mice can be initially immunized intraperitoneally or subcutaneously (SC) with antigen in Ribi's adjuvant, followed by every other week IP/SC immunizations (up to a total of 10) with antigen in Ribi's adjuvant. The immune response can be monitored over the course of the immunization protocol with plasma samples being obtained by retroorbital bleeds. The plasma can be screened by ELISA and FACS (as described below), and mice with sufficient titers of anti-NKG2A human immunoglobulin can be used for fusions. Mice can be boosted intravenously with antigen three days before sacrifice and removal of the spleen and lymph nodes. Two to three fusions for each immunization may be performed. Between 6 and 24 mice can be immunized for each antigen. In some embodiments, HCo7, HCo12, and KM strains are used. In addition, both HCo7 and HCo12 transgene can be bred together into a single mouse having two different human heavy chain transgenes (HCo7/HCo12).

Generation of Hybridomas Producing Monoclonal Antibodies to NKG2A Protein

To generate hybridomas producing monoclonal antibodies described herein, splenocytes and/or lymph node cells from immunized mice can be isolated and fused to an appropriate immortalized cell line, such as a mouse myeloma cell line. The resulting hybridomas can be screened for the production of antigen-specific antibodies. For example, single cell suspensions of splenic lymphocytes from immunized mice can be fused to Sp2/0 non-secreting mouse myeloma cells (ATCC, CRL 1581) with 50% PEG.

Cells are plated at approximately $2 \times 10^5$ in flat bottom microtiter plate, followed by a two week incubation in selective medium containing 10% fetal Clone Serum, 18% "653" conditioned media, 5% Origen (IGEN), 4 mM L-glutamine, 1 mM sodium pyruvate, 5 mM HEPES, 0.055 mM 2-mercaptoethanol, 50 units/ml penicillin, 50 mg/ml streptomycin, 50 mg/ml gentamycin and 1×HAT (Sigma). After approximately two weeks, cells can be cultured in medium in which the HAT is replaced with HT. Individual wells can then be screened by ELISA for human monoclonal IgM and IgG antibodies. Once extensive hybridoma growth occurs, medium can be observed usually after 10-14 days. The antibody secreting hybridomas can be re-plated, screened again, and, if still positive for human IgG, the monoclonal antibodies can be subcloned at least twice by limiting dilution. The stable subclones can then be cultured in vitro to generate small amounts of antibody in tissue culture medium for characterization.

To purify monoclonal antibodies, selected hybridomas can be grown in two-liter spinner-flasks for monoclonal antibody purification. Supernatants can be filtered and concentrated before affinity chromatography with protein A-sepharose (Pharmacia, Piscataway, N.J.). Eluted IgG can be checked by gel electrophoresis and high performance liquid chromatography to ensure purity. The buffer solution can be exchanged into PBS, and the concentration can be determined by OD280 using 1.43 extinction coefficient. The monoclonal antibodies can be aliquoted and stored at −80° C.

VI. Antibody Manufacture

Generation of Transfectomas Producing Monoclonal Antibodies to NKG2A

Antibodies of the present invention, including both specific antibodies for which sequences are provided and other, related anti-NKG2A antibodies, can be produced in a host cell transfectoma using, for example, a combination of recombinant DNA techniques and gene transfection methods well known in the art (Morrison, S. (1985) *Science* 229:1202).

For example, to express antibodies, or antibody fragments thereof, DNAs encoding partial or full-length light and heavy chains, can be obtained by standard molecular biology techniques (e.g., PCR amplification or cDNA cloning using a hybridoma that expresses the antibody of interest), and the DNAs can be inserted into expression vectors such that the genes are operatively linked to transcriptional and translational control sequences. In this context, the term "operatively linked" is intended to mean that an antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vector or both genes are inserted into the same expression vector. The antibody genes are inserted into the expression vector(s) by standard methods (e.g., ligation of complementary restriction sites on the antibody gene fragment and vector, or blunt end ligation if no restriction sites are present). The light and heavy chain variable regions of the antibodies described herein can be used to create full-length antibody genes of any antibody isotype by inserting them into expression vectors already encoding heavy chain constant and light chain constant regions of the desired isotype such that the $V_H$ segment is operatively linked to the $C_H$ segment(s) within the vector and the $V_L$ segment is operatively linked to the $C_L$ segment within the vector. Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

In addition to the antibody chain genes, recombinant expression vectors may carry regulatory sequences that control the expression of the antibody chain genes in a host cell. The term "regulatory sequence" includes promoters, enhancers, and other expression control elements (e.g., polyadenylation signals) that control the transcription or translation of the antibody chain genes. Such regulatory sequences are described, for example, in Goeddel (Gene Expression Technology. *Methods in Enzymology* 185, Academic Press, San Diego, CA (1990)). It will be appreciated by those skilled in the art that the design of the expression vector, including the selection of regulatory sequences, may depend on such factors as the choice of the host cell to be transformed, the level of expression of protein desired, amongst other factors. Preferred regulatory sequences for mammalian host cell expression include viral elements that direct high levels of protein expression in mammalian cells, such as promoters and/or enhancers derived from cytomegalovirus (CMV), Simian Virus 40 (SV40), adenovirus, (e.g., the adenovirus major late promoter (AdMLP), and polyomavirus. Alternatively, nonviral regulatory sequences may be used, such as the ubiquitin promoter or β-globin promoter. Still further, regulatory elements composed of sequences from different sources, such as the SRα promoter system, which contains sequences from the SV40 early promoter and the long terminal repeat of human T cell leukemia virus type 1 (Takebe, Y. et al. (1988) *Mol. Cell. Biol.* 8:466-472).

In addition to the antibody chain genes and regulatory sequences, recombinant expression vectors may carry additional sequences, such as sequences that regulate replication of the vector in host cells (e.g., origins of replication) and selectable marker genes. The selectable marker gene facilitates selection of host cells into which the vector has been introduced (see, e.g., U.S. Pat. Nos. 4,399,216, 4,634,665 and 5,179,017, all by Axel et al.). For example, typically the selectable marker gene confers resistance to drugs, such as G418, hygromycin or methotrexate, on a host cell into which the vector has been introduced. Exemplary selectable marker genes include the dihydrofolate reductase (DHFR) gene (for use in dhfr-host cells with methotrexate selection/amplification) and the neo gene (for G418 selection).

For expression of the light and heavy chains, the expression vector(s) encoding the heavy and light chains is transfected into a host cell by standard techniques. The various forms of the term "transfection" encompasses a wide variety of techniques commonly used for the introduction of exogenous DNA into a prokaryotic or eukaryotic host cell, e.g., electroporation, calcium-phosphate precipitation, DEAE-dextran transfection and the like. Although it is theoretically possible to express the antibodies described herein in either prokaryotic or eukaryotic host cells, expression of antibodies in eukaryotic cells, and most preferably mammalian host cells, is the most preferred because such eukaryotic cells, and in particular mammalian cells, are more likely than prokaryotic cells to assemble and secrete a properly folded and immunologically active antibody. Prokaryotic expression of antibody genes has been reported to be ineffective for production of high yields of active antibody (Boss, M. A. and Wood, C. R. (1985) *Immunology Today* 6:12-13). Antibodies of the present invention can also be produced in glycol-engineered strains of yeast. (*Pichia pastoris*. Li et al. (2006) *Nat. Biotechnol.* 24:210).

Exemplary mammalian host cells for expressing the recombinant antibodies described herein include CHO cells (including dhfr-CHO cells, described in Urlaub and Chasin, (1980) *Proc. Natl. Acad. Sci. USA* 77:4216-4220, used with a dihydrofolate reductase (DHFR) selectable marker, e.g., as described in R. J. Kaufman and P. A. Sharp (1982) *Mol. Biol.* 159:601-621), NSO myeloma cells, COS cells and SP2 cells. In particular, for use with NSO myeloma cells, another exemplary expression system is the GS gene expression system disclosed in WO 87/04462, WO 89/01036 and EP 338,841. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

The N- and C-termini of antibody polypeptide chains of the present invention may differ from the expected sequence due to commonly observed post-translational modifications. For example, C-terminal lysine residues are often missing from antibody heavy chains. (Dick et al. (2008) *Biotechnol. Bioeng.* 100:1132). N-terminal glutamine residues, and to a lesser extent glutamate residues, are frequently converted to pyroglutamate residues on both light and heavy chains of therapeutic antibodies. (Dick et al. (2007) *Biotechnol. Bioeng.* 97:544; Liu et al. (2011) *JBC* 28611211; Liu et al. (2011) *J. Biol. Chem.* 286:11211).

Amino acid sequences for various anti-hNKG2A antibodies of the present invention are provided in the Sequence Listing. For the reasons discussed above, the C-terminal lysine is not included in many of sequences in the Sequence Listing for heavy chains or heavy chain constant domains. However, in an alternative embodiment, each heavy chain for the anti-hNKG2A antibodies of the present invention, and/or genetic construct encoding such antibodies or the heavy or light chains thereof, includes this additional lysine residue at the C-terminus of the heavy chain(s).

VII. Assays

Antibodies described herein can be tested for binding to NKG2A by, for example, standard ELISA. For example, microtiter plates are coated with purified NKG2A at 1-2 µg/ml in PBS, and then blocked with 5% bovine serum albumin in PBS. Dilutions of antibody (e.g., dilutions of plasma from NKG2A-immunized mice) are added to each well and incubated for 1-2 hours at 37° C. The plates are washed with PBS/Tween and then incubated with secondary reagent (e.g., for human antibodies, or antibodies otherwise having a human heavy chain constant region, a goat-anti-human IgG Fc-specific polyclonal reagent) conjugated to horseradish peroxidase (HRP) for 1 hour at 37° C. After washing, the plates are developed with ABTS substrate (Moss Inc, product: ABTS-1000) and analyzed by a spectrophotometer at OD 415-495. Sera from immunized mice are then further screened by flow cytometry for binding to a cell line expressing human NKG2A, but not to a control cell line that does not express NKG2A. Briefly, the binding of anti-NKG2A antibodies is assessed by incubating NKG2A expressing CHO cells with the anti-NKG2A antibody at 1:20 dilution. The cells are washed and binding is detected with a PE-labeled anti-human IgG Ab. Flow cytometric analyses are performed using a FACScan flow cytometry (Becton Dickinson, San Jose, Calif.). Preferably, mice that develop the highest titers will be used for fusions. Analogous experiments may be performed using anti-mouse detection antibodies if mouse anti-HNKG2A antibodies are to be detected.

An ELISA, e.g., as described above can be used to screen for antibodies and, thus, hybridomas that produce antibodies that show positive reactivity with the NKG2A immunogen. Hybridomas that produce antibodies that bind, preferably with high affinity, to NKG2A can then be subcloned and further characterized. One clone from each hybridoma, which retains the reactivity of the parent cells (by ELISA), can then be chosen for making a cell bank, and for antibody purification.

To purify anti-NKG2A antibodies, selected hybridomas can be grown in two-liter spinner-flasks for monoclonal antibody purification. Supernatants can be filtered and concentrated before affinity chromatography with protein A-sepharose (Pharmacia, Piscataway, N.J.). Eluted IgG can be checked by gel electrophoresis and high performance liquid chromatography to ensure purity. The buffer solution can be exchanged into PBS, and the concentration can be determined by $OD_{280}$ using 1.43 extinction coefficient. The monoclonal antibodies can be aliquoted and stored at −80° C.

To determine if the selected anti-NKG2A monoclonal antibodies bind to unique epitopes, each antibody can be biotinylated using commercially available reagents (Pierce, Rockford, Ill.). Biotinylated MAb binding can be detected with a streptavidin labeled probe. Competition studies using unlabeled monoclonal antibodies and biotinylated monoclonal antibodies can be performed using NKG2A coated-ELISA plates as described above.

To determine the isotype of purified antibodies, isotype ELISAs can be performed using reagents specific for antibodies of a particular isotype. For example, to determine the isotype of a human monoclonal antibody, wells of microtiter plates can be coated with 1 µg/ml of anti-human immunoglobulin overnight at 4° C. After blocking with 1% BSA, the plates are reacted with 1 µg/ml or less of test monoclonal antibodies or purified isotype controls, at ambient temperature for one to two hours. The wells can then be reacted with either human IgG1 or human IgM-specific alkaline phosphatase-conjugated probes. Plates are developed and analyzed as described above.

To test the binding of monoclonal antibodies to live cells expressing NKG2A, flow cytometry can be used. Briefly, cell lines expressing membrane-bound NKG2A (grown under standard growth conditions) are mixed with A concentrations of monoclonal antibodies in PBS containing 0.1% BSA at 4° C. for one hour. After washing, the cells are reacted with Phycoerythrin (PE)-labeled anti-IgG antibody under the same conditions as the primary antibody staining. The samples can be analyzed by FACScan instrument using light and side scatter properties to gate on single cells and binding of the labeled antibodies is determined. An alternative assay using fluorescence microscopy may be used (in addition to or instead of) the flow cytometry assay. Cells can be stained exactly as described above and examined by fluorescence microscopy. This method allows visualization of individual cells, but may have diminished sensitivity depending on the density of the antigen.

Anti-hNKG2A antibodies can be further tested for reactivity with the NKG2A antigen by Western blotting. Briefly, cell extracts from cells expressing NKG2A can be prepared and subjected to sodium dodecyl sulfate polyacrylamide gel electrophoresis. After electrophoresis, the separated antigens will be transferred to nitrocellulose membranes, blocked with 20% mouse serum, and probed with the monoclonal antibodies to be tested. IgG binding can be detected using anti-IgG alkaline phosphatase and developed with BCIP/NBT substrate tablets (Sigma Chem. Co., St. Louis, Mo.).

Methods for analyzing binding affinity, cross-reactivity, and binding kinetics of various anti-NKG2A antibodies include standard assays known in the art, for example, Biolayer Interferometry (BLI) analysis, and Biacore SPR analysis using a Biacore SPR instrument.

In one embodiment, an anti-hNKG2A antibody specifically binds to the extracellular region of human NKG2A. In one embodiment, the antibody binds to a particular domain (e.g., a functional domain) within the extracellular domain of NKG2A. In one embodiment, the anti-hNKG2A antibody specifically binds to the extracellular region of human NKG2A and the extracellular region of cynomolgus NKG2A. In one embodiment, the anti-hNKG2A antibody binds to human NKG2A with high affinity.

VIII. Multispecific Molecules

In certain embodiments, antibodies described herein may be multispecific, e.g., bispecific or trispecific, molecules. Multispecific antigen-binding molecules, such as multispecific antibodies, comprise two or more antigen-binding site, each specific for a different epitope. The different epitope can be part of the same or different antigens. In one embodiment, one antigen-binding site is specific for human NKG2A and the other for a different antigen. In one embodiment, an anti-h NKG2A antibody, or antigen-binding fragments thereof, as described herein is linked to another antigen-binding molecule, e.g., another peptide or protein (e.g., another antibody or antibody fragment, or a ligand for a receptor) having a different binding specificity to generate a bispecific molecule that binds to at least two different binding sites or target molecules. In one embodiment, the antibody described herein is derivatized or linked to more than one other antigen-binding molecule to generate multispecific molecules that bind to more than two different binding sites and/or target molecules. Accordingly, provided herein are bispecific molecules comprising at least one first binding specificity for NKG2A and a second binding specificity for a second target epitope. In an embodiment described herein in which the bispecific molecule is multispecific, the molecule can further include a third binding specificity.

In one embodiment, the bispecific molecules described herein comprise as a binding specificity at least one antibody, or an antibody fragment thereof, including, e.g., an Fab, Fab', F(ab')$_2$, Fv, or a single chain Fv. The antibody may also be a light chain or heavy chain dimer, or any minimal fragment thereof such as a Fv or a single chain construct as described in Ladner et al. U.S. Pat. No. 4,946,778, the contents of which is expressly incorporated by reference.

While human monoclonal antibodies are preferred, other antibodies that can be employed in the bispecific molecules described herein are murine, chimeric and humanized monoclonal antibodies.

The bispecific molecules described herein can be prepared by conjugating the constituent binding specificities using methods known in the art. For example, each binding specificity of the bispecific molecule can be generated separately and then conjugated to one another. When the binding specificities are proteins or peptides, a variety of coupling or cross-linking agents can be used for covalent conjugation. Examples of cross-linking agents include protein A, carbodiimide, N-succinimidyl-S-acetyl-thioacetate (SATA), 5,5'-dithiobis(2-nitrobenzoic acid) (DTNB), o-phenylenedimaleimide (oPDM), N-succinimidyl-3-(2-pyridyldithio)propionate (SPDP), and sulfosuccinimidyl 4-(N-maleimidomethyl) cyclohaxane-1-carboxylate (sulfo-SMCC) (see e.g., Karpovsky et al. (1984) *J. Exp. Med.* 160:1686; Liu, M A et al. (1985) *Proc. Natl. Acad. Sci. USA* 82:8648). Other methods include those described in Paulus (1985) Behring Ins. Mitt. No. 78, 118-132; Brennan et al. (1985) *Science* 229:81-83), and Glennie et al. (1987) *J Immunol.* 139: 2367-2375). Preferred conjugating agents are SATA and sulfo-SMCC, both available from Pierce Chemical Co. (Rockford, Ill.).

When the binding specificities are antibodies, they can be conjugated via sulfhydryl bonding of the C-terminus hinge regions of the two heavy chains. In a particularly preferred embodiment, the hinge region is modified to contain an odd number of sulfhydryl residues, preferably one, prior to conjugation.

Alternatively, both binding specificities can be encoded in the same vector and expressed and assembled in the same host cell. This method is particularly useful where the bispecific molecule has a combination of binding specificities such as a (mAb×mAb), (mAb×Fab), (Fab×F(ab')$_2$) or (ligand×Fab) fusion protein. A bispecific molecule described herein can be a single chain molecule comprising one single chain antibody and a binding determinant, or a single chain bispecific molecule comprising two binding determinants. Bispecific molecules may comprise at least two single chain molecules. Methods for preparing bispecific molecules are described for example in U.S. Pat. Nos. 5,260,203; 5,455,030; 4,881,175; 5,132,405; 5,091,513; 5,476,786; 5,013,653; 5,258,498; and 5,482,858.

Binding of the bispecific molecules to their specific targets can be confirmed using art-recognized methods, such as using ELISA, radioimmunoassay (RIA), FACS analysis, bioassay (e.g., growth inhibition), or Western Blot assay. Each of these assays generally detects the presence of protein-antibody complexes of particular interest by employing a labeled reagent (e.g., an antibody) specific for the complex of interest.

IX. Compositions

Further provided are compositions, e.g., a pharmaceutical compositions, containing one or more anti-NKG2A antibodies, or antigen-binding fragment(s) thereof, as described herein, formulated together with a pharmaceutically acceptable carrier. Accordingly, the compositions of the present invention include the human or humanized anti-hNKG2A antibodies (or antigen-binding fragments thereof) having the CDR sequences, the heavy and/or light chain variable region sequences, or the full-length heavy and/or light chain sequences set forth herein. Compositions of the present invention also include anti-hNKG2A antibodies having sequences which are variants of the sequences set forth in the Sequence Listing. For example, such antibodies can comprise sequences that are at least 70%, 75%, 80%, 85%, 90%, or 95%, 96%, 97%, 98%, or 99% identical to the CDR sequences, the heavy and/or light chain variable region sequences, or full-length heavy and/or light chain sequences set forth in Sequence Listing.

Such compositions also may include one or a combination of (e.g., two or more different) antibodies, or immunoconjugates or bispecific molecules described herein. For example, a pharmaceutical composition described herein can comprise a combination of antibodies (or immunoconjugates or bispecific antibodies) that bind to different epitopes on the target antigen or that have complementary activities.

Pharmaceutical compositions described herein also can be administered as combination therapy, i.e., anti-NKG2A antibodies combined with other agents. For example, the combination therapy can include an anti-NKG2A antibody described herein combined with at least one other anti-cancer and/or T-cell stimulating (e.g., activating) agent. Examples of therapeutic agents that can be used in combination therapy are described in greater detail below in the section on uses of the antibodies described herein.

In some embodiments, pharmaceutical compositions disclosed herein can include other compounds, drugs, and/or agents used for the treatment of cancer. Such compounds, drugs, and/or agents can include, for example, chemotherapy drugs, small molecule drugs or antibodies that stimulate the immune response to a given cancer. In some embodiments, a pharmaceutical composition comprises a first antibody specific for anti-h NKG2A and a second antibody.

In some embodiments, the first antibody and the second antibody are present in the composition at a fixed dose (i.e., a fixed ratio). In other embodiments, this fixed dose is between at least about 1:200 to at least about 200:1, at least about 1:150 to at least about 150:1, at least about 1:100 to at least about 100:1, at least about 1:75 to at least about 75:1, at least about 1:50 to at least about 50:1, at least about 1:25 to at least about 25:1, at least about 1:10 to at least about 10:1, at least about 1:5 to at least about 5:1, at least about 1:4 to at least about 4:1, at least about 1:3 to at least about 3:1, or at least about 1:2 to at least about 2:1 mg anti-hNKG2A antibody to mg second antibody. In some embodiments, the fixed dose is at least about 1:1, about 1:2, about 1:3, about 1:4, about 1:5, about 1:6, about 1:7, about 1:8, about 1:9, about 1:10, about 1:15, about 1:20, about 1:30, about 1:40, about 1:50, about 1:60, about 1:70, about 1:80, about 1:90, about 1:100, about 1:120, about 1:140, about 1:160, about 1:180, or about 1:200 anti-h NKG2A antibody to second antibody. In some embodiments, the fixed dose is at least about 2:1, about 3:1, about 4:1, about 5:1, about 6:1, about 7:1, about 8:1, about 9:1, about 10:1, about 15:1, about 20:1, about 30:1, about 40:1, about 50:1, about 60:1, about 70:1, about 80:1, about 90:1, about 100:1, about 120:1, about 140:1, about 160:1, about 180:1, or about 200:1 mg first antibody to mg second antibody. For example, in one embodiment, the anti-h NKG2A antibody and the second antibody are administered as described in the Examples.

The additional antibodies include, for example, one or more of an anti-CTLA-4 antibody, an anti-PD-1 antibody, an anti-PD-L1 antibody, an anti-TIGIT antibody, an anti-OX40 (also known as CD134, TNFRSF4, ACT35 and/or TXGP1L) antibody, an anti-LAG-3 antibody, an anti-CD73 antibody, an anti-CD137 antibody, an anti-CD27 antibody, or an anti-CSF-1R antibody.

As used herein, "pharmaceutically acceptable carrier" includes any and all solvents, dispersion media, coatings, antibacterial and antifungal agents, isotonic and absorption delaying agents, and the like that are physiologically compatible. In some embodiments, the carrier is suitable for intravenous, intramuscular, subcutaneous, parenteral, spinal or epidermal administration (e.g., by injection or infusion). In some embodiments, the carrier is suitable for intravenous administration. In other embodiments, the carrier is suitable for subcutaneous administration. In some embodiments, the composition comprising anti-NKG2A antibody is delivered subcutaneously using Halozyme's ENHANZE® drug delivery technology, which includes a recombinant human hyaluronidase enzyme (rHuPH20) that temporarily degrades hyaluronan. In some embodiments, the ENHANZE® drug delivery technology allows for subcutaneous administrations of compositions that is more rapid as compared to intravenous administration. In other embodiments, depending on the route of administration, the active compound, i.e., antibody, immunoconjugate, or bispecific molecule, may be coated in a material to protect the compound from the action of acids and other natural conditions that may inactivate the compound.

The pharmaceutical compounds described herein may include one or more pharmaceutically acceptable salts. A "pharmaceutically acceptable salt" refers to a salt that retains the desired biological activity of the parent compound and does not impart any undesired toxicological effects (see e.g., Berge, S. M., et al. (1977) *J. Pharm. Sci.* 66:1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

A pharmaceutical composition described herein also may include a pharmaceutically acceptable anti-oxidant. Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Examples of suitable aqueous and non-aqueous carriers that may be employed in the pharmaceutical compositions described herein include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

Pharmaceutically acceptable carriers include sterile aqueous solutions or dispersions and sterile powders for the extemporaneous preparation of sterile injectable solutions or dispersion. Exemplary pharmaceutically acceptable carriers herein further include interstitial drug dispersion agents such as soluble neutral-active hyaluronidase glycoproteins (sHASEGP), for example, human soluble PH-20 hyaluronidase glycoproteins, such as rHuPH20 (HYLENEX™, Baxter International, Inc.). Certain exemplary sHASEGPs and methods of use, including rHuPH20, are described in US Patent Publication Nos. 2005/0260186 and 2006/0104968. In one aspect, a sHASEGP is combined with one or more additional glycosaminoglycanases such as chondroitinases.

The use of such media and agents for pharmaceutically active substances is known in the art. Except insofar as any conventional media or agent is incompatible with the active compound, use thereof in the pharmaceutical compositions described herein is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those described above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

The amount of active ingredient that can be combined with a carrier material to produce a single dosage form will vary depending upon the subject being treated, and the particular mode of administration. The amount of active ingredient that can be combined with a carrier material to produce a single dosage form will generally be that amount of the composition that produces a therapeutic effect. Out of one hundred percent, this amount may range from about 0.01 percent to about ninety-nine percent of active ingredient, e.g., from about 0.1 percent to about 70 percent, e.g., from about 1 percent to about 30 percent of active ingredient in combination with a pharmaceutically acceptable carrier.

In some embodiments, the composition includes an anti-NKG2A antibody, such as the NKG2A.9. The composition is a sterile, non-pyrogenic, single-use, preservative-free, isotonic aqueous solution for intravenous administration. The composition may be administered undiluted or further diluted with 0.9% sodium chloride injection to the required protein concentrations prior to infusion. In some embodiments, the anti-NKG2A antibody includes the following excipients: L-histine, L-histidine hydrochloride monohydrate, sucrose, pentetic acid (also known as diethylenetriaminepentaaceitc acid, polysorbate 80, and water for the injection.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms described herein are dictated by and directly dependent on (a) the unique characteristics of the active compound and the particular therapeutic effect to be achieved, and (b) the limitations inherent in the art of compounding such an active compound for the treatment of sensitivity in individuals.

For administration of the antibody, the dosage may range from about 0.0001 to 100 mg/kg, and more usually 0.01 to 5 mg/kg, of the host body weight. For example, dosages can be 0.3 mg/kg body weight, 1 mg/kg body weight, 3 mg/kg body weight, 5 mg/kg body weight or 10 mg/kg body weight or within the range of 1-10 mg/kg. Alternatively, administration of the antibody is a flat dose which may range from 2 mg to 800 mg, for example, a dose of 25 mg, 80 mg, 200 mg, or 400 mg. An exemplary treatment regimen entails administration once per week, once every two weeks, once every three weeks, once every four weeks, once a month, once every two months, once every three months, once every four months, once every five months, or once every six months. In some embodiments, the treatment regimen includes an initial dose, and then a maintenance dose of a different dose amount at an intermittent dose interval.

In some embodiments, two or more monoclonal antibodies with different binding specificities are administered simultaneously, in which case the dosage of each antibody administered falls within the ranges indicated. In some embodiments, the therapeutic antibody is administered on multiple occasions. Intervals between single dosages can be, for example, weekly, once every three weeks, once every four weeks, monthly, every three months or yearly. Intervals can also be irregular as indicated by measuring blood levels of antibody to the target antigen in the patient. In some embodiments, dosage is adjusted to achieve a plasma antibody concentration of about 1-1000 µg/ml and in some methods about 25-300 µg/ml.

In some embodiments, the antibody can be administered as a sustained release formulation. Administration via a sustained release formulations might require less frequent administration. Dosage and frequency vary depending on the half-life of the antibody in the patient. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In some embodiments, a relatively high dosage at relatively short intervals is administered for therapeutic treatment. In some embodiments, a relatively high dosage is administered until progression of the disease is reduced or terminated, e.g., until the patient shows partial or complete amelioration of symptoms of disease. In some embodiments, a prophylactic treatment is administered to patient following a therapeutic treatment.

Actual dosage levels of the active ingredients in the pharmaceutical compositions described herein may be varied so as to obtain an amount of the active ingredient that is effective to achieve the desired therapeutic response for a particular patient, composition, and mode of administration, without being toxic to the patient. The selected dosage level will depend upon a variety of pharmacokinetic factors including the activity of the particular compositions described herein employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

A "therapeutically effective dosage" of an anti-NKG2A antibody described herein preferably results in a decrease in severity of disease symptoms, an increase in frequency and duration of disease symptom-free periods, or a prevention of impairment or disability due to the disease affliction. In the context of cancer, a therapeutically effective dose preferably prevents further deterioration of physical symptoms associated with cancer. Symptoms of cancer are well-known in the art and include, for example, unusual mole features, a change in the appearance of a mole, including asymmetry, border, color and/or diameter, a newly pigmented skin area, an abnormal mole, darkened area under nail, breast lumps, nipple changes, breast cysts, breast pain, death, weight loss, weakness, excessive fatigue, difficulty eating, loss of appetite, chronic cough, worsening breathlessness, coughing up blood, blood in the urine, blood in stool, nausea, vomiting, liver metastases, lung metastases, bone metastases, abdominal fullness, bloating, fluid in peritoneal cavity, vaginal bleeding, constipation, abdominal distension, perforation of colon, acute peritonitis (infection, fever, pain), pain, vomiting blood, heavy sweating, fever, high blood pressure, anemia, diarrhea, jaundice, dizziness, chills, muscle spasms, colon metastases, lung metastases, bladder metastases, liver metastases, bone metastases, kidney metastases, and pancreatic metastases, difficulty swallowing, and the like. Therapeutic efficacy may be observable immediately after the first administration of an anti-hNKG2A monoclonal antibody of the present invention, or it may only be observed after a period of time and/or a series of doses. Such delayed efficacy my only be observed after several months of treatment, e.g., up to 6, 9 or 12 months.

A therapeutically effective dose may prevent or delay onset of cancer, such as may be desired when early or preliminary signs of the disease are present. Accordingly, any clinical or biochemical assay that monitors any of the foregoing may be used to determine whether a particular treatment is a therapeutically effective dose for treating cancer. One of ordinary skill in the art would be able to determine such amounts based on such factors as the subject's size, the severity of the subject's symptoms, and the particular composition or route of administration selected.

A composition described herein can be administered via one or more routes of administration using one or more of a variety of methods known in the art. As will be appreciated by the skilled artisan, the route and/or mode of administration will vary depending upon the desired results. Exemplary routes of administration for antibodies described herein include intravenous, intramuscular, intradermal, intraperitoneal, subcutaneous, spinal or other parenteral routes of administration, for example by injection or infusion.

Alternatively, an antibody described herein can be administered via a non-parenteral route, such as a topical, epidermal or mucosal route of administration, for example, intranasally, orally, vaginally, rectally, sublingually or topically.

The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems*, J. R. Robinson, ed., Marcel Dekker, Inc., New York, 1978.

Therapeutic compositions can be administered with medical devices known in the art. For example, in a preferred embodiment, a therapeutic composition described herein can be administered with a needleless hypodermic injection device, such as the devices disclosed in U.S. Pat. Nos. 5,399,163; 5,383,851; 5,312,335; 5,064,413; 4,941,880; 4,790,824; or 4,596,556. Examples of well-known implants and modules for use with anti-hNKG2A antibodies described herein include: U.S. Pat. No. 4,487,603, which discloses an implantable micro-infusion pump for dispensing medication at a controlled rate; U.S. Pat. No. 4,486,194, which discloses a therapeutic device for administering medicaments through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. These patents are incorporated herein by reference. Many other such implants, delivery systems, and modules are known to those skilled in the art.

In certain embodiments, the anti-hNKG2A antibodies described herein can be formulated to ensure proper distribution in vivo. For example, the blood-brain barrier (BBB) excludes many highly hydrophilic compounds. To ensure that the therapeutic compounds described herein cross the BBB (if desired), they can be formulated, for example, in liposomes. For methods of manufacturing liposomes, see, e.g., U.S. Pat. Nos. 4,522,811; 5,374,548; and 5,399,331. The liposomes may comprise one or more moieties that are selectively transported into specific cells or organs, thus enhance targeted drug delivery (see, e.g., V. V. Ranade (1989) *J. Clin. Pharmacol.* 29:685). Exemplary targeting moieties include folate or biotin (see, e.g., U.S. Pat. No. 5,416,016 to Low et al.); mannosides (Umezawa et al., (1988) *Biochem. Biophys. Res. Commun.* 153:1038); antibodies (P. G. Bloeman et al. (1995) *FEBS Lett.* 357:140; M. Owais et al. (1995) *Antimicrob. Agents Chemother.* 39:180); surfactant protein A receptor (Briscoe et al. (1995) *Am. J Physiol.* 1233:134); p120 (Schreier et al. (1994) *J. Biol. Chem.* 269:9090); see also K. Keinanen; M. L. Laukkanen (1994) *FEBS Lett* 346:123; J. J. Killion; I. J. Fidler (1994) *Immunomethods* 4:273.

Also within the scope described herein are kits comprising the antibody compositions described herein (e.g., human antibodies, bispecific or multispecific molecules, or immunoconjugates) and instructions for use. The kit can further contain at least one additional reagent, or one or more additional human antibodies described herein. Kits can include a label indicating the intended use of the contents of the kit. The term label includes any writing, or recorded material supplied on or with the kit, or that otherwise accompanies the kit.

X. Methods of Use

The antibodies, antibody compositions and methods described herein have numerous in vitro and in vivo uses involving, for example, enhancement of immune response by blocking the NKG2A/HLA-E interaction. In one embodiment, the anti-NKG2A antibodies described herein are monoclonal human or humanized antibodies. In one embodiment, anti-hNKG2A antibodies described herein (e.g., 13F3.A4, NKG2A.9, and NKG2A.11) can be administered to cells in culture, in vitro or ex vivo, or to human subjects to enhance immunity in a variety of diseases. In a particular embodiment, the anti-hNKG2A antibodies are antagonistic antibodies. Provided herein are methods of modifying an immune response in a subject comprising administering to the subject an anti-NKG2A antibody, or antigen-binding fragment thereof, described herein such that the immune response in the subject is enhanced, stimulated or up-regulated. In one embodiment, administering the anti-hNKG2A antibody according to the methods described herein enhances T cell and/or NK cell responses. In one embodiment, administering the anti-hNKG2A antibody according to the methods described herein stimulates, enhances or upregulates antigen-specific T cell responses to a tumor. The T cells can be Teff cells, e.g., CD4+ Teff cells, CD8+ Teff cells, T helper ($T_h$) cells and T cytotoxic ($T_c$) cells. A tumor may be a solid tumor or a liquid tumor, e.g., a hematological malignancy. In certain embodiments, a tumor is an immunogenic tumor. In certain embodiments, a tumor is non-immunogenic. In certain embodiments, a tumor is PD-L1 positive. In certain embodiments a tumor is PD-L1 negative. A subject may also be a virus-bearing subject and an immune response against the virus is enhanced. In one embodiment, administering the anti-hNKG2A antibody according to the methods described herein stimulates, enhances or upregulates NK cell responses.

In one embodiment, the methods result in an enhancement of an immune response in a human subject wherein such enhancement has a desirable effect. In one embodiment, the human subject is a human patients having a disorder that can be treated by augmenting an immune response, e.g., the T-cell mediated immune response. In a particular embodiment, the human patient has a cancer. In one embodiment, the anti-hNKG2A antibodies described herein can be administered together with an antigen of interest or the antigen may already be present in the subject to be treated, e.g., a tumor-bearing or virus-bearing subject. When anti-NKG2A antibodies are administered together with another agent, the two can be administered separately or simultaneously.

Further provided are methods for inhibiting growth of a tumor cell in a subject comprising administering to the subject an anti-hNKG2A antibody described herein such that growth of the tumor cell is inhibited in the subject, such as a human subject. Also provided are methods of treating chronic viral infection in a subject comprising administering to the subject an anti-NKG2A antibody described herein such that the chronic viral infection is treated in the subject, such as a human subject.

In some embodiments, an anti-NKG2A antibody is administered to a subject, e.g., a human patient, as an adjunctive therapy, adjuvant therapy, or neo-adjuvant therapy. In some embodiments, treatments of subjects having cancer with an anti-NKG2A antibody may lead to a long-term durable response relative to the current standard of care; long term survival of at least 1, 2, 3, 4, 5, 6, 7, 8, 9, 10 or more years, recurrence free survival of at least 1, 2, 3, 4, 5, 6, 7, 8, 9, or 10 or more years. In certain embodiments, treatment of a subject having cancer with an anti-hNKG2A antibody prevents recurrence of cancer or delays recurrence of cancer by, e.g., 1, 2, 3, 4, 5, 6, 7, 8, 9, or 10 or more years. An anti-NKG2A treatment can be used as a first, second, or subsequent line of treatment.

These and other methods described herein are discussed in further detail below.

Cancer

Provided herein are methods for treating a subject having cancer, comprising administering to the subject an anti-hNKG2A antibody described herein, such that the subject is treated, e.g., such that growth of cancerous tumors is inhibited or reduced and/or that the tumors regress. An anti-NKG2A antibody can be used alone to inhibit the growth of cancerous tumors. Alternatively, an anti-NKG2A antibody can be used in conjunction with another agent, e.g., other immunogenic agents, standard cancer treatments, or other antibodies, as described below. Combination with an inhibitor of PD-1, such as an anti-PD-1 or an anti-PD-L1 antibody, is also provided. Combination with an inhibitor of CTLA-4, such as an anti-CTLA-4 antibody, is also provided. Combination with an inhibitor of PD-1 and an inhibitor of CTLA-4 is also provided. Combination with an agonist antibody of ICOS is also provided.

In one aspect, provided herein are methods of treating cancer in a subject, comprising administering to the subject a therapeutically effective amount of an anti-NKG2A antibody described herein. In one embodiment, the anti-NKG2A antibody may be a chimeric antibody, a human antibody, or a humanized anti-NKG2A antibody. In one embodiment, the methods of treating a cancer described herein comprise administering an anti-NKG2A antibody that contacts human NKG2A at one or more amino acid residues of:

```
                                         (SEQ ID NO: 156)
(a) LSIDNEEMKF;

(SEQ ID NO: 157)
(b) PSSWIGVFRNSSHHPW;

(SEQ ID NO: 158)
(c) LAFKHEIKDSDN;
and (SEQ ID NO: 159)
(d) QVNRLKSAQQCGSSIIYHC.
```

In another embodiment, the methods of treating a cancer described herein comprise administering an anti-NKG2A antibody that contacts human NKG2A at one or more amino acid residues of:

```
                                         (SEQ ID NO: 156)
(a) LSIDNEEMKF;

(SEQ ID NO: 157)
(b) PSSWIGVFRNSSHHPW;

(SEQ ID NO: 158)
(c) LAFKHEIKDSDN;

(d) L;
and (SEQ ID NO: 159)
(e) QVNRLKSAQQCGSSIIYHC.
```

In another embodiment, the method comprises administering the NKG2A.9 antibody to treat cancer. In another embodiment, the method comprises administering a composition comprising the 13F3.A4 antibody to treat cancer. In another embodiment, the method comprises administering the NKG2A.11 antibody to treat cancer. In another embodiment, the method comprises administering a composition comprising the NKG2A.9 antibody to treat cancer. In another embodiment, the method comprises administering a composition comprising the NKG2A.11 antibody to treat cancer. In another embodiment, the method comprises administering the 13F3.A4 antibody or a variant thereof to treat cancer. In another embodiment, the method comprises administering a composition comprising the 13F3.A4 antibody or a variant thereof to treat cancer.

Examples of cancer include, but are not limited to, squamous cell carcinoma, small-cell lung cancer (SCLC), non-small cell lung cancer (NSCLC), squamous NSCLC, glioma, gastrointestinal cancer, renal cancer (e.g. clear cell carcinoma), ovarian cancer, liver cancer, colorectal cancer, endometrial cancer, kidney cancer (e.g., renal cell carcinoma (RCC)), prostate cancer (e.g. hormone refractory prostate adenocarcinoma), thyroid cancer, neuroblastoma, pancreatic cancer, glioblastoma (glioblastoma multiforme), cervical cancer, stomach cancer, bladder cancer, hepatoma, breast cancer, colon carcinoma, and head and neck cancer (or carcinoma), gastric cancer, germ cell tumor, pediatric sarcoma, sinonasal natural killer, melanoma (e.g., metastatic malignant melanoma, such as cutaneous or intraocular malignant melanoma), bone cancer, skin cancer, uterine cancer, cancer of the anal region, testicular cancer, carcinoma of the fallopian tubes, carcinoma of the endometrium, carcinoma of the cervix, carcinoma of the vagina, carcinoma of the vulva, cancer of the esophagus, cancer of the small intestine, cancer of the endocrine system, cancer of the parathyroid gland, cancer of the adrenal gland, sarcoma of soft tissue, cancer of the urethra, cancer of the penis, solid tumors of childhood, cancer of the ureter, carcinoma of the renal pelvis, neoplasm of the central nervous system (CNS), primary CNS lymphoma, tumor angiogenesis, spinal axis tumor, brain cancer including brain stem glioma, pituitary adenoma, Kaposi's sarcoma, epidermoid cancer, squamous cell cancer, T-cell lymphoma, environmentally-induced cancers including those induced by asbestos, virus-related cancers (e.g., human papilloma virus (HPV)-related tumor), and hematologic malignancies derived from either of the two major blood cell lineages, i.e., the myeloid cell line (which produces granulocytes, erythrocytes, thrombocytes, macrophages, and mast cells) or lymphoid cell line (which produces B, T, NK, and plasma cells), such as all types of leukemias, lymphomas, and myelomas, e.g., acute, chronic, lymphocytic and/or myelogenous leukemias, such as acute leukemia (ALL), acute myelogenous leukemia (AML), chronic lymphocytic leukemia (CLL), and chronic myelogenous leukemia (CML), undifferentiated AML (MO), myeloblastic leukemia (M1), myeloblastic leukemia M2; with cell maturation), promyelocytic leukemia (M3 or M3 variant [M3V]), myelomonocytic leukemia (M4 or M4 variant with eosinophilia [M4E]), monocytic leukemia (M5), erythroleukemia (M6), megakaryoblastic leukemia (M7), isolated granulocytic sarcoma, and chloroma; lymphomas, such as Hodgkin's lymphoma (HL), non-Hodgkin's lymphoma (NHL), B-cell lymphomas, T-cell lymphomas, lymphoplasmacytoid lymphoma, monocytoid B-cell lymphoma, mucosa-associated lymphoid tissue (MALT) lymphoma, anaplastic (e.g., Ki 1+) large-cell lymphoma, adult T-cell lymphoma/leukemia, mantle cell lymphoma, angioimmunoblastic T-cell lymphoma, angiocentric lymphoma, intestinal T-cell lymphoma, primary mediastinal B-cell lymphoma, precursor T-lymphoblastic lymphoma, T-lymphoblastic; and lymphoma/leukemia (T-Lbly/T-ALL), peripheral T-cell lymphoma, lymphoblastic lymphoma, post-transplantation lymphoproliferative disorder, true histiocytic lymphoma, primary central nervous system lymphoma, primary effusion lymphoma, lymphoblastic lymphoma (LBL), hematopoietic tumors of lymphoid lineage, acute lymphoblastic leukemia, diffuse large B-cell lymphoma, Burkitt's lymphoma, follicular lymphoma, diffuse histiocytic lymphoma (DHL), immunoblastic large cell lymphoma, precursor B-lymphoblastic lymphoma, cutaneous T-cell lymphoma (CTLC) (also called mycosis fungoides or Sézary syndrome), and lymphoplasmacytoid lymphoma (LPL) with Waldenstrom's macroglobulinemia; myelomas, such as IgG myeloma, light chain myeloma, nonsecretory myeloma, smoldering myeloma (also called indolent myeloma), solitary plasmocytoma, and multiple myelomas, chronic lymphocytic leukemia (CLL), hairy cell lymphoma; hematopoietic tumors of myeloid lineage, tumors of mesenchymal origin, including fibrosarcoma and rhabdomyoscarcoma; seminoma, teratocarcinoma, tumors of the central and peripheral nervous, including astrocytoma, schwannomas; tumors of mesenchymal origin, including fibrosarcoma, rhabdomyoscaroma, and osteosarcoma; and other tumors, including melanoma, xeroderma pigmentosum, keratoacanthoma, seminoma, thyroid follicular cancer and teratocarcinoma, hematopoietic tumors of lymphoid lineage, for example T-cell and B-cell tumors, including but not limited to T-cell disorders such as T-prolymphocytic leukemia (T-PLL), including of the small cell and cerebriform cell type; large granular lymphocyte leukemia (LGL) preferably of the T-cell type; a/d T-NHL hepatosplenic lymphoma; peripheral/post-thymic T cell lymphoma (pleomorphic and immunoblastic subtypes); angiocentric (nasal) T-cell lymphoma; cancer of the head or neck, renal cancer, rectal cancer, cancer of the thyroid gland; acute myeloid lymphoma, as well as any combinations of said cancers. In one embodiment, the methods described herein may also be used for treatment of metastatic cancers, refractory cancers (e.g., cancers refractory to previous immunotherapy, e.g., with a blocking CTLA-4 and/or PD-1 antibody), and recurrent cancers.

In one embodiment, the anti-hNKG2A antibody is administered as a monotherapy. In one embodiment, the anti-hNKG2A agonist antibody is administered as the only immunostimulating agent. In one embodiment, the anti-hNKG2A is administered to a patient with another agent. In one embodiment, an anti-hNKG2A antibody is administered with an immunogenic agent. In one embodiment, the anti-hNKG2A antibody is administered in conjunction with a cancer vaccine. In some embodiments, the cancer vaccine comprises cancerous cells, purified tumor antigens (including recombinant proteins, peptides, and carbohydrate molecules), cells, and cells transfected with genes encoding immune stimulating cytokines (He et al. (2004) *J. Immunol.* 173:4919-28). In some embodiments, the cancer vaccine is a peptide cancer vaccine, which in some embodiments is a personalized peptide vaccine. In some embodiments the peptide cancer vaccine is a multivalent long peptide, a multi-peptide, a peptide cocktail, a hybrid peptide, or a peptide-pulsed dendritic cell vaccine (see, e.g., Yamada et al., Cancer Sci, 104:14-21, 2013). In some embodiments, an anti-hNKG2A antibody is administered in conjunction with an adjuvant. Non-limiting examples of tumor vaccines that are used include peptides of melanoma antigens, such as peptides of gp100, MAGE antigens, Trp-2, MART1 and/or tyrosinase, or tumor cells transfected to express the cytokine GM-CSF. Many experimental strategies for vaccination against tumors have been devised (see Rosenberg, S., 2000, Development of Cancer Vaccines, ASCO Educational Book Spring: 60-62; Logothetis, C., 2000, ASCO Educational Book Spring: 300-302; Khayat, D. 2000, ASCO Educational Book Spring: 414-428; Foon, K. 2000, ASCO Educational Book Spring: 730-738; see also Restifo, N. and Sznol, M., Cancer Vaccines, Ch. 61, pp. 3023-3043 in DeVita et al. (eds.), 1997, Cancer: Principles and Practice of Oncology, Fifth Edition). In one of these strategies, a vaccine is prepared using autologous or allogeneic tumor cells. These cellular vaccines have been shown to be most effective when the tumor cells are transduced to express GM-CSF. GM-CSF has been shown to be a potent activator of antigen presentation for tumor vaccination. Dranoff et al. (1993) *Proc. Natl. Acad. Sci. U.S.A.* 90: 3539-43.

Other cancer vaccines are the proteins from viruses implicated in human cancers such a Human Papilloma Viruses (HPV), Hepatitis Viruses (HBV and HCV) and Kaposi's Herpes Sarcoma Virus (KHSV). In some embodiments, another form of tumor specific antigen that is used with NKG2A inhibition is purified heat shock proteins (HSP) isolated from the tumor tissue itself. These heat shock proteins contain fragments of proteins from the tumor cells and these HSPs are highly efficient at delivery to antigen presenting cells for eliciting tumor immunity (Suot & Srivastava (1995) *Science* 269:1585-1588; Tamura et al. (1997) *Science* 278:117-120).

In some embodiments, dendritic cells are potent antigen presenting cells that are used to prime antigen-specific responses. Dendritic cells can be produced ex vivo and loaded with various protein and peptide antigens as well as tumor cell extracts (Nestle et al. (1998) *Nature Medicine* 4: 328-332). Dendritic cells can also be transduced by genetic means to express these tumor antigens as well. DCs have also been fused directly to tumor cells for the purposes of immunization (Kugler et al. (2000) *Nature Medicine* 6:332-336). As a method of vaccination, Dendritic cell immunization can be effectively combined with anti-NKG2A antibodies to activate (unleash) more potent anti-tumor responses.

In some embodiments, an anti-hNKG2A is administered with standard of care treatment, e.g., surgery, radiation, and/or chemotherapy. In some embodiments, an anti-hNKG2A antibody is administered with a chemotherapeutic agent. In some embodiments, the anti-hNKG2A antibody is administered with one or more of carboplatin, cisplatin, paclitaxel, nab-paclitaxel, gemcitabine or FOLFOX. In some embodiment, an anti-hNKG2A antibody is administered with carboplatin or nab-paclitaxel. In some embodiments, an anti-hNKG2A antibody is administered in conjunction with carboplatin and paclitaxel. In some embodiments, an anti-hNKG2A antibody is administered with cisplatin and pemetrexed. In some embodiments, an anti-hNKG2A antibody is administered with cisplatin and gemcitabine. In some embodiments, an anti-hNKG2A antibody is administered with FOLFOX. In some embodiments, an anti-hNKG2A antibody is administered with FOLFIRI. In one embodiment, an anti-hNKG2A antibody is administered with dacarbazine for the treatment of melanoma. In some embodiments, cisplatin is intravenously administered as a 100 mg/ml dose once every four weeks. In some embodiments, an anti-hNKG2A antibody is administered in with doxorubicin (adriamycin), cisplatin bleomycin sulfate, carmustine, chlorambucil, dacarbazine and/or cyclophosphamide hydroxyurea. In some embodiments, adriamycin is intravenously administered as a 60 mg/ml to 75 mg/ml dose once every 21 days. In one embodiment, the anti-hNKG2A antibody is administered to a human patient that is resistant to treatment with at least one drug, wherein administration of the anti-hNKG2A antibody reduces, alleviates, or abrogates resistance to the at least one drug. In some embodiments, an anti-hNKG2A antibody is administered with an agonist antibody, such as an anti-ICOS antibody.

The combination therapies described above can be administered in various combinations with each other, and encompass combined administration (where two or more therapeutic agents are included in the same or separate formulations), and separate administration, in which case, administration of the antibody of the invention can occur prior to, simultaneously, and/or following, administration of the additional therapeutic agent and/or adjuvant. Antibodies of the invention can also be used in combination with radiation therapy.

In some embodiments, another example of such a combination is an anti-hNKG2A antibody administered antibody in combination with interleukin-2 (IL-2). In some embodiments, the combination of anti-hNKG2A antibody and IL-2 is to treat various cancers, including for the treatment of renal cell carcinoma and melanoma. In some embodiments, the anti-hNKG2A antibodies discussed herein is combined with an IL-2 pathway agonist to treat various cancers. The combination includes various IL-2 pathway agonists, such as those described in WO 2012/065086 (Nektar Therapeutics) and WO 2015/125159 (Nektar Therapeutics), the contents of which are incorporated by reference in their entireties. WO 2006/138572 (Nektar Therapeutics) provides conjugates having a degradable linkage and polymeric reagents useful in preparing such conjugates, as well as methods of making polymeric reagents and conjugates, and is incorporated by reference in its entirety.

In some embodiments, the combination of an anti-hNKG2A antibody as described herein, such as NKG2A.9, NKG2A.11, or 13F3.A4 antibodies, and an IL-2 pathway agonist, such as NKTR-214, is administered to patients to treat cancer. As described in more detail below, NKTR-214 is produced by conjugating on average around six FMOC (fluorenylmethyloxycarbonyl chloride)-based polyethylene glycol (PEG) reagents having the following structure (mPEG$_2$-C2-fomc-20K-N-Hydroxysuccinimidate Derivative, 200 kDa, ("mPED2-C2-fmoc-20K-NHS"):

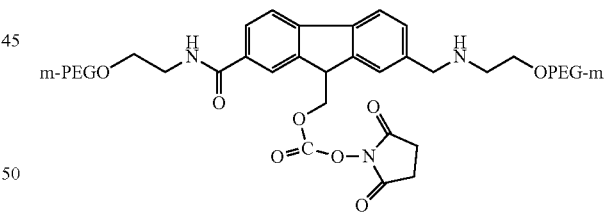

to a protein having the following 132-amino acid sequence:

```
                                                       (SEQ ID NO: 161)
PTSSSTKKTQLQLEHLLLDLQMILNGINNYKNPKLTRMLTFKFYMPKKATELKHLQCLEE    60

ELKPLEEVLNLAQSKNFHLRPRDLISNINVIVLELKGSETTFMCEYADETATIVEFLNRW   120

ITFSQSIISTLT                                                   132
```

WO 2012/065086 provides conjugates of an IL-2 moiety and one or more non-peptide, water-soluble polymers, including polyethylene glycol or a derivative thereof. Specifically, Example 2 (paragraphs 202-204) of WO 2012/

065086 describes PEGylation of rIL-2 with mPEG2-C2-fmoc-20K-NHS to result in the mPEG2-C2-fmoc-20K-NHS structure set forth above. Example 1 (paragraphs 63-66) WO 2015/125159 describes a scaled-up approach for PEGylating IL-2 with mPEG2-C2-fmoc-20K-NHS that results in RSLAIL-2 (NKTR-214). NKTR-214 is a cytokine that is designed to target CD122, (also known as interleukin-2 receptor beta subunit, IL-2Rβ), a protein found on certain immune cells (e.g., CD8+ T Cells and NK Cells), to expand these cells to promote their anti-tumor effects.

In some embodiments, an anti-hNKG2A antibody is administered in combination with an anti-angiogenic agent.

Other combination therapies that may result in synergy with the anti-hNKG2A antibodies described herein through cell death are radiation, surgery, and hormone deprivation.

In some embodiments, anti-hNKG2A antibodies described herein is administered in conjunction with bispecific antibodies. Bispecific antibodies can be used to target two different antigens. In some embodiments, anti-hNKG2A antibodies are used in combination with bispecific antibodies that target Fcα or Fcγ receptor-expressing effectors cells to treat tumor cells (see, e.g., U.S. Pat. Nos. 5,922,845 and 5,837,243). For example, anti-Fc receptor/anti-tumor antigen (e.g., Her-2/neu) bispecific antibodies have been used to target macrophages to sites of tumor. In some embodiments, the T cell arm of these responses is augmented by the functional activity of the anti-hNKG2A antibody. In some embodiments, antigen is delivered directly to DCs by the use of bispecific antibodies that bind to tumor antigen and a dendritic cell specific cell surface marker. In some embodiments, anti-hNKG2A antibodies are used in combination with antibodies that reduce or inactivate the immunosuppressive proteins expressed by a tumor, e.g., anti-TGF-β antibodies, anti-IL-10 antibodies, and anti-Fas ligand antibodies.

Infectious Diseases

In another aspect, the invention described herein provides a method of treating an infectious disease in a subject, including a human subject, comprising administering to the subject an anti-hNKG2A antibody, or antigen-binding fragment thereof, such that the subject is treated for the infectious disease. In other embodiments, the anti-NKG2A antibody is a chimeric or humanized antibody.

Similar to its treatment of tumors as discussed herein, anti-hNKG2A antibodies described herein can be administered alone, or as an adjuvant, in combination with vaccines, to enhance the immune response to pathogens, toxins, and self-antigens, including to treat chronic viral infections. Examples of pathogens for which this therapeutic approach can be particularly useful, include pathogens for which there is currently no effective vaccine, or pathogens for which conventional vaccines are less than completely effective. These pathogens include, but are not limited to HIV, hepatitis (A, B, & C), influenza, herpes, *Giardia*, malaria, *Leishmania, Staphylococcus aureus, Pseudomonas aeruginosa.*

Examples of pathogenic viruses causing infections treatable by methods described herein include HIV, hepatitis (A, B, or C), herpes virus (e.g., VZV, HSV-1, HAV-6, HSV-II, and CMV, Epstein Barr virus), adenovirus, influenza virus, flaviviruses, echovirus, rhinovirus, coxsackie virus, coronavirus, respiratory syncytial virus, mumps virus, rotavirus, measles virus, rubella virus, parvovirus, vaccinia virus, HTLV virus, dengue virus, papillomavirus, molluscum virus, poliovirus, rabies virus, JC virus and arboviral encephalitis virus.

Examples of pathogenic bacteria causing infections treatable by methods described herein include chlamydia, rickettsial bacteria, mycobacteria, staphylococci, streptococci, pneumonococci, meningococci and gonococci, klebsiella, proteus, serratia, pseudomonas, legionella, diphtheria, salmonella, bacilli, cholera, tetanus, botulism, anthrax, plague, leptospirosis, and Lyme disease bacteria.

Examples of pathogenic fungi causing infections treatable by methods described herein include *Candida* (albicans, krusei, glabrata, tropicalis, etc.), *Cryptococcus neoformans, Aspergillus* (fumigatus, niger, etc.), *Genus Mucorales* (mucor, absidia, rhizopus), *Sporothrix schenkii, Blastomyces dermatitides, Paracoccidioides brasiliensis, Coccidioides immitis* and *Histoplasma capsulatum.*

Examples of pathogenic parasites causing infections treatable by methods described herein include *Entamoeba histolytica, Balantidium coli, Naegleriafowleri, Acanthamoeba* sp., *Giardia lambia, Cryptosporidium* sp., *Pneumocystis carinii, Plasmodium vivax, Babesia micron, Trypanosoma brucei, Trypanosoma cruzi, Leishmania donovani, Toxoplasma gondii, Nippostrongylus brasiliensis.*

The methods described herein of administering anti-hNKG2A antibodies to a subject may be combined with other forms of immunotherapy such as cytokine treatment (e.g., interferons, GM-CSF, G-CSF, IL-2), or bispecific antibody therapy, which provides for enhanced presentation of tumor antigens (see, e.g., Holliger (1993) Proc. Natl. Acad. Sci. USA 90:6444-6448; Poljak (1994) Structure 2: 1121-1123).

Autoimmune Reactions

In some aspects, Anti-NKG2A antibodies increase autoimmune responses. Induction of anti-tumor responses using tumor cell and peptide vaccines reveals that many antitumor responses involve anti-self reactivities (van Elsas et al. (2001) J. Exp. Med. 194:481-489; Overwijk, et al. (1999) Proc. Natl. Acad. Sci. U.S.A. 96: 2982-2987; Hurwitz, (2000) supra; Rosenberg & White (1996) *J. Immunother Emphasis Tumor Immunol* 19 (1): 81-4). Therefore, anti-NKG2A antibodies are used with various self proteins to devise vaccination protocols to efficiently generate immune responses against these self proteins for disease treatment. For example, Alzheimer's disease involves inappropriate accumulation of Aβ peptide in amyloid deposits in the brain; antibody responses against amyloid are able to clear these amyloid deposits (Schenk et al., (1999) *Nature* 400: 173-177).

Other self proteins can also be used as targets such as IgE for the treatment of allergy and asthma, and TNF-α for rheumatoid arthritis. Finally, antibody responses to various hormones can be induced by the use of anti-NKG2A antibodies. Neutralizing antibody responses to reproductive hormones can be used for contraception. Neutralizing antibody response to hormones and other soluble factors that are required for the growth of particular tumors are additional vaccination targets.

Analogous methods as described above for the use of anti-NKG2A antibodies can be used for induction of therapeutic autoimmune responses to treat patients having an inappropriate accumulation of other self-antigens, such as amyloid deposits, including Aβ in Alzheimer's disease, cytokines such as TNF-α, and IgE.

Vaccines

In some aspects, anti-NKG2A antibodies described herein are used to stimulate antigen-specific immune responses administering an anti-NKG2A antibody along with an antigen of interest (e.g., a vaccine). Accordingly, provided herein are methods of enhancing an immune response to an antigen in a subject, comprising administering to the subject: (i) the antigen; and (ii) an anti-NKG2A antibody, or antigen-binding fragment thereof, such that an immune response to the antigen in the subject is enhanced. The antibody can be a human anti-human NKG2A antibody (such as any of the human anti-NKG2A antibodies described herein). In some embodiments, the anti-NKG2A antibody is a chimeric or humanized antibody. The antigen can be, for example, a tumor antigen, a viral antigen, a bacterial antigen or an antigen from a pathogen. Non-limiting examples of such antigens include those discussed in the sections herein, such as the tumor antigens (or tumor vaccines) discussed herein, or antigens from the viruses, bacteria or other pathogens described herein.

In certain embodiments, a peptide or fusion protein comprising the epitope to which an anti-NKG2A antibody binds is used as a vaccine instead of, or in addition to, an anti-NKG2A antibody.

Suitable routes of administering the antibody compositions (e.g., human monoclonal antibodies, multispecific and bispecific molecules and immunoconjugates) described herein in vivo and in vitro are well known in the art and can be selected by those of ordinary skill in the art. For example, the antibody compositions can be administered by intravenous or subcutaneous routes. Suitable dosages of the composition used will depend on the age and weight of the subject and the concentration and/or formulation of the antibody composition.

As previously described, anti-NKG2A antibodies described herein can be co-administered with one or other more therapeutic agents, e.g., a cytotoxic agent, a radiotoxic agent, or an immunosuppressive agent. The anti-NKG2A antibody can be linked to the agent (as an immuno-complex) or can be administered separately from the agent. In the latter case (separate administration), the anti-NKG2A antibody can be administered before, after, or concurrently with the agent or can be coadministered with other known therapies, e.g., an anti-cancer therapy, e.g., chemotherapy and/or radiation. Such therapeutic agents include, among others, anti-neoplastic agents such as doxorubicin (adriamycin), cisplatin bleomycin sulfate, carmustine, chlorambucil, dacarbazine and cyclophosphamide hydroxyurea which, by themselves, are only effective at levels which are toxic or subtoxic to a patient. Cisplatin is intravenously administered as a 100 mg/ml dose once every four weeks and adriamycin is intravenously administered as a 60-75 mg/ml dose once every 21 days. Co-administration of anti-NKG2A antibodies, or antigen binding fragments thereof, described herein with chemotherapeutic agents provides two anti-cancer agents that operate via different mechanisms to yield a cytotoxic effect to human tumor cells. Such coadministration can solve problems due to development of resistance to drugs or a change in the antigenicity of the tumor cells, which would render them unreactive with the antibody.

Also within the scope described herein are kits comprising the antibody compositions described herein (e.g., human antibodies, bispecific or multispecific molecules, or immunoconjugates) and instructions for use. The kit can further contain at least one additional reagent, or one or more additional human anti-NKG2A antibodies described herein (e.g., a human antibody having a complementary activity which binds to an epitope in NKG2A antigen distinct from the first human antibody). Kits typically include a label indicating the intended use of the contents of the kit. The term label includes any writing, or recorded material supplied on or with the kit, or which otherwise accompanies the kit.

Combination Therapies

In one aspect, provided herein are methods of combination therapy, e.g., for the treatment of cancer, in which an anti-hNKG2A antibody is administered in connection with one or more additional agents, e.g., antibodies, that are effective in stimulating immune responses to thereby further enhance, stimulate or upregulate immune responses in a subject, including a human subject. Provided herein are methods for treating or delaying progression of cancer in an individual comprising administering to the individual an anti-hNKG2A antibody (e.g., NKG2A.9, NKG2A.11, and 13F3.A4) in conjunction with another anti-cancer agent or cancer therapy. In some embodiments, an anti-hNKG2A antibody may be administered in conjunction with a chemotherapy or chemotherapeutic agent or with a radiation therapy or radiotherapeutic agent, as described above. In some embodiments, an anti-hNKG2A antibody may be administered in conjunction with an agonist antibody, such as anti-hICOS antibody. In some embodiments, an anti-hNKG2A antibody may be administered in conjunction with a targeted therapy or targeted therapeutic agent. In some embodiments, an anti-hNKG2A antibody may be administered in conjunction with an immunotherapy or immunotherapeutic agent, for example a monoclonal antibody.

In some embodiments, an anti-hNKG2A antibody described herein can be combined with (i) an agonist of another co-stimulatory receptor and/or (ii) an antagonist of an inhibitory signal on T cells. In some embodiments, a combination therapy comprising an anti-hNKG2A antibody and the agonist and/or antagonist results in an enhanced antigen-specific T cell response in a subject. In some embodiment, anti-hNKG2A antibodies described herein may be administered in conjunction with an agent that targets a co-stimulatory and co-inhibitory molecules that is a member of the immunoglobulin super family (IgSF) to increase an immune response. In some embodiment, anti-hNKG2A antibodies described herein may be administered in conjunction with an agent that targets a ligand of a co-stimulatory or co-inhibitory molecule. A family of membrane-bound ligands that bind to co-stimulatory or co-inhibitory receptors is the B7 family, which includes B7-1, B7-2, B7-H1 (PD-L1), B7-DC (PD-L2), B7-H2 (ICOS-L), B7-H3, B7-H4, B7-H5 (VISTA), and B7-H6. Another family of membrane bound ligands that bind to co-stimulatory or co-inhibitory receptors is the TNF family of molecules that bind to cognate TNF receptor family members, which include CD40, CD40L, OX-40, OX-40L, CD70, CD27L, CD30, CD30L, 4-1BBL, CD137/4-1BB, TRAIL/Apo2-L, TRAILR1/DR4, TRAILR2/DR5, TRAILR3, TRAILR4, OPG, RANK, RANKL, TWEAKR/Fn14, TWEAK, BAFFR, EDAR, XEDAR, TACI, APRIL, BCMA, LTβR, LIGHT, DcR3, HVEM, VEGI/TL1A, TRAMP/DR3, EDAR, EDA1, XEDAR, EDA2, TNFR1, Lymphotoxin α/TNFβ, TNFR2, TNFα, LTβR, Lymphotoxin α 1β2, FAS, FASL, RELT, DR6, TROY, NGFR.

In another aspect, anti-hNKG2A antibodies can be used in combination with antagonists of cytokines that inhibit T cell activation (e.g., IL-6, IL-10, TGF-β, VEGF; or other "immunosuppressive cytokines," or cytokines that stimulate T cell activation, for stimulating an immune response, e.g., for treating proliferative diseases, such as cancer.

In one aspect, T cell responses are stimulated by a combination of an anti-hNKG2A antibody described herein and one or more of (i) an antagonist of a protein that inhibits T cell activation (e.g., immune checkpoint inhibitors) such as CTLA-4, PD-1, PD-L1, PD-L2, LAG-3, TIM-3, Galectin 9, CEACAM-1, BTLA, CD69, Galectin-1, TIGIT, CD113, GPR56, VISTA, 2B4, CD48, GARP, PD1H, LAIR1, TIM-1, and TIM-4, and (ii) an agonist of a protein that stimulates T cell activation such as B7-1, B7-2, CD28, 4-1BB (CD137), 4-1BBL, CD40, ICOS-L, OX40, OX40L, GITR, GITRL, CD70, CD27, DR3 and CD28H.

Exemplary agents that modulate one of the above proteins and may be combined with anti-hNKG2A, e.g., those described herein, for treating cancer, include: YERVOY®/ ipilimumab or tremelimumab (to CTLA-4), galiximab (to B7.1), BMS-936558 (to PD-1), pidilizumab/CT-011 (to PD-1), KEYTRUDA®/pembrolizumab/MK-3475 (to PD-1), AMP224 (to B7-DC/PD-L2), BMS-936559 (to B7-H1), MPDL3280A (to B7-H1), CP-870893 or dacetuzumab/SGN-40 (CD40—Kirkwood et al. (2012) *CA Cancer J. Clin.* 62:309; Vanderheide & Glennie (2013) *Clin. Cancer Res.* 19:1035), AMG557 (to B7H2), MGA271 (to B7H3—WO 11/109400), IMP321 (to LAG-3), urelumab/ BMS-663513 and PF-05082566 (to CD137/4-1BB), varlilumab/CDX-1127 (to CD27), MEDI-6383 and MEDI-6469 (to OX40), RG-7888 (to OX40L—WO 06/029879), Atacicept (to TACI), muromonab-CD3 (to CD3), ipilumumab (to CTLA-4). Accordingly, in one embodiment an anti-hNKG2A antibody (such as NKG2A.9) is combined with an anti-PD-1 antibody (such as nivolumab) and/or an anti-CTLA-4 antibody (such as ipilimumab).

Other molecules that can be combined with anti-hNKG2A antibodies for the treatment of cancer include antagonists of inhibitory receptors on NK cells or agonists of activating receptors on NK cells. For example, anti-hNKG2A antibodies can be combined with antagonists of KIR (e.g., lirilumab).

Yet other agents for combination therapies include agents that inhibit or deplete macrophages or monocytes, including but not limited to CSF-1R antagonists such as CSF-1R antagonist antibodies including RG7155 (WO 11/70024, WO 11/107553, WO 11/131407, WO 13/87699, WO 13/119716, WO 13/132044) or FPA-008 (WO 11/140249; WO 13/169264; WO 14/036357).

In some embodiments, anti-hNKG2A antibodies described herein are used together with one or more of agonistic agents that ligate positive co-stimulatory receptors, blocking agents that attenuate signaling through inhibitory receptors, and one or more agents that increase systemically the frequency of anti-tumor T cells, agents that overcome distinct immune suppressive pathways within the tumor microenvironment (e.g., block inhibitory receptor engagement (e.g., PD-L1/PD-1 interactions), deplete or inhibit Tregs (e.g., using an anti-CD25 monoclonal antibody (e.g., daclizumab) or by ex vivo anti-CD25 bead depletion), inhibit metabolic enzymes such as IDO, or reverse/prevent T cell anergy or exhaustion) and agents that trigger innate immune activation and/or inflammation at tumor sites.

Provided herein are methods for stimulating an immune response in a subject comprising administering to the subject an anti-hNKG2A antibody and one or more additional immunostimulatory antibodies, such as a PD-1 antagonist, e.g., antagonist antibody, a PD-L1 antagonist, e.g., antagonist antibody, a CTLA-4 antagonist, e.g., antagonist antibody and/or a LAG3 antagonist, e.g., an antagonist antibody, such that an immune response is stimulated in the subject, for example to inhibit tumor growth or to stimulate an anti-viral response. In one embodiment, the subject is administered an anti-hNKG2A antibody and an antagonist anti-PD-1 antibody. In one embodiment, the subject is administered an anti-hNKG2A antibody and an antagonist anti-PD-L1 antibody. In one embodiment, the subject is administered an anti-hNKG2A antibody and an antagonist anti-CTLA-4 antibody. In one embodiment, the at least one additional immunostimulatory antibody (e.g., an antagonist anti-PD-1, an antagonist anti-PD-L1, an antagonist anti-CTLA-4 and/or an antagonist anti-LAG3 antibody) is a human antibody. Alternatively, the at least one additional immunostimulatory antibody can be, for example, a chimeric or humanized antibody (e.g., prepared from a mouse or hamster anti-PD-1, anti-PD-L1, anti-CTLA-4 and/or anti-LAG3 antibody).

Provided herein are methods for treating a hyperproliferative disease (e.g., cancer), comprising administering an anti-hNKG2A antibody and an antagonist PD-1 antibody to a subject. In some embodiments, the cancer is non-small cell lung cancer (NSCLC) or colorectal cancer (CRC). In some embodiments, the cancer is characterized by tumors with (i) elevated levels of HLA-E; and/or (ii) higher tumor mutation burden. In certain embodiments, the anti-hNKG2A antibody is administered at a subtherapeutic dose, the anti-PD-1 antibody is administered at a subtherapeutic dose, or both are administered at a subtherapeutic dose. Also provided herein are methods for altering an adverse event associated with treatment of a hyperproliferative disease with an immunostimulatory agent. In one embodiment, the method comprises administering an anti-hNKG2A antibody and a subtherapeutic dose of anti-PD-1 antibody to a subject. In some embodiments, the subject is a human. In some embodiments, the anti-PD-1 antibody is a human monoclonal antibody.

In some embodiments, anti-PD-1 antibodies that are known in the art are used in the presently described methods in combniatin on with the anti-NKG2A antibodies described herein. Various human monoclonal antibodies that bind specifically to PD-1 with high affinity have been disclosed in U.S. Pat. No. 8,008,449. Anti-PD-1 human antibodies disclosed in U.S. Pat. No. 8,008,449 have been demonstrated to exhibit one or more of the following characteristics: (a) bind to human PD-1 with a $K_D$ of $1\times10^{-7}$ M or less, as determined by surface plasmon resonance using a Biacore biosensor system; (b) do not substantially bind to human CD28, CTLA-4 or ICOS; (c) increase T-cell proliferation in a Mixed Lymphocyte Reaction (MLR) assay; (d) increase interferon-γ production in an MLR assay; (e) increase IL-2 secretion in an MLR assay; (0 bind to human PD-1 and cynomolgus monkey PD-1; (g) inhibit the binding of PD-L1 and/or PD-L2 to PD-1; (h) stimulate antigen-specific memory responses; (i) stimulate antibody responses; and (j) inhibit tumor cell growth in vivo. Anti-PD-1 antibodies usable in the present invention include monoclonal antibodies that bind specifically to human PD-1 and exhibit at least one, in some embodiments, at least five, of the preceding characteristics.

Other anti-PD-1 monoclonal antibodies have been described in, for example, U.S. Pat. Nos. 6,808,710, 7,488, 802, 8,168,757 and 8,354,509, US Publication No. 2016/ 0272708, and PCT Publication Nos. WO 2012/145493, WO 2008/156712, WO 2015/112900, WO 2012/145493, WO 2015/112800, WO 2014/206107, WO 2015/35606, WO 2015/085847, WO 2014/179664, WO 2017/020291, WO 2017/020858, WO 2016/197367, WO 2017/024515, WO 2017/025051, WO 2017/123557, WO 2016/106159, WO 2014/194302, WO 2017/040790, WO 2017/133540, WO 2017/132827, WO 2017/024465, WO 2017/025016, WO 2017/106061, WO 2017/19846, WO 2017/024465, WO 2017/025016, WO 2017/132825, and WO 2017/133540 each of which is incorporated by reference in its entirety.

In some embodiments, the anti-PD-1 antibody is nivolumab (also known as OPDIVO®, 5C4, BMS-936558, MDX-1106, and ONO-4538), pembrolizumab (Merck; also known as KEYTRUDA®, lambrolizumab, and MK-3475;

see WO2008/156712), PDR001 (Novartis; see WO 2015/112900), MEDI-0680 (AstraZeneca; also known as AMP-514; see WO 2012/145493), cemiplimab (Regeneron; also known as REGN-2810; see WO 2015/112800), JS001 (TAIZHOU JUNSHI PHARMA; see Si-Yang Liu et al., *J. Hematol. Oncol.* 10:136 (2017)), BGB-A317 (Beigene; see WO 2015/35606 and US 2015/0079109), INCSHR1210 (Jiangsu Hengrui Medicine; also known as SHR-1210; see WO 2015/085847; Si-Yang Liu et al., *J. Hematol. Oncol.* 10:136 (2017)), TSR-042 (Tesaro Biopharmaceutical; also known as ANB011; see WO2014/179664), GLS-010 (Wuxi/Harbin Gloria Pharmaceuticals; also known as WBP3055; see Si-Yang Liu et al., *J. Hematol. Oncol.* 10:136 (2017)), AM-0001 (Armo), STI-1110 (Sorrento Therapeutics; see WO 2014/194302), AGEN2034 (Agenus; see WO 2017/040790), MGA012 (Macrogenics, see WO 2017/19846), or IBI308 (Innovent; see WO 2017/024465, WO 2017/025016, WO 2017/132825, and WO 2017/133540).

In one embodiment, the anti-PD-1 antibody is nivolumab. Nivolumab is a fully human IgG4 (S228P) PD-1 immune checkpoint inhibitor antibody that selectively prevents interaction with PD-1 ligands (PD-L1 and PD-L2), thereby blocking the down-regulation of antitumor T-cell functions (U.S. Pat. No. 8,008,449; Wang et al., 2014 *Cancer Immunol Res.* 2(9):846-56).

In another embodiment, the anti-PD-1 antibody is pembrolizumab. Pembrolizumab is a humanized monoclonal IgG4 (S228P) antibody directed against human cell surface receptor PD-1 (programmed death-1 or programmed cell death-1). Pembrolizumab is described, for example, in U.S. Pat. Nos. 8,354,509 and 8,900,587.

Anti-PD-1 antibodies usable in the disclosed methods also include isolated antibodies that bind specifically to human PD-1 and cross-compete for binding to human PD-1 with any anti-PD-1 antibody disclosed herein, e.g., nivolumab (see, e.g., U.S. Pat. Nos. 8,008,449 and 8,779,105; WO 2013/173223). In some embodiments, the anti-PD-1 antibody binds the same epitope as any of the anti-PD-1 antibodies described herein, e.g., nivolumab. The ability of antibodies to cross-compete for binding to an antigen indicates that these monoclonal antibodies bind to the same epitope region of the antigen and sterically hinder the binding of other cross-competing antibodies to that particular epitope region. These cross-competing antibodies are expected to have functional properties very similar those of the reference antibody, e.g., nivolumab, by virtue of their binding to the same epitope region of PD-1. Cross-competing antibodies can be readily identified based on their ability to cross-compete with nivolumab in standard PD-1 binding assays such as Biacore analysis, ELISA assays or flow cytometry (see, e.g., WO 2013/173223).

In certain embodiments, the antibodies that cross-compete for binding to human PD-1 with, or bind to the same epitope region of human PD-1 antibody, nivolumab, are monoclonal antibodies. For administration to human subjects, these cross-competing antibodies are chimeric antibodies, engineered antibodies, or humanized or human antibodies. Such chimeric, engineered, humanized or human monoclonal antibodies can be prepared and isolated by methods well known in the art.

Anti-PD-1 antibodies usable in the methods of the disclosed invention also include antigen-binding portions of the above antibodies. It has been amply demonstrated that the antigen-binding function of an antibody can be performed by fragments of a full-length antibody.

Anti-PD-1 antibodies suitable for use in the disclosed methods or compositions are antibodies that bind to PD-1 with high specificity and affinity, block the binding of PD-L1 and or PD-L2, and inhibit the immunosuppressive effect of the PD-1 signaling pathway. In any of the compositions or methods disclosed herein, an anti-PD-1 "antibody" includes an antigen-binding portion or fragment that binds to the PD-1 receptor and exhibits the functional properties similar to those of whole antibodies in inhibiting ligand binding and up-regulating the immune system. In certain embodiments, the anti-PD-1 antibody or antigen-binding portion thereof cross-competes with nivolumab for binding to human PD-1.

Provided herein are methods for treating a hyperproliferative disease (e.g., cancer), comprising administering an anti-hNKG2A antibody and an antagonist PD-L1 antibody to a subject. In certain embodiments, the anti-hNKG2A antibody is administered at a subtherapeutic dose, the anti-PD-L1 antibody is administered at a subtherapeutic dose, or both are administered at a subtherapeutic dose. Provided herein are methods for altering an adverse event associated with treatment of a hyperproliferative disease with an immunostimulatory agent, comprising administering an anti-NKG2A antibody and a subtherapeutic dose of anti-PD-L1 antibody to a subject. In certain embodiments, the subject is human. In certain embodiments, the anti-PD-L1 antibody is a human sequence monoclonal antibody and the anti-hNKG2A antibody is a humanized monoclonal antibody, such as an antibody comprising the CDRs or variable regions of the antibodies disclosed herein.

Anti-PD-L1 antibodies that are known in the art can be used in the methods of the present disclosure. Examples of anti-PD-L1 antibodies useful in the methods of the present disclosure include the antibodies disclosed in U.S. Pat. No. 9,580,507. Anti-PD-L1 human monoclonal antibodies disclosed in U.S. Pat. No. 9,580,507 have been demonstrated to exhibit one or more of the following characteristics: (a) bind to human PD-L1 with a $K_D$ of $1\times10-7$ M or less, as determined by SPR using a Biacore biosensor system; (b) increase T-cell proliferation in a Mixed Lymphocyte Reaction (MLR) assay; (c) increase interferon-γ production in an MLR assay; (d) increase IL-2 secretion in an MLR assay; (e) stimulate antibody responses; and (f) reverse the effect of T regulatory cells on T cell effector cells and/or dendritic cells. Anti-PD-L1 antibodies usable in the present invention include monoclonal antibodies that bind specifically to human PD-L1 and exhibit at least one, in some embodiments, at least five, of the preceding characteristics.

In certain embodiments, the anti-PD-L1 antibody is BMS-936559 (also known as 12A4, MDX-1105; see, e.g., U.S. Pat. No. 7,943,743 and WO 2013/173223), atezolizumab (Roche; also known as TECENTRIQ®; MPDL3280A, RG7446; see U.S. Pat. No. 8,217,149; see, also, Herbst et al. (2013) J Clin Oncol 31(suppl):3000), durvalumab (AstraZeneca; also known as IMFINZI™, MEDI-4736; see WO 2011/066389), avelumab (Pfizer; also known as BAVENCIO®, MSB-0010718C; see WO 2013/079174), STI-1014 (Sorrento; see WO2013/181634), CX-072 (Cytomx; see WO2016/149201), KNO35 (3D Med/Alphamab; see Zhang et al., Cell Discov. 7:3 (March 2017), LY3300054 (Eli Lilly Co.; see, e.g., WO 2017/034916), or CK-301 (Checkpoint Therapeutics; see Gorelik et al., AACR:Abstract 4606 (April 2016)).

In certain embodiments, the PD-L1 antibody is atezolizumab (TECENTRIQ®). Atezolizumab is a fully humanized IgG1 monoclonal anti-PD-L1 antibody.

In certain embodiments, the PD-L1 antibody is durvalumab (IMFINZI™). Durvalumab is a human IgG1 kappa monoclonal anti-PD-L1 antibody.

In certain embodiments, the PD-L1 antibody is avelumab (BAVENCIO®). Avelumab is a human IgG1 lambda monoclonal anti-PD-L1 antibody.

In other embodiments, the anti-PD-L1 monoclonal antibody is 28-8, 28-1, 28-12, 29-8, 5H1, or any combination thereof.

Anti-PD-L1 antibodies usable in the disclosed methods also include isolated antibodies that bind specifically to human PD-L1 and cross-compete for binding to human PD-L1 with any anti-PD-L1 antibody disclosed herein, e.g., atezolizumab, durvalumab, and/or avelumab. In some embodiments, the anti-PD-L1 antibody binds the same epitope as any of the anti-PD-L1 antibodies described herein, e.g., atezolizumab, durvalumab, and/or avelumab. The ability of antibodies to cross-compete for binding to an antigen indicates that these antibodies bind to the same epitope region of the antigen and sterically hinder the binding of other cross-competing antibodies to that particular epitope region. These cross-competing antibodies are expected to have functional properties very similar those of the reference antibody, e.g., atezolizumab and/or avelumab, by virtue of their binding to the same epitope region of PD-L1. Cross-competing antibodies can be readily identified based on their ability to cross-compete with atezolizumab and/or avelumab in standard PD-L1 binding assays such as Biacore analysis, ELISA assays or flow cytometry (see, e.g., WO 2013/173223).

In certain embodiments, the antibodies that cross-compete for binding to human PD-L1 with, or bind to the same epitope region of human PD-L1 antibody as, atezolizumab, durvalumab, and/or avelumab, are monoclonal antibodies. For administration to human subjects, these cross-competing antibodies are chimeric antibodies, engineered antibodies, or humanized or human antibodies. Such chimeric, engineered, humanized or human monoclonal antibodies can be prepared and isolated by methods well known in the art.

Anti-PD-L1 antibodies usable in the methods of the disclosed invention also include antigen-binding portions of the above antibodies. It has been amply demonstrated that the antigen-binding function of an antibody can be performed by fragments of a full-length antibody.

Anti-PD-L1 antibodies suitable for use in the disclosed methods or compositions are antibodies that bind to PD-L1 with high specificity and affinity, block the binding of PD-1, and inhibit the immunosuppressive effect of the PD-1 signaling pathway. In any of the compositions or methods disclosed herein, an anti-PD-L1 "antibody" includes an antigen-binding portion or fragment that binds to PD-L1 and exhibits the functional properties similar to those of whole antibodies in inhibiting receptor binding and up-regulating the immune system. In certain embodiments, the anti-PD-L1 antibody or antigen-binding portion thereof cross-competes with atezolizumab, durvalumab, and/or avelumab for binding to human PD-L1.

In one embodiment, the anti-hNKG2A antibody of the present invention is combined with an antagonist of PD-1/PD-L1 signaling, such as a PD-1 antagonist (e.g., nivolumab, also known as MDX1106, as described in WO 06/121168) or a PD-L1 antagonist, in combination with a third immunotherapeutic agent (e.g., an anti-ICOS antibody, such as ICOS.33 IgG1f S267E (as described in U.S. Pat. No. 10,251,945), combined with nivolumab and ipilimumab). In one embodiment, the third immunotherapeutic agent is a CTLA-4 antagonist antibody. In certain embodiments, the anti-CTLA-4 antibody is YERVOY® (ipilimumab or antibody 10D1, described in PCT Publication WO 01/14424) or tremelimumab (formerly ticilimumab, CP-675,206). In one embodiment, the third immunotherapeutic agent is a GITR antagonist or an OX-40 antagonist, such as the anti-GITR or anti-OX40 antibodies disclosed herein. In one embodiment, the third immunotherapeutic agent is a GITR agonist, such as an agonistic GITR antibody. Suitable GITR antibodies include, for example, BMS-986153, BMS-986156, TRX-518 (WO06/105021, WO09/009116) and MK-4166 (WO11/028683). In one embodiment, the third immunotherapeutic agent is an IDO antagonist. Suitable IDO antagonists include, for example, INCB-024360 (WO2006/122150, WO07/75598, WO08/36653, WO08/36642), indoximod, or NLG-919 (WO09/73620, WO09/1156652, WO11/56652, WO12/142237).

Provided herein are methods for treating a hyperproliferative disease (e.g., cancer), comprising administering an anti-hNKG2A antibody described herein and a CTLA-4 antagonist antibody to a subject. In certain embodiments, the anti-hNKG2A antibody is administered at a subtherapeutic dose, the anti-CTLA-4 antibody is administered at a subtherapeutic dose, or both are administered at a subtherapeutic dose. Provided herein are methods for altering an adverse event associated with treatment of a hyperproliferative disease with an immunostimulatory agent, comprising administering an anti-hNKG2A antibody and a subtherapeutic dose of anti-CTLA-4 antibody to a subject. In certain embodiments, the subject is human.

Anti-CTLA-4 antibodies that are known in the art can be used in the methods of the present disclosure. Anti-CTLA-4 antibodies of the instant invention bind to human CTLA-4 so as to disrupt the interaction of CTLA-4 with a human B7 receptor. Because the interaction of CTLA-4 with B7 transduces a signal leading to inactivation of T-cells bearing the CTLA-4 receptor, disruption of the interaction effectively induces, enhances or prolongs the activation of such T cells, thereby inducing, enhancing or prolonging an immune response.

Human monoclonal antibodies that bind specifically to CTLA-4 with high affinity have been disclosed in U.S. Pat. No. 6,984,720. Other anti-CTLA-4 monoclonal antibodies have been described in, for example, U.S. Pat. Nos. 5,977,318, 6,051,227, 6,682,736, and 7,034,121 and International Publication Nos. WO 2012/122444, WO 2007/113648, WO 2016/196237, and WO 2000/037504, each of which is incorporated by reference herein in its entirety. Anti-CTLA-4 antibodies useful for the present invention include monoclonal antibodies that bind specifically to human CTLA-4 and exhibit at least one, at least two, or at least three of the preceding characteristics.

In certain embodiments, the CTLA-4 antibody is ipilimumab (also known as YERVOY®, MDX-010, 10D1; see U.S. Pat. No. 6,984,720), MK-1308 (Merck), AGEN-1884 (Agenus Inc.; see WO 2016/196237), or tremelimumab (AstraZeneca; also known as ticilimumab, CP-675,206; see WO 2000/037504 and Ribas, Update Cancer Ther. 2(3): 133-39 (2007)). In particular embodiments, the anti-CTLA-4 antibody is ipilimumab.

In particular embodiments, the CTLA-4 antibody is ipilimumab for use in the methods disclosed herein. Ipilimumab is a fully human, IgG1 monoclonal antibody that blocks the binding of CTLA-4 to its B7 ligands, thereby stimulating T cell activation and improving overall survival (OS) in patients with advanced melanoma.

In particular embodiments, the CTLA-4 antibody is tremelimumab.

In particular embodiments, the CTLA-4 antibody is MK-1308.

In particular embodiments, the CTLA-4 antibody is AGEN-1884.

Anti-CTLA-4 antibodies usable in the disclosed methods also include isolated antibodies that bind specifically to human CTLA-4 and cross-compete for binding to human CTLA-4 with any anti-CTLA-4 antibody disclosed herein, e.g., ipilimumab and/or tremelimumab. In some embodiments, the anti-CTLA-4 antibody binds the same epitope as any of the anti-CTLA-4 antibodies described herein, e.g., ipilimumab and/or tremelimumab. The ability of antibodies to cross-compete for binding to an antigen indicates that these antibodies bind to the same epitope region of the antigen and sterically hinder the binding of other cross-competing antibodies to that particular epitope region. These cross-competing antibodies are expected to have functional properties very similar those of the reference antibody, e.g., ipilimumab and/or tremelimumab, by virtue of their binding to the same epitope region of CTLA-4. Cross-competing antibodies can be readily identified based on their ability to cross-compete with ipilimumab and/or tremelimumab in standard CTLA-4 binding assays such as Biacore analysis, ELISA assays or flow cytometry (see, e.g., WO 2013/173223).

In certain embodiments, the antibodies that cross-compete for binding to human CTLA-4 with, or bind to the same epitope region of human CTLA-4 antibody as, ipilimumab and/or tremelimumab, are monoclonal antibodies. For administration to human subjects, these cross-competing antibodies are chimeric antibodies, engineered antibodies, or humanized or human antibodies. Such chimeric, engineered, humanized or human monoclonal antibodies can be prepared and isolated by methods well known in the art.

Anti-CTLA-4 antibodies usable in the methods of the disclosed invention also include antigen-binding portions of the above antibodies. It has been amply demonstrated that the antigen-binding function of an antibody can be performed by fragments of a full-length antibody.

Anti-CTLA-4 antibodies suitable for use in the disclosed methods or compositions are antibodies that bind to CTLA-4 with high specificity and affinity, block the activity of CTLA-4, and disrupt the interaction of CTLA-4 with a human B7 receptor. In any of the compositions or methods disclosed herein, an anti-CTLA-4 "antibody" includes an antigen-binding portion or fragment that binds to CTLA-4 and exhibits the functional properties similar to those of whole antibodies in inhibiting the interaction of CTLA-4 with a human B7 receptor and up-regulating the immune system. In certain embodiments, the anti-CTLA-4 antibody or antigen-binding portion thereof cross-competes with ipilimumab and/or tremelimumab for binding to human CTLA-4.

In one embodiment, the anti-hNKG2A antibody of the present invention is combined with an anti-CTLA-4 antibody, in combination with a third immunotherapeutic agent. In one embodiment the third immunotherapeutic agent is a GITR antagonist or an OX-40 antagonist, such as the anti-GITR or anti-OX40 antibodies disclosed herein. In one embodiment, the third immunotherapeutic agent is a GITR agonist, such as an agonistic GITR antibody. Suitable GITR antibodies include, for example, BMS-986153, BMS-986156, TRX-518 (WO06/105021, WO09/009116) and MK-4166 (WO11/028683). In one embodiment, the third immunotherapeutic agent is an IDO antagonist. Suitable IDO antagonists include, for example, INCB-024360 (WO2006/122150, WO07/75598, WO08/36653, WO08/36642), indoximod, or NLG-919 (WO09/73620, WO09/1156652, WO11/56652, WO12/142237).

Provided herein are methods for treating a hyperproliferative disease (e.g., cancer), comprising administering an anti-hNKG2A antibody and an anti-LAG-3 antibody to a subject. In further embodiments, the agonist anti-hNKG2A antibody is administered at a subtherapeutic dose, the anti-LAG-3 antibody is administered at a subtherapeutic dose, or both are administered at a subtherapeutic dose. Provided herein are methods for altering an adverse event associated with treatment of a hyperproliferative disease with an immunostimulatory agent, comprising administering an anti-hNKG2A antibody and a subtherapeutic dose of anti-LAG-3 antibody to a subject. In certain embodiments, the subject is human. In certain embodiments, the anti-hNKG2A antibody is a human sequence monoclonal antibody and the anti-hNKG2A antibody is a humanized monoclonal antibody, such as an antibody comprising the CDRs or variable regions of the antibodies disclosed herein. Examples of anti-LAG3 antibodies include antibodies comprising the CDRs or variable regions of antibodies 25F7, 26H10, 25E3, 8B7, 11F2 or 17E5, which are described in U.S. Patent Publication No. US2011/0150892 and WO2014/008218. In one embodiment, an anti-LAG-3 antibody is BMS-986016. Other anti-LAG-3 antibodies that can be used include IMP731 described in US 2011/007023 or IMP-321. Anti-LAG-3 antibodies that compete with and/or bind to the same epitope as that of any of these antibodies may also be used in combination treatments.

In certain embodiments, the anti-LAG-3 antibody binds to human LAG-3 with a $K_D$ of $5 \times 10^{-8}$ M or less, binds to human LAG-3 with a $K_D$ of $1 \times 10^{-8}$ M or less, binds to human LAG-3 with a $K_D$ of $5 \times 10^{-9}$ M or less, or binds to human LAG-3 with a $K_D$ of between $1 \times 10^{-8}$ M and $1 \times 10^{-10}$ M or less.

Administration of anti-hNKG2A antibodies described herein and other antagonists, e.g., antagonist antibodies, to one or more second target antigens such as LAG-3 and/or CTLA-4 and/or PD-1 and/or PD-L1 enhances the immune response to cancerous cells in the patient. Cancers whose growth may be inhibited using the antibodies of the instant disclosure include cancers typically responsive to immunotherapy. Examples of cancers for treatment with the combination therapy described herein include, but are not limited to, the described above in the discussion of monotherapy with anti-hNKG2A antibodies.

In certain embodiments, the combination of therapeutic antibodies discussed herein can be administered concurrently as a single composition in a pharmaceutically acceptable carrier, or concurrently as separate compositions with each antibody in a pharmaceutically acceptable carrier. In another embodiment, the combination of therapeutic antibodies can be administered sequentially. For example, an anti-CTLA-4 antibody and an anti-hNKG2A antibody can be administered sequentially, such as anti-CTLA-4 antibody being administered first and anti-hNKG2A antibody second, or anti-hNKG2A antibody being administered first and anti-CTLA-4 antibody second. Additionally or alternatively, an anti-PD-1 antibody and an anti-hNKG2A antibody can be administered sequentially, such as anti-PD-1 antibody being administered first and anti-hNKG2A antibody second, or anti-hNKG2A antibody being administered first and anti-PD-1 antibody second. Additionally or alternatively, an anti-PD-L1 antibody and anti-hNKG2A antibody can be administered sequentially, such as anti-PD-L1 antibody being administered first and anti-hNKG2A antibody second, or anti-hNKG2A antibody being administered first and anti-PD-L1 antibody second. Additionally or alternatively, an anti-LAG-3 antibody and anti-hNKG2A antibody can be administered sequentially, such as anti-LAG-3 antibody being administered first and anti-hNKG2A antibody second, or anti-hNKG2A antibody being administered first and anti-LAG-3 antibody second.

Furthermore, if more than one dose of the combination therapy is administered sequentially, the order of the sequential administration can be reversed or kept in the same order at each time point of administration, sequential administrations can be combined with concurrent administrations, or any combination thereof. For example, the first administration of a combination anti-CTLA-4 antibody and anti-hNKG2A antibody can be concurrent, the second administration can be sequential with anti-CTLA-4 antibody first and anti-hNKG2A antibody second, and the third administration can be sequential with anti-hNKG2A antibody first and anti-CTLA-4 antibody second, etc. Additionally or alternatively, the first administration of a combination anti-PD-1 antibody and anti-hNKG2A antibody can be concurrent, the second administration can be sequential with anti-PD-1 antibody first and anti-hNKG2A antibody second, and the third administration can be sequential with anti-hNKG2A antibody first and anti-PD-1 antibody second, etc. Additionally or alternatively, the first administration of a combination anti-PD-L1 antibody and anti-hNKG2A antibody can be concurrent, the second administration can be sequential with anti-PD-L1 antibody first and anti-hNKG2A antibody second, and the third administration can be sequential with anti-hNKG2A antibody first and anti-PD-L1 antibody second, etc. Additionally or alternatively, the first administration of a combination anti-LAG-3 antibody and anti-hNKG2A antibody can be concurrent, the second administration can be sequential with anti-LAG-3 antibody first and anti-hNKG2A antibody second, and the third administration can be sequential with anti-hNKG2A antibody first and anti-LAG-3 antibody second, etc. Another representative dosing scheme can involve a first administration that is sequential with anti-hNKG2A first and anti-CTLA-4 antibody (and/or anti-PD-1 antibody and/or anti-PD-L1 antibody and/or anti-LAG-3 antibody) second, and subsequent administrations may be concurrent.

In one embodiment, an anti-hNKG2A antibody, as sole immunotherapeutic agent, or the combination of an anti-hNKG2A antibody and one or more additional immunotherapeutic antibodies (e.g., anti-CTLA-4 and/or anti-PD-1 and/or anti-PD-L1 and/or anti-LAG-3 antibody) may be further combined with an immunogenic agent, such as cancerous cells, purified tumor antigens (including recombinant proteins, peptides, and carbohydrate molecules), cells, and cells transfected with genes encoding immune stimulating cytokines (He et al. (2004) *J. Immunol.* 173: 4919-28). Non-limiting examples of tumor vaccines that can be used include peptides of melanoma antigens, such as peptides of gp100, MAGE antigens, Trp-2, MART1 and/or tyrosinase, or tumor cells transfected to express the cytokine GM-CSF (discussed further below). An ICOS agonist and one or more additional antibodies (e.g., CTLA-4 and/or PD-1 and/or PD-L1 and/or LAG-3 blockade) can also be further combined with standard cancer treatments. For example, an ICOS agonist and one or more additional antibodies (e.g., CTLA-4 and/or PD-1 and/or PD-L1 and/or LAG-3 blockade) may be combined with chemotherapeutic regimes. In one embodiment, an anti-hNKG2A antibody is administered to a patient with an anti-CTLA-4 antibody and/or anti-PD-1 antibody and/or anti-PD-L1 antibody and/or anti-LAG-3 antibody in combination with dacarbazine for the treatment of melanoma. In one embodiment, an anti-hNKG2A antibody is administered to a patient with an anti-CTLA-4 antibody and/or anti-PD-1 antibody and/or anti-PD-L1 antibody and/or anti-LAG-3 antibody in combination with interleukin-2 (IL-2) for the treatment of cancer, including melanoma. Other combination therapies that may result in synergy with a combined anti-hNKG2A antibody with or without and CTLA-4 and/or PD-1 and/or PD-L1 and/or LAG-3 antagonism through cytotoxicity include radiation, surgery, or hormone deprivation. In another embodiment, angiogenesis inhibitors may be combined with an anti-hNKG2A antibody and CTLA-4 and/or PD-1 and/or PD-L1 and/or LAG-3 antagonism.

In one embodiment, an anti-hNKG2A antibody as sole immunotherapeutic agent, or a combination of an anti-hNKG2A antibody and CTLA-4 and/or PD-1 and/or PD-L1 and/or LAG-3 blocking antibodies can also be used in combination with bispecific antibodies that target Fcα or Fcγ receptor-expressing effector cells to tumor cells. See, e.g., U.S. Pat. Nos. 5,922,845 and 5,837,243. Bispecific antibodies can be used to target two separate antigens.

In one embodiment an anti-hNKG2A antibody as sole immunotherapeutic agent or a combination of an anti-hNKG2A antibody and additional immunostimulating agent, e.g., anti-CTLA-4 antibody and/or anti-PD-1 antibody and/or anti-PD-L1 antibody and/or anti-LAG-3 antibody, can be used in conjunction with an anti-neoplastic agent, such as RITUXAN® (rituximab), HERCEPTIN® (trastuzumab), BEXXAR® (tositumomab), ZEVALIN® (ibritumomab), CAMPATH® (alemtuzumab), LYMPHOCIDE® (eprtuzumab), AVASTIN® (bevacizumab), and TARCEVA® (erlotinib). By way of example and not wishing to be bound by theory, treatment with an anti-cancer antibody or an anti-cancer antibody conjugated to a toxin can lead to cancer cell death (e.g., tumor cells) which may potentiate an immune response mediated by the immunostimulating agent, e.g., anti-NKG2A antibody, anti-TIGIT antibody, anti-CTLA-4 antibody, anti-PD-1 antibody, anti-PD-L1 antibody, anti-ICOS antibody, and/or anti-LAG-3 antibody. In one embodiment, a treatment of a hyperproliferative disease (e.g., a cancer tumor) can include an anti-cancer agent, e.g., antibody, in combination with an anti-NKG2A antibody and optionally an additional immunostimulating agent, e.g., anti-CTLA-4 antibody and/or anti-PD-1 antibody and/or anti-PD-L1 antibody and/or anti-LAG-3 antibody, concurrently or sequentially or any combination thereof, which can potentiate an anti-tumor immune responses by the host.

Provided herein are methods for reducing, ameliorating or abrogating an adverse event associated with treatment of a hyperproliferative disease (e.g., cancer) with an immunostimulatory agent, comprising administering an anti-NKG2A antibody with or without an anti-CTLA-4 and/or anti-PD-1 and/or anti-PD-L1 and/or anti-LAG-3 antibody, to a subject. In one embodiment, the method reduces the incidence of immunostimulatory therapeutic antibody-induced colitis or diarrhea by administering a non-absorbable steroid to the patient. As used herein, a "non-absorbable steroid" is a glucocorticoid that exhibits extensive first pass metabolism such that, following metabolism in the liver, the bioavailability of the steroid is low, i.e., less than about 20%. In one embodiment described herein, the non-absorbable steroid is budesonide. Budesonide is a locally-acting glucocorticosteroid, which is extensively metabolized, primarily by the liver, following oral administration. ENTOCORT EC® (Astra-Zeneca) is a pH- and time-dependent oral formulation of budesonide developed to optimize drug delivery to the ileum and throughout the colon. ENTOCORT EC® is approved in the U.S. for the treatment of mild to moderate Crohn's disease involving the ileum and/or ascending colon. The usual oral dosage of ENTOCORT EC® for the treatment of Crohn's disease is 6 to 9 mg/day. ENTOCORT EC® is released in the intestines before being absorbed and retained in the gut mucosa. Once it passes through the gut mucosa target tissue, ENTOCORT EC® is extensively metabolized by the cytochrome P450 system in the liver to metabolites with negligible glucocorticoid activity. Therefore, the bioavailability is low (about 10%). The low bioavailability of budesonide results in an improved therapeutic ratio compared to other glucocorticoids with less extensive first-pass metabolism. Budesonide results in fewer adverse effects, including less hypothalamic-pituitary suppression, than systemically-acting corticosteroids. However, chronic administration of ENTOCORT EC® can result in systemic glucocorticoid effects such as hypercorticism and adrenal suppression. See PDR $58^{th}$ ed. 2004; 608-610.

In one embodiment, an anti-NKG2A antibody with or without CTLA-4 and/or PD-1 and/or PD-L1 and/or LAG-3 antagonist in conjunction with a non-absorbable steroid can be further combined with a salicylate. Salicylates include 5-ASA agents such as, for example: sulfasalazine (AZULFIDINE®, Pharmacia & UpJohn); olsalazine (DIPENTUM®, Pharmacia & UpJohn); balsalazide (COLAZAL®, Salix Pharmaceuticals, Inc.); and mesalamine (ASACOL®, Procter & Gamble Pharmaceuticals; PENTASA®, Shire US; CANASA®, Axcan Scandipharm, Inc.; ROWASA®, Solvay).

In accordance with the methods described herein, a salicylate administered in combination with an anti-NKG2A antibody with or without anti-CTLA-4 and/or anti-PD-1 and/or anti-PD-L1 and/or LAG-3 antibodies and a non-absorbable steroid includes any overlapping or sequential administration of the salicylate and the non-absorbable steroid for the purpose of decreasing the incidence of colitis induced by the immunostimulatory antibodies. Thus, for example, methods for reducing the incidence of colitis induced by the immunostimulatory antibodies described herein encompass administering a salicylate and a non-absorbable concurrently or sequentially (e.g., a salicylate is administered 6 hours after a non-absorbable steroid), or any combination thereof. Further, a salicylate and a non-absorbable steroid can be administered by the same route (e.g., both are administered orally) or by different routes (e.g., a salicylate is administered orally and a non-absorbable steroid is administered rectally), which may differ from the route(s) used to administer the anti-NKG2A antibody and anti-CTLA-4 and/or anti-PD-1 and/or anti-PD-L1 and/or anti-LAG-3 antibodies.

The anti-NKG2A antibody antibodies and combination antibody therapies described herein may also be used in conjunction with other well-known therapies that are selected for their particular usefulness against the indication being treated (e.g., cancer). Combinations of the anti-NKG2A antibody antibodies described herein may be used sequentially with known pharmaceutically acceptable agent(s).

In one embodiment, the anti-NKG2A antibody antibodies and combination antibody therapies described herein can be used in combination (e.g., simultaneously or separately) with an additional treatment, such as irradiation, chemotherapy (e.g., using camptothecin (CPT-11), 5-fluorouracil (5-FU), cisplatin, doxorubicin, irinotecan, paclitaxel, gemcitabine, cisplatin, paclitaxel, carboplatin-paclitaxel (Taxol), doxorubicin, 5-fu, or camptothecin+apo2l/TRAIL (a 6× combo)), one or more proteasome inhibitors (e.g., bortezomib or MG132), one or more Bcl-2 inhibitors (e.g., BH3I-2' (bcl-xl inhibitor), indoleamine dioxygenase-1 (IDO1) inhibitor (e.g., INCB24360), AT-101 (R-(–)-gossypol derivative), ABT-263 (small molecule), GX-15-070 (obatoclax), or MCL-1 (myeloid leukemia cell differentiation protein-1) antagonists), iAP (inhibitor of apoptosis protein) antagonists (e.g., smac7, smac4, small molecule smac mimetic, synthetic smac peptides (see Fulda et al., Nat Med 2002; 8:808-15), ISIS23722 (LY2181308), or AEG-35156 (GEM-640)), HDAC (histone deacetylase) inhibitors, anti-CD20 antibodies (e.g., rituximab), angiogenesis inhibitors (e.g., bevacizumab), anti-angiogenic agents targeting VEGF and VEGFR (e.g., AVASTIN®), synthetic triterpenoids (see Hyer et al., Cancer Research 2005; 65:4799-808), c-FLIP (cellular FLICE-inhibitory protein) modulators (e.g., natural and synthetic ligands of PPARγ (peroxisome proliferator-activated receptor γ), 5809354 or 5569100), kinase inhibitors (e.g., Sorafenib), trastuzumab, cetuximab, Temsirolimus, mTOR inhibitors such as rapamycin and temsirolimus, Bortezomib, JAK2 inhibitors, HSP90 inhibitors, PI3K-AKT inhibitors, Lenalildomide, GSK3β inhibitors, IAP inhibitors and/or genotoxic drugs.

The anti-NKG2A antibody antibodies and combination antibody therapies described herein can further be used in combination with one or more anti-proliferative cytotoxic agents. Classes of compounds that may be used as anti-proliferative cytotoxic agents include, but are not limited to, the following:

Alkylating agents (including, without limitation, nitrogen mustards, ethylenimine derivatives, alkyl sulfonates, nitrosoureas and triazenes): Uracil mustard, Chlormethine, Cyclophosphamide (CYTOXAN™) fosfamide, Melphalan, Chlorambucil, Pipobroman, Triethylenemelamine, Triethylenethiophosphoramine, Busulfan, Carmustine, Lomustine, Streptozocin, Dacarbazine, and Temozolomide.

Antimetabolites (including, without limitation, folic acid antagonists, pyrimidine analogs, purine analogs and adenosine deaminase inhibitors): Methotrexate, 5-Fluorouracil, Floxuridine, Cytarabine, 6-Mercaptopurine, 6-Thioguanine, Fludarabine phosphate, Pentostatine, and Gemcitabine.

Suitable anti-proliferative agents for combining with anti-NKG2A antibody antibodies, without limitation, taxanes, paclitaxel (paclitaxel is commercially available as TAXOL™), docetaxel, discodermolide (DDM), dictyostatin (DCT), Peloruside A, epothilones, epothilone A, epothilone B, epothilone C, epothilone D, epothilone E, epothilone F, furanoepothilone D, desoxyepothilone Bl, [17]-dehydrodesoxyepothilone B, [18]dehydrodesoxyepothilones B, C12,13-cyclopropyl-epothilone A, C6-C8 bridged epothilone A, trans-9,10-dehydroepothilone D, cis-9,10-dehydroepothilone D, 16-desmethylepothilone B, epothilone B10, discodermolide, patupilone (EPO-906), KOS-862, KOS-1584, ZK-EPO, ABJ-789, XAA296A (Discodermolide), TZT-1027 (soblidotin), ILX-651 (tasidotin hydrochloride), Halichondrin B, Eribulin mesylate (E-7389), Hemiasterlin (HTI-286), E-7974, Cyrptohycins, LY-355703, Maytansinoid immunoconjugates (DM-1), MKC-1, ABT-751, T1-38067, T-900607, SB-715992 (ispinesib), SB-743921, MK-0731, STA-5312, eleutherobin, 17beta-acetoxy-2-ethoxy-6-oxo-B-homo-estra-1,3,5(10)-trien-3-ol, cyclostreptin, isolaulimalide, laulimalide, 4-epi-7-dehydroxy-14,16-didemethyl-(+)-discodermolides, and cryptothilone 1, in addition to other microtubuline stabilizing agents known in the art.

In some embodiments it may be desirable to render aberrantly proliferative cells quiescent in conjunction with or prior to treatment with anti-NKG2A antibody antibodies described herein, e.g., by administering to the patient hormones and steroids (including synthetic analogs), such as 17a-Ethinylestradiol, Diethylstilbestrol, Testosterone, Prednisone, Fluoxymesterone, Dromostanolone propionate, Testolactone, Megestrolacetate, Methylprednisolone, Methyltestosterone, Prednisolone, Triamcinolone, Chlorotrianisene, Hydroxyprogesterone, Aminoglutethimide, Estramustine, Medroxyprogesteroneacetate, Leuprolide, Flutamide, Toremifene, ZOLADEX™. When employing the methods or compositions described herein, other agents used in the modulation of tumor growth or metastasis in a clinical setting, such as antimimetics, can also be administered as desired.

Methods for the safe and effective administration of chemotherapeutic agents are known to those skilled in the art. In addition, their administration is described in the standard literature. For example, the administration of many of the chemotherapeutic agents is described in the Physicians' Desk Reference (PDR), e.g., 1996 edition (Medical Economics Company, Montvale, N.J. 07645-1742, USA); the disclosure of which is incorporated herein by reference thereto.

The chemotherapeutic agent(s) and/or radiation therapy can be administered according to therapeutic protocols known in the art. It will be apparent to those skilled in the art that the administration of the chemotherapeutic agent(s) and/or radiation therapy can be varied depending on the disease being treated and the known effects of the chemotherapeutic agent(s) and/or radiation therapy on that disease. Also, in accordance with the knowledge of the skilled clinician, the therapeutic protocols (e.g., dosage amounts and times of administration) can be varied in view of the observed effects of the administered therapeutic agents on the patient, and in view of the observed responses of the disease to the administered therapeutic agents.

Outcomes

Tumor response is determined, for example, by modified Response Evaluation Criteria in Solid Tumors (RECIST) established by the NCI.

With respect to target lesions, responses to therapy may include:

| | |
|---|---|
| Complete Response (CR) (RECIST V1.1) | Disappearance of all target lesions. Any pathological lymph nodes (whether target or non-target) must have reduction in short axis to <10 mm. |
| Partial Response (PR) (RECIST V1.1) | At least a 30% decrease in the sum of the diameters of target lesions, taking as reference the baseline sum diameters. |
| Progressive Disease (PD) (RECIST V1.1) | At least a 20% increase in the sum of the diameters of target lesions, taking as reference the smallest sum on study (this includes the baseline sum if that is the smallest on study). In addition to the relative increase of 20%, the sum must also demonstrate an absolute increase of at least 5 mm. (Note: the appearance of one or more new lesions is also considered progression). |
| Stable Disease (SD) (RECIST V1.1) | Neither sufficient shrinkage to qualify for PR nor sufficient increase to qualify for PD, taking as reference the smallest sum diameters while on study. |
| Immune-related Complete Response (irCR) (irRECIST) | Disappearance of all target lesions. Any pathological lymph nodes (whether target or non-target) must have reduction in short axis to <10 mm. |
| Immune-related Partial Response (irPR) (irRECIST) | At least a 30% decrease in the sum of diameters of target lesions and all new measurable lesions (e.g., Percentage Change in Tumor Burden), taking as reference the baseline sum diameters. Note: the appearance of new measurable lesions is factored into the overall Tumor Burden, but does not automatically qualify as progressive disease until the sum of the diameters increases by ≥20% when compared to nadir. |
| Immune-related Progressive Disease (irPD) (irRECIST) | At least a 20% increase in Tumor Burden (e.g., the sum of diameters of target lesions, and any new measurable lesions) taking as reference the smallest sum on study (this includes the baseline sum if that is the smallest on study). In addition to the relative increase of 20%, the sum must also demonstrate an absolute increase of at least 5 mm. Tumor assessments using immune-related criteria for progressive disease incorporates the contribution of new measurable lesions. Each net percentage change in tumor burden per assessment accounts for the size and growth kinetics of both old and new lesions as they appear. |
| Immune-related Stable Disease (irSD) (irRECIST) | Neither sufficient shrinkage to qualify for irPR nor sufficient increase to qualify for irPD, taking as reference the smallest sum diameters while on study. |

With respect to non-target lesions, responses to therapy may include:

| | |
|---|---|
| Complete Response (CR) (RECIST V1.1) | Disappearance of all non-target lesions. All lymph nodes must be non-pathological in size (<10 mm short axis). |
| Non-CR/Non-PD (RECIST V1.1) | Persistence of one or more non-target lesion(s). |
| Progressive Disease (PD) (RECIST V1.1) | Unequivocal progression of existing non-target lesions. The appearance of one or more new lesions is also considered progression. |
| Immune-related Complete Response (irCR) (irRECIST) | Disappearance of all non-target lesions. All lymph nodes must be non-pathological in size (<10 mm short axis). |
| Immune-related Progressive Disease (irPD) (irRECIST) | Increases in number or size of non-target lesion(s) does not constitute progressive disease unless/until Tumor Burden increases by 20% (e.g., the sum of the diameters at nadir of target lesions and any new measurable lesions increases by the required amount). Non-target lesions are not considered in the definition of Stable Disease and Partial Response. |

Patients treated according to the methods disclosed herein preferably experience improvement in at least one sign of cancer. In one embodiment, improvement is measured by a reduction in the quantity and/or size of measurable tumor lesions. In another embodiment, lesions can be measured on chest x-rays or CT or MRI films. In another embodiment, cytology or histology can be used to evaluate responsiveness to a therapy.

In one embodiment, the patient treated exhibits a complete response (CR), a partial response (PR), stable disease (SD), immune-related complete disease (irCR), immune-related partial response (irPR), or immune-related stable disease (irSD). In another embodiment, the patient treated experiences tumor shrinkage and/or decrease in growth rate, i.e., suppression of tumor growth. In another embodiment, unwanted cell proliferation is reduced or inhibited. In yet another embodiment, one or more of the following can occur: the number of cancer cells can be reduced; tumor size can be reduced; cancer cell infiltration into peripheral organs can be inhibited, retarded, slowed, or stopped; tumor metastasis can be slowed or inhibited; tumor growth can be inhibited; recurrence of tumor can be prevented or delayed; one or more of the symptoms associated with cancer can be relieved to some extent.

In other embodiments, administration of effective amounts of the anti-NKG2A antibody (or combinations anti-NKG2A antibody and at least one additional antibody, e.g., an anti-PD-1 antibody or anti-CTLA-4 antibody) according to any of the methods provided herein produces a reduction in size of a tumor, reduction in number of metastatic lesions appearing over time, complete remission, partial remission, or stable disease. In still other embodiments, the methods of treatment produce a comparable clinical benefit rate (CBR=CR+PR+SD≥6 months) better than that achieved by an anti-NKG2A antibody alone (or any one of the combined antibodies alone). In other embodiments, the improvement of clinical benefit rate is about 20% about 30%, about 40%, about 50%, about 60%, about 70%, about 80%, about 90%, or more compared to the anti-NKG2A antibody alone (or any one of the combined antibodies alone).

Vaccine Adjuvants

Anti-NKG2A antibodies described herein can be used to enhance antigen-specific immune responses by co-administration of an anti-NKG2A antibody with an antigen of interest, e.g., a vaccine. Accordingly, provided herein are methods of enhancing an immune response to an antigen in a subject, comprising administering to the subject: (i) the antigen; and (ii) an anti-NKG2A antibody, or antigen-binding fragment thereof, such that an immune response to the antigen in the subject is enhanced. The antigen can be, for example, a tumor antigen, a viral antigen, a bacterial antigen or an antigen from a pathogen. Non-limiting examples of such antigens include those discussed in the sections above, such as the tumor antigens (or tumor vaccines) discussed above, or antigens from the viruses, bacteria or other pathogens described above.

Detection and Diagnostics

In another aspect, provided herein are methods for detecting the presence of human NKG2A antigen in a sample, or measuring the amount of human NKG2A antigen, comprising contacting the sample, and a control sample, with an anti-NKG2A antibody, e.g., a monoclonal anti-human NKG2A antibody, or an antigen binding fragment thereof, that specifically binds to human NKG2A, under conditions that allow for formation of a complex between the antibody or fragment thereof and human NKG2A. The formation of a complex is then detected, wherein a difference complex formation between the sample compared to the control sample is indicative the presence of human NKG2A antigen in the sample. Moreover, the anti-NKG2A antibodies described herein can be used to purify human NKG2A via immunoaffinity purification.

The present disclosure is further illustrated by the following examples, which should not be construed as limiting. The contents of all figures and all references, GenBank sequences, patents and published patent applications cited throughout this application are expressly incorporated herein by reference.

EXAMPLES

The following are non-limiting examples of anti-NKG2A antibodies, compositions, and methods of the invention. It is understood that various other embodiments may be practiced consistent with the general description provided herein.

Example 1

Generation of Anti-huNKG2A Antibodies

Fully human and chimeric anti-NKG2A monoclonal antibodies, and fully human and chimeric antibodies that bind to the same epitope and/or cross-block the binding of the anti-NKG2A antibodies are described in this disclosure. We desired antibodies that bound specifically to human and cynomolgus monkey NKG2A-expressing cells, but not to human and cynomolgus monkey NKG2C-expressing cells. The anti-NKG2A antibodies described herein may be generated using several methods as described in this example.

Generation, Screening, and Selection Methods of Anti-NKG2A Antibodies

1. Hybridoma Method and Development

Using a hybridoma method, anti-NKG2A antibodies were generated using transgenic mice that express human antibody genes. Human IgG transgenic Kunming (KM) mice were immunized through footpad injection with the plasma membrane of BAF3 (a murine pro-B cell line)-human NKG2A (BAF3-hNKG2A) and hCD94 cells or hNKG2A-hCD94-mFc protein. Lymph nodes from these mice were harvested, and hybridomas were generated using a CytoPulse electroporation instrument, which uses a pulse of electricity to increase permeability of the cell membrane, allowing, for example, DNA to be introduced into the cell. Antibodies specific for human NKG2A were selected in a primary screening by Fluorescent Microvolume Assay Technology (FMAT) for their ability to bind to CHO-S-human NKG2A. A secondary confirmation screen by Fluorescence-Activated Cell Sorting (FACS) analysis was performed to identify monoclonal antibodies that bind specifically to human NKG2A expressed on the cell surface of the CHO-S transfectant cells.

As shown in FIG. 1A, in step 101, 40 fusions of the lymph node cells fused to a myeloma cell line yielded 153 antibody clones.

Subsequently, in step 102, the hybridoma supernatants were tested for their ability to block binding of the HLA-E pentamer (a fluorescent labeled MHC-peptide complex, ProImmune) to human NKG2A-expressing cells. This assay identified antibodies that were able to block binding of the HLA-E pentamer to human NKG2A-expressing cells, and narrowed the number of antibody clones for further development from 153 to 28 antibody clones.

Next, antigen specificity was determined by the binding of purified antibodies to human or cynomolgus monkey NKG2A-expressing or NKG2C-expressing cells. Specifically, in Step 103, the 28 antibody clones that blocked the HLA-E/NKG2A interaction were further screened by the binding of purified antibodies to human NKG2A-expressing and screened against the binding to hCD94 or hNKG2C-expressing cells. In this step, three antibody clones (13F3.A4, 11H9.A4, and 4G5.D1) were discovered and selected for further investigation.

In Step 104, the three antibody clones (13F3.A4, 11H9.A4, and 4G5.D1) were screened for cross-reactivity to cynomolgus monkey NKG2A-expressing Chinese Hamster Ovary (CHO) cells.

In Step 105, various functional assays and epitope binning experiments described in the Examples herein were used to characterize the anti-NKG2A antibodies In Step 106, further antibody optimization and mutational scan analysis, allowed for the discovery of additional anti-NKG2A antibodies with desired functional properties as described herein.

2. Antibody Library Generation Method

In addition to the hybridoma method to generate antibodies, the antibody library method was also used to generate additional anti-NKG2A antibodies. This method generated anti-NKG2A antibodies including the P1-069366 antibody, which showed desirable specific binding to both human and cynomolgus monkey NKG2A expressing cell lines, while binding to human NKG2C-expressing cells was advantageously not observed.

Figure 1B:
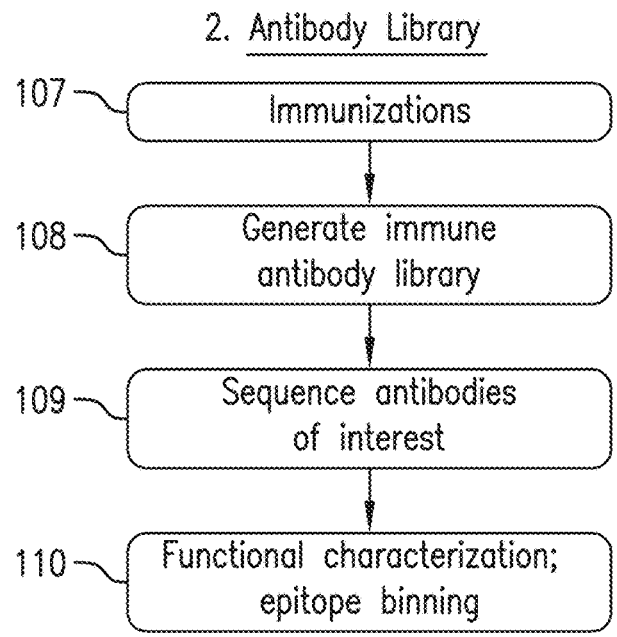

In this antibody library generation method, as shown in FIG. 1B, in step 107, nine transgenic mice expressing human antibodies were immunized with recombinant hNKG2A-hCD94-mFc fusion protein and plasma membranes from a cell line expressing cynomolgus monkey NKG2A. In step 108, the lymph nodes of the immunized animals were harvested and used to generate an immune antibody library. This library was expressed by yeast surface display and sorted using fluorescence-activated cell sorting (FACS) for antibodies that bound hNKG2A-hCD94-mFc recombinant protein, but not hNKG2C-hCD94-mFc recombinant protein. In step 109, the resulting population was sequenced using next generation sequencing (NGS), and antibodies of interest were synthesized and tested in assays. In step 110, functional characterization was performed. For example, to characterize the P1-069366 antibody, we measured binding of the antibody to CHO cell lines engineered to express human NKG2A-CD94, cynomolgus monkey NKG2A, or human NKG2C-CD94 by FACS. In addition, epitope binning was performed against, for example, the 13F3.A4 antibody and variants, including the NKG2A.9 antibody, as described in the Examples herein.

3. Single B Cell Cloning (SBCC) Method

Along with the hybridoma and antibody library methods to generate anti-NKG2A antibodies, a third method was used to generate over 200 additional anti-NKG2A antibodies.

Figure 1C:
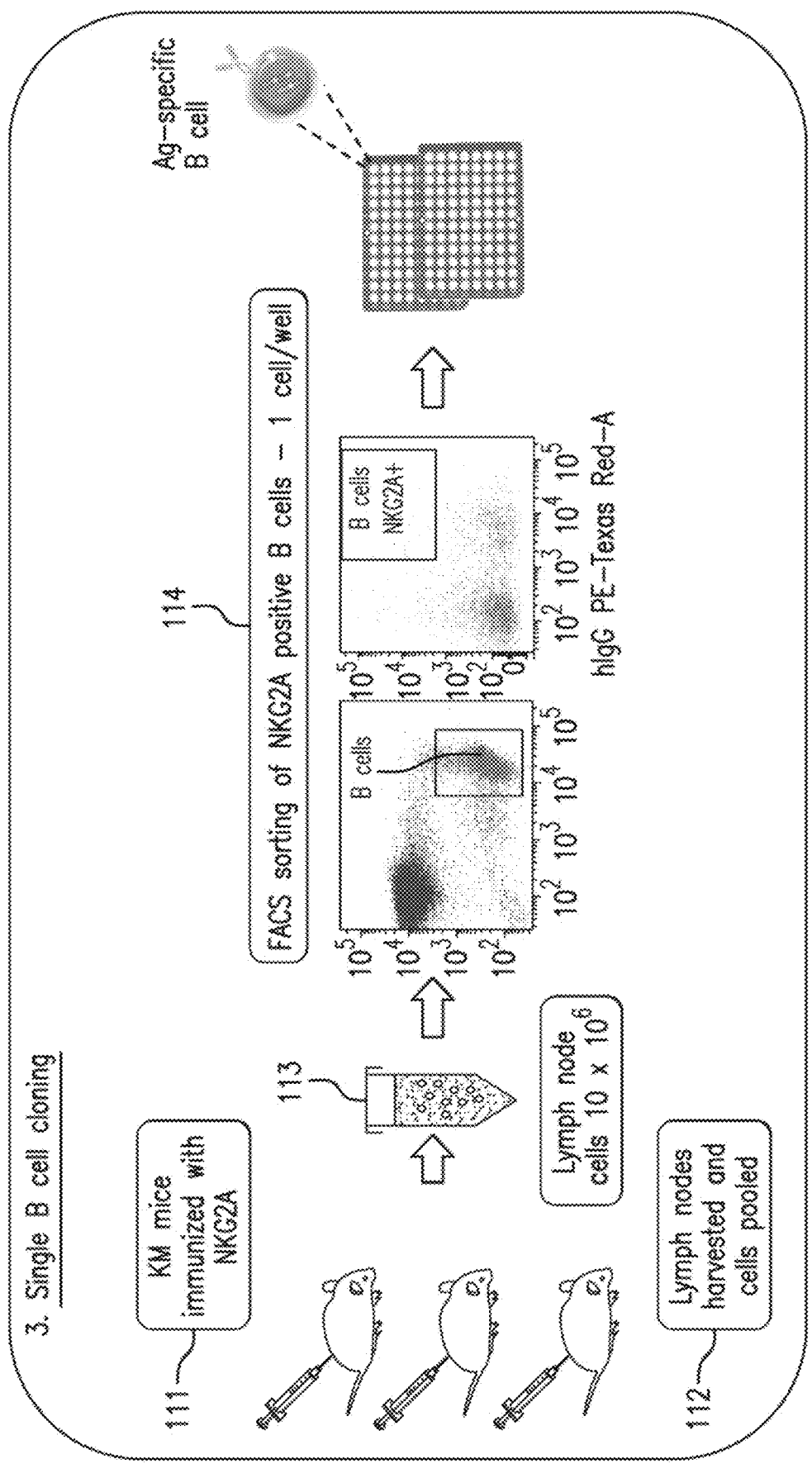

Anti-huNKG2A antibodies were generated using transgenic mice that express human antibody genes. This SBCC method was used to generate over 200 human anti-NKG2A monoclonal antibodies. As shown in FIG. 1C, in step 111, human IgG transgenic (KM) mice were immunized through footpad injection with the plasma membranes of BAF3 cell lines expressing-human NKG2A and cynomolgus monkey NKG2A, respectively, and hNKG2A-hCD94-mFc protein. In step 112, lymph nodes from these mice were harvested and cells derived were used for the SBCC method. In step 113, $10 \times 10^6$ lymph node cells were isolated from the lymph nodes. In step 114, the antigen specific B cell selection/sorting was based on cell surface human IgG expression, and we primarily used flow cytometry for sorting antigen positive (Ag+) B cells. The lymph nodes of the immunized animals were harvested and used to isolate antigen-specific B cells, that is, B cells specific to NKG2A.

Our FACS staining strategy required the use of soluble target antigen that is fluorescently labeled/biotinylated, and included a panel of B cell specific cell surface expressed markers, e.g. mouse CD19, mouse B220, and human IgG. This multiparametric FACS successfully resulted in the identification and sorting of NKG2A-specific B cells. Selective FACS staining resulted in isolation of hNKG2A-hCD94-mFc recombinant protein positive, but not hNKG2C-CD94-Fc recombinant protein B cells. The human IgG VH and VK genes from these sorted B cells were amplified by polymerase chain reaction (PCR) and molecularly expressed as recombinant human IgG1. The antibodies thus generated were tested in binding assays such as ELISA, HTRF and FACS.

The goal was to generate antibodies that specifically bound to NKG2A but not to NKG2C protein. We identified some antibodies that specifically bound to NKG2A, and some that were NKG2C negative. A very small number (rare) of B cell clones were identified that were cynomolgus and human NKG2A cross-reactive and NKG2C negative. NGS was performed on the SBCC derived B cell clones to generate human IgG VH and VK sequencing data. The selected panel of NKG2A specific antibodies were tested for further assays. However, none of the clones sufficiently blocked human NKG2A/HLA-E interaction, so these antibodies were not pursued for further development, as discussed in further detail in Example 3(2) below.

Example 2

Mutational Scan and Other Antibody Optimizations

A mutational scan was conducted in which a library of single-site mutations generated additional variants of anti-NKG2A antibodies, including the NKG2A.11 antibody (also known as 13F3.A4 VH I107T, VK N30P).

Figure 2:
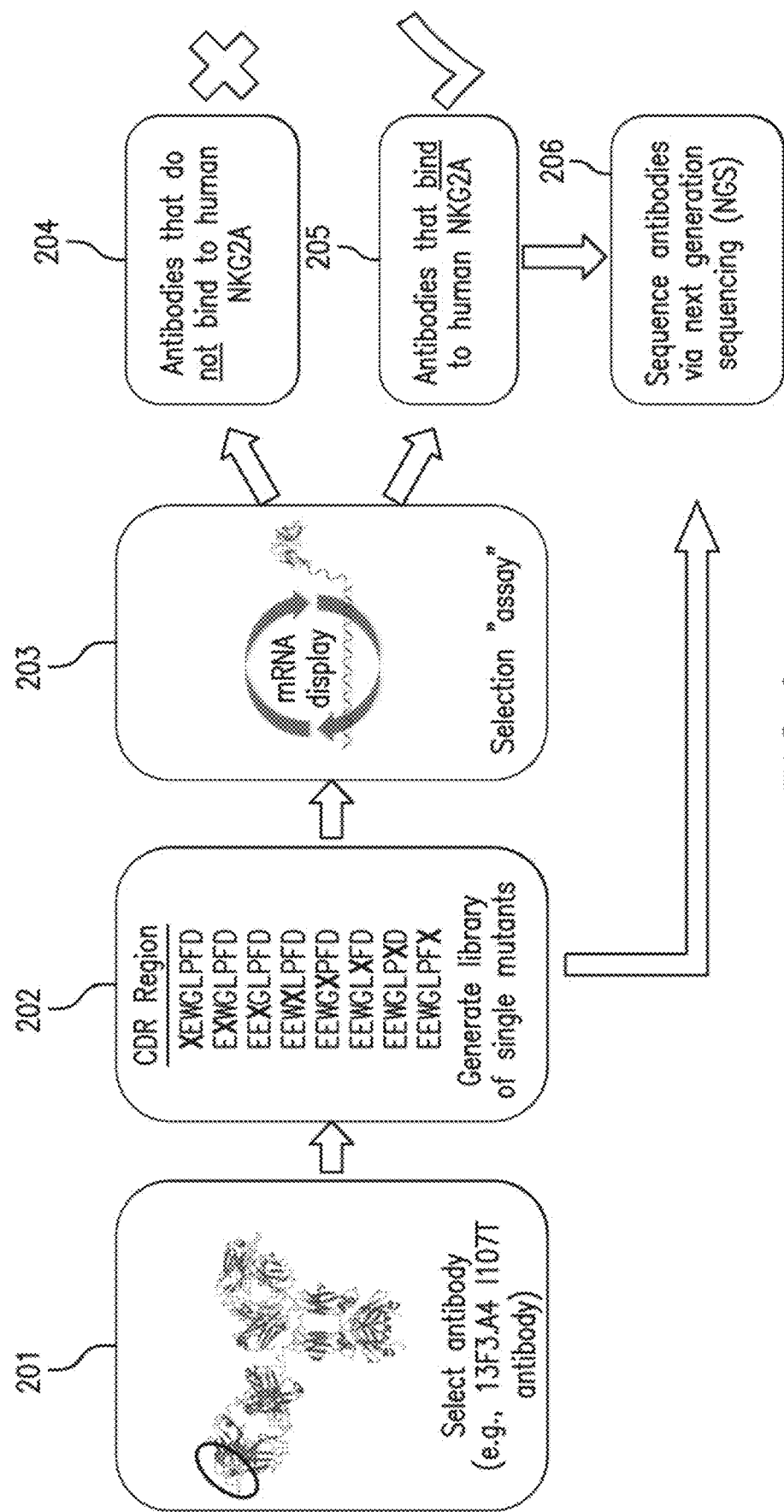
FIG. 2 illustrates the mutational scan analysis used to optimize the anti-NKG2A antibodies that were discovered. Specifically.

FIG. 2 illustrates the mutational scan analysis. High throughput sequencing was combined with protein display to allow simultaneous measurement of the relative fitness of every possible single-site CDR mutant on a scale that would be onerous for a more traditional approach. Deep mutational scanning approaches have been described in Araya et al., Trends in Biotechnology 29: 435-442 (2001); Forsynth et al., mAbs 5:523-53 (2013); and Wrenbeck et al. (2017) Curr. Opin. Struct. Biol. 45:36.

First, in step 201, an antibody of interest was selected to generate mutations of the antibody. Specifically, the 13F3.A4 I107T anti-NKG2A antibody was selected. The binding paratope of the 13F3.A4 I107T hybridoma antibody to NGK2A was investigated using a deep mutational scan. Second, in step 202, an scFv (single chain) library was created where each individual amino acid substitution in the light chain CDR1 region (LCDR1), light chain CDR3 region (LCDR3), and heavy chain CDR1-3 regions (HCDR1, HCDR2, and HCDR3) was generated using NNK oligonucleotides. This library of single mutants was sequenced using next generation sequencing (NGS) techniques. In generating this library of single mutants, for each CDR sequence, multiple oligonucleotides were designed that individually incorporated an NNK codon at each position, where N=A, C, G, T, and K=G, T. The use of these degenerate codons allowed encoding of all 20 naturally-occurring amino acids (plus a stop codon) at the position where the NNK codon was incorporated. The Kabat definition was used for all CDRs except HCDR1, where the AbM definition was used (Abhinandan and Martin (2008) Mol. Immunol. 45:3832; Swindells et al. (2017) J. Mol. Biol. 429:356), and position 102 of HCDR3 was not included in the analysis. Third, in step 203, using mRNA display (Xu L et al. (2002) Chemistry & Biology 9: 933; Roberts R W and J W Szostak (1997) Proc. Natl. Acad. Sci. USA 94:12297; Kurz et al. (2000) Nucleic Acids Res. 28(18): E83), the DNA library was taken through a single round of in vitro transcription and translation, during which the encoding mRNA was fused to its own scFv protein molecule via a puromycin linkage. During selection, any scFvs that bound biotin-labeled hNKG2A-hCD94-mFc fusion protein were captured by magnetic streptavidin beads, eluted, and amplified by PCR (step 205). As shown in step 204, antibodies that did not bind to human NKG2A were not selected for further testing and development. Finally, in step 206, the initial library generated in step 202 and the eluted DNA from step 205 were sequenced using next generation sequencing (NGS).

Next-Generation Sequencing (NGS) Data Analysis: During NGS data analysis, paired-end forward and reverse read sequences from NGS were assembled using FLASH (Magoc and Salzberg (2011) *Bioinformatics* 27:2957) and binned according to population, mutation position, and identity of the mutated amino acid. All sequences of poor quality and those containing multiple mutation sites were eliminated from the analysis. Next, the frequency of each sequence in the post-selection population was divided by the frequency in the starting population to derive an enrichment ratio (ER). In other words, the enrichment ratio is the counts of a particular sequence variant in the NKG2A-bound sample (step 205) divided by the counts in the initial library (step 202). This was then normalized to the enrichment ratio of the parental 13F3.A4 I107T antibody:

$$\text{Enrichment Ratio} = \frac{\text{Frequency after selection (step 205)}}{\text{Frequency in starting library (step 202)}}$$

→ Normalize to parental value at each position

Figure 3:
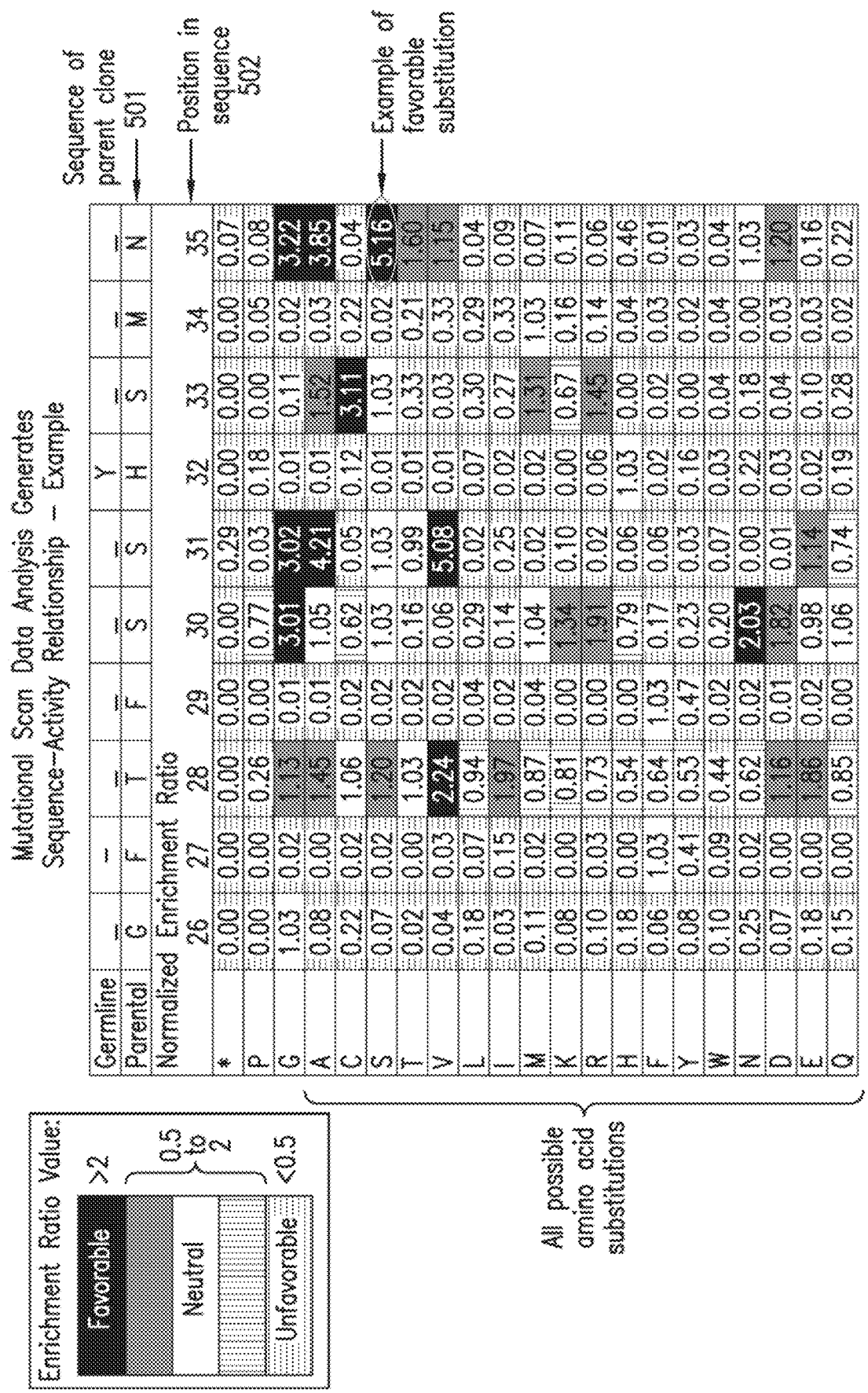
FIG. 3 is an exemplary heat map that was generated using mutational scan analysis, and allows for the interpretation of the sequence-activity relationship of single amino acid substitutions.

In this manner, the effect on NKG2A binding of every single amino acid substitution in the CDR regions as discussed herein was assessed. FIG. 3 is an exemplary heat map that was generated using the mutational scan data analysis, and allows for the interpretation of the sequence-activity relationship of single amino acid substitutions. The HCDR1 sequence (AbM definition) of the parental clone 501 is shown, and the position in the sequence 502 is also shown. Generally, the error in this method is approximately two-fold. Thus, enrichment ratio (ER) values from 0.5 to 2 are considered to be neutral substitutions, i.e., substitutions that maintain binding properties to NKG2A protein. ER values greater than 2 are considered favorable or preferred for binding, and ER values less than 0.5 are considered unfavorable for binding. As an example, a substitution from parental clone N in position 35 to S results in an ER value of 5.16, which is greater than 2 and is, thus, an example of a favorable or preferred substitution.

Figure 5A:
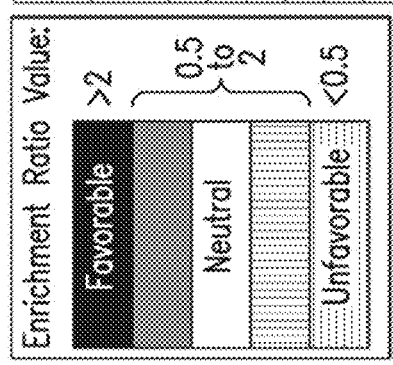
FIGS. 5A-E are the heat maps that were generated using the mutational scan analysis of 13F3.A4 I107T antibody for LCDR1 substitutions (SEQ ID NOs: 194 and 30, germline and parental, respectively) (FIG. 5A); LCDR3 substitutions (SEQ ID NOs: 195 and 15, germline and parental, respectively) (FIG. 5B); HCDR1 substitutions (SEQ ID NOs: 196 and 192, germline and parental, respectively) (FIG. 5C); HCDR2 substitutions (SEQ ID NOS: 42 and 11, germline and parental, respectively) (FIG. 5D); and HCDR3 substitutions (SEQ ID NOS: 193 and 193, germline and parental, respectively (FIG. 5E).

The CDR positions analyzed using the mutational scan method are shown in FIG. 4. As discussed herein, the Kabat definition was used for all CDRs except HCDR1, where the AbM definition was used. To develop an anti-NKG2A antibody with desirable biophysical properties, the mutational scan data was used to remove the "NS" deamidation chemical liability in LCDR1 by identifying amino acid substitutions that would retain similar binding to NKG2A protein as the 13F3.A4 I107T antibody. Based on this analysis, as shown in FIG. 5A, N30P in LCDR1 was chosen as a preferred (favorable) substitution, and the NKG2A.11 antibody (also known as 13F3 VH I107T VK N30P) was generated. This molecule was synthesized and cloned into an IgG expression vector with the human IgG1.3f Fc region and human constant kappa (light chain). The IgG protein was expressed for further downstream characterization.

The mutation scan analysis provided a rich set of information about the effect of single amino acid substitutions in the 13F3.A4 I107T anti-NKG2A antibody on binding to NKG2A protein, as shown in FIGS. 5A-E and summarized in Table 1 below.

TABLE 1

Single site mutations in the CDR sequences of 13F3.A4 I107T anti-NKG2A antibody that maintain or increase the ability of the antibody to bind to NKG2A.

| CDR Region | Position (Under Kabat definition except HCDR1 is under AbM definition) | Preferred substitutions that maintain or increase binding to NKG2A (heat maps are shown in FIG. 5A-E) | Amino acids that maintain binding to NKG2A, including parent amino acid sequence (heat maps are shown in FIG. 5A-E) |
|---|---|---|---|
| LCDR1 | 24, $X_1$ | | G, A, C, S, T, V, L, I, M, K, R (parent), H, F, Y, W, N, D, E, Q |
| | 25, $X_2$ | C, T, V, M | P, G, A (parent), S, L, I, F, Y, N, E, Q |
| | 26, $X_3$ | | P, G, A, C, S(parent), T, V, L, I, M, K, R, H, F, Y, W, N, D, E, Q |
| | 27, $X_4$ | G | P, A, C, S, T, V, L, I, M, K, R, H, F, Y, W, N, D, E, Q (parent) |
| | 28, $X_5$ | L | P, A, C, S, T, V, I, M, K, R, H, F, Y, W, N, D, E, Q, G (parent) |
| | 29, $X_6$ | C, H, F, N, D, E | P, G, A, S, T, V, L, I (parent) M, K, R, Y, W, Q |
| | 30, $X_7$ | P | G, A, C, S, T, V, L, I, M, K, H, F, Y, W, N (parent), D, E, Q |
| | 31, $X_8$ | P, G, C, D, E | A, S (parent), T, L, I, M, H, F, Y, W, N, Q |
| | 32, $X_9$ | V, I, F, Y, D, E | G, A (parent), C, S, T, L, M, H, W, N |
| | 33, $X_{10}$ | | A, C, T, V, L (parent), I |
| | 34, $X_{11}$ | E | A (parent), T, V |

TABLE 1-continued

Single site mutations in the CDR sequences of 13F3.A4 I107T anti-NKG2A antibody that maintain or increase the ability of the antibody to bind to NKG2A.

| CDR Region | Position (Under Kabat definition except HCDR1 is under AbM definition) | Preferred substitutions that maintain or increase binding to NKG2A (heat maps are shown in FIG. 5A-E) | Amino acids that maintain binding to NKG2A, including parent amino acid sequence (heat maps are shown in FIG. 5A-E) |
|---|---|---|---|
| LCDR3 | 89, $X_{12}$ | | Q (parent) |
| | 90, $X_{13}$ | D | A, S, T, K, N, E, Q (parent) |
| | 91, $X_{14}$ | C, M, H, W, N | A, T, L, F (parent) |
| | 92, $X_{15}$ | | P, A, C, S, I, H, F, Y, W, N (parent), D, E, Q |
| | 93, $X_{16}$ | V, D, E | G, A, C, S (parent), T, L, I, M, K, R, H, F, Y, W, N, Q |
| | 94, $X_{17}$ | | M, H, F, Y (parent), W |
| | 95, $X_{18}$ | | P (parent), G, A, S, M, D, E, Q |
| | 96, $X_{19}$ | | C, L (parent), F, W |
| | 97, $X_{20}$ | | G, A, C, S, T (parent), V, I, M, K, H, F, Y, W, N, D, E, Q |
| HCDR1 | 26, $X_{21}$ | | G (parent) |
| | 27, $X_{22}$ | | F (parent) |
| | 28, $X_{23}$ | V | G, A, C, S, T (parent), L, I, M, K, R, H, F, Y, N, D, E, Q |
| | 29, $X_{24}$ | | F (parent) |
| | 30, $X_{25}$ | G, N | P, A, C, S (parent), M, K, R, H, D, E, Q |
| | 31, $X_{26}$ | G, A, V | S (parent), T, E, Q |
| | 32, $X_{27}$ | | H (parent) |
| | 33, $X_{28}$ | C | A, S (parent), M, K, R |
| | 34, $X_{29}$ | | M (parent) |
| | 35, $X_{30}$ | G, A, S | T, V, N (parent), D |
| HCDR2 | 50, $X_{31}$ | S, Q | G, A (parent), C, L, M, K, F, D |
| | 51, $X_{32}$ | A | S, V, L, I (parent), M, N, E, Q |
| | 52, $X_{33}$ | | S (parent) |
| | 52a, $X_{34}$ | C | S (parent) |
| | 53, $X_{35}$ | Q | S (parent) |
| | 54, $X_{36}$ | | S (parent) |
| | 55, $X_{37}$ | F, Y, W | A, C, S (parent), T, M, R, H |
| | 56, $X_{38}$ | | Y (parent) |
| | 57, $X_{39}$ | | I (parent) |
| | 58, $X_{40}$ | | G, A, S, M, K, R, H, F, Y (parent), N, E, Q |
| | 59, $X_{41}$ | | G, S, T, V, M, R, H, F, Y (parent), W, N, Q |
| | 60, $X_{42}$ | H, Q | P, G, A (parent), C, S, T, V, L, I, M, K, R, F, Y, W, N, D, E |
| | 61, $X_{43}$ | | P, G, A, C, S, T, V, L, I, M, K, R, H, F, Y, W, N, D (parent), E, Q |
| | 62, $X_{44}$ | | P, G, A, C, S (parent), T, V, L, I, M, K, R, H, F, Y, W, N, D, E, Q |
| | 63, $X_{45}$ | | P, G, A, C, S, T, V (parent), L, I, M, K, R, H, F, Y, W, N, D, E, Q |
| | 64, $X_{46}$ | | P, G, A, C, S, T, V, L, I, M, K (parent), R, H, F, Y, W, N, D, E, Q |
| | 65, $X_{47}$ | | P, G (parent), A, C, S, T, V, L, I, M, K, R, H, F, Y, W, N, D, E, Q |

TABLE 1-continued

Single site mutations in the CDR sequences of 13F3.A4 I107T anti-NKG2A antibody that maintain or increase the ability of the antibody to bind to NKG2A.

| CDR Region | Position (Under Kabat definition except HCDR1 is under AbM definition) | Preferred substitutions that maintain or increase binding to NKG2A (heat maps are shown in FIG. 5A-E) | Amino acids that maintain binding to NKG2A, including parent amino acid sequence (heat maps are shown in FIG. 5A-E) |
|---|---|---|---|
| HCDR3 | 95, $X_{48}$ | | E (parent) |
| | 96, $X_{49}$ | | M, E (parent) |
| | 97, $X_{50}$ | | W (parent) |
| | 98, $X_{51}$ | | G (parent) |
| | 99, $X_{52}$ | | S, L (parent), H |
| | 100, $X_{53}$ | | P (parent) |
| | 100a, $X_{54}$ | | F (parent) |
| | 101, $X_{55}$ | | D (parent) |

Figure 5B:
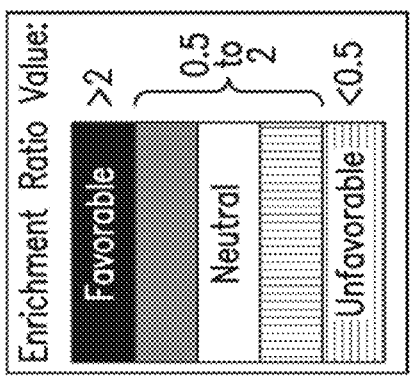
Figure 5C:
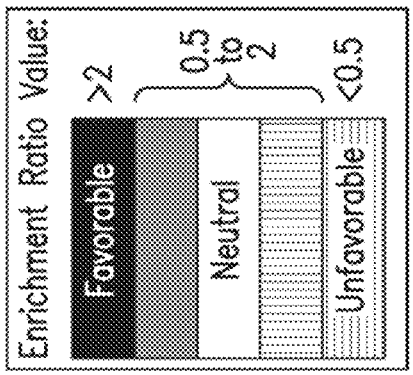
Figure 5D:
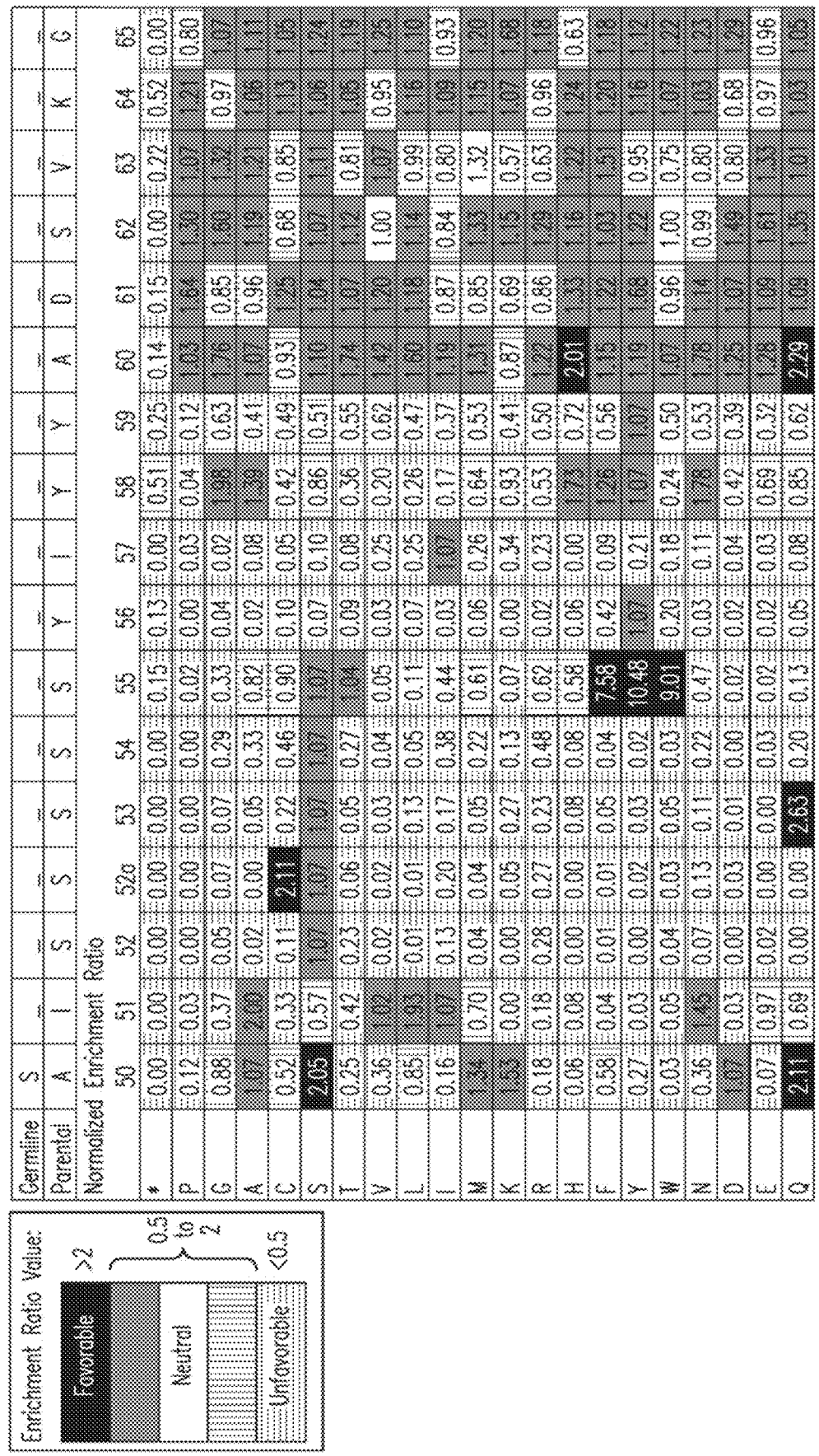
Figure 5E:
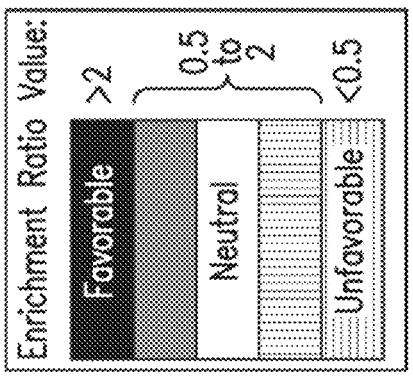

Using the full deep mutational scanning data, one of ordinary skill in the art would understand that many amino acid positions as shown in the data in FIG. 5A-E are tolerant to mutation, meaning that amino acid substitutions can be made at these positions and still maintain the desired functional ability to specifically bind to NKG2A protein. One of ordinary skill in the art would understand that certain positions, for example LCDR position 89 (as shown in FIG. 5B), as well as HCDR positions 26, 27, 29, 32, and 34 (as shown in FIG. 5C); HCDR positions 52, 52a, 53, 54, 56, 57 (as shown in FIG. 5D); and HDCR positions 95, 96, 97, 98, 99, 100, 100a, and 101 (as shown in FIG. 5E) were the most conserved, where only a single or a few amino acid types at these positions maintained binding to NKG2A protein. One of ordinary skill in the art would be able to design amino acid substitutions using this data to maintain binding to NKG2A protein.

Example 3

Discovery of Anti-NKG2A Antibodies with Desired, Unexpected Functional Characteristics After Analyzing Hundreds of Antibodies that Did Not Exhibit Such Characteristics.
(1) Discovery, Design, and Experimental Testing of Anti-NKG2A Antibodies Development of hundreds of anti-NKG2A antibodies was not pursued because the antibodies did not display certain desired functional properties as described herein. This difficulty in discovering anti-NKG2A antibodies with desired functional properties was partly due to the high sequence homology between the human NKG2A and human NKG2C proteins, as exemplified in FIG. 6. The sequence alignment was performed using Vector NTI software and the Align X program. FIG. 6 shows that 76% of amino acid residues (177 out of 233 amino acid residues) are conserved, and 6% of amino acid residues (13 of 233 amino acid residues) are similar between the canonical sequence of human NKG2A protein (SEQ ID NO: 182) and human NKG2C protein (hNKG2C, SEQ ID NO: 3).

It is well-known in the art that 20 different amino acids occur in nature, and that amino acids can be grouped together as in different classes and, thus, are "similar" based on their physicochemical properties. Amino acids that are physicochemically similar are often more interchangeable, that is, substitutable, than ones that are not. The following table provides a grouping of amino acids that have similar characteristics as defined, for example, by their side chains:

| Amino acid characteristic | | Examples | | |
|---|---|---|---|---|
| Polar | Polar, positively charged | Arginine | Arg | R |
| | | Histidine | His | H |
| | | Lysine | Lys | K |
| | Polar, negatively charged | Aspartic acid | Asp | D |
| | | Glumatic acid | Glu | E |
| | Polar, neutral | Serine | Ser | S |
| | | Threonine | Thr | T |
| | | Asparagine | Asn | N |
| | | Glutamine | Gln | Q |
| Non-polar | Non-polar aliphatic | Alanine | Ala | A |
| | | Valine | Val | V |
| | | Leucine | Leu | L |
| | | Isoleucine | Ile | I |
| | | Methionine | Met | M |
| | Non-polar aromatic | Phenylalanine | Phe | F |
| | | Tyrosine | Tyr | Y |
| | | Tryptophan | Trp | W |
| | | Proline | Pro | P |
| | | Glycine | Cys | C |
| Special characteristics | | Asparagine/ Aspartate | Asx | |
| | | Glutamine/ Glutamate | Glx | |

*Glycine does not have a side chain, and classification is not straight-forward. Glycine is generally found at the protein surface within loop or coil regions, which provides high flexibility to the polypeptide chain at these locations.

In summary, human NKG2A and human NKG2C share approximately 82% of the same or similar amino acid sequences. This high sequence homology between human NKG2A and human NKG2C made it a very difficult process to discover anti-NKG2A antibodies that not only bound with high affinity and specificity to the NKG2A protein, but also bound with low or no affinity and specificity to the NKG2C protein.

Surprisingly, the inventors discovered that the 13F3.A4 antibody exhibited certain desired functional characteristics as described in detail herein. FIG. 7A-B show the amino acid sequences of the heavy chain variable region (FIG. 7A) and light chain variable region (FIG. 7B) of the 13F3.A4 anti-NKG2A antibodies. Evidencing the difficulty of discovering anti-NKG2A antibodies that exhibited desired functional characteristics to, for example, treat cancer, even several variants of the 13F3.A4 antibody, which were at first considered potential lead antibodies, ultimately did not exhibit the desired functional properties. Table 2 summarizes certain anti-NKG2A antibodies including variants of the 13F3.A4 antibody that were generated and functionally characterized. Certain variants of the 13F3.A4 antibody, including the NKG2A.9 antibody, unexpectedly exhibited the desired functional characteristics described herein.

TABLE 2

| Anti-NKG2A Antibody and Functional Characterization | | | |
|---|---|---|---|
| Parental Hybridoma Clone | Recombinant Antibody Name | Antibody Isotype | Description and Functional Characterization |
| 11H9.A4 | NKG2A.5 | IgG1f | Tested in CHO-hNKG2A/HLA-E blocking assay<br>Tested in CHO-cynomolgus NKG2A binding assay. NKG2A.5 showed poor binding to cynomolgus NKG2A expressing CHO cells and was not further developed.<br>FIG. 9A-9B show the heavy chain and light variable region sequences of the 11H9 antibody. |
| 11H9.A4 | NKG2A.5 | IgG1.3f | Tested in CHO-hNKG2A/HLA-E blocking assay<br>Tested in CHO-cynomolgus NKG2A binding assay. Showed poor binding to cynomolgus NKG2A expressing CHO cells and was not further developed. |
| 13F3.A4 | NKG2A.6 | IgG1.3f and IgG1f | Tested in CHO-hNKG2A/HLA-E blocking assay. NKG2A.6 (the parental antibody of, for example, NKG2A.9 and NKG2A.11) blocked the hNKG2A/HLA-E interaction.<br>Tested in CHO-cynomolgus NKG2A binding assay. NKG2A.6 (the parental antibody of, for example, NKG2A.9 and NKG2A.11) bound to cynomolgus NKG2A<br>Based on the assay results, NKG2A.6-IgG1.3f antibody was further developed and led to the discovery and development of, for example, the NKG2A.9 and NKG2A.11-IgG1.3f antibodies. |
| 13F3.A4 | NKG2A.6 | IgG2.5 | Anti-NKG2A 13F3.A4 with human IgG2-C131S (codon-optimized)<br>Not tested in any assays |
| 13F3.A4 VH-I107T, VK-N30S | NKG2A.9 | IgG1.3f | 13F3.A4 with VH-I107T FW reversion and VK-N30S to remove deamidation site (codon-optimized)<br>Discovered and characterized in numerous functional assays as described in the Examples herein, and surprisingly showed desired functional characteristics.<br>FIG. 15 shows the light and heavy chain amino acid sequences of the NKG2A.9 antibody. |
| 13F3.A4 VH-I107T, VK-N30Q | NKG2A.10 | IgG1.3f | 13F3.A4 with VH-I107T FW reversion and VK-N30Q to remove deamidation site<br>Tested in CHO-hNKG2A/HLA-E blocking and CHO-hNKG2A binding assays |
| 13F3.A4 VH-I107T, VK-N30P | NKG2A.11 | IgG1.3f | 13F3.A4 with VH-I107T FW reversion and VK-N30P to remove deamidation site<br>Tested in CHO-hNKG2A/HLA-E blocking and CHO-hNKG2A binding assays |
| 13F3.A4 VH-I107T | NKG2A.12 | IgG1.3f | 13F3.A4 with VH-I107T FW reversion<br>Tested in CHO-hNKG2A/HLA-E blocking and CHO-hNKG2A binding assays |

TABLE 2-continued

Anti-NKG2A Antibody and Functional Characterization

| Parental Hybridoma Clone | Recombinant Antibody Name | Antibody Isotype | Description and Functional Characterization |
|---|---|---|---|
| 13F3.A4 VK-N30S | NKG2A.13 | IgG1.3f | 13F3.A4 with N30S to remove deamidation site<br>Not tested in any assays because the NKG2A.13 antibody did not have sufficient yield. |
| 13F3.A4 VK-N30Q | NKG2A.14 | IgG1.3f | 13F3.A4 with N30Q to remove deamidation site<br>Tested in CHO-hNKG2A/HLA-E blocking and CHO-hNKG2A binding assays |
| 13F3.A4 VK-N30P | NKG2A.15 | IgG1.3f | 13F3.A4 with N30P to remove deamidation site<br>Tested in CHO-hNKG2A/HLA-E blocking and CHO-hNKG2A binding assays |
| 2G6.C2 | NKG2A.16 | IgG1.3f and IgG1f-Fab6H | Tested in CHO-cynomolgus NKG2A binding assay.<br>The antibody showed poor binding to cynomolgus NKG2A expressing CHO cells and was not further developed.<br>The antibody also showed increased functionality of NKG2A-negative expressing cells, which suggested that the antibody does not directly affect the NKG2A/HLA-E pathway.<br>FIG. 8A-B shows the heavy chain (FIG. 8A) and light chain (FIG. 8B) amino acid sequences of the 2G6.C2 antibody. |
| 13F3 VH-I107T, VK-N30S-Y49S | NKG2A.18 | IgG1.3f | Hydrophobic patch mutants were generated to try and reduce undesired levels of aggregation.<br>None of the hydrophobic patch mutants were tested in any assays. |
| 13F3 VH-I107T, VK-N30S-Y94T | NKG2A.19 | | |
| 13F3 VH-I107T, VK-N30S-Y94A | NKG2A.20 | | |
| 13F3 VH-I107T, VK-N30S-Y94N | NKG2A.21 | | |
| 13F3 VH-Y56T-I107T, VK-N30S | NKG2A.22 | | |
| 13F3 VH-I57T-I107T, VK-N30S | NKG2A.23 | | |
| 13F3 VH-Y58N-I107T, VK-N30S | NKG2A.24 | | |
| 13F3 VH-Y58S-I107T, VK-N30S | NKG2A.25 | | |
| 27H4.D4 | NKG2A.17 | mIgG1-D265A | 27H4.D4 was re-expressed as NKG2A.17, a chimeric antibody with mouse IgG1-D265A and mouse kappa constant regions.<br>The 27H4.D4 antibody is a non-competing antibody that was generated to bind NKG2A |

TABLE 2-continued

Anti-NKG2A Antibody and Functional Characterization

| Parental Hybridoma Clone | Recombinant Antibody Name | Antibody Isotype | Description and Functional Characterization |
|---|---|---|---|
| | | | receptor in the presence of the anti-NKG2A antibody of interest, i.e., generated to bind to the same antigen as the target antibody (here, NKG2A), but not to the same epitope. This allowed measurement of the NKG2A receptor expression in the presence of the anti-NKG2A antibody of interest. |

For the reasons described herein and as shown by the numerous anti-NKG2A antibodies that were not selected for further development due to undesired functional characteristics, generating and discovering anti-NKG2A antibodies with the desired functional properties was an extremely difficult process. For example, even during advanced stages of anti-NKG2A antibody development, the 2G6.C2, 4G5.D1, 11H9.A4 and 1G5.B2 antibodies, which were initially considered potential lead antibodies, were ultimately not selected for further development because they did not exhibit all of the desired functional properties. FIG. 8A-B show the sequences of the heavy and light chain variable region of the 2G6.C2 antibody. FIG. 9A-B show the sequences of the heavy and light chain variable region of the 11H9.A4 antibody. FIG. 10A-B show the sequences of the heavy and light chain variable region of the 4G5.D1 antibody. FIG. 11A-B show the sequences of the heavy and light chain variable region of the 1G5.B2 antibody. These examples, amongst others described herein, demonstrate the difficulty of generating anti-NKG2A antibodies with the desired functional characteristics, including specific binding to NKG2A protein and not to NKG2C protein. As explained herein, part of the difficulty in discovering anti-NKG2A antibodies with desired functional properties was due to the high sequence homology between the human NKG2A and human NKG2C proteins.

Figure 12:
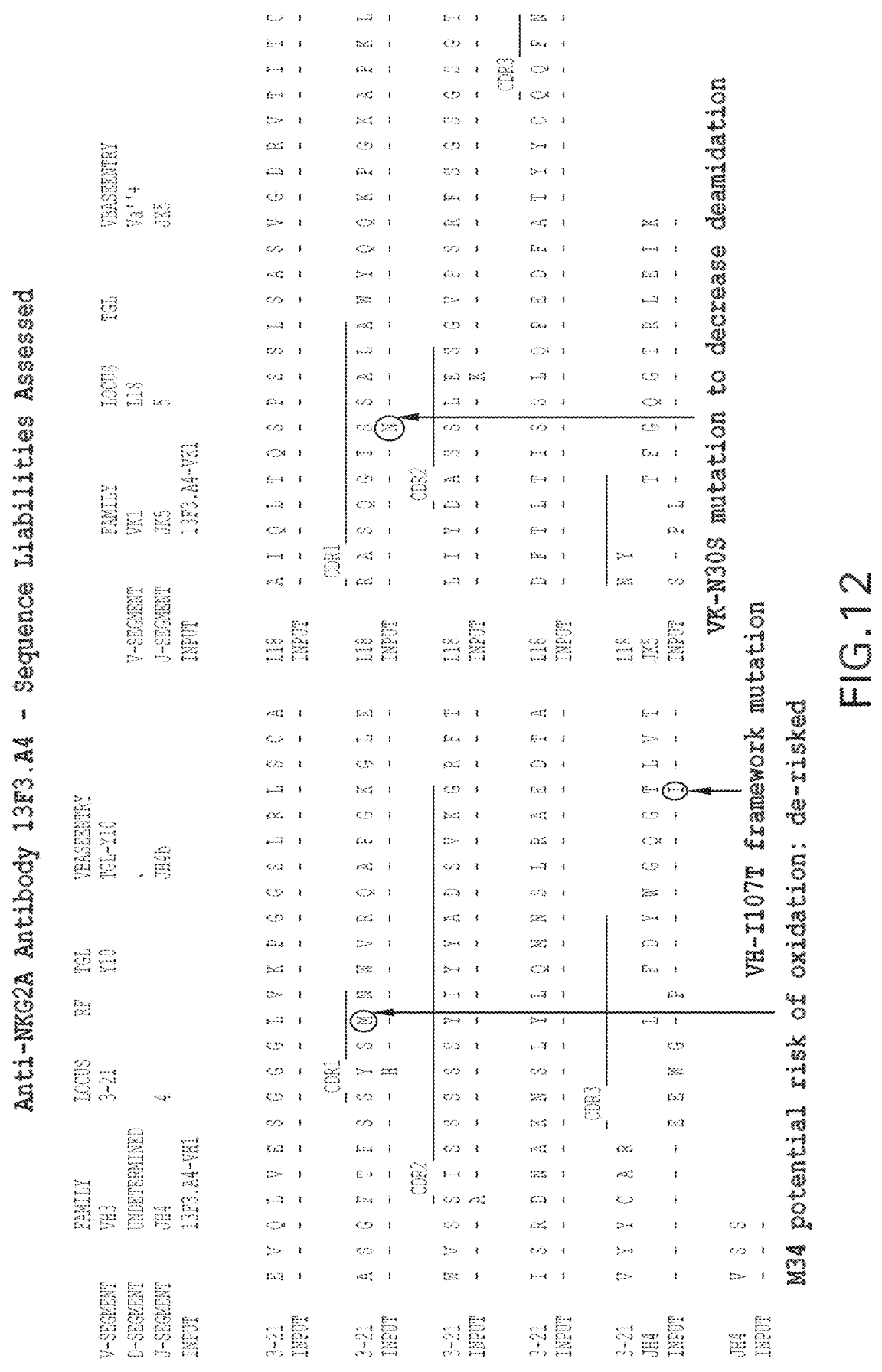

Variants of the 13F3.A4 antibody were discovered and further characterized. As shown in FIGS. 12-13, sequence liabilities were assessed in the 13F3.A4 antibody. The variable sequence of the fully human anti-NKG2A monoclonal antibody NKG2A.9 was derived from the 13F3.A4 hybridoma with a VH-I107T germline reversion mutation and a VK-N30S mutation to mitigate the deamidation liability of the VK-N30 residue. The constant region was derived from an IgG1f backbone (IgG1.3) and includes three mutations on the heavy chain: L234A, L235E, and G237A to minimize or eliminate antibody binding to Fcγ receptors and C1q. The M34 oxidation was identified as a potential risk for oxidation but was de-risked based on subsequent accelerated stability studies. The full length amino acid sequence of the NKG2A.9 antibody is shown in FIG. 14. The NKG2A.9 antibody was selected and tested in numerous functional assays as described herein to show safety and efficacy alone and in combination with other agents to treat, for example, cancer.

The full length amino acid sequence of the NKG2A.11 antibody is shown in FIG. 15. NKG2A.11 is derived from 13F3.A4 with a VH-I107T framework reversion and VK-N30P to remove the deamidation site. There is one amino acid difference between NKG2A.9 (N30S) and NKG2A.11 (N30P) in the light chain, and no amino acid differences in the heavy chain. NKG2A.9 and NKG2A.11 have similar thermal stability and solubility properties. NKG2A.9 has better thermal reversibility and better immunogenicity (in silico) than NKG2A.11. The immunogenicity of NKG2A.9 is described in more detail in Examples 16 and 26.

Figure 16:
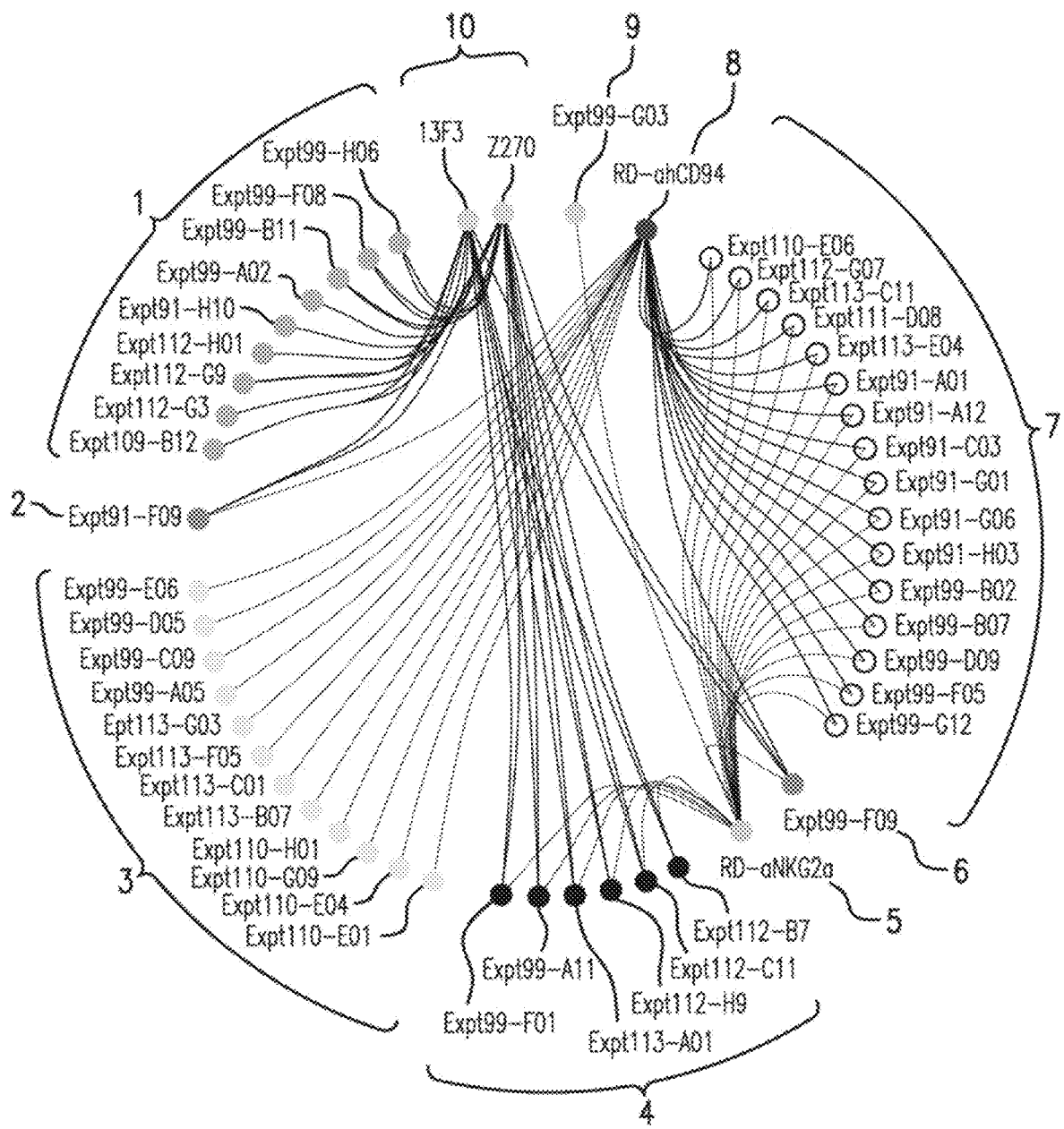
FIG. 16 shows a circle plot of epitope binning results of exemplary antibodies generated by the single B cell cloning method (SBCC), and shows the diversity of these antibodies. The antibodies that cross-block each other are connected by a line. Sample antibodies that have a similar blocking profile as compared to the benchmark antibodies (13F3.A4, Z270, RD-ahNKG2a (clone 131411, Catalog No. MAB1059), and RD-ahCD94 (clone 131412, Catalog No. MAB1058)) are grouped together into groups 1-4, 6-7, and 9. Benchmark antibodies with similar blocking profiles as the sample antibody sets are also grouped together into groups 5, 8 and 10.

(2) Hundreds of Antibodies Generated Using Single B Cell Cloning Method Lacked Desired Functional Characteristics FIG. 16 shows a circle plot epitope binning results of exemplary antibodies generated by the B cell cloning method. The epitope binning was performed on an Octet HTX instrument using the "in-tandem format." First, hNKG2A-hCD94-mFc fusion protein was captured on Octet sensor tips. Next, the remaining capture sites were blocked if required. Third, the antigen was saturated with single B cell cloning-derived antibodies from supernatant. Finally, the binding of reference antibodies was tested. The epitope binning experiment was repeated with reverse order of addition, saturating first with reference antibodies, and then probing for binding of supernatant containing single B cell cloning-derived antibodies. This epitope binning showed high diversity in binding and blocking behavior, corresponding to high diversity in the epitopes. FIG. 16 depicts the epitope binning results by displaying antibodies that cross-block each other connected by a line. Sample antibodies that have a similar blocking profile as compared to the benchmark antibodies (13F3.A4, Z270, RD-ahNKG2a (clone 131411, Catalog No. MAB1059), and RD-ahCD94 (clone 131412, Catalog No. MAB1058)) are grouped together into groups 1-4, 6-7, and 9. Benchmark antibodies with similar blocking profiles as the sample antibody sets are also grouped together into groups 5, 8 and 10. The antibodies in the same group could potentially cross-block each other as well, but this was not tested these experiments. Sample antibodies were not tested against each other, and benchmark antibodies were not tested against each other for cross-blocking.

Figure 17A:
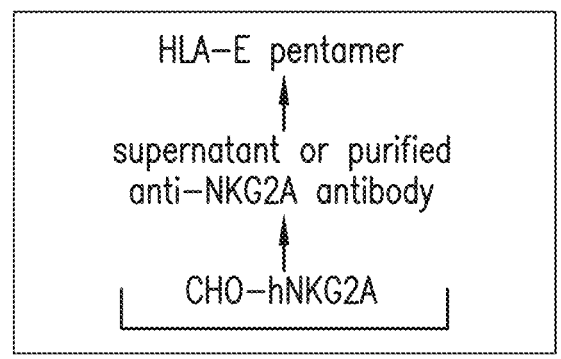
FIG. 17A shows the assay method to assess the ability of anti-human NKG2A antibodies generated using the SBCC method to block NKG2A/HLA-E interaction.
Figure 17B:
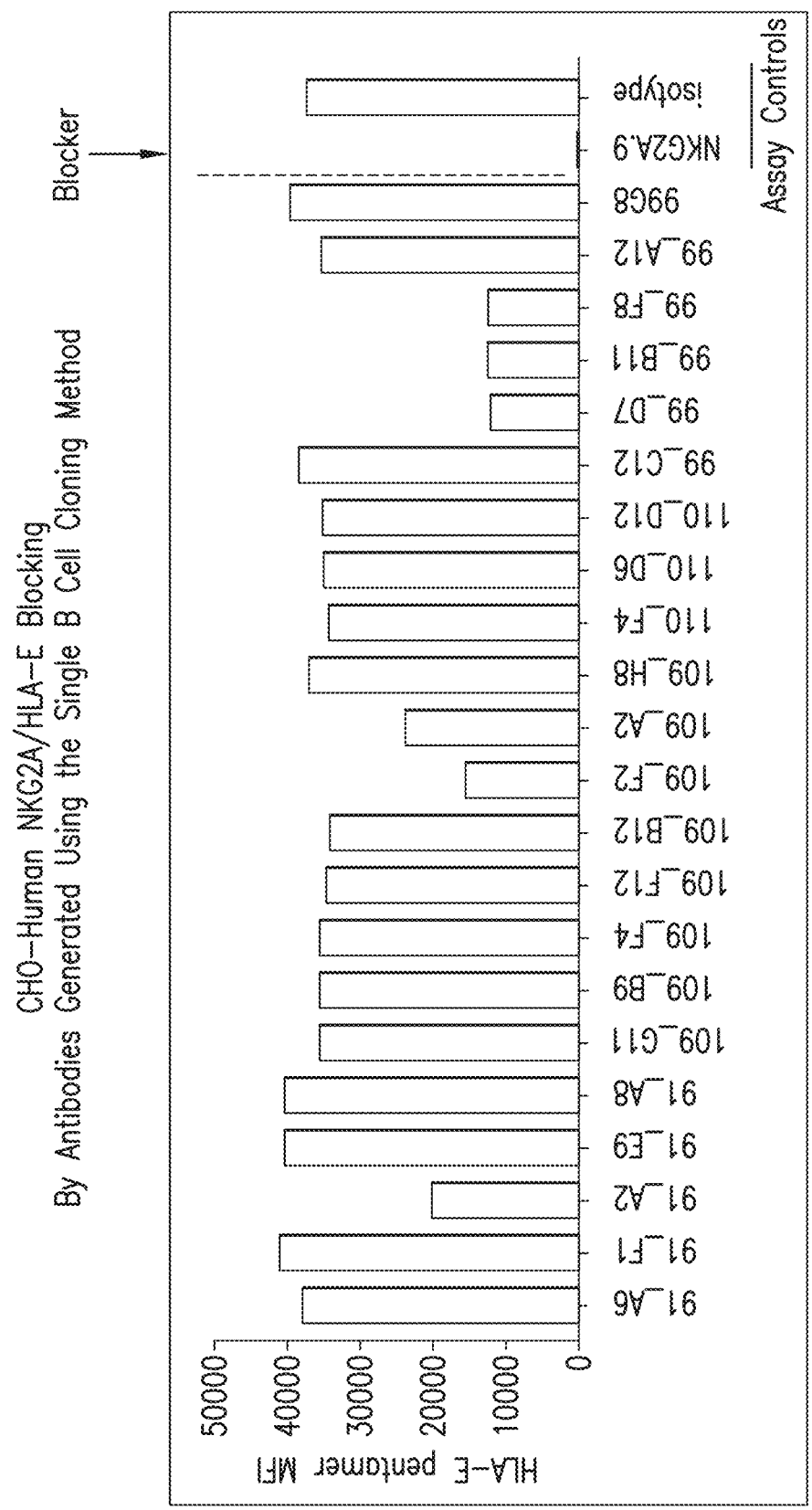
FIG. 17B shows that the sample antibodies only partially blocked or did not block the NKG2A/HLA-E interaction, as compared to the positive control (NKG2A.9 antibody) and negative control (isotype).

The ability of anti-human NKG2A antibodies generated using the single B cell cloning method to block NKG2A/HLA-E interaction was assessed. As depicted in FIG. 17A, $1 \times 10^6$ human NKG2A-expressing CHO cells were incubated with 1004 supernatant or 10 μg/mL purified antibody for 30 minutes at 4° C. Cells were washed and stained with fluorescently labeled HLA-E pentamer (Proimmune) to detect bound HLA-E on the cell surface. Cells were read fresh on the BD LSRFortessa. FIG. 17B shows the ability of anti-human NKG2A antibodies generated by B cell cloning to block HLA-E binding to human NKG2A-expressing CHO cells. The NKG2A.9 antibody served as the positive control, and the isotype served as the negative control. The hundreds of antibodies generated using the SBCC method only partially blocked or did not block the NKG2A/HLA-E interaction. None of these hundreds of antibodies were selected for further development, providing evidence of the difficulty of discovering anti-NKG2A antibodies with the desired functional characteristics.

(3) Anti-Human NKG2A Antibodies That Desirably Blocked the NKG2A/HLA-E Interaction and Not the NKG2C/HLAE-Interaction The ability of anti-human NKG2A antibodies to block the NKG2A/HLA-E and NKG2C/HLA-E interactions was assessed. As shown in FIG. 18D, $1\times10^6$ human NKG2A-expressing CHO cells were incubated with titrating amounts of anti-NKG2A antibody for 30 minutes at 4° C. Cells were washed and stained with fluorescently labeled HLA-E pentamer (Proimmune) to detect bound HLA-E on the cell surface. Cells were read fresh on the BD LSRFortessa. FIG. 18E-F show the HLA-E blocking curve and ICso of anti-NKG2A antibodies in blocking HLA-E binding to human NKG2A-expressing or NKG2C-expressing CHO cells. The 13F3.A4 and 11H9.A1 antibodies desirably showed specific binding to human NKG2A-expressing CHO cells (FIG. 18E), and desirably did not block the NKG2C/HLA-E interaction (FIG. 18F). However, the 2EB.B1 antibody undesirably bound to human NKG2C-expressing CHO cells and blocked the NKG2C/HLA-E interaction. Thus, the 2EB.B1 antibody was not selected for further development.

The ability of anti-NKG2A antibodies to block the NKG2A/HLA-E interaction in natural killer cells (NKLs) was also assessed. As shown in FIG. 19C, $1\times10^6$ endogenously expressing human NKL cells were incubated with titrating amounts of anti-NKG2A antibody for 30 minutes at 4° C. Cells were washed and stained with fluorescently labeled HLA-E pentamer (Proimmune) to detect bound HLA-E on the cell surface. Cells were read fresh on the BD LSRFortessa. FIG. 19D shows the HLA-E blocking curve and $IC_{50}$ values of anti-NKG2A antibodies in blocking HLA-E binding to human NKG2A expressing NKL cells. The 13F3.A4, 11H9.A1, 4G5.D1, and IG5.B2 antibodies showed blocking of the NKG2A/HLA-E interaction in NKL cells with $IC_{50}$ values of 0.2 nM, 0.1 nM, 0.3 nM, and 0.4 nM, respectively.

Figure 20A:
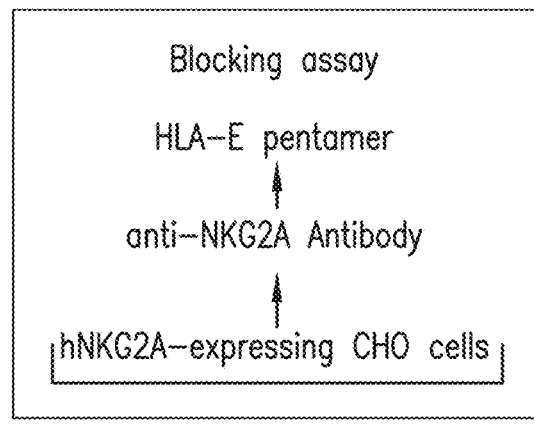
FIG. 20A-C illustrates the blocking assay method (FIG. 20A) used, which showed that the anti-human NKG2A antibodies tested blocked the NKG2A/HLA-E interaction in hNKG2A-expressing CHO cells, as shown in FIG. 20B-C.
Figure 20B:
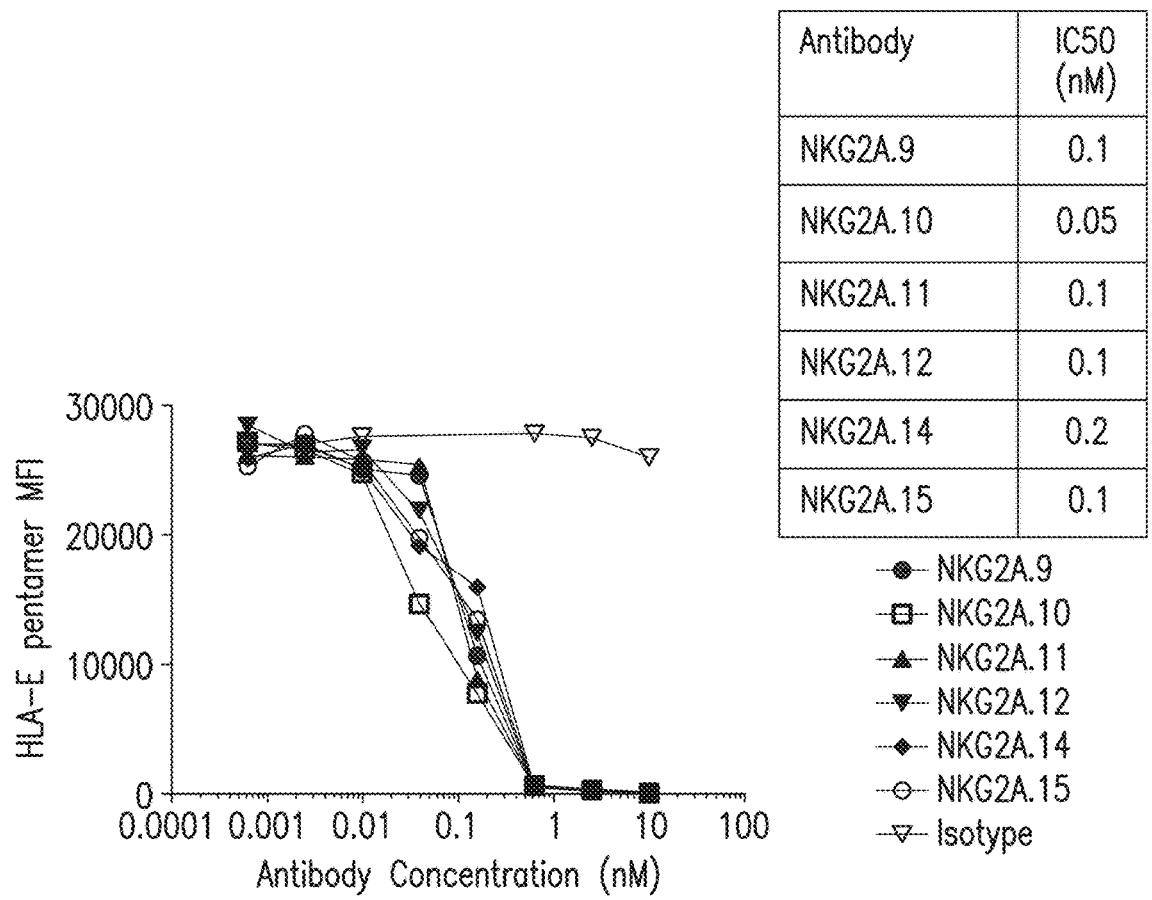
Figure 20C:
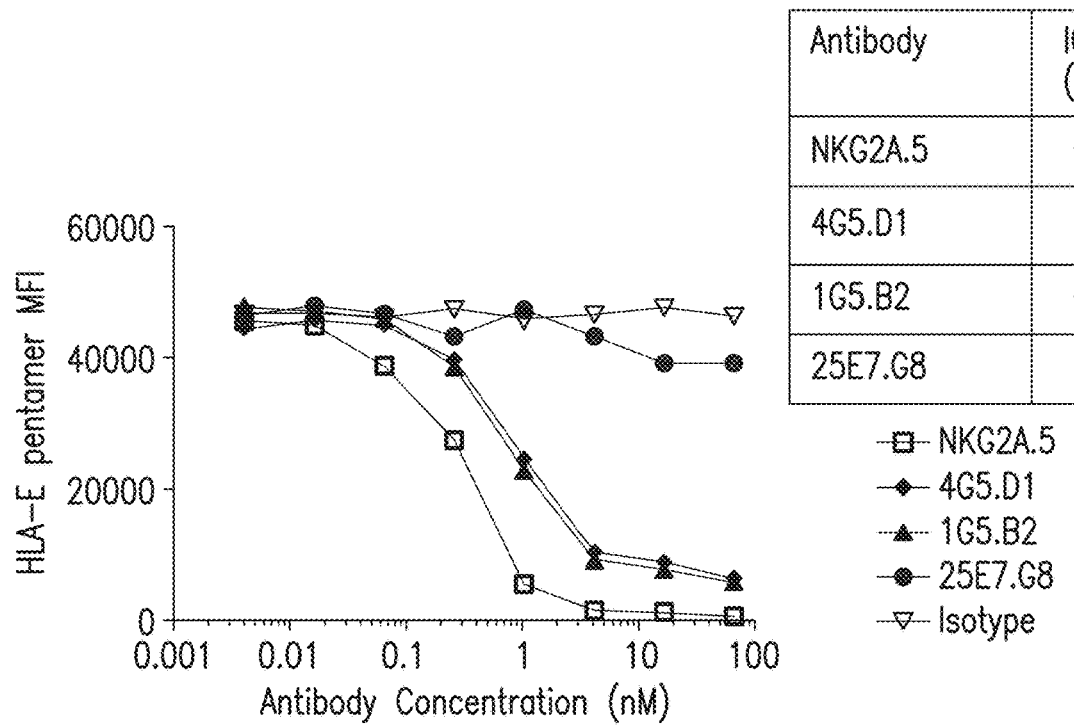

The ability of additional anti-human NKG2A antibodies to block the NKG2A/HLA-E interaction was assessed. As depicted in FIG. 20A, $1\times10^6$ human NKG2A-expressing CHO cells were incubated with titrating amounts of anti-NKG2A antibody (10 μg/ml) for 30 minutes at 4° C. Cells were washed and stained with fluorescently labeled HLA-E pentamer (Proimmune) to detect bound HLA-E on the cell surface. Cells were read fresh on the BD LSRFortessa. FIG. 20B-C show the HLA-E blocking curve, and $IC_{50}$ values of anti-human NKG2A antibodies in their ability to block HLA-E binding to human NKG2A-expressing CHO cells. As shown in FIG. 20B, the NKG2A.9, NKG2A.10, NKG2A.11, NKG2A.12, NKG2A.14, and NKG2A.15 antibodies all demonstrated relatively low $IC_{50}$ values (0.1, nM, 0.05 nM, 0.1 nM, 0.1 nM, 0.2 nM, and 0.1 nM, respectively), which indicated that the antibodies blocked the NKG2A/HLA-E interaction. Similarly, as shown in FIG. 20C, the NKG2A.5, 4G5.D1, and 1G5.B2 antibodies demonstrated relatively low $IC_{50}$ values of 0.3 nM, 0.9 nM, and 0.7 nM, respectively. Thus, these antibodies were selected for further development. However, as described herein, the NKG2A.5 and 4G5.D1 antibodies were later eliminated for further development due to their poor binding to cynomolgus NKG2A protein.

As shown in FIG. 20C, however, the 25E7.G8 antibody (depicted with a closed circle) did not block the NKG2A/HLA-E interaction, as shown by the relatively high $IC_{50}$ value of about 4 nM. Thus, the 25E7.G8 antibody was not selected for further development.

(4) Anti-NKG2A Antibodies That Showed Desirable Specific Binding to Human NKG2A-expressing CHO Cells.

Figure 18A:
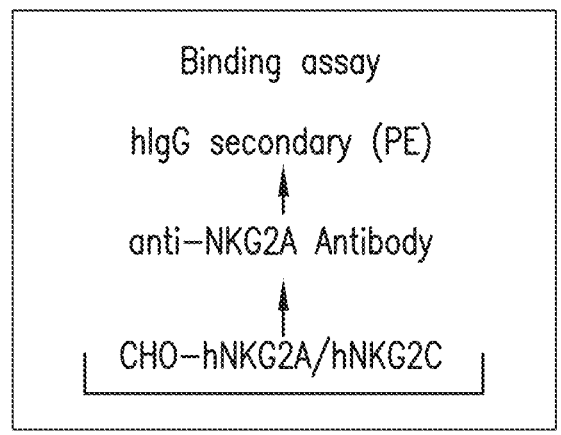
FIG. 18A-C show the binding assay method (FIG. 18A) to assess binding of anti-NKG2A antibodies to human NK2GA-expressing (FIG. 18B) and NKG2C-expressing CHO cells (FIG. 18C).
Figure 18B:
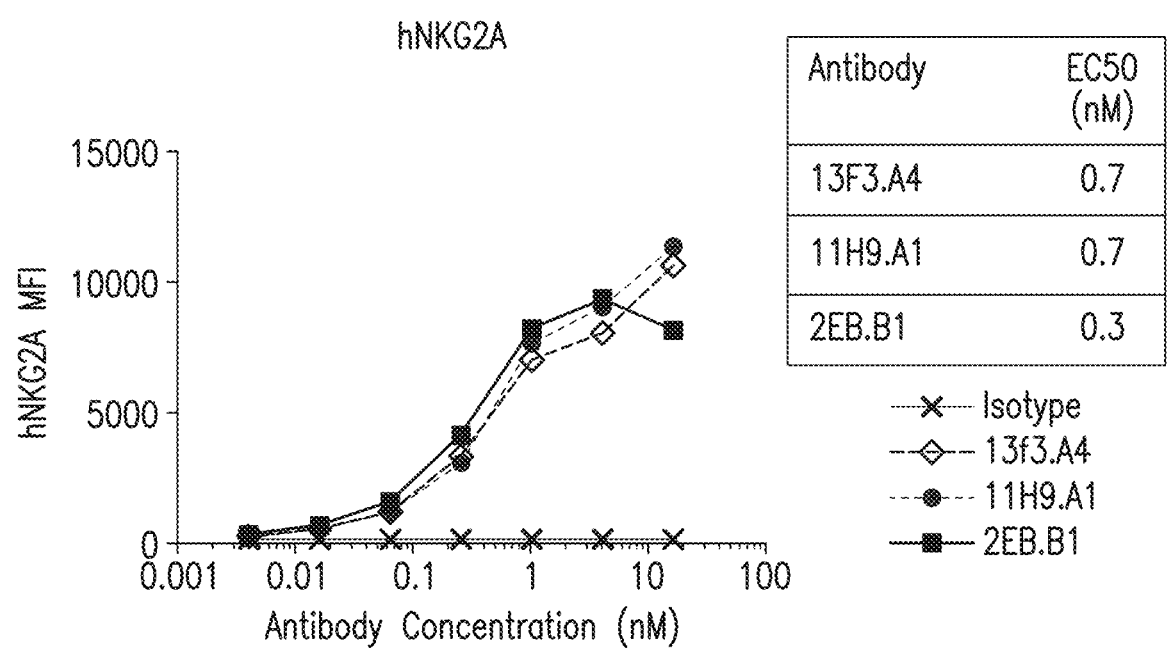
Figure 18C:
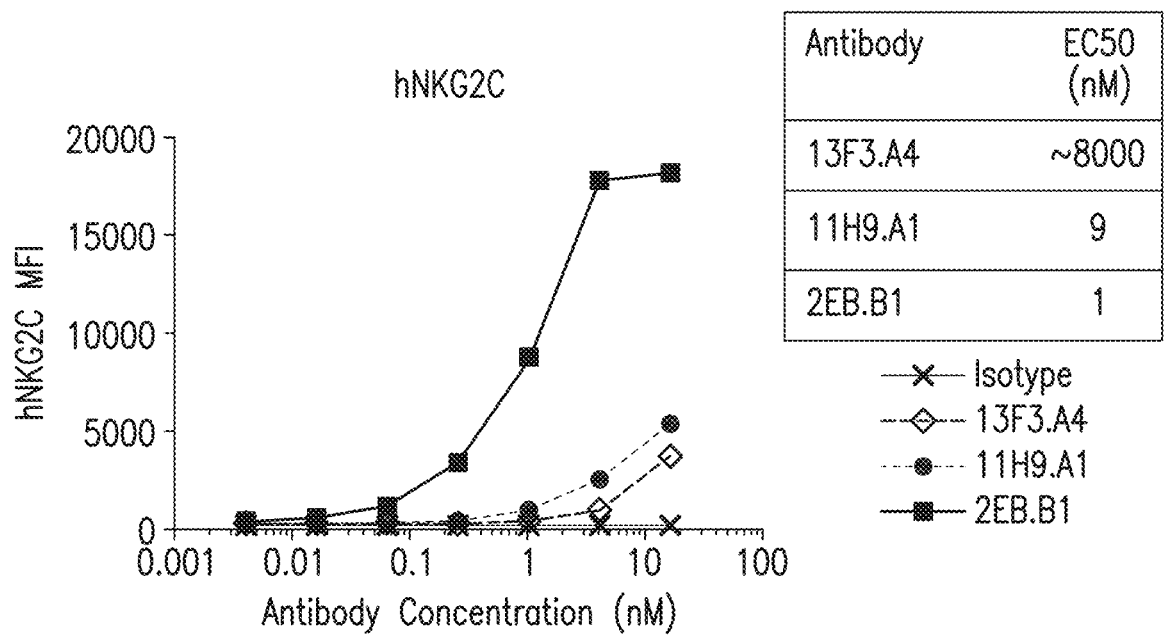
Figure 18D:
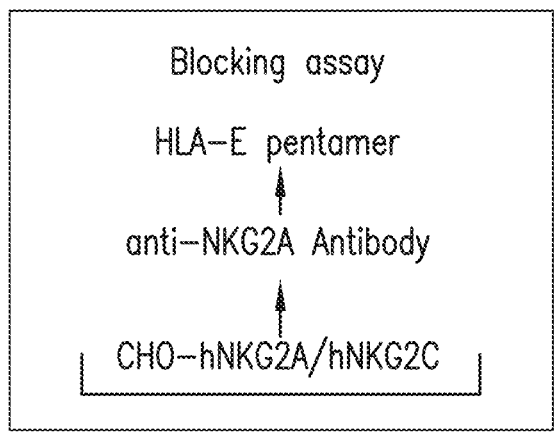
FIG. 18D-F show the blocking assay method (FIG. 18D) used to assess blocking of anti-NKG2A antibodies of the NKG2A/HLA-E interaction (FIG. 18E) and NKG2C/HLA-E interaction (FIG. 18F). The 13F3.A4 and 11H9.A1 antibodies showed specific binding to human NKG2A-expressing CHO cells (as shown in FIG. 18E), and did not block the NKG2C/HLA-E interaction (as shown in FIG. 18F).
Figure 18E:
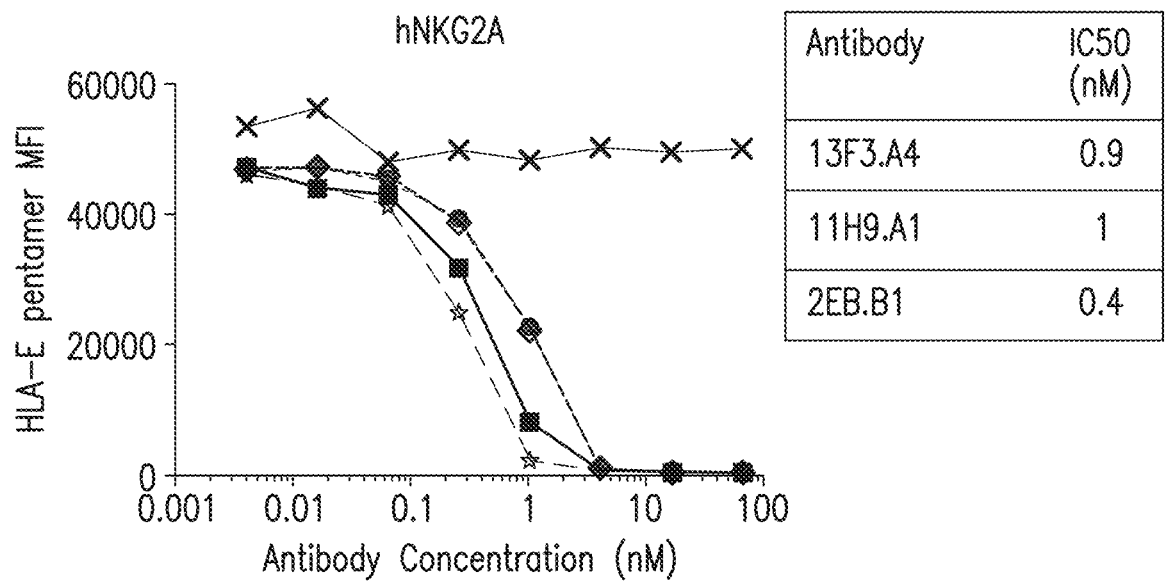
Figure 18F:
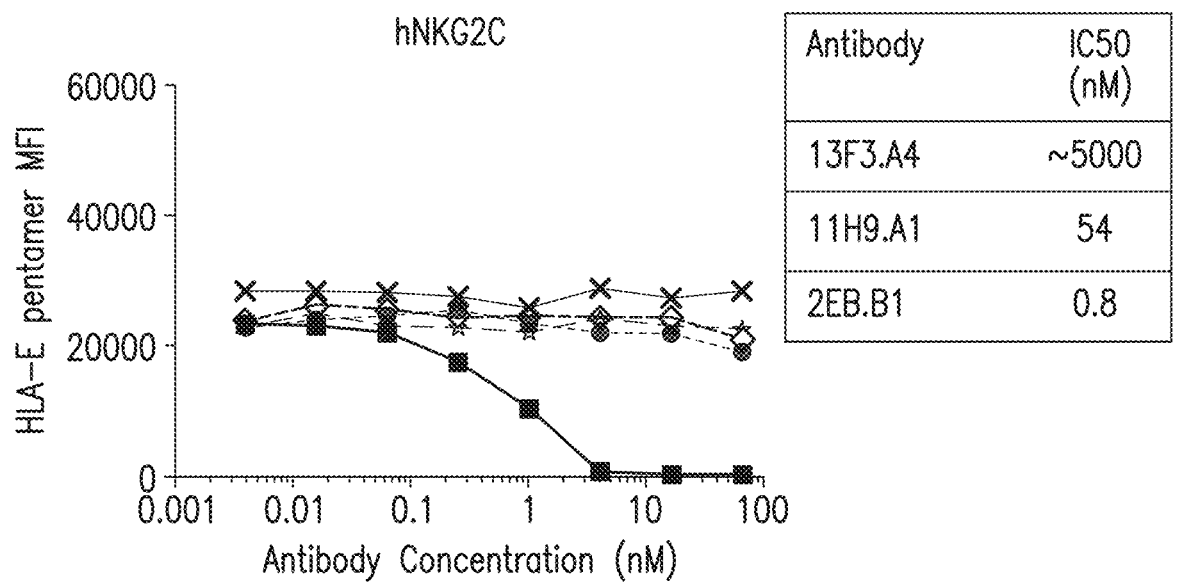

As depicted in FIG. 18A, $1\times10^6$ human NKG2A-expressing or human NKG2C-expressing CHO cells were incubated with titrating amounts of anti-NKG2A antibody for 30 minutes at 4° C. Cells were washed and stained with fluorescently labeled goat anti-human IgG-PE secondary antibody for 30 minutes at 4° C. to detect the bound antibody on the cell surface. Cells were read fresh on the BD LSRFortessa. FIG. 18B-C show the binding curve and $EC_{50}$ (nM) of anti-NKG2A antibodies to human NKG2A-expressing or NKG2C-expressing CHO cells. The 13F3.A4, 11H9.A1, and 2EB.B1 antibodies showed specific binding to the human NKG2A-expressing CHO cells, a shown by the $EC_{50}$ values of 0.7 nM, 0.7 nM, and 0.3 nM, respectively.

Figure 21A:
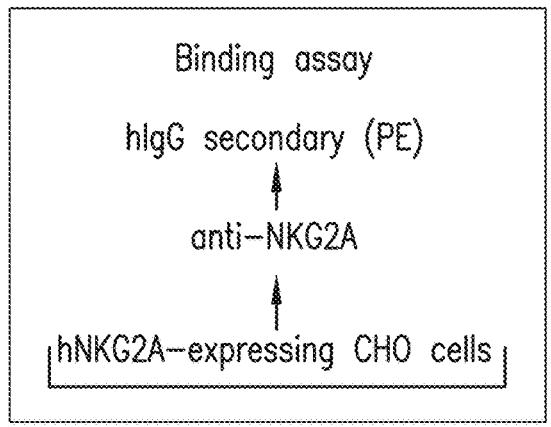
FIG. 21A-C illustrates the binding assay method (FIG. 21A) used, which showed that the anti-NKG2A antibodies tested bound to human NKG2A-expressing CHO cells, as shown in FIG. 21B-C.
Figure 21B:
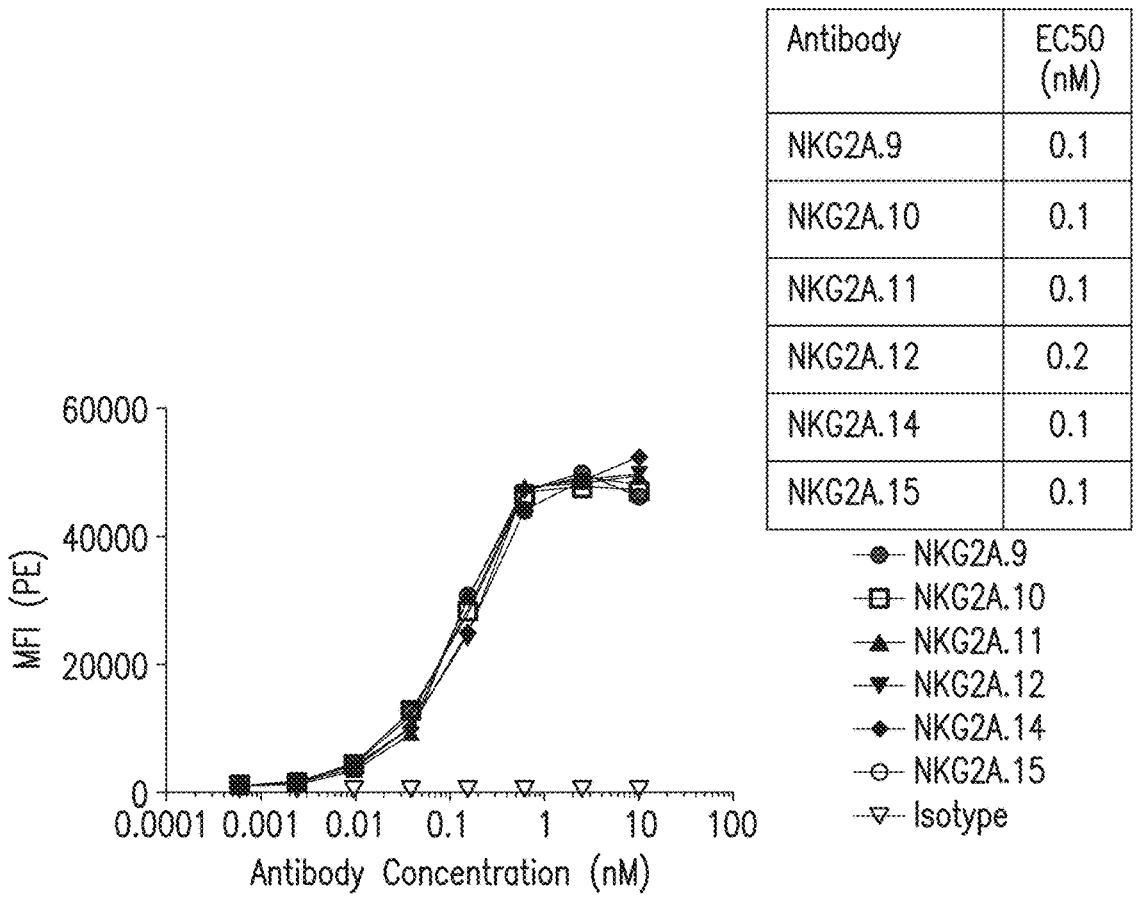
Figure 21C:
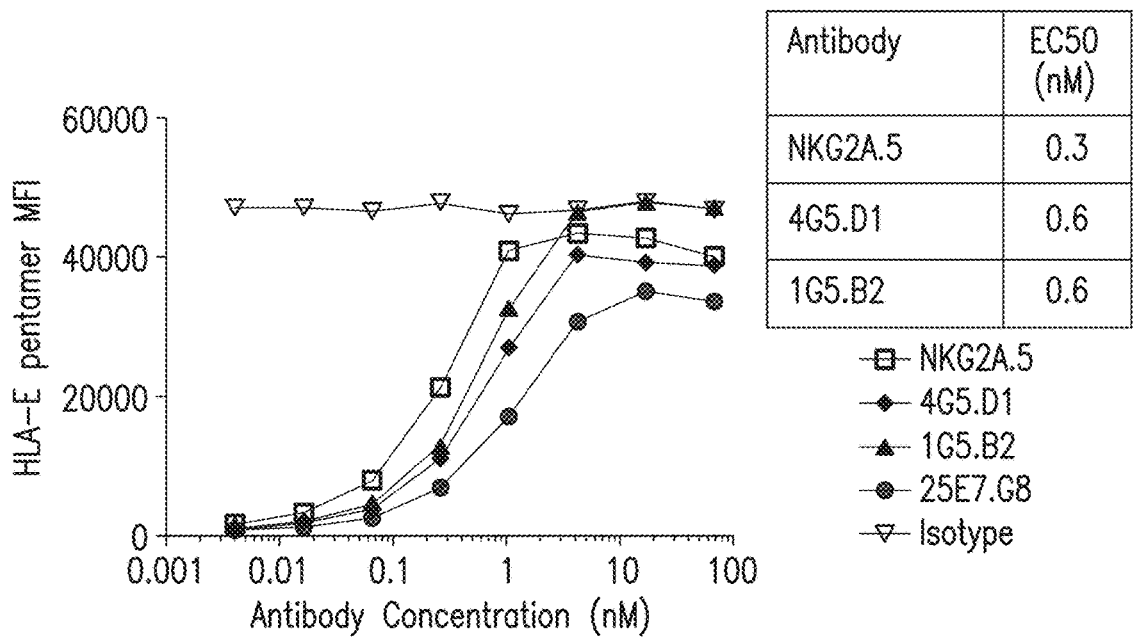

As shown in FIG. 21A, $1\times10^6$ human and cynomolgus NKG2A expressing CHO cells were incubated with titrating amounts of antibody (10 μg/ml) for 30 minutes at 4° C. Cells were washed and stained with fluorescently labeled goat anti-human IgG-PE secondary antibody for 30 minutes at 4° C. to detect the bound antibody on the cell surface. Cells were read fresh on the BD LSRFortessa. FIG. 21B-C show the binding curves, and $EC_{50}$ values of anti-human NKG2A antibodies to human NKG2A-expressing CHO cells.

As shown in FIG. 21B, the NKG2A.9, NKG2A.10, NKG2A.11, NKG2A.12, NKG2A.14, and NKG2A.15 antibodies all demonstrated relatively low $EC_{50}$ values (0.1 nM, 0.1 nM, 0.1 nM, 0.2 nM, 0.1 nM, and 0.1 nM, respectively), which indicated that the anti-NKG2A antibodies desirably bound with specificity to the NKG2A receptor in human NKG2A-expressing CHO cells. Similarly, as shown in FIG. 21C, the NKG2A.5, 4G5.D1, and 1G5.B2 antibodies demonstrated relatively low $EC_{50}$ values (0.3 nM, 0.6 nM, and 0.6 nM, respectively), which indicated the antibodies bound to the NKG2A receptor. Thus, the NKG2A.9, NKG2A.10, NKG2A.11, NKG2A.12, NKG2A.14, NKG2A.15, NKG2A.5, 4G5.D1, and 1G5.B2 were selected for further development at this stage.

(5) Anti-NKG2A Antibodies That Bound to Cynomolgus NKG2A-expressing CHO Cells

Figure 22A:
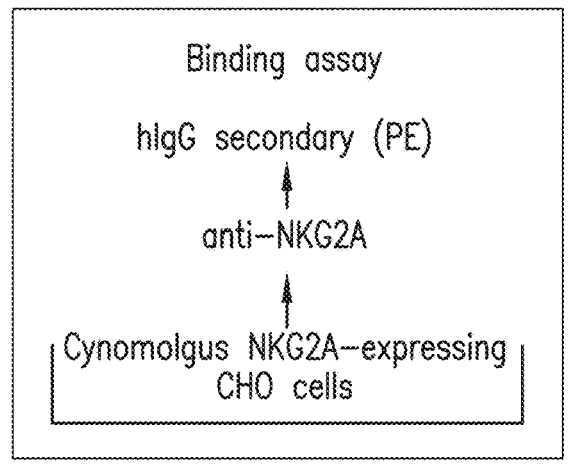
FIG. 22A-C illustrates the binding assay method (FIG. 22A) used, which assessed the ability of anti-NKG2A antibodies to bind to cynomolgus NKG2A-expressing CHO cells (results shown in FIG. 22B-C).
Figure 22B:
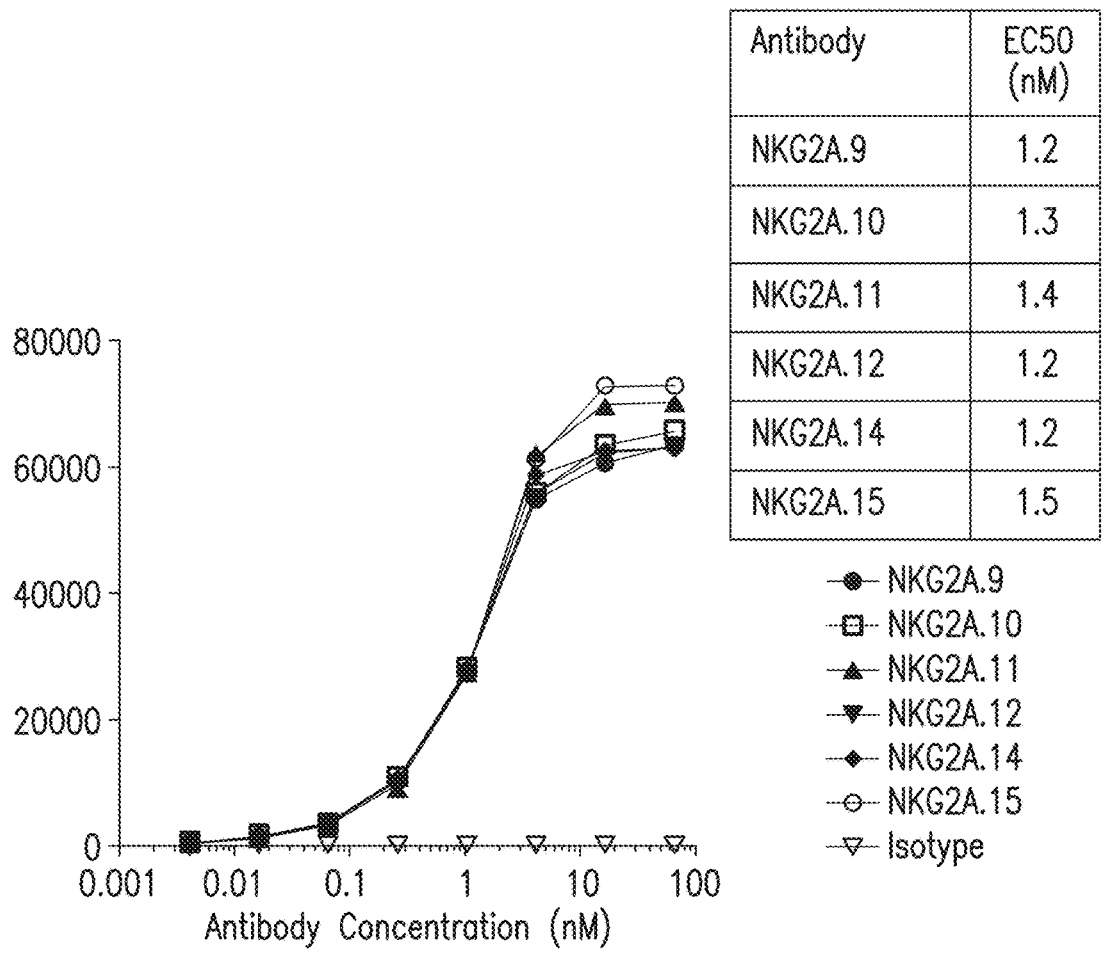
Figure 22C:
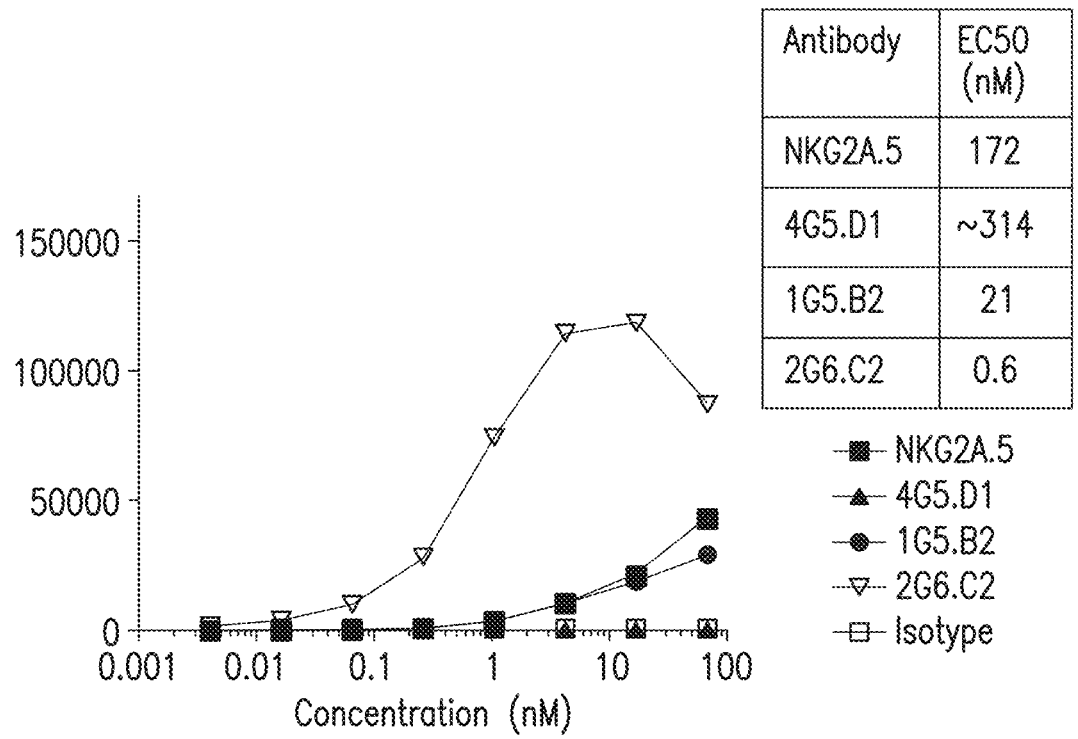

The ability of anti-NKG2A antibodies that bound to cynomolgus NKG2A-expressing CHO cells was assessed. As depicted in FIG. 22A, $1\times10^6$ cynomolgus NKG2A-expressing CHO cells were incubated with titrating amounts of anti-NKG2A antibody (10 μg/ml) 10 for 30 minutes at 4° C. Cells were washed and stained with fluorescently labeled HLA-E pentamer (Proimmune) to detect bound HLA-E on the cell surface. Cells were read fresh on the BD LSR-Fortessa. FIG. 22B-C show the binding curves, and $EC_{50}$ values of anti-human NKG2A antibodies to cynomolgus NKG2A-expressing CHO cells.

As shown in FIG. 22B, the NKG2A.9, NKG2A.10, NKG2A.11, NKG2A.12, NKG2A.14, and NKG2A.15 antibodies all demonstrated relatively low $EC_{50}$ values (1.2 nM, 1.3 nM, 1.4 nM, 1.2 nM, 1.2 nM, and 1.5\ nM, respectively), which indicated that the anti-NKG2A antibodies bound to the NKG2A receptor in cynomolgus monkey NKG2A-expressing CHO cells.

As shown in FIG. 22C, the NKG2A.5, 4G5.D1, and 1G5.B2 antibodies showed poor binding to cynomolgus monkey NKG2A expressing CHO cells, as demonstrated by the relatively high $EC_{50}$ values of 172 nM, about 314 nM, and 21 nM, respectively. Thus, these three antibodies were not selected for further development. The 2G6.C2 antibody had an $EC_{50}$ value of 0.6 nM, which desirably showed specific binding to cynomolgus monkey NKG2A expressing CHO cells; thus, the 2G6.C2 antibody was selected for further development.

Figure 23A:
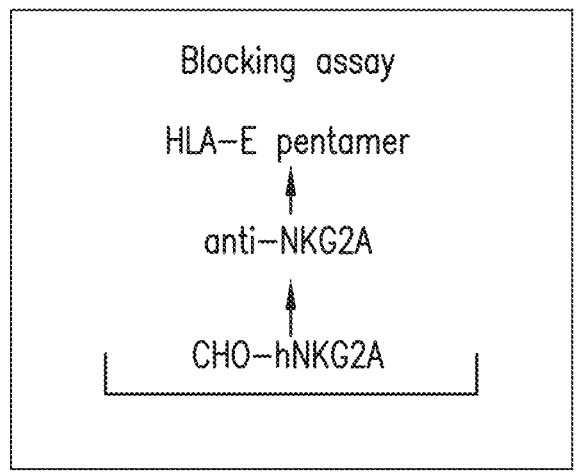
FIG. 23A-B illustrate the blocking assay method (FIG. 23A) used to assess ability of anti-NKG2A antibodies to desirably block the NKG2A/HLA-E interaction (FIG. 23B).
Figure 23B:
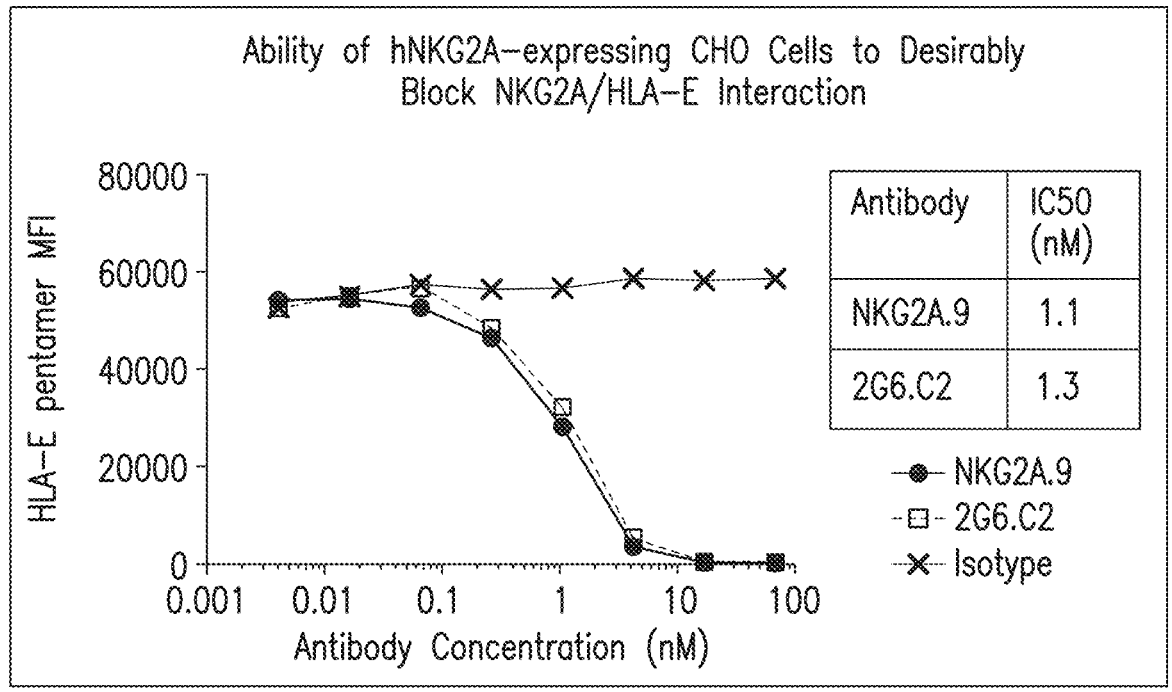
Figure 23C:
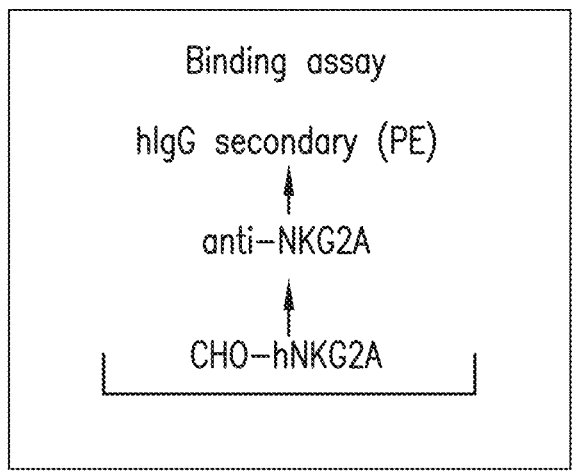
FIG. 23C-D show the binding assay method used (FIG. 23C) that showed the ability of anti-NKG2A antibodies to bind to NKG2A-expressing CHO cells (FIG. 23D).
Figure 23D:
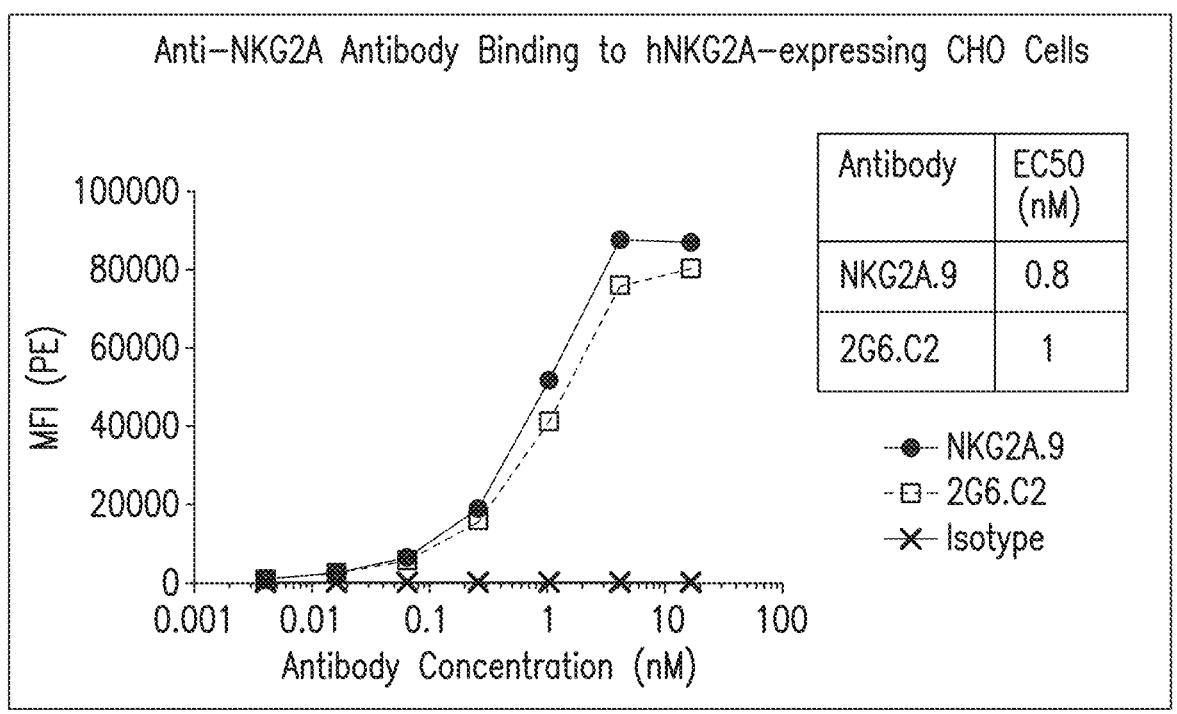

The ability of the 2G6.C2 antibody to specifically bind to the NKG2A receptor and to block the NKG2A/HLA-E interaction was assessed using the same methods as described above in this Example 3(3) and 3(4), and as depicted in FIGS. 23A and 23C. The 2G6.C2 antibody was comparable to, for example, the NKG2A.9 antibody in its ability to block the NKG2A/HLA-E interaction, as shown by the similar $IC_{50}$ values of 1.1 nM for the NKG2A.9 antibody and 1.3 nM for the 2G6.C2 antibody, ashown in FIG. 23B. Similarly, the 2G6.C2 antibody was comparable to, for example, the NKG2A.9 antibody in its ability to bind to the NKG2A receptor in human NKG2A-expressing CHO cells, as shown by the similar $EC_{50}$ values of 0.8 nM for the NKG2A.9 antibody and 1 nM for the 2G6.C2 antibody, as shown in FIG. 23D.

Despite being able to desirably block the NKG2A/HLA-E interaction and to bind to the NKG2A receptor, the 2G6.C2 antibody was not selected for further development because the 2G6.C2 non-specifically enhanced functionality among NKG2A negative (−) NK cells. This demonstrates the difficulty of discovering anti-NKG2A antibodies with the desired functional characteristics described herein to treat cancer.

(6) Anti-NKG2A Antibodies That Bound to Human NKG2A+ Natural Killer Cell Line (NKL)

Figure 19A:
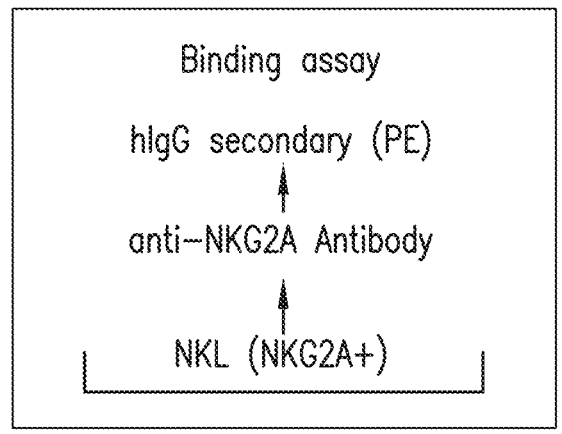
FIG. 19A-B illustrates the binding assay method (FIG. 19A) used, which assessed the ability of anti-NKG2A antibodies to bind to human NKG2A+ natural killer cell line (NKL)(as shown in FIG. 19B).
Figure 19B:
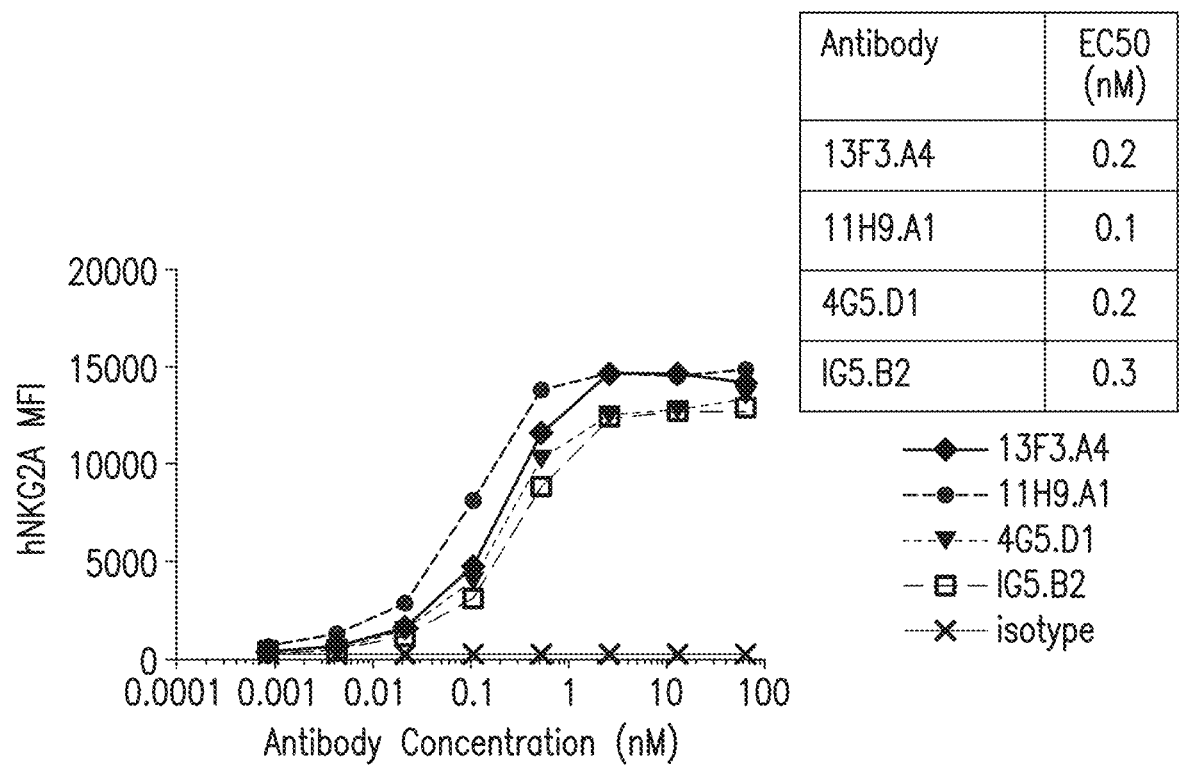
Figure 19C:
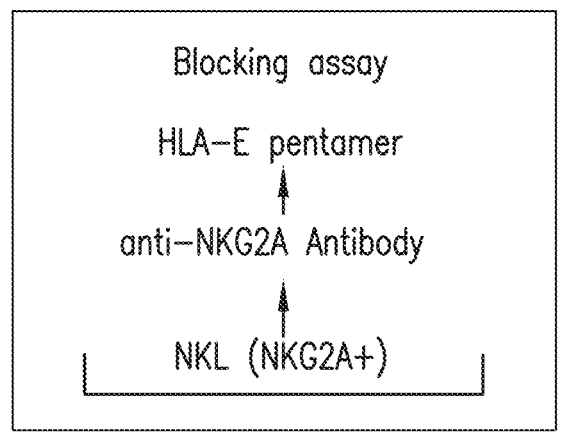
FIG. 19C-D illustrates the blocking assay method (FIG. 19C) used, which showed that the anti-NKG2A antibodies tested blocked HLA-E binding to human NKG2A expressing NKL cells, as shown in FIG. 19D.
Figure 19D:
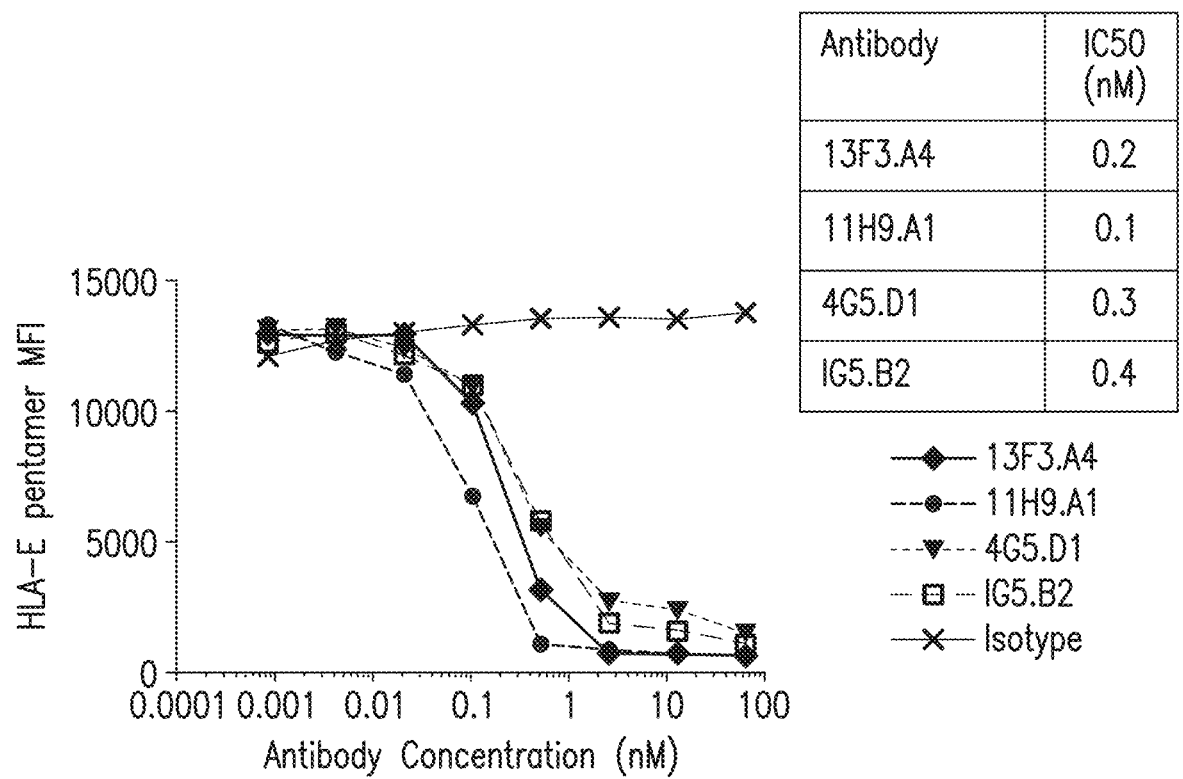

As shown in FIG. 19A, $1 \times 10^6$ endogenously expressing NKG2A human NKL cells were incubated with titrating amounts of anti-NKG2A antibody for 30 minutes at 4° C. Cells were washed and stained with fluorescently labeled goat anti-human IgG-PE secondary antibody for 30 minutes at 4° C. to detect the bound antibody on the cell surface. Cells were read fresh on the BD LSRFortessa. FIG. 19B shows the binding curve and $EC_{50}$ values (nM) of anti-NKG2A antibodies to human NKG2A expressing NKL cells. The $EC_{50}$ values for the 13F3.A4, 11H9.A1, 4G5.D1, and IG5.B2 antibodies were 0.2 nM, 0.1 nM, 0.2 nM, and 0.3 nM, respectively, and these values indicated that these anti-NKG2A antibodies desirably bound specifically to the NKG2A+ natural killer cells.

(7) Anti-NKG2A Antibodies That Bound to Cynomolgus NKG2A+ NKL

Figure 24A:
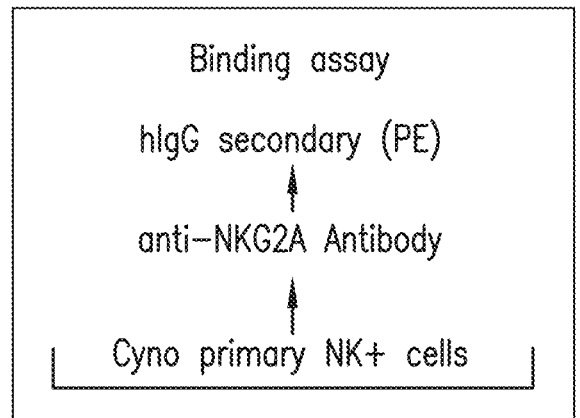
FIG. 24A-B show the binding assay method (FIG. 24A) used to assess whether anti-NKG2A antibodies bound to cynomolgus NKG2A+NKLs (FIG. 24B).
Figure 24B:
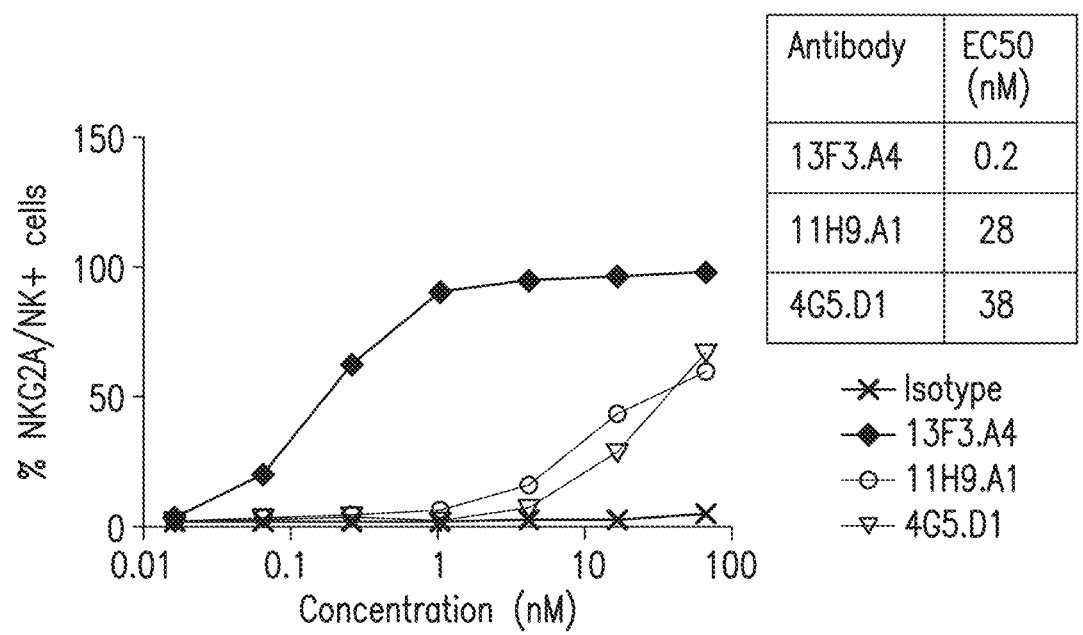

As depicted in FIG. 24A, $1 \times 10^6$ peripheral blood mononuclear cells (PBMC) isolated from cynomolgus monkeys were incubated with titrating amounts of anti-NKG2A antibody for 30 minutes at 4° C. Cells were washed and stained with fluorescently labeled goat anti-human IgG-PE secondary antibody for 30 minutes at 4° C. to detect the bound antibody on the cell surface. Cells were read fresh on the BD LSRFortessa. FIG. 24B shows the binding curve and $EC_{50}$ values (nM) of anti-NKG2A antibodies to cynomolgus NKG2A expressing NK cells. As shown in FIG. 24B, the 11H9.A1 and 4G5.D1 antibodies did not bind to cynomolgus NKG2A+ NK cells, as indicated by $EC_{50}$ values of 28 nM and 38 nM, respectively. Thus, because of their lack of binding to cynomolgus monkey NKG2A+ NK cells, the 11H9.A1 and 4G5.D1 antibodies were eliminated from further development to treat, for example, cancer. The 13F3.A4 antibody desirably bound to cynomolgus monkey NKG2A+NK cells, as indicated by the $EC_{50}$ value of 0.2 nM. Thus, the 13F3.A4 antibody demonstrated desirable binding functionality and was selected for further modification and development.

(8) Anti-NKG2A Antibodies That Enhanced Natural Killer (NK) Cell Response of Degranulation In in vitro experiments using peripheral blood mononuclear cells (PBMC) from healthy human donors, anti-NKG2A antibody blockade of NKG2A/HLA-E interaction among activated NK cells increased NK cell degranulation. One of the mechanisms by which NK cells eliminate their targets, such as tumor cells, is through a complicated, multi-stage process that concludes in the directed secretion of granules containing the lytic enzymes perforin and granzymes. This cellular process of directed secretion of molecules from granules is known as degranulation. After NK cells release secretory lytic granules to, for example, the target tumor cells, perforin generates pores in the target tumor cell membranes, and granzymes then access the target tumor cell cytoplasm and induce tumor cell death (also known as apoptosis). During this process, the lysosome-associated membrane protein-1 (LAMP-1, also known as CD107A) is transported to the surface of the NK cell, which renders it accessible for antibody binding, thus making it possible to identify NK cells that have been active in degranulation. We then measured the effect of the anti-NKG2A antibodies disclosed herein on NK cell activation and enhancement of NK cell functionality in the degranulation process, which results in increased tumor cell death. This process is partially illustrated in FIG. 25A. The X in the NK cell illustrates the inhibitory signal when NKG2A interacts with HLA-E. The dark circles in the NK cell represent granules.

NK cells isolated from normal PBMC donors were activated overnight with recombinant human (rh) interleukin-2 (IL-2). Specifically, NK cells were isolated from human whole blood using Ficoll gradient and the human NK cell isolation kit (Miltenyi Biotech). NK cells were cultured overnight with rh IL-2 (400 IU/ml). Following activation, the cell viability was more than 90%, as determined by cell counter. NK cells were then co-cultured for four hours with $5 \times 10^4$ of the human B-lymphoblastoid target cell line 721.221 expressing HLA-E in the presence of anti-human NKG2A antibodies (the NKG2A.9, NKG2A.10, NKG2A.11, NKG2A.14, NKG2A.15, NKG2A.5, 2G6.C2, 4G5.D1, 25E7.G8) and an isotype antibody (human IgG1.3). Cells were then collected and stained for the following markers: anti-human CD3, anti-human CD56, live/dead, and anti-human CD107a, and non-competing anti-human NKG2A antibody (the 27H4.D4 clone). Cells were acquired fresh on the BD LSRFortessa™. Percent degranulation (% CD107) among NKG2A+ or NKG2A− NK cells was subsequently analyzed on FlowJo Version 10 (flow cytometry software). Fold increase was calculated by increase in % CD107a over the isotype control.

In the presence of anti-human NKG2A monoclonal antibodies, there was an increase in NK cell degranulation as measured by CD107a expression by flow cytometry. The increase in NK cell response was not observed on NKG2A negative (−) NK cells, which showed that the antibody effect was specific to NKG2A expressing NK cells.

Figure 25B:
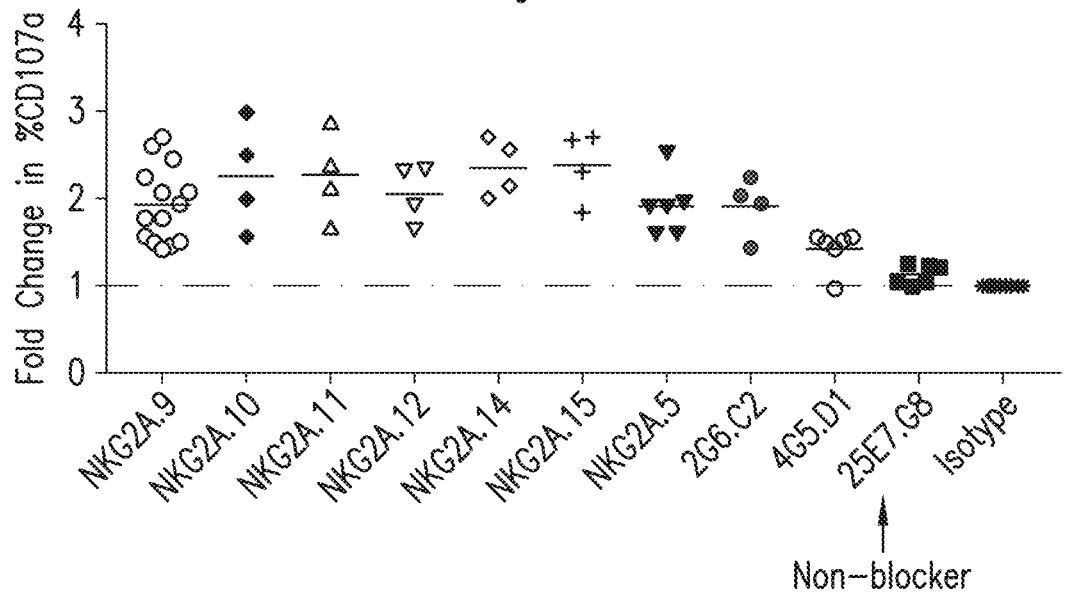
FIG. 25B-C are graphs of the flow cytometry analysis results, and shows that all tested anti-NKG2A antibodies (the NKG2A.9, NKG2A.10, NKG2A.11, NKG2A.12, NKG2A.14, NKG2A.15, NKG2A.5, 2G6.C2, and 4G5.D1 antibodies) enhanced NK cell degranulation (as measured by fold change in % CD107a compared to the isotype control) among NKG2A+ NK cells. The 25E7.G8 clone (as shown in FIG. 25B) is a non-blocking antibody that was used as a negative control.
Figure 25C:
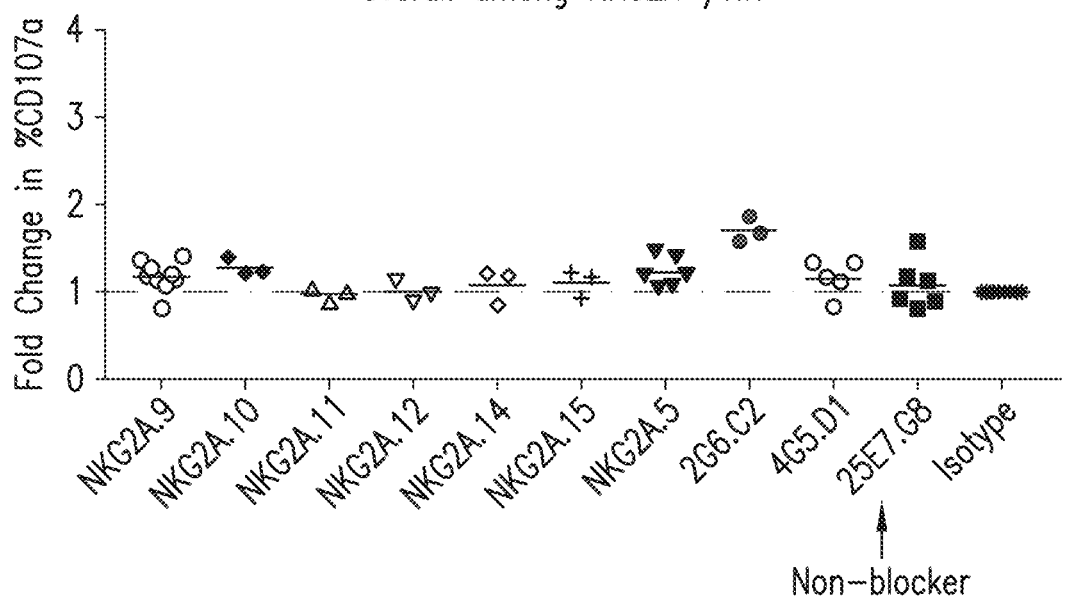

FIGS. 25B-C are graphical representations of the flow cytometry analyses, and shows that all tested anti-NKG2A antibodies (the NKG2A.9, NKG2A.10, NKG2A.11, NKG2A.12, NKG2A.14, NKG2A.15, NKG2A.5, 2G6.C2, and 4G5.D1 antibodies) enhanced NK cell degranulation (as measured by fold change in % CD107a compared to the isotype control) among NKG2A+ NK cells, except the 25E7.G8 clone (a non-blocking antibody) (as shown in FIG. 25B), which was included as a negative control. (In other words, it was expected that the 25E7.G8 antibody would not increase NK cell degranulation because the antibody does not block the NKG2A/HLA-E pathway).

Specifically, in assessing NK cells from several donors with a fixed concentration of 10 µg/ml of the NKG2A.9 antibody, there was an approximately two-fold increase in percent degranulation among NKG2A+ expressing NK cells compared to the human IgG1.3 isotype control. As shown in FIG. 25C, for the NKG2A.9, NKG2A.10, NKG2A.11, NKG2A.12, NKG2A.14, NKG2A.15, NKG2A.5, and 4G5.D1 antibodies, the increase in NK cell response was not observed on NKG2A negative (−)(also referred to herein as NKG2A-) NK cells, which showed that the % CD107 increase was specific to NKG2A expressing NK cells. In other words, for several of the anti-NKG2A antibodies (the NKG2A.9, NKG2A.10, NKG2A.11, NKG2A.12, NKG2A.14, NKG2A.15, NKG2A.5, 4G5.D1 antibodies), enhanced degranulation among NKG2A positive (+) (also referred to herein as NKG2A+) NK cells and lack of enhanced degranulation among NKG2A negative (−) NK cells showed that NKG2A receptor expression was needed to enhance functionality. One exception to this result, as shown in FIG. 25C, was the 2G6.C2 antibody, which showed enhanced NK cell degranulation even among NKG2A negative (−) NK cells. In other words, enhanced degranulation with the 2G6.C2 antibody was not specific to the NKG2A/HLA-E interaction. Thus, the 2G6.C2 antibody was not selected for further investigation.

Figure 53:
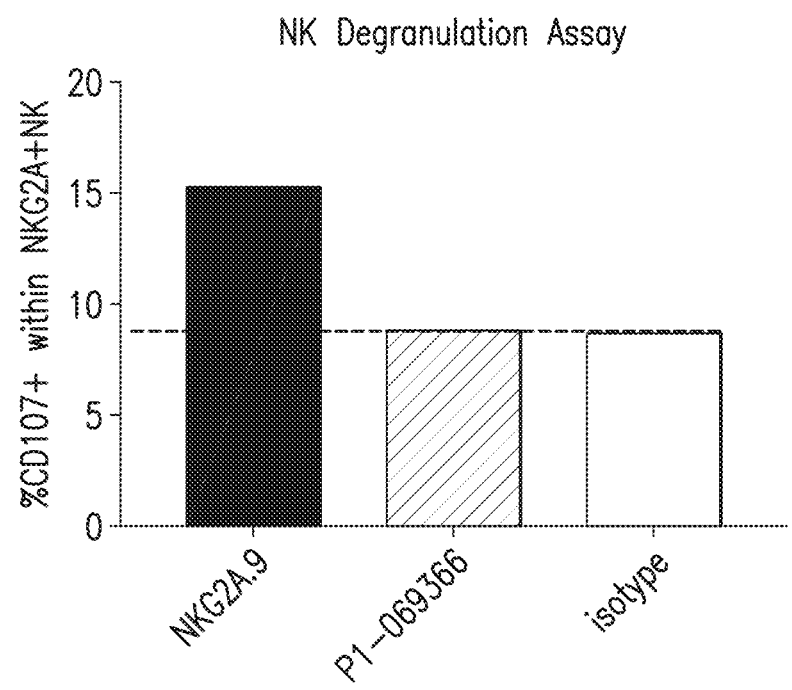
FIG. 53 shows the results of NK degranulation assay comparing P1-069366 to NKG2A.9 and isotype. The NKG2A.9 antibody showed functionality in the NK degranulation assay, while the P1-069366 antibody did not.

In summary, the NKG2A.9, NKG2A.10, NKG2A.11, NKG2A.12, NKG2A.14, NKG2A.15, NKG2A.5, and 4G5.D1 antibodies surprisingly and desirably specifically enhanced degranulation among NKG2A-expressing NK cells as compared to the isotype control. As shown in FIG. 25B, for the NKG2A.9 antibody, this enhanced degranulation was approximately two-fold compared to the isotype control. However, other anti-NKG2A antibodies were not selected for further development because they did not exhibit desired functional characteristics. For example, the 2G6.C2 antibody resulted in increased functionality of NKG2A negative (−) expressing cells, which suggested that the 2G6.C2 antibody did not directly affect the NKG2A/HLA-E interaction. The P1-069366 antibody also did not show functionality in the NK degranulation assay. As shown in FIG. 53, the P10069366 antibody had a similar % CD107[+] within NKG2A[+] NK cells are the isotype. Thus, the 2G6.C2 and P1-069366 antibodies were not selected for further development because they did not enhance degranulation in NK cells.

(9) Anti-NKG2A Antibodies That Enhanced NK Cell Response of Increased Interferon-gamma (IFNγ) Production.

Figure 26A:
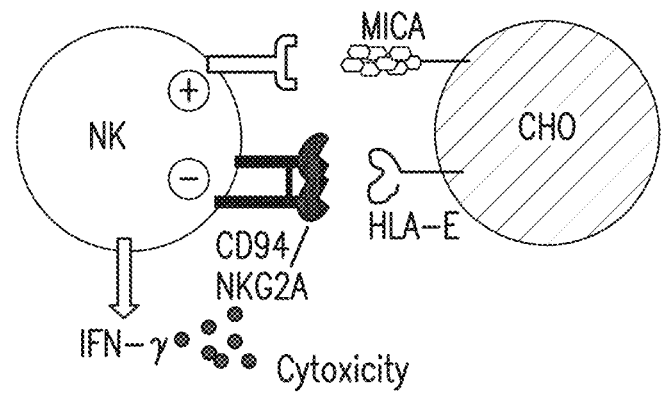
FIG. 26A illustrates the in vitro experiments using NKL cells and CHO/MICA/HLA-E to show that the anti-NKG2A antibodies blocked the NKG2A/HLA-E interaction among activated NK cells and increased IFN-γ production.

Anti-human NKG2A antibodies increased IFN-γ production in NKL cells co-cultured with CHO/MICA/HLA-E (CHO cells engineered to express HLA-E and MICA, the ligand for NK cell activating receptor NKG2D). As illustrated in FIG. 26A, in in vitro experiments using NKL cells and CHO/MICA/HLA-E, anti-NKG2A antibody blockade of the NKG2A/HLA-E interaction among activated NK cells (via the MICA-NKG2D pathway) desirably increased IFN-γ production. We first activated NKL cells using transfected MICA on CHO cells so that the activated NKL cells can kill the target cells, CHO/MICA/HLA-E cells. MICA functions as a ligand recognized by the activating receptor NKG2D that is expressed on the surface of NK cells. The antibodies were evaluated in an assay using a co-culture of NKL and CHO/MICA/HLA-E cells. In this assay, MICA on CHO cells served to activate NKL cells via NKG2A (positive signal), and the expression of HLA-E on CHO cells inhibits NKG2A expressing NKL cells (negative signal). The assay tested whether the anti-NKG2A antibody would block the NKG2A/HLA-E interaction and desirably increase IFN-γ production.

Figure 26B:
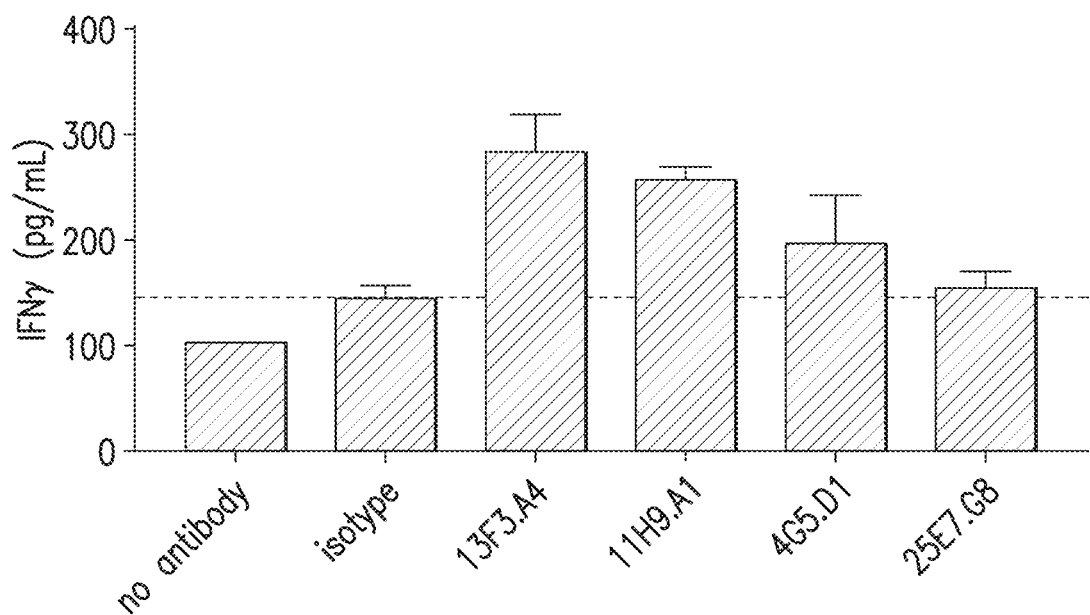
FIG. 26B shows that the 13F3.A4, 11H9.A1, and 4G5.D1 antibodies desirably increased IFN-γ production as compared to the isotype control (human IgG1.3 antibody). The 25E7.G8 clone was used as a negative control.

Specifically, NKL cells were co-cultured with CHO/MICA/HLA-E at an effector cell-to target cell ratio (E:T) of 4:1 in the presence of 10 µg/mL anti-human NKG2A antibody or isotype control antibody. Following overnight stimulation in a 37° C. incubator, IFN-γ production was measured in the supernatant by ELISA. As shown in FIG. 26B, the 13F3.A4, 11H9.A1, and 4G5.D1 antibodies desirably increased IFN-γ production as compared to the isotype control (human IgG1.3). The 25E7.G8 antibody, an anti-human NKG2A antibody that does not block NKG2A/HLA-E interaction, was used as a negative control, and, as expected, did not increase IFN-γ production compared to the isotype control.

(10) Anti-NKG2A Antibodies That Enhanced CD8+ T Cell Response of Increased IFNγ Production.

Anti-human NKG2A antibodies increased IFN-γ production among CD8+ T cells co-cultured with the pancreatic carcinoma cell line, Hs766T.

Figure 27A:
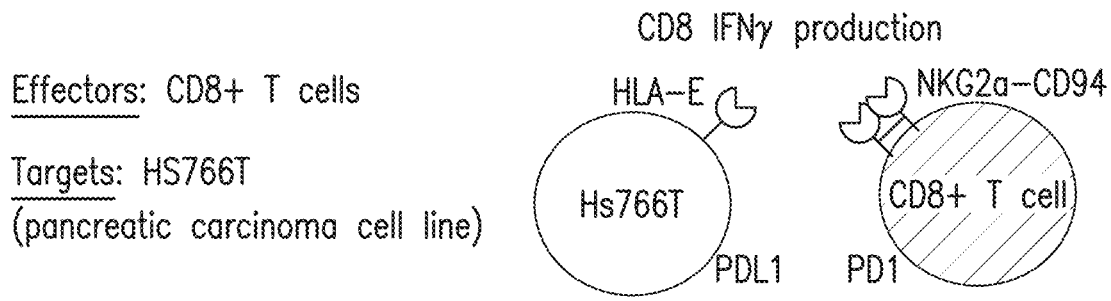
FIG. 27A illustrates the in vitro experiments used to assess whether anti-NKG2A antibodies enhanced the CD8+ T cell response of increased IFNγ in Hs766T target cells, a pancreatic carcinoma cell line.

Peripheral blood mononuclear cells (PBMC) from normal donors were activated for three days with plate-bound CD3 (OKT3) and rhIL-15 to increase expression of NKG2A among CD8+ T cells. As depicted in FIG. 27A, CD8+ T cells were co-cultured with Hs766T target cells (treated with mitomycin C) at an effector cell-to target cell ratio (E:T) of 1:1 in the presence of 10 µg/mL anti-human NKG2A antibodies or isotype control antibody (human IgG1.3). After five days of stimulation at 37° C., IFN-γ production was measured in the supernatant by ELISA.

Figure 27B:
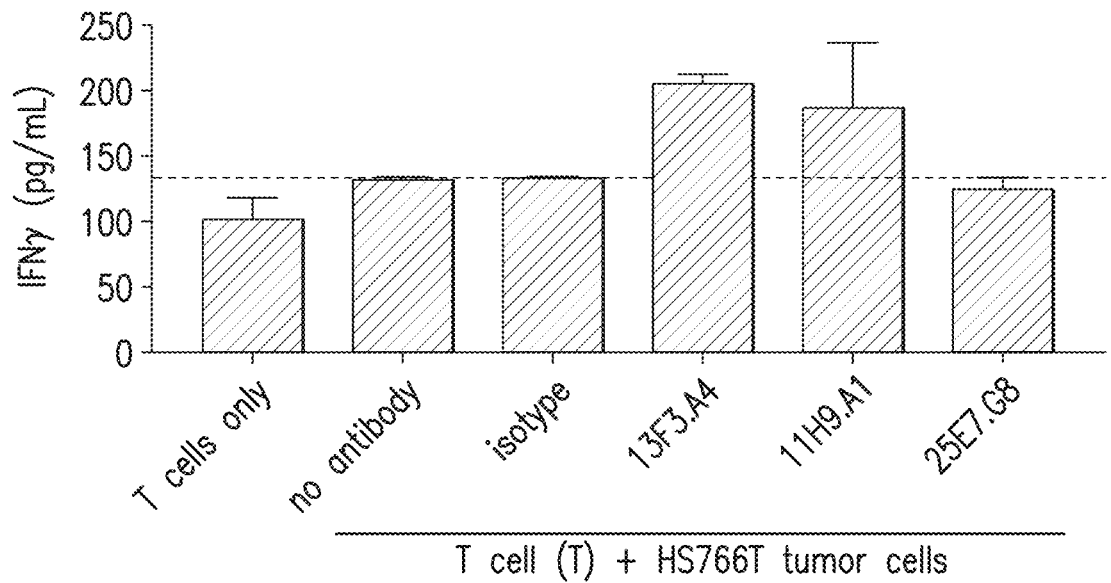
FIG. 27B is a graphical representation of the assay results and showed that the 13F3.A4 and 11H9.A1 antibodies increased IFN-γ production compared to the isotype control. The 25E7.G8 clone was used as a negative control.

As shown in FIG. 27B, the 13F3.A4 and 11H9.A1 antibodies increased IFN-γ production compared to the isotype control. The 25E7.G8 antibody, an anti-human NKG2A antibody that does not block NKG2A/HLA-E interaction, was used as a negative control and, as expected, did not increase IFN-γ production over isotype control. Specifically, HS766T is a pancreatic carcinoma cell line that endogenously expresses HLA-E. CD8+ T cells from healthy donor PBMC generally express low levels of NKG2A. However, with anti-CD3 and IL-15 stimulation, we were able to increase NKG2A expression on these cells. In this system, the CD8+ T cells express NKG2A, and the target HS766T cells express HLA-E. The 13F3.A4 and 11H9.A1 antibodies blocked NKG2A/HLA-E interaction and increased the cytotoxic functionality of CD8+ T cells, which was demonstrated by an increase in IFN-γ production.

(11) 13F3.A4 Antibody and Variants, Including the NKG2A.9 Antibody, Demonstrated Safe Levels of Undesirable Antibody Aggregation Antibody aggregates are clusters of denatured antibody molecules that are irreversibly formed during antibody expression in the cell culture, product purification, or storage as the antibody drug product. The process of aggregation is complicated and influenced by the biochemical and biophysical properties of the antibody as well as the physicochemical environmental in which the antibody is exposed during processing and storage. Antibody aggregation may expose normally unexposed epitopes, leading to increase immunogenicity. Purification processes for antibody products aims to achieve low aggregate levels, for example, less than 2% soluble aggregates. Accelerated stability studies (also known as forced degradation studies) were performed on eight variants of the 13F3.A4 antibody (NKG2A.9, NKG2A.13, NKG2A.18, NKG2A.19, NKG2A.21, NKG2A.22, NKG2A.23, and NKG2A.24) to ascertain the aggregation propensity of these antibodies at 4° C. and 25° C. storage for one month. NKG2A.20 stability was tested only at 4° C. due to limited material availability. A formulation with 20 mM histidine (pH 6.0), 260 mM sucrose, 50 µM DTPA and 0.05% polysorbate 80 was used as the test formulation for all the antibodies. Soluble aggregates were monitored by size exclusion chromatography (SEC) analysis. The tested concentrations were based on material availability. SEC revealed comparable aggregation propensities for all the antibodies except NKG2A.19, where multiple peaks are observed. Although not bound by any other mechanism, NKG2A.19 may have undergone degradation due to the presence of significant levels of protease in the batch of material tested.

Overall, the aggregation levels (less than 2% soluble aggregates at 25° C. after one-month storage) indicated suitability to formulate at pH 6.0 for the other antibodies that were tested. The physical stability data demonstrated less than 2% soluble aggregates after one month of storage at 25° C., which indicated that the tested formulation with the anti-NKG2A antibodies were suitable as a preliminary formulation imparting acceptable storage stability for drug substance at the tested concentration.

| NKG2A sequence | Tested concentration (mg/mL) | Soluble aggregate (%) 4° C. for one month | 25° C. for one month |
|---|---|---|---|
| NKG2A.9 | 150 | 0.7 | 0.8 |
| NKG2A.18 | 90 | Not detected | 1.2 |
| NKG2A.19 | 54 | Degraded sample | |
| NKG2A.20 | 6 | 1.2 | Not tested |
| NKG2A.21 | 43 | 1.3 | 1.9 |
| NKG2A.22 | 120 | 0.8 | 1.2 |
| NKG2A.23 | 130 | 0.8 | 1.1 |
| NKG2A.24 | 120 | 0.8 | 1.1 |

(12) NKG2A.9 Antibody Bound with High Affinity to NKG2A versus NKG2C Protein

The specificity of NKG2A.9 antibody for NKG2A protein over NKG2C protein was assessed by determining the kinetics and affinities using a Biacore T200 SPR instrument. The extracellular domains of NKG2A protein and NKG2C protein were each prepared as a heterodimer with the extracellular domain of CD94. The assay temperature was 37° C., and the running buffer was HEPES buffered saline (10 mM HEPES, 150 mM NaCl) at pH 7.4 supplemented with 0.05% Tween-20 and 1 g/L Bovine Serum Albumin (BSA). The NKG2A.9 antibody was captured on a CM4 sensor chip with pre-immobilized anti-human Fc capture reagent (Southern Biotech Catalog Number 2081-01). The NKG2A-CD94 and NKG2C-CD94 heterodimers were flowed as analytes over the captured antibody in two five-membered, three-fold dilution series each. One concentration series was used for single-cycle kinetics and the other one for multi-cycle kinetics. For the multi-cycle kinetics analysis, the second highest concentration was injected in duplicate. The top concentration for NKG2A-CD94 was 250 nM, and the top concentration for NKG2C-CD94 was 1.5 uM. All data were double-referenced and fitted to a 1:1 binding model with mass transport using the Biacore T200 Evaluation Software version 3.1

Generally, as discussed herein, two kinetic parameters determine binding affinity. The first parameter is how fast the complex is formed (the association rate, $k_a$), and the second parameter is how fast the complex dissociates or falls apart (the dissociation rate, $k_d$). Both kinetic parameters can be summarized in the equilibrium dissociation constant ($K_D$), which is defined as $k_d/k_a$. This comparative Biacore experiment addressed both interaction parameters: how fast the NKG2A.9 antibody/NKG2 protein complex was formed ($k_a$) and how fast it fell apart ($k_d$).

In this comparative Biacore experiment, the NKG2A.9 antibody showed 15-fold stronger binding to NKG2A protein than to NKG2C protein ($K_D$ of $3.9 \times 10^{-8}$ M for binding to NKG2A versus $K_D$ of $5.7 \times 10^{-7}$ M for binding to NKG2C). In other words, the NKG2A.9 antibody showed 15-fold weaker binding to NKG2C protein than to NKG2A protein. These results indicated that NKG2A.9 antibody had high selectivity for NKG2A protein compared to NKG2C protein, as summarized in the Table below. The NKG2A.9 antibody's stronger binding to NKG2A protein was driven by a faster association rate (ka), that is, how fast the NKG2A.9 antibody/NKG2A protein complex formed compared to the NKG2A.9 antibody/NKG2C protein complex. In other words, the NKG2A.9 antibody formed a complex 15 times more quickly with NKG2A protein than with NKG2C protein.

TABLE

Comparative Affinities of NKG2A.9 Antibody for NKG2A and NKG2C Proteins

| Ligand | Sample | $k_a$ (1/Ms) | $k_d$ (1/s) | $K_D$ (M) | $K_D$ ratio (NKG2C/NKG2A) |
|---|---|---|---|---|---|
| NKG2A.9 | hNKG2A-heterodimer | $3.9 \times 10^5$ | $1.5 \times 10^{-2}$ | $3.9 \times 10^{-8}$ | |
| NKG2A.9 | hNKG2C-heterodimer | $2.4 \times 10^4$ | $1.4 \times 10^{-2}$ | $5.7 \times 10^{-7}$ | 15 |

Figure 56B:
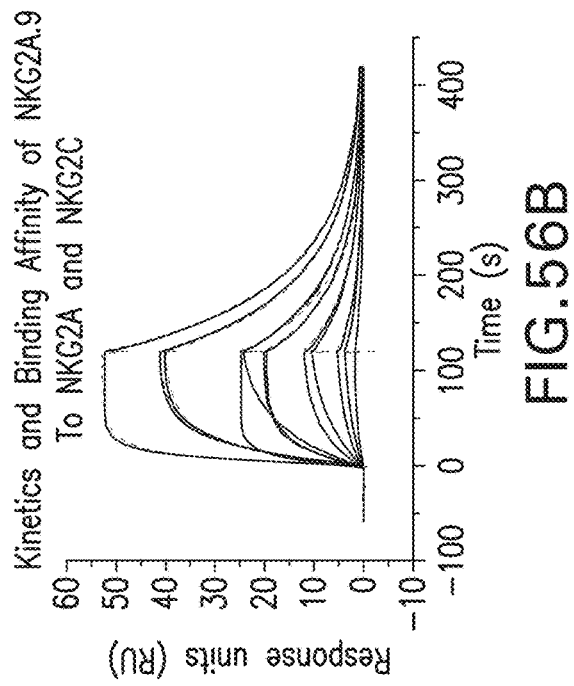
FIG. 56A-D show the binding affinity of the NKG2A.9 antibody to human NKG2A-CD94 heterodimers (FIG. 56A-B) and NKG2C-CD94 heterodimers (FIG. 56C-D) at 37° C. as determined by Biacore using both single-cycle kinetics (FIGS. 56A and 56C) and multi-cycle kinetics (FIGS. 56B and 56D). The SPR response is shown as a function of analyte association and dissociation.
Figure 56D:
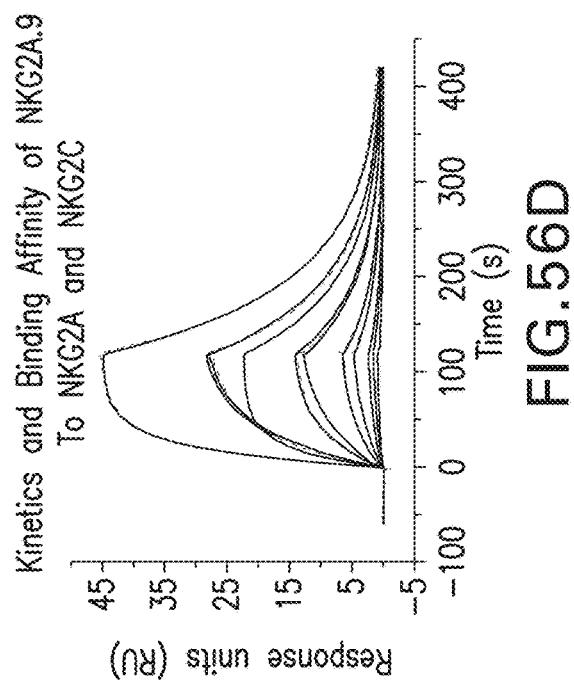
Figure 56A:
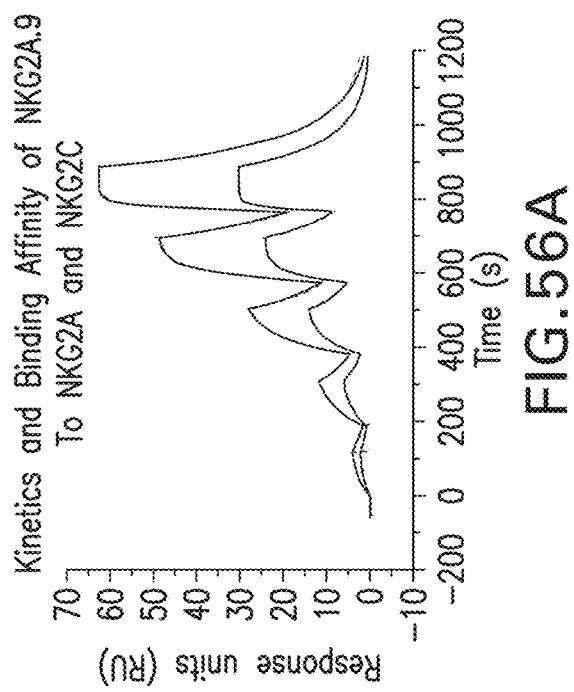
Figure 56C:
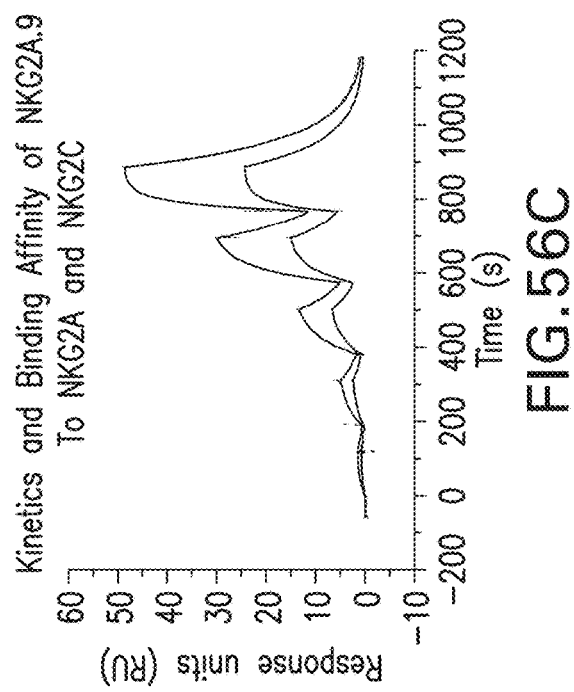

FIG. 56A-D show the binding affinity of the NKG2A.9 antibody to human NKG2A-CD94 heterodimers (FIG. 56A-B) and NKG2C-CD94 heterodimers (FIG. 56C-D) at 37° C. as determined by Biacore using both single-cycle kinetics (FIGS. 56A and 56C) and multi-cycle kinetics (FIGS. 56B and 56D). The SPR response is shown for analyte association and dissociation.

In other embodiments, the NKG2A.9 antibody forms a complex with NKG2A protein 14 times more quickly, 13 times more quickly, 12 times more quickly, 11 times more quickly, 10 times more quickly, 9 times more quickly, 8 times more quickly, 7 times more quickly, 6 times more quickly, 5 times more quickly, 4 more times more quickly, three time more quickly, or two times more quickly with than with NKG2C protein.

(13) Summary of Surprising and Desirable Functional Properties of Anti-NKG2A Antibodies In summary, the inventors unexpectedly discovered certain anti-NKG2A antibodies that exhibited various desired functional properties for treatment of, for example, cancer. In certain embodiments, these anti-NKG2A antibodies include the 13F3.A4 antibody clone and variants, including the NKG2A.9 and NKG2A.11 antibodies, which were identified and selected from hundreds of antibodies that did not exhibit the desired functional properties. Specifically, the NKG2A.9 antibody is an anti-hNKG2A antibody that is also known as 13F3.A4-VH-I107T-N30S IgG1.3, and will be referred to herein as the "NKG2A.9" antibody. Mutations in residue VH-107T (framework mutation reverted to germline) and residue VK-N30S to lower deamidation potential and reduce immunogenicity risk resulted in the discovery of the NKG2A.9 antibody. As described herein and shown in FIG. 13, various sequence liabilities were assessed in the 13F3.A4 antibody that led to the optimization and development of, for example, the NKG2A.9 antibody.

As described in further detail in Examples herein, anti-NKG2A antibodies, including the NKG2A.9 antibody, demonstrated, for example, the following surprising and desirable functional characteristics:
a) Blocked the NKG2A/HLA-E interaction;
b) Reversed NKG2A-mediated inhibitory signaling;
c) Did not bind, or bound with low affinity to, cells expressing human NKG2C protein;
d) Bound with high affinity to cells expressing human and cynomolgus NKG2A; and/or
e) Bound to human and cynomolgus NKG2A+ natural killer cells
f) Enhanced natural killer cell response, for example, of increased interferon-gamma (IFNγ); and/or
g) Enhanced CD8+ T cell response, for example, of increased IFNγ production; and/or
h) Formed a complex more quickly with NKG2A protein than with NKG2C protein; in some embodiments, formed a complex 15 times more quickly with NKG2A protein than with NKG2C protein.

The NKG2A.9 antibody was characterized and tested alone and in combination with additional antibodies as described in the Examples herein. The NKG2A.9 antibody bound with high affinity and specificity to human NKG2A protein. The $EC_{50}$ values for the binding of NKG2A.9 to NKG2A protein were as follows and demonstrated binding of NKG2A.9 to NKG2A protein:

| Cell lines | $EC_{50}$ |
| --- | --- |
| NKL (human NKG2A endogenously expressed on an NK cell line) | 0.4 nM |
| CHO-human NKG2A (human NKG2A ectopically expressed on CHO cells) | 0.6 nM |
| CHO-cyno NKG2A (cynomolgus monkey NKG2A ectopically expressed on CHO cells) | 1.2 nM |

The $EC_{50}$ values for the binding of NKG2A.9 to NKG2C protein were as follows and desirably demonstrated lack of binding of NKG2A.9 to human NKG2C protein:

| Cell lines | $EC_{50}$ |
| --- | --- |
| CHO-human NKG2C (human NKG2C ectopically expressed on CHO cells) | 9.0 nM |
| CHO-cyno NKG2C (cynomolgus monkey NKG2C ectopically expressed on CHO cells) | 0.8 nM |

The $IC_{50}$ values of NKG2A.9, which showed blocking of the NKG2A/HLA-E interaction in cell blocking assays, were as follows:

| Cell lines | $IC_{50}$ |
| --- | --- |
| NKL | 0.3 nM |
| CHO-human NKG2A | 1.0 nM |

The $EC_{50}$ values showed that the NKG2A.9 antibody blocked the NKG2A/HLA-E interaction. The $EC_{50}$ value of the NKG2A.9 antibody showed that binding to human NKG2A protein was about 15-fold less than to human NKG2C protein (0.6 nM for NKG2A vs. 9.0 nM for NKG2C). Furthermore, no specific binding of the NKG2A.9 antibody to human NKG2C was observed in SPR experiments. In contrast, the $EC_{50}$ values the NKG2A.9 antibody binding to cynomolgus NKG2A and cynomolgus NKG2C proteins were similar (1.2 nM for NKG2A vs. 0.8 nM for NKG2C). The NKG2A.9 antibody did not block the human NKG2C/HLA-E interaction as assessed by flow cytometry under the conditions discussed herein. No binding to mouse or rat NKG2A was observed by flow cytometry on primary NK cells.

Figure 52A:
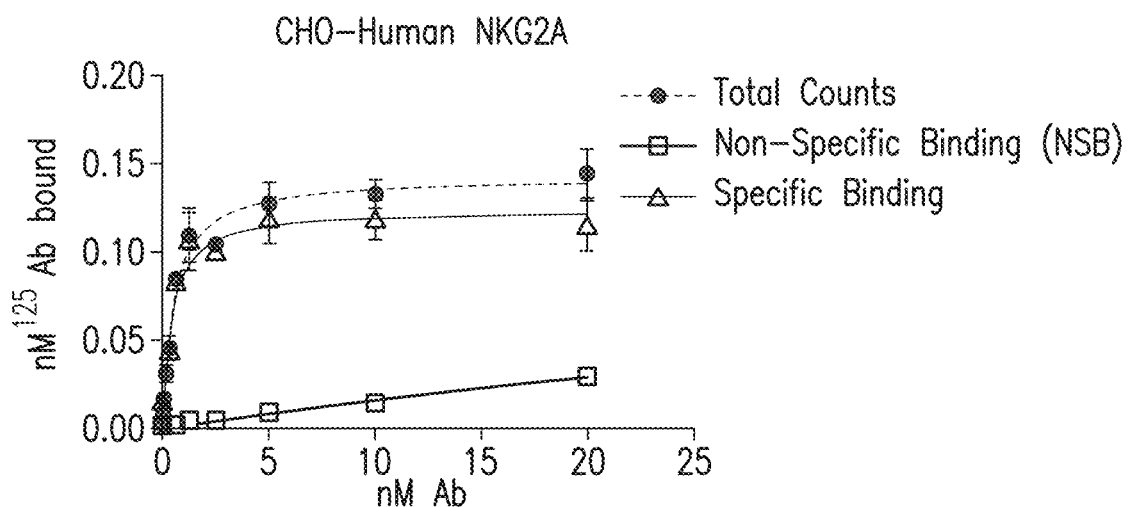
FIG. 52A-B shows the kinetic and binding affinities of NKG2A.9 as measured by Scatchard analysis.
Figure 52B:
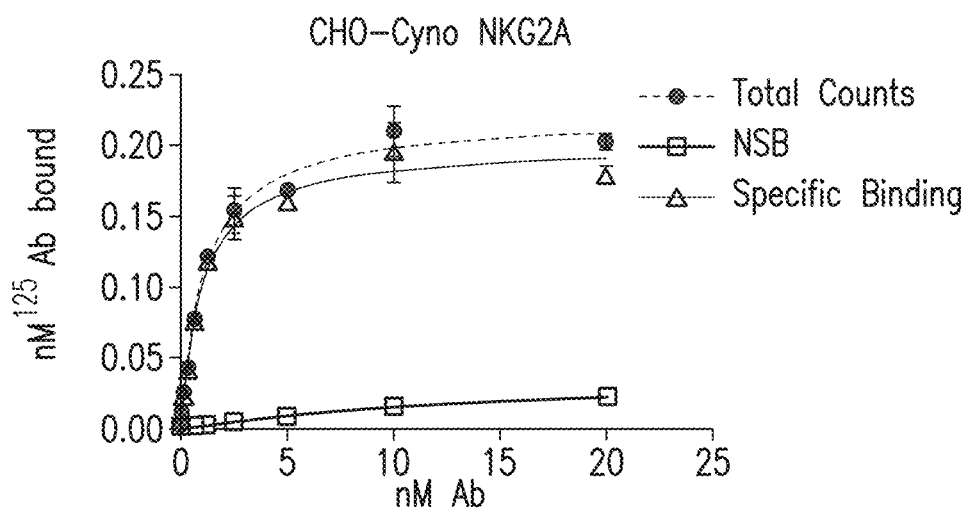

We used Scatchard analysis to measure binding affinities of NKG2A.9. For NKG2A.9, saturated cell binding and Scatchard analysis of CHO-hNKG2A and CHO-cynomolgus NKG2A established specific binding affinities ($K_D$ values) of about 0.4 nM and 1.0 nM, respectively, as shown in FIG. 52A-B. Specifically, NKG2A.9 was radioiodinated with $^{125}$I—Na (1 mCi; PerkinElmer Catalog NEZ033H001 MC) using IODO-GEN® solid phase iodination reagent (1,3,4,6-tetrachloro-3a-6a-diphenylglycouril; Pierce, Catalog 28601). Excess iodide was removed using a desalting column (Pierce, Catalog 43243). Fractions of labeled antibody were collected and analyzed for radioactivity on a Wizard 1470 gamma counter. The $^{125}$I-NKG2A.9 concentration in each fraction was calculated with the Qubit fluorometer from Invitrogen. Radiopurity was established by thin layer chromatography of peak protein and radioactive fractions. Radioiodinated NKG2A.9 binding to CHO overexpressed human or cynomolgnus NKG2A cells was demonstrated by incubating CHO-human or cynomolgus NKG2A cells with a titration of 125I-NKG2A.9. Nonspecific binding was determined by binding in the presence of a titration of a 100-fold molar excess of unlabeled antibody and was subtracted from total CPM to calculate specific binding. A linear standard curve of 125I-NKG2A.9 concentration versus CPM was used to extrapolate specific activity, maximal nM bound 125I-NKG2A.9 and thereby calculate receptor number per cell. Results of the Scatchard analysis showed that NKG2A.9 specifically bound to CHO-hNKG2A with an equilibrium dissociation constant ($K_D$) of 0.4 nM and to CHO-cynoNKG2A transfectants with a $K_D$ of 0.1 nM. The relative binding affinity of NKG2A.9 for cynomolgus NKG2A was determined via SPR by flowing NKG2A.9 Fab over a CM4 chip with immobilized monkey NKG2A-CD94-mFc (truncated construct to achieve expression). Human NKG2A-CD94-mFc coupled to a second flow cell served as a control. Another flow cell was left blank for reference-subtraction. The measurement was conducted on a Biacore T200 instrument at 37° C. using Hepes buffered saline (10 mM HEPES, 150 mM NaCl) at pH 7.4 supplemented with 0.05% Tween-20 and 1 g/L BSA as running buffer. A concentration series of NKG2A.9 Fab was injected over the different flow cells. All data were double-referenced and fitted to a 1:1 Langmuir model using the Biacore T200 Evaluation Software version 3.1. In this assay, the monovalent binding of NKG2A.9 Fab to human NKG2A was approximately 26-fold stronger than binding to cynomolgus NKG2A. The $K_D$ value as measured by SPR for human NKG2A was 61 nM, and $K_D$ value as measured by SPR for cynomolgus NKG2A was 1600 nM, as shown in the table below. These $K_D$ values indicated that the NKG2A.9 Fab binds to recombinant cynomolgus NKG2A, but higher Fab concentrations have to be used to achieve a binding level (saturation level) similar to that of human NKG2A.

| Analyte | hNKG2A-CD94 | | | cyNKG2A-CD94 | $K_D$ ratio (cy/h) |
|---|---|---|---|---|---|
| | $k_a$ (1/Ms) | $k_d$ (1/s) | $K_D$ (nM) | $K_D$ (nM) | |
| NKG2A.9 Fab | $3.4 \times 10^5$ | $2.0 \times 10^{-2}$ | 61 nM | 1600 nM | About 26 |

Example 4

Epitope Mapping of Anti-NKG2A Antibodies

Methods known in the art were used to probe regions of NKG2A to which anti-NKG2A antibodies, specifically, 13F3.A4 and NKG2A.9 antibodies, bind. Hydrogen/deuterium exchange mass spectrometry (HDX-MS) and fast photochemical oxidation of proteins (FPOP) were used to probe binding epitopes of hNKG2A with the 13F3.A4 and NKG2A.9 antibodies.

HDX-MS experiments on mFc-hNKG2A-hCD94/NKG2A.9 provided 95% sequence coverage for mFc-NKG2A-CD94. FPOP measurements yielded 99% sequence coverage on NKG2A. The total sequence coverage for NKG2A was 100% with the combined HDX-MS and FPOP dataset. Similarly, HDX-MS experiments on mFc-hNKG2A-hCD94/13F3 provided 95% sequence coverage for mFc-NKG2A-CD94. FPOP measurements yielded 99% sequence coverage on NKG2A. The total sequence coverage for NKG2A was 100% with the combined HDX-MS and FPOP dataset.

As discussed in more detail in this Example, certain embodiments of the present invention relates to an anti-NKG2A monoclonal antibody or antigen-binding portion thereof that specifically binds to an epitope located within discontinuous regions spanning approximately the following amino acid residues as determined by HDX-MS and/or FPOP epitope mapping:
- Region 1: $^{155}$LSIDNEEEMKF$^{165}$ (amino acid residues 155 to 165 of SEQ ID NO: 2 (native hNKG2A amino acid sequence);
- Region 2: $^{171}$PSSWIGVFRNSSHHPW$^{186}$ (amino acid residues 171 to 186 of SEQ ID NO: 2);
- Region 3: $^{192}$LAFKHEIKDSDN$^{203}$ (amino acid residues 192 to 203 of SEQ ID NO: 2);
- Region 4: L (amino acid residue 206 of SEQ ID NO: 2); and
- Region 5: $^{212}$QVNRLKSAQCGSSIIYHC$^{229}$ (amino acid residues 212 to 229 of SEQ ID NO: 2).

In some embodiments, the invention is directed to an anti-NKG2A monoclonal antibody or antigen-binding portion thereof that specifically binds to an epitope located within discontinuous regions consisting of the following amino acid residues as determined by HDX-MS:
- Region 1: $^{155}$LSIDNEEEMKF$^{165}$ (amino acid residues 155 to 165 of SEQ ID NO: 2);
- Region 2: $^{171}$PSSWIGVFRNSSHHPW$^{186}$ (amino acid residues 171 to 186 of SEQ ID NO: 2);
- Region 3: $^{192}$LAFKHEIKDSDN$^{203}$ (amino acid residues 192 to 203 of SEQ ID NO: 2); and
- Region 5: $^{212}$QVNRLKSAQCGSSIIYHC$^{229}$ (amino acid residues 212 to 229 of SEQ ID NO: 2).

Preparation for Epitope Mapping Experiments.

Prior to epitope mapping experiments, non-deuterated experiments were carried out to generate a list of common peptides for recombinant mFc-hNKG2A-hCD94 and protein complexes of mFc-NKG2A-CD94 and parental 13F3 Fab or NKG2A.9 Fab (15 µM, 1:1 molar ratio). In the HDX-MS experiments, 5 µL of each sample (mFc-hNKG2A-hCD94 or mFc-hNKG2A-hCD94 with Fab) was diluted into 55 µL of deuterium oxide ($D_2O$) buffer (10 mM phosphate buffer, D20, pD 7.0) to start the labeling reactions. The reactions were carried out for different time periods: 20 seconds, 1 minute, 10 minutes and 4 hours. By the end of each labeling reaction period, the reaction was quenched by adding quenching buffer (100 mM phosphate buffer with 4 M guanidine hydrochloride (GdnCl) and 0.4 M tris(2-carboxylethyl)phosphine (TCEP), pH 2.5, 1:1, volume/volume), and 50 µL of quenched sample was injected into Waters HDX-MS system for analysis. The deuterium uptake levels of common peptic peptides were monitored in the absence or presence of Fabs.

Epitope Mapping of 13F3 and NKG2A.9 by HDX-MS.

HDX-MS. HDX-MS probes protein conformation and conformational dynamics in solution by monitoring the rate and extent of deuterium exchange of backbone amide hydrogen atoms (R. Huang and G. Chen, *Analytical and Bioanalytical Chemistry*, 406: 6541-58 (2014); Wei et al., *Drug Discovery Today*, 19: 95-102 (2014). The level of HDX depends on the solvent accessibility of backbone amide hydrogen atoms and the protein hydrogen bonds. The mass increase of the protein upon HDX can be precisely measured by MS. When this technique is paired with enzymatic digestion, structure features at the peptide level can be resolved, enabling differentiation of surface-exposed peptides from those folded inside. Typically, the deuterium labeling and subsequent quenching experiments are performed followed by enzymatic digestion, peptide separation, and MS analysis.

Figure 28A:
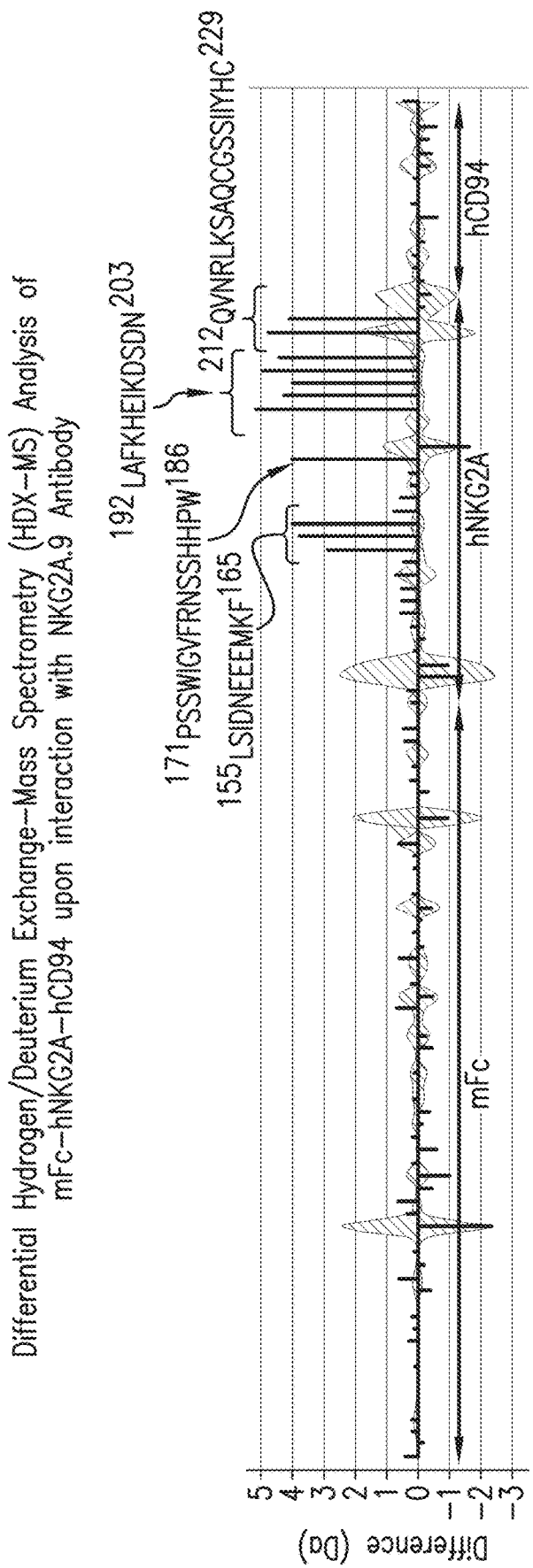
FIG. 28A-B show the results of differential hydrogen-deuterium exchange (HDX) analysis of mFc-hNKG2A-hCD94 upon interaction with NKG2A.9 antibody (FIG. 28A) and with 13F3.A4 antibody (FIG. 28B), respectively. The epitope sequences are labeled in FIGS. 28A-B (SEQ ID NOS: 119-122, disclosed from left to right along the analysis).
Figure 28B:
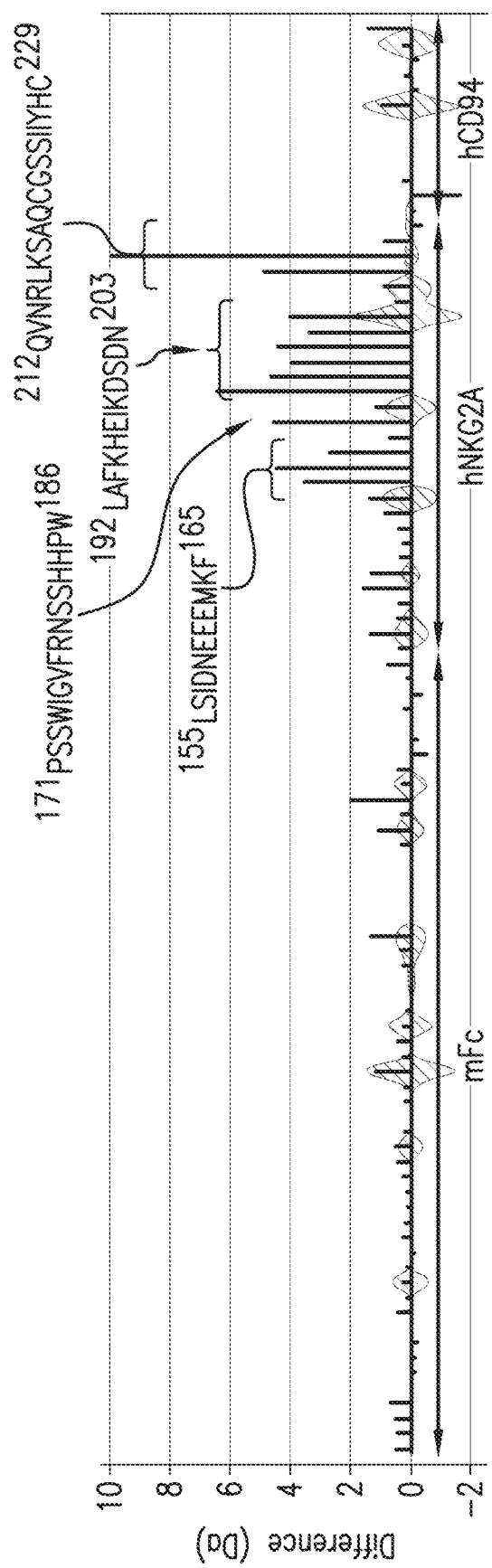

FIG. 28A shows differential HDX of mFc-hNKG2A-hCD94 upon interaction with NKG2A.9 antibody. FIG. 28B shows differential HDX of mFc-NKG2A-CD94 upon interaction with 13F3.A4. The data in FIGS. 28A-B show that the epitopes are the same for NGK2A.9 and 13F.3.A4 antibodies Specifically, HDX-MS data analysis on the NKG2A9 antibody in mFc-NKG2A-CD94 indicated that NKG2A9 and the 13F3.A4 parental monoclonal antibody share the same epitope, which is the following four discontinuous regions of hNKG2A (residue numbers correspond to native hNKG2A sequence):
- Region 1: $^{155}$LSIDNEEEMKF$^{165}$ (amino acid residues 155 to 165 of SEQ ID NO: 2);
- Region 2: $^{171}$PSSWIGVFRNSSHHPW$^{186}$ (amino acid residues 171 to 186 of SEQ ID NO: 2);
- Region 3: $^{192}$LAFKHEIKDSDN$^{203}$ (amino acid residues 192 to 203 of SEQ ID NO: 2); and
- Region 5: $^{212}$QVNRLKSAQCGSSIIYHC$^{229}$ (amino acid residues 212 to 229 of SEQ ID NO: 2).

Epitope Mapped to mFc-hNKG2A-hCD94 Sequence and Crystal Structure.

FPOP. Fast photochemical oxidation of proteins (FPOP) is a protein footprinting technique to determine structural information by mapping oxidation induced by hydroxyl (OH) radicals. (Li et al., *Analytical Chemistry*, 2017, 89, 2250-2258). The extent of hydroxyl radical-induced oxidation depends directly on solvent accessibility of amino acids side chains and chemical properties of exposed amino acids. Hydroxyl radicals, produced from hydrogen peroxide ($H_2O_2$) via laser activation, are highly reactive and produce covalent irreversible modifications to the side chains without causing backbone cleavages. FPOP coupled with enzymatic digestion and MS analysis allows peptide level assessment of the changes in solvent accessibilities of side chains due to protein-protein interactions. Residue-level information can be achieved by gas-phase fragmentation of the selected peptide regions by MS/MS. This technique provides complementary information to HDX.

Epitope mapping by FPOP was performed on mFc-NKG2A-CD94 and mFc-NKG2A-CD94 complexed with parental 13F3 Fab (15 µM, 1:1 molar ratio). Similarly, epitope mapping by FPOP was performed on mFc-NKG2A-CD94 and mFc-NKG2A-CD94 complexed with NKG2A.9 Fab (15 µM, 1:1 molar ratio).

For epitope mapping of both 13F3.A4 and NKG2A.9 antibodies, a krypton fluoride (KrF) excimer laser was used to generate hydroxyl radicals by the photolysis of $H_2O_2$, and the excitation wavelength was set as 248 nm to avoid any laser-induced conformation change of protein. Immediately before labeling, 5 µL of histidine and 5 µL of $H_2O_2$ were added to a protein aliquot. The final volume of protein solution was 50 µL, and the final concentrations of histidine was 500 µM and of $H_2O_2$ was 15 mM. The sample was then injected into fused silica tubing with an ultraviolet (UV) transparent window. The laser energy was adjusted to 70 mJ/pulse at a frequency of 7.4 Hz. Both FPOP and no laser control experiments were performed in triplicate. Each replicate was collected in a microcentrifuge tube containing 11 µL of quenching solution (50 nM of catalase and 20 mM of methionine). The samples were denatured, reduced, alkylated, deglycosylated, and digested with trypsin followed by liquid chromatography (LC)/MS analysis. The oxidation levels of tryptic peptides were monitored in the absence or presence of the NKG2A.9 Fab.

In FPOP experiments, four residues, M163, F179, H184, and L206, in hNKG2A exhibited significant reduction (P-value<0.025) in oxidation levels upon binding with parental 13F3 Fab. Similarly, in FPOP experiments, four residues, M163, F179, H184, and L206, in hNKG2A exhibited significant reduction (P-value<0.025) in oxidation levels upon binding with NKG2A.9.

For both 13F3.A4 and NKG2A.9 antibodies, FPOP protection percentage upon binding of Fab was calculated as:

$$\frac{(\text{Relative \% } FPOP \text{ difference in } hNKG2A) - (\text{Relative \% } FPOP \text{ difference in } hNKG2A/Fab \text{ complex})}{\text{Relative \% } FPOP \text{ difference in } hNKG2A} \times 100$$

Figure 29A:
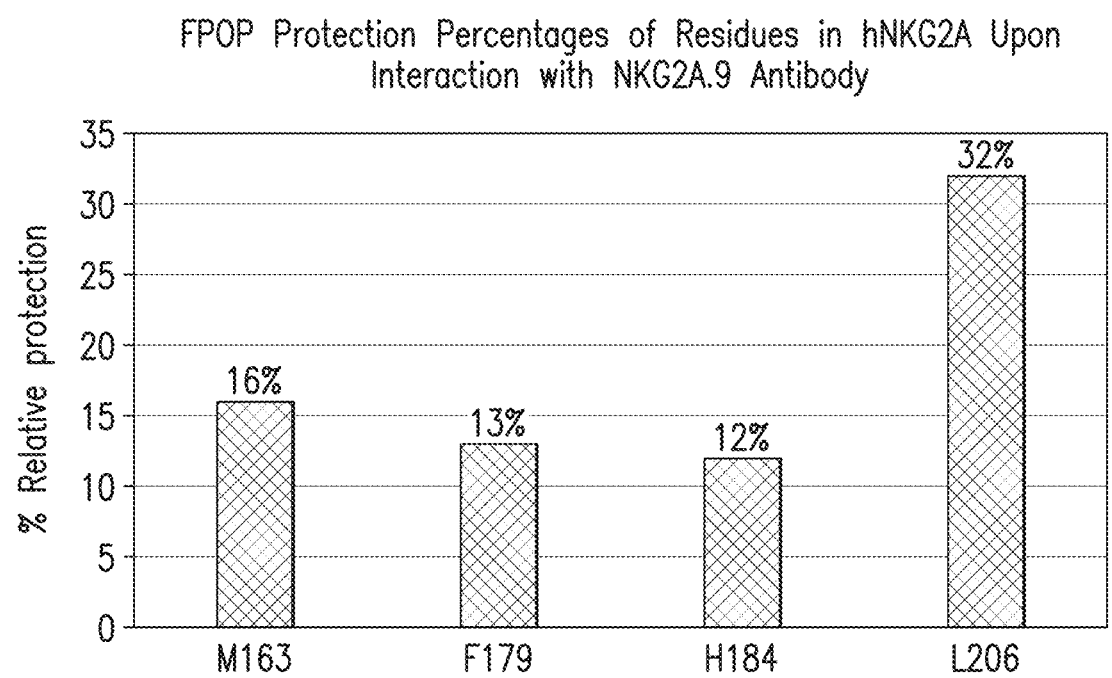
FIG. 29A-B show FPOP protection percentages for four residues (M163, F179, H184, L206) in hNKG2A upon interaction with NKG2A.9 antibody (FIG. 29A) and with 13F3.A4 antibody (FIG. 29B), respectively.
Figure 29B:
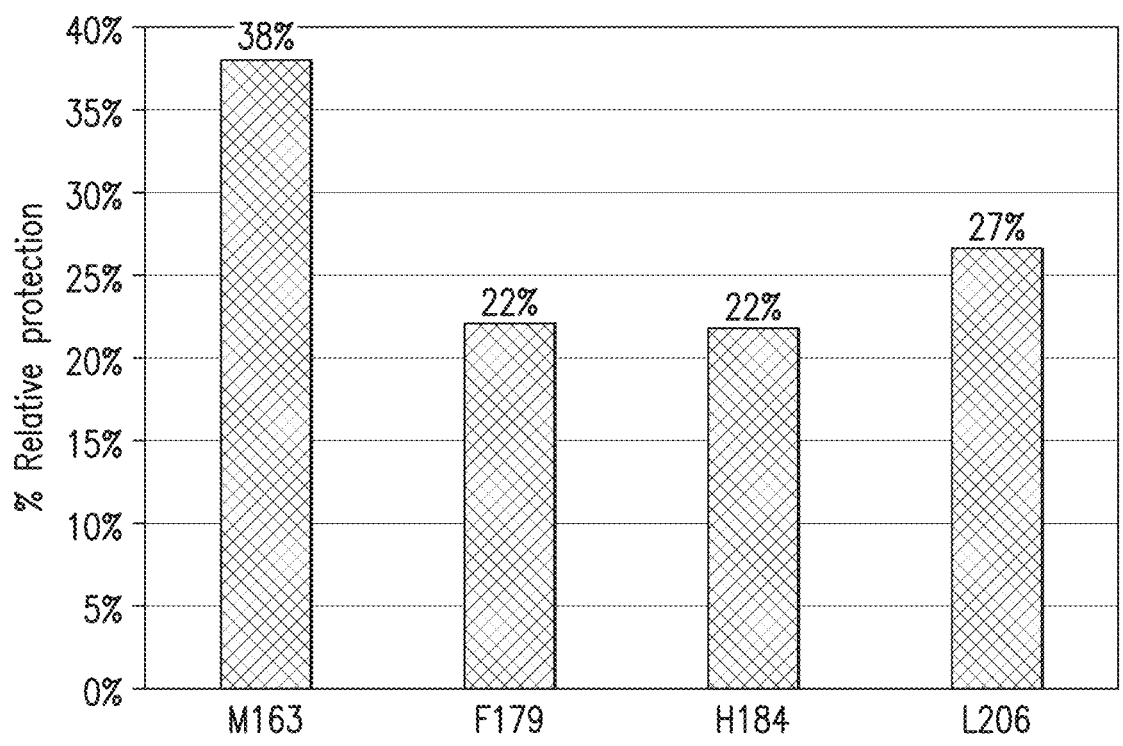

FIG. 29A displays protection percentages for four residues (M163, F179, H184, L206) in hNKG2A upon interaction with NKG2A.9. FIG. 29B displays FPOP protection percentages for four residues (M163, F179, H184, L206) in hNKG2A upon interaction with 13F3.A4.

Epitope Mapped to mFc-NKG2A-CD94 Sequence and Crystal Structure.

As shown in FIG. 30, the epitopes of NKG2A.9 and 13F3.A4 antibodies determined by HDX-MS and by FPOP were mapped to the mFc-hNKG2A-hCD94 sequence. In the mFc-hNKG2A-hCD94 sequence, mFc is the mouse Fc region, which is linked via a linker sequence ASIEGR (SEQ ID NO: 123) (shown by a box with dashed lines) to the extracellular domain of hNKG2A, which is linked via a linker sequence GGSGGS (SEQ ID NO: 124) (shown by a box with dashed lines) to hCD94, which is human CD94 protein.

Figure 31:
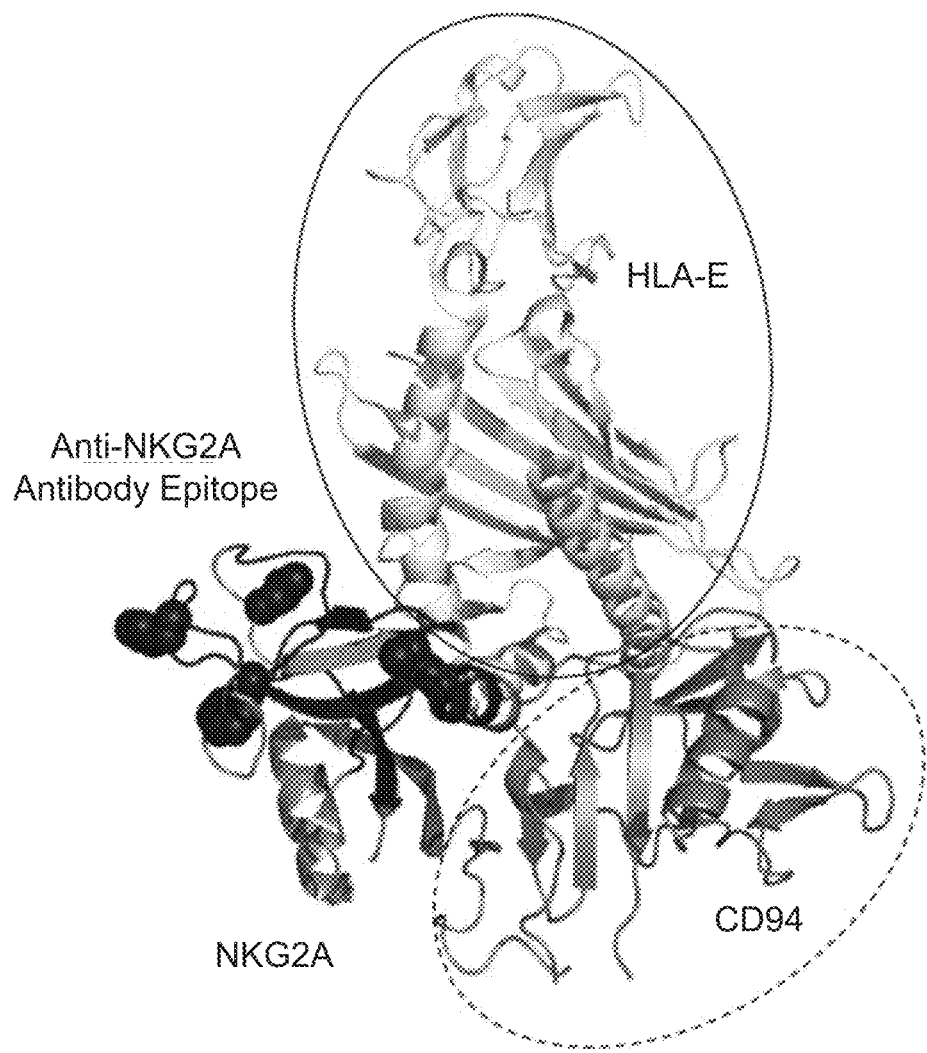
FIG. 31 shows the anti-NKG2A antibody epitope (for example, of the NKG2A.9 and 13F3.A4 antibodies) visualized on the NKG2A/CD94/HLA-E crystal structure. The anti-NKG2A antibody epitope is shown in black.

As shown in FIG. 31, the anti-NKG2A antibody epitope (for example, epitopes of NKG2A.9 and 13F3.A4 antibodies) can be visualized on the NKG2A/CD94/HLA-E crystal structure. Specifically, FIG. 31 depicts the anti-NKG2A antibody epitope (shown in black) on the NKG2A/CD94/HLA-E crystal structure (human CD94/NKG2A in complex with HLA-E crystal structure was published by Petrie et al., *J. Exp. Med.* 205: 725-35 (2008), which is incorporated by reference in its entirety.) The HLA-E crystal structure is indicated with a solid oval, and the CD94 crystal structure is indicated with a dotted oval.

In summary, based on the HDX-MS and FPOP experiments discussed herein, the NKG2A epitope to which the NKG2A.9 and 13F3.A4 antibodies bind includes the following discontinuous binding regions:

Region 1: LSIDNEEEMKF (amino acid residues 155 to 165 of SEQ ID NO: 2);
Region 2: PSSWIGVFRNSSHHPW (amino acid residues 171 to 186 of SEQ ID NO: 2);
Region 3: LAFKHEIKDSDN (amino acid residues 192 to 203 of SEQ ID NO: 2);
Region 4: L (amino acid residue 206 of SEQ ID NO: 2); and
Region 5: QVNRLKSAQCGSSIIYHC (amino acid residues 212 to 229 of SEQ ID NO: 2).

In other embodiments, based on the HDX-MS experiments discussed herein, the NKG2A epitope to which the NKG2A.9 and 13F3.A4 antibodies bind includes the following discontinuous binding regions:

Region 1: LSIDNEEEMKF (amino acid residues 155 to 165 of SEQ ID NO: 2);
Region 2: PSSWIGVFRNSSHHPW (amino acid residues 171 to 186 of SEQ ID NO: 2);
Region 3: LAFKHEIKDSDN (amino acid residues 192 to 203 of SEQ ID NO: 2); and
Region 5: QVNRLKSAQCGSSIIYHC (amino acid residues 212 to 229 of SEQ ID NO: 2).

Example 5

Epitope Binning Experiments
(1) P1-069366 Antibody Cross-Blocked 13F3.A4

An epitope binning experiment for P1-069366 and 13F3.A4 was performed by SPR using a "sandwich format", where antibody 1 is immobilized onto a Biacore T100 CMS chip, the recombinant human NKG2A-CD94 protein is flowed over the Biacore T100 CMS chip and allowed to bind, and then antibody 2 is flowed over the chip. Specifically, 13F3.A4 or P1-antibodies were immobilized onto a CMS sensor chip by amine coupling. A solution of recombinant NKG2A protein was flowed over the sensor chip where it was observed to bind both P1-069366 and 13F3.A4 antibodies. A solution of competing antibody was then flowed over the chip and additional binding was measured (indicative of co-binding to NKG2A). Finally, the sensor chip was regenerated using a solution of $MgCl_2$, which removed bound NKG2A and competing antibody. The experiment was conducted at 25° C. For analysis, non-specific binding to the reference flow cell was subtracted from binding to the analytical flow cells. P1-069366 antibody was directly immobilized to flow cell 2. Then, 200 nM NKG2A was flowered over flow cell 2, and approximately 600 RU was observed to bind. Subsequent injection of 13F3.A4 antibody, P1-069366 antibody, or buffer (HBS-P) did not result in increased binding signal. 13F3.A4 antibody was immobilized onto flow cell 3. Next, 200 nM NKG2A was flowed over flow cell 3, and approximately 900 RU was observed to bind. Subsequent injection of P1-069366 antibody, 13F3.A4 antibody, or buffer (HBS-P) did not result increased binding signal. In conclusion, P1-069366 antibody appeared to cross-block 13F3.A4 based on the results of the epitope binning experiment.

(2) 13F3.A4, 2G6.C2 Blocked Each Other as Well as HLA-E from Binding to Human NKG2A-CD94.

In another epitope binning and blocking experiment that was performed on an Octet HTX instrument using the "sandwich format", 13F3.A4 antibody, 2G6.C2 antibody as well as HLA-E were tested for simultaneous binding to human NKG2A. The antibodies and biotinylated HLA-E were captured on separate Octet sensor tips. Next, the remaining capture sites were blocked if required, and human NKG2A-CD94 was bound. Subsequent binding of 13F3.A4 antibody, 2G6.C2 antibody, and HLA-E to pre-bound NKG2A-CD94 was tested, probing all pairwise combinations of these three samples. These epitope binning experiments showed that the 13F3.A4 and 2G6.C2 antibodies block each other as well as HLA-E from binding to human NKG2A-CD94.

(3) Binding Activity of 2G6.C2 Antibody

Octet experiments also showed binding of 2G6.C2 antibody not only to human NKG2A-CD94 but also to a cynomolgus NKG2A-CD94-mFc construct. The kinetics of 2G6.C2 antibody binding to human NKG2A-CD94 and NKG2C-CD94 heterodimers were measured on a Biacore T200 instrument at 37° C. by capturing the antibody on a CM4 chip with pre-immobilized anti-hFc antibody and flowing the antigens as analytes with an appropriate concentration range. All data were double-referenced and fitted to a 1:1 binding model using the Biacore T200 Evaluation Software version 3.1. The Biacore experiments showed that the 2G6.C2 antibody had a weaker binding affinity than the 13F3.A4 antibody and that it has some cross-reactivity to NKG2C, as summarized below.

| Captured | Analyte | $k_a$ (1/Ms) | $k_d$ (1/s) | $K_D$ (M) | Half-Life of Antibody/Analyte Complex (seconds) |
|---|---|---|---|---|---|
| 2G6.C2 | hNKG2A-CD94 | $4.0 \times 10^5$ | $3.6 \times 10^{-2}$ | $9.1 \times 10^{-8}$ | 19 |
| 2G6.C2 | hNKG2C-CD94 | $2.8 \times 10^4$ | $3.0 \times 10^{-2}$ | $1.1 \times 10^{-6}$ | 23 |

Example 6

Discovery of Additional Anti-NKG2A Antibodies

As shown in FIGS. 32A-B, the heavy and light chain variable regions of certain anti-NKG2A antibodies (13F3.A4, NKG2A.9, and NKG2A.11) were aligned using Clutsal 2.1 software. This alignment resulted in the discovery of anti-NKG2A antibodies with the following consensus CDR sequences:

HCDR1:
(SEQ ID NO: 10)
SHSMN

HCDR2:
(SEQ ID NO: 11)
AISSSSSYIYYADSVKG

HCDR3:
(SEQ ID NO: 12)
EEWGLPFDY

LCDR1:
(SEQ ID NO: 13, for NKG2A.9 antibody)
RASQGISSALA;

(SEQ ID NO: 154, for NKG2A.11 antibody)
RASQGIPSALA;
or (SEQ ID NO: 155, for 13F3.A4 antibody)
RASQGINSALA.

LCDR2:
(SEQ ID NO: 14)
DASSLKS

LCDR3:
(SEQ ID NO: 15)
QQFNSYPLT

Example 7

Development of NKG2A.9 Antibody With an Inert Fc (IgG1.3) to Reduce or Prevent Fc gamma receptor (FcγR) Binding Since NKG2A is an inhibitory receptor expressed on CD8+ T and NK cells, we believe that avoiding or reducing agonism or depletion of NKG2A+ CD8+ T or NK cells enhances anti-tumor immunity. Thus, blockade of the NKG2A/HLA-E interaction was desired with an anti-NKG2A antibody unable to interact with human FcγRs.

As summarized in Study 1 below, we assessed the role of the isotype in mediating tumor growth inhibition in the 1956 sarcoma model. NKG2A.2 antibody is a mouse surrogate antibody generated as an mIgG2a or mIgG1-D265A isotype to evaluate the role of Fc in antitumor activity.

| Mouse Tumor Model Study 1 | | | | | |
|---|---|---|---|---|---|
| Purpose | Tumor Model | Recipient Mice | mAb(s) | Treatment Regimen | % Tumor Growth Inhibition (compared to isotype control) |
| Efficacy of anti-mNKG2A.2 IgG2a NKG2A.2 IgG1-D265A isotypes | 1956 sarcoma | C57Bl/6 n = 10/grp | NKG2A.2 (mIg2a) NKG2A.2 (mIgG1-D265A) | Day 0: 1 × 10⁶ cells per mouse subcutaneous (SC) Days 6, 9, 12: Each isotype 10 mg/kg intraperitoneal (IP) | At Day 21 NKG2A.2-g1 D265A: 41% NKG2A.2-g2a: 0% |

At Day 21 post implant, NKG2A.2-mIGg1 D265A inhibited tumor growth by 41% compared to the isotype control. In other words, treatment of tumor-bearing mice with an anti-mNKG2A mAb containing an inert Fc (mNKG2A.2 mIgG1-D265A) led to potent antitumor activity. However, when NKG2A.2 mIgG2a was administered, the antibody did not inhibit tumor growth. In other words, when the NKG2A.2 antibody was tested with an Fc capable of interacting with mouse FcγRs (mNKG2A.2 mIgG2a), tumors grew faster in vivo.

When anti-hNKG2A mAb with an IgG4 Fc was tested, it inhibited NK cell responses, particularly in the presence of strong stimulation.

Collectively, these data showed the advantageous functions of inert Fc human IgG1.3 was the preferred isotype for the NKG2A.9 antibody.

Example 8

NKG2A.9 Antibody Enhanced the Functional Activity of T Cells

In this assay, the NKG2A.9 antibody was tested for its functional activity of reversing the inhibition of NK-κB signaling in a NKG2A-expressing Jurkat T cell line stimulated by CHO/scOKT3/HLA-E (Chinese Hamster Ovary cells that have been engineered to express the single chain OKT3 and the ligand, HLA-E). NKG2A-expressing Jurkat effector cells were co-cultured with CHO/scOKT3/HLA-E target cells at an effector cell-to target cell ratio (E:T) of 1:1. The NKG2A.9 antibody or isotype antibody (human IgG1.3) was added to the co-culture at titrating concentrations. Following four hours of stimulation at 37° C., luciferase activity was quantified using Bio-Glo Reagent (100 μl/well) and EnVision plate reader. Relative Luciferase Units (RLU) data was plotted using Prism v5.01 software from GraphPad Inc.

Figure 33:
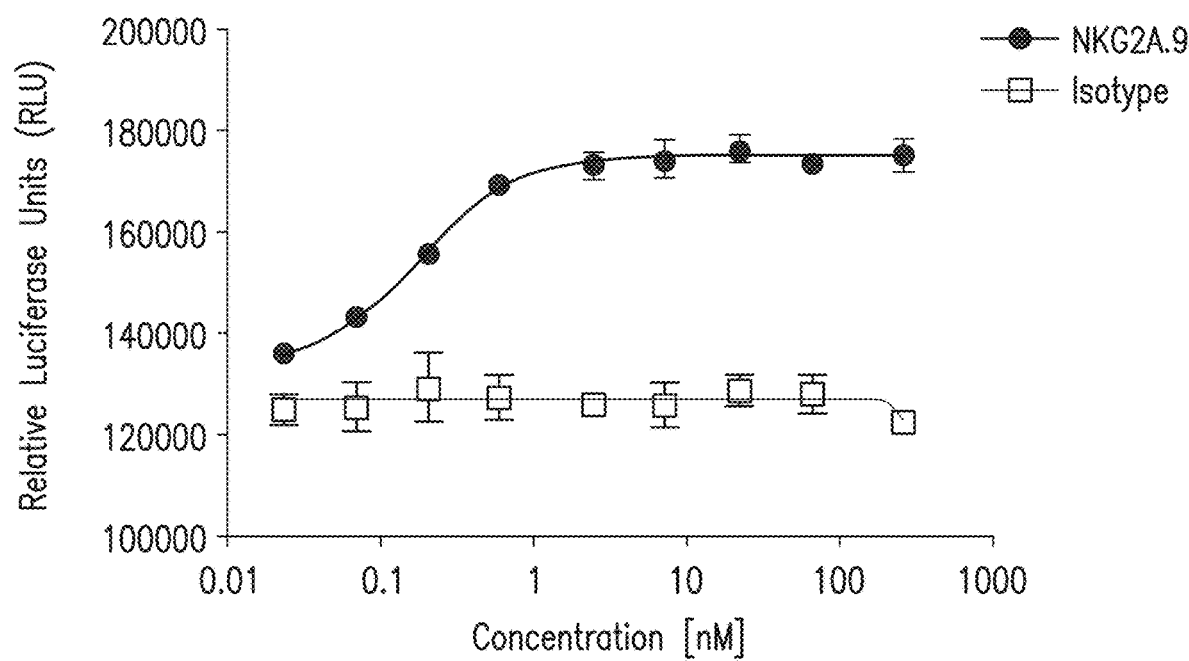
FIG. 33 shows assay results that the NKG2A.9 antibody, as compared to isotype, reversed the inhibition of NK-κB signaling in NKG2A-expressing Jurkat T cells stimulated by CHO/scOKT3/HLA-E.

The NKG2A.9 antibody reversed the NKG2A/HLA-E mediated inhibition of T cell responses. Specifically, as shown in FIG. 33, the NKG2A.9 antibody reversed the inhibition of NK-κB signaling in a NKG2A-expressing Jurkat T cell line stimulated by CHO/scOKT3/HLA-E, with an $EC_{50}$ value of 0.2 nM.

Example 9

NKG2A.9 Antibody IFN-γ Production Alone and In Combination with Anti-PD-L1 Monoclonal Antibody The NKG2A.9 antibody induced IFN-γ in NKG2A+ CD8 T isolated from healthy donor PBMC co-cultured with CHO/scOKT3/HLA-E/PD-L1 (Chinese Hamster Ovary cells that have been engineered to express the single chain OKT3 and the ligands HLA-E and PD-L1). Enhanced IFN-γ production is a measure of enhanced T-cell functionality. The effect was significantly amplified when NKG2A.9 was combined with anti-PD-L1 monoclonal antibody.

Figure 34A:
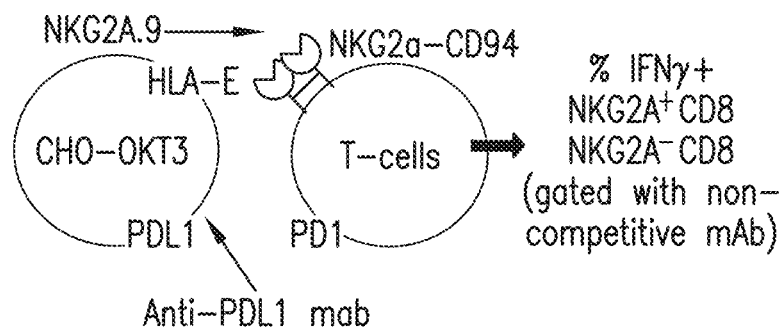
FIG. 34A illustrates the experimental method used to analyze the effect of NKG2A.9 and anti-PD-L1 antibodies, either alone or in combination, on IFN-γ induction by NKG2A$^+$ CD8+ T cells isolated from healthy peripheral blood mononuclear cells (PBMCs).

Briefly, as depicted in FIG. 34A, T cells isolated from healthy PBMCs were incubated with irradiated CHO/scOKT3/HLA-E/PD-L1 in the presence of NKG2A.9 antibody and an anti-PD-L1 antibody (BMS-936659), or a combination thereof for four days. The T cells were isolated from human whole blood using Ficoll gradient and the human T cell isolation kit (EasySep™ Human T Cell Isolation Kit, Stemcell Technologies). The cell viability was more than 90%, as determined by cell counter (Nexcelcom Cellometer Auto 2000). $1.5 \times 10^5$ cells were co-cultured for four days with $2.5 \times 10^4$ irradiated (67,000 RAD for 80 minutes; Rad Source Irradiator, RS-2000 Biological System) CHO/OKT3/HLA-E/PD-L1 cells in rhIL-15 (5 ng/ml) containing medium in the presence of either an isotype control antibody (human IgG1.3) or NKG2A.9 and/or anti-human PD-L1 antibody (BMS-936659). (CHO/scOKT3/HLAE/PD-L1 cells are Chinese Hamster Ovary cells that have been engineered to express the single chain OKT3 and the ligands HLA-E and PD-L1). At day four of the culture, cells were collected and stained with anti-human CD4, anti-human CD8, live/dead, anti-human NKG2A (27H4 clone). IFN-γ production was assessed by intracellular cytokine staining using the BD Cytofix/Cytoperm™ kit. Fixed cells were read on the BD LSRFortessa™. The percent of IFN-γ among NKG2A+ or NKG2A− CD8 T cells was calculated by FlowJo.

Figure 34B:
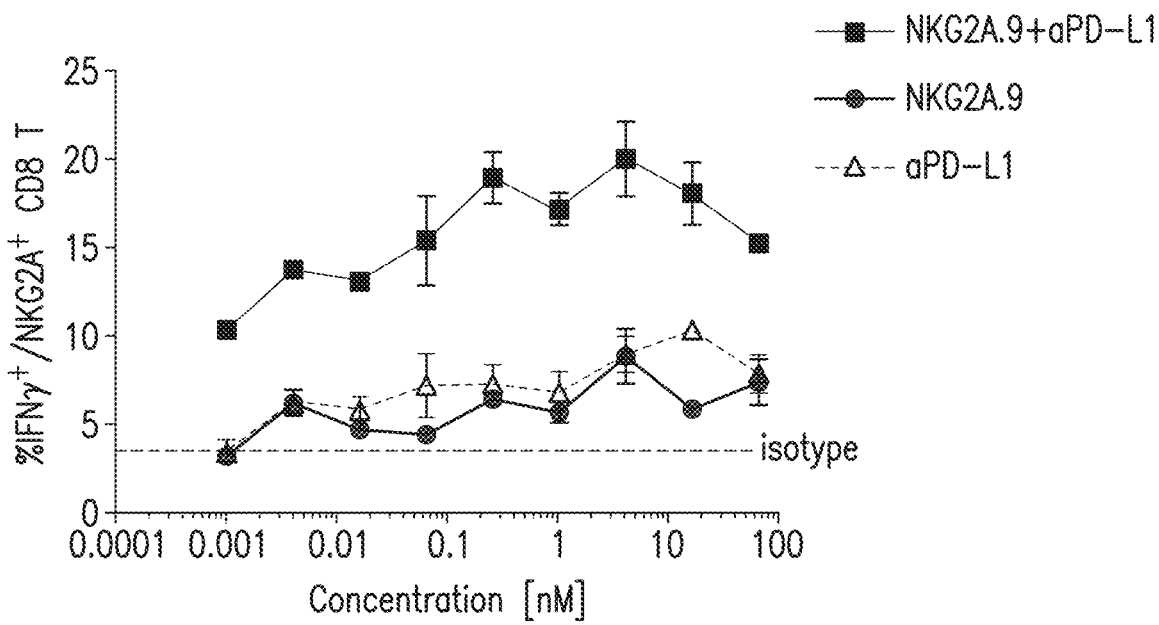
FIG. 34B shows the results of the method in which the combination of NKG2A.9 and anti-PD-L1 antibodies enhanced IFN-γ production by NKG2A$^+$ CD8+ T cells in a dose-dependent manner.

As shown in FIG. 34B, a dose-dependent enhancement of IFN-γ production by NKG2A+ CD8 T cells was observed when the NKG2A.9 antibody was combined with the anti-PD-L1 antibody. Notably, the increase in IFN-γ production was not observed on NKG2A− CD8 T cells, which indicated that the effect of the NKG2A.9 antibody was specific and intrinsic to NKG2A+ CD8 T cells.

Figure 35A:
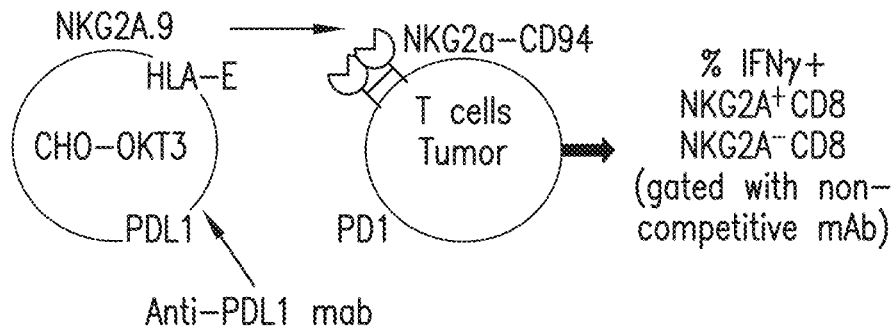
FIG. 35A-B illustrates the assay method (FIG. 35A) used to show that NKG2A.9 and/or anti-PD-L1 antibodies enhanced IFN-γ production in NKG2A$^+$ CD8+ T cells isolated from human tumors co-cultured with CHO/scOKT3/HLA-E/PD-L1 (FIG. 35B).
Figure 35B:
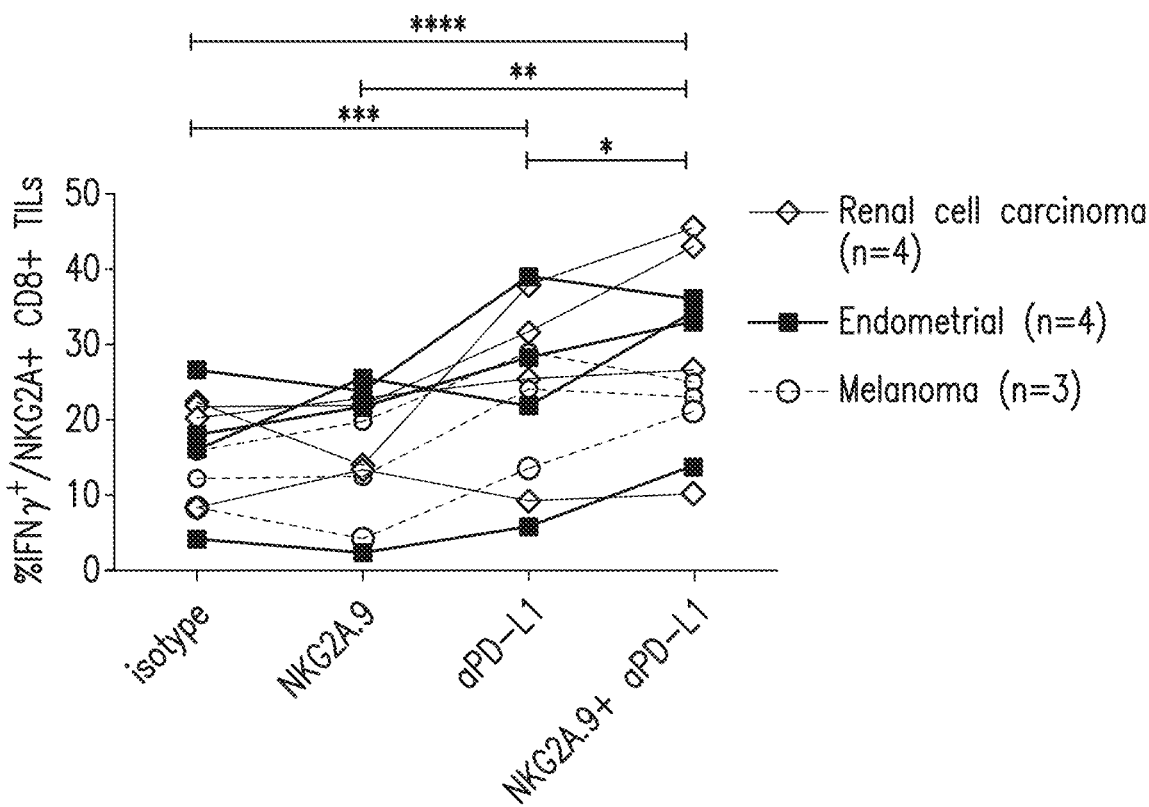

The NKG2A.9 antibody also induced IFN-γ in NKG2A+ CD8+ T cells isolated from human tumors co-cultured with CHO/scOKT3/HLA-E/PD-L1. The effect was significantly amplified when the NKG2A.9 antibody was combined with an anti-PD-L1 monoclonal antibody (BMS-936659). Briefly, as shown in in FIG. 35A-B, tumor-infiltrating lymphocytes (TIL) from renal cell carcinoma, melanoma, or endometrial tumor samples were co-cultured with irradiated CHO/scOKT3/HLA-E/PD-L1 in the presence of the NKG2A.9 antibody, anti-PD-L1, or their combination for four days. The NKG2A.9 antibody did not increase IFN-γ levels by NKG2A+ CD8 TIL over control monoclonal antibody, whereas anti-PD-L1 antibody stimulated IFN-γ levels by NKG2A+ CD8 TIL over isotype antibody (P=0.01). The greatest IFN-γ response was observed with the combination of the NKG2A.9 antibody and anti-PD-L1 mAb compared to isotype control antibody (P=0.003) as well as compared to anti-PD-L1 alone (P=0.04), as shown in FIG. 35B.

Example 10

Figure 36A:
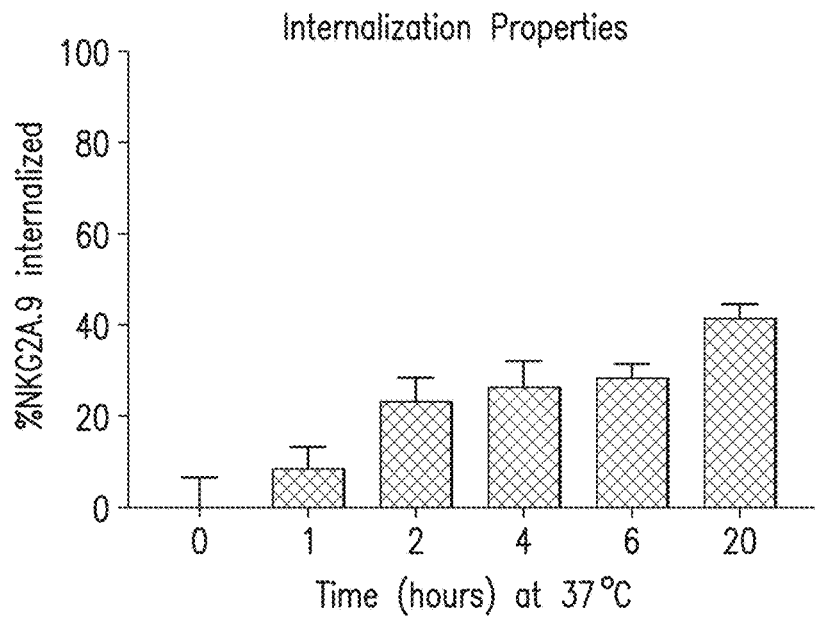
FIG. 36A is a graph showing that the NKG2A.9 antibody was internalized after binding to NKG2A-expressing cells.
Figure 36B:
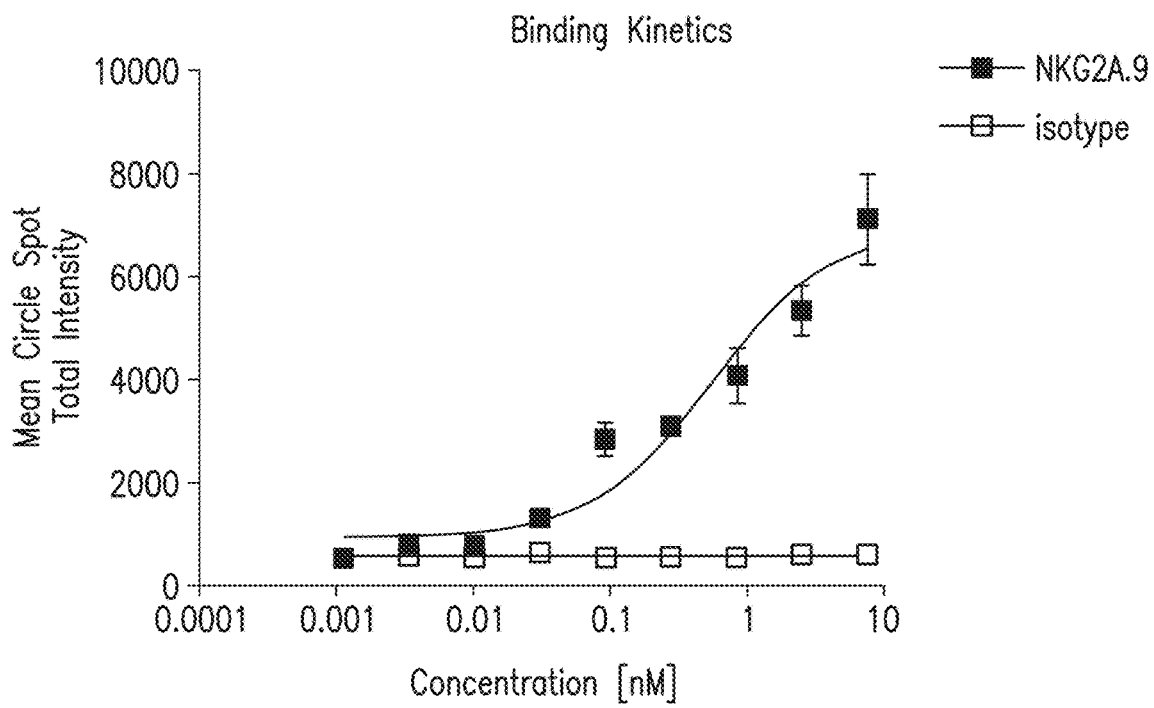
FIG. 36B is a graph showing the binding kinetics of the NKG2A.9 antibody and demonstrates that the NKG2A.9 antibody was internalized in a dose-dependent manner with an $EC_{50}$ of 0.5 nM.

NKG2A.9 Antibody Was Desirably Internalized After Binding to NKG2A-Expressing Cell As described in the Examples above, we observed downregulation of NKG2A surface expression after incubation of human CD8+ T or NK cells with the NKG2A.9 antibody. To determine whether the NKG2A.9 antibody was internalized into the cell, Alexa Fluor 488-labeled NKG2A.9 antibody or isotype control monoclonal antibody (KLH human IgG1 antibody) was added to NKL cells, and the levels of intracellular and surface-bound monoclonal antibodies were measured. Internationalization of the antibody shows target engagement of the antibody to the receptor. As shown in FIG. 36A, the NKG2A.9 antibody demonstrated internalization within one hour and increased over 20 hours. The NKG2A.9 antibody was gradually internalized by NKL cells and reached a plateau level of about 40% internalization by 20 hours. To quantify internalization of the NKG2A.9 antibody in a dose-response format, the pH sensitive dye assay was performed using NKL cells. As shown in FIG. 36B, at two hours, the NKG2A.9 antibody demonstrated a dose-dependent internalization with an $EC_{50}$ of 0.5 nM.

Example 11

Figure 37A:
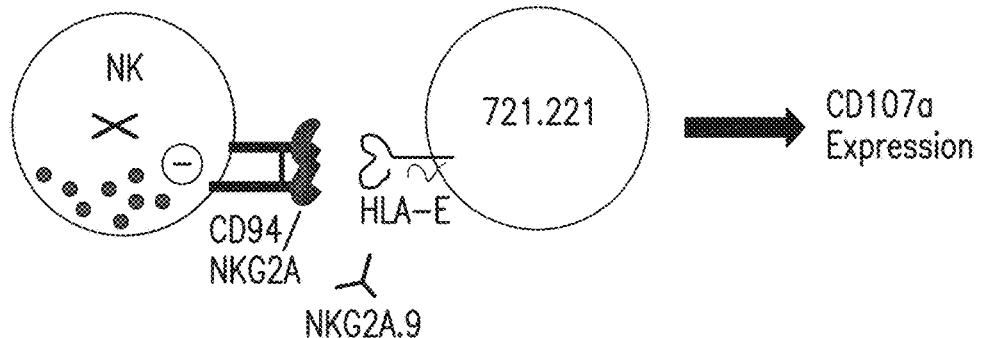
FIG. 37A-B illustrate the method used (FIG. 37A) to show that the NKG2A.9 antibody, as compared to isotype, increased NK cell degranulation in a dose-dependent manner, as measured by % CD107a expression measured by flow cytometry.
Figure 37B:
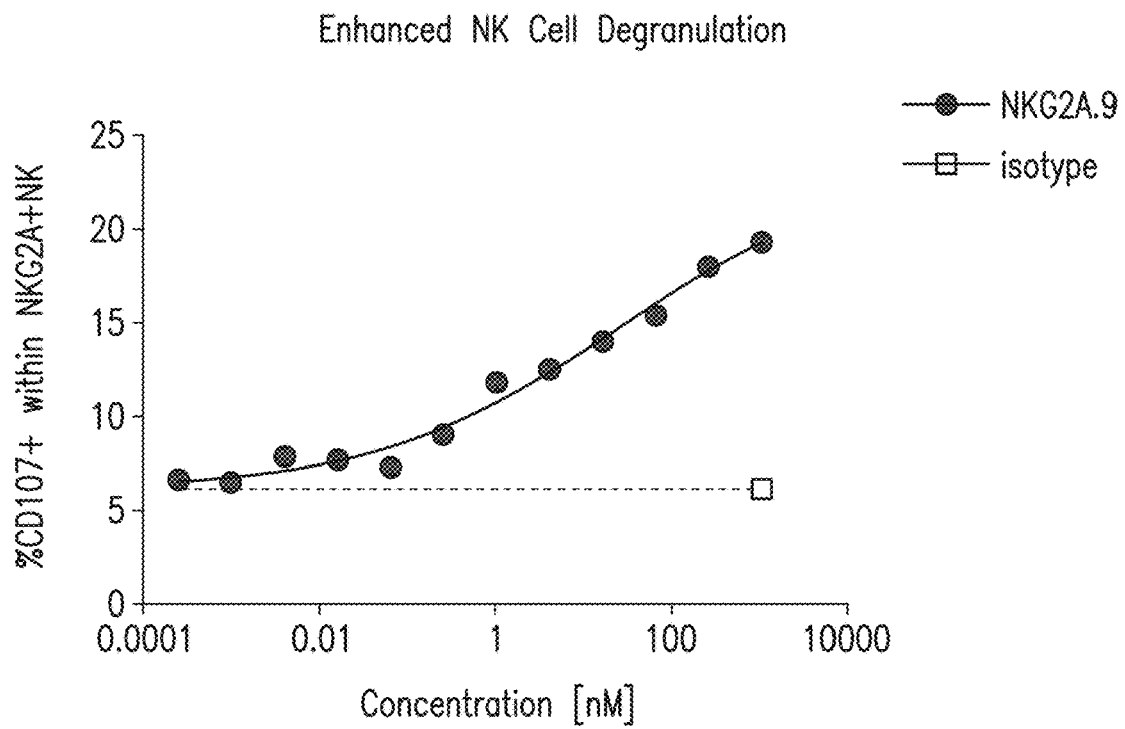
Figure 37C:
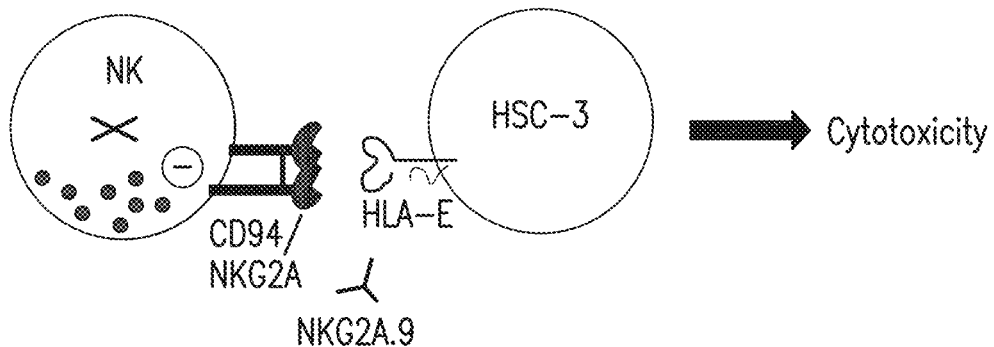
FIG. 37C-D illustrates the experimental method used (FIG. 37C) that showed that the NKG2A.9 antibody, as compared to isotype, increased lysis of HLA-E-expressing tumor cells in a dose-dependent manner (FIG. 37D).
Figure 37D:
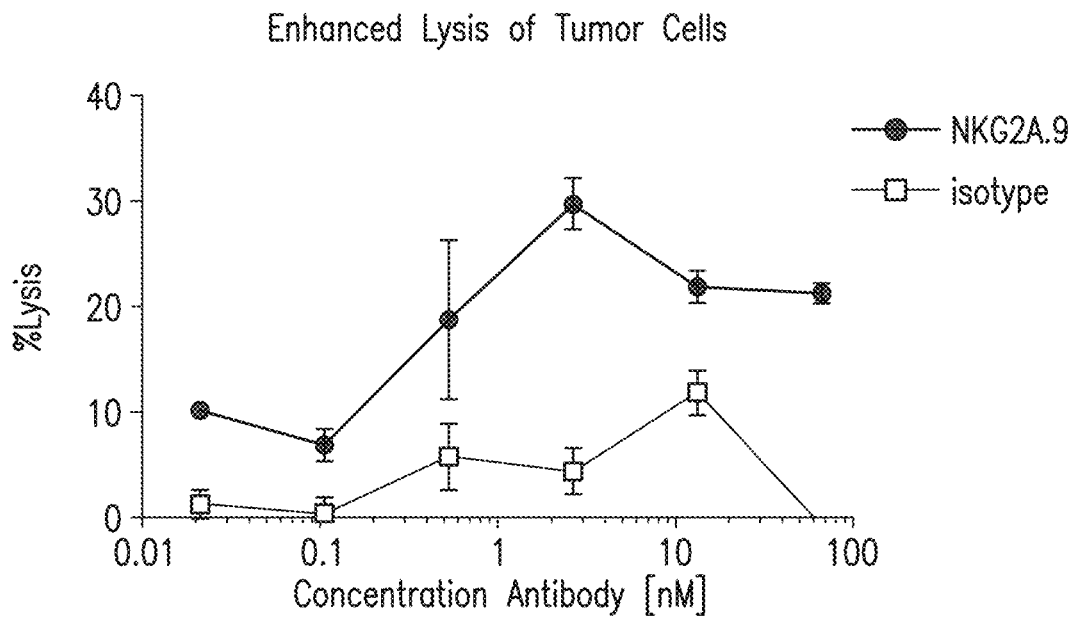

NKG2A.9 Antibody Increased Natural Killer Cell Degranulation and Lysis of HLA-E-Expressing Tumor Cells In in vitro experiments using PBMCs from normal donors, anti-NKG2A antibody blockade of the NKG2A/HLA-E interaction among activated NK cells resulted in increased NK cell degranulation. As depicted in FIG. 37A, NK cells isolated from normal PBMC donors were activated overnight with recombinant human (rh) IL-2. NK cells were then co-cultured with the human B-lymphoblastoid target cell line 721.221 expressing HLA-E. As shown in FIG. 37B, the NKG2A.9 antibody, as compared to isotype, increased NK cell degranulation in a dose-dependent manner, as measured by % CD107a expression by flow cytometry. Reversal of NKG2A/HLA-E mediated inhibition of NK cell cytotoxicity was assessed in vitro. As depicted in FIG. 37C, HSC-3, a human oral cancer cell line, was selected based on its endogenous expression of HLA-E. NKL cells were co-cultured with the HSC-3 target cells labeled with Calcein AM (a cell-permanent dye) at a 20:1 effector to target ratio in the presence of NKG2A.9 or isotype control antibody (human IgG1.3). The amount of Calcein released after two hours was measured and used to indicate the level of target cell lysis. As shown in FIG. 37D, the NKG2A.9 antibody, as compared to isotype, increased lysis of HLA-E expressing tumor cells in a dose dependent manner.

Example 12

13F3.A4 Antibody Showed Enhanced NK Cell Functionality

Figure 38A:
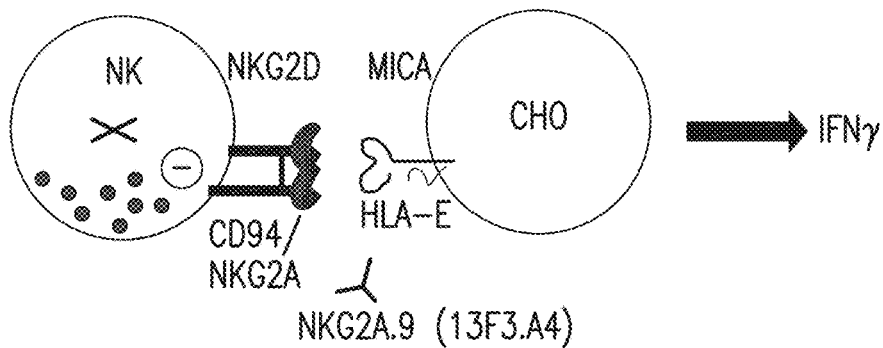
FIG. 38A illustrates the method used to measure the effect of the 13F3.A4 antibody on IFN-γ production in NKLs co-cultured with CHO/MICA/HLA-E.
Figure 38B:
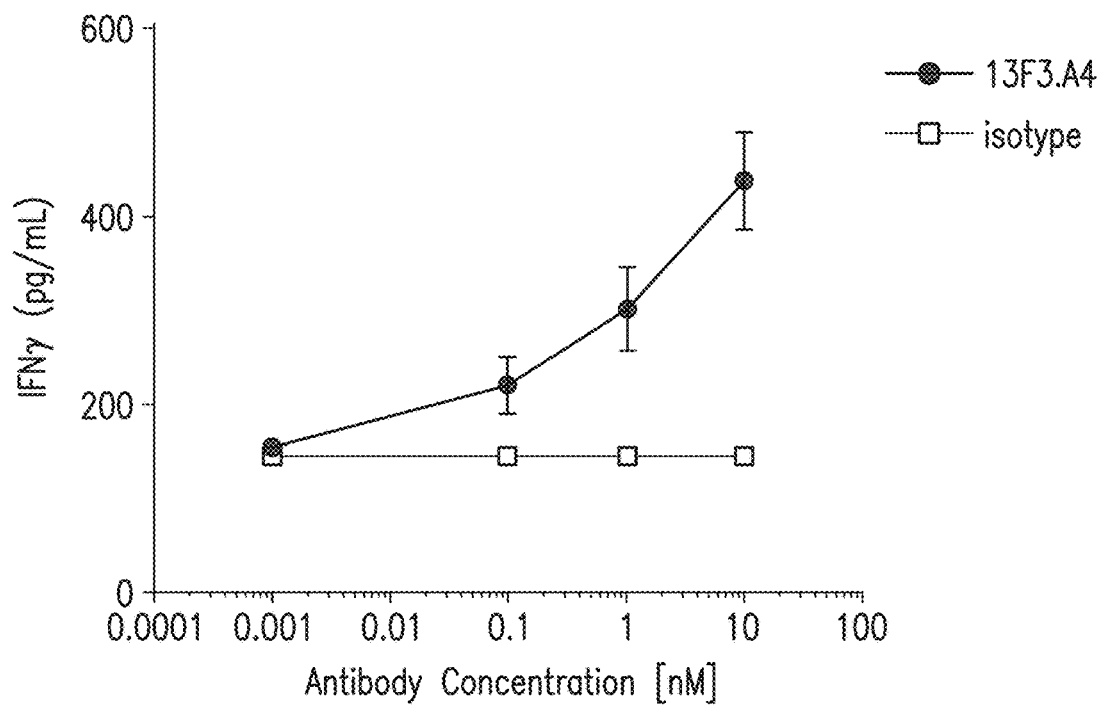
FIG. 38B shows that the 13F3.A4 antibody increased IFN-γ production in NKLs as compared to the isotype.

FIG. 38A illustrates the method used to measure the effect of the 13F3.A4 antibody on IFN-γ production in NKL cells co-cultured with CHO/MICA/HLA-E. Similar to the NKG2A.9 antibody, FIG. 38B shows that the 13F3.A4 antibody increased IFN-γ production in natural killer lymphocytes (NKL) co-cultured with CHO/MICA/HLA-E (Chinese Hamster Ovary cells that have been engineered to express MICA and HLA-E) as compared to the isotype.

Example 13

Comparative Binding Affinities of NKG2A.9

A comparison of the kinetics and binding affinities of NKG2A.9, Z270, and monalizumab for binding to hNKG2A-hCD94 was made using a Biacore T200 biosensor instrument and a heterodimer of the extracellular domains of human NKG2A and CD94. The temperature was 37° C. and the running buffer was Hepes buffered saline (10 mM HEPES, 150 mM NaCl) at pH 7.4 supplemented with 0.05% Tween-20 and 1 g/L BSA. The antibodies were captured on a C1 sensor chip with pre-immobilized anti-human Fc capture reagent (Southern Biotech catalog number 2081-01). The extracellular domain of human NKG2A was flowed as analyte over the captured antibodies in two five-membered, three-fold concentration series with 250 nM top concentration: one concentration series was used for single-cycle kinetics and the other one for multi-cycle kinetics with a duplicate injection at 83 nM. All data were double-referenced and fitted to a 1:1 binding model using Biacore T200 Evaluation Software version 3.1. Two independent runs were performed, using a different flow cell for each monoclonal antibody in the second run. Thus, four $K_D$ measurements were obtained. Where applicable, kinetic fit and steady state fit were both used to analyze the data.

FIG. 51A-D show the binding affinity of the NKG2A.9 antibody to human NKG2A-CD94 heterodimer at 37° C. as determined by Biacore in quadruplicate measurements using both single-cycle and multi-cycle kinetics. FIG. 51A-D show response units (RU) of NKG2A-CD94 binding versus time in seconds.

The NKG2A.9 antibody showed higher affinity ($K_D$=16 nM±0.4 nM; average±standard deviation) than Z270 ($K_D$=25 nM±3 nM) and monalizumab ($K_D$=26 nM 3 nM) in this assay, as summarized in the Table below. The overall affinity for NKG2A.9 is higher in this assay than in the experiment using NKG2A.9 Fab in Example 3; the difference may be due to a faster association rate ($k_a$), while the dissociation rate ($k_d$) is very similar. The faster association rate ($k_a$) in this assay may be reflective of by the more optimized conditions, in particular, the use of a flat sensor chip, which were used due to less reagent constraints for human versus cynomolgus NKG2A.

TABLE

Comparative Affinity of Anti-NKG2A Antibodies and Half-Life of Antibody/Analyte Complex

| Captured Antibody | Analyte | $k_a$ (1/Ms) | $k_d$ (1/s) | $K_D$ (nM) | Half-life of Antibody/Analyte Complex (seconds, s) |
|---|---|---|---|---|---|
| NKG2A.9 | hNKG2A-hCD94 | $1.1 \times 10^6 \pm 0.1 \times 10^6$ | $1.7 \times 10^{-2} \pm 0.2 \times 10^{-2}$ | 16.0 nM ± 0.4 nM | 37 to 45 s |
| Z270 | | $8 \times 10^6$ | $2 \times 10^{-1}$ | 25 nM ± 3 nM | 3 s to 4 s |
| Monalizumab | | $7 \times 10^6$ | $2 \times 10^{-1}$ | 26 nM ± 3 nM | 3 s to 4 s |

$K_D$ was averaged from four measurements. Standard deviation is shown where application.

The half-life of a 1:1 complex, such as one antibody binding site bound to one NKG2A-CD94 heterodimer, is time that it takes for half of the amount of the antibody/analyte complex (here, the antibody:NKG2A-CD94 complex) to dissociate. The half-life can mathematically be described as $\ln(2)/k_d$. The half-life of the antibody:NKG2A-CD94 complex was approximately 12-fold longer for NKG2A.9 (41 seconds) than for both Z270 and monalizumab (3 to 4 seconds).

Under conditions of monovalent binding on a cell surface (e.g., due to low antigen expression), NKG2A.9 can thus engage NKG2A-CD94 complex for a longer time period than Z270 and monalizumab. We believe that this longer half-life of the antibody/NKG2A-CD94 complex allows increased efficiency in ligand blocking. In other words, the longer half-life of the NKG2A.9/NKG2A-CD94 complex compared to monalizumab/NKG2A-CD94 or Z270/NKG2A-CD94 provided evidence for the ability of the NKG2A.9 antibody to better block the NKG2A/HLA-E interaction compared to monalizumab or Z270.

Example 14

Properties of Anti-mNKG2A Antibodies In Vitro

Anti-mNKG2A surrogate antibodies, NKG2A.2 (20D5 clone, eBioscience, mIgG1-D265A) and NKG2A.3 (7E6 clone, mIgG1-D265A), had similar functional properties to the NKG2A.9 antibody when evaluated in vitro, allowing these antibodies to serve as surrogate antibodies for proof-of-concept, mechanism of action (MOA), and human dose projection studies. The anti-NKG2A mouse antibodies NKG2A.2 and NKG2A.3 had the following functional properties:

1) $EC_{50}$ values for binding to mNKG2A-expressing CHO cells were 0.2 nM (NKG2A.2) and 0.3 nM (NKG2A.3).
2) $IC_{50}$ values for blockade of Qa-1b tetramer binding to mNKG2A-expressing CHO cells were 0.3 nM (NKG2A.2) and 0.4 nM (NKG2A.3). (Qa-1b is the house homolog to HLA-E in humans. Thus, this is comparable to the CHO hNKG2A/HLA-E blocking assay).
3) NKG2A.2 and NKG2A.3 bound specifically to mNKG2A, as they did not bind to NKG2A$^{-/-}$ NK or CD8 T cells.
4) NKG2A.2 and NKG2A.3 antibodies induced a dose-dependent increase in mouse NK cell degranulation.

Example 15

Anti-mNKG2A Antibodies, Both Alone and In Combination with Other Agents, Induced Anti-Tumor Activity In Vivo (1) Anti-mNKG2A Antibodies Induced Antitumor Activity as a Monotherapy in Mouse Models Anti-mNKG2A monoclonal antibodies (including the NKG2A.2 and NKG2A.3 antibodies) when administered as a single agent inhibited tumor growth in CT26 colon carcinoma, 1956 sarcoma, and A20 B cell lymphoma subcutaneous (SC) models as summarized in Study 2 below.

Summary of Mouse Tumor Model Studies 2-4

| Study No. | Purpose | Tumor Model | Recipient Mice | mAb(s) | Treatment Regimen | % Tumor Growth Inhibition (compared to isotype control) |
|---|---|---|---|---|---|---|
| 2 | Dose titration of anti-mNKG2A.3 | CT26 colon carcinoma | BALB/c n = 10/ group | NKG2A.3 (mIgG1-D265A) Anti-PD-1 Ab (mIGg1 D265A) | Day 0: 1 × 10$^6$ cells per mouse SC Days 6, 10, 13, 17, 20: NKG2A 10, 3, 1, 0.3 mg/kg intraperitoneal (IP) PD-1 (mPD1-4h2-mg1-D265A, mouse surrogate for nivolumab) 10 mg/kg IP Each antibody administered at 10 mg/kg IP | At Day 20 NKG2A.3 (10 mg/kg) + Anti-PD-1 Ab: 96% NKG2A.3 (1 mg/kg) + Anti-PD-1 Ab: 96% Anti-PD-1 Ab: 88% NKG2A.3(3 mg/kg) + Anti-PD-1 Ab: 76% NKG2A.3(0.3 mg/kg) + Anti-PD-1 Ab: 71% NKG2A.3 (3 mg/kg): 56% NKG2A.3(10 mg/kg): 49% NKG2A.3(1 mg/kg): 31% NKG2A.3(0.3 mg/kg): 0% |
| 3 | Efficacy of anti-mNKG2A.3 in combination with other checkpoint inhibitors | CT26 colon carcinoma | BALB/c n = 10/ group | NKG2A.3 (mIgG1-D265A) Anti-PD-1 Ab (mIgG1 D265A) Anti-TIGIT Ab (mIg2a) | Day 0: 1 × 10$^6$ cells per mouse SC Days 6, 10, 13,17, 20: Each antibody administered at 10 mg/kg IP | At Day 24 NKG2A.3 + anti-PD-1 Ab (Clone 4H2, mIgG1-D265aA: 91% NKG2A.3 + anti-TIGIT Ab (Clone 4H2, mIgG1-D265A: 88% NKG2A.3: 42% Anti-PD-1 Ab: 61% Anti-TIGIT Ab: 78% |
| 4 | Efficacy of anti-mNKG2A.2 in combination with checkpoint inhibitors in subcutaneous lymphoma model | A20 B cell lymphoma | BALB/c n = 10/ group | NKG2A.2 (mIgG1-D265A) Anti-PD-1 Ab (mIgG1-D265A) Anti-TIGIT Ab (mIg2a) | Day 0: 5 × 10$^6$ cells per mouse SC Days 6, 9, 12, 15, 18: Each antibodies dosed at 10 mg/kg IP | At Day 23 NKG2A.3 + Anti-PD-1 Ab: 94% Anti-PD-1 Ab: 75% NKG2A.3: 58% NKG2A.3 + Anti-TIGIT Ab: 51% Anti-TIGIT Ab: 32% Tumor-Free Mice at End of Study Anti-NKG2A A + Anti-PD-1 Ab: 8/9 tumor-free mice at the end of the study (TF) Anti-NKG2A Ab + Anti-TIGIT Ab: 4/9 TF Anti-PD-1 Ab: 3/9 TF Anti-NKG2A Ab: 1/9 TF Anti-TIGIT Ab: 0/9 TF Isotype: 0/9 TF |

Figure 39:
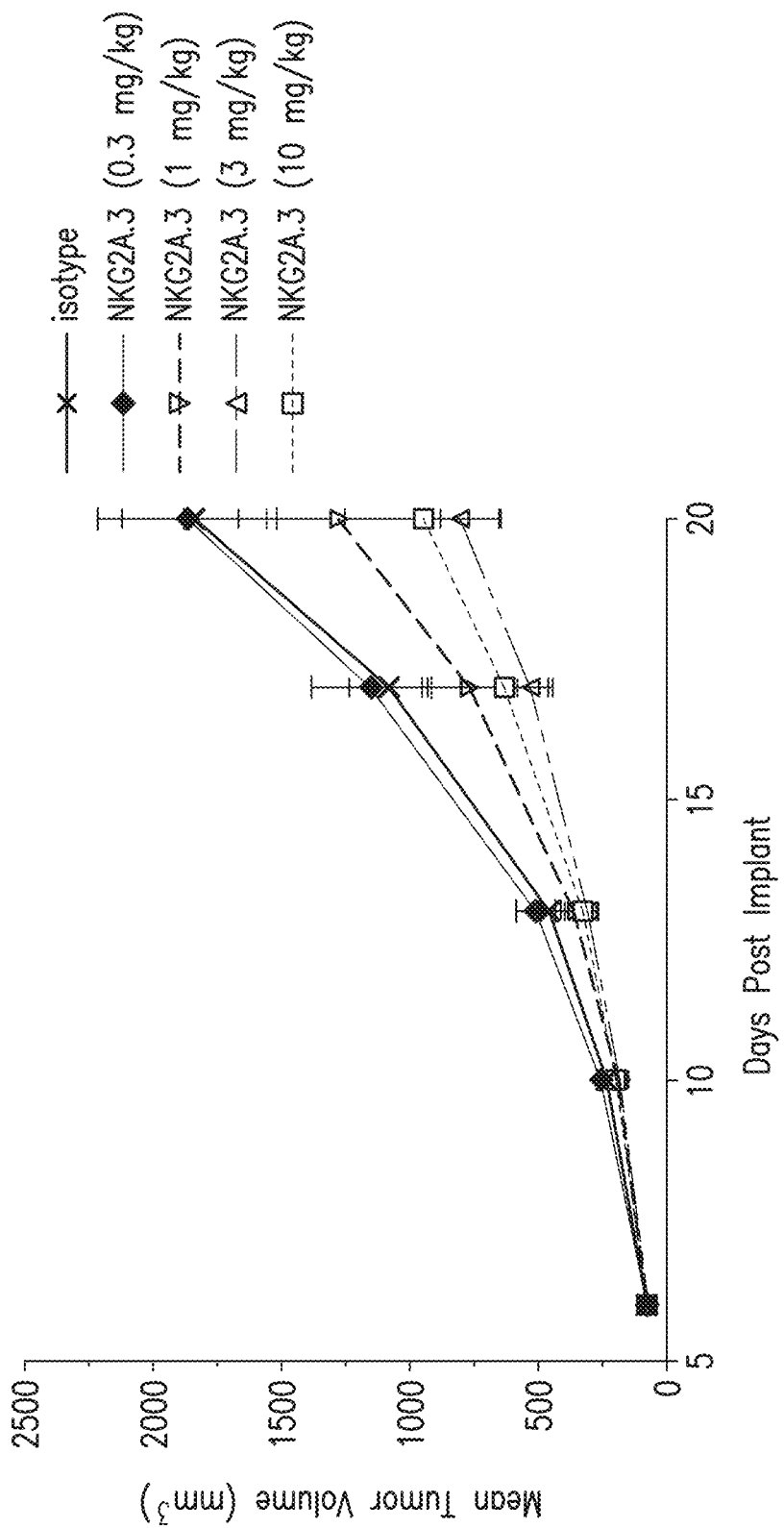
FIG. 39 shows the results of a dose titration study in which 10 mg/kg, 3 mg/kg, and 1 mg/kg of an anti-mNKG2A antibody (NKG2A.3) was administered as a monotherapy, and inhibited tumor growth in a colon carcinoma tumor model with a 48%, 56%, and 30% reduction in mean tumor volume, respectively. No efficacy was observed for the 0.3 mg/kg dose.

As shown in FIG. 39, in a dose titration study (Study No. 2 described above) with the CT26 tumor model, the NKG2A.3 antibody reduced tumor size when administered at 10 mg/kg, 3 mg/kg, and 1 mg/kg doses (48%, 56%, and 30% reduction in mean tumor volume, respectively).

(2) Combination of Anti-mPD-1 and Anti-mNKG2A Antibodies Enhanced Anti-Tumor Activity Compared to Either Single Agent Alone in Multiple Mouse Tumor Models.

Co-blockade with the anti-NKG2A (mNKG2A.3-mG1-D265A (7E6 clone) and anti-PD-1 antibodies (PD1-4H2-mG1-D265A, 6A1 clone) reduced tumor growth in models where anti-NKG2A monoclonal antibody alone showed single-agent activity. The combination of anti-mPD-1 and anti-mNKG2A antibodies demonstrated greater anti-tumor activity than either single agent alone in the CT26 tumor model.

Figure 40A:
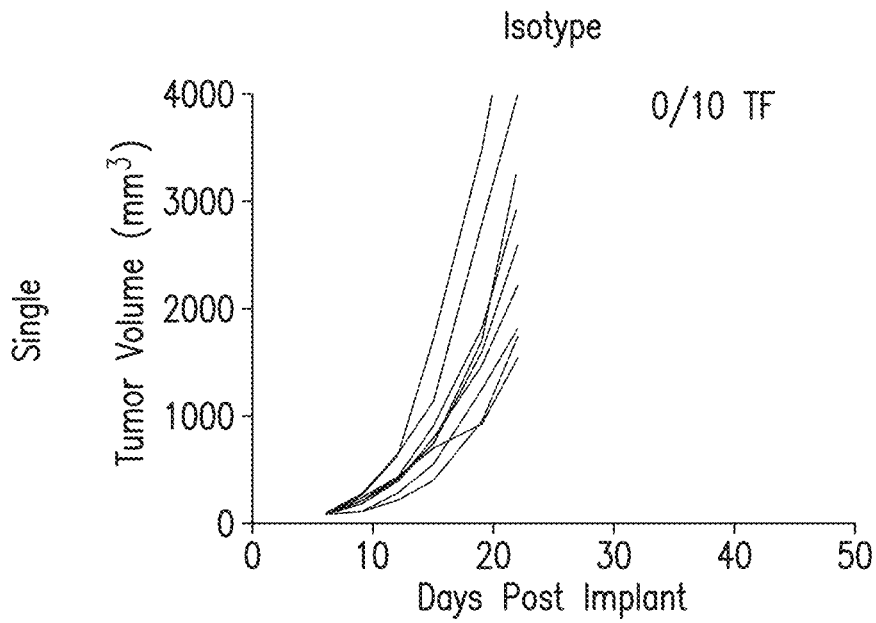
FIG. 40A-E show the results of in vivo studies in which anti-mNKG2A and anti-mPD-1 antibodies reduced tumor growth in mouse models where anti-mNKG2A antibody monotherapy showed single-agent activity in the CT26 colorectal tumor mouse model.
Figure 40B:
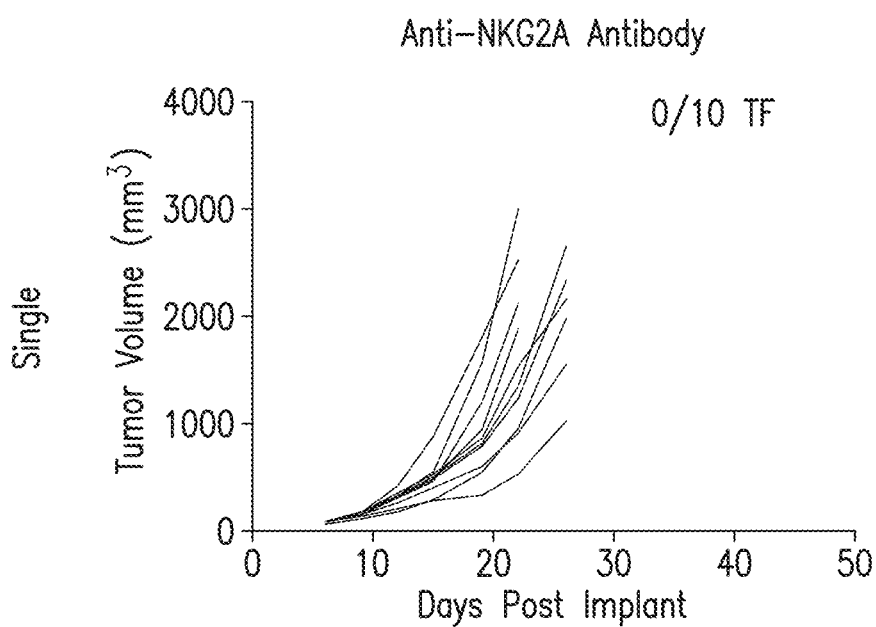
Figure 40C:
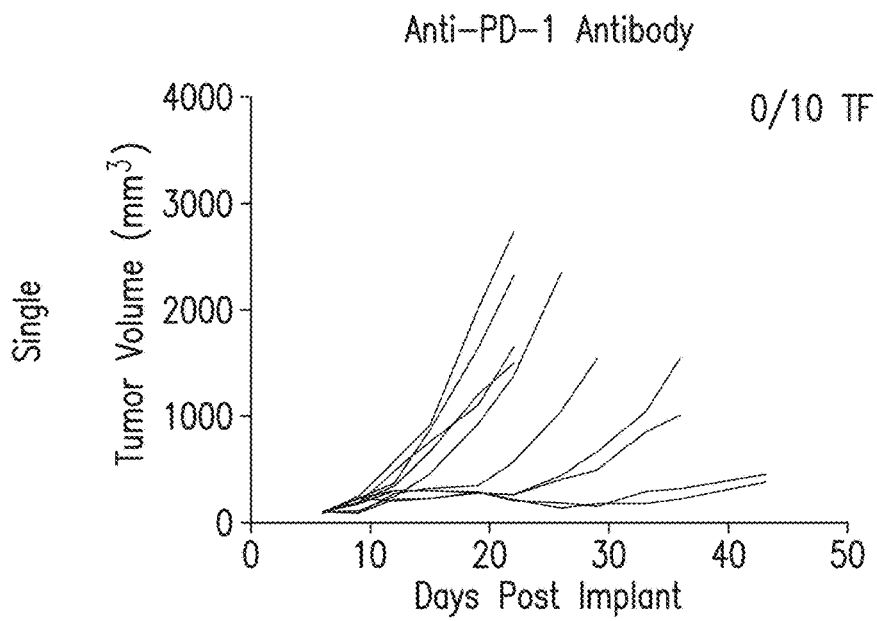
Figure 40D:
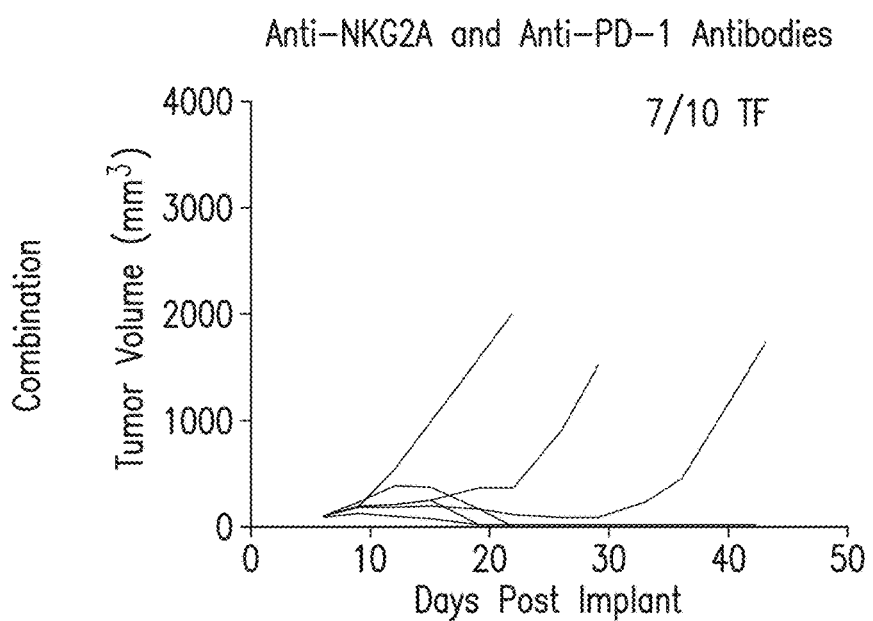
Figure 40E:
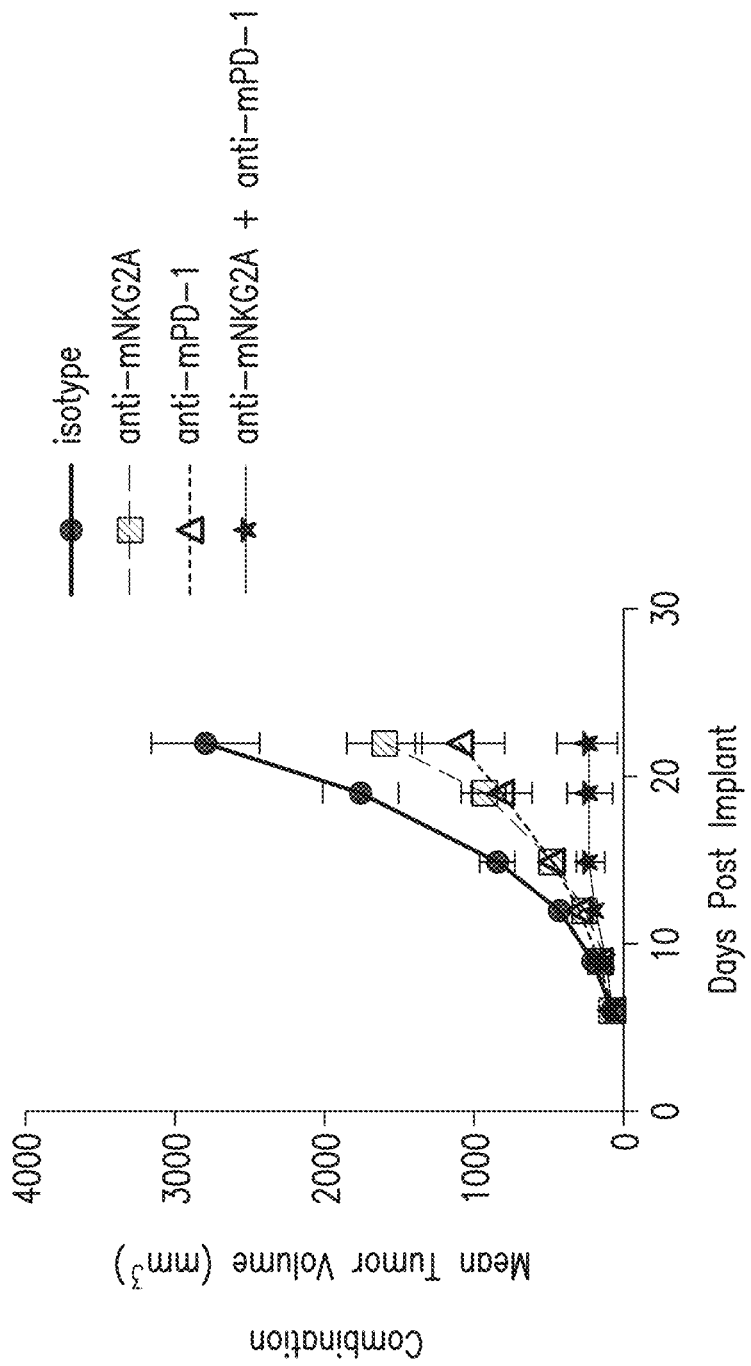

In the CT26 model, single-agent treatment with anti-mNKG2A or anti-mPD-1 antibodies reduced the mean tumor volume by 43% and 61%, respectively. Co-blockade of NKG2A and PD-1 led to a relatively stronger inhibition of tumor growth, with 7/10 mice tumor-free (TF) at the end of the study (FIG. 40D) and a 91% decrease in mean tumor volume (FIG. 40E). FIG. 40A-D show the tumor volume at various time points post tumor implantation in mice (n=10/group) treated with isotype (FIG. 40A), anti-mNKG2A antibody alone (FIG. 40B), anti-mPD-1 antibody alone (FIG. 40C), or a combination of anti-mNKG2A and anti-mPD1 antibodies (FIG. 40D). FIG. 40E shows the average tumor volume as a function of time (days post tumor implantation) in mice treated with isotype, anti-mNKG2A antibody alone, anti-mPD-1 antibody alone, or a combination of anti-mNKG2A and anti-mPD-1 antibodies.

Similar effects were observed in mice inoculated with 1956 sarcoma or A20 lymphoma SC tumors, as summarized in Studies 3 and 4 below.

| Study No. | Purpose | Tumor Model | Recipient Mice | mAb(s) | Treatment Regimen | % Tumor Growth Inhibition (compared to isotype control) |
|---|---|---|---|---|---|---|
| 3 | Efficacy of anti-mNKG2A.3 in combination with other checkpoint inhibitors | CT26 colon carcinoma | BALB/c n = 10/ group | NKG2A.3 (mIgG1-D265A) Anti-PD-1 Ab (mIGg1 D265A) Anti-TIGIT Ab (mIg2a) | Day 0: 1 × 10⁶ cells per mouse SC Days 6, 10, 13, 17, 20: Each antibody administered at 10 mg/kg IP | At Day 24 NKG2A.3 + anti-PD-1 Ab: 91% NKG2A.3 + anti-TIGIT Ab (10A7 clone, mIgG1-D265A): 88% NKG2A.3: 42% Anti-PD-1 Ab: 61% Anti-TIGIT Ab: 78% |
| 4 | Efficacy of anti-mNKG2A.2 in combination with checkpoint inhibitors in subcutaneous lymphoma model | A20 B cell lymphoma | BALB/c n = 10/ group | NKG2A.2 (mIgG1-D265A) Anti-PD-1 (mIgG1-D265A) Ab Anti-TIGIT (mIg2a) Ab | Day 0: 5 × 10⁶ cells per mouse SC Days 6, 9, 12, 15, 18: Each antibodies dosed at 10 mg/kg IP | At Day 23 NKG2A.3 + anti-PD-1 Ab: 94% Anti-PD-1 Ab: 75% NKG2A.3: 58% NKG2A.3 + anti-TIGIT Ab: 51% Anti-TIGIT Ab: 32% Tumor-Free Mice at End of Study NKG2A + anti-PD-1 Ab: 8/9 tumor-free mice at the end of the study (TF) NKG2A + Anti-TIGIT Ab: 4/9 TF Anti-PD-1 Ab: 3/9 TF NKG2A: 1/9 TF Anti-TIGIT Ab: 0/9 TF Isotype: 0/9 TF |

Summary of Mouse Tumor Model Studies 3 and 4

NKG2A/PD-1 co-blockade improved tumor growth inhibition even in models where anti-NKG2A monoclonal antibodies alone (NKG2A.3-mG1-D265A (7E6 clone) or NKG2A.2-mg1-D265A (4F12 clone)) did not show single-agent activity. In the M109 lung tumor model, co-blockade of anti-NKG2A and anti-PD-1 antibodies led to a 72% decrease in the mean tumor volume compared to isotype control, as summarized in Study 5 below.

Summary of Mouse Tumor Model Study 5

| Study No. | Purpose | Tumor Model | Recipient Mice | mAb(s) | Treatment Regimen | % Tumor Growth Inhibition (compared to isotype control) |
|---|---|---|---|---|---|---|
| 5 | Efficacy of anti-mNKG2A.2 in combination with anti-mPD-1 | M109 lung carcinoma | BALB/c n = 10/group | NKG2A.2 (mIgG1-D265A) Anti-PD-1 Ab (mIgG1-D265A) | Day 0: $2 \times 10^5$ cells per mouse SC Day 7, 10, 13: Each antibody administered at 10 mg/kg IP | At Day 25 NKG2A + Anti-PD-1 Ab: 72% Anti-PD-1 Ab: 17% Anti-NKG2A Ab: 11% |

In the BR5.1 ovarian tumor model, co-blockade of NKG2A and PD-1 led to a 36% decrease in the mean tumor volume compared to isotype control, as summarized in Study 6 below.

Summary of Mouse Tumor Model Study 6

| Study No. | Purpose | Tumor Model | Recipient Mice | mAb(s) | Treatment Regimen | % Tumor Growth Inhibition (compared to isotype control) |
|---|---|---|---|---|---|---|
| 6 | Efficacy of anti-mNKG2A.2 in combination with anti-mPD-1 | BR5.1 ovarian | FVB/NJ n = 15/group | NKG2A.2 (mIgG1-D265A) PD-1 (mIgG1-D265A) | Day 0: Fragmented tumors SC Days 5, 8, 11, 14, 17: NKG2A.2 10 mg/kg IP PD-1 5 mg/kg IP | At Day 26 NKG2A + PD-1: 36% NKG2A: 5% PD-1: 0% |

We did not observe activity of anti-mNKG2A alone or in combination with anti-mPD-1 in the MC38 colon carcinoma model, as shown in Study 7 below.

Summary of Mouse Tumor Model Study 7

| Study No. | Purpose | Tumor Model | Recipient Mice | mAb(s) | Treatment Regimen | % Tumor Growth Inhibition (compared to isotype control) |
|---|---|---|---|---|---|---|
| 7 | Efficacy of anti-mNKG2A.3 with anti-mPD-1 | MC38 colon adenocarcinoma | C57Bl/6 n = 10/group | NKG2A.3 (mIgG1-D265A) PD-1 (mIgG1-D265A) | Day 0: 1e6 cells per mouse SC Days 6, 8: Each antibody administered at 10 mg/kg IP | No efficacy observed |

(3) Anti-NKG2A and anti-PD-1 Antibodies Enhanced Antitumor Activity and Functionality of Mouse Natural Killer (NK) Cells and CD8 Tumor Infiltrating Lymphocytes (TILs).

NKG2A/PD-1 co-blockade efficacy was dependent on both CD8+ T and NK cells. CT26− bearing mice were depleted of either CD8+ T or NK cells prior to treatment with anti-mNKG2A and anti-mPD-1 monoclonal antibodies. Mice treated with anti-mNKG2A (NKG2A.3, 7E6 clone, mIgG1-D265A)/anti-mPD-1 (4H2 clone, mIgG1-D265A) antibodies had an increase in mean tumor volume when depleted of either CD8+ T cells (191% increase, mean tumor volume 2271±699 mm$^3$) or NK cells (94% increase, mean tumor volume 1509±800 mm$^3$) compared to mice that did not receive depleting monoclonal antibodies (mean tumor volume 778±686 mm$^3$), as summarized in Study 8 below.

Summary of Mouse Tumor Model Study 8

| Study No. | Purpose | Tumor Model | Recipient Mice | mAb(s) | Treatment Regimen | % Tumor Growth Inhibition (compared to isotype control) |
|---|---|---|---|---|---|---|
| 8 | Depletion of NK and CD8 T-cells | CT26 colon carcinoma | BALB/c n = 10/group | NKG2A.3 (mIgG1-D265A) PD-1 (mIgG1-D265A) Anti-asialo GM1 (e-Bioscience) Anti-CD8a (53.6.7, BioXCell) | Day 0: 1e6 cells per mouse SC Days 5, 12, 19: anti-asialo GM1 (50 μg/mouse) or anti-CD8a (200 μg/mouse) IP Days 6, 10, 13, 17, 20: Each antibody administered at 10 mg/kg IP | At Day 21 NKG2A.3 + PD-1: 60% NKG2A.3 + PD-1 + anti-asialo GM1: 22% NKG2A.3 + PD-1 + anti-CD8: 0% |

Figure 41A:
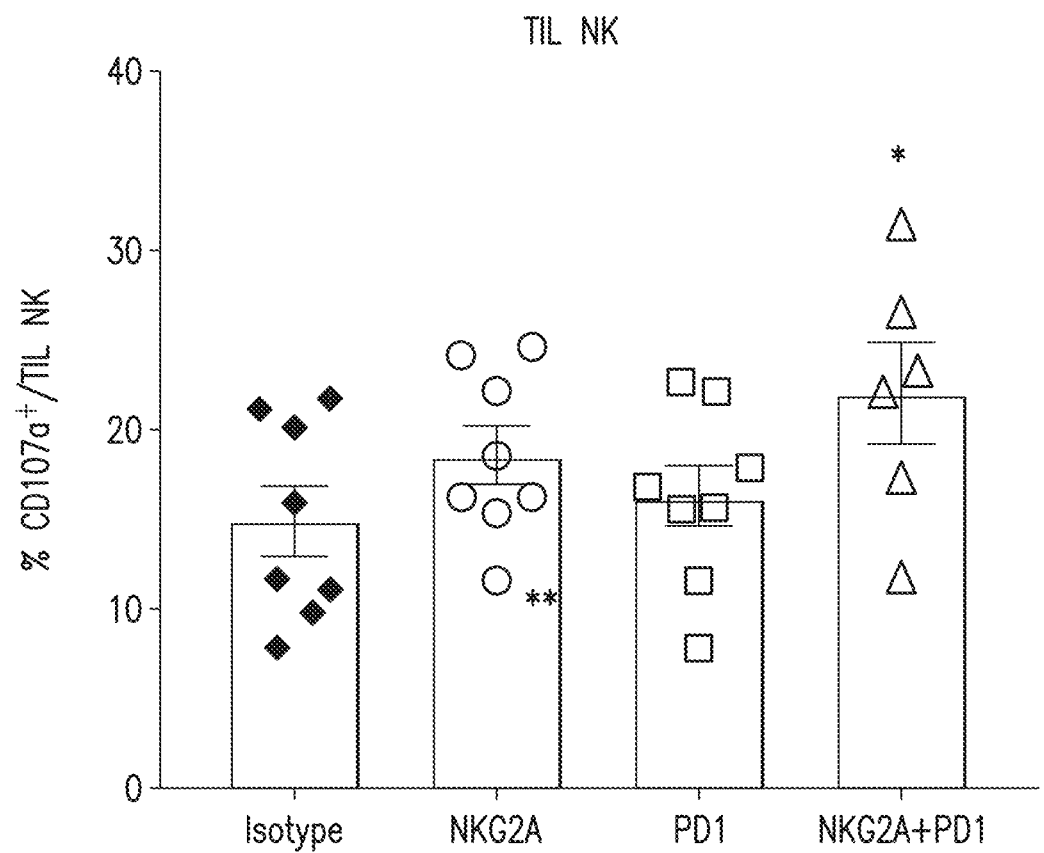
FIG. 41A-C are graphs showing the results of in vivo studies in which anti-NKG2A and anti-PD-1 antibodies increased NK (FIG. 41A) and tumor-specific CD8+ T cell cytotoxicity and IFN-γ in a murine colon carcinoma model (FIG. 41B-C).
Figure 41B:
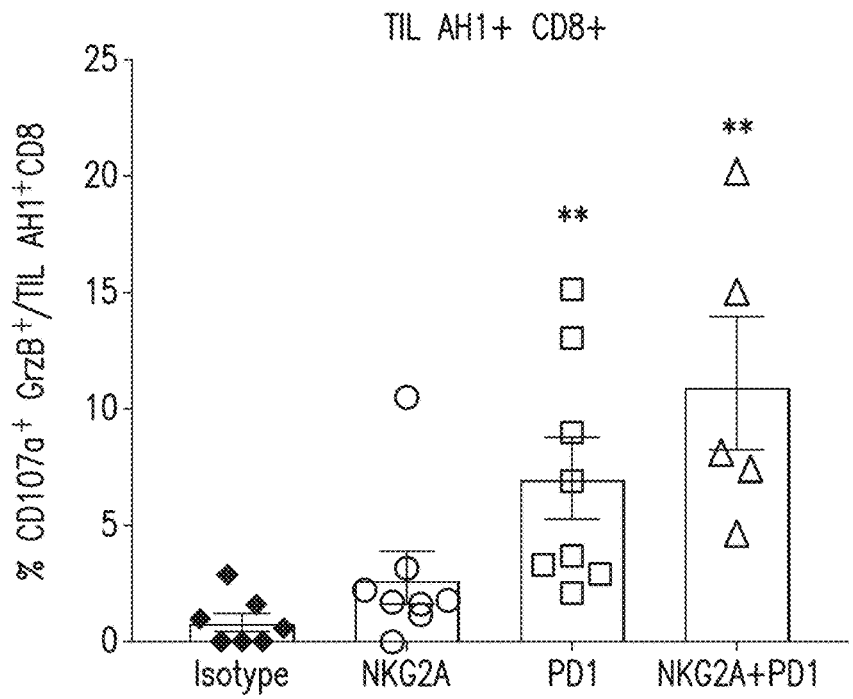
Figure 41C:
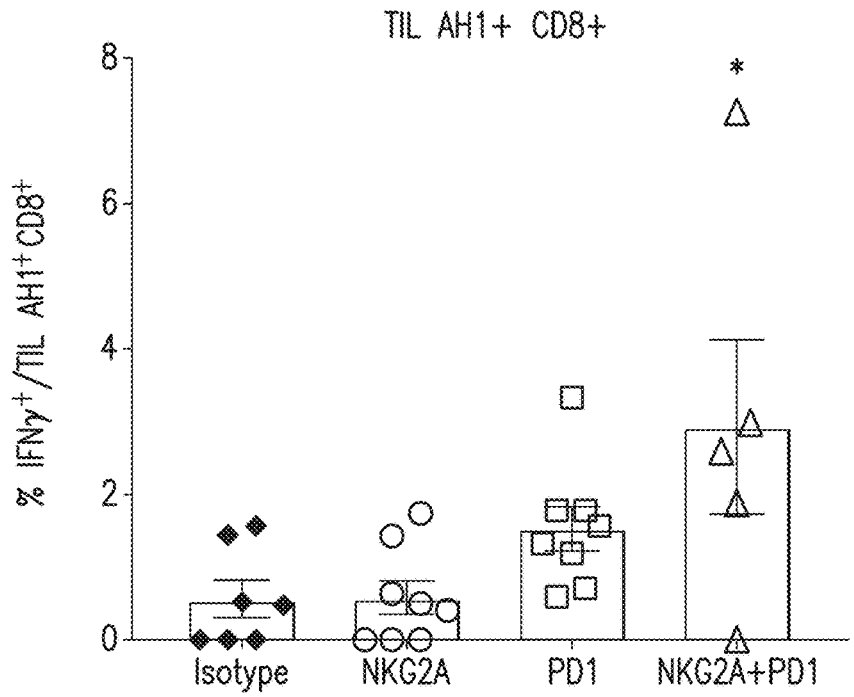

NKG2A/PD-1 co-blockade enhanced functionality of NK and CD8+ T TIL. After four doses of monoclonal antibodies (Day 12 post treatment initiation), NK and CD8+ T TILs were analyzed by flow cytometry. Anti-mNKG2A/anti-mPD-1 treatment led to an increased frequency of CD107a+ NK cells relative to isotype control-treated groups, as shown in FIG. 41A. Immuno-phenotyping studies in the CT26 model showed that co-blockade with the anti-NKG2A and anti-PD-1 antibodies showed a statistically significant increase in NK and tumor specific CD8+ T-cell cytotoxicity and IFN-γ. Anti-mNKG2A/anti-mPD-1 treatment led to an increased frequency of CD107a+ NK cells with an approximately 1.5-fold increase relative to isotype control-treated group. A similar increase in the frequency of cytotoxic CD8+ T cells was seen among tumor-specific AH-1+ CD8+ T cells, as shown in FIG. 41B with an approximately 13-fold increase in CD107a+ Granzyme B+ AH1+ CD8 T cells relative to isotype control-treated group. NKG2A/PD-1 co-blockade also increased the frequency of IFN-γ producing AH-1+ CD8+ T cells with an approximately 5.5-fold increase in IFN-γ+ AH-1+ CD8+ T cells relative to isotype control-treated group, as shown in FIG. 41C.

In summary, anti-NKG2A and anti-PD-1 antibodies, either alone or in combination, increased the frequency of cytotoxic CD8+ T cells among tumor-specific AH-1+ CD8 T cells. The administration of anti-NKG2A and anti-PD-1 antibodies increased NK and tumor-specific CD8 T cell cytotoxicity and IFN-γ in the CT model.

(4) Anti-mPD-1 Antibodies Inhibited Tumor Growth to a Greater Extent when Combined with Anti-mNKG2A Compared to Combination with Anti-mLAG-3 or Anti-mTIGIT Antibodies in a Mouse Model of Sarcoma.

It was previously shown that dual blockade of PD-1 with anti-LAG-3 and anti-PD-1 antibodies with anti-TIGIT antibodies synergistically delayed tumor growth as compared with single agent treatment in mouse tumor models. (Woo et al., "Immune inhibitory molecules LAG-3 and PD-1 synergistically regulate T-cell function to promote tumoral immune escape." Cancer Res 72:917-27 (2012); Johnston R J et al., "The immunoreceptor TIGIT regulates antitumor and antiviral CD8 (+) T cell effector function." Cancer Cell 26:923-937 (2014).

We examined the effect of combining anti-mPD-1 antibody with either anti-mNKG2A (NKG2A.3, 7E6 clone, mIgG1-D265a), anti-mLAG-3 (1A5 clone, mIgG1-D265A), or anti-mTIGIT (10A7 clone, mIgG1-D265A) antibodies on tumor growth control in the 1956 sarcoma model, as summarized in Study 9 below.

Summary of Mouse Tumor Model Study 9

| Study No. | Purpose | Tumor Model | Recipient Mice | mAb(s) | Treatment Regimen | % Tumor Growth Inhibition (compared to isotype control) |
|---|---|---|---|---|---|---|
| 9 | Efficacy of anti-mPD-1 in combination with anti-mNKG2A.3 and other checkpoint inhibitors | 1956 sarcoma | C57Bl/6 n = 10/group | NKG2A.3 (mIgG1-D265A) Anti-PD-1 Ab (mIgG1-D265A) TTGIT (mIgG1-D265A) Anti-LAG-3 Ab (mIgG1-D265A) | Day 0: 1 × 10^6 cells per mouse SC Days 6, 9, 12, 15, 18: Each antibody administered at 10 mg/kg IP | At Day 27 NKG2A.3 + Anti-PD-1 Ab: 97% Anti-PD-1 Ab + Anti-LAG-3 Ab: 91% Anti-PD-1 Ab: 77% Anti PD-1 Ab + Anti-TIGIT Ab: 72% NKG2A.3-D265A: 24% Anti-LAG-3-D265A Ab: 0% Anti-TIGIT-D265A Ab: 0% Tumor-Free Mice at End of Study (TF) NKG2A + PD-1: 6/10 TF LAG-3 + PD-1: 4/10 TF PD-1: 2/10 TF PD-1 + TIGIT: 1/10 TF NKG2A: 1/10 TF LAG-3: 0/10 TF |

Summary of Mouse Tumor Model Study 9

| Study No. | Purpose | Tumor Model | Recipient Mice | mAb(s) | Treatment Regimen | % Tumor Growth Inhibition (compared to isotype control) |
|---|---|---|---|---|---|---|
| | | | | | | TIGIT: 0/10 TF<br>Isotype: 0/10 TF |

PD-1/NKG2A dual blockade showed the strongest antitumor efficacy (6/10 tumor-free mice) compared to the combination of 1) antiPD-1/anti-LAG-3 antibodies (4/10 tumor-free mice) and 2) anti-PD-1/anti-TIGIT antibodies (1/10 tumor-free mice).

Anti-mNKG2A antibodies was combined with other checkpoint inhibitors including anti-mCTLA-4 and anti-LAG-3 antibodies to enhance antitumor efficacy in several mouse tumor models. In the 1956 model, anti-mNKG2A antibody demonstrated strong activity when combined with anti-mCTLA-4, with 87% reduction in mean tumor growth volume and 3/10 mice tumor-free compared to isotype control, as described in studies summarized in Study 10 and FIG. 42A-E.

Summary of Mouse Tumor Model Study 10

| Study No. | Purpose | Tumor Model | Recipient Mice | mAb(s) (with isotype in parenthesis) | Treatment Regimen | % Tumor Growth Inhibition (compared to isotype control) |
|---|---|---|---|---|---|---|
| 10 | Efficacy of anti-mNKG2A.3 in combination with lower doses of other checkpoint inhibitors | 1956 sarcoma | C57Bl/6 n = 10/ group | NKG2A.3 (mIgG1-D265A) Anti-PD-1 Ab (mIgG1-D265A) Anti-CTLA-4 Ab (mIgG2a) | Day 0: 1 × 10$^6$ cells per mouse SC Days 6, 9, 12: NKG2A: 10 mg/kg IP Anti-PD-1 Ab: 0.3 mg/kg IP Anti-CTLA-4 Ab: 0.1 mg/kg IP | At Day 22 NKG2A.3 + Anti-CTLA-4 Ab: 86% NKG2A.3 + Anti-PD-1 Ab: 76% Anti-CTLA-4 mIgG2a Ab: 51% NKG2A.3: 26% Anti-PD-1 mIgG1 D265A Ab: 25% |

Figure 42A:
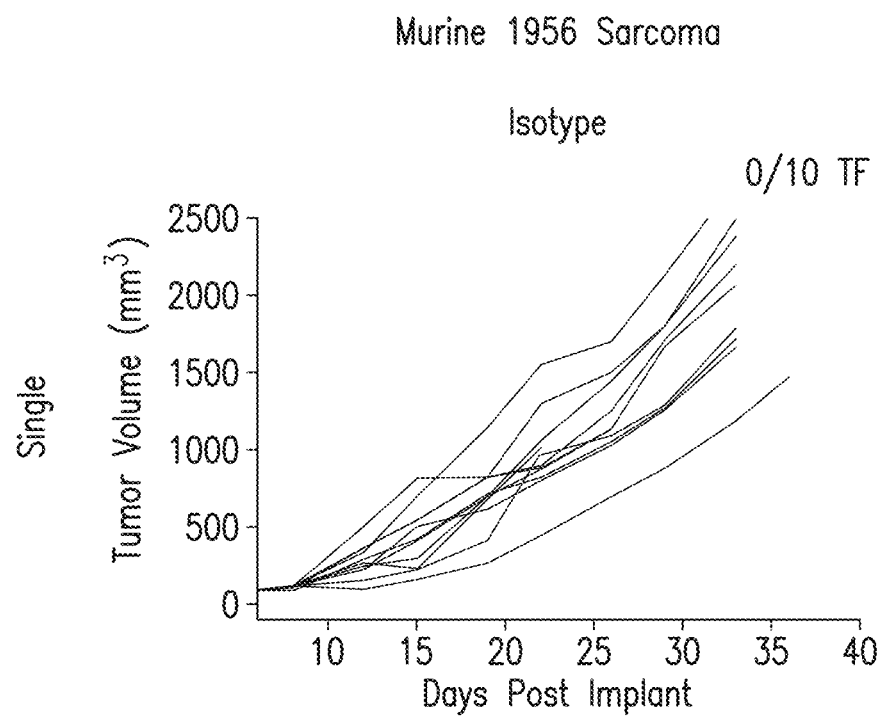
FIG. 42A-E shows the anti-tumor activity of anti-mNKG2A and anti-mCTLA-4 antibodies, either alone or in combination, in the 1956 mouse sarcoma model.
Figure 42B:
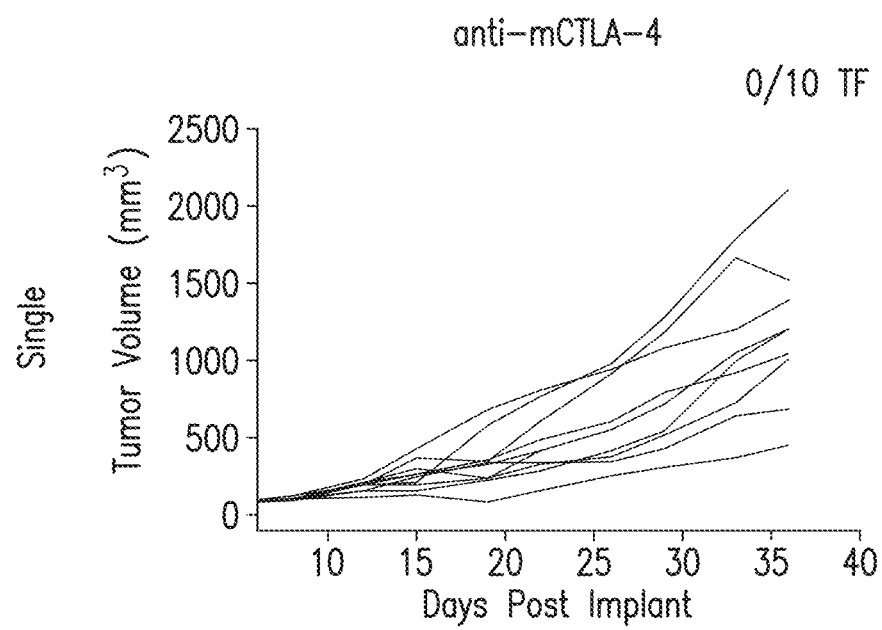
Figure 42C:
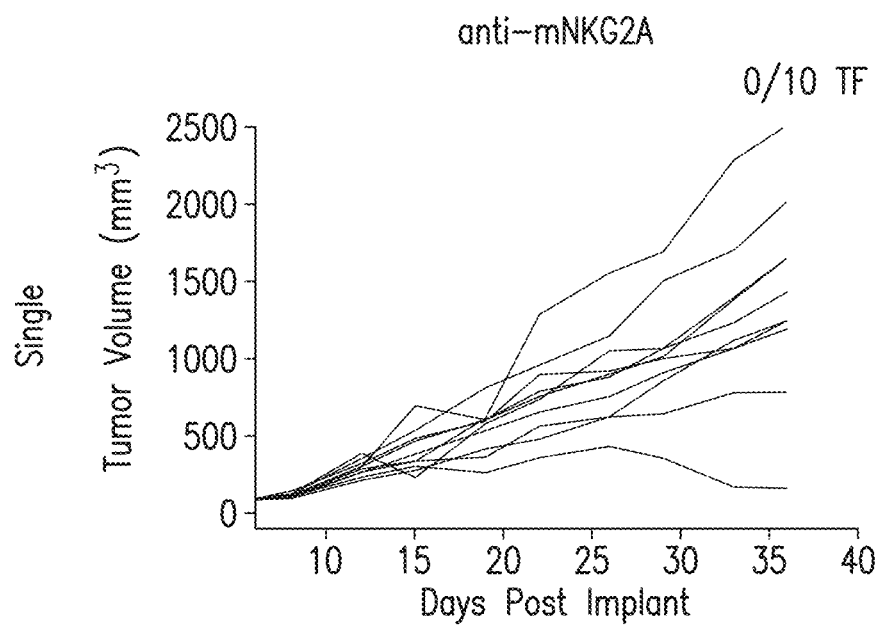
Figure 42D:
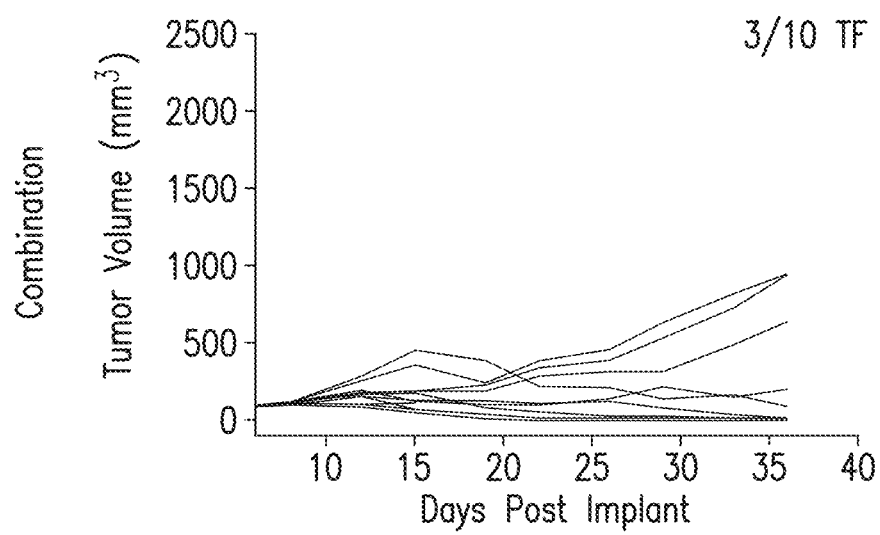
Figure 42E:
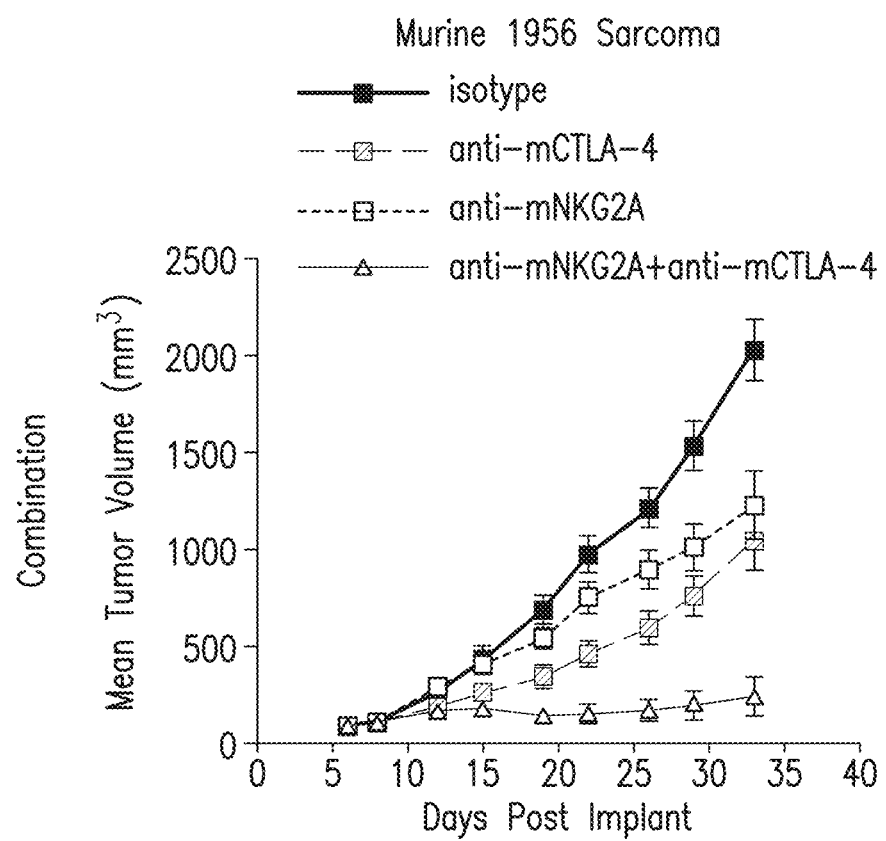

FIG. 42A-E shows the anti-tumor activity of anti-mNKG2A (10 mg/kg) and anti-mCTLA-4 (0.1 mg/kg) antibodies, either alone or in combination, in the 1956 mouse sarcoma model. FIG. 42A-D show the tumor volume at various time points post tumor implantation in mice treated with isotype (FIG. 42A), anti-mCTLA-4 antibody (FIG. 42B, CTLA-4 IgG2a, 0.1 mg/kg), anti-mNKG2A antibody (FIG. 42C, 10 mg/kg), or combination of anti-mNKG2A and anti-mCTLA-4 (FIG. 42D). FIG. 42E shows the average tumor volume as a function of time (days post tumor implantation) in mice treated with isotype, anti-mCTLA-4 alone, anti-mNKG2A alone, or combination of anti-mNKG2A and anti-mCTLA-4.

In the A20 lymphoma intravenous model, anti-NKG2A antibody alone had a survival benefit, with a 10% survival rate. Combination therapy with either anti-mPD-1 or anti-mLAG-3 antibodies extended the survival benefit to 50% and 70%, respectively. The triple combination of anti-mNKG2A, anti-mPD-1, and anti-mLAG-3 antibodies provided the greatest benefit with an 80% survival rate as summarized in Study 11 below and shown in FIG. 43.

Summary of Mouse Tumor Model Study 11

| Study No. | Purpose | Tumor Model | Recipient Mice | mAb(s)(with isotype in parenthesis) | Treatment Regimen | % Tumor Growth Inhibition (compared to isotype control) |
|---|---|---|---|---|---|---|
| 11 | Survival following treatment with anti-mNKG2A.3 in combination with checkpoint inhibitors in IV lymphoma model | A20 B cell lymphoma | BALB/c n = 10/group | NKG2A.3 (mIgG1-D265A) Anti-PD-1 Ab (mIgG1-D265A) Anto-LAG-3 (mIgG1-D265A) | Day 0: $2 \times 10^5$ cells per mouse IV Days 4, 7, 10, 13, 16: Each antibody administered at 10 mg/kg IP | % Survival on Day 60: Anti-NKG2A + Anti-PD-1 + Anti-LAG-3 Abs: 80%, P = <0.0001 Anti-NKG2A + Anti-LAG-3 Abs: 70%, P = 0.0004 Anti-NKG2A + Anti-PD-1 Abs: 50%, P = 0.006 Anti-LAG-3 Ab: 40%, P = 0.001 Anti-PD-1 Ab: 20%, P = <0.0001 Anti-NKG2A Ab: 10%, P = 0.028 (P value compared to isotype control) |

Figure 43:
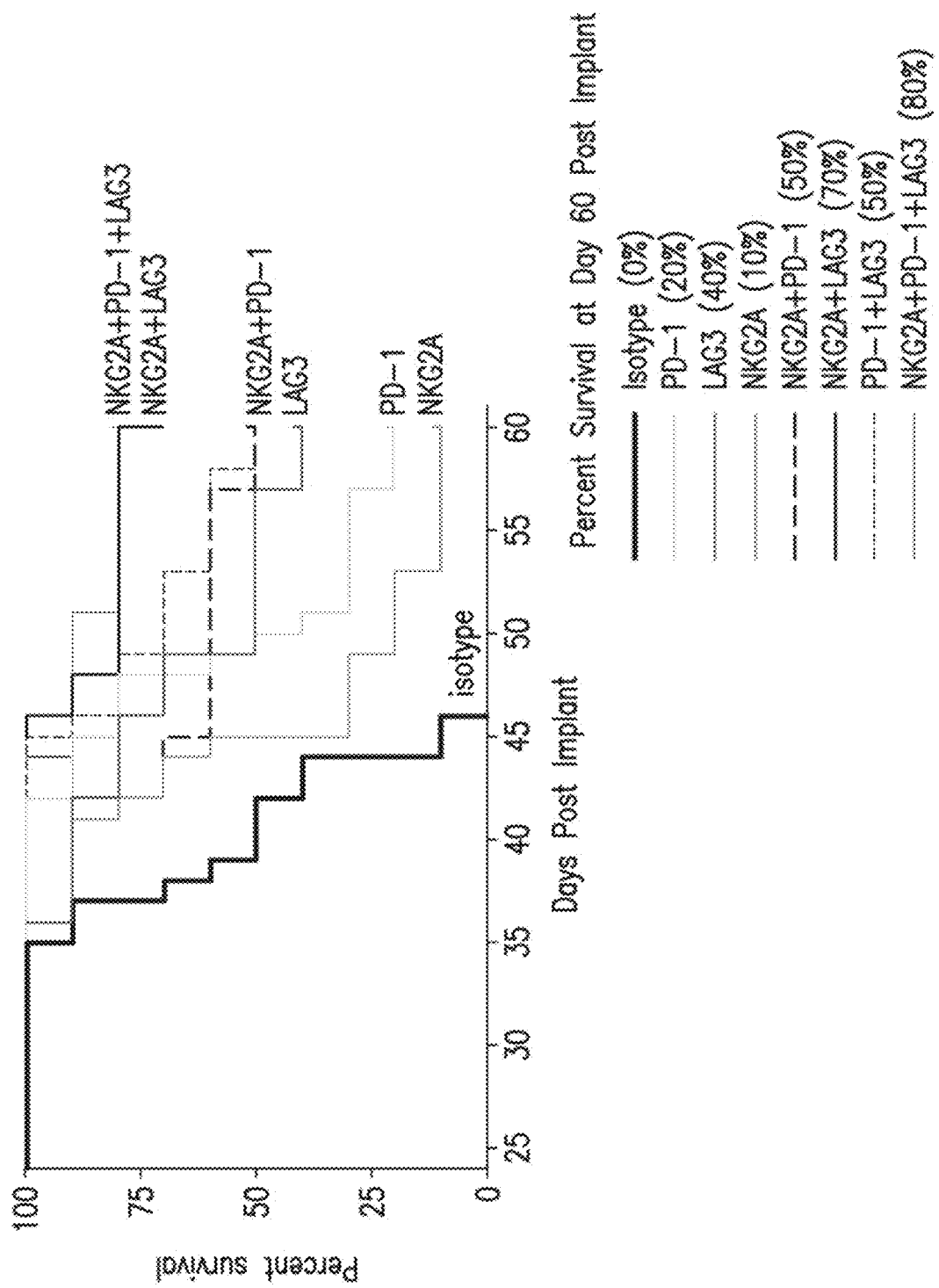
FIG. 43 shows anti-tumor activity of anti-NKG2A, anti-PD-1, and anti-LAG3 antibodies and combinations thereof in a murine lymphoma model. Administering anti-NKG2A antibody alone had a survival benefit, with a 10% survival rate. Combination therapy of anti-NKG2A antibody with either anti-mPD-1 or anti-mLAG-3 antibodies extended the survival rate to 50% and 70%, respectively. The triple combination of anti-mNKG2A, anti-mPD-1, and anti-mLAG-3 antibodies provided the greatest benefit with an 80% survival rate.

FIG. 43 shows the anti-tumor activity of anti-mNKG2A, anti-PD-1, anti-LAG3 antibodies, both alone and in combination in the A20 systemic lymphoma model. Specifically, FIG. 43 shows the percent survival at various time points post tumor implantation in mice (n=10/group) treated with isotype, anti-mNKG2A, anti-mPD-1, anti-LAG3 alone, or a combination thereof.

Taken together, these data showed that combinatorial blockade of anti-NKG2A, anti-PD-1, anti-CTLA-4, and anti-LAG-3 antibodies has enhanced efficacy in reducing mouse tumor growth.

Figure 44:
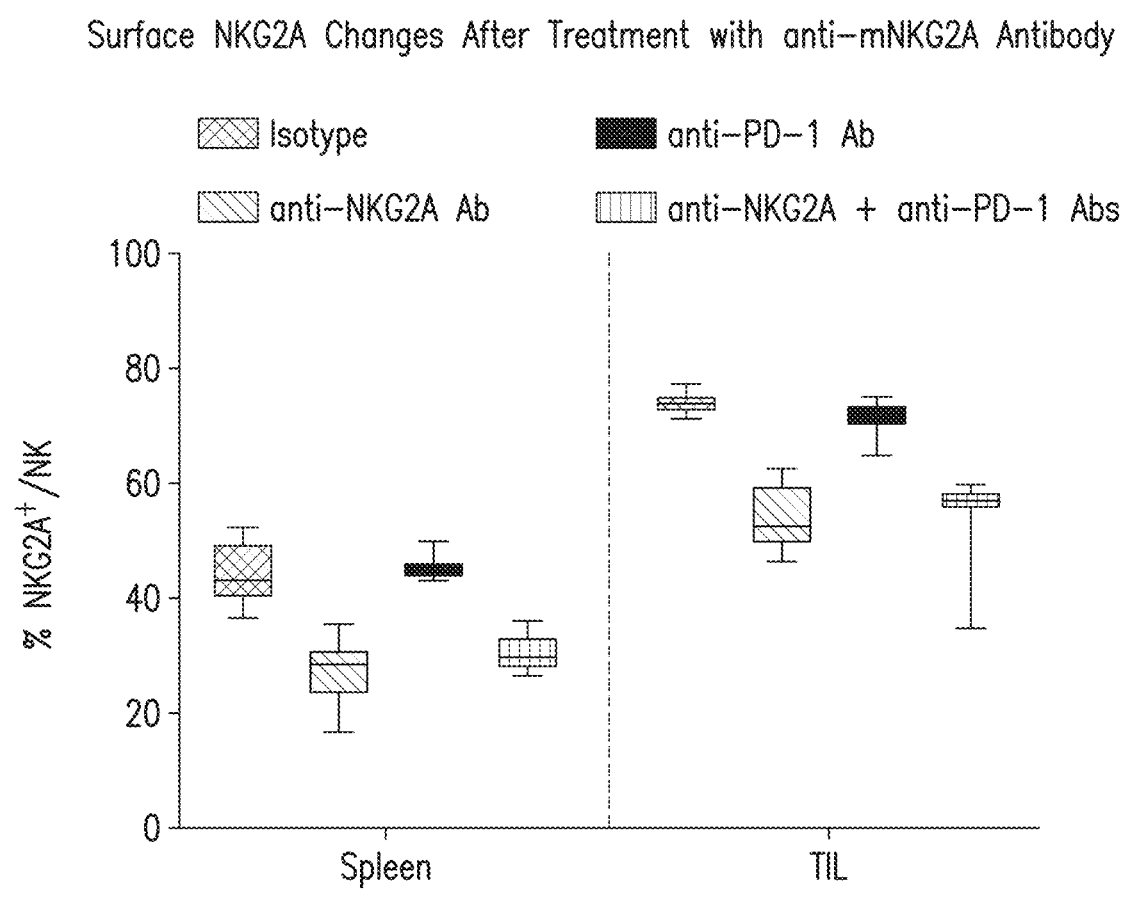
FIG. 44 shows that after treatment with anti-mNKG2A antibody in a murine CT26 colon carcinoma model, the NKG2A expression level was reduced on both splenic and tumor infiltrating lymphocyte (TIL) NK cells as compared with the isotype.

(5) Anti-mNKG2A Monoclonal Antibody Administered In Vivo Downregulated Surface NKG2A on Mouse NK Cells After treatment with anti-mNKG2A monoclonal antibody (NKG2A.3 (7E6 clone), mIgG1-D265A), the NKG2A expression level was reduced on both splenic and TIL NK cells as compared with the isotype, as shown in FIG. 44. FIG. 44 shows the percent of NKG2A-expressing NK cells among NKG2A+ NK cells as measured on day five after first treatment in spleen and tumor in a murine CT26 colon carcinoma model. We observed downregulation of the NKG2A expression after administration of the anti-NKG2A antibody, which indicated that it can be used as a marker of target engagement. Downregulation refers to the downregulation of the surface NKG2A expression. Target engagement means that the anti-NKG2A antibody engages with the NKG2A receptor.

Together with the internalization data discussed herein, these data support that NKG2A downregulation will serve as a target engagement marker for the NKG2A.9 antibody.

Example 16

Biophysical Properties, Affinity and Epitope Mapping, and Immunogenicity

As described herein, the variable sequence of fully human anti-NKG2A monoclonal antibody NKG2A.9 is derived from the 13F3.A4 hybridoma with a VH-I107T germline reversion mutation and a VK-N30S mutation to mitigate the deamidation liability of the VK-N30 amino acid residue. The constant region was derived from an IgG1f backbone (IgG1.3) and includes three mutations on the heavy chain: L234A, L235E, and G237A to minimize or eliminate antibody binding to Fcγ receptors and C1q. The NKG2A.9 antibody is also known as 13F3-VH-I107T-VH-N30S IgGf1.3 and NKG2A.9 IgGf1.3. The Table below summarizes the biophysical characteristics of the NKG2A.9 antibody based on the analysis of the material derived from the ExpiCHO transient expression system.

| Property | Method | Results |
|---|---|---|
| Identity | SDS-PAGE (sodium dodecyl sulfate-polyacryamide gel electrophoresis) | Heavy and light chain bands confirmed Deglycosylated molecular weight (MW) = 143,683 Dalton (Da) (as predicted) |
| | LC-MS/MS peptide map | *Heavy Chain (HC): observed 48,893 Da, inferred 48,900 Da, predicted 48,900 Da *Light Chain (LC) = observed 23,207 Da, inferred 23,211 Da, predicted 23,210 Da >99% sequence and disulfide structure confirmed by peptide mapping and mass spectrometry. Isoform and N-297 glycosylation on heavy chain were confirmed. |
| Purity/ Homogeneity | CE-SDS (capillary electrophoresis sodium dodecyl sulfate) | Non-reduced (NR): 97.0% monomer, impurities include 2.1% HHL (heavy chain-heavy chain-light chain), 0.4% HL (heavy chain-light chain), 0.1% HH (heavy chain-heavy chain), 0.3% Reduced (R): LC 29.5%, HC 69.8%, NGHC 0.7% |
| | SEC (Size Exclusion Chromatography) SE-MALS (combination of | 98.1% monomer |

-continued

| Property | Method | Results |
|---|---|---|
| | Size Exclusion Chromatography with Multi-Angle Light Scattering analysis) HIC-HPLC (Hydrophobic Interaction Chromatography-High Performance Liquid Chromatography) CE (Capillary electrophoresis, Glycans) cIEF (Capillary isoelectric focusing) | 95.2%(146 kDa), 2.63% (505 kDa), 1.6% (109 kDa) 86.4% main peak at 35.5 minutes, 13.6% pre-main peak. G0F (78%), G1F (17%), G2F (1%), Man5 (4%), Main peak pI = 8.9 (59%), Acidic species 35%, Basic species 7%; pI range 8.6-9.1 |
| Chemical Modifications | LC-MS/MS (Liquid Chromatography-Tandem mass spectrometry) peptide map | Very low |
| Affinity human NKG2A** | Biacore | $K_D$ = 36 nM (1:1 binding model); $k_a$ (1/Ms) = 3.0 × $10^5$, $k_d$ (1/s) = 1.1 × $10^{-2}$ at 37° C.; cross-reacts with cynomolgus NKG2A |
| Thermal Stability and Reversibility | DSC (Differential scanning colorimeter) (diluted into storage buffer) | Tm1 = 68° C., Tm2 = 75° C., Tm3 = 83° C. Reversibility at 68° C. = 92%, at 75° C. = 49% |

*Deglycosylation and partial reduction method used for light and heavy chain mass confirmation.
** Human NKG2A-CD94 heterodimer (hNKG2A-CD94-mFc) used as antigen for binding studies.

The biophysical properties of the NKG2A.9 antibody were favorable. The identity of the NKG2A.9 antibody was confirmed by SDS-PAGE and mass spectrometry analysis. The purity of the antibody was greater than 98% as tested by size exclusion chromatography (SEC). A single N-glycosylation site was confirmed at N297 on the heavy chain, with a glycan profile that was consistent with the glycan profile of IgG1 monoclonal antibodies expressed in CHO cells. Only fucosylated glycans (G0f, G1f, G2f, and Man5) were found on them. The NKG2A.9 antibody had good thermal stability and reversibility, meaning that the antibody retained its structural integrity under thermal stress and had modest refolding properties when stress was released.

Example 17

Preclinical Pharmacokinetics Studies

The pharmacokinetics data supported efficacy of the NKG2A.9 antibody. After intravenous (IV) administration to cynomolgus monkeys, the NKG2A.9 exhibited linear antibody pharmacokinetic (PK) characteristics at doses≥0.5 mg/kg, with a predicted human half-life (T1/2) of 16 days. The human efficacious dose targeting the steady-state trough concentration ($C_{trough,ss}$) for achieving complete (99%) receptor occupancy (RO) in blood was projected to be 2.5 mg/kg IV, every four weeks. The dose after subcutaneous (SC) administration may vary depending on SC bioavailability in humans (typically 50-100%) and whether a slow SC absorption rate improves the $C_{trough,ss}$.

Formulation efforts showed that a platform formulation approach can be used for a ready-to-use (RTU) formulation. Preliminary viscosity and stability evaluation of the NKG2A.9 antibody at high (150 mg/mL) concentration and the predicted human efficacious dose (2.5 mg/kg) indicate that subcutaneous administration may be possible under optimized formulation conditions.

The toxicology data showed that the NKG2A.9 antibody can be safely administered. Doses of 0 mg/kg, 0.5 mg/kg, 10 mg/kg, and 50 mg/kg in cynomolgus monkeys were well tolerated with no abnormalities identified. Receptor occupancy at Day 43 (36%, 84%, and 97% at 0.1 mg/kg, 10 mg/kg, and 50 mg/kg, respectively) and target engagement (downregulation of surface NKG2A) were demonstrated at all doses. Downregulation refers to the downregulation of the surface NKG2A expression. We observed downregulation of the NKG2A expression following administration of the antibody, which indicated that it can be used as a marker of target engagement (i.e. anti-NKG2A antibody engages with the NKG2A receptor).

Example 18

Pharmacokinetics of Anti-mNKG2A.3 in Mice

Pharmacokinetic studies were conducted with an anti-mNKG2A mouse surrogate (NKG2A.3) that has similar properties to the NKG2A.9 antibody following intravenous (IV) or intraperitoneal (IP) administration to C57BL6 mice. Table 3 summarizes the pharmacokinetic parameters obtained from the studies.

TABLE 3

Pharmacokinetic Parameters of an Anti-mNKG2A Mouse Surrogate (NKG2A.3) after IV and IP Administration to C57BL6 Mice (Mean ± Standard Deviation (SD), n = 4 or 5)*

| Route of administration | Dose (mg/kg) | Cmax (nM) | Tmax (hours) | AUCtot (μM × day) | T½ (days) | CLT (mL/day/kg) | Vss (mL/kg) |
|---|---|---|---|---|---|---|---|
| IV (non-tumor- | 0.3 | 24 ± 6.8 | 0.25 ± 0** | 0.075 ± 0.010 | 3.2 ± 0.2 | 26 ± 3.5 | 121 ± 16 |
| | 1 | 79 ± 7.8 | 0.25 ± 0** | 0.38 ± 0.036 | 3.9 ± 0.5 | 17 ± 1.7 | 108 ± 15 |

TABLE 3-continued

Pharmacokinetic Parameters of an Anti-mNKG2A Mouse Surrogate (NKG2A.3) after IV and IP Administration to C57BL6 Mice (Mean ± Standard Deviation (SD), n = 4 or 5)*

| Route of administration | Dose (mg/kg) | Cmax (nM) | Tmax (hours) | AUCtot (μM × day) | T½ (days) | CLT (mL/day/kg) | Vss (mL/kg) |
|---|---|---|---|---|---|---|---|
| bearing) | 10 | 940 ± 327 | 0.25 ± 0** | 7.3 ± 2.0 | 9.4 ± 2.5 | 9.7 ± 2.5 | 128 ± 19 |
| IP | 0.1 | 6.9 ± 0.8 | 2 ± 0 | 0.014 ± 0.004 | n.a. | n.a. | n.a. |
| (tumor-bearing) | 10 | 993 ± 87 | 2 ± 0 | 8.0 ± 1.1 | n.a. | n.a. | n.a. |

Note:
PK parameters were obtained using non-compartmental analysis of serum drug concentration-time data. n.a. stands for not applicable.
*Serum drug levels were obtained from serial micro-sampling and corrected for either a theoretical dilution factor of 17 or an experimentally determined dilution factor of 20;
**First sampling time point.

The NKG2A.3 antibody exhibited nonlinear pharmacokinetics in mice. With an intravenous dose ratio of 1:3:30, the Area Under the Curve (AUC) ratio was 1:5.1:97. The terminal half-life increased from 3.2 days to 9.4 days when the doses increased from 0.3 mg/kg to 10 mg/kg. Similarly, with an IP dose ratio of 1:100, the AUC ratio was 1:571 between 0.1 and 10 mg/kg. In addition, the formation of anti-drug antibodies (ADAs) did not affect the PK of NKG2A.3 significantly. Collectively, these data showed that the NKG2A.3 antibody underwent target-mediated drug disposition (TMDD) in mice.

The IP bioavailability was complete when comparing the AUC values at 10 mg/kg between IV and IP routes. In addition, there was no apparent difference in the systemic exposure between tumor- and non-tumor-bearing mice as well as between C57BL6 and BALB/c mice.

In addition, a single-dose PK/pharmacodynamic (PD) study was conducted with the NKG2A.3 antibody in the CT26 model, where the time course of drug levels and receptor occupancy (RO) was determined in both the circulation and tumors. The average tumor-to-serum drug concentration ratio was 0.10±0.07 (N=33), with the RO in blood and tumor infiltrating lymphocytes (TILs) being complete at the mouse efficacious dose of 1 mg/kg.

Example 19

Pharmacokinetics of the NKG2A.9 Antibody in Cynomolgus Monkeys

We characterized the pharmacokinetic characteristics of the NKG2A.9 antibody in cynomolgus monkeys at a dose range of 0.5 mg-50 mg/kg). The PK parameters of the NKG2A.9 antibody obtained from a single-dose toxicokinetic (TK)/PD and tolerability study are summarized in Table 4 below.

TABLE 4

Pharmacokinetic Parameters of the NKG2A.9 Antibody after IV Administration to Cynomolgus Monkeys (Mean ± SD, N = 3)

| Dose (mg/kg) | Cmax (nM) | Tmax (hour) | AUC0-42 d (μM × day) | T½ (day) | CLT (mL/day/kg) | Vss (mL/kg) |
|---|---|---|---|---|---|---|
| 0.5 | 0.11 ± 0.01 | 0.5 ± 0* | 1 ± 0.2 | 14 ± 6 | 3.1 ± 0.9 | 53 ± 7 |
| 10 | 2.5 ± 0.29 | 0.5 ± 0* | 22 ± 4 | 18 ± 3** | 2.4 ± 0.5 | 57 ± 6 |
| 50 | 9.8 ± 2.5 | 0.5 ± 0* | 101 ± 18 | 23 ± 4 | 2.5 ± 0.5 | 77 ± 12 |

Note:
PK parameters were obtained using non-compartmental analysis of serum drug concentration-time data.
*First sampling time point;
**Two drug concentrations affected by ADAs were not included for T½ calculation.

The $AUC_{0\text{-}42\ d}$ was dose-proportional between 0.5 mg/kg and 50 mg/kg IV doses, with half-life ranging from 14 days to 23 days. In addition, the PK results were affected by ADAs only in one monkey. Furthermore, PK/PD modeling of the monkey blood RO data revealed that the serum drug $EC_{50}$ was 20±5.4 nM, which is in agreement with the in vitro $EC_{50}$ of 31±5.4 nM.

In conclusion, the studies demonstrated that the anti-NKG2A antibody showed good receptor occupancy and was well tolerated in cynomolgus monkeys.

Example 20

Human Pharmacokinetics of the NKG2A.9 Antibody

The human PK of the NKG2A.9 antibody is assumed to be same as that in monkeys. As a result, the predicted human intravenous dose of the NKG2A.9 antibody is 10 mg/kg, and the predicted half-life of the NKG2A.9 antibody in humans is 16 days, as summarized in Table 5 below.

TABLE 5

Predicted Human Pharmacokinetic Parameters of the NKG2A.9 Antibody

| IV Dose (mg/kg) | AUCtot (μM × day) | T½ (day) | CLT (mL/day/kg) | Vss (mL/kg) |
|---|---|---|---|---|
| 10 | 24 | 16 | 2.7 | 61 |

Example 21

Projection of Human Efficacious Dose

The human efficacious dose of the NKG2A.9 antibody was projected using an RO-based approach. The available in vitro and in vivo preclinical data, including RO in mice and monkeys as well as mouse antitumor efficacy, were evaluated. The maximum antitumor efficacy in combination with anti-mPD-1 was demonstrated in 1956 and CT26 syngeneic models at a dosage regimen of 1 mg/kg administered every three to four days for a total of five doses (Q3/4D×5), with no further improvement in efficacy at doses up to 10 mg/kg. Importantly, at 1 mg/kg, the NKG2A receptors in both blood and tumors (i.e., TIL) were fully occupied, indicating complete RO. In addition, PK/PD modeling of monkey blood RO data revealed agreement between the in vitro and in vivo RO $EC_{50}$, which suggested that the in vitro $EC_{50}$ can be used to predict the in vivo RO. Taken together, the human efficacious dose of the NKG2A.9 antibody is projected by targeting 99% RO in blood at trough, using an in vitro human RO $EC_{50}$ of 1 nM. Because the average tumor-to-serum drug concentration ratio observed with NKG2A.3 in mice was about 0.10, along with the fact that a similar ratio was observed with an anti-OX40 antibody (BMS-986178) in human tumor biopsies samples, targeting 99% RO in blood at trough would lead to about 90% RO in tumors throughout the treatment period. Consequently, the projected human efficacious dose is 2.5 mg/kg administered every four weeks. At this dose, the predicted human steady-state AUC and $C_{trough}$ cover the exposure achieved at the maximum efficacious dose of 1 mg/kg Q3/4D×5 in mice.

Example 22

Stability and Formulation of the NKG2A.9 Antibody

Formulation efforts have shown that a platform formulation approach can be used for the development of a ready-to-use (RTU) formulation for the NKG2A.9 antibody. Preliminary viscosity and stability evaluation at 150 mg/mL indicated that the NKG2A.9 antibody can be administered via subcutaneous administration under optimized formulation conditions.

A formulation evaluation including a freeze-thaw stability study and an accelerated stability study have been performed for the NKG2A.9 antibody at a concentration of 25 mg/mL, as summarized in Table 6 below.

No physical stability issues were observed during freeze-thaw stress (five cycles) at 25 mg/mL in platform formulation (20 mM histidine buffer pH 6.0, 260 mM sucrose, 50 µM pentetic acid, 0.05% polysorbate 80). Accelerated stability studies in platform buffer at 25 mg/mL were conducted at 4° C., 25° C., and 40° C. Over three months under the conditions tested, minor chemical modifications that did not affect functional activity were observed in the CDR region of the NKG2A.9 antibody. These minor chemical modifications in the NKG2A.9 antibody included changes in oxidation, deamidation, and isomerization of amino acid residues that are expected due to storage of the solution in, for example, an elevated temperature, did not adversely affect the binding activity of the antibody. Deamidation of N326 in the VSNK region (SEQ ID NO: 162) of the Fc was observed under stressed conditions (about 18% after three months at 40° C.), which is typical for IgG1 monoclonal antibodies. After storage at 25° C. for three months, deamidation was observed to be acceptable at about 1.4%. No physical stability issues or loss of functional activity were observed over three months under tested conditions.

No issues with viscosity (apparent viscosity=7.3 centipoise (cP)) or aggregation (0.4% soluble aggregates) were observed upon concentration of the NKG2A.9 antibody to 150 mg/mL. No physical stability issues were observed during freeze-thaw stress (five cycles) at 150 mg/mL in platform formulation. The NKG2A.9 antibody at 150 mg/mL in platform formulation was subjected to accelerated stability for three months at 4° C., 25° C., and 40° C., as summarized in Table 7 below.

TABLE 6

Stability of the NKG2A.9 Antibody at 25 mg/mL in Platform Formulation

| Property | Method(s) | Results |
| --- | --- | --- |
| Freeze/Thaw (F/T) (1 hour at −80° C., 1 hour at room temperature (RT) × 5) | UV, SEC | No F/T stability risk revealed |
| Solubility/Concentration Profile | UV, SEC | At least 25 mg/mL in platform buffer (20 mM histidine, pH 6.0, 260 mM sucrose, 0.05 mM DTPA, 0.05% polysorbate 80) |
| Accelerated Stability 25 mg/mL 3 months at 4° C., 25° C., and 40° C. in platform formulation | UV, SEC, cIEF, LC-MS/MS peptide mapping, functional (flow cytometry) | 3 months at 40° C. = 5% increase in LMW* <br> 3 months at 40° C. = 4% increase in HMW* <br> 3 months at 40° C. = 12%/month increase in acidic variant <br> 3 months at 40° C. = 18% increase in deamidation of N326 in VSNK region (SEQ ID NO: 162) |

*LMW = Low Molecular Weight,
HMW = High Molecular Weight

TABLE 7

Stability of the NKG2A.9 Antibody at 150 mg/mL in Platform Formulation

| Property | Method(s) | Results |
|---|---|---|
| Solubility/Concentration Profile | UV, SEC, Viscosity (viscometer) | At least 150 mg/mL in platform buffer (20 mM histidine, pH 6.0, 260 mM sucrose, 0.05 mM DTPA, 0.05% polysorbate 80) Apparent viscosity = 7.3 ± 0.1 CP |
| Accelerated Stability 150 mg/mL 3 months at 4° C., 25° C. and 40° C. in platform formulation | UV, SEC | 3 months at 4° C. = 0.1% increase in LMW 3 months at 4° C. = 0.8% increase in HMW 1 month at 25° C. = 0.4% increase in LMW 1 month at 25° C. = 0.8% increase in HMW Significant aggregation and clipping observed at 25° C. and 40° C. beyond 1 month. |

Minor physical stability issues were observed at 4° C. after three months and at 25° C. after one month on stability (0.8% increase in high molecular weight aggregates, HMW, at both temperatures). Clipping and physical instability were observed at elevated temperatures of 25° C. and 40° C. after storage for more than one month. The instability seen after storage for longer time at elevated temperature could potentially be explained by a slight contamination of the discovery lot used for the evaluation.

Example 23

Tissue Distribution of the NKG2A.9 Antibody

Immunohistochemistry using the NKG2A.9 Antibody on a panel of 20 frozen human tissues showed occasional mononuclear cell expression, but no unexpected binding. There was strong staining in small subsets of mononuclear cells, mainly in the spleen, and rare staining of mononuclear cells in tonsil, uterus, stomach, small intestines, thymus, and liver.

Example 24

Single-Dose Pharmacokinetics, Toxicokinetics, Tolerability, and Pharmacodynamics Study of NKG2A.9 in Cynomolgus Monkeys Cynomolgus monkey is the preclinical toxicology species because of similar binding of the whole antibody to NKG2A. In addition, immunohistochemistry analysis of monkey tissues, using the NKG2A.9 antibody, is similar to that of humans, showing positive staining in small subsets of mononuclear cells. As discussed herein, the NKG2A.9 antibody binds to both NKG2A and NKG2C in monkeys, whereas it selectively binds to NKG2A and not NKG2C in humans. Since NKG2C is an activating receptor, it is possible that in monkeys there could be simultaneous upregulation of immune responses (due to NKG2A blockade) and downregulation of immune responses (due to NKG2C blockade).

The NKG2A.9 antibody was administered as a single intravenous dose to cynomolgus monkeys (n=3 per group, mixed sex) at 0 mg/kg, 0.5 mg/kg, 10 mg/kg, and 50 mg/kg, and animals were observed for 42 days. Study endpoints included clinical observations, body weight, clinical pathology, pharmacokinetics and toxicokinetics, anti-drug antibody (ADA) formation, RO, surface NKG2A expression, and PBMC immunophenotyping. All animals were immunized with simian immunodeficiency virus (SIV) Gag and Nef, expressed in two separate adenovirus-5 vectors, to evaluate enhancement of immune responses as a potential PD endpoint (SIV-reactive T cell [tetramer] assay on Day 22; ex vivo T cell response to antigen on Day 22). This was a non-terminal study, without necropsy or histopathology.

All doses were well tolerated at dosages up to 50 mg/kg ($AUC_{0-42\ days} \leq 101$ μM·day). There were no NKG2A.9 antibody-related clinical signs, changes in body weight, or NKG2A.9 antibody-related changes in hematology or clinical chemistry, as summarized in Table 8 below.

TABLE 8

Summary of Results for the NKG2A.9 Antibody: Single-dose IV TK, Tolerability, and PD in Monkeys (n = 3/group)

| Study Endpoint | NKG2A.9 Antibody-Related Results |
|---|---|
| Clinical signs | None |
| Body weight | No significant changes |
| Hematology, clinical chemistry | No significant changes |
| Receptor occupancy | Day 1, 4 hours: 81%, 99%, and 100% at 0.5 mg/kg, 10 mg/kg, and 50 mg/kg, respectively |
| | Day 43: 36%, 84%, and 97% at 0.5 mg/kg, 10 mg/kg, and 50 mg/kg, respectively |
| Downregulation of surface NKG2A (target engagement marker) | Day 1 (4 hours post-dosing): Surface expression was 50%, 52%, and 58% (relative to pre-dose) at 0.5 mg/kg, 10 mg/kg, and 50 mg/kg |
| | Day 43: Surface expression was 65-80%, 47-107%, and 41-51% at 0.5 mg/kg, 10 mg/kg, and 50 mg/kg, respectively |

TABLE 8-continued

Summary of Results for the NKG2A.9 Antibody: Single-dose
IV TK, Tolerability, and PD in Monkeys (n = 3/group)

| Study Endpoint | NKG2A.9 Antibody-Related Results |
| --- | --- |
| Response to immunization | No change in ex vivo recall response to SIV Gag or Nef. An apparent NKG2A.9-mediated trend of decrease in the percentages of Nef- and Gag-specific (tetramer+) CD8+ cells. Within the antigen-specific CD8+ T cell populations, there was an apparent trend of decrease in the percentage of $T_{EM}$ cells. |
| Toxicokinetics | At 50 mg/kg, the Cmax was 9.8 µM on Day 1, 0.5 h, and the $AUC_{0-42\ days}$ was 101 µM · day |
| Anti-drug antibody (ADA) | ADA observed in one animal (10 mg/kg) beginning at the first time point, Day 8 |

ADA was observed in one animal (10 mg/kg) beginning at the first time point, Day 8. Pharmacokinetics/toxicokinetics were linear in the dose range evaluated. At the high dosage of 50 mg/kg, the Cmax was 9.8 µM (on Day 1, 0.5 h) and the $AUC_{0-42\ days}$ was 101 µM·day. In summary, the single-dose monkey study showed RO, downregulation of surface expression of NKG2A as a marker of target engagement, and acceptable TK without any adverse findings for a single dose administered at dosages up to 50 mg/kg ($AUC_{0-42\ days} \leq 101$ µM·day).

Example 25

Cytokine Release Assays

An in vitro cytokine release assay was performed using soluble NKG2A.9 antibody and whole blood from 15 human donors. Cytokines and chemokines were evaluated by a Luminex panel of 75 cytokines/chemokines to determine if treatment with the NKG2A.9 antibody poses a safety risk of cytokine release syndrome. No NKG2A.9-related induction of the human cytokines or chemokines assayed was observed.

Example 26

Immunogenicity Risk Assessment for Anti-NKG2A Antibodies

Therapeutic antibodies have the potential to elicit an immune response in patients against the therapeutic antibody. This immune response is usually manifested by the generation of anti-drug antibodies (ADA), such as through a human anti-human antibody (HAHA) response, which can alter exposure, neutralize therapeutic function, and/or even result in serious clinical consequences for the patient. The "foreignness" of the therapeutic antibody, which is recognized as "non-self" by the immune system, is thought to be the main driver of an MHC class II-mediated ADA immune response. It is important for a safe and effective anti-NKG2A antibody as described herein to have low or no immunogenicity. The potential for human immunogenicity of several anti-NKG2A monoclonal antibodies was evaluated by in silico HLA binding tools and in vitro by DC:T cell proliferation assays. As discussed herein, the NKG2A.9 antibody was engineered to have low human immunogenicity liabilities as assessed by in silico HLA binding tools. The risk of various anti-NKG2A antibodies (NKG2A.6, NKG2A.9, and NKG2A.11 antibodies) to elicit an undesirable immune response in humans against the antibodies was determined to be low based on in vitro DC:T cell proliferation assays.

1. In Silico HLA Binding Analysis Was Used to Engineer Anti-NKG2A Antibodies with Low Immunogenicity Risk T cell activation and proliferation are required steps to develop an immune response. Specifically, HLA Class II binding of peptide antigen is a critical step in developing high affinity IgG antibody mediated immune response. Using an in silico HLA binding tool (IEDB) (See, e.g., Wang P, et al., PLoS Comput Biol. 4(4) (2008)), we analyzed the CDR regions of monoclonal antibodies by dividing the amino acid sequence into overlapping 15 peptides and ranking the binding for 27 HLA DRB1 alleles (which covers about 95% of the human population) against all other peptides submitted to IEDB database. Peptides that rank in the top 10 percentile for a given HLA allele are considered a "binder," and a region that shows a binder for 50% of the alleles is designated as a "binding cluster." A "binder" or "binding clusters" within a biologic molecule are considered to be a driving factor in the development of immunogenicity (Sinu, P et al., *Clinical & Developmental Immunology* Vol. 2013 (2013)).

Figure 54A:
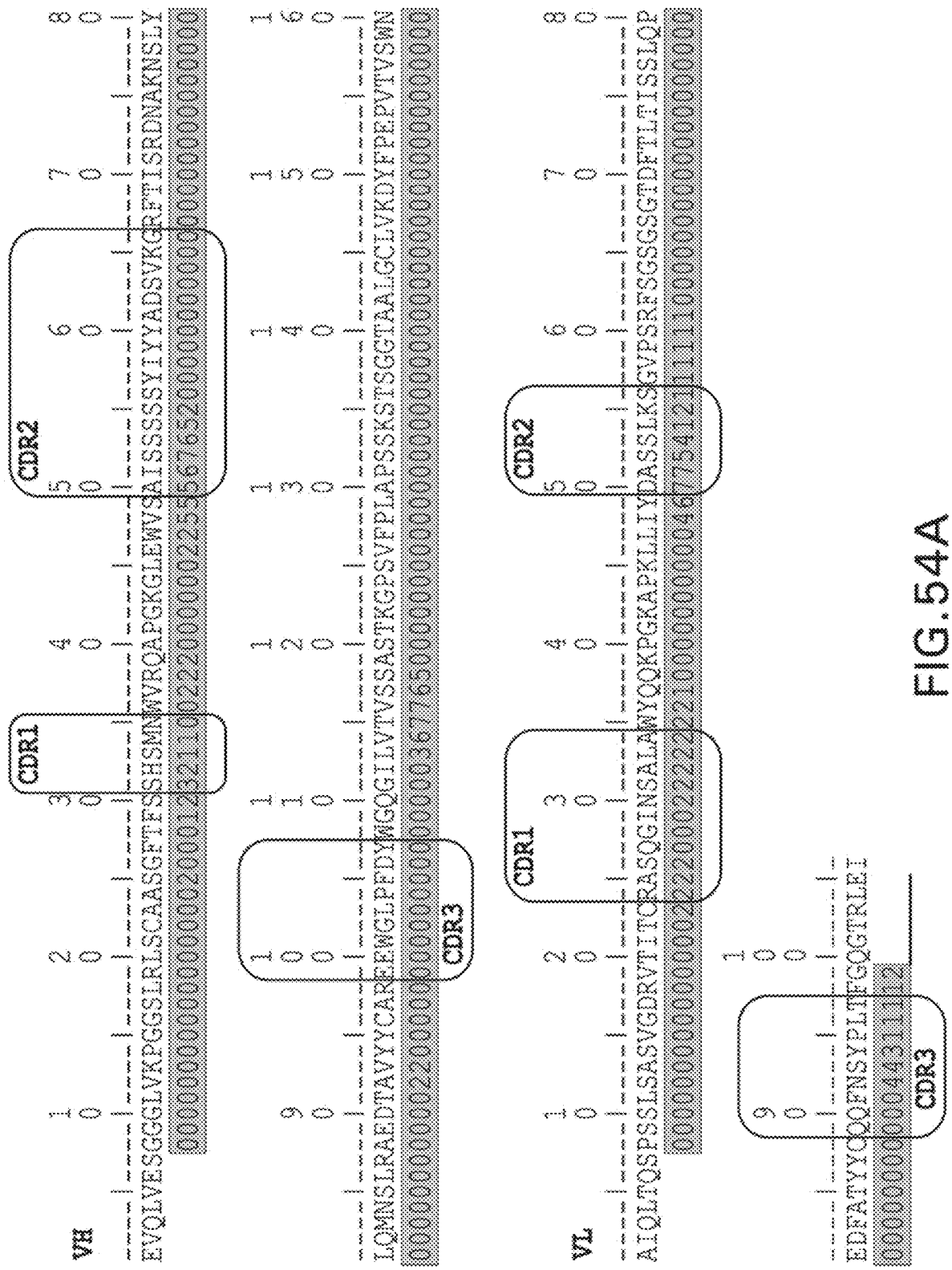

As shown in FIG. 54A, the 13F3.A4 antibody contains two HLA binding clusters; multiple peptides spanning the VH CDR 2 region and the VL CDR2 region were predicted to bind to up to 70% or 19/27 HLA call II DRB1 alleles (as denoted by the shaded numbers under the sequence in FIG. 54A). As discussed herein, a "binding cluster" is a region that shows a binder for 50% of the alleles; a shaded number 6 means that 60% of the alleles show binding and is, therefore, a "binding cluster."

Figures 54B, 54C:
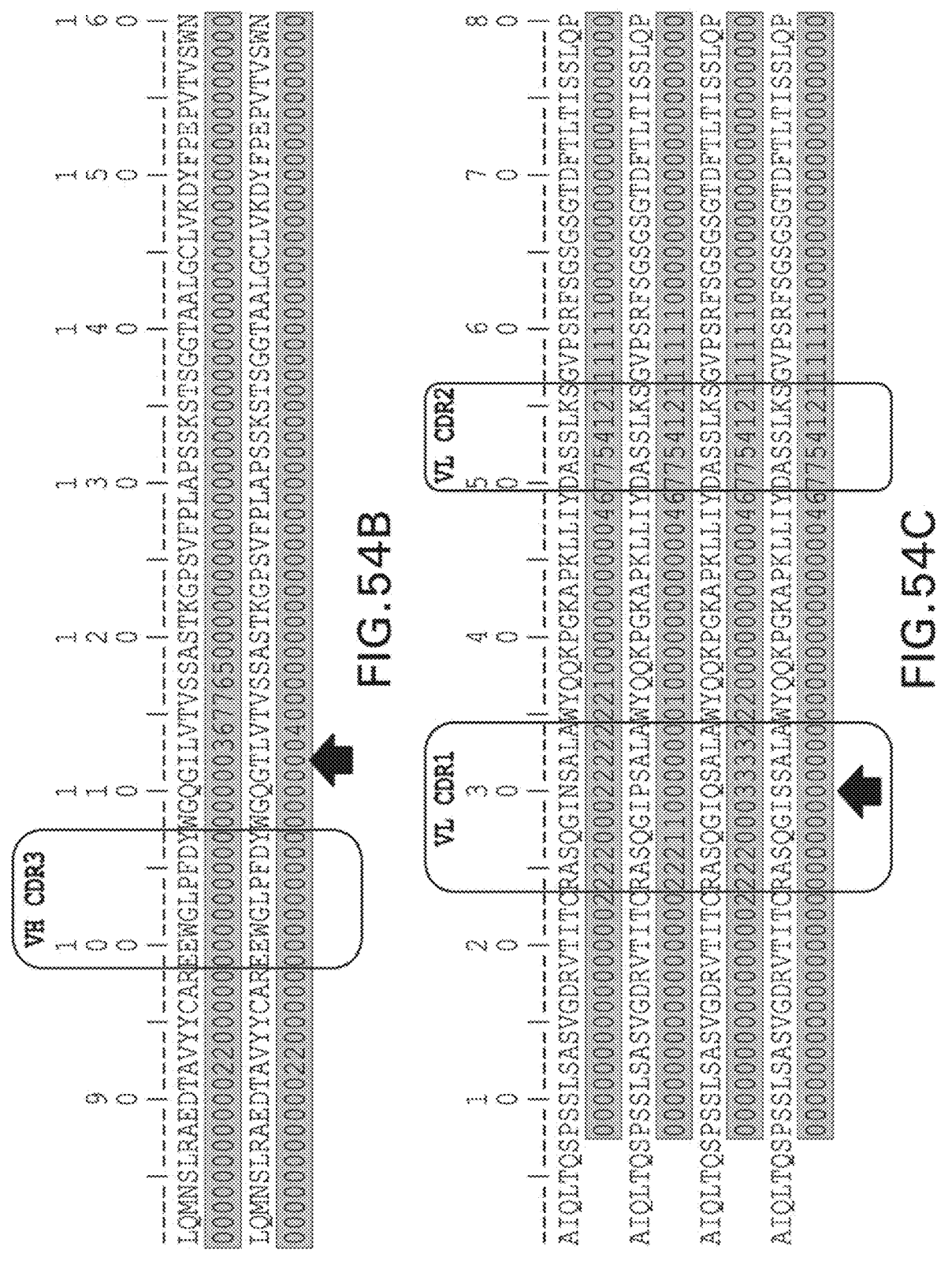

In addition, as shown in FIG. 54B and described herein, a VH-I107T framework reversion (that is, substituting isoleucine with threonine at position 107) removed a binding cluster from the 13F3.A4 antibody. This I107T substitution of the 13F3.A4 antibody was selected, such as isoleucine at position 107 was selected in the NKG2A.9 antibody (T a position 107 is shown by the arrow in the second row of FIG. 54B).

As shown in FIG. 54C and described herein, to engineer and minimize immunogenicity potential of the 13F3.A4 antibody, in the light chain CDR1 of the 13F3.A4 antibody, the asparagine (N) at the 30 position (first row of FIG. 54C) was engineered to a proline (P) (second row of FIG. 54c), glutamine (Q) (third row of FIG. 54C) or serine (S) (fourth row of FIG. 54C). The N30S substitution (as shown in the fourth row of FIG. 54C) was selected because it showed no HLA binding potential (as indicated by "0" in the shaded region). This N30S substitution of the 13F3.A4 antibody (N at position 30) was selected for inclusion in the NKG2A.9 antibody (S at position 30). In FIG. 54B-C, only certain portions of the sequences of the 13F3.A4 are shown for clarity.

2. Immunogenicity Risk of Anti-NKG2A Antibodies (NKG2A.6, NKG2A.9, and NKG2A.11) Was Low Based on In Vitro DC:T Cell Proliferation Assay Results After an HLA Class II molecule binds a peptide antigen, the next critical step in developing an immune response to a therapeutic antibody is the activation of CD4+ T cells. This T cell activation occurs as a result of the recognition of a cognate peptide-MHC complex (HLA) on an antigen presenting cell. T cell activation and proliferation (amongst multiple other factors) are required to develop an immune response. In vitro, peripheral blood mononuclear cell (PBMC)-based immunogenicity prediction assays using diverse donor sets are used to determine whether a molecule is potentially immunogenic by its ability to stimulate these specific, activated CD4+ T cells ex vivo.

An in vitro DC:T cell proliferation assay (see, e.g., methods described in Joubert M K, et al., PLOS ONE 11(8) (2016)) was conducted for several anti-human NKG2A antibodies (NKG2A.6, NKG2A.9, and NKG2A.11 antibodies) to further assess the human immunogenicity potential of these antibodies. Briefly, PBMCs from healthy volunteers were isolated by Ficoll (GE Healthcare). Gradient centrifugation and human lymphocyte antigen (HLA) Class II weres characterized using polymerase chain reaction (PCR) amplification and hybridization with oligonucleotide probes (Pro-Immune). A panel of 40 PBMC donors composed of HLA Class II types closely matching the world population frequencies was used for an assay run.

Monocytes isolated from PBMC using a negative bead based method (Intellicyt) were cultured in DC Media (Lonza) containing Il-4 and GM-CSF to generate immature dendritic cells (DC), pulsed with anti-human NKG2A antibodies (NKG2A.6, NKG2A.9, and NKG2A.11 antibodies) and quality control proteins for four hours followed by a two-day DC maturation step in media containing TNF-a, IL-1b, IL-6, and PGE2.

Pulsed DC were added to autologous PBMC-labeled with carboxyfluorescein succinimidyl ester (CFSE) (Invitrogen) to monitor proliferation and plated in 96-well plates in six replicates at 200,000 cells per well in DC media (Lonzo) containing pen-strep (Gibco) for seven days, after which media was washed away and cells were labeled with an anti-human CD4 APC (BD Biosciences) monoclonal antibodies. After removal of the unbound anti-CD4 monoclonal antibody cells with a wash step, cells were fixed with 3.7% formalin (Sigma,) in PBS analyzed by flow cytometry to determine the percentage of proliferating CD4+ T cells.

Figure 55:
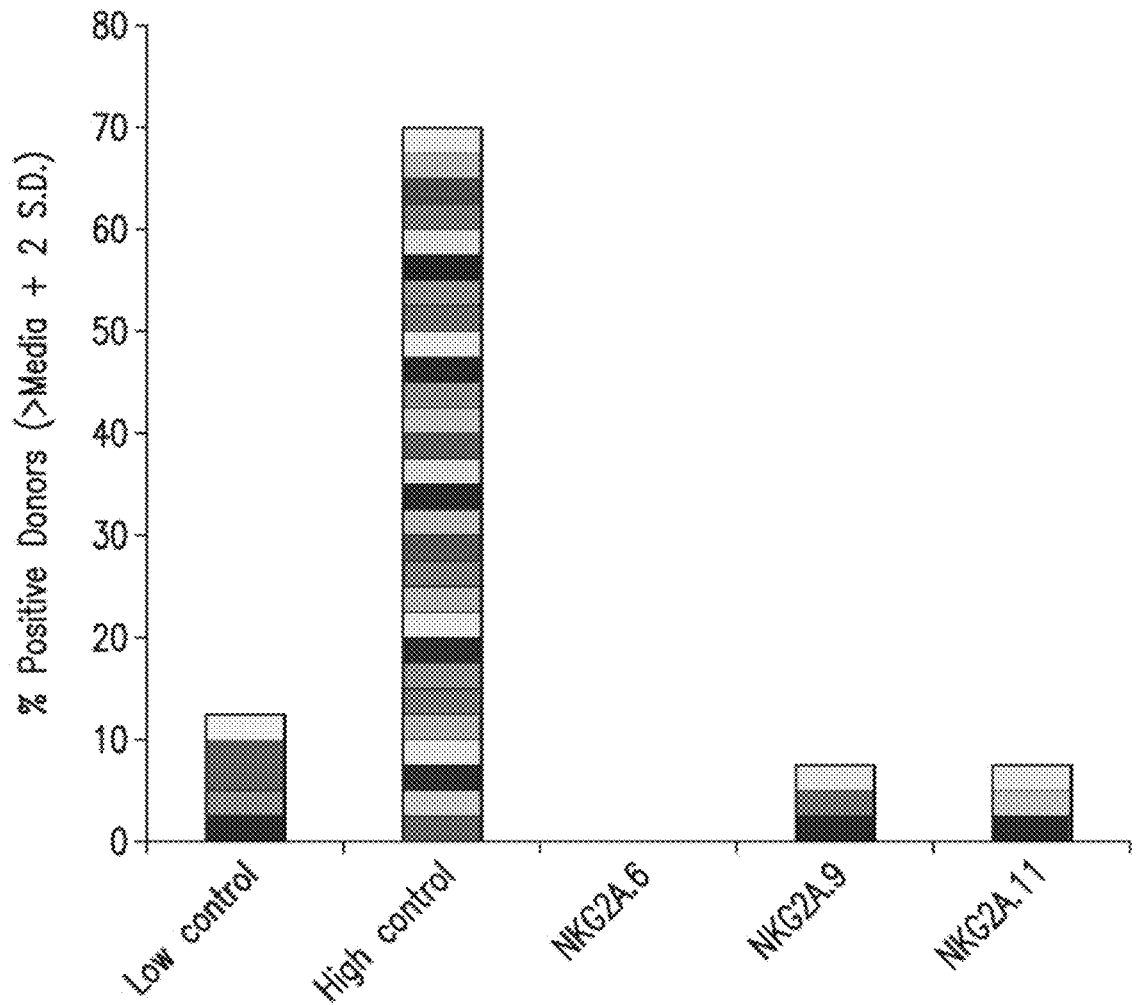
FIG. 55 show the results of an in vitro DC:T cell proliferation assay in demonstrating the low immunogenicity risk of anti-NKG2A antibodies, specifically, the NKG2A.6, NKG2A.9, and NKG2A.11 antibodies.

As shown in FIG. 55, NKG2A.9 produced CD4+ T cell proliferation response compared to media pulsed dendritic cells in only three out of 40 donors (7.5%) in this in vitro DC:T cell assay. This result was comparable to the 12.5% CD4+ proliferation for the control monoclonal antibody (bevacizumab), which has been demonstrated to have a very low immunogenicity in the clinic ("low control") (Saffari F., et al., Int J Cancer Manag.; 11(11)(2018)). The "high control" antibody (ATR-107) showed CD4+ proliferation in 70% of donors, and has been shown to have a high ADA rate of 76% in clinical studies (Hua, F., et al., The Journal of Clinical Pharmacology, 54: 14-22 (2014)).

NKG2A.11 also produced CD4+ proliferation response in only 3 out of 40 donors. The NKG2A.6 antibody did not produce CD4+ proliferative response in any donor. Repeatability data for the high and low control antibodies for this assay show a Coefficient of Variation % (CV %) of 5-10%. Therefore, none of these monoclonal antibodies are significantly differently in their low immunogenicity risk. To summarize, the risk of the NKG2A.6, NKG2A.9, and NKG2A.11 antibodies to elicit an undesirable immune response in humans against the antibodies was determined to be low based on in vitro DC:T cell proliferation assays.

Example 27

Single-Dose Intravenous Toxicokinetic, Tolerability, and Pharmacodynamics Study in Monkeys The NKG2A.9 antibody was well tolerated when given intravenously as a single dose to cynomolgus monkeys at 0.5 mg/kg, 10 mg/kg, and 50 mg/kg ($AUC_{0-42\ days} \leq 101$ µM·day), and no abnormalities were identified by clinical pathology.

Specifically, this study was conducted to determine the potential toxicity of the NKG2A.9 antibody when given intravenously as a single dose to monkeys (1) to determine the systemic exposure to NKG2A.9, and (2) to assess the pharmacodynamic response to NKG2A.9, after immunization with adenovirus serotype 5 (Ad5) vectors expressing simian immunodeficiency virus proteins gag and nef (Ad5-gag and Ad5-nef, respectively). The NKG2A.9 antibody was administered intravenously as a slow bolus injection at doses of 0 mg/kg (vehicle), 0.5 mg/kg, 10 mg/kg, or 50 mg/kg to groups of three protein-naive monkeys (1 or 2 per sex). Doses were administered at 0.25 mL/kg, 0.5 mL/kg, or 2.5 mL/kg in a vehicle/carrier of 20 mM histidine, 260 mM sucrose, pH 6.0. The 2 Ad5 vectors were administered intramuscularly in the posterior quadriceps or caudal thighs in 1 injection with approximately $3.3 \times 10^9$ viral particles at 0.5 mL. Criteria for evaluation included survival, toxicokinetics, clinical observations, body weights, clinical pathology evaluations, and immunotoxicological and pharmacodynamic assessments (anti-drug antibodies, peripheral blood lymphocyte phenotyping, natural killer and T-cell activation, ex vivo recall responses to Nef and Gag, antigen-specific T-cell phenotyping, and NKG2A receptor occupancy and receptor expression). The monkeys were observed throughout the six-week post-dose period, after which they were returned to stock.

The NKG2A.9 antibody AUC(0-T) and Cmax exposures increased in a dose proportional manner at the dose levels evaluated. After intravenous administration, the systemic exposures in males were comparable to those in females at all dose levels. Because there were no substantial sex differences in systemic exposure values, all results and conclusions were based upon sex-combined data. One out of nine monkeys given the NKG2A.9 antibody at 10 mg/kg developed anti-drug antibodies, and the same monkey affected by the anti-drug antibodies exhibited a more rapid decline in drug concentrations compared to other monkeys.

The toxicokinetic summary for the NKG2A.9 antibody is shown below:

| Toxicokinetic Summary - Mean Sex-combined Values | | | |
|---|---|---|---|
| | NKG2A.9 Antibody Dose | | |
| Parameter | 0.5 mg/kg | 10 mg/kg | 50 mg/kg |
| Cmax; µg/mL | 16.8 | 380 | 1,470 |
| AUC(0-1008 h); | 3,620 | 79,000 | 365,000 |

All animals survived and were returned to stock at the end of the study. The NGK2A.9 antibody was well tolerated at all doses with no effects on clinical observations, body weight, or clinical pathology. There were no NKG2A.9-mediated changes in percentages of peripheral blood T cells, helper T cells, cytotoxic T cells, B cells, NK cells, activated CD4+, CD8+, effector memory CD8+ T cells, or NK cell enriched lymphocytes. Ex vivo recall responses to gag and nef peptides were also not altered. Percentages of antigen-specific CD8+ T cells were not altered, although there was high variability across all doses.

At four hours following dosing on Day 1, group mean NKG2A receptor occupancy on NK cell enriched lymphocytes was 81%, 99%, and 100% relative to pretest at 0.5 mg/kg, 10 mg/kg, and 50 mg/kg NKG2A.9, respectively. By Day 43, for monkeys dosed with 0.5 mg/kg NKG2A.9, receptor occupancy decreased to a range from 21% to 45%; for monkeys dosed with 10 mg/kg NKG2A.9, receptor occupancy decreased to a range from 72% to 95%. By 4 hours after dosing on Day 1, group mean NKG2A receptor expression on NK cell enriched lymphocytes was 50%, 52%, and 58% relative to pretest at 0.5 mg/kg, 10 mg/kg, and 50 mg/kg NKG2A.9, respectively, which showed internalization or downregulation of the receptor following dosing with NKG2A.9. By Day 43, NKG2A receptor expression ranged from 65% to 80%, 47% to 99%, and 41% to 46% at 0.5 mg/kg, 10 mg/kg, and 50 mg/kg NKG2A.9 antibody, respectively.

logic) and ophthalmologic examinations, clinical pathology evaluations, immunophenotyping, natural killer (NK) cell activation, receptor expression (RE), receptor occupancy (RO), organ weights, and gross and microscopic pathology analyses. Scheduled necropsies were conducted after 1 month of weekly dosing—5 doses total—(3/sex/group) and following an 8-week recovery period (2/sex/group).

On Day 22, mean NKG2A.9 systemic exposures (AUC [0-168h]) increased dose proportionally between 10 mg/kg and 100 mg/kg. There were no substantial sex differences at any dose. Accumulation of NKG2A.9 was observed following repeated administration at all dose levels, with mean systemic exposures (MX[0-168h]) that were approximately 2.5-fold to 2.9-fold those on Day 1, The presence of treatment-emergent anti-drug/NKG2A.9 antibodies were detected in 1 of 10, 2 of 10, and 3 of 10 monkeys at 1 mg/kg (intravenous), 10 mg/kg (subcutaneous), or 100 (subcutaneous) mg/kg, respectively, on and/or after Day 8; these had no substantial impact on mean systemic exposures to NKG2A. 9

The toxicokinetic summary for the NKG2A.9 antibody is presented in the following table:

| | | NKG2A.9 Dose | | |
|---|---|---|---|---|
| Parameter[a] | Period | 1 mg/kg (Intravenous) | 10 mg/kg (Subcutaneous with 2000 U/mL rHuPH20) | 100 mg/kg (Subcutaneous with 2000 U/mL |
| Cmax (µg/mL) | Day 1 | 29.4 | 143 | 1,270 |
| | Day 22 | 49.3/49.9 | 416/372 | 3,120/3,100 |
| AUC(0-168 h) (µg · h/mL) | Day 1 | 1,960 | 19,200 | 170,000 |
| | Day 22 | 4,820/4,850 | 55,500/52,700 | 425,000/424,000 |

[a]Values were calculated with data from all available monkeys/only monkeys without detectable treatment-emergent anti-NKG2A.9 antibodies (ADAs), which were detected on and/or after Day 8 (i.e., 168 hours after dosing on Day 1).

In conclusion, the NKG2A.9 antibody was well tolerated by monkeys following a single intravenous administration at ≤50 mg/kg (mean sex-combined AUC[0-1008h]≤365,000 µg·h/mL). Receptor occupancy and reduced receptor expression were observed at all doses tested.

Example 28

One-Month Intermittent Dose Subcutaneous and Intravenous Toxicity Study In Cynomolgus Monkeys A one-month study was conducted to determine the potential toxicity of the NKG2A.9 antibody when administered to cynomolgus monkeys once weekly for one month (1) to evaluate the potential reversibility of any findings, (2) to determine systemic exposure to NKG2A.9, and (3) to provide data to support use of NKG2A.9 in humans. NKG2A.9 was administered by subcutaneous injection at doses of 0 mg/kg (vehicle), 10 mg/kg or 100 mg/kg to three groups of five monkeys/sex/group. Formulations for the subcutaneous doses of 10 mg/kg or 100 mg/kg NKG2A.9 included 2000 U/mL rHuPH20. In addition, NKG2A.9 was administered by intravenous injection (slow bolus) at a dose of 1 mg/kg to a single group of five monkeys/sex. All doses were administered at 2 mL/kg in a vehicle of 20 mM histidine, 250 mM sucrose, 0.05 mM diethvlenetriamine pentaacetic acid (DTPA), and 0.05% (w/v) polysorbate-80 (PS-80), pH 6.

Criteria for evaluation included survival, toxicokinetics, clinical observations, body weights, visual food consumption estimates, physical (including respiratory and neuro- There were no NKG2A.9-related mortalities; all monkeys survived to their scheduled necropsies. NKG2A.9 was well tolerated at all doses with no effects on clinical observations, body weight, visual food consumption estimates, cardiovascular, neurological, ophthalmologic, clinical pathology, or histopathologic parameters.

There were no NKG2A.9-related changes in T cell (total T, helper T, or cytotoxic T), B cell, or NK cell numbers or activation of NK cell-enriched peripheral blood cell populations.

Dose-dependent receptor occupancy (RO) on NK cells was observed, (84%, 95%, and 100% at 1 mg/kg, 10 mg/kg, and 100 mg/kg NKG2A.9, respectively), four hours after the first dose. Thereafter, at all timepoints through Day 29, the group mean RO range was 72% to 84% and 94% to 98% at 1 mg/kg and 10 mg/kg, respectively, with maximal (100%) RC) at 100 mg/kg. While RO was complete and sustained throughout the recovery phase (through Day 85) at 100 mg/kg, partial loss of RO was observed at 1 mg/kg and 10 mg/kg. At 1 mg/kg, partial loss of RO was observed from Day 71 through Day 85 (Group mean RO of 39%), which correlated with a drop in serum NKG2A.9 concentrations below 4 µg/mL. At 10 mg/kg, partial loss of occupancy was observed on Day 85 (Group mean RO of 74%), which correlated with a drop in serum NKG2A.9concentrations below 50 µg/mL.

Engagement of NKG2 by NKG2A.9 is known to result in partial down regul an on as a consequence of receptor internalization. There was a non-dose-dependent reduction of NKG2 RE on NK cells during the dosing phase (overall range of 36 to 75% of pretest values across all doses) with minimal recovery during the recovery phase at 1 mg/kg, and no recovery at 10 mg/kg or 100 mg/kg.

In conclusion, NKG2A.9 was well tolerated by cynomolgus monkeys for one month at ≤100 mg/kg/week (mean AUC≤425,000 μg·h/mL) with evidence of robust target engagement at all doses. NKG2A.9-mediated in vivo blockade of NK cell NKG2A/HLA-E interaction in cynomolgus monkeys did not induce immune cell activation, suggesting the lack of, or minimal contribution of the NKG2A pathway in the context of a disease-free, physiological setting. Based on the tolerability and lack of anatomic or clinical pathology findings, the no-observed-adverse-effect level (NOAEL) was considered to be 100 mg/kg, which is also considered the highest non severely toxic dose (HNSTD).

Example 29

Immunohistochemical Analysis of NKG2A Expression in Tumors

We believe that the activity of the NKG2A.9 antibody reduces the inhibitory activity of NKG2A and leads to enhanced cytotoxicity at the tumor site. Consequently, criteria for tumor prioritization includes the expression of NKG2A and HLA-E.

Figure 45:
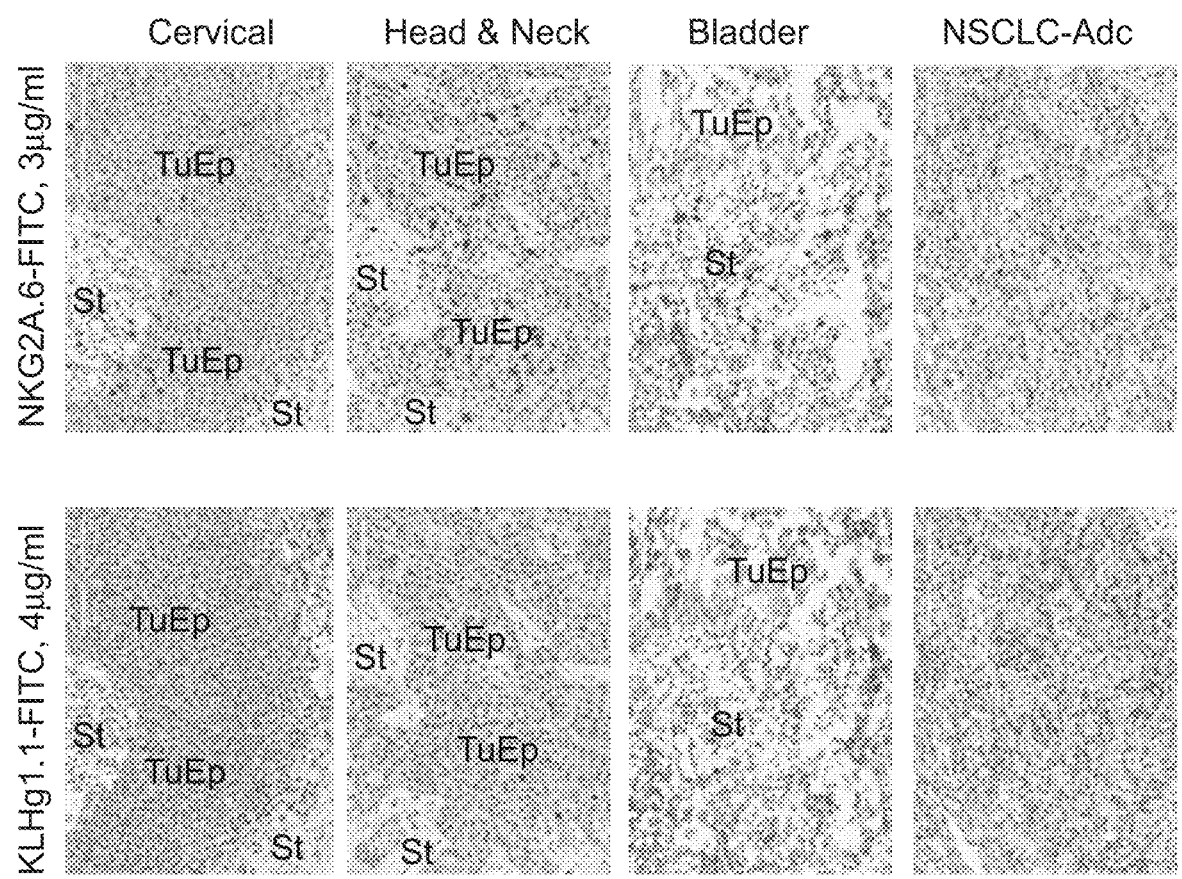
FIG. 45 shows the results of NKG2A expression as evaluated by immunohistochemistry on different tumor types.

To identify potential tumor indications, preliminary profiling of NKG2A in selected tumor types was assessed with FITC-conjugated NKG2A.6 (the parent clone of the NKG2A.9 antibody) on frozen sections. NKG2A was present in a small fraction of mononuclear cells and primarily distributed in the tumor stroma, as shown in FIG. 45. FIG. 45 shows representative examples of NKG2A staining in commercially procured human tumor samples stained with FITC-conjugated NKG2A.6 antibody and negative control reagent (anti-KLH human IgG1.1-FITC). In FIG. 45, "Cervical" indicates cervical carcinoma; "head & neck" indicates head and neck squamous cell carcinoma; "bladder" indicates bladder carcinoma; and NSCLC-Adc indicates non-small cell lung cancer, adenocarcinoma. "St" are tumor stroma, and "TuEp" are tumor epithelial cells.

Figure 46:
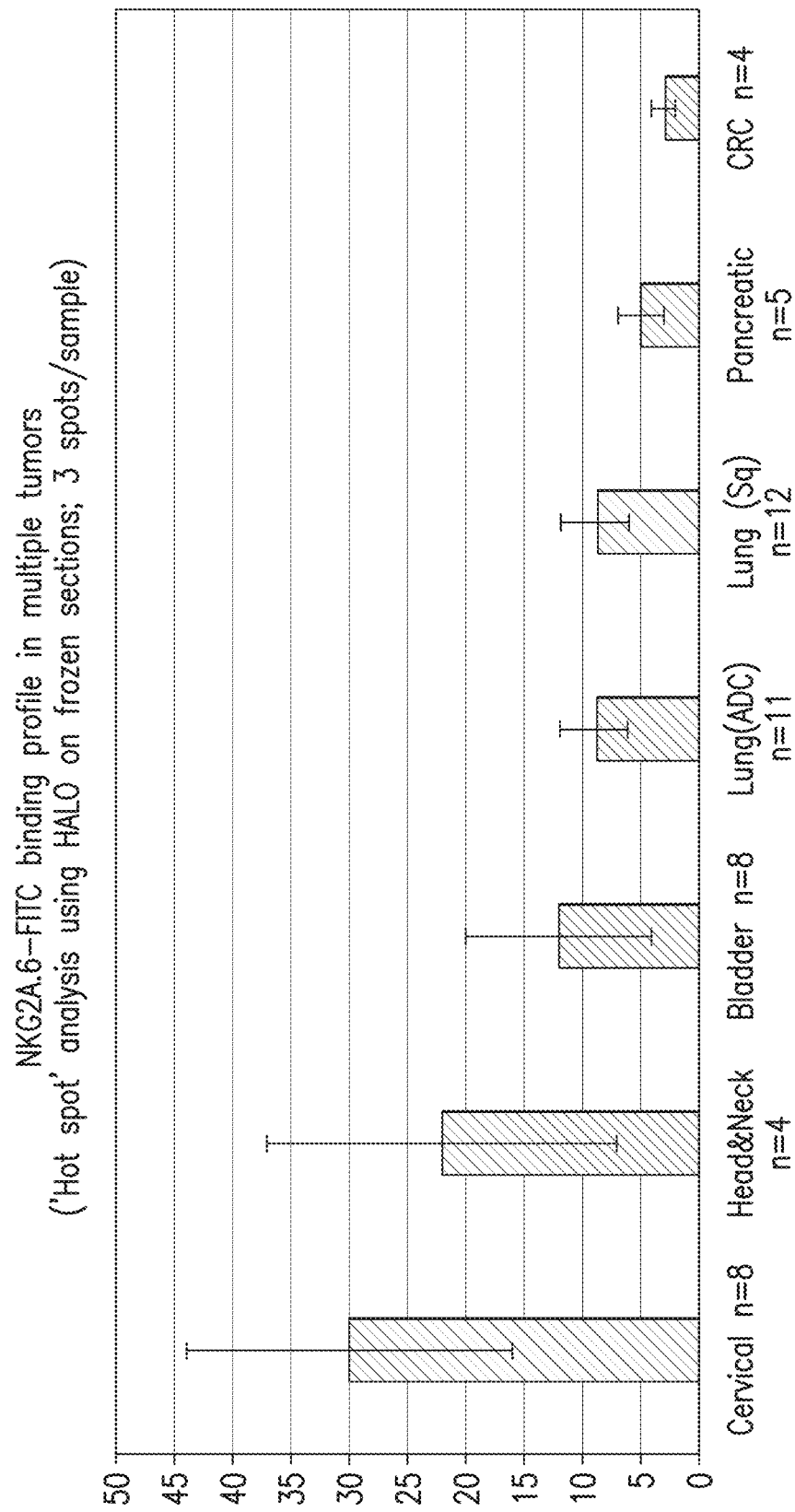
FIG. 46 shows the binding profile of the FITC-conjugated NKG2A.6 antibody in multiple tumors.

Image analysis of NKG2A expression by immunohistochemistry on frozen tumor sections was performed. "Hot spot" image analysis using HALO™ software was performed on three spots per sample. Staining with isotype control was substracted from staining with the FITC-conjugated NKG2A.6 antibody. This image analysis revealed a relatively high abundance of NKG2A expression in cervical and head and neck carcinomas, moderate expression in bladder and non-small cell lung carcinomas, and low expression in pancreatic and colorectal carcinomas, as shown in FIG. 46. FIG. 46 shows NKG2A expression levels across different tumor types. The Y-axis represents the number of positive cells per 1.15 mm² spot, and the results are shown as means plus standard error.

Example 30

Immunohistochemical Analysis of HLA-E Expression in 7 Tumor Types

Figure 47:
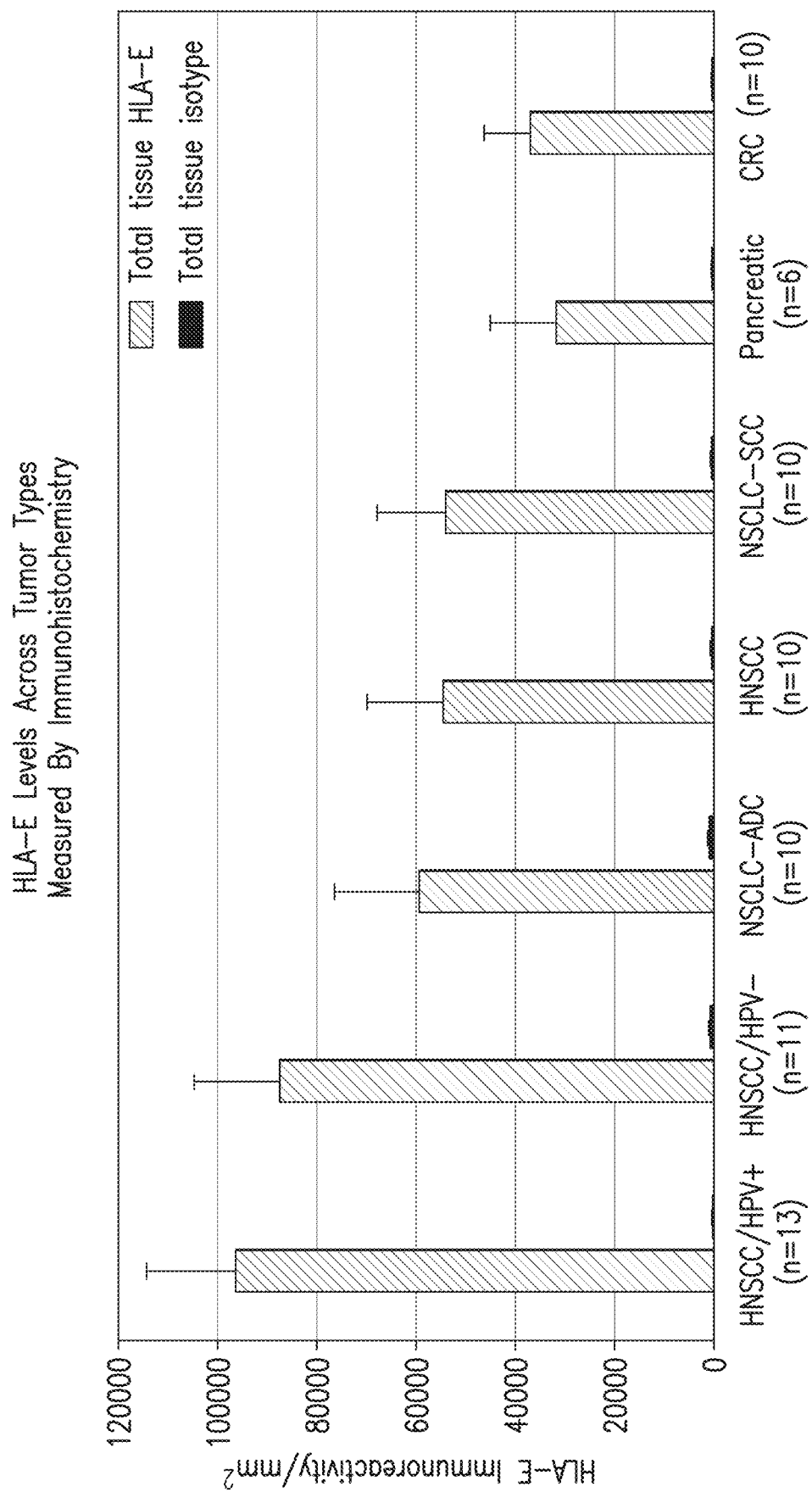
FIG. 47 shows the results of HLA-E expression in 7 different tumor types as evaluated by immunohistochemistry.

To evaluate HLA-E expression, a commercial anti-HLA-E antibody (clone MEM-E/02) was validated for immunohistochemistry in formalin-fixed paraffin-embedded (FFPE) tissues. HLA-E was broadly expressed in tumor samples examined. Positive staining was observed in both tumor epithelium and stroma. Whole slide image analysis using HALO™ software revealed a relatively higher abundance of HLA-E in HNSCC and NSCLC, and a lower abundance in pancreatic carcinoma and colorectal cancer (CRC), as shown in FIG. 47. FIG. 47 shows the results of whole slide image analysis of HLA-E expression using HALO software in 13 HPV+ head and neck squamous cell carcinoma (NNSCC/HPV+), 11 HPV− head and neck squamous cell carcinoma (HNSCC/HPV−), 10 non-small cell lung adenocarcinoma (NSCLC-ADC), 10 HNSCC, 10 non-small cell lung squamous cell carcinoma (NSCLC-SCC), 6 pancreatic carcinoma, and 10 colon carcinoma (CRC) samples. Immunoreactivity of HLA-E was calculated as follows: total area of 'brown' x average OD of 'brown'/total area of tissue. Data was normalized to mm². The results are shown as means plus standard error.

Figure 48:
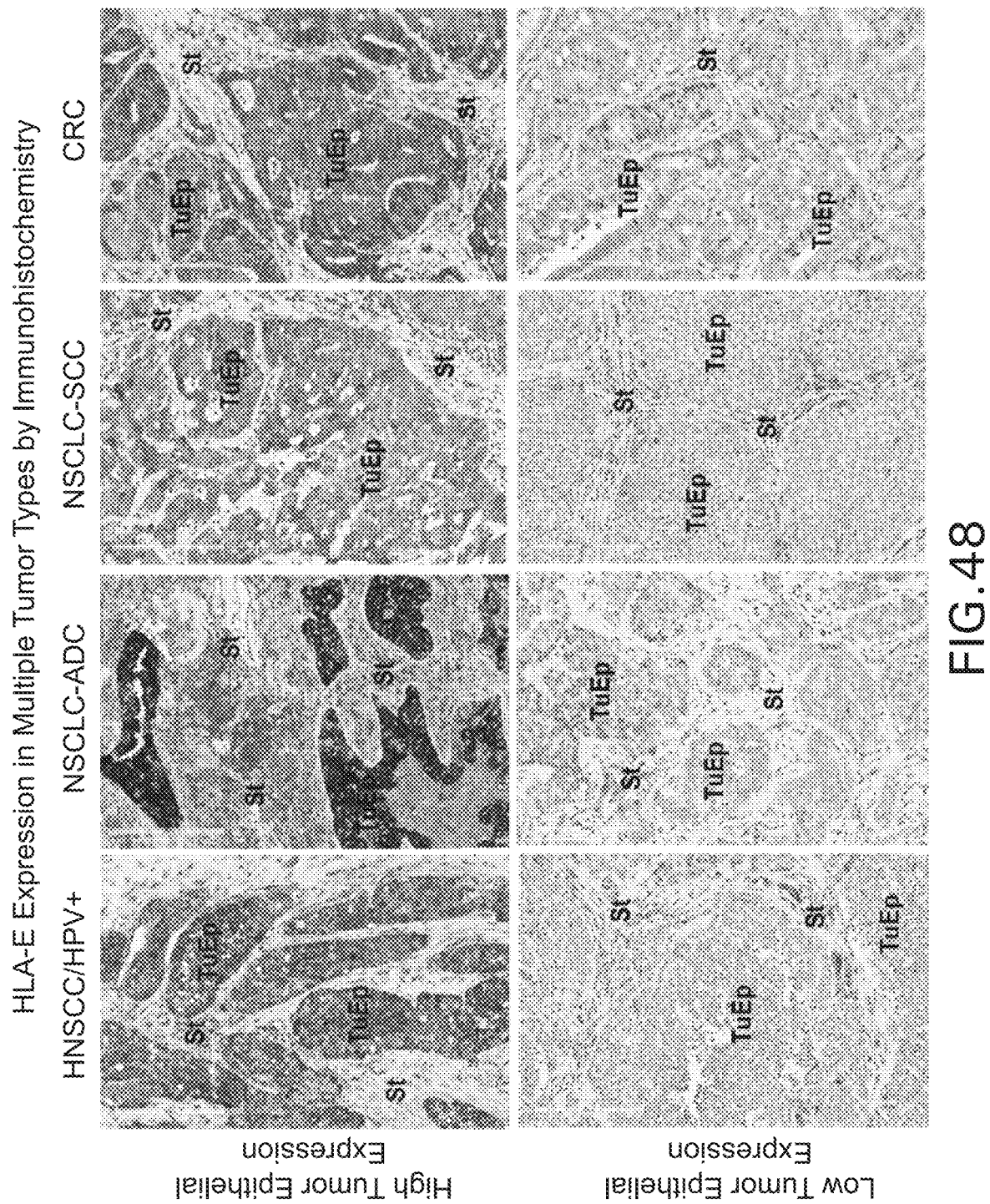
FIG. 48 shows representative images of HLA-E expression in different tumor types as evaluated by immunohistochemistry.

In tumor epithelial cells, the positive staining was primarily cytoplasmic. Notable membrane staining was also exhibited in some tumor cells. In tumor stroma, positive staining was primarily distributed in mononuclear cells and subsets of interstitial cells, as well as occasionally in microvasculature and neutrophils in some cases. In general, HLA-E expression in stroma was present in almost all cases. However, the expression in tumor epithelial cells varied significantly from sample to sample in all tumor types examined. High-level tumor epithelial expression was seen in most cases, while negative or very low expression was seen in small number of cases, as shown in FIG. 48. In FIG. 48, "St" are tumor stroma, and "TuEp" are tumor epithelial cells. FIG. 48 shows representative images of HLA-E expression in multiple tumors. Immunohistochemistry with a validated commercial monoclonal antibody on FFPE sections from HPV+ head and neck squamous cell carcinoma (NNSCC/HPV+), non-small cell lung adenocarcinoma (NSCLC-ADC), non-small cell squamous cell carcinoma (NSCLC-SCC), and colon carcinoma (CRC).

Patients with virus-derived tumors: Viral infections can induce NKG2A expression on NK cells, as was observed in hepatitis C chronically infected patients. (Harrison R J et al., "Association of NKG2A with treatment for chronic hepatitis C virus infection." *Clin Exp Immuno* 161:306-14 (2010)). In addition, the frequency of NKG2A+ CD8 T cells was shown to be higher in TIL from patients with HPV-16+ head and neck carcinomas, compared to HPV-16 tumors. (van Hall T, et al. "NKG2A checkpoint receptor expression on tumor-infiltrating CD8+ T cells restrains efficacy of immunotherapy." *Cancer Res Supplement*; Abstract 2999 (2017)). We evaluated an association between HPV status in head and neck tumors and expression of the NKG2A/HLA-E pathway by measuring HLA-E expression by IHC between biopsies from HPV+ and HPV− head and neck tumors. Our initial assessment in a relatively small number of samples showed that HLA-E expression by IHC was not significantly different between HPV+ and HPV− samples, as shown in FIG. 48. We will test HPV status in head and neck tumors and expression of the NKG2A/HLA-E pathway by measuring CD8 (as a surrogate for NKG2A expression) and HLA-E expression by IHC between biopsies from HPV+ and HPV− head and neck tumors. We also continued the IHC analysis with additional tumor types and larger sample sizes, and this analysis is described in Example 31 below.

Example 31

Immunohistochemical Analysis of HLA-E Expression in 17 Tumor Types

We profiled HLA-E expression across 17 tumor types by immunohistochemical (IHC) assessment. We believe that cancer patients are most likely to respond to anti-tumor treatment with the anti-NKG2A antibodies described herein for tumor types that express higher levels of HLA-E.

To assess HLA-E expression, immunohistochemistry (IHC) was performed on formalin-fixed paraffin-embedded (FFPE) sections from 17 tumor types/subtypes, including cervical, bladder, breast, colorectal adenocarcinoma (CRC), endometrial, head & neck squamous cell carcinoma (HN-SCC), gastric, glioblastoma (GBM), melanoma, non-Hodgkin lymphoma (follicular lymphoma), ovarian, renal cell (RCC), pancreatic, prostate, small cell lung carcinoma (SCLC), non-small cell lung adenocarcinoma (NSCLC-AD), and non-small cell lung squamous cell carcinoma (NSCLC-SQC), with well-characterized commercial monoclonal antibody (clone MEM/02). There were 14 to 43 samples per tumor type/subtype. Stained slides were evaluated by the study pathologists to identify the tissue or cell type. All slides were judged for adequacy of tissue elements and staining. A conventional/manual scoring was performed by study pathologists.

Figure 57:
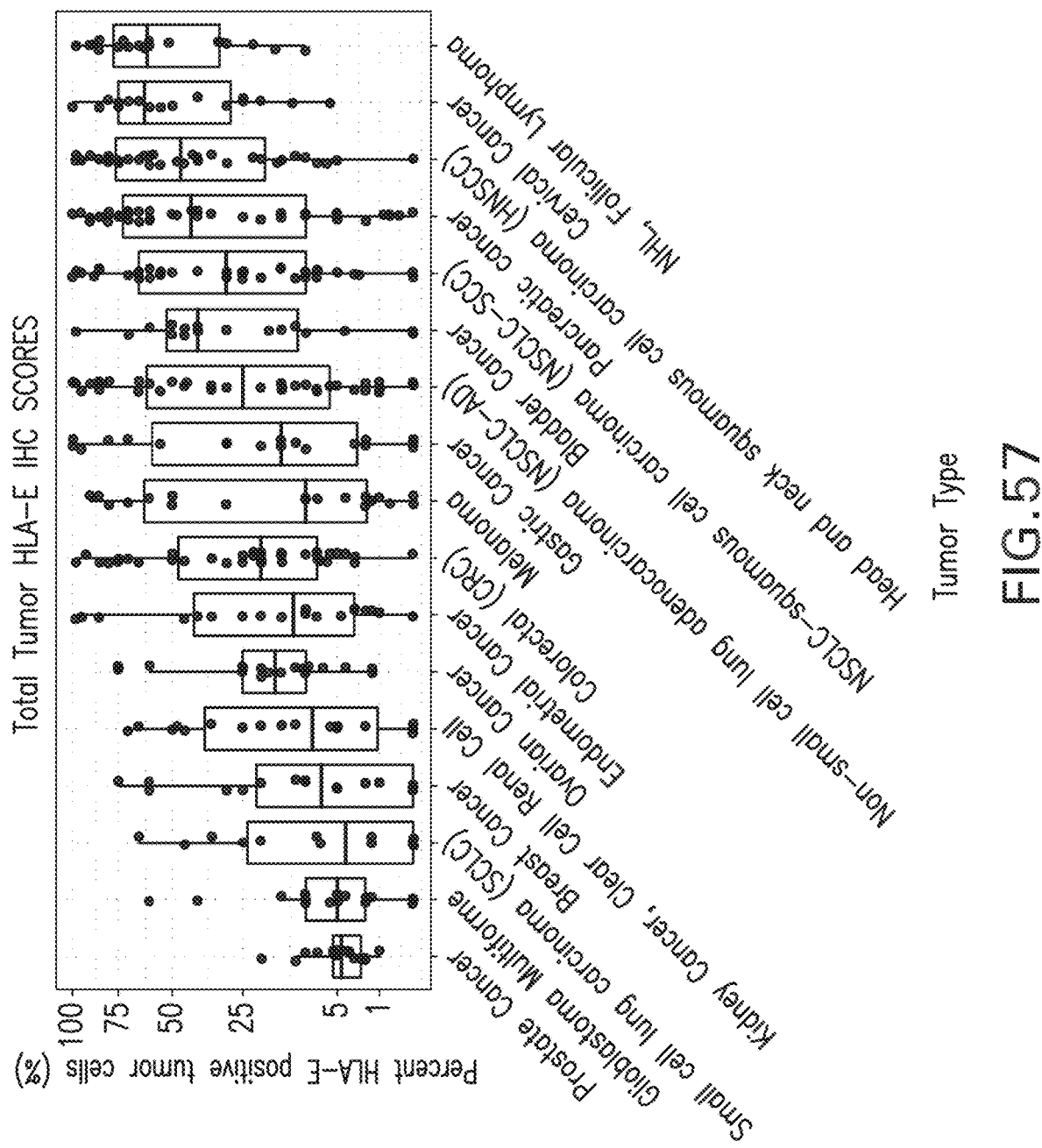
FIG. 57 shows a boxplot of total HLA-E positivity score across 16 different tumor types as evaluated by immunohistochemistry. Total HLA-E score is defined as percent of combined cytoplasmic and/or membrane HLA-E positivity in the tumor cells.

The results showed that HLA-E expression was observed in the tumor cell, immune, and endothelial cell compartments across various indications. In tumor cells, positive staining was predominantly cytoplasmic across human tumor types with limited expression noted at the surface plasma membrane. Total HLA-E expression ranged from diffuse tumor cell positivity to heterogeneous expression to some cases with low to almost no HLA-E expression. FIG. 57 shows a boxplot of total HLA-E positivity score across 17 different tumor types as evaluated by immunohistochemistry. Total HLA-E score is defined as percent of combined cytoplasmic and/or membrane HLA-E positivity in the tumor cells. The data used to generate FIG. 57 is shown in the Table below.

In conclusion, there was a dynamic range of total HLA-E expression across and within the tumor indications. We believe that cancer patients with high HLA-E expression in tumor cells are more likely to respond to anti-tumor treatment with the anti-NKG2A antibodies described herein. Non-Hodgkin lymphoma (follicular lymphoma), cervical, HNSCC, pancreatic, NSCLC, and bladder tumors had the highest level of total HLA-E expression; thus, patients with these cancers have the highest likelihood of responding to anti-tumor treatment with the anti-NKG2A antibodies described herein. This study provided tumor profiling data to support the prioritization of indication selection to include, for example, HNSCC, RCC, NSCLC, and CRC cancers in clinical development.

Prostate, GBM, and SCLC demonstrated the lowest level of HLA-E expression. Nevertheless, we believe that patients with tumor types that have lower HLA-E expression will also respond to anti-tumor treatment with the anti-NKG2A antibodies described herein. This study is described in more detail below.

Materials and Methods

Tissue Samples

Overall, 17 cancer types/subtypes from two sets of samples were studied. Full size FFPE slides of 6 tumor types/subtypes, including colorectal adenocarcinoma (CRC), head and neck squamous cell carcinoma (HNSCC), non-small cell lung adenocarcinoma (NSCLC-AD), non-small cell lung squamous cell carcinoma (NSCLC-SQC), pancreatic carcinoma, and small cell lung carcinoma (SCLC), with 14-24 samples per tumor type, were studied. FFPE tissue samples were obtained from various commer-

| Tumor Type | Samples (N) | Total Tumor HLA-E Positive Score[1] | Total Tumor HLA-E Positive Percentage[2] | Mean | Median | Standard Deviation | 25$^{th}$ Percentile | 75$^{th}$ Percentile |
|---|---|---|---|---|---|---|---|---|
| Bladder Cancer | 20 | 17 | 85% | 37.3 | 40.0 | 30.4 | 11.5 | 52.5 |
| Breast Cancer | 20 | 14 | 70% | 16.3 | 7.5 | 22.9 | 0 | 21.25 |
| Glioblastoma Multiforme | 19 | 16 | 84.21% | 9.9 | 5.0 | 15.1 | 2 | 10 |
| Gastric Cancer | 20 | 17 | 85% | 32.7 | 15.0 | 36.4 | 2.75 | 58.75 |
| Kidney Cancer, Clear Cell Renal Cell | 20 | 15 | 75% | 20.4 | 9.0 | 23.4 | 1.5 | 37.5 |
| NSCLC-AD | 40 | 38 | 95% | 35.8 | 25.0 | 33.6 | 6 | 61.25 |
| NSCLC-SCC | 40 | 37 | 92.50% | 39.1 | 30.0 | 32.0 | 10 | 65 |
| Melanoma | 20 | 18 | 90% | 32.0 | 10.0 | 35.0 | 1.88 | 62.5 |
| Endometrial Cancer | 20 | 19 | 95% | 27.3 | 12.5 | 31.9 | 3 | 41.25 |
| Ovarian Cancer | 20 | 20 | 100% | 25.0 | 16.5 | 25.0 | 9.88 | 25 |
| CRC | 39 | 38 | 97.44% | 30.2 | 20.0 | 28.7 | 8 | 47.5 |
| NHL, Follicular Lymphoma | 20 | 20 | 100% | 58.3 | 61.3 | 26.3 | 32.38 | 77.5 |
| HNSCC | 40 | 39 | 97.50% | 48.7 | 46.5 | 30.9 | 19 | 76.25 |
| Prostate Cancer | 20 | 20 | 100% | 5.4 | 4.5 | 4.4 | 2.38 | 5.5 |
| Cervical Cancer | 20 | 20 | 100% | 54.7 | 62.5 | 27.2 | 28.75 | 75 |
| Pancreatic | 43 | 41 | 95.35% | 44.1 | 42.5 | 33.7 | 10 | 72.5 |
| SCLC | 14 | 9 | 64.29% | 14.9 | 4.5 | 20.6 | 0 | 23.75 |

[1]To calculate the "Total Tumor HLA-E Positive score," a 1% cutoff on the HLA-E values was used. In other words, if greater than or equal to 1% of the tumors were HLA-E positive (cytoplasmic and/or membrane HLA-E), then the sample was labeled as "positive."
[2]"Total tumor HLA-E positive percentage" is the percentage of HLA-E positive patients in the tumor type.

In FIG. 57, each of the boxes in the boxplots show the total tumor HLA-E positive value at the 25$^{th}$ percentile; the middle line of each of the boxes is the median value; and the upper limit of each of the boxes show the value at the 75$^{th}$ percentile.

cial tissue vendors (BioIVT, Detroit, Mich.; BioChain Institute Inc. Newark, Calif.; Conversant Biologics Inc, Huntsville, Ala.; Cooperative Human Tissue Network, Philadelphia, Pa.; Indivumed GmbH, Lewisburg, Pa.; The MT Group Inc. Van Nuys, Calif.; TriStar Technology Group LLC, Rockville, Md.). In addition, multi-tumor blocks (MTBs) containing 16 tumor types/subtypes including bladder, breast, GBM, gastric, RCC, NSCLC-AD, NSCLC-SQC, melanoma, endometrial, ovarian, CRC, HNSCC, prostate, cervical, pancreatic carcinoma, and non-Hodgkin lymphoma (follicular lymphoma), with 20 cases/tumor types, were studied. Each MTB contained 5 cases of a single indication per FFPE block and 1 hyperplastic tonsil as positive control. The MTBs were made by Folio Biosciences (now Discovery Life Sciences) for BMS.

Antibodies and Reagents
  Mouse monoclonal antibody anti-human HLA-E, Clone MEM/02 (Abcam, Cambridge, Mass., Catalog ab2216, Lot GR251472-15)
  Mouse IgG1 Isotype, Clone 11711 (R&D Systems, Minneapolis, Minn., Catalog MAB002, Lot IX2415091)
  Bond Polymer Refine Detection (Leica Biosystems, Buffalo Grove, Ill., Catalog DS9800, Lot 46396 and 46794)
  Bond Epitope Retrieval 2 (Leica Biosystems, Buffalo Grove, Ill., Catalog AR9640, Lot ER20180)
  Protein Block, Serum-Free (Agilent Technologies, Santa Clara, Calif., Catalog X0909, Lot 10117172) Human gamma globulin (Sigma-Aldrich, St. Louis, Mo., Catalog G-4386, Lot SLV M0524V)

IHC Methods FFPE sections at 4 µm were prepared, paraffin dipped and stored at 4° C. until use. For MTBs, 4 µm sections were cut and stored at 4° C. in vacuum sealed bags until use. All IHC assays including respective isotype controls were optimized for automated IHC using the Leica BondRX platform. FFPE sections from the same hyperplastic human tonsil tissue block were used as positive controls for all IHC runs.

For immunostaining, FFPE slides were baked, deparaffinized in xylenes, and rehydrated through a graded ethanol series following routine histology procedures. Antigen retrieval was performed on the Leica Bond RX instrument. Automated IHC staining procedures were carried out at room temperature on the Leica Bond RX. Briefly, slides were blocked in peroxidase block for 10 minutes followed by non-specific protein block for 20 minutes. Primary antibodies were incubated for 60 minutes followed by Refine Linker for 30 minutes. Slides were then incubated with Refine Polymer for 30 minutes. Finally, slides were reacted with the DAB substrate-chromogen solution for 6 minutes, counterstained for 8 minutes with Leica Hematoxylin, and then dehydrated, cleared, and coverslipped with Permount following routine histological procedure.

After immunostaining, all slides were scanned at 20× using the Aperio AT2 whole slide scanner (Leica Biosystems Imaging, Vista, Calif.), and the images were stored and organized with the Aperio eSlide Manager Software.

Pathology Assessment and Manual Scoring Methods

The study pathologist evaluated the slides to determine tissue adequacy and staining quality. The study pathologist manually scored the HLA-E IHC stained slides and reviewed isotype and positive control slides. Pathology assessment consisted of H&E evaluation to determine the tumor content and confirm tumor type. HLA-E immunohistochemistry (IHC) stained slides were scored manually using whole slide scanned images for tumor and immune cell positivity. No background staining was observed in the isotype control slides. HLA-E expression in tumor cells (TC), immune cells (IC) and endothelial cells were evaluated. Percentage of cytoplasmic HLA-E and membrane HLA-E were recorded. The total HLA-E score was the key reportable data for HLA-E expression, which is composed of combined cytoplasmic and/or membrane HLA-E positivity in the tumor cells, and was reported as percent HLA-E positive of total tumor cells. The percent HLA-E immune cell positivity along with predominant geographical location of HLA-E positive immune cells and endothelium were also assessed.

Results

HLA-E was diffusely positive in hyperplastic tonsil. HLA-E membranous/cytoplasmic staining was noted within the crypt epithelium, germinal centers, and interfollicular zones with strongest intensity in the mantle zones. In the tumor tissues, specific HLA-E expression was observed in tumor cells, immune cells, and endothelial cells. Cytoplasmic and membranous localization of HLA-E were noted within the tumor cells across indications and exhibited a dynamic range of intensity ranging from weak (1+ intensity) to strong (3+ intensity). HLA-E expression was predominantly cytoplasmic across human tumor types with limited expression noted at the plasma membrane. Total HLA-E expression ranged from diffuse tumor cell positivity to heterogeneous expression to some cases with low to very low HLA-E expression. Cervical, HNSCC, pancreatic, NSCLC, bladder, and non-Hodgkin lymphoma tumors had the highest level of total HLA-E expression with prostate, GBM and SCLC being the lowest, as shown in FIG. 59. RCC had the highest level of expression of membranous HLA-E among tumor types examined, although the total HLA-E level was relatively low.

Conclusion

In conclusion, the data showed a dynamic range of expression of total HLA-E across and within various tumor indications. Cervical, HNSCC, pancreatic, NSCLC, and bladder tumors had the highest level of total HLA-E expression, while prostate, GBM and SCLC demonstrated the lowest frequency of expression. This study provided tumor profiling data to support the prioritization of indication selection to include, for example, HNSCC, RCC, NSCLC, and CRC cancers in the clinical development of anti-NKG2A antibodies described herein. In some embodiments, we believe that patients with tumor types that have lower HLA-E expression will also respond to anti-tumor treatment with the anti-NKG2A antibodies described herein.

Example 32

Patients with High Serum Levels of soluble HLA-E

Cancer patients with melanoma show greater titers of soluble HLA-E in their serum compared to healthy donors. (Allard M et al., "Serum soluble HLA-E in melanoma: a new potential immune-related marker in cancer," PLoS One, 6:e21118 (2011)).

Recent data from a nivolumab clinical trial in patients with NSCLC (Checkmate 063) suggest that patients with high sHLA-E have a lower response rate to nivolumab. (Rebmann V et al., "Soluble HLA-G and -E (sHLA-G/E) as potential biomarkers of clinical outcomes in patients (pts) with advanced, refractory squamous (SQ) NSCLC treated with nivolumab (NIVO): CheckMate 063", Cancer Res; AM2017-CT126 (2017)).

We believe that patients with a high level of HLA-E expression in tumors are more likely to benefit from treatment with the anti-NKG2A antibodies described herein, including the NKG2A.9 antibody, either alone or in combination with, for example, nivolumab. In some embodiments, a healthcare provider selects patients with a specific level of HLA-E, such as soluble HLA-E, for treatment with the anti-NKG2A.9 antibodies described herein. In other embodiments, a healthcare provider selects patients with a specific level of CD8+ expression (as a surrogate for NKG2A expression) for treatment with the anti-NKG2A.9 antibodies described herein.

Figure 49A:
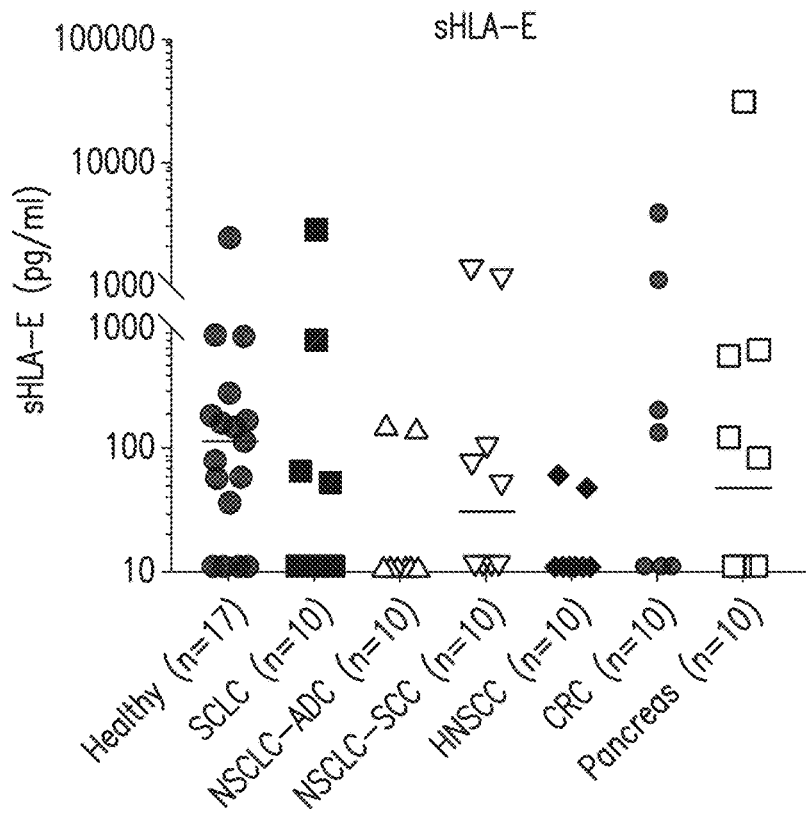
FIG. 49A-B show levels of soluble HLA-E levels across healthy control patients and cancer patients.
Figure 49B:
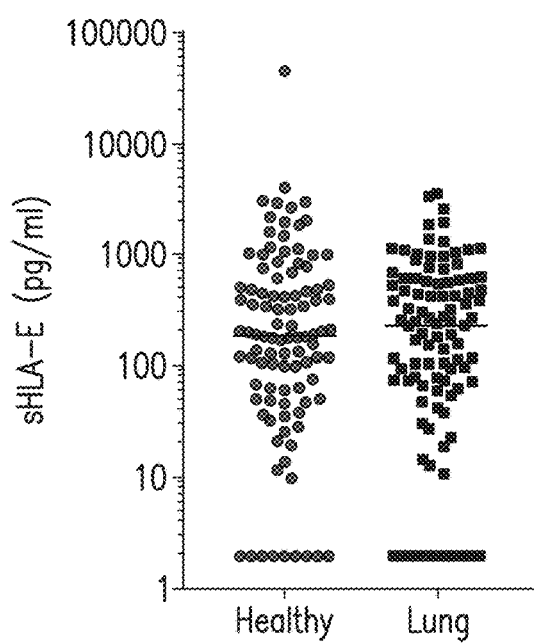

A selective and sensitive SIMOA-based immunoassay to measure sHLA-E (LLOQ: 11 pg/mL) was developed and used to test two independent sample sets: (A) a first set that contains sera and plasma from healthy controls (n=17) and from patients from six cancer types (n=10 patients per cancer type) (FIG. 49A) and (B) a second set of 100 healthy controls and 100 lung cancer patients (FIG. 49B). In both sets, interpatient variability was observed, with similar ranges in healthy donors and cancer patients. This assay will confirm soluble HLA-E levels as a predictive marker of response to nivolumab using this assay.

Within each tumor type, significant inter-patient variability for HLA-E expression was observed, as shown in FIG. 49. We believe patients with higher tumor HLA-E and higher CD8+ (using CD8+ as a surrogate for NKG2A expression) will benefit from NKG2A inhibition to restore antitumor activity of CD8+ T and NK cells.

Example 33

Phase 1/Phase 2 Study with the NKG2A.9 Antibody

We will conduct a Phase I/II study with the NKG2A.9 antibody to develop a safe and efficacious therapy to treat cancer. Although not bound by any mechanism, the therapy will restore T cell response to checkpoint inhibitors in PD-L1 resistant/refractory tumors and/or enhance NK activity in NK-enriched solid tumors.

Figure 50:
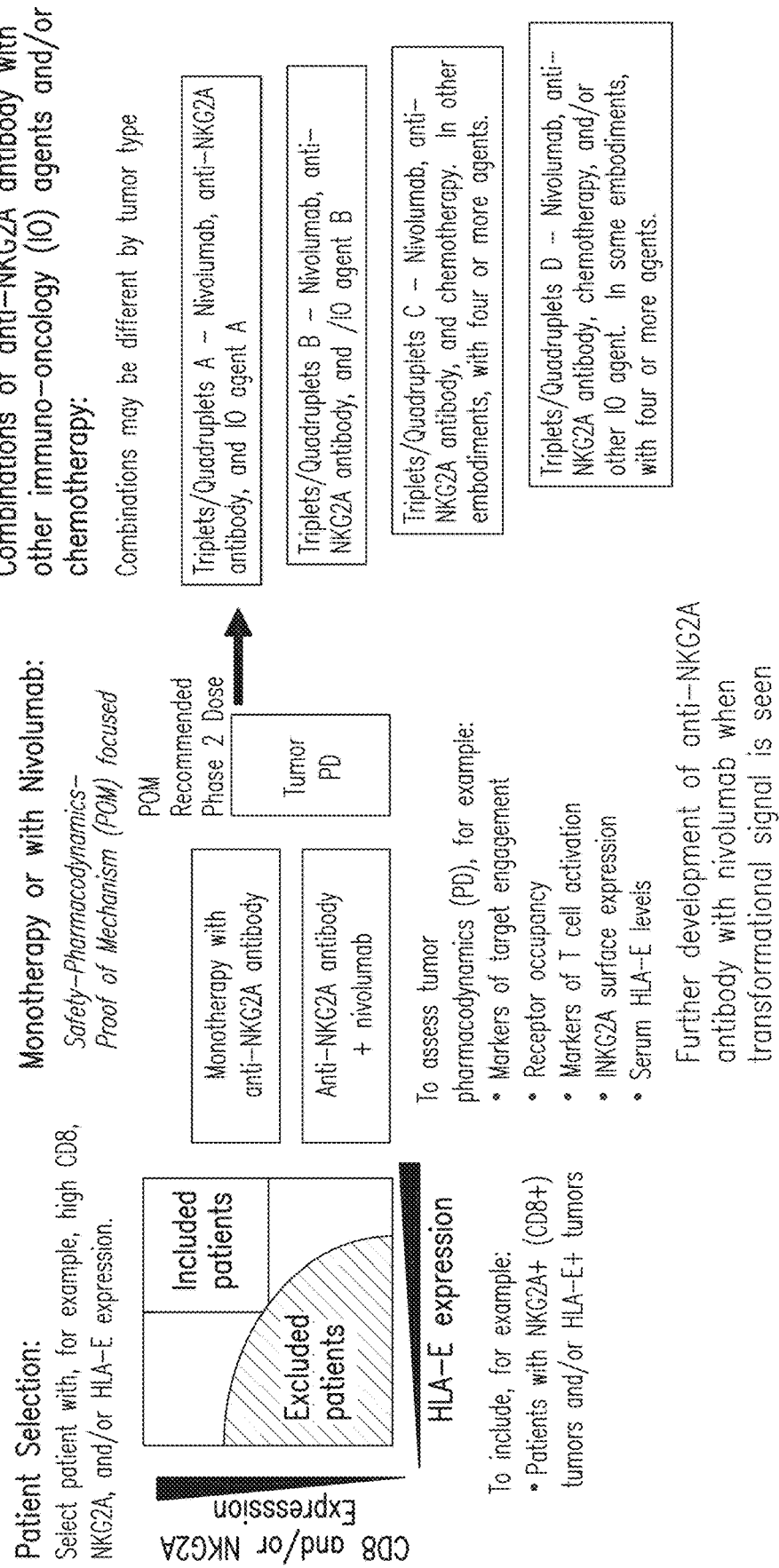
FIG. 50 shows the clinical development plan for anti-NKG2A antibodies discussed herein, including patient selections steps and various combination therapies with the anti-NKG2A antibodies described herein.
Figure 51A:
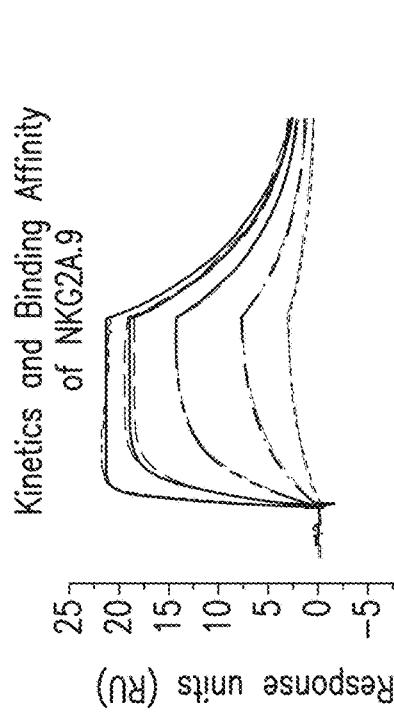
FIG. 51A-D are graphs showing the kinetics and binding affinity of the NKG2A.9 antibody as determined by Biacore analysis.
Figure 51B:
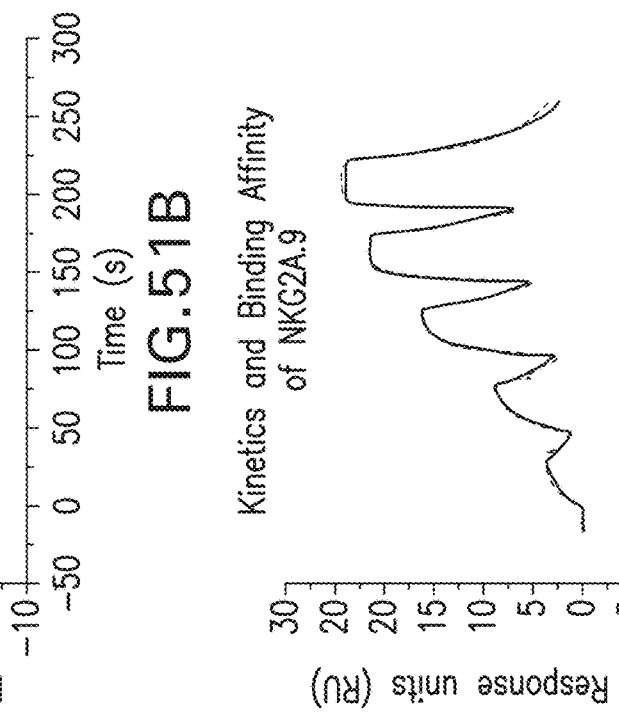
Figure 51C:
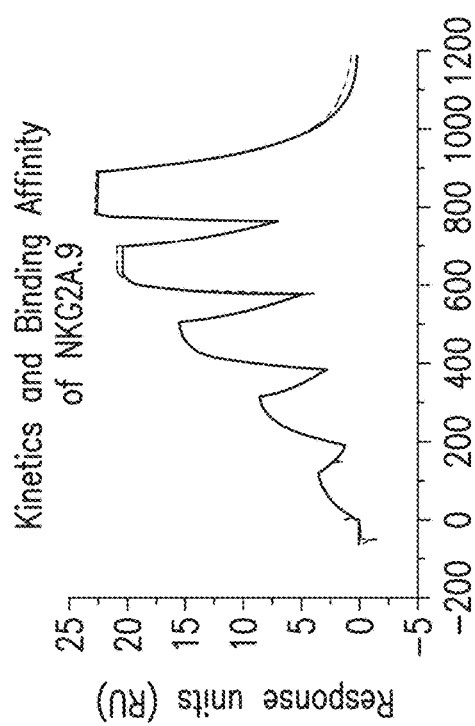
Figure 51D:
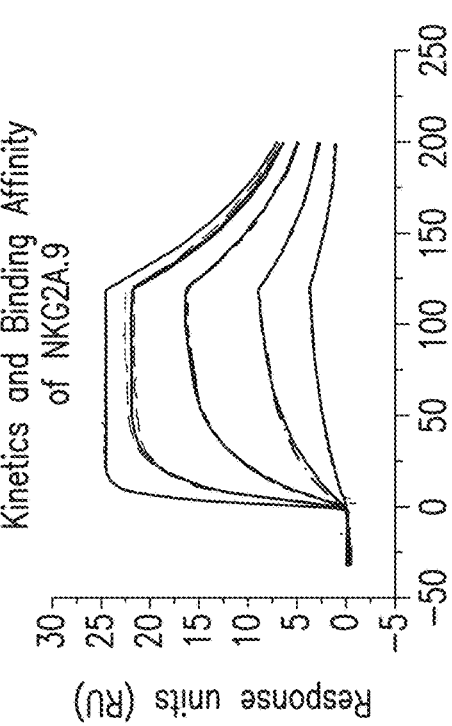

The clinical development plan is summarized in Table 9 below.

body combination with nivolumab, as illustrated in FIG. 50. The safety, MTD or maximum administered dose, PK, PD, and preliminary evaluation of clinical activity will next be evaluated with the combination therapy. Triplet checkpoint blockade combinations will also be evaluated during dose escalation and include the NKG2A.9 antibody, nivolumab, and other checkpoint inhibitors including but not limited to relatlimab (anti-LAG-3), anti-TIM-3, anti-TIGIT, ipilimumab, CTLA-4 NF or Probody, or other anti-cancer therapies, including, for example, chemotherapy, signal transduction agents such as cetuximab, amongst other therapies.

Patient/tumor selection for escalation and expansion cohorts will be based on ongoing analysis of The Cancer Genome Atlas (TCGA) expression profiles, expression profiles from internal nivolumab trials, profiling of tumor samples for CD8 levels (as a surrogate for NKG2A levels), and profiling of tumor and serum samples for HLA-E, including virally-induced tumors. For example, patient selection will be based on choosing patients whose tumors are CD8+ (as a surrogate for NKG2A) and HLA-E+, as illustrated in FIG. 50. In another embodiment, patient selection will also be based on tumors with high inflammation or tumor mutation burden.

Patients enrolled in this study will be required to provide pre-treatment and on-treatment biopsies as well as serial peripheral blood samples to test the hypothesis that treatment with anti-NKG2A alone or in combination with nivolumab increases the number or functional activities of CD8+ T and NK cells in the tumor. Particular attention will be dedicated to analyzing whether such changes in the tumor immune microenvironment correlate with clinical response. Pharmacodynamic studies will evaluate markers of target engagement, T cell activation, changes in NKG2A surface

TABLE 9

Anti-NKG2A Antibody Clinical Development Plan

| Anti-NKG2A Antibody with Nivolumab | |
| --- | --- |
| Checkpoint blockade with anti-NKG2A antibody in combination with nivolumab will synergize to extend the benefit and deepen response in tumors resistant or refractory to anti-PD-L1 therapy or associated with poor response to anti-PD-L1 therapy | Selection of patients with: Inflamed or high-TMB tumors with known anti-PD-1 activity but less than complete response AND high expression of HLA-E and/or CD8 (as a surrogate for NKG2A expression); and/or Tumors associated with a viral etiology AND high expression of CD8 (NKG2A surrogate) and/or HLA-E; and/or Tumors that relapse after anti-PD-1 treatment AND have high expression of CD8 (NKG2A surrogate) and/or total tumor HLA-E. |
| Anti-NKG2A Antibody with Other I-O Agents and Multi-Checkpoint Combinations | |
| Anti-NKG2A antibody in combination with multiple checkpoint inhibitors will overcome I-O resistance by redundant checkpoint pathways and optimize clinical benefit. | Selection of patients with: Inflamed or high-TMB tumors with expression of multiple immune checkpoint proteins |

The clinical development of the NKG2A.9 antibody will begin with a first in human (FIH), Phase 1/2 study. An initial monotherapy dose escalation will be performed to determine the safety, maximum tolerated dose (MTD) or maximum administered dose, PK, PD, and preliminary evaluation of clinical activity. Intravenous administration route will initially be used in the study, with subcutaneous administration in other arms of the study. Alternatively, an intravenous administration route can be used. With a staggered start, a parallel dose escalation will occur with the NKG2A.9 anti-expression, IFN-γ, and serum sHLA-E. Subjects with NKG2A-positive and HLA-E+ tumors (including but not limited to non-small cell lung cancer (NSCLC), renal cell carcinoma (RCC), and head and neck squamous cell carcinoma (HNSCC)) and tumors of viral origin (head and neck, cervical, hepatocellular cancers) will optionally be included. Subjects may have tumors that are resistant/refractory to anti-PD-1/PD-L1 therapy or tumors that are reported to be insensitive to anti-PD-1/PD-L1 therapy. Alternatively, subjects may be naïve to PD-1/PD-L1 treatment.

The Sequence Listing is provided in the Table below.

| SEQ ID NO | Name | Sequence | |
|---|---|---|---|
| 1 | Human NKG2A nucleotide sequence (CCDS8625.1) | ATGGATAACC AAGGAGTAAT CTACTCAGAC CTGAATCTGC CCCCAAACCC | 50 |
| | | AAAGAGGCAG CAACGAAAAC CTAAAGGCAA TAAAAACTCC ATTTTAGCAA | 100 |
| | | CTGAACAGGA AATAACCTAT GCGGAATTAA ACCTTCAAAA AGCTTCTCAG | 150 |
| | | GATTTTCAAG GGAATGACAA AACCTATCAC TGCAAAGATT TACCATCAGC | 200 |
| | | TCCAGAGAAG CTCATTGTTG GGATCCTGGG AATTATCTGT CTTATCTTAA | 250 |
| | | TGGCCTCTGT GGTAACGATA GTTGTTATTC CCTCTACATT AATACAGAGG | 300 |
| | | CACAACAATT CTTCCCTGAA TACAAGAACT CAGAAAGCAC GTCATTGTGG | 350 |
| | | CCATTGTCCT GAGGAGTGGA TTACATATTC CAACAGTTGT TACTACATTG | 400 |
| | | GTAAGGAAAG AAGAACTTGG GAAGAGAGTT TGCTGGCCTG TACTTCGAAG | 450 |
| | | AACTCCAGTC TGCTTTCTAT AGATAATGAA GAAGAAATGA AATTTCTGTC | 500 |
| | | CATCATTTCA CCATCCTCAT GGATTGGTGT GTTTCGTAAC AGCAGTCATC | 550 |
| | | ATCCATGGGT GACAATGAAT GGTTTGGCTT TCAAACATGA GATAAAAGAC | 600 |
| | | TCAGATAATG CTGAACTTAA CTGTGCAGTG CTACAAGTAA ATCGACTTAA | 650 |
| | | ATCAGCCCAG TGTGGATCTT CAATAATATA TCATTGTAAG CATAAGCTTT | 700 |
| | | AG | 702 |
| 2 | Human NKG2A amino acid sequence (GenBank NP_002250.2 | MDNQGVIYSD LNLPPNPKR QQRKPKGNKNS ILATEQEITY AELNLQKASQ | 50 |
| | | DFQGNDKTYH CKDLPSAPE KLIVGILGIIC LILMASVVTI VVIPSTLIQR | 100 |
| | | HNNSSLNTRT QKARHCGHC PEEWITYSNSC YYIGKERRTW EESLLACTSK | 150 |
| | | NSSLLSIDNE EEMKFLSII SPSSWIGVFRN SSHHPWVTMN GLAFKHEIKD | 200 |
| | | SDNAELNCAV LQVNRLKSA QCGSSIIYHCK HKL | 233 |
| 3 | Human NKG2C amino acid sequence (GenBank: CAA04922.1) | MSKQRGTFSE VSLAQDPKRQ QRKPKGNKSS ISGTEQEIFQ VELNLQNPSL | 50 |
| | | NHQGIDKIYD CQGLLPPPEK LTAEVLGIIC IVLMATVLKT IVLIPFLEQN | 100 |
| | | NSSPNTRTQK ARHCGHCPEE WITYSNSCYY IGKERRTWEE SLLACTSKNS | 150 |
| | | SLLSIDNEEE MKFLASILPS SWIGVFRNSS HHPWVTINGL AFKHKIKDSD | 200 |
| | | NAELNCAVLQ VNRLKSAQCG SSMIYHCKHK L | 231 |

NKG2A.9 Antibody (13F3.A4 antibody with VH-I107T framework reversion and VK-N30S to remove deamidation site) (SEQ ID NOs: 4-17, 163)

| 4 | NKG2A.9 light chain nucleotide sequence (including C-terminal "tag" stop codon) | gccatccagt tgacccagtc tccatcctcc ctgtctgcat ctgtaggaga | 50 |
|---|---|---|---|
| | | cagagtcacc atcacttgcc gggcaagtca gggcattcc agtgctttag | 100 |
| | | cctggtatca gcagaaacca gggaaagctc ctaagctcct gatctatgat | 150 |
| | | gcctccagtt tgaaaagtgg ggtcccatca aggttcagcg cagtggatc | 200 |
| | | tgggacagat ttcactctca ccatcagcag cctgcagcct gaagattttg | 250 |
| | | caacttatta ctgtcaacag tttaatagtt accctctcac cttcggccaa | 300 |
| | | gggacacgac tggagattaa acgtacggtg gctgcaccat ctgtcttcat | 350 |
| | | cttcccgcca tctgatgagc agttgaaatc tggaactgcc tctgttgtgt | 400 |
| | | gcctgctgaa taacttctat cccagagagg ccaaagtaca gtggaaggtg | 450 |
| | | gataacgccc tccaatcggg taactcccag gagagtgtca cagagcagga | 500 |
| | | cagcaaggac agcacctaca gcctcagcag caccctgacg ctgagcaaag | 550 |
| | | cagactacga gaaacacaaa gtctacgcct gcgaagtcac ccatcagggc | 600 |
| | | ctgagctcgc ccgtcacaaa gagcttcaac aggggagagt gttag | 645 |
| 5 | NKG2A.9 light chain amino acid sequence | AIQLTQSPSS LSASVGDRVT ITCRASQGIS SALAWYQQKP GKAPKLLIYD | 50 |
| | | ASSLKSGVPS RFSGSGSGTD FTLTISSLQP EDFATYYCQQ FNSYPLTFGQ | 100 |
| | | GTRLEIKRTV AAPSVFIFPP SDEQLKSGTA SVVCLLNNFY PREAKVQWKV | 150 |
| | | DNALQSGNSQ ESVTEQDSKD STYSLSSTLT LSKADYEKHK VYACEVTHQG | 200 |
| | | LSSPVTKSFN RGEC | 214 |
| 6 | NKG2A.9 heavy chain nucleotide sequence (same as NKG2A.11-G1.3f heavy chain nucleotide sequence) (including C-terminal "tga" stop codon) | gaggtgcagc tggtggagtc tgggggaggc ctggtcaagc cggggggtc | 50 |
| | | cctgagactc tcctgtgcag cctctggatt caccttcagt tcccatagta | 100 |
| | | tgaactgggt ccgccaggct ccagggaagg ggctggagtg ggtctcatcc | 150 |
| | | ataagtagta gtagtagtta catatactac gcagactcag tgaagggccg | 200 |
| | | attcaccatc tccagagaca cgccaagaa ctcactgtat ctgcaaatga | 250 |
| | | acagcctgag agccgaggac acggctgtgt attactgtgc gagagaagag | 300 |
| | | tgggggctac cctttgacta ctggggccag ggaaccctgg tcaccgtctc | 350 |
| | | ctcagctagc accaagggcc catcggtctt ccccctggca ccctcctcca | 400 |
| | | agagcacctc tgggggcaca gcggccctgg gctgcctggt caaggactac | 450 |
| | | ttccccgaac cggtgacggt gtcgtggaac tcaggcgccc tgaccagcgg | 500 |
| | | cgtgcacacc ttccggctg tcctacagtc tcaggactc tactccctca | 550 |
| | | gcagcgtggt gaccgtgccc tccagcagct gggcaccca gacctacatc | 600 |
| | | tgcaacgtga atcacaagcc cagcaacacc aaggtggaca gagagttga | 650 |
| | | gcccaaatct tgtgacaaaa ctcacacatg cccaccgtgc ccagcacctg | 700 |
| | | aagccgaagg ggccccgtca gtcttcctct tccccccaaa acccaaggac | 750 |
| | | accctcatga tctcccggac ccctgaggtc acatgcgtgg tggtggacgt | 800 |
| | | gagccacgaa gaccctgagg tcaagttcaa ctggtacgtg gacggcgtgg | 850 |
| | | aggtgcataa tgccaagaca aagccgcggg aggagcagta caacagcacg | 900 |
| | | taccgtgtgg tcagcgtcct caccgtcctg caccaggact ggctgaatgg | 950 |

| SEQ ID NO | Name | Sequence | |
|---|---|---|---|
| | | caaggagtac aagtgcaagg tctccaacaa agccctccca gcccccatcg | 1000 |
| | | agaaaaccat ctccaaagcc aaagggcagc cccgagaacc acaggtgtac | 1050 |
| | | accctgcccc catcccggga ggagatgacc aagaaccagg tcagcctgac | 1100 |
| | | ctgcctggtc aaaggcttct atcccagcga catcgccgtg gagtgggaga | 1150 |
| | | gcaatgggca gccggagaac aactacaaga ccacgcctcc cgtgctggac | 1200 |
| | | tccgacggct ccttcttcct ctatagcaag ctcaccgtgg acaagagcag | 1250 |
| | | gtggcagcag gggaacgtct tctcatgctc cgtgatgcat gaggctctgc | 1300 |
| | | acaaccacta cacgcagaag agcctctccc tgtccccggg ttga | 1344 |
| 7 | NKG2A.9 heavy chain amino acid sequence (same as NKG2A.11-G1.3f heavy chain amino acid sequence) (terminal lysine is absent) | EVQLVESGGG LVKPGGSLRL SCAASGFTFS SHSMNWVRQA PGKGLEWVSA | 50 |
| | | ISSSSSYIYY ADSVKGRFTI SRDNAKNSLY LQMNSLRAED TAVYYCAREE | 100 |
| | | WGLPFDYWGQ GTLVTVSSAS TKGPSVFPLA PSSKSTSGGT AALGCLVKDY | 150 |
| | | FPEPVTVSWN SGALTSGVHT FPAVLQSSGL YSLSSVVTVP SSSLGTQTYI | 200 |
| | | CNVNHKPSNT KVDKRVEPKS CDKTHTCPPC PAPEAEGAPS VFLFPPKPKD | 250 |
| | | TLMISRTPEV TCVVVDVSHE DPEVKFNWYV DGVEVHNAKT KPREEQYNST | 300 |
| | | YRVVSVLTVL HQDWLNGKEY KCKVSNKALP APIEKTISKA KGQPREPQVY | 350 |
| | | TLPPSREEMT KNQVSLTCLV KGFYPSDIAV EWESNGQPEN NYKTTPPVLD | 400 |
| | | SDGSFFLYSK LTVDKSRWQQ GNVFSCSVMH EALHNHYTQK SLSLSPG | 447 |
| 163 | NKG2A.9 heavy chain amino acid sequence (same as NKG2A.11-G1.3f heavy chain amino acid sequence) (shown with the terminal lysine) | EVQLVESGGG LVKPGGSLRL SCAASGFTFS SHSMNWVRQA PGKGLEWVSA | 50 |
| | | ISSSSSYIYY ADSVKGRFTI SRDNAKNSLY LQMNSLRAED TAVYYCAREE | 100 |
| | | WGLPFDYWGQ GTLVTVSSAS TKGPSVFPLA PSSKSTSGGT AALGCLVKDY | 150 |
| | | FPEPVTVSWN SGALTSGVHT FPAVLQSSGL YSLSSVVTVP SSSLGTQTYI | 200 |
| | | CNVNHKPSNT KVDKRVEPKS CDKTHTCPPC PAPEAEGAPS VFLFPPKPKD | 250 |
| | | TLMISRTPEV TCVVVDVSHE DPEVKFNWYV DGVEVHNAKT KPREEQYNST | 300 |
| | | YRVVSVLTVL HQDWLNGKEY KCKVSNKALP APIEKTISKA KGQPREPQVY | 350 |
| | | TLPPSREEMT KNQVSLTCLV KGFYPSDIAV EWESNGQPEN NYKTTPPVLD | 400 |
| | | SDGSFFLYSK LTVDKSRWQQ GNVFSCSVMH EALHNHYTQK SLSLSPGK | 447 |
| 8 | NKG2A.9 heavy chain variable domain (same as NKG2A.11 heavy chain variable domain) | EVQLVESGGG LVKPGGSLRL SCAASGFTFS SHSMNWVRQA PGKGLEWVSA | 50 |
| | | ISSSSSYIYY ADSVKGRFTI SRDNAKNSLY LQMNSLRAED TAVYYCAREE | 100 |
| | | WGLPFDYWGQ GTLVTVSS | 118 |
| 9 | NKG2A.9 light chain variable domain | AIQLTQSPSS LSASVGDRVT ITCRASQGIS SALAWYQQKP GKAPKLLIYD | 50 |
| | | ASSLKSGVPS RFSGSGSGTD FTLTISSLQP EDFATYYCQQ FNSYPLTFGQ | 100 |
| | | GTRLEIK | 107 |
| 10 | NKG2A.9 VH CDR1 | SHSMN | 5 |
| 11 | NKG2A.9 VH CDR2 | AISSSSSYIY YADSVKG | 17 |
| 12 | NKG2A.9 VH CDR3 | EEWGLPFDY | 9 |
| 13 | NKG2A.9 VL CDR1 | RASQGISSAL A | 11 |
| 14 | NKG2A.9 VL CDR2 | DASSLKS | 7 |
| 15 | NKG2A.9 VL CDR3 | QQFNSYPLT | 9 |

| SEQ ID NO | Name | Sequence | |
|---|---|---|---|
| 16 | NKG2A.9 heavy chain constant domain | ASTKGPSVFP LAPSSKSTSG GTAALGCLVK DYFPEPVTVS WNSGALTSGV<br>HTFPAVLQSS GLYSLSSVVT VPSSSLGTQT YICNVNHKPS NTKVDKRVEP<br>KSCDKTHTCP PCPAPEAEGA PSVFLFPPKP KDTLMISRTP EVTCVVVDVS<br>HEDPEVKFNW YVDGVEVHNA KTKPREEQYN STYRVVSVLT VLHQDWLNGK<br>EYKCKVSNKA LPAPIEKTIS KAKGQPREPQ VYTLPPSREE MTKNQVSLTC<br>LVKGFYPSDI AVEWESNGQP ENNYKTTPPV LDSDGSFFLY SKLTVDKSRW<br>QQGNVFSCSV MHEALHNHYT QKSLSLSPG | 50<br>100<br>150<br>200<br>250<br>300<br>329 |
| 17 | NKG2A.9 light chain constant domain | RTVAAPSVFI FPPSDEQLKS GTASVVCLLN NFYPREAKVQ WKVDNALQSG<br>NSQESVTEQD SKDSTYSLSS TLTLSKADYE KHKVYACEVT HQGLSSPVTK<br>SFNRGEC | 50<br>100<br>107 |

NKG2A.11 Antibody (13F3.A4 VH-I107T, VK-N30P) (13F3.A4 with VH-I107T
framework reversion and VK-N30P to remove deamidation site)
(SEQ ID NOs: 18-21, 164-165)
(SEQ ID NOs: 6-7 (NKG2A.11 heavy chain sequences nucleotide
and amino acid sequences, respectively))

| SEQ ID NO | Name | Sequence | |
|---|---|---|---|
| 18 | NKG2A.11 light chain nucleotide sequence (including C-terminal "tag" stop codon) | gccatccagt tgacccagtc tccatcctcc ctgtctgcat ctgtaggaga<br>cagagtcacc atcacttgcc gggcaagtca gggcattccc agtgctttag<br>cctggtatca gcagaaacca gggaaagctc ctaagctcct gatctatgat<br>gcctccagtt tgaaaagtgg ggtcccatca aggttcagcg gcagtggatc<br>tgggacagat ttcactctca ccatcagcag cctgcagcct gaagattttg<br>caacttatta ctgtcaacag tttaatagtt accctctcac cttcggccaa<br>gggacacgac tggagattaa acgtacggtg gctgcaccat ctgtcttcat<br>cttcccgcca tctgatgagc agttgaaatc tggaactgcc tctgttgtgt<br>gcctgctgaa taacttctat cccagagagg ccaaagtaca gtggaaggtg<br>gataacgccc tccaatcggg taactcccag gagagtgtca cagagcagga<br>cagcaaggac agcacctaca gcctcagcag caccctgacg ctgagcaaag<br>cagactacga gaaacacaaa gtctacgcct gcgaagtcac ccatcagggc<br>ctgagctcgc ccgtcacaaa gagcttcaac aggggagagt gttag | 50<br>100<br>150<br>200<br>250<br>300<br>350<br>400<br>450<br>500<br>550<br>600<br>645 |
| 19 | NKG2A.11 light chain amino acid sequence | AIQLTQSPSS LSASVGDRVT ITCRASQGIP SALAWYQQKP GKAPKLLIYD<br>ASSLKSGVPS RFSGSGSGTD FTLTISSLQP EDFATYYCQQ FNSYPLTFGQ<br>GTRLEIKRTV AAPSVFIFPP SDEQLKSGTA SVVCLLNNFY PREAKVQWKV<br>DNALQSGNSQ ESVTEQDSKD STYSLSSTLT LSKADYEKHK VYACEVTHQG<br>LSSPVTKSFN RGEC | 50<br>100<br>150<br>200<br>214 |
| 164 | NKG2A.11 light chain variable domain amino acid sequence | AIQLTQSPSS LSASVGDRVT ITCRASQGIP SALAWYQQKP GKAPKLLIYD<br>ASSLKSGVPS RFSGSGSGTD FTLTISSLQP EDFATYYCQQ FNSYPLTFGQ<br>GTRLEIK | 50<br>100<br>107 |
| 165 | NKG2A.11 light chain constant domain amino acid sequence | RTVAAPSVFI FPPSDEQLKS GTASVVCLLN NFYPREAKVQ WKVDNALQSG<br>NSQESVTEQD SKDSTYSLSS TLTLSKADYE KHKVYACEVT HQGLSSPVTK<br>SFNRGEC | 50<br>100<br>107 |
| 20 | Osteonectin signal nucleotide sequence | atgagggctt ggatcttctt tctgctctgc ctggccgggc gcgccttggc<br>c | 50<br>51 |
| 21 | Osteonectin signal amino acid sequence | MRAWIFFLLC LAGRALA | 17 |

NKG2A.6 Antibody (13F3.A4 antibody) (SEQ ID NOs: 22-36, 166-169)

| SEQ ID NO | Name | Sequence | |
|---|---|---|---|
| 22 | Signal amino acid sequence for 13F3.A4 heavy chain | MELGLRWVFL VAILEGVQC | 19 |

| SEQ ID NO | Name | Sequence | |
|---|---|---|---|
| 23 | 13F3.A4 VH (heavy chain variable region nucleotide sequence) (with 57-nucleotide signal sequence) | ATGGAACTGG GGCTCCGCTG GGTTTTCCTT GTTGCTATTT TAGAAGGTGT<br>CCAGTGT<br>GAGGTGCAGC TGGTGGAGTC TGGGGGAGGC CTGGTCAAGC CGGGGGGGTC<br>CCTGAGACTC TCCTGTGCAG CCTCTGGATT CACCTTCAGT TCCCATAGTA<br>TGAACTGGGT CCGCCAGGCT CCAGGGAAGG GGCTGGAGTG GGTCTCAGCC<br>ATAAGTAGTA GTAGTAGTTA CATATACTAC GCAGACTCAG TGAAGGGCCG<br>ATTCACCATC TCCAGAGACA ACGCCAAGAA CTCACTGTAT CTGCAAATGA<br>ACAGCCTGAG AGCCGAGGAC ACGGCTGTGT ATTACTGTGC GAGAGAAGAG<br>TGGGGGCTAC CCTTTGACTA CTGGGGCCAG GGAATCCTGG TCACCGTCTC<br>CTCA | -57<br>-7<br>50<br>100<br>150<br>200<br>250<br>300<br>350<br>354 |
| 166 | 13F3.A4 VH (heavy chain variable region nucleotide sequence) (without signal sequence) | GAGGTGCAGC TGGTGGAGTC TGGGGGAGGC CTGGTCAAGC CGGGGGGGTC<br>CCTGAGACTC TCCTGTGCAG CCTCTGGATT CACCTTCAGT TCCCATAGTA<br>TGAACTGGGT CCGCCAGGCT CCAGGGAAGG GGCTGGAGTG GGTCTCAGCC<br>ATAAGTAGTA GTAGTAGTTA CATATACTAC GCAGACTCAG TGAAGGGCCG<br>ATTCACCATC TCCAGAGACA ACGCCAAGAA CTCACTGTAT CTGCAAATGA<br>ACAGCCTGAG AGCCGAGGAC ACGGCTGTGT ATTACTGTGC GAGAGAAGAG<br>TGGGGGCTAC CCTTTGACTA CTGGGGCCAG GGAATCCTGG TCACCGTCTC<br>CTCA | 50<br>100<br>150<br>200<br>250<br>300<br>350<br>354 |
| 24 | 13F3.A4 VH heavy chain variable region amino acid sequence (with 19-amino acid signal sequence) | MELGLRWVFL VAILEGVQC<br>EVQLVESGGG LVKPGGSLRL SCAASGFTFS SHSMNWVRQA PGKGLEWVSA<br>ISSSSSYIYY ADSVKGRFTI SRDNAKNSLY LQMNSLRAED TAVYYCAREE<br>WGLPFDYWGQ GILVTVSS | -19<br>50<br>100<br>118 |
| 167 | 13F3.A4 VH amino acid sequence (without signal sequence) | EVQLVESGGG LVKPGGSLRL SCAASGFTFS SHSMNWVRQA PGKGLEWVSA<br>ISSSSSYIYY ADSVKGRFTI SRDNAKNSLY LQMNSLRAED TAVYYCAREE<br>WGLPFDYWGQ GILVTVSS | 50<br>100<br>118 |
| 25 | 13F3.A4 VL nucleotide sequence (with 66-nucleotide signal sequence) | ATGGACATGA GGGTCCCCGC TCAGCTCCTG GGGCTTCTGC TGCTCTGGCT<br>CCCAGGTGCC AGATGT<br>GCCATCCAGT TGACCCAGTC TCCATCCTCC CTGTCTGCAT CTGTAGGAGA<br>CAGAGTCACC ATCACTTGCC GGGCAAGTCA GGGCATTAAC AGTGCTTTAG<br>CCTGGTATCA GCAGAAACCA GGGAAAGCTC CTAAGCTCCT GATCTATGAT<br>GCCTCCAGTT TGAAAGTGG GGTCCCATCA AGGTTCAGCG GCAGTGGATC<br>TGGGACAGAT TTCACTCTCA CCATCAGCAG CCTGCAGCCT GAAGATTTTG<br>CAACTTATTA CTGTCAACAG TTTAATAGTT ACCCTCTCAC CTTCGGCCAA<br>GGGACACGAC TGGAGATTAA A | -66<br>-16<br>50<br>100<br>150<br>200<br>250<br>300<br>321 |
| 168 | 13F3.A4 VL nucleotide sequence (without signal sequence) | GCCATCCAGT TGACCCAGTC TCCATCCTCC CTGTCTGCAT CTGTAGGAGA<br>CAGAGTCACC ATCACTTGCC GGGCAAGTCA GGGCATTAAC AGTGCTTTAG<br>CCTGGTATCA GCAGAAACCA GGGAAAGCTC CTAAGCTCCT GATCTATGAT<br>GCCTCCAGTT TGAAAGTGG GGTCCCATCA AGGTTCAGCG GCAGTGGATC<br>TGGGACAGAT TTCACTCTCA CCATCAGCAG CCTGCAGCCT GAAGATTTTG<br>CAACTTATTA CTGTCAACAG TTTAATAGTT ACCCTCTCAC CTTCGGCCAA<br>GGGACACGAC TGGAGATTAA A | 50<br>100<br>150<br>200<br>250<br>300<br>321 |
| 26 | 13F3.A4 VL (light chain variable region amino acid sequence) (with 22-amino acid signal sequence) | MDMRVPAQLL GLLLLWLPGA RC<br>AIQLTQSPSS LSASVGDRVT ITCRASQGIN SALAWYQQKP GKAPKLLIYD<br>ASSLKSGVPS RFSGSGSGTD FTLTISSLQP EDFATYYCQQ FNSYPLTFGQ<br>GTRLEIK | -22<br>50<br>100<br>107 |

| SEQ ID NO | Name | Sequence | |
|---|---|---|---|
| 169 | 13F3.A4 VL amino acid sequence (without signal sequence) | AIQLTQSPSS LSASVGDRVT ITCRASQGIN SALAWYQQKP GKAPKLLIYD<br>ASSLKSGVPS RFSGSGSGTD FTLTISSLQP EDFATYYCQQ FNSYPLTFGQ<br>GTRLEIK | 50<br>100<br>107 |
| 27 | 13F3.A4 VH CDR1 | SHSMN | 5 |
| 28 | 13F3.A4 VH CDR2 | AISSSSSYIY YADSVKG | 17 |
| 29 | 13F3.A4 VH CDR3 | EEWGLPFDY | 9 |
| 30 | 13F3.A4 VL CDR1 | RASQGINSAL A | 11 |
| 31 | 13F3.A4 VL CDR2 | DASSLKS | 7 |
| 32 | 13F3.A4 VL CDR3 | QQFNSYPLT | 9 |
| 33 | 13F3.A4 CH heavy chain constant region | ASTKGPSVFP LAPSSKSTSG GTAALGCLVK DYFPEPVTVS WNSGALTSGV<br>HTFPAVLQSS GLYSLSSVVT VPSSSLGTQT YICNVNHKPS NTKVDKKVEP<br>KSCDKTHTCP PCPAPELLGG PSVFLFPPKP KDTLMISRTP EVTCVVVDVS<br>HEDPEVKFNW YVDGVEVHNA KTKPREEQYN STYRVVSVLT VLHQDWLNGK<br>EYKCKVSNKA LPAPIEKTIS KAKGQPREPQ VYTLPPSRDE LTKNQVSLTC<br>LVKGFYPSDI AVEWESNGQP ENNYKTTPPV LDSDGSFFLY SKLTVDKSRW<br>QQGNVFSCSV MHEALHNHYT QKSLSLSPGK | 50<br>100<br>150<br>200<br>250<br>300<br>330 |
| 34 | 13F3.A4 CL light chain constant region | RTVAAPSVFI FPPSDEQLKS GTASVVCLLN NFYPREAKVQ WKVDNALQSG<br>NSQESVTEQD SKDSTYSLSS TLTLSKADYE KHKVYACEVT HQGLSSPVTK<br>SFNRGEC | 50<br>100<br>107 |
| 35 | 13F3.A4 heavy chain amino acid sequence (without signal sequence) Terminal lysine can be absent. | EVQLVESGGG LVKPGGSLRL SCAASGFTFS SHSMNWVRQA PGKGLEWVSA<br>ISSSSSYIYY ADSVKGRFTI SRDNAKNSLY LQMNSLRAED TAVYYCAREE<br>WGLPFDYWGQ GILVTVSSAS TKGPSVFPLA PSSKSTSGGT AALGCLVKDY<br>FPEPVTVSWN SGALTSGVHT FPAVLQSSGL YSLSSVVTVP SSSLGTQTYI<br>CNVNHKPSNT KVDKKVEPKS CDKTHTCPPC PAPELLGGPS VFLFPPKPKD<br>TLMISRTPEV TCVVVDVSHE DPEVKFNWYV DGVEVHNAKT KPREEQYNST<br>YRVVSVLTVL HQDWLNGKEY KCKVSNKALP APIEKTISKA KGQPREPQVY<br>TLPPSRDELT KNQVSLTCLV KGFYPSDIAV EWESNGQPEN NYKTTPPVLD<br>SDGSFFLYSK LTVDKSRWQQ GNVFSCSVMH EALHNHYTQK SLSLSPG(K) | 50<br>100<br>150<br>200<br>250<br>300<br>350<br>400<br>448 |
| 36 | 13F3.A4 light chain amino acid sequence (without signal sequence) | AIQLTQSPSS LSASVGDRVT ITCRASQGIN SALAWYQQKP GKAPKLLIYD<br>ASSLKSGVPS RFSGSGSGTD FTLTISSLQP EDFATYYCQQ FNSYPLTFGQ<br>GTRLEIKRTV AAPSVFIFPP SDEQLKSGTA SVVCLLNNFY PREAKVQWKV<br>DNALQSGNSQ ESVTEQDSKD STYSLSSTLT LSKADYEKHK VYACEVTHQG<br>LSSPVTKSFN RGEC | 50<br>100<br>150<br>200<br>214 |

NKG2A.5 Antibody (11H9.A1 antibody (SEQ ID NOs: 37-50, 170-173)

| SEQ ID NO | Name | Sequence | |
|---|---|---|---|
| 37 | 11H9.A1 VH (heavy chain variable region nucleotide sequence) (with 57-nucleotide signal sequence) | ATGGAACTGG GGCTCCGCTG GTTTTCCTT GTTGCTATTT TAGAAGGTGT<br>CCAGTGT<br>GAGGTGCAGT TGGTGGAGTC TGGGGGAGGC CTGGTCAAGC CTGGGGGGTC<br>CCTGAGACTC TCCTGTGCAG CCTCTGGATT CACCTTCAGT AGCTATAGCA<br>TGAACTGGGT CCGCCAGGCT CCAGGGAAGG GGCTGGAGTG GGTCTCATCC<br>ATTAGTAGTA GTAGTAGTTA CATATACTAC GCAGACTCAG TGAAGGGCCG<br>ATTCACCATC TCCAGAGACA ACGCCAAGAA CTCACTGTAT CTGCAAATGA<br>ACAGCCTGAG AGCCGAGGAC ACGGCTGTGT ATTACTGTGC GAGACTACTA<br>TGGTTCGGGG AGATTTTTGA CTACTGGGGC CAGGGAACCC TGGTCACCGT<br>CTCCTCA | -57<br>-7<br>50<br>100<br>150<br>200<br>250<br>300<br>350<br>357 |

| SEQ ID NO | Name | Sequence | |
|---|---|---|---|
| 170 | 11H9.A1 VH (heavy chain variable region nucleotide sequence) (without signal sequence) | GAGGTGCAGT TGGTGGAGTC TGGGGGAGGC CTGGTCAAGC CTGGGGGGTC<br>CCTGAGACTC TCCTGTGCAG CCTCTGGATT CACCTTCAGT AGCTATAGCA<br>TGAACTGGGT CCGCCAGGCT CCAGGGAAGG GGCTGGAGTG GGTCTCATCC<br>ATTAGTAGTA GTAGTAGTTA CATATACTAC GCAGACTCAG TGAAGGGCCG<br>ATTCACCATC TCCAGAGACA ACGCCAAGAA CTCACTGTAT CTGCAAATGA<br>ACAGCCTGAG AGCCGAGGAC ACGGCTGTGT ATTACTGTGC GAGACTACTA<br>TGGTTCGGGG AGATTTTTGA CTACTGGGGC CAGGGAACCC TGGTCACCGT<br>CTCCTCA | 50<br>100<br>150<br>200<br>250<br>300<br>350<br>357 |
| 38 | 11H9.A1 VH (heavy chain variable region amino acid sequence) (with 19-amino acid signal sequence) | MELGLRWVFL VAILEGVQC<br>EVQLVESGGG LVKPGGSLRL SCAASGFTFS SYSMNWVRQA PGKGLEWVSS<br>ISSSSSYIYY ADSVKGRFTI SRDNAKNSLY LQMNSLRAED TAVYYCARLL<br>WFGEIFDYWG QGTLVTVSS | -19<br>50<br>100<br>119 |
| 171 | 11H9.A1 VH (heavy chain variable region amino acid sequence) (without signal sequence) | EVQLVESGGG LVKPGGSLRL SCAASGFTFS SYSMNWVRQA PGKGLEWVSS<br>ISSSSSYIYY ADSVKGRFTI SRDNAKNSLY LQMNSLRAED TAVYYCARLL<br>WFGEIFDYWG QGTLVTVSS | 50<br>100<br>119 |
| 39 | 11H9.A1 VL (light chain variable region nucleotide sequence) (with 66-nucleotide signal sequence) | ATGGACATGA GGGTCCCCGC TCAGCTCCTG GGGCTTCTGC TGCTCTGGCT<br>CCCAGGTGCC AGATGT<br>GCCATCCAGT TGACCCAGTC TCCATCCTCC CTGTCTGCAT CTGTAGGAGA<br>CAGAGTCACC ATCACTTGCC GGGCAAGTCA GGGCATTAGC AGTGCTTTAG<br>CCTGGTATCA GCAGAAACCA GGGAAAGCTC CTAAGCTCCT GATCTATGAT<br>GCCTCCAGTT TGAAAAGTGG GGTCCCATCA AGGTTCAGCG GCAGTGGATC<br>TGGGACAGAT TTCACTCTCA CCATCAGCAG CCTGCAGCCT GAAGATTTTG<br>CAACTTATTA CTGTCAACAG TTTAATAGTT ACCCGATCAC CTTCGGCCAA<br>GGGACACGAC TGGAGATTAA A | -66<br>-16<br>50<br>100<br>150<br>200<br>250<br>300<br>321 |
| 172 | 11H9.A1 VL (light chain variable region nucleotide sequence) (without signal sequence) | GCCATCCAGT TGACCCAGTC TCCATCCTCC CTGTCTGCAT CTGTAGGAGA<br>CAGAGTCACC ATCACTTGCC GGGCAAGTCA GGGCATTAGC AGTGCTTTAG<br>CCTGGTATCA GCAGAAACCA GGGAAAGCTC CTAAGCTCCT GATCTATGAT<br>GCCTCCAGTT TGAAAAGTGG GGTCCCATCA AGGTTCAGCG GCAGTGGATC<br>TGGGACAGAT TTCACTCTCA CCATCAGCAG CCTGCAGCCT GAAGATTTTG<br>CAACTTATTA CTGTCAACAG TTTAATAGTT ACCCGATCAC CTTCGGCCAA<br>GGGACACGAC TGGAGATTAA A | 50<br>100<br>150<br>200<br>250<br>300<br>321 |
| 40 | 11H9.A1 VL (light chain variable region amino acid sequence) (with 22-amino acid signal sequence) | MDMRVPAQLL GLLLLWLPGA RC<br>AIQLTQSPSS LSASVGDRVT ITCRASQGIS SALAWYQQKP GKAPKLLIYD<br>ASSLKSGVPS RFSGSGSGTD FTLTISSLQP EDFATYYCQQ FNSYPITFGQ<br>GTRLEIK | -22<br>50<br>100<br>107 |
| 173 | 11H9.A1 VL (light chain variable | AIQLTQSPSS LSASVGDRVT ITCRASQGIS SALAWYQQKP GKAPKLLIYD<br>ASSLKSGVPS RFSGSGSGTD FTLTISSLQP EDFATYYCQQ FNSYPITFGQ<br>GTRLEIK | 50<br>100<br>107 |

Sequence Listing

| SEQ ID NO | Name | Sequence | |
|---|---|---|---|
| | region amino acid sequence) (without signal sequence) | | |
| 41 | 11H9.A1 VH CDR1 | SYSMN | 5 |
| 42 | 11H9.A1 VH CDR2 | SISSSSSYIY YADSVKG | 17 |
| 43 | 11H9.A1 VH CDR3 | LLWFGEIFDY | 10 |
| 44 | 11H9.A1 VL CDR1 | RASQGISSAL A | 11 |
| 45 | 11H9.A1 VL CDR2 | DASSLKS | 7 |
| 46 | 11H9.A1 VL CDR3 | QQFNSYPIT | 9 |
| 47 | 11H9.A1 CH heavy chain constant region | ASTKGPSVFP LAPSSKSTSG GTAALGCLVK DYFPEPVTVS WNSGALTSGV<br>HTFPAVLQSS GLYSLSSVVT VPSSSLGTQT YICNVNHKPS NTKVDKKVEP<br>KSCDKTHTCP PCPAPELLGG PSVFLFPPKP KDTLMISRTP EVTCVVVDVS<br>HEDPEVKFNW YVDGVEVHNA KTKPREEQYN STYRVVSVLT VLHQDWLNGK<br>EYKCKVSNKA LPAPIEKTIS KAKGQPREPQ VYTLPPSRDE LTKNQVSLTC<br>LVKGFYPSDI AVEWESNGQP ENNYKTTPPV LDSDGSFFLY SKLTVDKSRW<br>QQGNVFSCSV MHEALHNHYT QKSLSLSPGK | 50<br>100<br>150<br>200<br>250<br>300<br>330 |
| 48 | 11H9.A1 CL light chain constant region | RTVAAPSVFI FPPSDEQLKS GTASVVCLLN NFYPREAKVQ WKVDNALQSG<br>NSQESVTEQD SKDSTYSLSS TLTLSKADYE KHKVYACEVT HQGLSSPVTK<br>SFNRGEC | 50<br>100<br>107 |
| 49 | 11H9.A1 heavy chain (without signal sequence) | EVQLVESGGG LVKPGGSLRL SCAASGFTFS SYSMNWVRQA PGKGLEWVSS<br>ISSSSSYIYY ADSVKGRFTI SRDNAKNSLY LQMNSLRAED TAVYYCARLL<br>WFGEIFDYWG QGTLVTVSSA STKGPSVFPL APSSKSTSGG TAALGCLVKD<br>YFPEPVTVSW NSGALTSGVH TFPAVLQSSG LYSLSSVVTV PSSSLGTQTY<br>ICNVNHKPSN TKVDKKVEPK SCDKTHTCPP CPAPELLGGP SVFLFPPKPK<br>DTLMISRTPE VTCVVVDVSH EDPEVKFNWY VDGVEVHNAK TKPREEQYNS<br>TYRVVSVLTV LHQDWLNGKE YKCKVSNKAL PAPIEKTISK AKGQPREPQV<br>YTLPPSRDEL TKNQVSLTCL VKGFYPSDIA VEWESNGQPE NNYKTTPPVL<br>DSDGSFFLYS KLTVDKSRWQ QGNVFSCSVM HEALHNHYTQ KSLSLSPGK | 50<br>100<br>150<br>200<br>250<br>300<br>350<br>400<br>449 |
| 50 | 11H9.A1 light chain (without signal sequence) | AIQLTQSPSS LSASVGDRVT ITCRASQGIS SALAWYQQKP GKAPKLLIYD<br>ASSLKSGVPS RFSGSGSGTD FTLTISSLQP EDFATYYCQQ FNSYPITFGQ<br>GTRLEIKRTV AAPSVFIFPP SDEQLKSGTA SVVCLLNNFY PREAKVQWKV<br>DNALQSGNSQ ESVTEQDSKD STYSLSSTLT LSKADYEKHK VYACEVTHQG<br>LSSPVTKSFN RGEC | 50<br>100<br>150<br>200<br>214 |
| | NKG2A.16 Antibody (2G6.C2 antibody) (SEQ ID NOs: 51-64) | | |
| 51 | 2G6.C2 VH (heavy chain variable region nucleotide sequence) | GAGGTGCAAC TGGTGGAGTC TGGGGGAGGC TTGGTACAGC GGGGGGGGTC<br>CCTGAGACTC TCCTGTGCAG CCTCTGGATT CACCTTCAGT AGCAATAGCA<br>TGAACTGGAT CCGCCAGGCT CCAGGGAAGG GGCTGGAGTG GGTTGCACAC<br>ATTAGTAGTG GTAGCAGTTT CATATACTAC GCAGACTCTG TGAAGGGCCG<br>ATTCACCATC TCCAGAGACA ATGCCAAGAA CTCTCTGTCT CTGCAAATGA<br>ACAGCCTGAG AGACGAAGAC ACGGCTGTGT ATTACTGTGC GAGAGATGAC<br>TGGGGAATTG ATGCTTTTAA TATCTGGGGC CAAGGGACAA TGGTCACCGT<br>CTCTTCA | 50<br>100<br>150<br>200<br>250<br>300<br>350<br>357 |
| 52 | 2G6.C2 VH (heavy chain variable region amino acid sequence) | EVQLVESGGG LVQRGGSLRL SCAASGFTFS SNSMNWIRQA PGKGLEWVAH<br>ISSGSSFIYY ADSVKGRFTI SRDNAKNSLS LQMNSLRDED TAVYYCARDD<br>WGIDAFNIWG QGTMVTVSS | 50<br>100<br>119 |

| SEQ ID NO | Name | Sequence | |
|---|---|---|---|
| 53 | 2G6.C2 VL (light chain variable region nucleotide sequence) | GAAATTGTGT TGACACAGTC TCCAGCCACC CTGTCTTTGT CTCCAGGGGA AAGAGCCACC CTCTCCTGCA GGGCCAGTCA GAGTGTTAGC AGCTCCTTAG CCTGGTACCA ACAGAAACCT GGCCAGGCTC CCAGGCTCCT CATCTATGAT GCATCCAACA GGGCCACTGG CATCCCAGCC AGGTTCAGTG GCAGTGGGTC TGGGACAGAC TTCACTCTCA CCATCAGCAG CCTAGAGCCT GAAGATTTTG CAGTTTATTA CTGTCAGCAG CGTAGCAACT GGATATTCAC TTTCGGCCCT GGGACCAAAG TGGATATCAA A | 50 100 150 200 250 300 321 |
| 54 | 2G6.C2 VL (light chain variable region amino acid sequence) | EIVLTQSPAT LSLSPGERAT LSCRASQSVS SSLAWYQQKP GQAPRLLIYD ASNRATGIPA RFSGSGSGTD FTLTISSLEP EDFAVYYCQQ RSNWIFTFGP GTKVDIK | 50 100 107 |
| 55 | 2G6.C2 VH CDR1 | SNSMN | 5 |
| 56 | 2G6.C2 VH CDR2 | HISSGSSFIY YADSVKG | 107 |
| 57 | 2G6.C2 VH CDR3 | DDWGIDAFNI | 10 |
| 58 | 2G6.C2 VL CDR1 | RASQSVSSSL A | 11 |
| 59 | 2G6.C2 VL CDR2 | DASNRAT | 7 |
| 60 | 2G6.C2 VL CDR3 | QQRSNWIFT | 9 |
| 61 | 2G6.C2 CH heavy chain constant region | ASTKGPSVFP LAPSSKSTSG GTAALGCLVK DYFPEPVTVS WNSGALTSGV HTFPAVLQSS GLYSLSSVVT VPSSSLGTQT YICNVNHKPS NTKVDKRVEP KSCDKTHTCP PCPAPELLGG PSVFLFPPKP KDTLMISRTP EVTCVVVDVS HEDPEVKFNW YVDGVEVHNA KTKPREEQYN STYRVVSVLT VLHQDWLNGK EYKCKVSNKA LPAPIEKTIS KAKGQPREPQ VYTLPPSRDE LTKNQVSLTC LVKGFYPSDI AVEWESNGQP ENNYKTTPPV LDSDGSFFLY SKLTVDKSRW QQGNVFSCSV MHEALHNHYT QKSLSLSPGK | 50 100 150 200 250 300 330 |
| 62 | 2G6.C2 CL light chain constant region | RTVAAPSVFI FPPSDEQLKS GTASVVCLLN NFYPREAKVQ WKVDNALQSG NSQESVTEQD SKDSTYSLSS TLTLSKADYE KHKVYACEVT HQGLSSPVTK SFNRGEC | 50 100 107 |
| 63 | 2G6.C2 heavy chain | EVQLVESGGG LVQRGGSLRL SCAASGFTFS SNSMNWIRQA PGKGLEWVAH ISSGSSFIYY ADSVKGRFTI SRDNAKNSLS LQMNSLRDED TAVYYCARDD WGIDAFNIWG QGMTVTVSSA STKGPSVFPL APSSKSTSGG TAALGCLVKD YFPEPVTVSW NSGALTSGVH TFPAVLQSSG LYSLSSVVTV PSSSLGTQTY ICNVNHKPSN TKVDKRVEPK SCDKTHTCPP CPAPELLGGP SVFLFPPKPK DTLMISRTPE VTCVVVDVSH EDPEVKFNWY VDGVEVHNAK TKPREEQYNS TYRVVSVLTV LHQDWLNGKE YKCKVSNKAL PAPIEKTISK AKGQPREPQV YTLPPSRDEL TKNQVSLTCL VKGFYPSDIA VEWESNGQPE NNYKTTPPVL DSDGSFFLYS KLTVDKSRWQ QGNVFSCSVM HEALHNHYTQ KSLSLSPGK | 50 100 150 200 250 300 350 400 459 |
| 64 | 2G6.C2 light chain | EIVLTQSPAT LSLSPGERAT LSCRASQSVS SSLAWYQQKP GQAPRLLIYD ASNRATGIPA RFSGSGSGTD FTLTISSLEP EDFAVYYCQQ RSNWIFTFGP GTKVDIKRTV AAPSVFIFPP SDEQLKSGTA SVVCLLNNFY PREAKVQWKV DNALQSGNSQ ESVTEQDSKD STYSLSSTLT LSKADYEKHK VYACEVTHQG LSSPVTKSFN RGEC | 50 100 150 200 214 |
| 4G5.D1 Antibody (SEQ ID NOs: 65-78, 174-177) | | | |
| 65 | 4G5.D1 VH (heavy chain variable region nucleotide | ATGAACACCC TGTGGTTCTT CCTCCTCCTG GTGGCAGCTC CCAGATGGGT CCTGTCC CAGATGCAGC TGCAGGAGTC GGGCCCAGGA CTGGTGAAGC CTTCGGAGAC CCTGTCCCTC ACCTGCACTG TCTCTGGTGG CTCCGTCAGC AGTGGTCGTT ACTACTGGAG TTGGATCCGG CAGCCCCCCG GGAAGGGACT GGAGTGGATT GGGTATATCT ATTACAGTGG GAGCACCAAC TACAACCCCT CCCTCAAGAG | -57 -7 50 100 150 200 |

| SEQ ID NO | Name | Sequence | |
|---|---|---|---|
| | sequence) (with 57-nucleotide signal sequence) | TCGAGTCACC ATATCAGTAG ACACGTCCAA GAACCAGTTC TCCCTGAAGC<br>TGACCTCTGT GACCGCTGCG GACACGGCCG TGTATTACTG TGCGAGAGAG<br>GGTGGAGACT ACTACTACTA CAATATGGAC GTCTGGGGCC CAGGGACCAC<br>GGTCACCGTC TCCTCA | 250<br>300<br>350<br>367 |
| 174 | 4G5.D1 VH nucleotide sequence (without signal sequence) | CAGATGCAGC TGCAGGAGTC GGGCCCAGGA CTGGTGAAGC CTTCGGAGAC<br>CCTGTCCCTC ACCTGCACTG TCTCTGGTGG CTCCGTCAGC AGTGGTCGTT<br>ACTACTGGAG TTGGATCCGG CAGCCCCCCG GGAAGGGACT GGAGTGGATT<br>GGGTATATCT ATTACAGTGG GAGCACCAAC TACAACCCCT CCCTCAAGAG<br>TCGAGTCACC ATATCAGTAG ACACGTCCAA GAACCAGTTC TCCCTGAAGC<br>TGACCTCTGT GACCGCTGCG GACACGGCCG TGTATTACTG TGCGAGAGAG<br>GGTGGAGACT ACTACTACTA CAATATGGAC GTCTGGGGCC CAGGGACCAC<br>GGTCACCGTC TCCTCA | 50<br>100<br>150<br>200<br>250<br>300<br>350<br>367 |
| 66 | 4G5.D1 VH amino acid sequence (with 19-amino acid signal sequence) | MKHLWFFLLL VAAPRWVLS<br>QMQLQESGPG LVKPSETLSL TCTVSGGSVS SGRYYWSWIR QPPGKGLEWI<br>GYIYYSGSTN YNPSLKSRVT ISVDTSKNQF SLKLTSVTAA DTAVYYCARE<br>GGDYYYYNMD VWGPGTTVTV SS | -19<br>50<br>100<br>122 |
| 175 | 4G5.D1 VH amino acid sequence (without signal sequence) | QMQLQESGPG LVKPSETLSL TCTVSGGSVS SGRYYWSWIR QPPGKGLEWI<br>GYIYYSGSTN YNPSLKSRVT ISVDTSKNQF SLKLTSVTAA DTAVYYCARE<br>GGDYYYYNMD VWGPGTTVTV SS | 50<br>100<br>122 |
| 67 | 4G5.D1 VL nucleotide sequence (with 60-nucleotide signal sequence) | ATGGAAACCC CAGCGCAGCT TCTCTTCCTC CTGCTACTCT GGCTCCCAGA<br>TACCACCGGA<br>GAAATTGTGT TGACGCAGTC TCCAGGCACC CTGTCTTTGT CTCCAGGGGA<br>AAGAGCCACC CTCTCCTGCA GGGCCAGTCA GAGTGTTAGC AGCAGCTACT<br>TAGCCTGGTA CCAGCAGAAA CCTGGCCAGG CTCCCAGGCT CCTCATCTAT<br>GGTGCATCCA GCAGGGCCAC TGGCATCCCA GACAGGTTCA GTGGCAGTGG<br>GTCTGGGACA GACTTCACTC TCACCATCAG CAGACTGGAG CCTGAAGATT<br>TTGCAGTGTA TTACTGTCAG CAGTATGGTA GCTCACCGTA CACTTTTGGC<br>CAGGGGACCA AGCTGGAGAT CAAA | -60<br>-10<br>50<br>100<br>150<br>200<br>250<br>300<br>324 |
| 176 | 4G5.D1 VL nucleotide sequence (without signal sequence) | GAAATTGTGT TGACGCAGTC TCCAGGCACC CTGTCTTTGT CTCCAGGGGA<br>AAGAGCCACC CTCTCCTGCA GGGCCAGTCA GAGTGTTAGC AGCAGCTACT<br>TAGCCTGGTA CCAGCAGAAA CCTGGCCAGG CTCCCAGGCT CCTCATCTAT<br>GGTGCATCCA GCAGGGCCAC TGGCATCCCA GACAGGTTCA GTGGCAGTGG<br>GTCTGGGACA GACTTCACTC TCACCATCAG CAGACTGGAG CCTGAAGATT<br>TTGCAGTGTA TTACTGTCAG CAGTATGGTA GCTCACCGTA CACTTTTGGC<br>CAGGGGACCA AGCTGGAGAT CAAA | 50<br>100<br>150<br>200<br>250<br>300<br>324 |
| 68 | 4G5.D1 VL amino acid sequence (with 20-amino acid signal sequence) | METPAQLLFL LLLWLPDTTG<br>EIVLTQSPGT LSLSPGERAT LSCRASQSVS SSYLAWYQQK PGQAPRLLIY<br>GASSRATGIP DRFSGSGSGT DFTLTISRLE PEDFAVYYCQ QYGSSPYTFG<br>QGTKLEIK | -20<br>50<br>100<br>108 |
| 177 | 4G5.D1 VL amino acid sequence (without signal sequence) | EIVLTQSPGT LSLSPGERAT LSCRASQSVS SSYLAWYQQK PGQAPRLLIY<br>GASSRATGIP DRFSGSGSGT DFTLTISRLE PEDFAVYYCQ QYGSSPYTFG<br>QGTKLEIK | 50<br>100<br>108 |
| 69 | 4G5.D1 VH CDR1 | SGRYYWS | 8 |
| 70 | 4G5.D1 VH CDR2 | YIYYSGSTNY NPSLKS | 16 |

| SEQ ID NO | Name | Sequence | |
|---|---|---|---|
| 71 | 4G5.D1 VH CDR3 | EGGDYYYYNM DV | 12 |
| 72 | 4G5.D1 VL CDR1 | RASQSVSSSY LA | 12 |
| 73 | 4G5.D1 VL CDR2 | GASSRAT | 7 |
| 74 | 4G5.D1 VL CDR3 | QQYGSSPYT | 9 |
| 75 | 4G5.D1 CH heavy chain constant region | ASTKGPSVFP LAPSSKSTSG GTAALGCLVK DYFPEPVTVS WNSGALTSGV<br>HTFPAVLQSS GLYSLSSVVT VPSSSLGTQT YICNVNHKPS NTKVDKRVEP<br>KSCDKTHTCP PCPAPELLGG PSVFLFPPKP KDTLMISRTP EVTCVVVDVS<br>HEDPEVKFNW YVDGVEVHNA KTKPREEQYN STYRVVSVLT VLHQDWLNGK<br>EYKCKVSNKA LPAPIEKTIS KAKGQPREPQ VYTLPPSRDE LTKNQVSLTC<br>LVKGFYPSDI AVEWESNGQP ENNYKTTPPV LDSDGSFFLY SKLTVDKSRW<br>QQGNVFSCSV MHEALHNHYT QKSLSLSPGK | 50<br>100<br>150<br>200<br>250<br>300<br>330 |
| 76 | 4G5.D1 CL light chain constant region | RTVAAPSVFI FPPSDEQLKS GTASVVCLLN NFYPREAKVQ WKVDNALQSG<br>NSQESVTEQD SKDSTYSLSS TLTLSKADYE KHKVYACEVT HQGLSSPVTK<br>SFNRGEC | 50<br>100<br>107 |
| 77 | 4G5.D1 heavy chain | QMQLQESGPG LVKPSETLSL TCTVSGGSVS SGRYYWSWIR QPPGKGLEWI<br>GYIYYSGSTN YNPSLKSRVT ISVDTSKNQF SLKLTSVTAA DTAVYYCARE<br>GGDYYYYNMD VWGPGTTVTV SSASTKGPSV FPLAPSSKST SGGTAALGCL<br>VKDYFPEPVT VSWNSGALTS GVHTFPAVLQ SSGLYSLSSV VTVPSSSLGT<br>QTYICNVNHK PSNTKVDKRV EPKSCDKTHT CPPCPAPELL GGPSVFLFPP<br>KPKDTLMISR TPEVTCVVVD VSHEDPEVKF NWYVDGVEVH NAKTKPREEQ<br>YNSTYRVVSV LTVLHQDWLN GKEYKCKVSN KALPAPIEKT ISKAKGQPRE<br>PQVYTLPPSR DELTKNQVSL TCLVKGFYPS DIAVEWESNG QPENNYKTTP<br>PVLDSDGSFF LYSKLTVDKS RWQQGNVFSC SVMHEALHNH YTQKSLSLSP<br>GK | 50<br>100<br>150<br>200<br>250<br>300<br>350<br>400<br>450<br>452 |
| 78 | 4G5.D1 light chain | EIVLTQSPGT LSLSPGERAT LSCRASQSVS SSYLAWYQQK PGQAPRLLIY<br>GASSRATGIP DRFSGSGSGT DFTLTISRLE PEDFAVYYCQ QYGSSPYTFG<br>QGTKLEIKRT VAAPSVFIFP PSDEQLKSGT ASVVCLLNNF YPREAKVQWK<br>VDNALQSGNS QESVTEQDSK DSTYSLSSTL TLSKADYEKH KVYACEVTHQ<br>GLSSPVTKSF NRGEC | 50<br>100<br>150<br>200<br>215 |
| | 1G5.B2 Antibody (SEQ ID NOs: 79-92, 178-181) | | |
| 79 | 1G5.B2 VH nucleotide sequence (with 57-nucleotide signal sequence) | ATGGAGTTTG GGCTGAGCTG GGTTTTCCTC GTTGCTCTTT TAAGAGGTGT<br>CCAGTGT<br>CAGGTGCAGC TGGTGGAGTC TGGGGGAGGC GTGGTCCAGC CTGGGAGGTC<br>CCTGAGACTC TCCTGTGCAG CCTCTGGATT CACCTTCAGT GACTATGCTA<br>TGCACTGGGT CCGCCAGACT CCAGGCAGGG GGCTGGAGTG GCTGACATTT<br>ATATCATATG ATGGAAGCAA TAAATACCAC GCAGACTCCG TGAAGGGCCG<br>ATTCACCATC TCCAGAGACA ATTCCAAGAA CACGCTGTTT CTGCAAATGA<br>ACAGTCTGAG AGCTGAGGAC ACGGCTGTTT ATTACTGTGC GAGAGATTCC<br>TGGGATCGGG GGTACTTCGA TCTCTGGGGC CGTGGCACCC TGGTCACTGT<br>CTCCTCA | -57<br>-7<br>50<br>100<br>150<br>200<br>250<br>300<br>350<br>357 |
| 178 | 1G5.B2 VH nucleotide sequence (without signal sequence) | CAGGTGCAGC TGGTGGAGTC TGGGGGAGGC GTGGTCCAGC CTGGGAGGTC<br>CCTGAGACTC TCCTGTGCAG CCTCTGGATT CACCTTCAGT GACTATGCTA<br>TGCACTGGGT CCGCCAGACT CCAGGCAGGG GGCTGGAGTG GCTGACATTT<br>ATATCATATG ATGGAAGCAA TAAATACCAC GCAGACTCCG TGAAGGGCCG<br>ATTCACCATC TCCAGAGACA ATTCCAAGAA CACGCTGTTT CTGCAAATGA<br>ACAGTCTGAG AGCTGAGGAC ACGGCTGTTT ATTACTGTGC GAGAGATTCC<br>TGGGATCGGG GGTACTTCGA TCTCTGGGGC CGTGGCACCC TGGTCACTGT<br>CTCCTCA | 50<br>100<br>150<br>200<br>250<br>300<br>350<br>357 |
| 80 | 1G5.B2 VH amino acid sequence (with 19-amino acid signal sequence) | MEFGLSWVFL VALLRGVQC<br>QVQLVESGGG VVQPGRSLRL SCAASGFTFS DYAMHWVRQT PGRGLEWLTF<br>ISYDGSNKYH ADSVKGRFTI SRDNSKNTLF LQMNSLRAED TAVYYCARDS<br>WDRGYFDLWG RGTLVTVSS | -19<br>50<br>100<br>119 |

| SEQ ID NO | Name | Sequence | |
|---|---|---|---|
| 179 | 1G5.B2 VH amino acid sequence (without signal sequence) | QVQLVESGGG VVQPGRSLRL SCAASGFTFS DYAMHWVRQT PGRGLEWLTF<br>ISYDGSNKYH ADSVKGRFTI SRDNSKNTLF LQMNSLRAED TAVYYCARDS<br>WDRGYFDLWG RGTLVTVSS | 50<br>100<br>119 |
| 81 | 1G5.B2 VL nucleotide sequence (with 60-nucleotide signal sequence) | ATGGAAGCCC CAGCTCAGCT TCTCTTCCTC CTGCTACTCT GGCTCCCAGA<br>TACCACCGGA<br>GAAATTGTGT TGACACAGTC TCCAGCCACC CTGTCTTTGT CTCCAGGGGA<br>AAGAGCCACC CTCTCCTGCA GGGCCAGTCA GAGTGTTAGC AGCTACTTAG<br>CCTGGTACCA ACAGAAACCT GGCCAGGCTC CCAGGCTCCT CATCTATGAT<br>GCATCCAACA GGGCCACTGG CATCCCAGCC AGGTTCAGTG GCAGTGGGTC<br>TGGGACAGAC TTCACTCTCA CCATCAGCAG CCTAGAGCCT GAAGATTTTG<br>CAGTTTATTA CTGTCAGCAG CGTAGCAACT GGTGGACGTT CGGCCAAGGG<br>ACCAAGGTGG AAATCAAA | -60<br>-10<br>50<br>100<br>150<br>200<br>250<br>300<br>318 |
| 180 | 1G5.B2 VL nucleotide sequence (without signal sequence) | GAAATTGTGT TGACACAGTC TCCAGCCACC CTGTCTTTGT CTCCAGGGGA<br>AAGAGCCACC CTCTCCTGCA GGGCCAGTCA GAGTGTTAGC AGCTACTTAG<br>CCTGGTACCA ACAGAAACCT GGCCAGGCTC CCAGGCTCCT CATCTATGAT<br>GCATCCAACA GGGCCACTGG CATCCCAGCC AGGTTCAGTG GCAGTGGGTC<br>TGGGACAGAC TTCACTCTCA CCATCAGCAG CCTAGAGCCT GAAGATTTTG<br>CAGTTTATTA CTGTCAGCAG CGTAGCAACT GGTGGACGTT CGGCCAAGGG<br>ACCAAGGTGG AAATCAAA | 50<br>100<br>150<br>200<br>250<br>300<br>318 |
| 82 | 1G5.B2 VL amino acid sequence (with 20-amino acid signal sequence) | MEAPAQLLFL LLLWLPDTTG<br>EIVLTQSPAT LSLSPGERAT LSCRASQSVS SYLAWYQQKP GQAPRLLIYD<br>ASNRATGIPA RFSGSGSGTD FTLTISSLEP EDFAVYYCQQ RSNWWTFGQG<br>TKVEIK | -20<br>50<br>100<br>106 |
| 181 | 1G5.B2 VL amino acid sequence (without signal sequence) | EIVLTQSPAT LSLSPGERAT LSCRASQSVS SYLAWYQQKP GQAPRLLIYD<br>ASNRATGIPA RFSGSGSGTD FTLTISSLEP EDFAVYYCQQ RSNWWTFGQG<br>TKVEIK | 50<br>100<br>106 |
| 83 | 1G5.B2 VH CDR1 | DYAMH | 5 |
| 84 | 1G5.B2 VH CDR2 | FISYDGSNKY HADSVKG | 17 |
| 85 | 1G5.B2 VH CDR3 | DSWDRGYFDL | 10 |
| 86 | 1G5.B2 VL CDR1 | RASQSVSSYL A | 11 |
| 87 | 1G5.B2 VL CDR2 | DASNRAT | 7 |
| 88 | 1G5.B2 VL CDR3 | QQRSNWWT | 8 |
| 89 | 1G5.B2 CH heavy chain constant region | ASTKGPSVFP LAPSSKSTSG GTAALGCLVK DYFPEPVTVS WNSGALTSGV<br>HTPPAVLQSS GLYSLSSVVT VPSSSLGTQT YICNVNHKPS NTKVDKRVEP<br>KSCDKTHTCP PCPAPELLGG PSVFLFPPKP KDTLMISRTP EVTCVVVDVS<br>HEDPEVKFNW YVDGVEVHNA KTKPREEQYN STYRVVSVLT VLHQDWLNGK<br>EYKCKVSNKA LPAPIEKTIS KAKGQPREPQ VYTLPPSRDE LTKNQVSLTC<br>LVKGFYPSDI AVEWESNGQP ENNYKTTPPV LDSDGSFFLY SKLTVDKSRW<br>QQGNVFSCSV MHEALHNHYT QKSLSLSPGK | 50<br>100<br>150<br>200<br>250<br>300<br>330 |

| SEQ ID NO | Name | Sequence | |
|---|---|---|---|
| 90 | 1G5.B2 CL light chain constant region | RTVAAPSVFI FPPSDEQLKS GTASWCLLN NFYPREAKVQ WKVDNALQSG<br>NSQESVTEQD SKDSTYSLSS TLTLSKADYE KHKVYACEVT HQGLSSPVTK<br>SFNRGEC | 50<br>100<br>107 |
| 91 | 1G5.B2 heavy chain (without signal sequence) | QVQLVESGGG WQPGRSLRL SCAASGFTFS DYAMHWVRQT PGRGLEWLTF<br>ISYDGSNKYH ADSVKGRFTI SRDNSKNTLF LQMNSLRAED TAVYYCARDS<br>WDRGYFDLWG RGTLVTVSSA STKGPSVFPL APSSKSTSGG TAALGCLVKD<br>YFPEPVTVSW NSGALTSGVH TFPAVLQSSG LYSLSSVVTV PSSSLGTQTY<br>ICNVNHKPSN TKVDKRVEPK SCDKTHTCPP CPAPELLGGP SVFLFPPKPK<br>DTLMISRTPE VTCVVVDVSH EDPEVKFNWY VDGVEVHNAK TKPREEQYNS<br>TYRVVSVLTV LHQDWLNGKE YKCKVSNKAL PAPIEKTISK AKGQPREPQV<br>YTLPPSRDEL TKNQVSLTCL VKGFYPSDIA VEWESNGQPE NNYKTTPPVL<br>DSDGSFFLYS KLTVDKSRWQ QGNVFSCSVM HEALHNHYTQ KSLSLSPGK | 50<br>100<br>150<br>200<br>250<br>300<br>350<br>400<br>449 |
| 92 | 1G5.B2 light chain (without signal sequence) | EIVLTQSPAT LSLSPGERAT LSCRASQSVS SYLAWYQQKP GQAPRLLIYD<br>ASNRATGIPA RFSGSGSGTD FTLTISSLEP EDFAVYYCQQ RSNWWTFGQG<br>TKVEIKRTVA APSVFIFPPS DEQLKSGTAS VVCLLNNFYP REAKVQWKVD<br>NALQSGNSQE SVTEQDSKDS TYSLSSTLTL SKADYEKHKV YACEVTHQGL<br>SSPVTKSFNR GEC | 50<br>100<br>150<br>200<br>213 |
| | P1-069366 Antibody (SEQ ID NOs: 93-104) | | |
| 93 | P1-069366 VH (heavy chain variable region amino acid sequence) | QVQLVESGGG VVQPGRSLRL SCAASGFTFS SYAMHWVRQA PGKGLEWVAV<br>ISYDGSYKEY ADSVKGRFTI SRDSSKNTLY LQMNSLRAED TAVYYCARAQ<br>ISEYFDYWGQ GTLVTVSS | 50<br>100<br>118 |
| 94 | P1-069366 VL (light chain variable region amino acid sequence) | DIQMTQSPSS LSASVGDRVT ITCRASQGIS SWLAWYQQKP EKAPKSLIYA<br>ASSLQSGVPS RFSGSGSGTD FTLTISSLQP EDFATYYCQQ YNSYPLTFGQ<br>GTKVEIK | 50<br>100<br>107 |
| 95 | P1-069366 VH CDR1 | SYAMH | 5 |
| 96 | P1-069366 VH CDR2 | VISYDGSYKEYADSVKG | |
| 97 | P1-069366 VH CDR3 | AQISEYFDY | |
| 98 | P1-069366 VL CDR1 | RASQGISSWLA | |
| 99 | P1-069366 VL CDR2 | AASSLQS | |
| 100 | P1-069366 VL CDR3 | QQYNSYPLT | |
| 101 | P1-069366 CH heavy chain constant region | ASTKGPSVFP LAPSSKSTSG GTAALGCLVK DYFPEPVTVS WNSGALTSGV<br>HTFPAVLQSS GLYSLSSWT VPSSSLGTQT YICNVNHKPS NTKVDKRVEP<br>KSCDKTHTCP PCPAPEAEGA PSVFLFPPKP KDTLMISRTP EVTCVVVDVS<br>HEDPEVKFNW YVDGVEVHNA KTKPREEQYN STYRVVSVLT VLHQDWLNGK<br>EYKCKVSNKA LPAPIEKTIS KAKGQPREPQ VYTLPPSREE MTKNQVSLTC<br>LVKGFYPSDI AVEWESNGQP ENNYKTTPPV LDSDGSFFLY SKLTVDKSRW<br>QQGNVFSCSV MHEALHNHYT QKSLSLSPG | 50<br>100<br>150<br>200<br>250<br>300<br>329 |
| 102 | P1-069366 CL light chain constant region | RTVAAPSVFI FPPSDEQLKS GTASVVCLLN NFYPREAKVQ WKVDNALQSG<br>NSQESVTEQD SKDSTYSLSS TLTLSKADYE KHKVYACEVT HQGLSSPVTK<br>SFNRGEC | 50<br>100<br>107 |

| SEQ ID NO | Name | Sequence | |
|---|---|---|---|
| 103 | P1-069366 heavy chain without signal sequence | QVQLVESGGG VVQPGRSLRL SCAASGFTFS SYAMHWVRQA PGKGLEWVAV<br>ISYDGSYKEY ADSVKGRFTI SRDSSKNTLY LQMNSLRAED TAVYYCARAQ<br>ISEYFDYWGQ GTLVTVSSAS TKGPSVFPLA PSSKSTSGGT AALGCLVKDY<br>FPEPVTVSWN SGALTSGVHT FPAVLQSSGL YSLSSVVTVP SSSLGTQTYI<br>CNVNHKPSNT KVDKRVEPKS CDKTHTCPPC PAPEAEGAPS VFLFPPKPKD<br>TLMISRTPEV TCVVVDVSHE DPEVKFNWYV DGVEVHNAKT KPREEQYNST<br>YRVVSVLTVL HQDWLNGKEY KCKVSNKALP APIEKTISKA KGQPREPQVY<br>TLPPSREEMT KNQVSLTCLV KGFYPSDIAV EWESNGQPEN NYKTTPPVLD<br>SDGSFFLYSK LTVDKSRWQQ GNVFSCSVMH EALHNHYTQK SLSLSPG | 50<br>100<br>150<br>200<br>250<br>300<br>350<br>400<br>447 |
| 104 | P1-069366 light chain without signal sequence | DIQMTQSPSS LSASVGDRVT ITCRASQGIS SWLAWYQQKP EKAPKSLIYA<br>ASSLQSGVPS RFSGSGSGTD FTLTISSLQP EDFATYYCQQ YNSYPLTFGQ<br>GTKVEIKRTV AAPSVFIFPP SDEQLKSGTA SVVCLLNNFY PREAKVQWKV<br>DNALQSGNSQ ESVTEQDSKD STYSLSSTLT LSKADYEKHK VYACEVTHQG<br>LSSPVTKSFN RGEC | 50<br>100<br>150<br>200<br>214 |

NKG2A.17 Antibody (chimeric anti-NKG2A 27H4.D4) (mG1-D265A isotype)
(SEQ ID NOs: 105-118)

| | | | |
|---|---|---|---|
| 105 | 27H4.D4 VH (heavy chain variable region nucleotide sequence) | CAGGTGCAAC TAGTGGAGTC TGGGGGAGGC TTGGTCAAGC CTGGAGGGTC<br>CCTCAGACTC TCCTGTGCAG CCTCTGGGTT CACCTTCAGT GACTTCTACA<br>TGAGCTGGAT CCGCCAGGCT CCAGGGAAGG GGCTGGAGTG GATTTCATAC<br>ATTAGTAGTA GTGATTTTAC CATATACTAC GCAGACTCTG TGGAGGGCCG<br>ATTCACCATC TCCAGGGACA ACGCCAAGAA CTCACTGTTT CTGCAAATGA<br>ACAGCCTGAG AGCCGAGGAC ACGGCTGTGT ATTACTGTGC GAGAAGAGGG<br>AGCCTTCCTT TCAACTACGA TATGGACGTC TGGGGCCAAG GGACCACGGT<br>CACCGTCTCC TCA | 50<br>100<br>150<br>200<br>250<br>300<br>350<br>363 |
| 106 | 27H4.D4 VH (heavy chain variable region amino acid sequence) | QVQLVESGGG LVKPGGSLRL SCAASGFTFS DFYMSWIRQA PGKGLEWISY<br>ISSSDFTIYY ADSVEGRFTI SRDNAKNSLF LQMNSLRAED TAVYYCARRG<br>SLPFNYDMDV WGQGTTVTVS S | 50<br>100<br>121 |
| 107 | 27H4.D4 VL (light chain variable region nucleotide sequence) | GACATCCAGA TGACCCAGTC TCCATCTTCC GTGTCTGCAT CTGTAGGAGA<br>CAGAGTCACC ATCTCTTGTC GGGCGAGTCA GGGTATTAGC AGCTACTTAG<br>CCTGGTATCA GCATAAACCA GGGAAAGCCC CTAAGCTCCT GATCTATGCT<br>GCATCCAGTT TGCAAAGTGG GGTCCCATCA AGGTTCAGCG GCAGTGGATC<br>TGGGACAGCT TCACTCTCA CCATCAGCAG CCTGCAGCCT GAAGATTTTG<br>CAACTTACTA TTGTCAACAG GCTAATAGTT TCCCGCTCAC TTTCGGCGGA<br>GGGACCAAGG TGGAGATCAA A | 50<br>100<br>150<br>200<br>250<br>500<br>521 |
| 108 | 27H4.D4 VL (light chain variable region amino acid sequence) | DIQMTQSPSS VSASVGDRVT ISCRASQGIS SYLAWYQHKP GKAPKLLIYA<br>ASSLQSGVPS RFSGSGSGTA FTLTISSLQP EDFATYYCQQ ANSFPLTFGG<br>GTKVEIK | 50<br>100<br>107 |
| 109 | 27H4.D4 VH CDR1 | DFYMS | 5 |
| 110 | 27H4.D4 VH CDR2 | YISSSDFTIY YADSVEG | 17 |
| 111 | 27H4.D4 VH CDR3 | RGSLPFNYDM DV | 12 |
| 112 | 27H4.D4 VL CDR1 | RASQGISSYL A | 11 |
| 113 | 27H4.D4 VL CDR2 | AASSLQS | 7 |
| 114 | 27H4.D4 VL CDR3 | QQANSFPLT | 9 |

| SEQ ID NO | Name | Sequence | |
|---|---|---|---|
| 115 | 27H4.D4 CH heavy chain constant region | ASTKGPSVFP LAPSSKSTSG GTAALGCLVK DYFPEPVTVS WNSGALTSGV<br>HTFPAVLQSS GLYSLSSVVT VPSSSLGTQT YICNVNHKPS NTKVDKKVEP<br>KSCDKTHTCP PCPAPELLGG PSVFLFPPKP KDTLMISRTP EVTCVVVDVS<br>HEDPEVKFNW YVDGVEVHNA KTKPREEQYN STYRVVSVLT VLHQDWLNGK<br>EYKCKVSNKA LPAPIEKTIS KAKGQPREPQ VYTLPPSRDE LTKNQVSLTC<br>LVKGFYPSDI AVEWESNGQP ENNYKTTPPV LDSDGSFFLY SKLTVDKSRW<br>QQGNVFSCSV MHEALHNHYT QKSLSLSPGK | 50<br>100<br>150<br>200<br>250<br>300<br>330 |
| 116 | 27H4.D4 CL light chain constant region | RTVAAPSVFI FPPSDEQLKS GTASVVCLLN NFYPREAKVQ WKVDNALQSG<br>NSQESVTEQD SKDSTYSLSS TLTLSKADYE KHKVYACEVT HQGLSSPVTK<br>SFNRGEC | 50<br>100<br>107 |
| 117 | 27H4.D4 heavy chain without signal sequence | QVQLVESGGG LVKPGGSLRL SCAASGFTFS DFYMSWIRQA PGKGLEWISY<br>ISSSDFTIYY ADSVEGRFTI SRDNAKNSLF LQMNSLRAED TAVYYCARRG<br>SLPFNYDMDV WGQGTTVTVS SASTKGPSVF PLAPSSKSTS GGTAALGCLV<br>KDYFPEPVTV SWNSGALTSG VHTFPAVLQS SGLYSLSSVV TVPSSSLGTQ<br>TYICNVNHKP SNTKVDKKVE PKSCDKTHTC PPCPAPELLG GPSVFLFPPK<br>PKDTLMISRT PEVTCVVVDV SHEDPEVKFN WYVDGVEVHN AKTKPREEQY<br>NSTYRVVSVL TVLHQDWLNG KEYKCKVSNK ALPAPIEKTI SKAKGQPREP<br>QVYTLPPSRD ELTKNQVSLT CLVKGFYPSD IAVEWESNGQ PENNYKTTPP<br>VLDSDGSFFL YSKLTVDKSR WQQGNVFSCS VMHEALHNHY TQKSLSLSPG<br>K | 50<br>100<br>150<br>200<br>250<br>300<br>350<br>400<br>450<br>451 |
| 118 | 27H4.D4 light chain without signal sequence | DIQMTQSPSS VSASVGDRVT ISCRASQGIS SYLAWYQHKP GKAPKLLIYA<br>ASSLQSGVPS RFSGSGSGTA FTLTISSLQP EDFATYYCQQ ANSFPLTFGG<br>GTKVEIKRTV AAPSVFIFPP SDEQLKSGTA SVVCLLNNFY PREAKVQWKV<br>DNALQSGNSQ ESVTEQDSKD STYSLSSTLT LSKADYEKHK VYACEVTHQG<br>LSSPVTKSFN RGEC | 50<br>100<br>150<br>200<br>214 |

NKG2A.10 Antibody (13F3.A4 VH-I107T, VK-N30Q)) (13F3.A4 with VH-I107T framework reversion and VK-N30Q to remove deamidation site) (SEQ ID NOs: 126-127)

| 126 | NKG2A.10 heavy chain | EVQLVESGGG LVKPGGSLRL SCAASGFTFS SHSMNWVRQA PGKGLEWVSA<br>ISSSSSYIYY ADSVKGRFTI SRDNAKNSLY LQMNSLRAED TAVYYCAREE<br>WGLPFDYWGQ GTLVTVSSAS TKGPSVFPLA PSSKSTSGGT AALGCLVKDY<br>FPEPVTVSWN SGALTSGVHT FPA | 50<br>100<br>150<br>173 |
| 127 | NKG2A.10 light chain | AIQLTQSPSS LSASVGDRVT ITCRASQGIQ SALAWYQQKP GKAPKLLIYD<br>ASSLKSGVPS RFSGSGSGTD FTLTISSLQP EDFATYYCQQ FNSYPLTFGQ<br>GTRLEIKRTV AAPSVFIFPP SDEQLKSGTA SVVCLLNNFY PREAKVQWKV<br>DNALQSGNSQ ESVTEQDSKD STYSLSSTLT LSKADYEKHK VYACEVTHQG<br>LSSPVTKSFN RGEC | 50<br>100<br>150<br>200<br>214 |

NKG2A.12 Antibody (13F3.A4 VH-I107T) (13F3.A4 antibody with VH-107T framework reversion) (SEQ ID NOs: 128-129)

| 128 | NKG2A.12 heavy chain | EVQLVESGGG LVKPGGSLRL SCAASGFTFS SHSMNWVRQA PGKGLEWVSA<br>ISSSSSYIYY ADSVKGRFTI SRDNAKNSLY LQMNSLRAED TAVYYCAREE<br>WGLPFDYWGQ GTLVTVSSAS TKGPSVFPLA PSSKSTSGGT AALGCLVKDY<br>FPEPVTVSWN SGALTSGVHT FPAVLQSSGL YSLSSVVTVP SSSLGTQTYI<br>CNVNHKPSNT KVDKRVEPKS CDKTHTCPPC PAPEAEGAPS VFLFPPKPKD<br>TLMISRTPEV TCVVVDVSHE DPEVKFNWYV DGVEVHNAKT KPREEQYNST<br>YRVVSVLTVL HQDWLNGKEY KCKVSNKALP APIEKTISKA KGQPREPQVY<br>TLPPSREEMT KNQVSLTCLV KGFYPSDIAV EWESNGQPEN NYKTTPPVLD<br>SDGSFFLYSK LTVDKSRWQQ GNVFSCSVMH EALHNHYTQK SLSLSPGK | 50<br>100<br>150<br>200<br>250<br>300<br>350<br>400<br>448 |
| 129 | NKG2A.12 light chain | AIQLTQSPSS LSASVGDRVT ITCRASQGIN SALAWYQQKP GKAPKLLIYD<br>ASSLKSGVPS RFSGSGSGTD FTLTISSLQP EDFATYYCQQ FNSYPLTFGQ<br>GTRLEIKRTV AAPSVFIFPP SDEQLKSGTA SVVCLLNNFY PREAKVQWKV<br>DNALQSGNSQ ESVTEQDSKD STYSLSSTLT LSKADYEKHK VYACEVTHQG<br>LSSPVTKSFN RGEC | 50<br>100<br>150<br>200<br>214 |

NKG2A.14 Antibody (13F3.A4 VK-N30Q) (13F3.A4 antibody with N30Q to remove deamidation site) (SEQ ID NOs: 130-131)

| 130 | NKG2A.14 heavy chain | EVQLVESGGG LVKPGGSLRL SCAASGFTFS SHSMNWVRQA PGKGLEWVSA<br>ISSSSSYIYY ADSVKGRFTI SRDNAKNSLY LQMNSLRAED TAVYYCAREE<br>WGLPFDYWGQ GILVTVSSAS TKGPSVFPLA PSSKSTSGGT AALGCLVKDY<br>FPEPVTVSWN SGALTSGVHT FPAVLQSSGL YSLSSVVTVP SSSLGTQTYI<br>CNVNHKPSNT KVDKRVEPKS CDKTHTCPPC PAPEAEGAPS VFLFPPKPKD | 50<br>100<br>150<br>200<br>250 |

| SEQ ID NO | Name | Sequence | |
|---|---|---|---|
| | | TLMISRTPEV TCVVVDVSHE DPEVKFNWYV DGVEVHNAKT KPREEQYNST | 300 |
| | | YRVVSVLTVL HQDWLNGKEY KCKVSNKALP APIEKTISKA KGQPREPQVY | 350 |
| | | TLPPSREEMT KNQVSLTCLV KGFYPSDIAV EWESNGQPEN NYKTTPPVLD | 400 |
| | | SDGSFFLYSK LTVDKSRWQQ GNVFSCSVMH EALHNHYTQK SLSLSPGK | 448 |
| 131 | NKG2A.14 light chain | AIQLTQSPSS LSASVGDRVT ITCRASQGIQ SALAWYQQKP GKAPKLLIYD | 50 |
| | | ASSLKSGVPS RFSGSGSGTD FTLTISSLQP EDFATYYCQQ FNSYPLTFGQ | 100 |
| | | GTRLEIKRTV AAPSVFIFPP SDEQLKSGTA SVVCLLNNFY PREAKVQWKV | 150 |
| | | DNALQSGNSQ ESVTEQDSKD STYSLSSTLT LSKADYEKHK VYACEVTHQG | 200 |
| | | LSSPVTKSFN RGEC | 214 |

NKG2A.15 Antibody (13F3.A4 VK-N30P) (13F3.A4 antibody with N30P to remove deamidation site) (SEQ ID NOs: 132-133)

| 132 | NKG2A.15 heavy chain | EVQLVESGGG LVKPGGSLRL SCAASGFTFS SHSMNWVRQA PGKGLEWVSA | 50 |
|---|---|---|---|
| | | ISSSSSYIYY ADSVKGRFTI SRDNAKNSLY LQMNSLRAED TAVYYCAREE | 100 |
| | | WGLPFDYWGQ GILVTVSSAS TKGPSVFPLA PSSKSTSGGT AALGCLVKDY | 150 |
| | | FPEPVTVSWN SGALTSGVHT FPAVLQSSGL YSLSSVVTVP SSSLGTQTYI | 200 |
| | | CNVNHKPSNT KVDKRVEPKS CDKTHTCPPC PAPEAEGAPS VFLFPPKPKD | 250 |
| | | TLMISRTPEV TCVVVDVSHE DPEVKFNWYV DGVEVHNAKT KPREEQYNST | 300 |
| | | YRVVSVLTVL HQDWLNGKEY KCKVSNKALP APIEKTISKA KGQPREPQVY | 350 |
| | | TLPPSREEMT KNQVSLTCLV KGFYPSDIAV EWESNGQPEN NYKTTPPVLD | 400 |
| | | SDGSFFLYSK LTVDKSRWQQ GNVFSCSVMH EALHNHYTQK SLSLSPGK | 448 |
| 133 | NKG2A.15 light chain | AIQLTQSPSS LSASVGDRVT ITCRASQGIP SALAWYQQKP GKAPKLLIYD | 50 |
| | | ASSLKSGVPS RFSGSGSGTD FTLTISSLQP EDFATYYCQQ FNSYPLTFGQ | 100 |
| | | GTRLEIKRTV AAPSVFIFPP SDEQLKSGTA SVVCLLNNFY PREAKVQWKV | 150 |
| | | DNALQSGNSQ ESVTEQDSKD STYSLSSTLT LSKADYEKHK VYACEVTHQG | 200 |
| | | LSSPVTKSFN RGEC | 214 |

NKG2A.18 Antibody (13F3.A4 VH-I107T, VK-N30S-Y49S) (SEQ ID NOs: 134-135)

| 134 | NKG2A.18 VH (heavy chain variable region nucleotide sequence) | EVQLVESGGG LVKPGGSLRL SCAASGFTFS SHSMNWVRQA PGKGLEWVSA | 50 |
|---|---|---|---|
| | | ISSSSSYIYY ADSVKGRFTI SRDNAKNSLY LQMNSLRAED TAVYYCAREE | 100 |
| | | WGLPFDYWGQ GTLVTVSSAS TKGPSVFPLA PSSKSTSGGT AALGCLVKDY | 150 |
| | | FPEPVTVSWN SGALTSGVHT FPAVLQSSGL YSLSSVVTVP SSSLGTQTYI | 200 |
| | | CNVNHKPSNT KVDKRVEPKS CDKTHTCPPC PAPEAEGAPS VFLFPPKPKD | 250 |
| | | TLMISRTPEV TCVVVDVSHE DPEVKFNWYV DGVEVHNAKT KPREEQYNST | 300 |
| | | YRVVSVLTVL HQDWLNGKEY KCKVSNKALP APIEKTISKA KGQPREPQVY | 350 |
| | | TLPPSREEMT KNQVSLTCLV KGFYPSDIAV EWESNGQPEN NYKTTPPVLD | 400 |
| | | SDGSFFLYSK LTVDKSRWQQ GNVFSCSVMH EALHNHYTQK SLSLSPGK | 448 |
| 135 | NKG2A.18 LH (light chain variable region nucleotide sequence) | AIQLTQSPSS LSASVGDRVT ITCRASQGIS SALAWYQQKP GKAPKLLISD | 50 |
| | | ASSLKSGVPS RFSGSGSGTD FTLTISSLQP EDFATYYCQQ FNSYPLTFGQ | 100 |
| | | GTRLEIKRTV AAPSVFIFPP SDEQLKSGTA SVVCLLNNFY PREAKVQWKV | 150 |
| | | DNALQSGNSQ ESVTEQDSKD STYSLSSTLT LSKADYEKHK VYACEVTHQG | 200 |
| | | LSSPVTKSFN RGEC | 214 |

NKG2A.19 Antibody (13F3.A4 VH-I107T, VK-N30S-Y94T) (SEQ ID NOs: 136-137)

| 136 | NKG2A.19 VH (heavy chain variable region nucleotide sequence) | EVQLVESGGG LVKPGGSLRL SCAASGFTFS SHSMNWVRQA PGKGLEWVSA | 50 |
|---|---|---|---|
| | | ISSSSSYIYY ADSVKGRFTI SRDNAKNSLY LQMNSLRAED TAVYYCAREE | 100 |
| | | WGLPFDYWGQ GTLVTVSSAS TKGPSVFPLA PSSKSTSGGT AALGCLVKDY | 150 |
| | | FPEPVTVSWN SGALTSGVHT FPAVLQSSGL YSLSSVVTVP SSSLGTQTYI | 200 |
| | | CNVNHKPSNT KVDKRVEPKS CDKTHTCPPC PAPEAEGAPS VFLFPPKPKD | 250 |
| | | TLMISRTPEV TCVVVDVSHE DPEVKFNWYV DGVEVHNAKT KPREEQYNST | 300 |
| | | YRVVSVLTVL HQDWLNGKEY KCKVSNKALP APIEKTISKA KGQPREPQVY | 350 |
| | | TLPPSREEMT KNQVSLTCLV KGFYPSDIAV EWESNGQPEN NYKTTPPVLD | 400 |
| | | SDGSFFLYSK LTVDKSRWQQ GNVFSCSVMH EALHNHYTQK SLSLSPGK | 448 |
| 137 | NKG2A.19 LH (light chain variable region nucleotide sequence) | AIQLTQSPSS LSASVGDRVT ITCRASQGIS SALAWYQQKP GKAPKLLIYD | 50 |
| | | ASSLKSGVPS RFSGSGSGTD FTLTISSLQP EDFATYYCQQ FNSTPLTFGQ | 100 |
| | | GTRLEIKRTV AAPSVFIFPP SDEQLKSGTA SVVCLLNNFY PREAKVQWKV | 150 |
| | | DNALQSGNSQ ESVTEQDSKD STYSLSSTLT LSKADYEKHK VYACEVTHQG | 200 |
| | | LSSPVTKSFN RGEC | 214 |

Sequence Listing

| SEQ ID NO | Name | Sequence | |
|---|---|---|---|
| | NKG2 A. 20 Antibody (13F3.A4 VH-I107T, VK-N30S-Y94A) (SEQ ID NOs: 138-139) | | |
| 138 | NKG2A.20 VH (heavy chain variable region nucleotide sequence) | EVQLVESGGG LVKPGGSLRL SCAASGFTFS SHSMNWVRQA PGKGLEWVSA | 50 |
| | | ISSSSSYIYY ADSVKGRFTI SRDNAKNSLY LQMNSLRAED TAVYYCAREE | 100 |
| | | WGLPFDYWGQ GTLVTVSSAS TKGPSVFPLA PSSKSTSGGT AALGCLVKDY | 150 |
| | | FPEPVTVSWN SGALTSGVHT FPAVLQSSGL YSLSSVVTVP SSSLGTQTYI | 200 |
| | | CNVNHKPSNT KVDKRVEPKS CDKTHTCPPC PAPEAEGAPS VFLFPPKPKD | 250 |
| | | TLMISRTPEV TCVVVDVSHE DPEVKFNWYV DGVEVHNAKT KPREEQYNST | 300 |
| | | YRVVSVLTVL HQDWLNGKEY KCKVSNKALP APIEKTISKA KGQPREPQVY | 350 |
| | | TLPPSREEMT KNQVSLTCLV KGFYPSDIAV EWESNGQPEN NYKTTPPVLD | 400 |
| | | SDGSFFLYSK LTVDKSRWQQ GNVFSCSVMH EALHNHYTQK SLSLSPGK | 448 |
| 139 | NKG2A.20 VH (light chain variable region nucleotide sequence) | AIQLTQSPSS LSASVGDRVT ITCRASQGIS SALAWYQQKP GKAPKLLIYD | 50 |
| | | ASSLKSGVPS RFSGSGSGTD FTLTISSLQP EDFATYYCQQ FNSAPLTFGQ | 100 |
| | | GTRLEIKRTV AAPSVFIFPP SDEQLKSGTA SVVCLLNNFY PREAKVQWKV | 150 |
| | | DNALQSGNSQ ESVTEQDSKD STYSLSSTLT LSKADYEKHK VYACEVTHQG | 200 |
| | | LSSPVTKSFN RGEC | 214 |
| | NKG2A.21 Antibody (13F3.A4 VH-I107T, VK-N30S-Y94N) (SEQ ID NOs: 140-141) | | |
| 140 | NKG2A.21 VH (heavy chain variable region nucleotide sequence) | EVQLVESGGG LVKPGGSLRL SCAASGFTFS SHSMNWVRQA PGKGLEWVSA | 50 |
| | | ISSSSSYIYY ADSVKGRFTI SRDNAKNSLY LQMNSLRAED TAVYYCAREE | 100 |
| | | WGLPFDYWGQ GTLVTVSSAS TKGPSVFPLA PSSKSTSGGT AALGCLVKDY | 150 |
| | | FPEPVTVSWN SGALTSGVHT FPAVLQSSGL YSLSSVVTVP SSSLGTQTYI | 200 |
| | | CNVNHKPSNT KVDKRVEPKS CDKTHTCPPC PAPEAEGAPS VFLFPPKPKD | 250 |
| | | TLMISRTPEV TCVVVDVSHE DPEVKFNWYV DGVEVHNAKT KPREEQYNST | 300 |
| | | YRVVSVLTVL HQDWLNGKEY KCKVSNKALP APIEKTISKA KGQPREPQVY | 350 |
| | | TLPPSREEMT KNQVSLTCLV KGFYPSDIAV EWESNGQPEN NYKTTPPVLD | 400 |
| | | SDGSFFLYSK LTVDKSRWQQ GNVFSCSVMH EALHNHYTQK SLSLSPGK | 448 |
| 141 | NKG2A.21 LH (light chain variable region nucleotide sequence) | AIQLTQSPSS LSASVGDRVT ITCRASQGIS SALAWYQQKP GKAPKLLIYD | 50 |
| | | ASSLKSGVPS RFSGSGSGTD FTLTISSLQP EDFATYYCQQ FNSNPLTFGQ | 100 |
| | | GTRLEIKRTV AAPSVFIFPP SDEQLKSGTA SVVCLLNNFY PREAKVQWKV | 150 |
| | | DNALQSGNSQ ESVTEQDSKD STYSLSSTLT LSKADYEKHK VYACEVTHQG | 200 |
| | | LSSPVTKSFN RGEC | 214 |
| | NKG2A.22 Antibody (13F3.A4 VH-Y56T-I107T, VK-N30S) (SEQ ID NOs: 142-143) | | |
| 142 | NKG2A.22 VH (heavy chain variable region nucleotide sequence) | EVQLVESGGG LVKPGGSLRL SCAASGFTFS SHSMNWVRQA PGKGLEWVSA | 50 |
| | | ISSSSSTIYY ADSVKGRFTI SRDNAKNSLY LQMNSLRAED TAVYYCAREE | 100 |
| | | WGLPFDYWGQ GTLVTVSSAS TKGPSVFPLA PSSKSTSGGT AALGCLVKDY | 150 |
| | | FPEPVTVSWN SGALTSGVHT FPAVLQSSGL YSLSSVVTVP SSSLGTQTYI | 200 |
| | | CNVNHKPSNT KVDKRVEPKS CDKTHTCPPC PAPEAEGAPS VFLFPPKPKD | 250 |
| | | TLMISRTPEV TCVVVDVSHE DPEVKFNWYV DGVEVHNAKT KPREEQYNST | 300 |
| | | YRVVSVLTVL HQDWLNGKEY KCKVSNKALP APIEKTISKA KGQPREPQVY | 350 |
| | | TLPPSREEMT KNQVSLTCLV KGFYPSDIAV EWESNGQPEN NYKTTPPVLD | 400 |
| | | SDGSFFLYSK LTVDKSRWQQ GNVFSCSVMH EALHNHYTQK SLSLSPGK | 448 |
| 143 | NKG2A.22 LH (light chain variable region nucleotide sequence) | AIQLTQSPSS LSASVGDRVT ITCRASQGIS SALAWYQQKP GKAPKLLIYD | 50 |
| | | ASSLKSGVPS RFSGSGSGTD FTLTISSLQP EDFATYYCQQ FNSYPLTFGQ | 100 |
| | | GTRLEIKRTV AAPSVFIFPP SDEQLKSGTA SVVCLLNNFY PREAKVQWKV | 150 |
| | | DNALQSGNSQ ESVTEQDSKD STYSLSSTLT LSKADYEKHK VYACEVTHQG | 200 |
| | | LSSPVTKSFN RGEC | 214 |
| | NKG2A.23 Antibody (13F3.A4 VH-I57T-I107T, VK-N30S) (SEQ ID NOs: 144-145) | | |
| 144 | NKG2A.23 VH (heavy chain variable region nucleotide sequence) | EVQLVESGGG LVKPGGSLRL SCAASGFTFS SHSMNWVRQA PGKGLEWVSA | 50 |
| | | ISSSSSYTYY ADSVKGRFTI SRDNAKNSLY LQMNSLRAED TAVYYCAREE | 100 |
| | | WGLPFDYWGQ GTLVTVSSAS TKGPSVFPLA PSSKSTSGGT AALGCLVKDY | 150 |
| | | FPEPVTVSWN SGALTSGVHT FPAVLQSSGL YSLSSVVTVP SSSLGTQTYI | 200 |
| | | CNVNHKPSNT KVDKRVEPKS CDKTHTCPPC PAPEAEGAPS VFLFPPKPKD | 250 |
| | | TLMISRTPEV TCVVVDVSHE DPEVKFNWYV DGVEVHNAKT KPREEQYNST | 300 |
| | | YRVVSVLTVL HQDWLNGKEY KCKVSNKALP APIEKTISKA KGQPREPQVY | 350 |
| | | TLPPSREEMT KNQVSLTCLV KGFYPSDIAV EWESNGQPEN NYKTTPPVLD | 400 |
| | | SDGSFFLYSK LTVDKSRWQQ GNVFSCSVMH EALHNHYTQK SLSLSPGK | 448 |

| SEQ ID NO | Name | Sequence | |
|---|---|---|---|
| 145 | NKG2A.23 LH (light chain variable region nucleotide sequence) | AIQLTQSPSS LSASVGDRVT ITCRASQGIS SALAWYQQKP GKAPKLLIYD<br>ASSLKSGVPS RFSGSGSGTD FTLTISSLQP EDFATYYCQQ FNSYPLTFGQ<br>GTRLEIKRTV AAPSVFIFPP SDEQLKSGTA SVVCLLNNFY PREAKVQWKV<br>DNALQSGNSQ ESVTEQDSKD STYSLSSTLT LSKADYEKHK VYACEVTHQG<br>LSSPVTKSFN RGEC | 50<br>100<br>150<br>200<br>214 |

NKG2A.24 Antibody (13F3.A4 VH-Y58N-I107T, VK-N30S) (SEQ ID NOs: 146-147)

| 146 | NKG2A.24 VH (heavy chain variable region nucleotide sequence) | EVQLVESGGG LVKPGGSLRL SCAASGFTFS SHSMNWVRQA PGKGLEWVSA<br>ISSSSSYINY ADSVKGRFTI SRDNAKNSLY LQMNSLRAED TAVYYCAREE<br>WGLPFDYWGQ GTLVTVSSAS TKGPSVFPLA PSSKSTSGGT AALGCLVKDY<br>FPEPVTVSWN SGALTSGVHT FPAVLQSSGL YSLSSVVTVP SSSLGTQTYI<br>CNVNHKPSNT KVDKRVEPKS CDKTHTCPPC PAPEAEGAPS VFLFPPKPKD<br>TLMISRTPEV TCVVVDVSHE DPEVKFNWYV DGVEVHNAKT KPREEQYNST<br>YRVVSVLTVL HQDWLNGKEY KCKVSNKALP APIEKTISKA KGQPREPQVY<br>TLPPSREEMT KNQVSLTCLV KGFYPSDIAV EWESNGQPEN NYKTTPPVLD<br>SDGSFFLYSK LTVDKSRWQQ GNVFSCSVMH EALHNHYTQK SLSLSPGK | 50<br>100<br>150<br>200<br>250<br>300<br>350<br>400<br>448 |
| 147 | NKG2A.24 LH (light chain variable region nucleotide sequence) | AIQLTQSPSS LSASVGDRVT ITCRASQGIS SALAWYQQKP GKAPKLLIYD<br>ASSLKSGVPS RFSGSGSGTD FTLTISSLQP EDFATYYCQQ FNSYPLTFGQ<br>GTRLEIKRTV AAPSVFIFPP SDEQLKSGTA SVVCLLNNFY PREAKVQWKV<br>DNALQSGNSQ ESVTEQDSKD STYSLSSTLT LSKADYEKHK VYACEVTHQG<br>LSSPVTKSFN RGEC | 50<br>100<br>150<br>200<br>214 |

NKG2A.25 Antibody (13F3.A4 VH-Y58S-I107T, VK-N30S) (SEQ ID NOs: 148-149)

| 148 | NKG2A.25 VH (heavy chain variable region nucleotide sequence) | EVQLVESGGG LVKPGGSLRL SCAASGFTFS SHSMNWVRQA PGKGLEWVSA<br>ISSSSSYISY ADSVKGRFTI SRDNAKNSLY LQMNSLRAED TAVYYCAREE<br>WGLPFDYWGQ GTLVTVSSAS TKGPSVFPLA PSSKSTSGGT AALGCLVKDY<br>FPEPVTVSWN SGALTSGVHT FPAVLQSSGL YSLSSVVTVP SSSLGTQTYI<br>CNVNHKPSNT KVDKRVEPKS CDKTHTCPPC PAPEAEGAPS VFLFPPKPKD<br>TLMISRTPEV TCVVVDVSHE DPEVKFNWYV DGVEVHNAKT KPREEQYNST<br>YRVVSVLTVL HQDWLNGKEY KCKVSNKALP APIEKTISKA KGQPREPQVY<br>TLPPSREEMT KNQVSLTCLV KGFYPSDIAV EWESNGQPEN NYKTTPPVLD<br>SDGSFFLYSK LTVDKSRWQQ GNVFSCSVMH EALHNHYTQK SLSLSPGK | 50<br>100<br>150<br>200<br>250<br>300<br>350<br>400<br>448 |
| 149 | NKG2A.25 LH (light chain variable region nucleotide sequence) | AIQLTQSPSS LSASVGDRVT ITCRASQGIS SALAWYQQKP GKAPKLLIYD<br>ASSLKSGVPS RFSGSGSGTD FTLTISSLQP EDFATYYCQQ FNSYPLTFGQ<br>GTRLEIKRTV AAPSVFIFPP SDEQLKSGTA SVVCLLNNFY PREAKVQWKV<br>DNALQSGNSQ ESVTEQDSKD STYSLSSTLT LSKADYEKHK VYACEVTHQG<br>LSSPVTKSFN RGEC | 50<br>100<br>150<br>200<br>214 |

NKG2A.13-G1.3f (SEQ ID NOs: 150-151)

| 150 | NKG2A.13-G1.3f (light chain sequence) | AIQLTQSPSS LSASVGDRVT ITCRASQGIS SALAWYQQKP GKAPKLLIYD<br>ASSLKSGVPS FSGSGSGTDF TLTISSLQPE DFATYYCQQF NSYPLTFGQG<br>TRLEIKRTVA APSVFIFPPS DEQLKSGTAS VVCLLNNFYP REAKVQWKVD<br>NALQSGNSQE SVTEQDSKDS TYSLSSTLTL SKADYEKHKV YACEVTHQGL<br>SSPVTKSFNR GEC | 50<br>100<br>150<br>200<br>213 |
| 151 | NKG2A.13-G1.3f (heavy chain sequence) | EVQLVESGGG LVKPGGSLRL SCAASGFTFS SHSMNWVRQA PGKGLEWVSA<br>ISSSSSYIYY ADSVKGRFTI SRDNAKNSLY LQMNSLRAED TAVYYCAREE<br>WGLPFDYWGQ GILVTVSSAS TKGPSVFPLA PSSKSTSGGT AALGCLVKDY<br>FPEPVTVSWN SGALTSGVHT FPAVLQSSGL YSLSSVVTVP SSSLGTQTYI<br>CNVNHKPSNT KVDKRVEPKS CDKTHTCPPC PAPEAEGAPS VFLFPPKPKD<br>TLMISRTPEV TCVVVDVSHE DPEVKFNWYV DGVEVHNAKT KPREEQYNST<br>YRVVSVLTVL HQDWLNGKEY KCKVSNKALP APIEKTISKA KGQPREPQVY<br>TLPPSREEMT KNQVSLTCLV KGFYPSDIAV EWESNGQPEN NYKTTPPVLD<br>SDGSFFLYSK LTVDKSRWQQ GNVFSCSVMH EALHNHYTQK SLSLSPGK | 50<br>100<br>150<br>200<br>250<br>300<br>350<br>400<br>448 | mNKG2A.3-mG1-D265A (SEQ ID NOs: 152-153)

| 152 | mNKG2A.3-mG1-D265A (Light chain sequence) | DIVMTQSPSS LAVSAGDKVT INCKSSQTLF SGRYNYLAWY QQKTGQAPKL<br>LIYYTSTRHT GVPDRFIGSG SGTDFTLTIN NLQTEDLGNY YCQHYSTPY<br>TFGAGTNLEI RRADAAPTVS IFPPSSEQLT SGGASVVCFL NNFYPKDINV<br>KWKIDGSERQ NGVLNSWTDQ DSKDSTYSMS STLTLTKDEY ERHNSYTCEA<br>THKTSTSPIV KSFNRNEC | 50<br>100<br>150<br>200<br>218 |

| SEQ ID NO | Name | Sequence | |
|---|---|---|---|
| 153 | mNKG2A.3-mG1-D265A (Heavy chain sequence) | QVQLKQSGAE LVKPGASVKI SCKTSGYTFT DGYMHWVEQN PGQGLEWIGR | 50 |
| | | IDPDSGYTMY NQKFQDKATL TRDKSSSTVY MELRSLTSED SAVYYCAINY | 100 |
| | | GEYWYFDFWG QGTQVTVSSA KTTPPSVYPL APGSAAQTNS MVTLGCLVKG | 150 |
| | | YFPEPVTVTW NSGSLSSGVH TFPAVLQSDL YTLSSSVTVP SSTWPSETVT | 200 |
| | | CNVAHPASST KVDKKIVPRD CGCKPCICTV PEVSSVFIFP PKPKDVLTIT | 250 |
| | | LTPKVTCVVV AISKDDPEVQ FSWFVDDVEV HTAQTQPREE QFNSTFRSVS | 300 |
| | | ELPIMHQDWL NGKEFKCRVN SAAFPAPIEK TISKTKGRPK APQVYTIPPP | 350 |
| | | KEQMAKDKVS LTCMITDFFP EDITVEWQWN GQPAENYKNT QPIMDTDGSY | 400 |
| | | FVYSKLNVQK SNWEAGNTFT CSVLHEGLHN HHTEKSLSHS PGK | 443 |
| 154 | | RASQGIPSAL A | 11 |
| 155 | | RASQGINSAL A | 11 |
| 156 | | LSIDNEEMKF | 10 |
| 157 | | PSSWIGVFRN SSHHPW | 16 |
| 158 | | LAFKHEIKDS DN | 12 |
| 159 | | QVNRLKSAQQ CGSSIIYHC | 19 |
| 160 | | GGGGSGGGGS GGGGS | 15 |
| 161 | | PTSSSTKKTQ LQLEHLLLDL QMILNGINNY KNPKLTRMLT FKFYMPKKAT | 50 |
| | | ELKHLQCLEE ELKPLEEVLN LAQSKNFHLR PRDLISNINV IVLELKGSET | 100 |
| | | TFMCEYADET ATIVEFLNRW ITFSQSIIST LT | 132 |
| 162 | | VSNK | 4 |
| 163 | | EVQLVESGGG LVKPGGSLRL SCAASGFTFS SHSMNWVRQA PGKGLEWVSA | 50 |
| | | ISSSSSYIYY ADSVKGRFTI SRDNAKNSLY LQMNSLRAED TAVYYCAREE | 100 |
| | | WGLPFDYWGQ GTLVTVSSAS TKGPSVFPLA PSSKSTSGGT AALGCLVKDY | 150 |
| | | FPEPVTVSWN SGALTSGVHT FPAVLQSSGL YSLSSVVTVP SSSLGTQTYI | 200 |
| | | CNVNHKPSNT KVDKRVEPKS CDKTHTCPPC PAPEAEGAPS VFLFPPKPKD | 250 |
| | | TLMISRTPEV TCVVVDVSHE DPEVKFNWYV DGVEVHNAKT KPREEQYNST | 300 |
| | | YRVVSVLTVL HQDWLNGKEY KCKVSNKALP APIEKTISKA KGQPREPQVY | 350 |
| | | TLPPSREEMT KNQVSLTCLV KGFYPSDIAV EWESNGQPEN NYKTTPPVLD | 400 |
| | | SDGSFFLYSK LTVDKSRWQQ GNVFSCSVMH EALHNHYTQK SLSLSPGK | 448 |
| 164 | | AIQLTQSPSS LSASVGDRVT ITCRASQGIP SALAWYQQKP GKAPKLLIYD | 50 |
| | | ASSLKSGVPS RFSGSGSGTD FTLTISSLQP EDFATYYCQQ FNSYPLTFGQ | 100 |
| | | GTRLEIK | 107 |
| 165 | | RTVAAPSVFI FPPSDEQLKS GTASVVCLLN NFYPREAKVQ WKVDNALQSG | 50 |
| | | NSQESVTEQD SKDSTYSLSS TLTLSKADYE KHKVYACEVT HQGLSSPVTK | 100 |
| | | SFNRGEC | 107 |
| 166 | | GAGGTGCAGC TGGTGGAGTC TGGGGGAGGC CTGGTCAAGC CGGGGGGGTC | 50 |
| | | CCTGAGACTC TCCTGTGCAG CCTCTGGATT CACCTTCAGT TCCCATAGTA | 100 |
| | | TGAACTGGGT CCGCCAGGCT CCAGGGAAGG GGCTGGAGTG GGTCTCAGCC | 150 |
| | | ATAAGTAGTA GTAGTAGTTA CATATACTAC GCAGACTCAG TGAAGGGCCG | 200 |
| | | ATTCACCATC TCCAGAGACA ACGCCAAGAA CTCACTGTAT CTGCAAATGA | 250 |
| | | ACAGCCTGAG AGCCGAGGAC ACGGCTGTGT ATTACTGTGC GAGAGAAGAG | 300 |
| | | TGGGGGCTAC CCTTTGACTA CTGGGGCCAG GGAATCCTGG TCACCGTCTC | 350 |
| | | CTCA | 354 |
| 167 | | EVQLVESGGG LVKPGGSLRL SCAASGFTFS SHSMNWVRQA PGKGLEWVSA | 50 |
| | | ISSSSSYIYY ADSVKGRFTI SRDNAKNSLY LQMNSLRAED TAVYYCAREE | 100 |
| | | WGLPFDYWGQ GILVTVSS | 118 |
| 168 | | GCCATCCAGT TGACCCAGTC TCCATCCTCC CTGTCTGCAT CTGTAGGAGA | 50 |
| | | CAGAGTCACC ATCACTTGCC GGGCAAGTCA GGGCATTAAC AGTGCTTTAG | 100 |
| | | CCTGGTATCA GCAGAAACCA GGGAAAGCTC CTAAGCTCCT GATCTATGAT | 150 |
| | | GCCTCCAGTT TGAAAAGTGG GGTCCCATCA AGGTTCAGCG GCAGTGGATC | 200 |
| | | TGGGACAGAT TTCACTCTCA CCATCAGCAG CCTGCAGCCT GAAGATTTTG | 250 |
| | | CAACTTATTA CTGTCAACAG TTTAATAGTT ACCCTCTCAC CTTCGGCCAA | 300 |
| | | GGGACACGAC TGGAGATTAA A | 321 |
| 169 | | AIQLTQSPSS LSASVGDRVT ITCRASQGIN SALAWYQQKP GKAPKLLIYD | 50 |
| | | ASSLKSGVPS RFSGSGSGTD FTLTISSLQP EDFATYYCQQ FNSYPLTFGQ | 100 |
| | | GTRLEIK | 107 |

| SEQ ID NO | Name | Sequence | |
|---|---|---|---|
| 170 | | GAGGTGCAGT TGGTGGAGTC TGGGGGAGGC CTGGTCAAGC CTGGGGGGTC | 50 |
| | | CCTGAGACTC TCCTGTGCAG CCTCTGGATT CACCTTCAGT AGCTATAGCA | 100 |
| | | TGAACTGGGT CCGCCAGGCT CCAGGGAAGG GGCTGGAGTG GGTCTCATCC | 150 |
| | | ATTAGTAGTA GTAGTAGTTA CATATACTAC GCAGACTCAG TGAAGGGCCG | 200 |
| | | ATTCACCATC TCCAGAGACA ACGCCAAGAA CTCACTGTAT CTGCAAATGA | 250 |
| | | ACAGCCTGAG AGCCGAGGAC ACGGCTGTGT ATTACTGTGC GAGACTACTA | 300 |
| | | TGGTTCGGGG AGATTTTTGA CTACTGGGGC CAGGGAACCC TGGTCACCGT | 350 |
| | | CTCCTCA | 357 |
| 171 | | EVQLVESGGG LVKPGGSLRL SCAASGFTFS SYSMNWVRQA PGKGLEWVSS | 50 |
| | | ISSSSSYIYY ADSVKGRFTI SRDNAKNSLY LQMNSLRAED TAVYYCARLL | 100 |
| | | WFGEIFDYWG QGTLVTVSS | 119 |
| 172 | | GCCATCCAGT TGACCCAGTC TCCATCCTCC CTGTCTGCAT CTGTAGGAGA | 50 |
| | | CAGAGTCACC ATCACTTGCC GGGCAAGTCA GGGCATTAGC AGTGCTTTAG | 100 |
| | | CCTGGTATCA GCAGAAACCA GGGAAAGCTC CTAAGCTCCT GATCTATGAT | 150 |
| | | GCCTCCAGTT TGAAAAGTGG GGTCCCATCA AGGTTCAGCG GCAGTGGATC | 200 |
| | | TGGGACAGAT TTCACTCTCA CCATCAGCAG CCTGCAGCCT GAAGATTTTG | 250 |
| | | CAACTTATTA CTGTCAACAG TTTAATAGTT ACCCGATCAC CTTCGGCCAA | 300 |
| | | GGGACACGAC TGGAGATTAA A | 321 |
| 173 | | AIQLTQSPSS LSASVGDRVT ITCRASQGIS SALAWYQQKP GKAPKLLIYD | 50 |
| | | ASSLKSGVPS RFSGSGSGTD FTLTISSLQP EDFATYYCQQ FNSYPITFGQ | 100 |
| | | GTRLEIK | 107 |
| 174 | | CAGATGCAGC TGCAGGAGTC GGGCCCAGGA CTGGTGAAGC CTTCGGAGAC | 50 |
| | | CCTGTCCCTC ACCTGCACTG TCTCTGGTGG CTCCGTCAGC AGTGGTCGTT | 100 |
| | | ACTACTGGAG TTGGATCCGG CAGCCCCCCG GGAAGGGACT GGAGTGGATT | 150 |
| | | GGGTATATCT ATTACAGTGG GAGCACCAAC TACAACCCCT CCCTCAAGAG | 200 |
| | | TCGAGTCACC ATATCAGTAG ACACGTCCAA GAACCAGTTC TCCCTGAAGC | 250 |
| | | TGACCTCTGT GACCGCTGCG GACACGGCCG TGTATTACTG TGCGAGAGAG | 300 |
| | | GGTGGAGACT ACTACTACTA CAATATGGAC GTCTGGGCC CAGGGACCAC | 350 |
| | | GGTCACCGTC TCCTCA | 366 |
| 175 | | QMQLQESGPG LVKPSETLSL TCTVSGGSVS SGRYYWSWIR QPPGKGLEWI | 50 |
| | | GYIYYSGSTN YNPSLKSRVT ISVDTSKNQF SLKLTSVTAA DTAVYYCARE | 100 |
| | | GGDYYYYNMD VWGPGTTVTV SS | 122 |
| 176 | | GAAATTGTGT TGACGCAGTC TCCAGGCACC CTGTCTTTGT CTCCAGGGGA | 50 |
| | | AAGAGCCACC CTCTCCTGCA GGGCCAGTCA GAGTGTTAGC AGCAGCTACT | 100 |
| | | TAGCCTGGTA CCAGCAGAAA CCTGGCCAGG CTCCCAGGCT CCTCATCTAT | 150 |
| | | GGTGCATCCA GCAGGGCCAC TGGCATCCCA GACAGGTTCA GTGGCAGTGG | 200 |
| | | GTCTGGGACA GACTTCACTC TCACCATCAG CAGACTGGAG CCTGAAGATT | 250 |
| | | TTGCAGTGTA TTACTGTCAG CAGTATGGTA GCTCACCGTA CACTTTTGGC | 300 |
| | | CAGGGGACCA AGCTGGAGAT CAAA | 324 |
| 177 | | EIVLTQSPGT LSLSPGERAT LSCRASQSVS SSYLAWYQQK PGQAPRLLIY | 50 |
| | | GASSRATGIP DRFSGSGSGT DFTLTISRLE PEDFAVYYCQ QYGSSPYTFG | 100 |
| | | QGTKLEIK | 108 |
| 178 | | CAGGTGCAGC TGGTGGAGTC TGGGGGAGGC GTGGTCCAGC CTGGGAGGTC | 50 |
| | | CCTGAGACTC TCCTGTGCAG CCTCTGGATT CACCTTCAGT GACTATGCTA | 100 |
| | | TGCACTGGGT CCGCCAGACT CCAGGCAGGG GGCTGGAGTG GCTGACATTT | 150 |
| | | ATATCATATG ATGGAAGCAA TAAATACCAC GCAGACTCCG TGAAGGGCCG | 200 |
| | | ATTCACCATC TCCAGAGACA ATTCCAAGAA CACGCTGTTT CTGCAAATGA | 250 |
| | | ACAGTCTGAG AGCTGAGGAC ACGGCTGTTT ATTACTGTGC GAGAGATTCC | 300 |
| | | TGGGATCGGG GTACTTCGA TCTCTGGGGC CGTGGCACCC TGGTCACTGT | 350 |
| | | CTCCTCA | 357 |
| 179 | | QVQLVESGGG VVQPGRSLRL SCAASGFTFS DYAMHWVRQT PGRGLEWLTF | 50 |
| | | ISYDGSNKYH ADSVKGRFTI SRDNSKNTLF LQMNSLRAED TAVYYCARDS | 100 |
| | | WDRGYFDLWG RGTLVTVSS | 119 |
| 180 | | GAAATTGTGT TGACACAGTC TCCAGCCACC CTGTCTTTGT CTCCAGGGGA | 50 |
| | | AAGAGCCACC CTCTCCTGCA GGGCCAGTCA GAGTGTTAGC AGCTACTTAG | 100 |
| | | CCTGGTACCA ACAGAAACCT GGCCAGGCTC CCAGGCTCCT CATCTATGAT | 150 |
| | | GCATCCAACA GGGCCACTGG CATCCCAGCC AGGTTCAGTG GCAGTGGGTC | 200 |
| | | TGGGACAGAC TTCACTCTCA CCATCAGCAG CCTAGAGCCT GAAGATTTTG | 250 |
| | | CAGTTTATTA CTGTCAGCAG CGTAGCAACT GGTGGACGTT CGGCCAAGGG | 300 |
| | | ACCAAGGTGG AAATCAAA | 318 |

Sequence Listing

| SEQ ID NO | Name | Sequence | |
|---|---|---|---|
| 181 | | EIVLTQSPAT LSLSPGERAT LSCRASQSVS SYLAWYQQKP GQAPRLLIYD | 50 |
| | | ASNRATGIPA RFSGSGSGTD FTLTISSLEP EDFAVYYCQQ RSNWWTFGQG | 100 |
| | | TKVEIK | 106 |
| 182 | | MDNQGVIYSD LNLPPNPKRQ QRKPKGNKSS ILATEQEITY AELNLQKASQ | 50 |
| | | DFQGNDKTYH CKDLPSAPEK LIVGILGIIC LILMASVVTI VVIPSTLIQR | 100 |
| | | HNNSSLNTRT QKARHCGHCP EEWITYSNSC YYIGKERRTW EESLLACTSK | 150 |
| | | NSSLLSIDNE EEMKFLSIIS PSSWIGVFRN SSHHPWVTMN GLAFKHEIKD | 200 |
| | | SDNAELNCAV LQVNRLKSAQ CGSSIIYHCK HKL | 233 |
| 183 | | XEWGLPFD | 8 |
| 184 | | EXWGLPFD | 8 |
| 185 | | EEXGLPFD | 8 |
| 186 | | EEWXLPFD | 8 |
| 187 | | EEWGXPFD | 8 |
| 188 | | EEWGLXFD | 8 |
| 189 | | EEWGLPXD | 8 |
| 190 | | EEWGLPFX | 8 |
| 191 | | GTFSSYSMN | 9 |
| 192 | | GFTFSSHSMN | 10 |
| 193 | | EEWGLPFD | 8 |
| 194 | | RASQGSNSAL A | 11 |
| 195 | | QQFNNYPLT | 9 |
| 196 | | GFTFSSYSMN | 10 |
| 197 | | EVQLVESGGG LVKPGGSLRL SCAASGFTFS SHSMNWVRQA PGKGLEWVSA | 50 |
| | | ISSSSSYIYY ADSVKGRFTI SRDNAKNSLY LQMNSLRAED TAVYYCAREE | 100 |
| | | WGLPFDYWGQ GILVTVSSAS TKGPSVFPLA PSSKSTSGGT AALGCLVKDY | 150 |
| | | FPEPVTVSWN | 160 |
| 198 | | AIQLTQSPSS LSASVGDRVT ITCRASQGIN SALAWYQQKP GKAPKLLIYD | 50 |
| | | ASSLKSGVPS RFSGSGSGTD FTLTISSLQP EDFATYYcQQ FNSYPLTFGQ | 100 |
| | | GTRLEI | 106 |
| 199 | | LQMNSLRAED TAVYYCAREE WGLPFDYWGQ GILVTVSSAS TKGPSVFPLA | 50 |
| | | PSSKSTSGGT AALGCLVKDY FPEPVTVSWN | 80 |
| 200 | | LQMNSLRAED TAVYYCAREE WGLPFDYWGQ GTLVTVSSAS TKGPSVFPLA | 50 |
| | | PSSKSTSGGT AALGCLVKDY FPEPVTVSWN | 80 |
| 201 | | AIQLTQSPSS LSASVGDRVT ITCRASQGIN SALAWYQQKP GKAPKLLIYD | 50 |
| | | ASSLKSGVPS RFSGSGSGTD FTLTISSLQP | 80 |
| 202 | | AIQLTQSPSS LSASVGDRVT ITCRASQGIP SALAWYQQKP GKAPKLLIYD | 50 |
| | | ASSLKSGVPS RFSGSGSGTD FTLTISSLQP | 80 |
| 203 | | AIQLTQSPSS LSASVGDRVT ITCRASQGIQ SALAWYQQKP GKAPKLLIYD | 50 |
| | | ASSLKSGVPS RFSGSGSGTD FTLTISSLQP | 80 |
| 204 | | AIQLTQSPSS LSASVGDRVT ITCRASQGIS SALAWYQQKP GKAPKLLIYD | 50 |
| | | ASSLKSGVPS RFSGSGSGTD FTLTISSLQP | 80 |
| 205 | NP_001291377.1 | MDNQGVIYSD LNLPPNPKRQ QRKPKGNKSS ILATEQEITY AELNLQKASQ | 50 |
| | | DFQGNDKTYH CKDLPSAPEK LIVGILGIIC LILMASVVTI VVIPSTLIQR | 100 |
| | | HNNSSLNTRT QKARHCGHCP EEWITYSNSC YYIGKERRTW EESLLACTSK | 150 |
| | | NSSLLSIDNE EEMKFLSIIS PSSWIGVFRN SSHHPWVTMN GLAFKHEIKD | 200 |
| | | SDNAELNCAV LQVNRLKSAQ CGSSIIYH | 228 |

| SEQ ID NO | Name | Sequence | |
|---|---|---|---|
| 206 | NP_015567.2 | MDNQGVIYSD LNLPPNPKRQ QRKPKGNKNS ILATEQEITY AELNLQKASQ | 50 |
| | | DFQGNDKTYH CKDLPSAPEK LIVGILGIIC LILMASVVTI VVIPSRHCGH | 100 |
| | | CPEEWITYSN SCYYIGKERR TWEESLLACT SKNSSLLSID NEEEMKFLSI | 150 |
| | | ISPSSWIGVF RNSSHHPWVT MNGLAFKHEI KDSDNAELNC AVLQVNRLKS | 200 |
| | | AQCGSSIIYH CKHKL | 215 |
| 207 | NP_998822.1 | MDNQGVIYSD LNLPPNPKRQ QRKPKGNKSS ILATEQEITY AELNLQKASQ | 50 |
| | | DFQGNDKTYH CKDLPSAPEK LIVGILGIIC LILMASVVTI VVIPSRHCGH | 100 |
| | | CPEEWITYSN SCYYIGKERR TWEESLLACT SKNSSLLSID NEEEMKFLSI | 150 |
| | | ISPSSWIGVF RNSSHHPWVT MNGLAFKHEI KDSDNAELNC AVLQVNRLKS | 200 |
| | | AQCGSSIIYH CKHKL | 215 |
| 208 | NM_001304448.1 | ACAGTTGAGA GGAGTTTGAG TGGAGATTCA GGGCCATTTT AGTATCTTCT | 50 |
| | | GTAGGACAGA GGTCAGCAAG CATGCCCCAG AGGTACAGAT GTATATGTCT | 100 |
| | | CCCAGGAAGT CTCTGTGGGT GAAGGACTGA TCTCAAGTTG TGGCTGACAC | 150 |
| | | TAGTTAAAGC CAAGTTAGAG GGCTGTTTCA GGGTCTACAT TGAGACTACA | 200 |
| | | GTTGATATGC CTACCTCCTG AGACACTAGT GTGTGAGTCT CCTCCTGGGC | 250 |
| | | CCCTGGGCAA ATGGTTTTGG CAGCATGACC AAGGCCTAAA TGGGGCTGAA | 300 |
| | | GGCAAGCACA GGAGGATGGG TCCCTTTTCA GGTCTGGAGA TGGAATCACT | 350 |
| | | GTTGCTATAG CAGGCCTTTT TATGAGACTA ACCTGGCCTC TCCACTAAAG | 400 |
| | | GATGTGTGAC TTTCTGGGGA CAGAAGAGTA CAGTCCCTGA CATCACACAC | 450 |
| | | TGCAGAGATG GATAACCAAG GAGTAATCTA CTCAGACCTG AATCTGCCCC | 500 |
| | | CAAACCCAAA GAGGCAGCAA CGAAACCTA AAGGCAATAA AAGCTCCATT | 550 |
| | | TTAGCAACTG AACAGGAAAT AACCTATGCG GAATTAAACC TTCAAAAAGC | 600 |
| | | TTCTCAGGAT TTTCAAGGGA ATGACAAAAC CTATCACTGC AAAGATTTAC | 650 |
| | | CATCAGCTCC AGAGAAGCTC ATTGTTGGGA TCCTGGGAAT TATCTGTCTT | 700 |
| | | ATCTTAATGG CCTCTGTGGT AACGATAGTT GTTATTCCCT CTACATTAAT | 750 |
| | | ACAGAGGCAC AACAATTCTT CCCTGAATAC AAGAACTCAG AAAGCACGTC | 800 |
| | | ATTGTGGCCA TTGTCCTGAG GAGTGGATTA CATATTCAA CAGTTGTTAC | 850 |
| | | TACATTGGTA AGGAAAGAAG AACTTGGGAA GAGAGTTTGC TGGCCTGTAC | 900 |
| | | TTCGAAGAAC TCCAGTCTGC TTTCTATAGA ATGAAGAA GAAATGAAAT | 950 |
| | | TTCTGTCCAT CATTTCACCA TCCTCATGGA TTGGTGTGTT TCGTAACAGC | 1000 |
| | | AGTCATCATC CATGGGTGAC AATGAATGGT TTGGCTTTCA AACATGAGAT | 1050 |
| | | AAAAGACTCA GATAATGCTG AACTTAACTG TGCAGTGCTA CAAGTAAATC | 1100 |
| | | GACTTAAATC AGCCCAGTGT GGATCTTCAA TAATATATCA TTAAACTTGT | 1150 |
| | | TAATTTAATA CAATTTACAA CACACCTGC | 1179 |
| 209 | NM_002259.5 | CCACTCTTGA CTCACTCTGA GCCTTCACAG GGCAGTCTGC GAAGATTGCA | 50 |
| | | GGCATTGTTT GTTCTTGTCT TGGATTTATG CCTTTAAATT TCACCTTTTA | 100 |
| | | TTACACAGCT ATAGCAGGCC TTTTTATGAG ACTAACCTGG CCTCTCCACT | 150 |
| | | AAAGGATGTG TGACTTTCTG GGGACAGAAG AGTACAGTCC CTGACATCAC | 200 |
| | | ACACTGCAGA GATGGATAAC CAAGGAGTAA TCTACTCAGA CCTGAATCTG | 250 |
| | | CCCCCAAACC CAAAGAGGCA GCAACGAAAA CCTAAAGGCA ATAAAAACTC | 300 |
| | | CATTTTAGCA ACTGAACAGG AAATAACCTA TGCGGAATTA AACCTTCAAA | 350 |
| | | AAGCTTCTCA GGATTTTCAA GGGAATGACA AAACCTATCA CTGCAAAGAT | 400 |
| | | TTACCATCAG CTCCAGAGAA GCTCATTGTT GGGATCCTGG GAATTATCTG | 450 |
| | | TCTTATCTTA ATGGCCTCTG TGGTAACGAT AGTTGTTATT CCCTCTACAT | 500 |
| | | TAATACAGAG GCACAACAAT TCTTCCCTGA ATACAAGAAC TCAGAAAGCA | 550 |
| | | CGTCATTGTG GCCATTGTCC TGAGGAGTGG ATTACATATT CCAACAGTTG | 600 |
| | | TTACTACATT GGTAAGGAAA GAAGAACTTG GAAGAGAGT TTGCTGGCCT | 650 |
| | | GTACTTCGAA GAACTCCAGT CTGCTTTCTA TAGAATAATGA AGAAGAAATG | 700 |
| | | AAATTTCTGT CCATCATTTC ACCATCCTCA TGGATTGGTG TGTTTCGTAA | 750 |
| | | CAGCAGTCAT CATCCATGGG TGACAATGAA TGGTTTGGCT TCAAACATG | 800 |
| | | AGATAAAAGA CTCAGATAAT GCTGAACTTA ACTGTGCAGT GCTACAAGTA | 850 |
| | | AATCGACTTA AATCAGCCCA GTGTGGATCT TCAATAATAT ATCATTGTAA | 900 |
| | | GCATAAGCTT TAGAGGTAAA GCGTTTGCAT TTGCAGTGCA TCAGATAAAT | 950 |
| | | TGTATATTTC TTAAAATAGA AATATATTAT GATTGCATAA ATCTTAAAAT | 1000 |
| | | GAATTATGTT ATTTGCTCTA ATAAGAAAAT TCTAAATCAA TTATTGAAAC | 1050 |
| | | AGGATACACA CAATTACTAA AGTACAGACA TCCTAGCATT TGTGTCGGGC | 1100 |
| | | TCATTTTGCT CAACATGGTA TTTGTGGTTT TCAGCCTTTC TAAAAGTTGC | 1150 |
| | | ATGTTATGTG AGTCAGCTTA TAGGAAGTAC CAAGAACAGT CAAACCCATG | 1200 |
| | | GAGACAGAAA GTAGAATAGT GGTTGCCAAT GTCTGAGGGA GGTTGAAATA | 1250 |
| | | GGAGATGACC TCTAACTGAT AGAACGTTAC TTTGTGTCGT GATGAAAACT | 1300 |
| | | TTCTAAATTT CAGTAGTGGG GATGGTTGTA ACTCTGCGAA TATACTAAAC | 1350 |
| | | ATCATTGATT TTAATCATT TTAAGTGCAT GAAATGTATG CTTTGTACAC | 1400 |
| | | GACACTTCAA TAAAGCTATC CAGAAAAAAA AAAAA | 1436 |
| 210 | NM_007328.4 | CCACTCTTGA CTCACTCTGA GCCTTCACAG GGCAGTCTGC GAAGATTGCA | 50 |
| | | GGCATTGTTT GTTCTTGTCT TGGATTTATG CCTTTAAATT TCACCTTTTA | 100 |
| | | TTACACAGCT ATAGCAGGCC TTTTTATGAG ACTAACCTGG CCTCTCCACT | 150 |
| | | AAAGGATGTG TGACTTTCTG GGGACAGAAG AGTACAGTCC CTGACATCAC | 200 |
| | | ACACTGCAGA GATGGATAAC CAAGGAGTAA TCTACTCAGA CCTGAATCTG | 250 |
| | | CCCCCAAACC CAAAGAGGCA GCAACGAAAA CCTAAAGGCA ATAAAAACTC | 300 |

| SEQ ID NO | Name | Sequence | |
|---|---|---|---|
| | | CATTTTAGCA ACTGAACAGG AAATAACCTA TGCGGAATTA AACCTTCAAA | 350 |
| | | AAGCTTCTCA GGATTTTCAA GGGAATGACA AAACCTATCA CTGCAAAGAT | 400 |
| | | TTACCATCAG CTCCAGAGAA GCTCATTGTT GGGATCCTGG GAATTATCTG | 450 |
| | | TCTTATCTTA ATGGCCTCTG TGGTAACGAT AGTTGTTATT CCCTCACGTC | 500 |
| | | ATTGTGGCCA TTGTCCTGAG GAGTGGATTA CATATTCCAA CAGTTGTTAC | 550 |
| | | TACATTGGTA AGGAAAGAAG AACTTGGGAA GAGAGTTTGC TGGCCTGTAC | 600 |
| | | TTCGAAGAAC TCCAGTCTGC TTTCTATAGA TAATGAAGAA GAAATGAAAT | 650 |
| | | TTCTGTCCAT CATTTCACCA TCCTCATGGA TTGGTGTGTT TCGTAACAGC | 700 |
| | | AGTCATCATC CATGGGTGAC AATGAATGGT TTGGCTTTCA AACATGAGAT | 750 |
| | | AAAAGACTCA GATAATGCTG AACTTAACTG TGCAGTGCTA CAAGTAAATC | 800 |
| | | GACTTAAATC AGCCCAGTGT GGATCTTCAA TAATATATCA TTGTAAGCAT | 850 |
| | | AAGCTTTAGA GGTAAAGCGT TTGCATTTGC AGTGCATCAG ATAAATTGTA | 900 |
| | | TATTTCTTAA AATAGAAATA TATTATGATT GCATAAATCT TAAAATGAAT | 950 |
| | | TATGTTATTT GCTCTAATAA GAAATTCTA AATCAATTAT TGAAACAGGA | 1000 |
| | | TACACACAAT TACTAAAGTA CAGACATCCT AGCATTTGTG TCGGGCTCAT | 1050 |
| | | TTTGCTCAAC ATGGTATTTG TGGTTTTCAG CCTTTCTAAA AGTTGCATGT | 1100 |
| | | TATGTGAGTC AGCTTATAGG AAGTACCAAG AACAGTCAAA CCCATGGAGA | 1150 |
| | | CAGAAAGTAG AATAGTGGTT GCCATGTCT GAGGGAGGTT GAAATAGGAG | 1200 |
| | | ATGACCTCTA ACTGATAGAA CGTTACTTTG TGTCGTGATG AAAACTTTCT | 1250 |
| | | AAATTTCAGT AGTGGTGATG GTTGTAACTC TGCGAATATA CTAAACATCA | 1300 |
| | | TTGATTTTTA ATCATTTTAA GTGCATGAAA TGTATGCTTT GTACACGACA | 1350 |
| | | CTTCAATAAA GCTATCCAGA AAAAAAAAAA AA | 1382 |
| 211 | NM_213657.2 | GCATGCCCCA GAGGTACAGA TGTATATGTC TCCCAGGAAG TCTCTGTGGG | 50 |
| | | TGAAGGACTG ATCTCAAGTT GTGGCTGACA CTAGTTAAAG CCAAGTTAGA | 100 |
| | | GGGCTGTTTC AGGGTCTACA TTGAGACTAC AGTTGATATG CCTACCTCCT | 150 |
| | | GAGACACTAG TGTGTGAGTC TCCTCCTGGG CCCCTGGGCA ATGGTTTTG | 200 |
| | | GCAGCATGAC CAAGGCCTAA ATGGGGCTGA AGGCAAGCAC AGGAGGATGG | 250 |
| | | GTCCCTTTTC AGGTCTGGAG ATGGAATCAC TGTTGCTATA GCAGGCCTTT | 300 |
| | | TTATGAGACT AACCTGGCCT CTCCACTAAA GGATGTGTGA CTTTCTGGGG | 350 |
| | | ACAGAAGAGT ACAGTCCCTG ACATCACACA CTGCAGAGAT GGATAACCAA | 400 |
| | | GGAGTAATCT ACTCAGACCT GAATCTGCCC CCAAACCCAA AGAGGCAGCA | 450 |
| | | ACGAAAACCT AAAGGCAATA AAAGCTCCAT TTTAGCAACT GAACAGGAAA | 500 |
| | | TAACCTATGC GGAATTAAAC CTTCAAAAAG CTTCTCAGGA TTTTCAAGGG | 550 |
| | | AATGACAAAA CCTATCACTG CAAAGATTTA CCATCAGCTC CAGAGAAGCT | 600 |
| | | CATTGTTGGG ATCCTGGGAA TTATCTGTCT TATCTTAATG GCCTCTGTGG | 650 |
| | | TAACGATAGT TGTTATTCCC TCACGTCATT GTGGCCATTG TCCTGAGGAG | 700 |
| | | TGGATTACAT ATTCCAACAG TTGTTACTAC ATTGGTAAGG AAAGAAGAAC | 750 |
| | | TTGGGAAGAG AGTTTGCTGG CCTGTACTTC GAAGAACTCC AGTCTGCTTT | 800 |
| | | CTATAGATAA TGAAGAAGAA ATGAAATTTC TGTCCATCAT TTCACCATCC | 850 |
| | | TCATGGATTG GTGTGTTTCG TAACAGCAGT CATCATCCAT GGGTGACAAT | 900 |
| | | GAATGGTTTG CTTTCAAAC ATGAGATAAA AGACTCAGAT AATGCTGAAC | 950 |
| | | TTAACTGTGC AGTGCTACAA GTAAATCGAC TTAAATCAGC CCAGTGTGGA | 1000 |
| | | TCTTCAATAA TATATCATTG TAAGCATAAG CTTTAGAGGT AAAGCGTTTG | 1050 |
| | | CATTTGCAGT GCATCAGATA AATTGTATAT TTCTTAAAAT AGAAATATAT | 1100 |
| | | TATGATTGCA TAAATCTTAA AATGAATTAT GTTATTTGCT CTAATAAGAA | 1150 |
| | | AATTCTAAAT CAATTATTGA AACAGGATAC ACACAATTAC TAAAGTACAG | 1200 |
| | | ACATCCTAGC ATTTGTGTCG GGCTCATTTT GCTCAACATG GTATTTGTGG | 1250 |
| | | TTTTCAGCCT TTCTAAAAGT TGCATGTTAT GTGAGTCAGC TTATAGGAAG | 1300 |
| | | TACCAAGAAC AGTCAAACCC ATGGAGACAG AAAGTAGAAT AGTGGTTGCC | 1350 |
| | | AATGTCTGAG GGAGGTTGAA ATAGGAGATG ACCTCTAACT GATAGAACGT | 1400 |
| | | TACTTTGTGT CGTGATGAAA ACTTTCTAAA TTTCAGTAGT GGTGATGGTT | 1450 |
| | | GTAACTCTGC GAATATACTA AACATCATTG ATTTTTAATC ATTTTAAGTG | 1500 |
| | | CATGAAATGT ATGCTTTGTA CACGACACTT CAATAAAGCT ATCCAGAAAA | 1550 |
| | | AAAAAAAAA AAA | 1563 |
| 212 | NM_213658.2 | GCATGCCCCA GAGGTACAGA TGTATATGTC TCCCAGGAAG TCTCTGTGGG | 50 |
| | | TGAAGGACTG ATCTCAAGTT GTGGCTGACA CTAGTTAAAG CCAAGTTAGA | 100 |
| | | GGGCTGTTTC AGGGTCTACA TTGAGACTAC AGTTGATATG CCTACCTCCT | 150 |
| | | GAGACACTAG TGTGTGAGTC TCCTCCTGGG CCCCTGGGCA ATGGTTTTG | 200 |
| | | GCAGCATGAC CAAGGCCTAA ATGGGGCTGA AGGCAAGCAC AGGAGGATGG | 250 |
| | | GTCCCTTTTC AGGTCTGGAG ATGGAATCAC TGTTGCTATA GCAGGCCTTT | 300 |
| | | TTATGAGACT AACCTGGCCT CTCCACTAAA GGATGTGTGA CTTTCTGGGG | 350 |
| | | ACAGAAGAGT ACAGTCCCTG ACATCACACA CTGCAGAGAT GGATAACCAA | 400 |
| | | GGAGTAATCT ACTCAGACCT GAATCTGCCC CCAAACCCAA AGAGGCAGCA | 450 |
| | | ACGAAAACCT AAAGGCAATA AAAGCTCCAT TTTAGCAACT GAACAGGAAA | 500 |
| | | TAACCTATGC GGAATTAAAC CTTCAAAAAG CTTCTCAGGA TTTTCAAGGG | 550 |
| | | AATGACAAAA CCTATCACTG CAAAGATTTA CCATCAGCTC CAGAGAAGCT | 600 |
| | | CATTGTTGGG ATCCTGGGAA TTATCTGTCT TATCTTAATG GCCTCTGTGG | 650 |
| | | TAACGATAGT TGTTATTCCC TCTACATTAA TACAGAGGCA CAACAATTCT | 700 |
| | | TCCCTGAATA CAAGAACTCA GAAAGCACGT CATTGTGGCC ATTGTCCTGA | 750 |
| | | GGAGTGGATT ACATATTCCA ACAGTTGTTA CTACATTGGT AAGGAAAGAA | 800 |
| | | GAACTTGGGA AGAGAGTTTG CTGGCCTGTA CTTCGAAGAA CTCCAGTCTG | 850 |

| Sequence Listing | | |
|---|---|---|
| SEQ ID NO | Name | Sequence |
| | | CTTTCTATAG ATAATGAAGA AGAAATGAAA TTTCTGTCCA TCATTTCACC   900 |
| | | ATCCTCATGG ATTGGTGTGT TTCGTAACAG CAGTCATCAT CCATGGGTGA   950 |
| | | CAATGAATGG TTTGGCTTTC AAACATGAGA TAAAAGACTC AGATAATGCT  1000 |
| | | GAACTTAACT GTGCAGTGCT ACAAGTAAAT CGACTTAAAT CAGCCCAGTG  1050 |
| | | TGGATCTTCA ATAATATATC ATTGTAAGCA TAAGCTTTAG AGGTAAAGCG  1100 |
| | | TTTGCATTTG CAGTGCATCA GATAAATTGT ATATTCTTA AAATAGAAAT   1150 |
| | | ATATTATGAT TGCATAAATC TTAAAATGAA TTATGTTATT TGCTCTAATA  1200 |
| | | AGAAAATTCT AAATCAATTA TTGAAACAGG ATACACACAA TTACTAAAGT  1250 |
| | | ACAGACATCC TAGCATTTGT GTCGGGCTCA TTTTGCTCAA CATGGTATTT  1300 |
| | | GTGGTTTTCA GCCTTTCTAA AAGTTGCATG TTATGTGAGT CAGCTTATAG  1350 |
| | | GAAGTACCAA GAACAGTCAA ACCCATGGAG ACAGAAAGTA GAATAGTGGT  1400 |
| | | TGCCAATGTC TGAGGGAGGT TGAAATAGGA GATGACCTCT AACTGATAGA  1450 |
| | | ACGTTACTTT GTGTCGTGAT GAAACTTTC TAAATTTCAG TAGTGGTGAT   1500 |
| | | GGTTGTAACT CTGCGAATAT ACTAAACATC ATTGATTTTT AATCATTTTA  1550 |
| | | AGTGCATGAA ATGTATGCTT TGTACACGAC ACTTCAATAA AGCTATCCAG  1600 |
| | | AAAAAAAAAA AAAAAAA  1617 |

TABLE 2

$V_H$, $V_L$, $C_H$, $C_L$, Heavy Chain, and Light Chain Amino Acid Sequences of NKG2A.9 Monoclonal Antibody (also known as 13F3-VH-I107T-Vk-N30S IgG1.3) (hereinafter referred to as "NKG2A.9 Antibody")

| | Amino Acid Sequences (SEQ ID NOs) | |
|---|---|---|
| Heavy chain ($V_H$) variable domain | EVQLVESGGG LVKPGGSLRL SCAASGFTFS SHSMNWVRQA PGKGLEWVSA<br>ISSSSSYIYY ADSVKGRFTI SRDNAKNSLY LQMNSLRAED TAVYYCAREE<br>WGLPFDYWGQ GTLVTVSS<br>(SEQ ID NO: 8) | 50<br>100<br>118 |
| Light chain variable domain ($V_L$) | AIQLTQSPSS LSASVGDRVT ITCRASQGIS SALAWYQQKP GKAPKLLIYD<br>ASSLKSGVPS RFSGSGSGTD FTLTISSLQP EDFATYYCQQ FNSYPLTFGQ<br>GTRLEIK<br>(SEQ ID NO: 9) | 50<br>100<br>107 |
| Heavy chain constant domain ($C_H$) (C-terminal lysine (K) is not shown but may be included in some embodiments) | ASTKGPSVFP LAPSSKSTSG GTAALGCLVK DYFPEPVTVS WNSGALTSGV<br>HTFPAVLQSS GLYSLSSVVT VPSSSLGTQT YICNVNHKPS NTKVDKRVEP<br>KSCDKTHTCP PCPAPEAEGA PSVFLFPPKP KDTLMISRTP EVTCVVVDVS<br>HEDPEVKFNW YVDGVEVHNA KTKPREEQYN STYRVVSVLT VLHQDWLNGK<br>EYKCKVSNKA LPAPIEKTIS KAKGQPREPQ VYTLPPSREE MTKNQVSLTC<br>LVKGFYPSDI AVEWESNGQP ENNYKTTPPV LDSDGSFFLY SKLTVDKSRW<br>QQGNVFSCSV MHEALHNHYT QKSLSLSPG<br>(SEQ ID NO: 16) | 50<br>100<br>150<br>200<br>250<br>300<br>329 |
| Light chain constant domain ($C_L$) | RTVAAPSVFI FPPSDEQLKS GTASVVCLLN NFYPREAKVQ WKVDNALQSG<br>NSQESVTEQD SKDSTYSLSS TLTLSKADYE KHKVYACEVT HQGLSSPVTK<br>SFNRGEC<br>(SEQ ID NO: 17) | 50<br>100<br>107 |
| Heavy Chain (C-terminal lysine (K) is not shown but may be included in some embodiments) | EVQLVESGGG LVKPGGSLRL SCAASGFTFS SHSMNWVRQA PGKGLEWVSA<br>ISSSSSYIYY ADSVKGRFTI SRDNAKNSLY LQMNSLRAED TAVYYCAREE<br>WGLPFDYWGQ GTLVTVSSAS TKGPSVFPLA PSSKSTSGGT AALGCLVKDY<br>FPEPVTVSWN SGALTSGVHT PFAVLQSSGL YSLSSVVTVP SSSLGTQTYI<br>CNVNHKPSNT KVDKRVEPKS CDKTHTCPPC PAPEAEGAPS VFLFPPKPKD<br>TLMISRTPEV TCVVVDVSHE DPEVKFNWYV DGVEVHNAKT KPREEQYNST<br>YRVVSVLTVL HQDWLNGKEY KCKVSNKALP APIEKTISKA KGQPREPQVY<br>TLPPSREEMT KNQVSLTCLV KGFYPSDIAV EWESNGQPEN NYKTTPPVLD<br>SDGSFFLYSK LTVDKSRWQQ GNVFSCSVMH EALHNHYTQK SLSLSPG<br>(SEQ ID NO: 7) | 50<br>100<br>150<br>200<br>250<br>300<br>350<br>400<br>447 |
| Light Chain | AIQLTQSPSS LSASVGDRVT ITCRASQGIS SALAWYQQKP GKAPKLLIYD<br>ASSLKSGVPS RFSGSGSGTD FTLTISSLQP EDFATYYCQQ FNSYPLTFGQ<br>GTRLEIKRTV AAPSVFIFPP SDEQLKSGTA SVVCLLNNFY PREAKVQWKV<br>DNALQSGNSQ ESVTEQDSKD STYSLSSTLT LSKADYEKHK VYACEVTHQG<br>LSSPVTKSFN RGEC<br>(SEQ ID NO: 5) | 50<br>100<br>150<br>200<br>214 |

TABLE 3

Amino Acid Sequences for the Six CDR Domains of NKG2A.9 Antibody
Amino Acid Sequences (SEQ ID NOs)

| VH CDR1 | VH CDR2 | VH CDR3 | VL CDR1 | VL CDR2 | VL CDR3 |
|---|---|---|---|---|---|
| SHSMN (SEQ ID NO: 10) | AISSSSSYI YYADSVKG (SEQ ID NO: 11) | EEWGLPFDY (SEQ ID NO: 12) | RASQGISSALA (SEQ ID NO: 13) | DASSLKS (SEQ ID NO: 14) | QQFNSYPLT (SEQ ID NO: 15) |

TABLE 4

Amino Acid Sequences for the Six CDR Domains of NKG2A.11 Antibody
Amino Acid Sequences (SEQ ID NOs)

| VH CDR1 | VH CDR2 | VH CDR3 | VL CDR1 | VL CDR2 | VL CDR3 |
|---|---|---|---|---|---|
| SHSMN (SEQ ID NO: 10) | AISSSSSYI YYADSVKG (SEQ ID NO: 11) | EEWGLPFDY (SEQ ID NO: 12) | RASQGIPSALA (SEQ ID NO: 154) | DASSLKS (SEQ ID NO: 14) | QQFNSYPLT (SEQ ID NO: 15) |

TABLE 5

Amino Acid Sequences for the Six CDR Domains of 13F3.A4 Antibody
Amino Acid Sequences (SEQ ID NOs)

| VH CDR1 | VH CDR2 | VH CDR3 | VL CDR1 | VL CDR2 | VL CDR3 |
|---|---|---|---|---|---|
| SHSMN (SEQ ID NO: 10) | AISSSSSYI YYADSVKG (SEQ ID NO: 11) | EEWGLPFDY (SEQ ID NO: 12) | RASQGINSALA (SEQ ID NO: 155) | DASSLKS (SEQ ID NO: 14) | QQFNSYPLT (SEQ ID NO: 15) |

---

What is claimed is:

1. A method of treating a cancer expressing HLA-E in a subject in need thereof comprising administering to the subject an isolated antibody or antigen-binding fragment thereof that binds human NKG2A wherein said antibody comprises an HCDR1, an HCDR2 and an HCDR3 of a VH of the amino acid sequence of SEQ ID NO:8 and a LCDR1, an LCDR2 and an LCDR3 of a VL of the amino acid sequence of SEQ ID NO:9.

2. The method of claim 1, wherein the isolated antibody or antigen-binding fragment thereof comprises a VH consisting essentially of the amino acid sequence of SEQ ID NO:8 and a VL consisting essentially of the amino acid sequence of SEQ ID NO:9.

3. The method of claim 1, wherein the isolated antibody or antigen-binding fragment thereof comprises a VH at least 95% identical to the amino acid sequence of SEQ ID NO:8 and a VL at least 95% identical to the amino acid sequence of SEQ ID NO:9.

4. The method of claim 1, wherein the isolated antibody or antigen-binding fragment thereof comprises a VH at least 98% identical to the amino acid sequence of SEQ ID NO:8 and a VL at least 98% identical to the amino acid sequence of SEQ ID NO:9.

5. The method of claim 1, wherein the isolated antibody or antigen-binding fragment thereof comprises a VH at least 99% identical to the amino acid sequence of SEQ ID NO:8 and a VL at least 99% identical to the amino acid sequence of SEQ ID NO:9.

6. The method of claim 1, wherein the antibody is a full-length antibody.

7. The method of claim 1, wherein the cancer is bladder cancer, breast cancer, uterine cancer, cervical cancer, ovarian cancer, prostate cancer, testicular cancer, esophageal cancer, gastrointestinal cancer, pancreatic cancer, colorectal cancer, head and neck cancer, lung cancer, stomach cancer, germ cell cancer, bone cancer, liver cancer, thyroid cancer, skin cancer, neoplasm of the central nervous system, lymphoma, leukemia, myeloma, sarcoma, endometrial cancer, gastric cancer, melanoma, renal cancer, urothelial cancer, or glioblastoma multiforme.

8. The method of claim 7, wherein the head and neck cancer is squamous cell carcinoma of the head and neck.

9. The method of claim 7, wherein the lung cancer is non-small cell lung cancer.

10. The method of claim 7, wherein the lymphoma is non-Hodgkin lymphoma.

11. The method of claim 7, wherein the renal cancer is renal cell carcinoma.

12. The method of claim 1, wherein said antibody or antigen-binding fragment thereof is administered in combination with one or more additional therapeutic agents.

13. The method of claim 12 wherein the additional therapeutic agent is an anti-PD-1 antibody, anti-PD-L1 antibody, or an anti-CTLA-4 antibody.

14. The method of claim 13, wherein the anti-PD-1 antibody is nivolumab.

15. The method of claim 13, wherein the anti-CTLA-4 antibody is ipilimumab.

16. The method of claim 12, wherein the additional therapeutic agent is cetuximab.

17. A method of treating a cancer expressing HLA-E in a subject in need thereof comprising administering to the subject an isolated antibody or antigen-binding fragment thereof that binds human NKG2A wherein said antibody comprises an HCDR1 of the amino acid sequence of SEQ ID NO:10, an HCDR2 of the amino acid sequence of SEQ ID NO:11 and an HCDR3 of the amino acid sequence of SEQ ID NO: 12 and an LCDR1 of the amino acid sequence of SEQ ID NO:13, an LCDR2 of the amino acid sequence of SEQ ID NO:14 and an LCDR3 of the amino acid sequence of SEQ ID NO:15.

18. The method of claim 17, wherein the isolated antibody or antigen-binding fragment thereof comprises a VH at least 90% identical to the amino acid sequence of SEQ ID NO:8 and a VL at least 90% identical to the amino acid sequence of SEQ ID NO:9.

19. The method of claim 17, wherein the isolated antibody, or antigen-binding fragment thereof, comprises a VH at least 95% identical to the amino acid sequence of SEQ ID NO:8 and a VL at least 95% identical to the amino acid sequence of SEQ ID NO:9.

20. The method of claim 17, wherein the isolated antibody, or antigen-binding fragment thereof, comprises a VH at least 98% identical to the amino acid sequence of SEQ ID NO:8 and a VL at least 98% identical to the amino acid sequence of SEQ ID NO:9.

21. The method of claim 17, wherein the isolated antibody, or antigen-binding fragment thereof, comprises a VH at least 99% identical to the amino acid sequence of SEQ ID NO:8 and a VL at least 99% identical to the amino acid sequence of SEQ ID NO:9.

22. The method of claim 17, wherein the antibody is a full-length antibody.

23. The method of claim 17, wherein the cancer is bladder cancer, breast cancer, uterine cancer, cervical cancer, ovarian cancer, prostate cancer, testicular cancer, esophageal cancer, gastrointestinal cancer, pancreatic cancer, colorectal cancer, head and neck cancer, lung cancer, stomach cancer, germ cell cancer, bone cancer, liver cancer, thyroid cancer, skin cancer, neoplasm of the central nervous system, lymphoma, leukemia, myeloma, sarcoma, endometrial cancer, gastric cancer, melanoma, renal cancer, urothelial cancer, or glioblastoma multiforme.

24. The method of claim 23, wherein the head and neck cancer is squamous cell carcinoma of the head and neck.

25. The method of claim 23, wherein the lung cancer is non-small cell lung cancer.

26. The method of claim 23, wherein the lymphoma is non-Hodgkin lymphoma.

27. The method of claim 23, wherein the renal cancer is renal cell carcinoma.

28. The method of claim 17, wherein said antibody or antigen-binding fragment thereof is administered in combination with one or more additional therapeutic agents.

29. The method of claim 28 wherein the additional therapeutic agent is an anti-PD-1 antibody, anti-PD-L1 antibody, or an anti-CTLA-4 antibody.

30. The method of claim 29, wherein the anti-PD-1 antibody is nivolumab.

31. The method of claim 29, wherein the anti-CTLA-4 antibody is ipilimumab.

32. The method of claim 28, wherein the additional therapeutic agent is cetuximab.

33. A method of treating a cancer expressing HLA-E in a subject in need thereof comprising administering to the subject an isolated antibody or antigen-binding fragment thereof that binds human NKG2A wherein said antibody comprises a VH of the amino acid sequence of SEQ ID NO:8 and a VL of the amino acid sequence of SEQ ID NO:9.

34. The method of claim 33, wherein the isolated antibody comprises a HC at least 90% identical to an amino acid sequence of SEQ ID NO:7 and a LC at least 90% identical to an amino acid sequence of SEQ ID NO:5.

35. The method of claim 33, wherein the isolated antibody comprises a HC at least 95% identical to an amino acid sequence of SEQ ID NO:7 and a LC at least 95% identical to an amino acid sequence of SEQ ID NO:5.

36. The method of claim 33, wherein isolated antibody comprises a HC at least 98% identical to an amino acid sequence of SEQ ID NO:7 and a LC at least 98% identical to an amino acid sequence of SEQ ID NO:5.

37. The method of claim 33, wherein isolated antibody comprises a HC at least 99% identical to an amino acid sequence of SEQ ID NO:7 and a LC at least 99% identical to an amino acid sequence of SEQ ID NO:5.

38. The method of claim 33, wherein the antibody is a full-length antibody.

39. The method of claim 33, wherein the cancer is bladder cancer, breast cancer, uterine cancer, cervical cancer, ovarian cancer, prostate cancer, testicular cancer, esophageal cancer, gastrointestinal cancer, pancreatic cancer, colorectal cancer, head and neck cancer, lung cancer, stomach cancer, germ cell cancer, bone cancer, liver cancer, thyroid cancer, skin cancer, neoplasm of the central nervous system, lymphoma, leukemia, myeloma, sarcoma, endometrial cancer, gastric cancer, melanoma, renal cancer, urothelial cancer, or glioblastoma multiforme.

40. The method of claim 39, wherein the head and neck cancer is squamous cell carcinoma of the head and neck.

41. The method of claim 39, wherein the lung cancer is non-small cell lung cancer.

42. The method of claim 39, wherein the lymphoma is non-Hodgkin lymphoma.

43. The method of claim 39, wherein the renal cancer is renal cell carcinoma.

44. The method of claim 33, wherein said antibody or antigen-binding fragment thereof is administered in combination with one or more additional therapeutic agents.

45. The method of claim 44 wherein the additional therapeutic agent is an anti-PD-1 antibody, anti-PD-L1 antibody, or an anti-CTLA-4 antibody.

46. The method of claim 45, wherein the anti-PD-1 antibody is nivolumab.

47. The method of claim 45, wherein the anti-CTLA-4 antibody is ipilimumab.

48. The method of claim 44, wherein the additional therapeutic agent is cetuximab.

49. A method of treating a cancer expressing HLA-E in a subject in need thereof comprising administering to the subject an isolated antibody that binds human NKG2A wherein said antibody comprises a HC of the amino acid sequence of SEQ ID NO:7 and a LC of the amino acid sequence of SEQ ID NO:5.

50. The method of claim 49, wherein the cancer is bladder cancer, breast cancer, uterine cancer, cervical cancer, ovarian cancer, prostate cancer, testicular cancer, esophageal cancer, gastrointestinal cancer, pancreatic cancer, colorectal cancer, head and neck cancer, lung cancer, stomach cancer, germ cell cancer, bone cancer, liver cancer, thyroid cancer, skin cancer, neoplasm of the central nervous system, lymphoma, leukemia, myeloma, sarcoma, endometrial cancer, gastric cancer, melanoma, renal cancer, urothelial cancer, or glioblastoma multiforme.

51. The method of claim 50, wherein the head and neck cancer is squamous cell carcinoma of the head and neck.

52. The method of claim 50, wherein the lung cancer is non-small cell lung cancer.

53. The method of claim 50, wherein the lymphoma is non-Hodgkin lymphoma.

54. The method of claim 50, wherein the renal cancer is renal cell carcinoma.

55. The method of claim 50, wherein said antibody or antigen-binding fragment thereof is administered in combination with one or more additional therapeutic agents.

56. The method of claim 55 wherein the additional therapeutic agent is an anti-PD-1 antibody, anti-PD-L1 antibody, or an anti-CTLA-4 antibody.

57. The method of claim 56, wherein the anti-PD-1 antibody is nivolumab.

58. The method of claim 56, wherein the anti-CTLA-4 antibody is ipilimumab.

59. The method of claim 55, wherein the additional therapeutic agent is cetuximab.

60. A method of treating a cancer expressing HLA-E in a subject in need thereof comprising administering to the subject an isolated antibody or antigen-binding fragment thereof that binds human NKG2A wherein said antibody or antigen-binding fragment thereof comprises an HCDR1 of the amino acid sequence of SEQ ID NO:10, an HCDR2 of the amino acid sequence of SEQ ID NO:11 and an HCDR3 of the amino acid sequence of SEQ ID NO:12 and a LCDR1 of the amino acid sequence of SEQ ID NO: 154, an LCDR2 of the amino acid sequence of SEQ ID NO: 14 and an LCDR3 of the amino acid sequence of SEQ ID NO:15.

61. The method of claim 60, wherein the isolated antibody or antigen-binding fragment thereof comprises a VH at least 90% identical to the amino acid sequence of SEQ ID NO:8 and a VL at least 90% identical to the amino acid sequence of SEQ ID NO: 164.

62. The method of claim 60, wherein the isolated antibody or antigen-binding fragment thereof comprises a VH at least 95% identical to the amino acid sequence of SEQ ID NO:8 and a VL at least 95% identical to the amino acid sequence of SEQ ID NO:164.

63. The method of claim 60, wherein the isolated antibody, or antigen-binding fragment thereof, comprises a VH at least 99% identical to the amino acid sequence of SEQ ID NO:8 and a VL at least 99% identical to the amino acid sequence of SEQ ID NO:164.

64. The method of claim 60, wherein the isolated antibody, or antigen-binding fragment thereof, comprises a VH of the amino acid sequence of SEQ ID NO:8 and a VL of the amino acid sequence of SEQ ID NO: 164.

65. The method of claim 60, wherein the isolated antibody comprises a HC of the amino acid sequence of SEQ ID NO:7 and a LC of the amino acid sequence of SEQ ID NO: 19.

66. The method of claim 60, wherein the antibody is a full-length antibody.

67. The method of claim 60, wherein the cancer is bladder cancer, breast cancer, uterine cancer, cervical cancer, ovarian cancer, prostate cancer, testicular cancer, esophageal cancer, gastrointestinal cancer, pancreatic cancer, colorectal cancer, head and neck cancer, lung cancer, stomach cancer, germ cell cancer, bone cancer, liver cancer, thyroid cancer, skin cancer, neoplasm of the central nervous system, lymphoma, leukemia, myeloma, sarcoma, endometrial cancer, gastric cancer, melanoma, renal cancer, urothelial cancer, or glioblastoma multiforme.

68. The method of claim 67, wherein the head and neck cancer is squamous cell carcinoma of the head and neck.

69. The method of claim 67, wherein the lung cancer is non-small cell lung cancer.

70. The method of claim 67, wherein the lymphoma is non-Hodgkin lymphoma.

71. The method of claim 67, wherein the renal cancer is renal cell carcinoma.

72. The method of claim 60, wherein said antibody or antigen-binding fragment thereof is administered in combination with one or more additional therapeutic agents.

73. The method of claim 72 wherein the additional therapeutic agent is an anti-PD-1 antibody, anti-PD-L1 antibody, or an anti-CTLA-4 antibody.

74. The method of claim 73, wherein the anti-PD-1 antibody is nivolumab.

75. The method of claim 73, wherein the anti-CTLA-4 antibody is ipilimumab.

76. The method of claim 72, wherein the additional therapeutic agent is cetuximab.

* * * * *

SEQUENCE LISTING

<160> NUMBER OF SEQ ID NOS: 212

<210> SEQ ID NO 1
<211> LENGTH: 702
<212> TYPE: DNA
<213> ORGANISM: Homo sapiens

<400> SEQUENCE: 1

```
atggataacc aaggagtaat ctactcagac ctgaatctgc ccccaaaccc aaagaggcag      60
caacgaaaac ctaaaggcaa taaaaactcc attttagcaa ctgaacagga aataacctat     120
gcggaattaa accttcaaaa agcttctcag gattttcaag ggaatgacaa aacctatcac     180
tgcaaagatt taccatcagc tccagagaag ctcattgttg ggatcctggg aattatctgt     240
cttatcttaa tggcctctgt ggtaacgata gttgttattc cctctacatt aatacagagg     300
cacaacaatt cttccctgaa tacaagaact cagaaagcac gtcattgtgg ccattgtcct     360
gaggagtgga ttacatattc aacagttgt tactacattg gtaaggaaag aagaacttgg     420
gaagagagtt tgctggcctg tacttcgaag aactccagtc tgctttctat agataatgaa     480
gaagaaatga aatttctgtc catcatttca ccatcctcat ggattggtgt gtttcgtaac     540
agcagtcatc atccatgggt gacaatgaat ggtttggctt tcaaacatga gataaaagac     600
tcagataatg ctgaacttaa ctgtgcagtg ctacaagtaa atcgacttaa atcagcccag     660
```
tgtggatctt caataatata tcattgtaag cataagcttt ag         702

<210> SEQ ID NO 2
<211> LENGTH: 233
<212> TYPE: PRT
<213> ORGANISM: Homo sapiens

<400> SEQUENCE: 2

Met Asp Asn Gln Gly Val Ile Tyr Ser Asp Leu Asn Leu Pro Pro Asn
1               5                   10                  15

Pro Lys Arg Gln Gln Arg Lys Pro Lys Gly Asn Lys Asn Ser Ile Leu
                20                  25                  30

Ala Thr Glu Gln Glu Ile Thr Tyr Ala Glu Leu Asn Leu Gln Lys Ala
            35                  40                  45

Ser Gln Asp Phe Gln Gly Asn Asp Lys Thr Tyr His Cys Lys Asp Leu
        50                  55                  60

Pro Ser Ala Pro Glu Lys Leu Ile Val Gly Ile Leu Gly Ile Ile Cys
65                  70                  75                  80

Leu Ile Leu Met Ala Ser Val Val Thr Ile Val Val Ile Pro Ser Thr
                85                  90                  95

Leu Ile Gln Arg His Asn Asn Ser Ser Leu Asn Thr Arg Thr Gln Lys
                100                 105                 110

Ala Arg His Cys Gly His Cys Pro Glu Glu Trp Ile Thr Tyr Ser Asn
            115                 120                 125

Ser Cys Tyr Tyr Ile Gly Lys Glu Arg Arg Thr Trp Glu Glu Ser Leu
        130                 135                 140

Leu Ala Cys Thr Ser Lys Asn Ser Ser Leu Leu Ser Ile Asp Asn Glu
145                 150                 155                 160

Glu Glu Met Lys Phe Leu Ser Ile Ile Ser Pro Ser Ser Trp Ile Gly
                165                 170                 175

Val Phe Arg Asn Ser Ser His His Pro Trp Val Thr Met Asn Gly Leu
                180                 185                 190

Ala Phe Lys His Glu Ile Lys Asp Ser Asp Asn Ala Glu Leu Asn Cys
            195                 200                 205

Ala Val Leu Gln Val Asn Arg Leu Lys Ser Ala Gln Cys Gly Ser Ser
        210                 215                 220

Ile Ile Tyr His Cys Lys His Lys Leu
225                 230

<210> SEQ ID NO 3
<211> LENGTH: 231
<212> TYPE: PRT
<213> ORGANISM: Homo sapiens

<400> SEQUENCE: 3

Met Ser Lys Gln Arg Gly Thr Phe Ser Glu Val Ser Leu Ala Gln Asp
1               5                   10                  15

Pro Lys Arg Gln Gln Arg Lys Pro Lys Gly Asn Lys Ser Ser Ile Ser
                20                  25                  30

Gly Thr Glu Gln Glu Ile Phe Gln Val Glu Leu Asn Leu Gln Asn Pro
            35                  40                  45

Ser Leu Asn His Gln Gly Ile Asp Lys Ile Tyr Asp Cys Gln Gly Leu
        50                  55                  60

Leu Pro Pro Pro Glu Lys Leu Thr Ala Glu Val Leu Gly Ile Ile Cys
65                  70                  75                  80

Ile Val Leu Met Ala Thr Val Leu Lys Thr Ile Val Leu Ile Pro Phe
                85                  90                  95

Leu Glu Gln Asn Asn Ser Ser Pro Asn Thr Arg Thr Gln Lys Ala Arg
            100                 105                 110

His Cys Gly His Cys Pro Glu Glu Trp Ile Thr Tyr Ser Asn Ser Cys
        115                 120                 125

Tyr Tyr Ile Gly Lys Glu Arg Arg Thr Trp Glu Glu Ser Leu Leu Ala
    130                 135                 140

Cys Thr Ser Lys Asn Ser Ser Leu Leu Ser Ile Asp Asn Glu Glu Glu
145                 150                 155                 160

Met Lys Phe Leu Ala Ser Ile Leu Pro Ser Ser Trp Ile Gly Val Phe
                165                 170                 175

Arg Asn Ser Ser His His Pro Trp Val Thr Ile Asn Gly Leu Ala Phe
            180                 185                 190

Lys His Lys Ile Lys Asp Ser Asp Asn Ala Glu Leu Asn Cys Ala Val
        195                 200                 205

Leu Gln Val Asn Arg Leu Lys Ser Ala Gln Cys Gly Ser Ser Met Ile
    210                 215                 220

Tyr His Cys Lys His Lys Leu
225                 230

<210> SEQ ID NO 4
<211> LENGTH: 645
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4
gccatccagt tgacccagtc tccatcctcc ctgtctgcat ctgtaggaga cagagtcacc      60
atcacttgcc gggcaagtca gggcatttcc agtgctttag cctggtatca gcagaaacca     120
gggaaagctc ctaagctcct gatctatgat gcctccagtt tgaaaagtgg ggtcccatca     180
aggttcagcg gcagtggatc tgggacagat ttcactctca ccatcagcag cctgcagcct     240
gaagattttg caacttatta ctgtcaacag tttaatagtt accctctcac cttcggccaa     300
gggacacgac tggagattaa acgtacggtg gctgcaccat ctgtcttcat cttcccgcca     360
tctgatgagc agttgaaatc tggaactgcc tctgttgtgt gcctgctgaa taacttctat     420
cccagagagg ccaaagtaca gtggaaggtg gataacgccc tccaatcggg taactcccag     480
gagagtgtca cagagcagga cagcaaggac agcacctaca gcctcagcag caccctgacg     540
ctgagcaaag cagactacga gaaacacaaa gtctacgcct gcgaagtcac ccatcagggc     600
ctgagctcgc ccgtcacaaa gagcttcaac aggggagagt gttag                    645

<210> SEQ ID NO 5
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Leu Leu Ile
            35                  40                  45

Tyr Asp Ala Ser Ser Leu Lys Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Phe Asn Ser Tyr Pro Leu
                85                  90                  95

Thr Phe Gly Gln Gly Thr Arg Leu Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
        210

<210> SEQ ID NO 6
<211> LENGTH: 1344
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6
gaggtgcagc tggtggagtc tgggggaggc ctggtcaagc cggggggggtc cctgagactc        60 tcctgtgcag cctctggatt cacctttcagt tcccatagta tgaactgggt ccgccaggct       120
ccagggaagg gctggagtg gtctcagcc ataagtagta gtagtagtta catatactac          180
gcagactcag tgaagggccg attcaccatc tccagagaca acgccaagaa ctcactgtat        240
ctgcaaatga acagcctgag agccgaggac acggctgtgt attactgtgc gagagaagag        300
tgggggctac cctttgacta ctggggccag ggaaccctgg tcaccgtctc ctcagctagc        360
accaagggcc catcggtctt ccccctggca ccctcctcca agagcacctc tgggggcaca        420
gcggccctgg gctgcctggt caaggactac ttccccgaac cggtgacggt gtcgtggaac        480
tcaggcgccc tgaccagcgg cgtgcacacc ttcccggctg tcctacagtc ctcaggactc        540
tactccctca gcagcgtggt gaccgtgccc tccagcagct gggcacccca gacctacatc        600
tgcaacgtga atcacaagcc cagcaacacc aaggtggaca gagagttga gcccaaatct        660 tgtgacaaaa ctcacacatg cccaccgtgc ccagcacctg aagccgaagg ggccccgtca        720
gtcttcctct tccccccaaa acccaaggac accctcatga tctcccggac ccctgaggtc        780
acatgcgtgg tggtggacgt gagccacgaa gaccctgagg tcaagttcaa ctggtacgtg        840
gacggcgtgg aggtgcataa tgccaagaca aagccgcggg aggagcagta caacagcacg        900
taccgtgtgg tcagcgtcct caccgtcctg caccaggact ggctgaatgg caaggagtac        960

-continued

```
aagtgcaagg tctccaacaa agccctccca gcccccatcg agaaaaccat ctccaaagcc    1020
aaagggcagc cccgagaacc acaggtgtac accctgcccc catcccggga ggagatgacc    1080
aagaaccagg tcagcctgac ctgcctggtc aaaggcttct atcccagcga catcgccgtg    1140
gagtgggaga gcaatgggca gccggagaac aactacaaga ccacgcctcc cgtgctggac    1200
tccgacggct ccttcttcct ctatagcaag ctcaccgtgg acaagagcag gtggcagcag    1260
gggaacgtct tctcatgctc cgtgatgcat gaggctctgc acaaccacta cacgcagaag    1320
agcctctccc tgtccccggg ttga                                          1344
```

<210> SEQ ID NO 7
<211> LENGTH: 447
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 7

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser His
            20                  25                  30

Ser Met Asn Trp Val Arg Gln Ala Pro Gly Lys Gly Leu Glu Trp Val
        35                  40                  45

Ser Ala Ile Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Glu Trp Gly Leu Pro Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Ala Glu Gly Ala Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285
```

Lys Thr Lys Pro Arg Glu Glu Gln Tyr Asn Ser Thr Tyr Arg Val Val
            290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
            355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
            435                 440                 445

<210> SEQ ID NO 8
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser His
            20                  25                  30

Ser Met Asn Trp Val Arg Gln Ala Pro Gly Lys Gly Leu Glu Trp Val
        35                  40                  45

Ser Ala Ile Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Glu Trp Gly Leu Pro Phe Asp Tyr Trp Gly Gln Gly Thr
            100                 105                 110

Leu Val Thr Val Ser Ser
        115

<210> SEQ ID NO 9
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Ala Ile Gln Leu Thr Gln Ser Pro Ser Ser Leu Ser Ala Ser Val Gly
1               5                   10                  15

```
Asp Arg Val Thr Ile Thr Cys Arg Ala Ser Gln Gly Ile Ser Ser Ala
             20                  25                  30

Leu Ala Trp Tyr Gln Gln Lys Pro Gly Lys Ala Pro Lys Leu Leu Ile
         35                  40                  45

Tyr Asp Ala Ser Ser Leu Lys Ser Gly Val Pro Ser Arg Phe Ser Gly
     50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Leu
                 85                  90                  95

Thr Phe Gly Gln Gly Thr Arg Leu Glu Ile Lys
            100                 105

<210> SEQ ID NO 10
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Ser His Ser Met Asn
1               5

<210> SEQ ID NO 11
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Ala Ile Ser Ser Ser Ser Ser Tyr Ile Tyr Tyr Ala Asp Ser Val Lys
1               5                   10                  15

Gly

<210> SEQ ID NO 12
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Glu Glu Trp Gly Leu Pro Phe Asp Tyr
1               5

<210> SEQ ID NO 13
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Arg Ala Ser Gln Gly Ile Ser Ser Ala Leu Ala
1               5                   10

<210> SEQ ID NO 14
```

```
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Asp Ala Ser Ser Leu Lys Ser
1               5

<210> SEQ ID NO 15
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Gln Gln Phe Asn Ser Tyr Pro Leu Thr
1               5

<210> SEQ ID NO 16
<211> LENGTH: 329
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Ala Glu Gly Ala Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220
```

```
Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325
```

<210> SEQ ID NO 17
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

```
Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

<210> SEQ ID NO 18
<211> LENGTH: 645
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 18

```
gccatccagt tgacccagtc tccatcctcc ctgtctgcat ctgtaggaga cagagtcacc      60
atcacttgcc gggcaagtca gggcattccc agtgctttag cctggtatca gcagaaacca     120
gggaaagctc ctaagctcct gatctatgat gcctccagtt tgaaaagtgg ggtcccatca     180
aggttcagcg gcagtggatc tgggacagat tcactctca ccatcagcag cctgcagcct     240
gaagattttg caacttatta ctgtcaacag tttaatagtt accctctcac cttcggccaa    300
gggacacgac tggagattaa acgtacggtg gctgcaccat ctgtcttcat cttcccgcca    360
tctgatgagc agttgaaatc tggaactgcc tctgttgtgt gcctgctgaa taacttctat    420
cccagagagg ccaaagtaca gtggaaggtg gataacgccc tccaatcggg taactcccag    480
```

-continued

```
gagagtgtca cagagcagga cagcaaggac agcacctaca gcctcagcag caccctgacg    540
ctgagcaaag cagactacga gaaacacaaa gtctacgcct gcgaagtcac ccatcagggc    600
ctgagctcgc ccgtcacaaa gagcttcaac aggggagagt gttag                    645
```

```
<210> SEQ ID NO 19
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Pro Ser Ala
            20                  25                  30

Leu Ala Trp Tyr Gln Gln Lys Pro Gly Lys Ala Pro Lys Leu Leu Ile
        35                  40                  45

Tyr Asp Ala Ser Ser Leu Lys Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Leu
                85                  90                  95

Thr Phe Gly Gln Gly Thr Arg Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

```
<210> SEQ ID NO 20
<211> LENGTH: 51
<212> TYPE: DNA
<213> ORGANISM: Unknown
<220> FEATURE:
<223> OTHER INFORMATION: Description of Unknown: Osteonectin
      oligonucleotide

<400> SEQUENCE: 20
atgagggctt ggatcttctt tctgctctgc ctggccgggc gcgccttggc c             51
```

```
<210> SEQ ID NO 21
<211> LENGTH: 17
<212> TYPE: PRT
<213> ORGANISM: Unknown
<220> FEATURE:
```

<223> OTHER INFORMATION: Description of Unknown: Osteonectin
    peptide

<400> SEQUENCE: 21

Met Arg Ala Trp Ile Phe Phe Leu Leu Cys Leu Ala Gly Arg Ala Leu
1               5                   10                  15

Ala

<210> SEQ ID NO 22
<211> LENGTH: 19
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 22

Met Glu Leu Gly Leu Arg Trp Val Phe Leu Val Ala Ile Leu Glu Gly
1               5                   10                  15

Val Gln Cys

<210> SEQ ID NO 23
<211> LENGTH: 411
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 23
atggaactgg ggctccgctg ggttttcctt gttgctattt tagaaggtgt ccagtgtgag      60
gtgcagctgg tggagtctgg gggaggcctg gtcaagccgg ggggtccct gagactctcc     120 tgtgcagcct ctggattcac cttcagttcc catagtatga actgggtccg ccaggctcca    180
gggaaggggc tggagtgggt ctcagccata agtagtagta gtagttacat atactacgca    240
gactcagtga agggccgatt caccatctcc agagacaacg ccaagaactc actgtatctg    300
caaatgaaca gcctgagagc cgaggacacg gctgtgtatt actgtgcgag agaagagtgg    360
gggctaccct ttgactactg gggccaggga atcctggtca ccgtctcctc a             411

<210> SEQ ID NO 24
<211> LENGTH: 137
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 24

Met Glu Leu Gly Leu Arg Trp Val Phe Leu Val Ala Ile Leu Glu Gly
1               5                   10                  15

Val Gln Cys Glu Val Gln Leu Val Glu Ser Gly Gly Gly Leu Val Lys
            20                  25                  30

Pro Gly Gly Ser Leu Arg Leu Ser Cys Ala Ala Ser Gly Phe Thr Phe
        35                  40                  45

Ser Ser His Ser Met Asn Trp Val Arg Gln Ala Pro Gly Lys Gly Leu
    50                  55                  60

Glu Trp Val Ser Ala Ile Ser Ser Ser Ser Ser Tyr Ile Tyr Tyr Ala
65                  70                  75                  80

Asp Ser Val Lys Gly Arg Phe Thr Ile Ser Arg Asp Asn Ala Lys Asn
                85                  90                  95

```
Ser Leu Tyr Leu Gln Met Asn Ser Leu Arg Ala Glu Asp Thr Ala Val
            100                 105                 110

Tyr Tyr Cys Ala Arg Glu Glu Trp Gly Leu Pro Phe Asp Tyr Trp Gly
        115                 120                 125

Gln Gly Ile Leu Val Thr Val Ser Ser
    130                 135

<210> SEQ ID NO 25
<211> LENGTH: 387
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 25
atggacatga gggtccccgc tcagctcctg gggcttctgc tgctctggct cccaggtgcc      60
agatgtgcca tccagttgac ccagtctcca tcctccctgt ctgcatctgt aggagacaga    120
gtcaccatca cttgccgggc aagtcagggc attaacagtg ctttagcctg gtatcagcag    180
aaaccaggga aagctcctaa gctcctgatc tatgatgcct ccagtttgaa aagtggggtc    240
ccatcaaggt tcagcggcag tggatctggg acagatttca ctctcaccat cagcagcctg    300
cagcctgaag attttgcaac ttattactgt caacagttta atagttaccc tctcaccttc    360
ggccaaggga cacgactgga gattaaa                                       387

<210> SEQ ID NO 26
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Met Asp Met Arg Val Pro Ala Gln Leu Leu Gly Leu Leu Leu Leu Trp
1               5                   10                  15

Leu Pro Gly Ala Arg Cys Ala Ile Gln Leu Thr Gln Ser Pro Ser Ser
            20                  25                  30

Leu Ser Ala Ser Val Gly Asp Arg Val Thr Ile Thr Cys Arg Ala Ser
        35                  40                  45

Gln Gly Ile Asn Ser Ala Leu Ala Trp Tyr Gln Gln Lys Pro Gly Lys
    50                  55                  60

Ala Pro Lys Leu Leu Ile Tyr Asp Ala Ser Ser Leu Lys Ser Gly Val
65                  70                  75                  80

Pro Ser Arg Phe Ser Gly Ser Gly Ser Gly Thr Asp Phe Thr Leu Thr
                85                  90                  95

Ile Ser Ser Leu Gln Pro Glu Asp Phe Ala Thr Tyr Tyr Cys Gln Gln
            100                 105                 110

Phe Asn Ser Tyr Pro Leu Thr Phe Gly Gln Gly Thr Arg Leu Glu Ile
        115                 120                 125

Lys

<210> SEQ ID NO 27
<211> LENGTH: 5
<212> TYPE: PRT
<213> ORGANISM: Artificial Sequence
<220> FEATURE:
<223> OTHER INFORMATION: Description of Artificial Sequence: Synthetic
```

```
        peptide

<400> SEQUENCE: 27

Ser His Ser Met Asn
1               5

<210> SEQ ID NO 28
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Ala Ile Ser Ser Ser Ser Ser Tyr Ile Tyr Tyr Ala Asp Ser Val Lys
1               5                   10                  15

Gly

<210> SEQ ID NO 29
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Glu Glu Trp Gly Leu Pro Phe Asp Tyr
1               5

<210> SEQ ID NO 30
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Arg Ala Ser Gln Gly Ile Asn Ser Ala Leu Ala
1               5                   10

<210> SEQ ID NO 31
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Asp Ala Ser Ser Leu Lys Ser
1               5

<210> SEQ ID NO 32
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Gln Gln Phe Asn Ser Tyr Pro Leu Thr
1               5
```

<210> SEQ ID NO 33
<211> LENGTH: 330
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 33

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 34
<211> LENGTH: 107
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 34

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 35
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (448)..(448)
<223> OTHER INFORMATION: May or may not be present

<400> SEQUENCE: 35

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser His
            20                  25                  30

Ser Met Asn Trp Val Arg Gln Ala Pro Gly Lys Gly Leu Glu Trp Val
        35                  40                  45

Ser Ala Ile Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Glu Trp Gly Leu Pro Phe Asp Tyr Trp Gly Gln Gly Ile
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
```

```
                195                 200                 205
Asn Thr Lys Val Asp Lys Lys Val Glu Pro Lys Ser Cys Asp Lys Thr
210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
                260                 265                 270

Glu Val Lys Phe Asn Trp Tyr Val Asp Gly Val Glu Val His Asn Ala
                275                 280                 285

Lys Thr Lys Pro Arg Glu Glu Gln Tyr Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
                340                 345                 350

Pro Pro Ser Arg Asp Glu Leu Thr Lys Asn Gln Val Ser Leu Thr Cys
                355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly Lys
                435                 440                 445

<210> SEQ ID NO 36
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Asn Ser Ala
                20                  25                  30

Leu Ala Trp Tyr Gln Gln Lys Pro Gly Lys Ala Pro Lys Leu Leu Ile
            35                  40                  45

Tyr Asp Ala Ser Ser Leu Lys Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Leu
                85                  90                  95

Thr Phe Gly Gln Gly Thr Arg Leu Glu Ile Lys Arg Thr Val Ala Ala
                100                 105                 110
```

```
Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
        165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 37
<211> LENGTH: 414
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 37

```
atggaactgg ggctccgctg ggttttcctt gttgctattt tagaaggtgt ccagtgtgag      60
gtgcagttgg tggagtctgg gggaggcctg gtcaagcctg gggggtccct gagactctcc     120
tgtgcagcct ctggattcac cttcagtagc tatagcatga actgggtccg ccaggctcca     180
gggaaggggc tggagtgggt ctcatccatt agtagtagta gtagttacat atactacgca     240
gactcagtga aggccgatt caccatctcc agagacaacg ccaagaactc actgtatctg     300
caaatgaaca gcctgagagc cgaggacacg gctgtgtatt actgtgcgag actactatgg     360
ttcggggaga ttttgacta ctggggccag ggaaccctgg tcaccgtctc ctca           414
```

<210> SEQ ID NO 38
<211> LENGTH: 138
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 38

```
Met Glu Leu Gly Leu Arg Trp Val Phe Leu Val Ala Ile Leu Glu Gly
1               5                   10                  15

Val Gln Cys Glu Val Gln Leu Val Glu Ser Gly Gly Gly Leu Val Lys
            20                  25                  30

Pro Gly Gly Ser Leu Arg Leu Ser Cys Ala Ala Ser Gly Phe Thr Phe
        35                  40                  45

Ser Ser Tyr Ser Met Asn Trp Val Arg Gln Ala Pro Gly Lys Gly Leu
    50                  55                  60

Glu Trp Val Ser Ser Ile Ser Ser Ser Ser Tyr Ile Tyr Tyr Ala
65                  70                  75                  80

Asp Ser Val Lys Gly Arg Phe Thr Ile Ser Arg Asp Asn Ala Lys Asn
                85                  90                  95

Ser Leu Tyr Leu Gln Met Asn Ser Leu Arg Ala Glu Asp Thr Ala Val
            100                 105                 110

Tyr Tyr Cys Ala Arg Leu Leu Trp Phe Gly Glu Ile Phe Asp Tyr Trp
```

115                 120                 125
Gly Gln Gly Thr Leu Val Thr Val Ser Ser
        130                 135

<210> SEQ ID NO 39
<211> LENGTH: 387
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 39
atggacatga gggtccccgc tcagctcctg gggcttctgc tgctctggct cccaggtgcc        60
agatgtgcca tccagttgac ccagtctcca tcctccctgt ctgcatctgt aggagacaga       120
gtcaccatca cttgccgggc aagtcagggc attagcagtg ctttagcctg gtatcagcag       180
aaaccaggga agctcctaa gctcctgatc tatgatgcct ccagtttgaa aagtggggtc        240
ccatcaaggt tcagcggcag tggatctggg acagatttca ctctcaccat cagcagcctg       300
cagcctgaag attttgcaac ttattactgt caacagttta atagttaccc gatcaccttc       360
ggccaaggga cacgactgga gattaaa                                           387

<210> SEQ ID NO 40
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Met Asp Met Arg Val Pro Ala Gln Leu Leu Gly Leu Leu Leu Leu Trp
1               5                   10                  15

Leu Pro Gly Ala Arg Cys Ala Ile Gln Leu Thr Gln Ser Pro Ser Ser
            20                  25                  30

Leu Ser Ala Ser Val Gly Asp Arg Val Thr Ile Thr Cys Arg Ala Ser
        35                  40                  45

Gln Gly Ile Ser Ser Ala Leu Ala Trp Tyr Gln Gln Lys Pro Gly Lys
    50                  55                  60

Ala Pro Lys Leu Leu Ile Tyr Asp Ala Ser Ser Leu Lys Ser Gly Val
65                  70                  75                  80

Pro Ser Arg Phe Ser Gly Ser Gly Ser Gly Thr Asp Phe Thr Leu Thr
                85                  90                  95

Ile Ser Ser Leu Gln Pro Glu Asp Phe Ala Thr Tyr Tyr Cys Gln Gln
            100                 105                 110

Phe Asn Ser Tyr Pro Ile Thr Phe Gly Gln Gly Thr Arg Leu Glu Ile
        115                 120                 125

Lys

<210> SEQ ID NO 41
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Ser Tyr Ser Met Asn

```
<210> SEQ ID NO 42
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Ser Ile Ser Ser Ser Ser Ser Tyr Ile Tyr Tyr Ala Asp Ser Val Lys
1               5                   10                  15

Gly

<210> SEQ ID NO 43
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Leu Leu Trp Phe Gly Glu Ile Phe Asp Tyr
1               5                   10

<210> SEQ ID NO 44
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Arg Ala Ser Gln Gly Ile Ser Ser Ala Leu Ala
1               5                   10

<210> SEQ ID NO 45
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Asp Ala Ser Ser Leu Lys Ser
1               5

<210> SEQ ID NO 46
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Gln Gln Phe Asn Ser Tyr Pro Ile Thr
1               5

<210> SEQ ID NO 47
<211> LENGTH: 330
<212> TYPE: PRT
<213> ORGANISM: Artificial Sequence
```

<220> FEATURE:
<223> OTHER INFORMATION: Description of Artificial Sequence: Synthetic
      polypeptide

<400> SEQUENCE: 47

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 48
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

```
Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 49
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Tyr Ile Tyr Tyr Ala Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Leu Leu Trp Phe Gly Glu Ile Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
```

```
                        245                 250                 255
Arg Thr Pro Glu Val Thr Cys Val Val Asp Val Ser His Glu Asp
            260                 265                 270

Pro Glu Val Lys Phe Asn Trp Tyr Val Asp Gly Val Glu Val His Asn
                275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
                355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
                435                 440                 445

Lys

<210> SEQ ID NO 50
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Leu Leu Ile
        35                  40                  45

Tyr Asp Ala Ser Ser Leu Lys Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Ile
                85                  90                  95

Thr Phe Gly Gln Gly Thr Arg Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
```

```
                145                 150                 155                 160
Glu Ser Val Thr Glu Gln Asp Ser Lys Asp Ser Thr Tyr Ser Leu Ser
                    165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 51
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 51
gaggtgcaac tggtggagtc tgggggaggc ttggtacagc ggggggggtc cctgagactc      60
tcctgtgcag cctctggatt caccttcagt agcaatagca tgaactggat ccgccaggct     120
ccagggaagg ggctggagtg ggttgcacac attagtagtg gtagcagttt catatactac     180
gcagactctg tgaagggccg attcaccatc tccagagaca tgccaagaa ctctctgtct      240 ctgcaaatga acagcctgag agacgaagac acggctgtgt attactgtgc gagagatgac     300
tggggaattg atgcttttaa tatctggggc caagggacaa tggtcaccgt ctcttca        357

<210> SEQ ID NO 52
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Glu Val Gln Leu Val Glu Ser Gly Gly Gly Leu Val Gln Arg Gly Gly
1               5                   10                  15

Ser Leu Arg Leu Ser Cys Ala Ala Ser Gly Phe Thr Phe Ser Ser Asn
            20                  25                  30

Ser Met Asn Trp Ile Arg Gln Ala Pro Gly Lys Gly Leu Glu Trp Val
        35                  40                  45

Ala His Ile Ser Ser Gly Ser Ser Phe Ile Tyr Tyr Ala Asp Ser Val
    50                  55                  60

Lys Gly Arg Phe Thr Ile Ser Arg Asp Asn Ala Lys Asn Ser Leu Ser
65                  70                  75                  80

Leu Gln Met Asn Ser Leu Arg Asp Glu Asp Thr Ala Val Tyr Tyr Cys
                85                  90                  95

Ala Arg Asp Asp Trp Gly Ile Asp Ala Phe Asn Ile Trp Gly Gln Gly
            100                 105                 110

Thr Met Val Thr Val Ser Ser
        115

<210> SEQ ID NO 53
<211> LENGTH: 321
<212> TYPE: DNA
<213> ORGANISM: Artificial Sequence
<220> FEATURE:
<223> OTHER INFORMATION: Description of Artificial Sequence: Synthetic
``` polynucleotide

<400> SEQUENCE: 53

```
gaaattgtgt tgacacagtc tccagccacc ctgtctttgt ctccagggga aagagccacc    60
ctctcctgca gggccagtca gagtgttagc agctccttag cctggtacca acagaaacct   120
ggccaggctc ccaggctcct catctatgat gcatccaaca gggccactgg catcccagcc   180
aggttcagtg gcagtgggtc tgggacagac ttcactctca ccatcagcag cctagagcct   240
gaagattttg cagtttatta ctgtcagcag cgtagcaact ggatattcac tttcggccct   300
gggaccaaag tggatatcaa a                                             321
```

<210> SEQ ID NO 54
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Ile Phe
                85                  90                  95

Thr Phe Gly Pro Gly Thr Lys Val Asp Ile Lys
            100                 105
```

<210> SEQ ID NO 55
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

```
Ser Asn Ser Met Asn
1               5
```

<210> SEQ ID NO 56
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

```
His Ile Ser Ser Gly Ser Ser Phe Ile Tyr Tyr Ala Asp Ser Val Lys
1               5                   10                  15

Gly
```

```
<210> SEQ ID NO 57
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Asp Asp Trp Gly Ile Asp Ala Phe Asn Ile
1               5                   10

<210> SEQ ID NO 58
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Arg Ala Ser Gln Ser Val Ser Ser Ser Leu Ala
1               5                   10

<210> SEQ ID NO 59
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Asp Ala Ser Asn Arg Ala Thr
1               5

<210> SEQ ID NO 60
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Gln Gln Arg Ser Asn Trp Ile Phe Thr
1               5

<210> SEQ ID NO 61
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
```

65                  70                  75                  80
Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
        130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 62
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

```
Pro Val Thr Lys Ser Phe Asn Arg Gly Glu Cys
            100                 105
```

<210> SEQ ID NO 63
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

```
Glu Val Gln Leu Val Glu Ser Gly Gly Gly Leu Val Gln Arg Gly Gly
1               5                   10                  15

Ser Leu Arg Leu Ser Cys Ala Ala Ser Gly Phe Thr Phe Ser Ser Asn
            20                  25                  30

Ser Met Asn Trp Ile Arg Gln Ala Pro Gly Lys Gly Leu Glu Trp Val
        35                  40                  45

Ala His Ile Ser Ser Gly Ser Ser Phe Ile Tyr Tyr Ala Asp Ser Val
    50                  55                  60

Lys Gly Arg Phe Thr Ile Ser Arg Asp Asn Ala Lys Asn Ser Leu Ser
65                  70                  75                  80

Leu Gln Met Asn Ser Leu Arg Asp Glu Asp Thr Ala Val Tyr Tyr Cys
                85                  90                  95

Ala Arg Asp Asp Trp Gly Ile Asp Ala Phe Asn Ile Trp Gly Gln Gly
            100                 105                 110

Thr Met Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350
```

```
Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys

<210> SEQ ID NO 64
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Ile Phe
                85                  90                  95

Thr Phe Gly Pro Gly Thr Lys Val Asp Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 65
<211> LENGTH: 423
<212> TYPE: DNA
<213> ORGANISM: Artificial Sequence
```

<220> FEATURE:
<223> OTHER INFORMATION: Description of Artificial Sequence: Synthetic
      polynucleotide

<400> SEQUENCE: 65
atgaaacacc tgtggttctt cctcctcctg gtggcagctc ccagatgggt cctgtcccag      60
atgcagctgc aggagtcggg cccaggactg gtgaagcctt cggagaccct gtccctcacc     120
tgcactgtct ctggtggctc cgtcagcagt ggtcgttact actggagttg gatccggcag     180
ccccccggga agggactgga gtggattggg tatatctatt acagtgggag caccaactac     240
aacccctccc tcaagagtcg agtcaccata tcagtagaca cgtccaagaa ccagttctcc     300
ctgaagctga cctctgtgac cgctgcggac acggccgtgt attactgtgc gagagagggt     360
ggagactact actactacaa tatggacgtc tggggcccag gaccacggt caccgtctcc     420 tca                                                                    423

<210> SEQ ID NO 66
<211> LENGTH: 141
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Met Lys His Leu Trp Phe Phe Leu Leu Leu Val Ala Ala Pro Arg Trp
1               5                   10                  15

Val Leu Ser Gln Met Gln Leu Gln Glu Ser Gly Pro Gly Leu Val Lys
            20                  25                  30

Pro Ser Glu Thr Leu Ser Leu Thr Cys Thr Val Ser Gly Gly Ser Val
        35                  40                  45

Ser Ser Gly Arg Tyr Tyr Trp Ser Trp Ile Arg Gln Pro Pro Gly Lys
    50                  55                  60

Gly Leu Glu Trp Ile Gly Tyr Ile Tyr Tyr Ser Gly Ser Thr Asn Tyr
65                  70                  75                  80

Asn Pro Ser Leu Lys Ser Arg Val Thr Ile Ser Val Asp Thr Ser Lys
                85                  90                  95

Asn Gln Phe Ser Leu Lys Leu Thr Ser Val Thr Ala Ala Asp Thr Ala
            100                 105                 110

Val Tyr Tyr Cys Ala Arg Glu Gly Gly Asp Tyr Tyr Tyr Tyr Asn Met
        115                 120                 125

Asp Val Trp Gly Pro Gly Thr Thr Val Thr Val Ser Ser
    130                 135                 140

<210> SEQ ID NO 67
<211> LENGTH: 384
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 67
atggaaaccc cagcgcagct tctcttcctc ctgctactct ggctcccaga taccaccgga      60
gaaattgtgt tgacgcagtc tccaggcacc ctgtctttgt ctccagggga aagagccacc     120
ctctcctgca gggccagtca gagtgttagc agcagctact tagcctggta ccagcagaaa     180
cctggccagg ctcccaggct cctcatctat ggtgcatcca gcagggccac tggcatccca     240

```
gacaggttca gtggcagtgg gtctgggaca gacttcactc tcaccatcag cagactggag    300
cctgaagatt tgcagtgta ttactgtcag cagtatggta gctcaccgta cacttttggc    360
caggggacca agctggagat caaa                                          384
```

<210> SEQ ID NO 68
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

Met Glu Thr Pro Ala Gln Leu Leu Phe Leu Leu Leu Leu Trp Leu Pro
1               5                   10                  15

Asp Thr Thr Gly Glu Ile Val Leu Thr Gln Ser Pro Gly Thr Leu Ser
            20                  25                  30

Leu Ser Pro Gly Glu Arg Ala Thr Leu Ser Cys Arg Ala Ser Gln Ser
        35                  40                  45

Val Ser Ser Ser Tyr Leu Ala Trp Tyr Gln Gln Lys Pro Gly Gln Ala
    50                  55                  60

Pro Arg Leu Leu Ile Tyr Gly Ala Ser Ser Arg Ala Thr Gly Ile Pro
65                  70                  75                  80

Asp Arg Phe Ser Gly Ser Gly Ser Gly Thr Asp Phe Thr Leu Thr Ile
                85                  90                  95

Ser Arg Leu Glu Pro Glu Asp Phe Ala Val Tyr Tyr Cys Gln Gln Tyr
            100                 105                 110

Gly Ser Ser Pro Tyr Thr Phe Gly Gln Gly Thr Lys Leu Glu Ile Lys
        115                 120                 125

<210> SEQ ID NO 69
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Ser Gly Arg Tyr Tyr Trp Ser
1               5

<210> SEQ ID NO 70
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Tyr Ile Tyr Tyr Ser Gly Ser Thr Asn Tyr Asn Pro Ser Leu Lys Ser
1               5                   10                  15

<210> SEQ ID NO 71
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

```
Glu Gly Gly Asp Tyr Tyr Tyr Asn Met Asp Val
1               5                  10

<210> SEQ ID NO 72
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Arg Ala Ser Gln Ser Val Ser Ser Ser Tyr Leu Ala
1               5                  10

<210> SEQ ID NO 73
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Gly Ala Ser Ser Arg Ala Thr
1               5

<210> SEQ ID NO 74
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Gln Gln Tyr Gly Ser Ser Pro Tyr Thr
1               5

<210> SEQ ID NO 75
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
```

```
            115                 120                 125
Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 76
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 77
<211> LENGTH: 452
<212> TYPE: PRT
<213> ORGANISM: Artificial Sequence
<220> FEATURE:
```

<223> OTHER INFORMATION: Description of Artificial Sequence: Synthetic
polypeptide

<400> SEQUENCE: 77

```
Gln Met Gln Leu Gln Glu Ser Gly Pro Gly Leu Val Lys Pro Ser Glu
1               5                   10                  15

Thr Leu Ser Leu Thr Cys Thr Val Ser Gly Gly Ser Val Ser Ser Gly
            20                  25                  30

Arg Tyr Tyr Trp Ser Trp Ile Arg Gln Pro Pro Gly Lys Gly Leu Glu
        35                  40                  45

Trp Ile Gly Tyr Ile Tyr Tyr Ser Gly Ser Thr Asn Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Thr Ser Val Thr Ala Ala Asp Thr Ala Val Tyr Tyr
                85                  90                  95

Cys Ala Arg Glu Gly Gly Asp Tyr Tyr Tyr Asn Met Asp Val Trp
            100                 105                 110

Gly Pro Gly Thr Thr Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400
```

```
Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450

<210> SEQ ID NO 78
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Tyr Thr Phe Gly Gln Gly Thr Lys Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 79
<211> LENGTH: 414
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 79
atggagtttg ggctgagctg ggttttcctc gttgctcttt taagaggtgt ccagtgtcag    60
```

```
gtgcagctgg tggagtctgg gggaggcgtg gtccagcctg ggaggtccct gagactctcc    120
tgtgcagcct ctggattcac cttcagtgac tatgctatgc actgggtccg ccagactcca    180
ggcagggggc tggagtggct gacatttata tcatatgatg gaagcaataa ataccacgca    240
gactccgtga agggccgatt caccatctcc agagacaatt ccaagaacac gctgtttctg    300
caaatgaaca gtctgagagc tgaggacacg gctgtttatt actgtgcgag agattcctgg    360
gatcgggggt acttcgatct ctggggccgt ggcaccctgg tcactgtctc ctca          414
```

<210> SEQ ID NO 80
<211> LENGTH: 138
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

```
Met Glu Phe Gly Leu Ser Trp Val Phe Leu Val Ala Leu Leu Arg Gly
1               5                   10                  15

Val Gln Cys Gln Val Gln Leu Val Glu Ser Gly Gly Gly Val Val Gln
            20                  25                  30

Pro Gly Arg Ser Leu Arg Leu Ser Cys Ala Ala Ser Gly Phe Thr Phe
        35                  40                  45

Ser Asp Tyr Ala Met His Trp Val Arg Gln Thr Pro Gly Arg Gly Leu
    50                  55                  60

Glu Trp Leu Thr Phe Ile Ser Tyr Asp Gly Ser Asn Lys Tyr His Ala
65                  70                  75                  80

Asp Ser Val Lys Gly Arg Phe Thr Ile Ser Arg Asp Asn Ser Lys Asn
                85                  90                  95

Thr Leu Phe Leu Gln Met Asn Ser Leu Arg Ala Glu Asp Thr Ala Val
            100                 105                 110

Tyr Tyr Cys Ala Arg Asp Ser Trp Asp Arg Gly Tyr Phe Asp Leu Trp
        115                 120                 125

Gly Arg Gly Thr Leu Val Thr Val Ser Ser
    130                 135
```

<210> SEQ ID NO 81
<211> LENGTH: 378
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 81

```
atggaagccc agctcagct tctcttcctc ctgctactct ggctcccaga taccaccgga     60
gaaattgtgt tgacacagtc tccagccacc ctgtctttgt ctccagggga aagagccacc    120
ctctcctgca gggccagtca gagtgttagc agctacttag cctggtacca acagaaacct    180
ggccaggctc ccaggctcct catctatgat gcatccaaca gggccactgg catcccagcc    240
aggttcagtg gcagtgggtc tgggacagac ttcactctca ccatcagcag cctagagcct    300
gaagattttg cagtttatta ctgtcagcag cgtagcaact ggtggacgtt cggccaaggg    360
accaaggtgg aaatcaaa                                                  378
```

<210> SEQ ID NO 82
<211> LENGTH: 126
<212> TYPE: PRT

```
<213> ORGANISM: Artificial Sequence
<220> FEATURE:
<223> OTHER INFORMATION: Description of Artificial Sequence: Synthetic
      polypeptide

<400> SEQUENCE: 82

Met Glu Ala Pro Ala Gln Leu Leu Phe Leu Leu Leu Leu Trp Leu Pro
1               5                   10                  15

Asp Thr Thr Gly Glu Ile Val Leu Thr Gln Ser Pro Ala Thr Leu Ser
            20                  25                  30

Leu Ser Pro Gly Glu Arg Ala Thr Leu Ser Cys Arg Ala Ser Gln Ser
        35                  40                  45

Val Ser Ser Tyr Leu Ala Trp Tyr Gln Gln Lys Pro Gly Gln Ala Pro
    50                  55                  60

Arg Leu Leu Ile Tyr Asp Ala Ser Asn Arg Ala Thr Gly Ile Pro Ala
65                  70                  75                  80

Arg Phe Ser Gly Ser Gly Ser Gly Thr Asp Phe Thr Leu Thr Ile Ser
                85                  90                  95

Ser Leu Glu Pro Glu Asp Phe Ala Val Tyr Tyr Cys Gln Gln Arg Ser
            100                 105                 110

Asn Trp Trp Thr Phe Gly Gln Gly Thr Lys Val Glu Ile Lys
        115                 120                 125

<210> SEQ ID NO 83
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Asp Tyr Ala Met His
1               5

<210> SEQ ID NO 84
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Phe Ile Ser Tyr Asp Gly Ser Asn Lys Tyr His Ala Asp Ser Val Lys
1               5                   10                  15

Gly

<210> SEQ ID NO 85
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Asp Ser Trp Asp Arg Gly Tyr Phe Asp Leu
1               5                   10

<210> SEQ ID NO 86
<211> LENGTH: 11
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 86

Arg Ala Ser Gln Ser Val Ser Ser Tyr Leu Ala
1               5                   10

<210> SEQ ID NO 87
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Asp Ala Ser Asn Arg Ala Thr
1               5

<210> SEQ ID NO 88
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Gln Gln Arg Ser Asn Trp Trp Thr
1               5

<210> SEQ ID NO 89
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 89

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160
```

```
Tyr Val Asp Gly Val Glu Val His Asn Ala Lys Thr Lys Pro Arg Glu
            165                 170                 175

Glu Gln Tyr Asn Ser Thr Tyr Arg Val Val Ser Val Leu Thr Val Leu
        180                 185                 190

His Gln Asp Trp Leu Asn Gly Lys Glu Tyr Lys Cys Lys Val Ser Asn
    195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
        260                 265                 270

Asn Tyr Lys Thr Thr Pro Pro Val Leu Asp Ser Asp Gly Ser Phe Phe
    275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 90
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 90

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 91
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 91

Gln Val Gln Leu Val Glu Ser Gly Gly Gly Val Val Gln Pro Gly Arg
1               5                   10                  15
```

```
Ser Leu Arg Leu Ser Cys Ala Ala Ser Gly Phe Thr Phe Ser Asp Tyr
            20                  25                  30

Ala Met His Trp Val Arg Gln Thr Pro Gly Arg Gly Leu Glu Trp Leu
        35                  40                  45

Thr Phe Ile Ser Tyr Asp Gly Ser Asn Lys Tyr His Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Arg Asp Ser Trp Asp Arg Gly Tyr Phe Asp Leu Trp Gly Arg Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
```

Lys

<210> SEQ ID NO 92
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 92

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Trp Thr
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 93
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 93

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Tyr Lys Glu Tyr Ala Asp Ser Val
    50                  55                  60

```
Lys Gly Arg Phe Thr Ile Ser Arg Asp Ser Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Ala Gln Ile Ser Glu Tyr Phe Asp Tyr Trp Gly Gln Gly Thr
            100                 105                 110

Leu Val Thr Val Ser Ser
        115
```

<210> SEQ ID NO 94
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 94

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Ser Ser Trp
             20                  25                  30

Leu Ala Trp Tyr Gln Gln Lys Pro Glu Lys Ala Pro Lys Ser Leu Ile
         35                  40                  45

Tyr Ala Ala Ser Ser Leu Gln Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Asn Ser Tyr Pro Leu
                 85                  90                  95

Thr Phe Gly Gln Gly Thr Lys Val Glu Ile Lys
            100                 105
```

<210> SEQ ID NO 95
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

```
Ser Tyr Ala Met His
 1               5
```

<210> SEQ ID NO 96
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

```
Val Ile Ser Tyr Asp Gly Ser Tyr Lys Glu Tyr Ala Asp Ser Val Lys
 1               5                  10                  15

Gly
```

<210> SEQ ID NO 97
<211> LENGTH: 9
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 97

Ala Gln Ile Ser Glu Tyr Phe Asp Tyr
1               5

<210> SEQ ID NO 98
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Arg Ala Ser Gln Gly Ile Ser Ser Trp Leu Ala
1               5                   10

<210> SEQ ID NO 99
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Ala Ala Ser Ser Leu Gln Ser
1               5

<210> SEQ ID NO 100
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Gln Gln Tyr Asn Ser Tyr Pro Leu Thr
1               5

<210> SEQ ID NO 101
<211> LENGTH: 329
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 101

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
```

```
                    85                  90                  95
Arg Val Glu Pro Lys Ser Cys Asp Lys Thr His Thr Cys Pro Pro Cys
                100                 105                 110

Pro Ala Pro Glu Ala Glu Gly Ala Pro Ser Val Phe Leu Phe Pro Pro
                115                 120                 125

Lys Pro Lys Asp Thr Leu Met Ile Ser Arg Thr Pro Glu Val Thr Cys
            130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 102
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 102

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

<210> SEQ ID NO 103
<211> LENGTH: 447
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 103

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Val Arg Gln Ala Pro Gly Lys Gly Leu Glu Trp Val
        35                  40                  45

Ala Val Ile Ser Tyr Asp Gly Ser Tyr Lys Glu Tyr Ala Asp Ser Val
    50                  55                  60

Lys Gly Arg Phe Thr Ile Ser Arg Asp Ser Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Gln Ile Ser Glu Tyr Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Ala Glu Gly Ala Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
            370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
            435                 440                 445

<210> SEQ ID NO 104
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 104

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 105
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 105

```
caggtgcaac tagtggagtc tgggggaggc ttggtcaagc ctggagggtc cctcagactc    60
tcctgtgcag cctctgggtt caccttcagt gacttctaca tgagctggat ccgccaggct   120
ccagggaagg ggctggagtg gatttcatac attagtagta gtgattttac catatactac   180
gcagactctg tggagggccg attcaccatc tccaggaca acgccaagaa ctcactgttt    240
ctgcaaatga acagcctgag agccgaggac acggctgtgt attactgtgc gagaagaggg   300
agccttcctt tcaactacga tatggacgtc tggggccaag gaccacggt caccgtctcc    360 tca                                                                  363
```

<210> SEQ ID NO 106
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 106

```
Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Phe
            20                  25                  30

Tyr Met Ser Trp Ile Arg Gln Ala Pro Gly Lys Gly Leu Glu Trp Ile
        35                  40                  45

Ser Tyr Ile Ser Ser Ser Asp Phe Thr Ile Tyr Tyr Ala Asp Ser Val
    50                  55                  60

Glu Gly Arg Phe Thr Ile Ser Arg Asp Asn Ala Lys Asn Ser Leu Phe
65                  70                  75                  80

Leu Gln Met Asn Ser Leu Arg Ala Glu Asp Thr Ala Val Tyr Tyr Cys
                85                  90                  95

Ala Arg Arg Gly Ser Leu Pro Phe Asn Tyr Asp Met Asp Val Trp Gly
            100                 105                 110

Gln Gly Thr Thr Val Thr Val Ser Ser
        115                 120
```

<210> SEQ ID NO 107
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 107

```
gacatccaga tgacccagtc tccatcttcc gtgtctgcat ctgtaggaga cagagtcacc    60
atctcttgtc gggcgagtca gggtattagc agctacttag cctggtatca gcataaacca   120
gggaaagccc ctaagctcct gatctatgct gcatccagtt tgcaaagtgg ggtcccatca   180
aggttcagcg gcagtggatc tgggacagct ttcactctca ccatcagcag cctgcagcct   240
gaagattttg caacttacta ttgtcaacag gctaatagtt tcccgctcac tttcggcgga   300
gggaccaagg tggagatcaa a                                              321
```

<210> SEQ ID NO 108
<211> LENGTH: 107
<212> TYPE: PRT
<213> ORGANISM: Artificial Sequence
<220> FEATURE:

<223> OTHER INFORMATION: Description of Artificial Sequence: Synthetic
       polypeptide

<400> SEQUENCE: 108

Asp Ile Gln Met Thr Gln Ser Pro Ser Ser Val Ser Ala Ser Val Gly
1               5                   10                  15

Asp Arg Val Thr Ile Ser Cys Arg Ala Ser Gln Gly Ile Ser Ser Tyr
            20                  25                  30

Leu Ala Trp Tyr Gln His Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Ala Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Leu
                85                  90                  95

Thr Phe Gly Gly Gly Thr Lys Val Glu Ile Lys
            100                 105

<210> SEQ ID NO 109
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Asp Phe Tyr Met Ser
1               5

<210> SEQ ID NO 110
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Tyr Ile Ser Ser Ser Asp Phe Thr Ile Tyr Tyr Ala Asp Ser Val Glu
1               5                   10                  15

Gly

<210> SEQ ID NO 111
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Arg Gly Ser Leu Pro Phe Asn Tyr Asp Met Asp Val
1               5                   10

<210> SEQ ID NO 112
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Arg Ala Ser Gln Gly Ile Ser Ser Tyr Leu Ala
1               5                   10

<210> SEQ ID NO 113
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Ala Ala Ser Ser Leu Gln Ser
1               5

<210> SEQ ID NO 114
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Gln Gln Ala Asn Ser Phe Pro Leu Thr
1               5

<210> SEQ ID NO 115
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 115

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

```
His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 116
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 116

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 117
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 117

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Phe
            20                  25                  30

Tyr Met Ser Trp Ile Arg Gln Ala Pro Gly Lys Gly Leu Glu Trp Ile
        35                  40                  45
```

```
Ser Tyr Ile Ser Ser Ser Asp Phe Thr Ile Tyr Tyr Ala Asp Ser Val
    50                  55                  60

Glu Gly Arg Phe Thr Ile Ser Arg Asp Asn Ala Lys Asn Ser Leu Phe
65                  70                  75                  80

Leu Gln Met Asn Ser Leu Arg Ala Glu Asp Thr Ala Val Tyr Tyr Cys
                85                  90                  95

Ala Arg Arg Gly Ser Leu Pro Phe Asn Tyr Asp Met Asp Val Trp Gly
            100                 105                 110

Gln Gly Thr Thr Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450
```

<210> SEQ ID NO 118
<211> LENGTH: 214
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 118

Asp Ile Gln Met Thr Gln Ser Pro Ser Ser Val Ser Ala Ser Val Gly
1               5                   10                  15

Asp Arg Val Thr Ile Ser Cys Arg Ala Ser Gln Gly Ile Ser Ser Tyr
            20                  25                  30

Leu Ala Trp Tyr Gln His Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Ala Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 119
<211> LENGTH: 11
<212> TYPE: PRT
<213> ORGANISM: Homo sapiens

<400> SEQUENCE: 119

Leu Ser Ile Asp Asn Glu Glu Glu Met Lys Phe
1               5                   10

<210> SEQ ID NO 120
<211> LENGTH: 16
<212> TYPE: PRT
<213> ORGANISM: Homo sapiens

<400> SEQUENCE: 120

Pro Ser Ser Trp Ile Gly Val Phe Arg Asn Ser Ser His His Pro Trp
1               5                   10                  15

<210> SEQ ID NO 121
<211> LENGTH: 12
<212> TYPE: PRT

<213> ORGANISM: Homo sapiens

<400> SEQUENCE: 121

Leu Ala Phe Lys His Glu Ile Lys Asp Ser Asp Asn
1               5                   10

<210> SEQ ID NO 122
<211> LENGTH: 18
<212> TYPE: PRT
<213> ORGANISM: Homo sapiens

<400> SEQUENCE: 122

Gln Val Asn Arg Leu Lys Ser Ala Gln Cys Gly Ser Ser Ile Ile Tyr
1               5                   10                  15

His Cys

<210> SEQ ID NO 123
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Ala Ser Ile Glu Gly Arg
1               5

<210> SEQ ID NO 124
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Gly Gly Ser Gly Gly Ser
1               5

<210> SEQ ID NO 125
<211> LENGTH: 479
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 125

Val Pro Arg Asp Ser Gly Ser Lys Pro Ser Ile Ser Thr Val Pro Glu
1               5                   10                  15

Val Ser Ser Val Phe Ile Phe Pro Pro Lys Pro Lys Asp Val Leu Thr
                20                  25                  30

Ile Thr Leu Thr Pro Lys Val Thr Cys Val Val Val Asp Ile Ser Lys
            35                  40                  45

Asp Asp Pro Glu Val Gln Phe Ser Trp Phe Val Asp Asp Val Glu Val
        50                  55                  60

His Thr Ala Gln Thr Gln Pro Arg Glu Glu Gln Phe Asn Ser Thr Phe
65                  70                  75                  80

Arg Ser Val Ser Glu Leu Pro Ile Met His Gln Asp Trp Leu Asn Gly
                85                  90                  95

Lys Glu Phe Lys Cys Arg Val Asn Ser Ala Ala Phe Pro Ala Pro Ile
                100                 105                 110

Glu Lys Thr Ile Ser Lys Thr Lys Gly Arg Pro Lys Ala Pro Gln Val
            115                 120                 125

Tyr Thr Ile Pro Pro Lys Glu Gln Met Ala Lys Asp Lys Val Ser
    130                 135                 140

Leu Thr Cys Met Ile Thr Asp Phe Phe Pro Glu Asp Ile Thr Val Glu
145                 150                 155                 160

Trp Gln Trp Asn Gly Gln Pro Ala Glu Asn Tyr Lys Asn Thr Gln Pro
                165                 170                 175

Ile Met Asp Thr Asp Gly Ser Tyr Phe Val Tyr Ser Lys Leu Asn Val
            180                 185                 190

Gln Lys Ser Asn Trp Glu Ala Gly Asn Thr Phe Thr Cys Ser Val Leu
        195                 200                 205

His Glu Gly Leu His Asn His His Thr Glu Lys Ser Leu Ser His Ser
210                 215                 220

Pro Gly Lys Ala Ser Ile Glu Gly Arg Cys Gly His Cys Pro Glu Glu
225                 230                 235                 240

Trp Ile Thr Tyr Ser Asn Ser Cys Tyr Tyr Ile Gly Lys Glu Arg Arg
                245                 250                 255

Thr Trp Glu Glu Ser Leu Leu Ala Cys Thr Ser Lys Asn Ser Ser Leu
            260                 265                 270

Leu Ser Ile Asp Asn Glu Glu Glu Met Lys Phe Leu Ser Ile Ile Ser
        275                 280                 285

Pro Ser Ser Trp Ile Gly Val Phe Arg Asn Ser Ser His Pro Trp
    290                 295                 300

Val Thr Met Asn Gly Leu Ala Phe Lys His Glu Ile Lys Asp Ser Asp
305                 310                 315                 320

Asn Ala Glu Leu Asn Cys Ala Val Leu Gln Val Asn Arg Leu Lys Ser
                325                 330                 335

Ala Gln Cys Gly Ser Ser Ile Ile Tyr His Cys Lys His Lys Leu Gly
            340                 345                 350

Gly Ser Gly Gly Ser Cys Cys Ser Cys Gln Glu Lys Trp Val Gly Tyr
        355                 360                 365

Arg Cys Asn Cys Tyr Phe Ile Ser Ser Glu Gln Lys Thr Trp Asn Glu
    370                 375                 380

Ser Arg His Leu Cys Ala Ser Gln Lys Ser Ser Leu Leu Gln Leu Gln
385                 390                 395                 400

Asn Thr Asp Glu Leu Asp Phe Met Ser Ser Ser Gln Gln Phe Tyr Trp
                405                 410                 415

Ile Gly Leu Ser Tyr Ser Glu Glu His Thr Ala Trp Leu Trp Glu Asn
            420                 425                 430

Gly Ser Ala Leu Ser Gln Tyr Leu Phe Pro Ser Phe Glu Thr Phe Asn
        435                 440                 445

Thr Lys Asn Cys Ile Ala Tyr Asn Pro Asn Gly Asn Ala Leu Asp Glu
    450                 455                 460

Ser Cys Glu Asp Lys Asn Arg Tyr Ile Cys Lys Gln Gln Leu Ile
465                 470                 475

<210> SEQ ID NO 126
<211> LENGTH: 173
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 126

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser His
            20                  25                  30

Ser Met Asn Trp Val Arg Gln Ala Pro Gly Lys Gly Leu Glu Trp Val
        35                  40                  45

Ser Ala Ile Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Glu Trp Gly Leu Pro Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala
                165                 170

<210> SEQ ID NO 127
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 127

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Gln Ser Ala
            20                  25                  30

Leu Ala Trp Tyr Gln Gln Lys Pro Gly Lys Ala Pro Lys Leu Leu Ile
        35                  40                  45

Tyr Asp Ala Ser Ser Leu Lys Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Leu
                85                  90                  95

Thr Phe Gly Gln Gly Thr Arg Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

```
Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 128
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 128

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser His
            20                  25                  30

Ser Met Asn Trp Val Arg Gln Ala Pro Gly Lys Gly Leu Glu Trp Val
        35                  40                  45

Ser Ala Ile Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
            85                  90                  95

Ala Arg Glu Glu Trp Gly Leu Pro Phe Asp Tyr Trp Gly Gln Gly Thr
        100                 105                 110

Leu Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
            165                 170                 175

Ser Ser Gly Leu Tyr Ser Leu Ser Ser Val Val Thr Val Pro Ser Ser
        180                 185                 190

Ser Leu Gly Thr Gln Thr Tyr Ile Cys Asn Val Asn His Lys Pro Ser
            195                 200                 205

Asn Thr Lys Val Asp Lys Arg Val Glu Pro Lys Ser Cys Asp Lys Thr
        210                 215                 220

His Thr Cys Pro Pro Cys Pro Ala Pro Glu Ala Glu Gly Ala Pro Ser
225                 230                 235                 240

Val Phe Leu Phe Pro Pro Lys Pro Lys Asp Thr Leu Met Ile Ser Arg
            245                 250                 255

Thr Pro Glu Val Thr Cys Val Val Val Asp Val Ser His Glu Asp Pro
        260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
        290                 295                 300

Ser Val Leu Thr Val Leu His Gln Asp Trp Leu Asn Gly Lys Glu Tyr
305                 310                 315                 320
```

```
Lys Cys Lys Val Ser Asn Lys Ala Leu Pro Ala Pro Ile Glu Lys Thr
            325                 330                 335

Ile Ser Lys Ala Lys Gly Gln Pro Arg Glu Pro Gln Val Tyr Thr Leu
        340                 345                 350

Pro Pro Ser Arg Glu Glu Met Thr Lys Asn Gln Val Ser Leu Thr Cys
            355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 129
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 129

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Asn Ser Ala
            20                  25                  30

Leu Ala Trp Tyr Gln Gln Lys Pro Gly Lys Ala Pro Lys Leu Leu Ile
        35                  40                  45

Tyr Asp Ala Ser Ser Leu Lys Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Leu
                85                  90                  95

Thr Phe Gly Gln Gly Thr Arg Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 130
<211> LENGTH: 448
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 130

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser His
            20                  25                  30

Ser Met Asn Trp Val Arg Gln Ala Pro Gly Lys Gly Leu Glu Trp Val
        35                  40                  45

Ser Ala Ile Ser Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Glu Trp Gly Leu Pro Phe Asp Tyr Trp Gly Gln Gly Ile
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Ala Glu Gly Ala Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365
```

```
Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
                435                 440                 445

<210> SEQ ID NO 131
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 131

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Gln Ser Ala
            20                  25                  30

Leu Ala Trp Tyr Gln Gln Lys Pro Gly Lys Ala Pro Lys Leu Leu Ile
        35                  40                  45

Tyr Asp Ala Ser Ser Leu Lys Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Leu
                85                  90                  95

Thr Phe Gly Gln Gly Thr Arg Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 132
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 132
```

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser His
            20                  25                  30

Ser Met Asn Trp Val Arg Gln Ala Pro Gly Lys Gly Leu Glu Trp Val
        35                  40                  45

Ser Ala Ile Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Glu Trp Gly Leu Pro Phe Asp Tyr Trp Gly Gln Gly Ile
            100                 105                 110

Leu Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
            130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Arg Val Glu Pro Lys Ser Cys Asp Lys Thr
210                 215                 220

His Thr Cys Pro Pro Cys Pro Ala Pro Glu Ala Glu Gly Ala Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
            355                 360                 365

Leu Val Lys Gly Phe Tyr Pro Ser Asp Ile Ala Val Glu Trp Glu Ser
370                 375                 380

Asn Gly Gln Pro Glu Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
```

```
                420             425             430
Leu His Asn His Tyr Thr Gln Lys Ser Leu Ser Leu Ser Pro Gly Lys
            435             440             445
```

<210> SEQ ID NO 133
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 133

```
Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Pro Ser Ala
            20                  25                  30

Leu Ala Trp Tyr Gln Gln Lys Pro Gly Lys Ala Pro Lys Leu Leu Ile
        35                  40                  45

Tyr Asp Ala Ser Ser Leu Lys Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Leu
                85                  90                  95

Thr Phe Gly Gln Gly Thr Arg Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 134
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 134

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser His
            20                  25                  30

Ser Met Asn Trp Val Arg Gln Ala Pro Gly Lys Gly Leu Glu Trp Val
        35                  40                  45

Ser Ala Ile Ser Ser Ser Ser Ser Tyr Ile Tyr Tyr Ala Asp Ser Val
```

```
            50                  55                  60
Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Glu Glu Trp Gly Leu Pro Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
210                 215                 220

His Thr Cys Pro Pro Cys Pro Ala Pro Glu Ala Glu Gly Ala Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
        290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
        370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 135
<211> LENGTH: 214
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 135

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Leu Leu Ile
        35                  40                  45

Ser Asp Ala Ser Ser Leu Lys Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Leu
                85                  90                  95

Thr Phe Gly Gln Gly Thr Arg Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 136
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 136

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser His
            20                  25                  30

Ser Met Asn Trp Val Arg Gln Ala Pro Gly Lys Gly Leu Glu Trp Val
        35                  40                  45

Ser Ala Ile Ser Ser Ser Ser Tyr Ile Tyr Tyr Ala Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Glu Trp Gly Leu Pro Phe Asp Tyr Trp Gly Gln Gly Thr
            100                 105                 110
```

Leu Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
                180                 185                 190

Ser Leu Gly Thr Gln Thr Tyr Ile Cys Asn Val Asn His Lys Pro Ser
            195                 200                 205

Asn Thr Lys Val Asp Lys Arg Val Glu Pro Lys Ser Cys Asp Lys Thr
        210                 215                 220

His Thr Cys Pro Pro Cys Pro Ala Pro Glu Ala Glu Gly Ala Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
        290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
        370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 137
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 137

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala

-continued

```
                20                  25                  30
Leu Ala Trp Tyr Gln Gln Lys Pro Gly Lys Ala Pro Lys Leu Leu Ile
            35                  40                  45

Tyr Asp Ala Ser Ser Leu Lys Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Phe Asn Ser Thr Pro Leu
                85                  90                  95

Thr Phe Gly Gln Gly Thr Arg Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 138
<211> LENGTH: 448
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 138

```
Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Ser His
            20                  25                  30

Ser Met Asn Trp Val Arg Gln Ala Pro Gly Lys Gly Leu Glu Trp Val
        35                  40                  45

Ser Ala Ile Ser Ser Ser Ser Tyr Ile Tyr Tyr Ala Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                85                  90                  95

Ala Arg Glu Glu Trp Gly Leu Pro Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160
```

Ser Gly Ala Leu Thr Ser Gly Val His Thr Phe Pro Ala Val Leu Gln
            165                 170                 175

Ser Ser Gly Leu Tyr Ser Leu Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Arg Val Glu Pro Lys Ser Cys Asp Lys Thr
        210                 215                 220

His Thr Cys Pro Pro Cys Pro Ala Pro Glu Ala Glu Gly Ala Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
        290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 139
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 139

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Leu Leu Ile
        35                  40                  45

Tyr Asp Ala Ser Ser Leu Lys Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

```
Glu Asp Phe Ala Thr Tyr Tyr Cys Gln Gln Phe Asn Ser Ala Pro Leu
                85                  90                  95

Thr Phe Gly Gln Gly Thr Arg Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 140
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 140

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser His
            20                  25                  30

Ser Met Asn Trp Val Arg Gln Ala Pro Gly Lys Gly Leu Glu Trp Val
        35                  40                  45

Ser Ala Ile Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Glu Trp Gly Leu Pro Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
```

```
                 210                 215                 220

His Thr Cys Pro Pro Cys Pro Ala Pro Glu Ala Glu Gly Ala Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Asp Val Ser His Glu Asp Pro
            260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
            290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
            355                 360                 365

Leu Val Lys Gly Phe Tyr Pro Ser Asp Ile Ala Val Glu Trp Glu Ser
            370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
            435                 440                 445

<210> SEQ ID NO 141
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 141

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Leu Leu Ile
        35                  40                  45

Tyr Asp Ala Ser Ser Leu Lys Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Asn Pro Leu
                85                  90                  95

Thr Phe Gly Gln Gly Thr Arg Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125
```

```
Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 142
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 142

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser His
            20                  25                  30

Ser Met Asn Trp Val Arg Gln Ala Pro Gly Lys Gly Leu Glu Trp Val
        35                  40                  45

Ser Ala Ile Ser Ser Ser Ser Thr Ile Tyr Tyr Ala Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
            85                  90                  95

Ala Arg Glu Glu Trp Gly Leu Pro Phe Asp Tyr Trp Gly Gln Gly Thr
        100                 105                 110

Leu Val Thr Val Ser Ser Ala Ser Thr Lys Gly Pro Ser Val Phe Pro
    115                 120                 125

Leu Ala Pro Ser Ser Lys Ser Thr Ser Gly Gly Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Ala Glu Gly Ala Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270
```

```
Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
            355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
            435                 440                 445

<210> SEQ ID NO 143
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 143

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Leu Leu Ile
        35                  40                  45

Tyr Asp Ala Ser Ser Leu Lys Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Leu
                85                  90                  95

Thr Phe Gly Gln Gly Thr Arg Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
```

```
                       180                 185                 190
Ala Cys Glu Val Thr His Gln Gly Leu Ser Ser Pro Val Thr Lys Ser
            195                 200                 205

Phe Asn Arg Gly Glu Cys
            210

<210> SEQ ID NO 144
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 144

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser His
            20                  25                  30

Ser Met Asn Trp Val Arg Gln Ala Pro Gly Lys Gly Leu Glu Trp Val
        35                  40                  45

Ser Ala Ile Ser Ser Ser Ser Ser Tyr Thr Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Glu Trp Gly Leu Pro Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Ala Glu Gly Ala Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320
```

```
Lys Cys Lys Val Ser Asn Lys Ala Leu Pro Ala Pro Ile Glu Lys Thr
            325                 330                 335

Ile Ser Lys Ala Lys Gly Gln Pro Arg Glu Pro Gln Val Tyr Thr Leu
        340                 345                 350

Pro Pro Ser Arg Glu Glu Met Thr Lys Asn Gln Val Ser Leu Thr Cys
            355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly Lys
                435                 440                 445

<210> SEQ ID NO 145
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 145

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Leu Leu Ile
        35                  40                  45

Tyr Asp Ala Ser Ser Leu Lys Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Leu
                85                  90                  95

Thr Phe Gly Gln Gly Thr Arg Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 146
```

```
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 146

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser His
            20                  25                  30

Ser Met Asn Trp Val Arg Gln Ala Pro Gly Lys Gly Leu Glu Trp Val
        35                  40                  45

Ser Ala Ile Ser Ser Ser Ser Tyr Ile Asn Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Glu Trp Gly Leu Pro Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Ala Glu Gly Ala Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
```

```
                    370                 375                 380
Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly Lys
                435                 440                 445

<210> SEQ ID NO 147
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 147

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Leu Leu Ile
        35                  40                  45

Tyr Asp Ala Ser Ser Leu Lys Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Leu
                85                  90                  95

Thr Phe Gly Gln Gly Thr Arg Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 148
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 148

Glu Val Gln Leu Val Glu Ser Gly Gly Gly Leu Val Lys Pro Gly Gly
```

-continued

```
1               5                   10                  15
Ser Leu Arg Leu Ser Cys Ala Ala Ser Gly Phe Thr Phe Ser Ser His
            20                  25                  30

Ser Met Asn Trp Val Arg Gln Ala Pro Gly Lys Gly Leu Glu Trp Val
            35                  40                  45

Ser Ala Ile Ser Ser Ser Ser Tyr Ile Ser Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Glu Trp Gly Leu Pro Phe Asp Tyr Trp Gly Gln Gly Thr
            100                 105                 110

Leu Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
            130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Arg Val Glu Pro Lys Ser Cys Asp Lys Thr
            210                 215                 220

His Thr Cys Pro Pro Cys Pro Ala Pro Glu Ala Glu Gly Ala Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
            290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
            355                 360                 365

Leu Val Lys Gly Phe Tyr Pro Ser Asp Ile Ala Val Glu Trp Glu Ser
            370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430
```

```
Leu His Asn His Tyr Thr Gln Lys Ser Leu Ser Leu Ser Pro Gly Lys
        435                 440                 445
```

<210> SEQ ID NO 149
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 149

```
Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Leu Leu Ile
        35                  40                  45

Tyr Asp Ala Ser Ser Leu Lys Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Leu
                85                  90                  95

Thr Phe Gly Gln Gly Thr Arg Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 150
<211> LENGTH: 213
<212> TYPE: PRT
<213> ORGANISM: Homo sapiens

<400> SEQUENCE: 150

```
Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Leu Leu Ile
        35                  40                  45

Tyr Asp Ala Ser Ser Leu Lys Ser Gly Val Pro Ser Phe Ser Gly Ser
    50                  55                  60

Gly Ser Gly Thr Asp Phe Thr Leu Thr Ile Ser Ser Leu Gln Pro Glu
65                  70                  75                  80
```

-continued

```
Asp Phe Ala Thr Tyr Tyr Cys Gln Gln Phe Asn Ser Tyr Pro Leu Thr
                85                  90                  95

Phe Gly Gln Gly Thr Arg Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210
```

<210> SEQ ID NO 151
<211> LENGTH: 448
<212> TYPE: PRT
<213> ORGANISM: Homo sapiens

<400> SEQUENCE: 151

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser His
            20                  25                  30

Ser Met Asn Trp Val Arg Gln Ala Pro Gly Lys Gly Leu Glu Trp Val
        35                  40                  45

Ser Ala Ile Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Glu Trp Gly Leu Pro Phe Asp Tyr Trp Gly Gln Gly Ile
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Ala Glu Gly Ala Pro Ser
```

```
               225                 230                 235                 240
Val Phe Leu Phe Pro Lys Pro Lys Asp Thr Leu Met Ile Ser Arg
            245                 250                 255

Thr Pro Glu Val Thr Cys Val Val Asp Val Ser His Glu Asp Pro
            260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
            290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
            325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
            355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
            405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
    435                 440                 445

<210> SEQ ID NO 152
<211> LENGTH: 218
<212> TYPE: PRT
<213> ORGANISM: Mus musculus

<400> SEQUENCE: 152

Asp Ile Val Met Thr Gln Ser Pro Ser Ser Leu Ala Val Ser Ala Gly
1               5                   10                  15

Asp Lys Val Thr Ile Asn Cys Lys Ser Ser Gln Thr Leu Phe Ser Gly
            20                  25                  30

Arg Tyr Asn Tyr Leu Ala Trp Tyr Gln Gln Lys Thr Gly Gln Ala Pro
        35                  40                  45

Lys Leu Leu Ile Tyr Tyr Thr Ser Thr Arg His Thr Gly Val Pro Gly
    50                  55                  60

Arg Phe Ile Gly Ser Gly Ser Gly Thr Asp Phe Thr Leu Thr Ile Asn
65                  70                  75                  80

Asn Leu Gln Thr Glu Asp Leu Gly Asn Tyr Tyr Cys Gln Gln His Tyr
                85                  90                  95

Ser Thr Pro Tyr Thr Phe Gly Ala Gly Thr Asn Leu Glu Ile Arg Arg
            100                 105                 110

Ala Asp Ala Ala Pro Thr Val Ser Ile Phe Pro Pro Ser Ser Glu Gln
        115                 120                 125

Leu Thr Ser Gly Gly Ala Ser Val Val Cys Phe Leu Asn Asn Phe Tyr
    130                 135                 140

Pro Lys Asp Ile Asn Val Lys Trp Lys Ile Asp Gly Ser Glu Arg Gln
145                 150                 155                 160
```

```
Asn Gly Val Leu Asn Ser Trp Thr Asp Gln Asp Ser Lys Asp Ser Thr
                165                 170                 175
Tyr Ser Met Ser Ser Thr Leu Thr Leu Thr Lys Asp Glu Tyr Glu Arg
            180                 185                 190
His Asn Ser Tyr Thr Cys Glu Ala Thr His Lys Thr Ser Thr Ser Pro
        195                 200                 205
Ile Val Lys Ser Phe Asn Arg Asn Glu Cys
    210                 215

<210> SEQ ID NO 153
<211> LENGTH: 443
<212> TYPE: PRT
<213> ORGANISM: Mus musculus

<400> SEQUENCE: 153

Gln Val Gln Leu Lys Gln Ser Gly Ala Glu Leu Val Lys Pro Gly Ala
1               5                   10                  15
Ser Val Lys Ile Ser Cys Lys Thr Ser Gly Tyr Thr Phe Thr Asp Gly
            20                  25                  30
Tyr Met His Trp Val Glu Gln Asn Pro Gly Gln Gly Leu Glu Trp Ile
        35                  40                  45
Gly Arg Ile Asp Pro Asp Ser Gly Tyr Thr Met Tyr Asn Gln Lys Phe
    50                  55                  60
Gln Asp Lys Ala Thr Leu Thr Arg Asp Lys Ser Ser Ser Thr Val Tyr
65                  70                  75                  80
Met Glu Leu Arg Ser Leu Thr Ser Glu Asp Ser Ala Val Tyr Tyr Cys
                85                  90                  95
Ala Ile Asn Tyr Gly Glu Tyr Trp Tyr Phe Asp Phe Trp Gly Gln Gly
            100                 105                 110
Thr Gln Val Thr Val Ser Ser Ala Lys Thr Thr Pro Pro Ser Val Tyr
        115                 120                 125
Pro Leu Ala Pro Gly Ser Ala Ala Gln Thr Asn Ser Met Val Thr Leu
    130                 135                 140
Gly Cys Leu Val Lys Gly Tyr Phe Pro Glu Pro Val Thr Val Thr Trp
145                 150                 155                 160
Asn Ser Gly Ser Leu Ser Ser Gly Val His Thr Phe Pro Ala Val Leu
                165                 170                 175
Gln Ser Asp Leu Tyr Thr Leu Ser Ser Ser Val Thr Val Pro Ser Ser
            180                 185                 190
Thr Trp Pro Ser Glu Thr Val Thr Cys Asn Val Ala His Pro Ala Ser
        195                 200                 205
Ser Thr Lys Val Asp Lys Lys Ile Val Pro Arg Asp Cys Gly Cys Lys
    210                 215                 220
Pro Cys Ile Cys Thr Val Pro Glu Val Ser Ser Val Phe Ile Phe Pro
225                 230                 235                 240
Pro Lys Pro Lys Asp Val Leu Thr Ile Thr Leu Thr Pro Lys Val Thr
                245                 250                 255
Cys Val Val Val Ala Ile Ser Lys Asp Asp Pro Glu Val Gln Phe Ser
            260                 265                 270
Trp Phe Val Asp Asp Val Glu Val His Thr Ala Gln Thr Gln Pro Arg
        275                 280                 285
Glu Glu Gln Phe Asn Ser Thr Phe Arg Ser Val Ser Glu Leu Pro Ile
    290                 295                 300
Met His Gln Asp Trp Leu Asn Gly Lys Glu Phe Lys Cys Arg Val Asn
305                 310                 315                 320
```

```
Ser Ala Ala Phe Pro Ala Pro Ile Glu Lys Thr Ile Ser Lys Thr Lys
                325                 330                 335

Gly Arg Pro Lys Ala Pro Gln Val Tyr Thr Ile Pro Pro Lys Glu
            340                 345                 350

Gln Met Ala Lys Asp Lys Val Ser Leu Thr Cys Met Ile Thr Asp Phe
        355                 360                 365

Phe Pro Glu Asp Ile Thr Val Glu Trp Gln Trp Asn Gly Gln Pro Ala
    370                 375                 380

Glu Asn Tyr Lys Asn Thr Gln Pro Ile Met Asp Thr Asp Gly Ser Tyr
385                 390                 395                 400

Phe Val Tyr Ser Lys Leu Asn Val Gln Lys Ser Asn Trp Glu Ala Gly
                405                 410                 415

Asn Thr Phe Thr Cys Ser Val Leu His Glu Gly Leu His Asn His His
            420                 425                 430

Thr Glu Lys Ser Leu Ser His Ser Pro Gly Lys
        435                 440

<210> SEQ ID NO 154
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 154

Arg Ala Ser Gln Gly Ile Pro Ser Ala Leu Ala
1               5                   10

<210> SEQ ID NO 155
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 155

Arg Ala Ser Gln Gly Ile Asn Ser Ala Leu Ala
1               5                   10

<210> SEQ ID NO 156
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 156

Leu Ser Ile Asp Asn Glu Glu Met Lys Phe
1               5                   10

<210> SEQ ID NO 157
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 157

Pro Ser Ser Trp Ile Gly Val Phe Arg Asn Ser Ser His His Pro Trp
```

<210> SEQ ID NO 158
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 158

Leu Ala Phe Lys His Glu Ile Lys Asp Ser Asp Asn
1               5                   10

<210> SEQ ID NO 159
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 159

Gln Val Asn Arg Leu Lys Ser Ala Gln Gln Cys Gly Ser Ser Ile Ile
1               5                   10                  15

Tyr His Cys

<210> SEQ ID NO 160
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 160

Gly Gly Gly Gly Ser Gly Gly Gly Ser Gly Gly Gly Gly Ser
1               5                   10                  15

<210> SEQ ID NO 161
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 161

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
                20                  25                  30

Pro Lys Leu Thr Arg Met Leu Thr Phe Lys Phe Tyr Met Pro Lys Lys
            35                  40                  45

Ala Thr Glu Leu Lys His Leu Gln Cys Leu Glu Glu Leu Lys Pro
        50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
                100                 105                 110

Ile Val Glu Phe Leu Asn Arg Trp Ile Thr Phe Ser Gln Ser Ile Ile

```
                115                 120                 125
Ser Thr Leu Thr
    130

<210> SEQ ID NO 162
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 162

Val Ser Asn Lys
1

<210> SEQ ID NO 163
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 163

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser His
            20                  25                  30

Ser Met Asn Trp Val Arg Gln Ala Pro Gly Lys Gly Leu Glu Trp Val
        35                  40                  45

Ser Ala Ile Ser Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Glu Trp Gly Leu Pro Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Ala Glu Gly Ala Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
```

```
                260                 265                 270
Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
        290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 164
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 164

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Pro Ser Ala
            20                  25                  30

Leu Ala Trp Tyr Gln Gln Lys Pro Gly Lys Ala Pro Lys Leu Leu Ile
        35                  40                  45

Tyr Asp Ala Ser Ser Leu Lys Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Leu
                85                  90                  95

Thr Phe Gly Gln Gly Thr Arg Leu Glu Ile Lys
            100                 105

<210> SEQ ID NO 165
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 165

Arg Thr Val Ala Ala Pro Ser Val Phe Ile Phe Pro Pro Ser Asp Glu
```

```
                1               5                  10                 15
Gln Leu Lys Ser Gly Thr Ala Ser Val Val Cys Leu Leu Asn Asn Phe
            20                  25                 30
Tyr Pro Arg Glu Ala Lys Val Gln Trp Lys Val Asp Asn Ala Leu Gln
            35                  40                 45
Ser Gly Asn Ser Gln Glu Ser Val Thr Glu Gln Asp Ser Lys Asp Ser
    50                  55                 60
Thr Tyr Ser Leu Ser Ser Thr Leu Thr Leu Ser Lys Ala Asp Tyr Glu
65                  70                 75                  80
Lys His Lys Val Tyr Ala Cys Glu Val Thr His Gln Gly Leu Ser Ser
                85                  90                 95
Pro Val Thr Lys Ser Phe Asn Arg Gly Glu Cys
                100                 105
```

<210> SEQ ID NO 166
<211> LENGTH: 354
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 166

```
gaggtgcagc tggtggagtc tgggggaggc ctggtcaagc cggggggtc cctgagactc        60
tcctgtgcag cctctggatt caccttcagt tcccatagta tgaactgggt ccgccaggct      120
ccagggaagg gctggagtg gtctcagcc ataagtagta gtagtagtta catatactac        180
gcagactcag tgaagggccg attcaccatc tccagagaca acgccaagaa ctcactgtat      240
ctgcaaatga acagcctgag agccgaggac acggctgtgt attactgtgc gagagaagag      300
tgggggctac cctttgacta ctgggccag ggaatcctgg tcaccgtctc ctca            354
```

<210> SEQ ID NO 167
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 167

```
Glu Val Gln Leu Val Glu Ser Gly Gly Gly Leu Val Lys Pro Gly Gly
1               5                   10                  15
Ser Leu Arg Leu Ser Cys Ala Ala Ser Gly Phe Thr Phe Ser Ser His
            20                  25                  30
Ser Met Asn Trp Val Arg Gln Ala Pro Gly Lys Gly Leu Glu Trp Val
        35                  40                  45
Ser Ala Ile Ser Ser Ser Ser Ser Tyr Ile Tyr Tyr Ala Asp Ser Val
    50                  55                  60
Lys Gly Arg Phe Thr Ile Ser Arg Asp Asn Ala Lys Asn Ser Leu Tyr
65                  70                  75                  80
Leu Gln Met Asn Ser Leu Arg Ala Glu Asp Thr Ala Val Tyr Tyr Cys
                85                  90                  95
Ala Arg Glu Glu Trp Gly Leu Pro Phe Asp Tyr Trp Gly Gln Gly Ile
                100                 105                 110
Leu Val Thr Val Ser Ser
            115
```

<210> SEQ ID NO 168
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 168
gccatccagt tgacccagtc tccatcctcc ctgtctgcat ctgtaggaga cagagtcacc    60
atcacttgcc gggcaagtca gggcattaac agtgctttag cctggtatca gcagaaacca   120
gggaaagctc ctaagctcct gatctatgat gcctccagtt tgaaaagtgg ggtcccatca   180
aggttcagcg gcagtggatc tgggacagat ttcactctca ccatcagcag cctgcagcct   240
gaagattttg caacttatta ctgtcaacag tttaatagtt accctctcac cttcggccaa   300
gggacacgac tggagattaa a                                              321

<210> SEQ ID NO 169
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 169

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Asn Ser Ala
            20                  25                  30

Leu Ala Trp Tyr Gln Gln Lys Pro Gly Lys Ala Pro Lys Leu Leu Ile
        35                  40                  45

Tyr Asp Ala Ser Ser Leu Lys Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Leu
                85                  90                  95

Thr Phe Gly Gln Gly Thr Arg Leu Glu Ile Lys
            100                 105

<210> SEQ ID NO 170
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 170
gaggtgcagt tggtggagtc tgggggaggc ctggtcaagc ctgggggtc cctgagactc     60 tcctgtgcag cctctggatt caccttcagt agctatagca tgaactgggt ccgccaggct   120
ccagggaagg ggctggagtg ggtctcatcc attagtagta gtagtagtta catatactac   180
gcagactcag tgaagggccg attcaccatc tccagagaca acgccaagaa ctcactgtat   240
ctgcaaatga acagcctgag agccgaggac acggctgtgt attactgtgc gagactacta   300
tggttcgggg agattttga ctactggggc cagggaaccc tggtcaccgt ctcctca      357

<210> SEQ ID NO 171

```
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 171

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Leu Leu Trp Phe Gly Glu Ile Phe Asp Tyr Trp Gly Gln Gly
            100                 105                 110

Thr Leu Val Thr Val Ser Ser
        115

<210> SEQ ID NO 172
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 172
gccatccagt tgacccagtc tccatcctcc ctgtctgcat ctgtaggaga cagagtcacc      60
atcacttgcc gggcaagtca gggcattagc agtgctttag cctggtatca gcagaaacca    120
gggaaagctc ctaagctcct gatctatgat gcctccagtt tgaaaagtgg ggtcccatca    180
aggttcagcg gcagtggatc tgggacagat ttcactctca ccatcagcag cctgcagcct    240
gaagattttg caacttatta ctgtcaacag tttaatagtt acccgatcac cttcggccaa    300
gggacacgac tggagattaa a                                               321

<210> SEQ ID NO 173
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 173

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Leu Leu Ile
        35                  40                  45

Tyr Asp Ala Ser Ser Leu Lys Ser Gly Val Pro Ser Arg Phe Ser Gly
    50                  55                  60
```

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Ile
                85                  90                  95

Thr Phe Gly Gln Gly Thr Arg Leu Glu Ile Lys
            100                 105

<210> SEQ ID NO 174
<211> LENGTH: 366
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 174
cagatgcagc tgcaggagtc gggcccagga ctggtgaagc cttcggagac cctgtccctc       60
acctgcactg tctctggtgg ctccgtcagc agtggtcgtt actactggag ttggatccgg      120
cagccccccg ggaagggact ggagtggatt gggtatatct attacagtgg gagcaccaac      180
tacaacccct ccctcaagag tcgagtcacc atatcagtag acacgtccaa gaaccagttc      240
tccctgaagc tgacctctgt gaccgctgcg gacacggccg tgtattactg tgcgagagag      300
ggtggagact actactacta caatatggac gtctggggcc cagggaccac ggtcaccgtc      360
tcctca                                                                 366

<210> SEQ ID NO 175
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 175

Gln Met Gln Leu Gln Glu Ser Gly Pro Gly Leu Val Lys Pro Ser Glu
1               5                   10                  15

Thr Leu Ser Leu Thr Cys Thr Val Ser Gly Gly Ser Val Ser Ser Gly
            20                  25                  30

Arg Tyr Tyr Trp Ser Trp Ile Arg Gln Pro Pro Gly Lys Gly Leu Glu
        35                  40                  45

Trp Ile Gly Tyr Ile Tyr Tyr Ser Gly Ser Thr Asn Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Thr Ser Val Thr Ala Ala Asp Thr Ala Val Tyr Tyr
                85                  90                  95

Cys Ala Arg Glu Gly Gly Asp Tyr Tyr Tyr Tyr Asn Met Asp Val Trp
            100                 105                 110

Gly Pro Gly Thr Thr Val Thr Val Ser Ser
        115                 120

<210> SEQ ID NO 176
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 176

```
gaaattgtgt tgacgcagtc tccaggcacc ctgtctttgt ctccagggga aagagccacc    60
ctctcctgca gggccagtca gagtgttagc agcagctact tagcctggta ccagcagaaa   120
cctggccagg ctcccaggct cctcatctat ggtgcatcca gcagggccac tggcatccca   180
gacaggttca gtggcagtgg gtctgggaca gacttcactc tcaccatcag cagactggag   240
cctgaagatt ttgcagtgta ttactgtcag cagtatggta gctcaccgta cacttttggc   300
caggggacca agctggagat caaa                                          324
```

```
<210> SEQ ID NO 177
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 177
```

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Tyr Thr Phe Gly Gln Gly Thr Lys Leu Glu Ile Lys
            100                 105

```
<210> SEQ ID NO 178
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 178
caggtgcagc tggtggagtc tgggggaggc gtggtccagc ctgggaggtc cctgagactc    60
tcctgtgcag cctctggatt caccttcagt gactatgcta tgcactgggt ccgccagact   120
ccaggcaggg gctggagtg gctgacattt atatcatatg atggaagcaa taaataccac    180
gcagactccg tgaagggccg attcaccatc tccagagaca attccaagaa cacgctgttt    240
ctgcaaatga acagtctgag agctgaggac acggctgttt attactgtgc gagagattcc   300
tgggatcggg ggtacttcga tctctgggc cgtggcaccc tggtcactgt ctcctca       357
```

```
<210> SEQ ID NO 179
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 179
```

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asp Tyr
            20                  25                  30

Ala Met His Trp Val Arg Gln Thr Pro Gly Arg Gly Leu Glu Trp Leu
        35                  40                  45

Thr Phe Ile Ser Tyr Asp Gly Ser Asn Lys Tyr His Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Arg Asp Ser Trp Asp Arg Gly Tyr Phe Asp Leu Trp Gly Arg Gly
            100                 105                 110

Thr Leu Val Thr Val Ser Ser
        115
```

```
<210> SEQ ID NO 180
<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 180
gaaattgtgt tgacacagtc tccagccacc ctgtctttgt ctccagggga aagagccacc    60
ctctcctgca gggccagtca gagtgttagc agctacttag cctggtacca acagaaacct   120
ggccaggctc ccaggctcct catctatgat gcatccaaca gggccactgg catcccagcc   180
aggttcagtg gcagtgggtc tgggacagac ttcactctca ccatcagcag cctagagcct   240
gaagattttg cagtttatta ctgtcagcag cgtagcaact ggtggacgtt cggccaaggg   300
accaaggtgg aaatcaaa                                                 318

<210> SEQ ID NO 181
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 181

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Trp Thr
                85                  90                  95

Phe Gly Gln Gly Thr Lys Val Glu Ile Lys
            100                 105
```

<210> SEQ ID NO 182
<211> LENGTH: 233
<212> TYPE: PRT
<213> ORGANISM: Homo sapiens

<400> SEQUENCE: 182

```
Met Asp Asn Gln Gly Val Ile Tyr Ser Asp Leu Asn Leu Pro Pro Asn
1               5                   10                  15

Pro Lys Arg Gln Gln Arg Lys Pro Lys Gly Asn Lys Ser Ser Ile Leu
            20                  25                  30

Ala Thr Glu Gln Glu Ile Thr Tyr Ala Glu Leu Asn Leu Gln Lys Ala
        35                  40                  45

Ser Gln Asp Phe Gln Gly Asn Asp Lys Thr Tyr His Cys Lys Asp Leu
    50                  55                  60

Pro Ser Ala Pro Glu Lys Leu Ile Val Gly Ile Leu Gly Ile Ile Cys
65                  70                  75                  80

Leu Ile Leu Met Ala Ser Val Val Thr Ile Val Val Ile Pro Ser Thr
                85                  90                  95

Leu Ile Gln Arg His Asn Asn Ser Ser Leu Asn Thr Arg Thr Gln Lys
            100                 105                 110

Ala Arg His Cys Gly His Cys Pro Glu Glu Trp Ile Thr Tyr Ser Asn
        115                 120                 125

Ser Cys Tyr Tyr Ile Gly Lys Glu Arg Arg Thr Trp Glu Glu Ser Leu
    130                 135                 140

Leu Ala Cys Thr Ser Lys Asn Ser Ser Leu Leu Ser Ile Asp Asn Glu
145                 150                 155                 160

Glu Glu Met Lys Phe Leu Ser Ile Ile Ser Pro Ser Ser Trp Ile Gly
                165                 170                 175

Val Phe Arg Asn Ser Ser His His Pro Trp Val Thr Met Asn Gly Leu
            180                 185                 190

Ala Phe Lys His Glu Ile Lys Asp Ser Asp Asn Ala Glu Leu Asn Cys
        195                 200                 205

Ala Val Leu Gln Val Asn Arg Leu Lys Ser Ala Gln Cys Gly Ser Ser
    210                 215                 220

Ile Ile Tyr His Cys Lys His Lys Leu
225                 230
```

<210> SEQ ID NO 183
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid

<400> SEQUENCE: 183

```
Xaa Glu Trp Gly Leu Pro Phe Asp
1               5
```

<210> SEQ ID NO 184
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

```
<220> FEATURE:
<221> NAME/KEY: MOD_RES
<222> LOCATION: (2)..(2)
<223> OTHER INFORMATION: Any amino acid

<400> SEQUENCE: 184

Glu Xaa Trp Gly Leu Pro Phe Asp
1               5

<210> SEQ ID NO 185
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any amino acid

<400> SEQUENCE: 185

Glu Glu Xaa Gly Leu Pro Phe Asp
1               5

<210> SEQ ID NO 186
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Any amino acid

<400> SEQUENCE: 186

Glu Glu Trp Xaa Leu Pro Phe Asp
1               5

<210> SEQ ID NO 187
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Any amino acid

<400> SEQUENCE: 187

Glu Glu Trp Gly Xaa Pro Phe Asp
1               5

<210> SEQ ID NO 188
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Any amino acid

<400> SEQUENCE: 188
```

```
Glu Glu Trp Gly Leu Xaa Phe Asp
1               5

<210> SEQ ID NO 189
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Any amino acid

<400> SEQUENCE: 189

Glu Glu Trp Gly Leu Pro Xaa Asp
1               5

<210> SEQ ID NO 190
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Any amino acid

<400> SEQUENCE: 190

Glu Glu Trp Gly Leu Pro Phe Xaa
1               5

<210> SEQ ID NO 191
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 191

Gly Thr Phe Ser Ser Tyr Ser Met Asn
1               5

<210> SEQ ID NO 192
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 192

Gly Phe Thr Phe Ser Ser His Ser Met Asn
1               5                   10

<210> SEQ ID NO 193
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 193

Glu Glu Trp Gly Leu Pro Phe Asp
```

<210> SEQ ID NO 194
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 194

Arg Ala Ser Gln Gly Ser Asn Ser Ala Leu Ala
1               5                   10

<210> SEQ ID NO 195
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 195

Gln Gln Phe Asn Asn Tyr Pro Leu Thr
1               5

<210> SEQ ID NO 196
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 196

Gly Phe Thr Phe Ser Ser Tyr Ser Met Asn
1               5                   10

<210> SEQ ID NO 197
<211> LENGTH: 160
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 197

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser His
            20                  25                  30

Ser Met Asn Trp Val Arg Gln Ala Pro Gly Lys Gly Leu Glu Trp Val
        35                  40                  45

Ser Ala Ile Ser Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Glu Trp Gly Leu Pro Phe Asp Tyr Trp Gly Gln Gly Ile
            100                 105                 110

Leu Val Thr Val Ser Ser Ala Ser Thr Lys Gly Pro Ser Val Phe Pro
        115                 120                 125

```
Leu Ala Pro Ser Ser Lys Ser Thr Ser Gly Gly Thr Ala Ala Leu Gly
        130                 135                 140

Cys Leu Val Lys Asp Tyr Phe Pro Glu Pro Val Thr Val Ser Trp Asn
145                 150                 155                 160

<210> SEQ ID NO 198
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 198

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Asn Ser Ala
            20                  25                  30

Leu Ala Trp Tyr Gln Gln Lys Pro Gly Lys Ala Pro Lys Leu Leu Ile
        35                  40                  45

Tyr Asp Ala Ser Ser Leu Lys Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Leu
                85                  90                  95

Thr Phe Gly Gln Gly Thr Arg Leu Glu Ile
            100                 105

<210> SEQ ID NO 199
<211> LENGTH: 80
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 199

Leu Gln Met Asn Ser Leu Arg Ala Glu Asp Thr Ala Val Tyr Tyr Cys
1               5                   10                  15

Ala Arg Glu Glu Trp Gly Leu Pro Phe Asp Tyr Trp Gly Gln Gly Ile
            20                  25                  30

Leu Val Thr Val Ser Ser Ala Ser Thr Lys Gly Pro Ser Val Phe Pro
        35                  40                  45

Leu Ala Pro Ser Ser Lys Ser Thr Ser Gly Gly Thr Ala Ala Leu Gly
    50                  55                  60

Cys Leu Val Lys Asp Tyr Phe Pro Glu Pro Val Thr Val Ser Trp Asn
65                  70                  75                  80

<210> SEQ ID NO 200
<211> LENGTH: 80
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 200

Leu Gln Met Asn Ser Leu Arg Ala Glu Asp Thr Ala Val Tyr Tyr Cys
1               5                   10                  15

Ala Arg Glu Glu Trp Gly Leu Pro Phe Asp Tyr Trp Gly Gln Gly Thr
```

```
                    20                  25                  30

Leu Val Thr Val Ser Ser Ala Ser Thr Lys Gly Pro Ser Val Phe Pro
                35                  40                  45

Leu Ala Pro Ser Ser Lys Ser Thr Ser Gly Gly Thr Ala Ala Leu Gly
            50                  55                  60

Cys Leu Val Lys Asp Tyr Phe Pro Glu Pro Val Thr Val Ser Trp Asn
65                  70                  75                  80

<210> SEQ ID NO 201
<211> LENGTH: 80
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 201

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Asn Ser Ala
                20                  25                  30

Leu Ala Trp Tyr Gln Lys Pro Gly Lys Ala Pro Lys Leu Leu Ile
                35                  40                  45

Tyr Asp Ala Ser Ser Leu Lys Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

<210> SEQ ID NO 202
<211> LENGTH: 80
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 202

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Pro Ser Ala
                20                  25                  30

Leu Ala Trp Tyr Gln Lys Pro Gly Lys Ala Pro Lys Leu Leu Ile
                35                  40                  45

Tyr Asp Ala Ser Ser Leu Lys Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

<210> SEQ ID NO 203
<211> LENGTH: 80
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 203

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Gln Ser Ala
                20                  25                  30
```

```
Leu Ala Trp Tyr Gln Gln Lys Pro Gly Lys Ala Pro Lys Leu Leu Ile
            35                  40                  45

Tyr Asp Ala Ser Ser Leu Lys Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

<210> SEQ ID NO 204
<211> LENGTH: 80
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 204

Ala Ile Gln Leu Thr Gln Ser Pro Ser Ser Leu Ser Ala Ser Val Gly
 1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Leu Leu Ile
            35                  40                  45

Tyr Asp Ala Ser Ser Leu Lys Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

<210> SEQ ID NO 205
<211> LENGTH: 228
<212> TYPE: PRT
<213> ORGANISM: Homo sapiens

<400> SEQUENCE: 205

Met Asp Asn Gln Gly Val Ile Tyr Ser Asp Leu Asn Leu Pro Pro Asn
 1               5                   10                  15

Pro Lys Arg Gln Gln Arg Lys Pro Lys Gly Asn Lys Ser Ser Ile Leu
            20                  25                  30

Ala Thr Glu Gln Glu Ile Thr Tyr Ala Glu Leu Asn Leu Gln Lys Ala
            35                  40                  45

Ser Gln Asp Phe Gln Gly Asn Asp Lys Thr Tyr His Cys Lys Asp Leu
 50                  55                  60

Pro Ser Ala Pro Glu Lys Leu Ile Val Gly Ile Leu Gly Ile Ile Cys
 65                  70                  75                  80

Leu Ile Leu Met Ala Ser Val Val Thr Ile Val Val Ile Pro Ser Thr
            85                  90                  95

Leu Ile Gln Arg His Asn Asn Ser Ser Leu Asn Thr Arg Thr Gln Lys
            100                 105                 110

Ala Arg His Cys Gly His Cys Pro Glu Glu Trp Ile Thr Tyr Ser Asn
            115                 120                 125

Ser Cys Tyr Tyr Ile Gly Lys Glu Arg Arg Thr Trp Glu Glu Ser Leu
 130                 135                 140

Leu Ala Cys Thr Ser Lys Asn Ser Ser Leu Leu Ser Ile Asp Asn Glu
 145                 150                 155                 160

Glu Glu Met Lys Phe Leu Ser Ile Ile Ser Pro Ser Ser Trp Ile Gly
            165                 170                 175

Val Phe Arg Asn Ser Ser His His Pro Trp Val Thr Met Asn Gly Leu
            180                 185                 190
```

Ala Phe Lys His Glu Ile Lys Asp Ser Asp Asn Ala Glu Leu Asn Cys
            195                 200                 205

Ala Val Leu Gln Val Asn Arg Leu Lys Ser Ala Gln Cys Gly Ser Ser
210                 215                 220

Ile Ile Tyr His
225

<210> SEQ ID NO 206
<211> LENGTH: 215
<212> TYPE: PRT
<213> ORGANISM: Homo sapiens

<400> SEQUENCE: 206

Met Asp Asn Gln Gly Val Ile Tyr Ser Asp Leu Asn Leu Pro Pro Asn
1               5                   10                  15

Pro Lys Arg Gln Gln Arg Lys Pro Lys Gly Asn Lys Asn Ser Ile Leu
            20                  25                  30

Ala Thr Glu Gln Glu Ile Thr Tyr Ala Glu Leu Asn Leu Gln Lys Ala
        35                  40                  45

Ser Gln Asp Phe Gln Gly Asn Asp Lys Thr Tyr His Cys Lys Asp Leu
50                  55                  60

Pro Ser Ala Pro Glu Lys Leu Ile Val Gly Ile Leu Gly Ile Ile Cys
65                  70                  75                  80

Leu Ile Leu Met Ala Ser Val Val Thr Ile Val Ile Pro Ser Arg
                85                  90                  95

His Cys Gly His Cys Pro Glu Glu Trp Ile Thr Tyr Ser Asn Ser Cys
                100                 105                 110

Tyr Tyr Ile Gly Lys Glu Arg Arg Thr Trp Glu Glu Ser Leu Leu Ala
            115                 120                 125

Cys Thr Ser Lys Asn Ser Ser Leu Leu Ser Ile Asp Asn Glu Glu Glu
130                 135                 140

Met Lys Phe Leu Ser Ile Ile Ser Pro Ser Ser Trp Ile Gly Val Phe
145                 150                 155                 160

Arg Asn Ser Ser His His Pro Trp Val Thr Met Asn Gly Leu Ala Phe
                165                 170                 175

Lys His Glu Ile Lys Asp Ser Asp Asn Ala Glu Leu Asn Cys Ala Val
            180                 185                 190

Leu Gln Val Asn Arg Leu Lys Ser Ala Gln Cys Gly Ser Ser Ile Ile
        195                 200                 205

Tyr His Cys Lys His Lys Leu
    210                 215

<210> SEQ ID NO 207
<211> LENGTH: 215
<212> TYPE: PRT
<213> ORGANISM: Homo sapiens

<400> SEQUENCE: 207

Met Asp Asn Gln Gly Val Ile Tyr Ser Asp Leu Asn Leu Pro Pro Asn
1               5                   10                  15

Pro Lys Arg Gln Gln Arg Lys Pro Lys Gly Asn Lys Asn Ser Ile Leu
            20                  25                  30

Ala Thr Glu Gln Glu Ile Thr Tyr Ala Glu Leu Asn Leu Gln Lys Ala
        35                  40                  45

Ser Gln Asp Phe Gln Gly Asn Asp Lys Thr Tyr His Cys Lys Asp Leu
50                  55                  60

```
Pro Ser Ala Pro Glu Lys Leu Ile Val Gly Ile Gly Ile Ile Cys
65              70                  75                  80

Leu Ile Leu Met Ala Ser Val Val Thr Ile Val Ile Pro Ser Arg
                85                  90                  95

His Cys Gly His Cys Pro Glu Glu Trp Ile Thr Tyr Ser Asn Ser Cys
            100                 105                 110

Tyr Tyr Ile Gly Lys Glu Arg Arg Thr Trp Glu Glu Ser Leu Leu Ala
            115                 120                 125

Cys Thr Ser Lys Asn Ser Ser Leu Leu Ser Ile Asp Asn Glu Glu Glu
            130                 135                 140

Met Lys Phe Leu Ser Ile Ile Ser Pro Ser Ser Trp Ile Gly Val Phe
145                 150                 155                 160

Arg Asn Ser Ser His His Pro Trp Val Thr Met Asn Gly Leu Ala Phe
                165                 170                 175

Lys His Glu Ile Lys Asp Ser Asp Asn Ala Glu Leu Asn Cys Ala Val
            180                 185                 190

Leu Gln Val Asn Arg Leu Lys Ser Ala Gln Cys Gly Ser Ser Ile Ile
            195                 200                 205

Tyr His Cys Lys His Lys Leu
    210                 215

<210> SEQ ID NO 208
<211> LENGTH: 1179
<212> TYPE: DNA
<213> ORGANISM: Homo sapiens

<400> SEQUENCE: 208
acagttgaga ggagtttgag tggagattca gggccatttt agtatcttct gtaggacaga      60
ggtcagcaag catgccccag aggtacagat gtatatgtct cccaggaagt ctctgtgggt    120
gaaggactga tctcaagttg tggctgacac tagttaaagc caagttagag ggctgtttca    180
gggtctacat tgagactaca gttgatatgc ctacctcctg agacactagt gtgtgagtct    240
cctcctgggc ccctgggcaa atggttttgg cagcatgacc aaggcctaaa tggggctgaa    300
ggcaagcaca ggaggatggg tccctttca ggtctggaga tggaatcact gttgctatag     360
caggcctttt tatgagacta acctggcctc tccactaaag gatgtgtgac tttctgggga    420
cagaagagta cagtccctga catcacacac tgcagagatg gataaccaag gagtaatcta    480
ctcagacctg aatctgcccc caaacccaaa gaggcagcaa cgaaaaccta aaggcaataa    540
aagctccatt ttagcaactg aacaggaaat aacctatgcg gaattaaacc ttcaaaaagc    600
ttctcaggat tttcaaggga atgacaaaac ctatcactgc aaagatttac catcagctcc    660
agagaagctc attgttggga tcctgggaat tatctgtctt atcttaatgg cctctgtggt    720
aacgatagtt gttattccct ctacattaat acagaggcac aacaattctt ccctgaatac    780
aagaactcag aaagcacgtc attgtggcca ttgtcctgag gagtggatta catattccaa    840
cagttgttac tacattggta aggaaagaag aacttgggaa gagagtttgc tggcctgtac    900
ttcgaagaac tccagtctgc tttctataga taatgaagaa gaaatgaaat ttctgtccat    960
catttcacca tcctcatgga ttggtgtgtt tcgtaacagc agtcatcatc catgggtgac   1020
aatgaatggt ttggctttca aacatgagat aaaagactca gataatgctg aacttaactg   1080
tgcagtgcta caagtaaatc gacttaaatc agcccagtgt ggatcttcaa taatatatca   1140
ttaaacttgt taatttaata caatttacaa cacacctgc                          1179
```

<210> SEQ ID NO 209
<211> LENGTH: 1436
<212> TYPE: DNA
<213> ORGANISM: Homo sapiens

<400> SEQUENCE: 209

| | | | | | |
|---|---|---|---|---|---|
| ccactcttga | ctcactctga | gccttcacag | ggcagtctgc | gaagattgca | ggcattgttt | 60 |
| gttcttgtct | tggatttatg | cctttaaatt | tcaccttta | ttacacagct | atagcaggcc | 120 |
| tttttatgag | actaacctgg | cctctccact | aaaggatgtg | tgactttctg | gggacagaag | 180 |
| agtacagtcc | ctgacatcac | acactgcaga | gatggataac | caaggagtaa | tctactcaga | 240 |
| cctgaatctg | cccccaaacc | caagaggca | gcaacgaaaa | cctaaaggca | ataaaaactc | 300 |
| cattttagca | actgaacagg | aaataaccta | tgcggaatta | aaccttcaaa | aagcttctca | 360 |
| ggattttcaa | gggaatgaca | aaacctatca | ctgcaaagat | ttaccatcag | ctccagagaa | 420 |
| gctcattgtt | gggatcctgg | gaattatctg | tcttatctta | atggcctctg | tggtaacgat | 480 |
| agttgttatt | ccctctacat | taatacagag | gcacaacaat | tcttccctga | atacaagaac | 540 |
| tcagaaagca | cgtcattgtg | gccattgtcc | tgaggagtgg | attacatatt | ccaacagttg | 600 |
| ttactacatt | ggtaaggaaa | gaagaacttg | ggaagagagt | ttgctggcct | gtacttcgaa | 660 |
| gaactccagt | ctgctttcta | tagataatga | agaagaaatg | aaatttctgt | ccatcatttc | 720 |
| accatcctca | tggattggtg | tgtttcgtaa | cagcagtcat | catccatggg | tgacaatgaa | 780 |
| tggtttggct | ttcaaacatg | agataaaaga | ctcagataat | gctgaactta | actgtgcagt | 840 |
| gctacaagta | aatcgactta | aatcagccca | gtgtggatct | tcaataatat | atcattgtaa | 900 |
| gcataagctt | tagaggtaaa | gcgtttgcat | ttgcagtgca | tcagataaat | tgtatatttc | 960 |
| ttaaaataga | aatatattat | gattgcataa | atcttaaaat | gaattatgtt | atttgctcta | 1020 |
| ataagaaaat | tctaaatcaa | ttattgaaac | aggatacaca | caattactaa | agtacagaca | 1080 |
| tcctagcatt | tgtgtcgggc | tcatttgct | caacatggta | tttgtggttt | tcagcctttc | 1140 |
| taaaagttgc | atgttatgtg | agtcagctta | taggaagtac | caagaacagt | caaacccatg | 1200 |
| gagacagaaa | gtagaatagt | ggttgccaat | gtctgaggga | ggttgaaata | ggagatgacc | 1260 |
| tctaactgat | agaacgttac | tttgtgtcgt | gatgaaaact | ttctaaattt | cagtagtggt | 1320 |
| gatggttgta | actctgcgaa | tatactaaac | atcattgatt | tttaatcatt | ttaagtgcat | 1380 |
| gaaatgtatg | ctttgtacac | gacacttcaa | taaagctatc | cagaaaaaaa | aaaaaa | 1436 |

<210> SEQ ID NO 210
<211> LENGTH: 1382
<212> TYPE: DNA
<213> ORGANISM: Homo sapiens

<400> SEQUENCE: 210

| | | | | | |
|---|---|---|---|---|---|
| ccactcttga | ctcactctga | gccttcacag | ggcagtctgc | gaagattgca | ggcattgttt | 60 |
| gttcttgtct | tggatttatg | cctttaaatt | tcaccttta | ttacacagct | atagcaggcc | 120 |
| tttttatgag | actaacctgg | cctctccact | aaaggatgtg | tgactttctg | gggacagaag | 180 |
| agtacagtcc | ctgacatcac | acactgcaga | gatggataac | caaggagtaa | tctactcaga | 240 |
| cctgaatctg | cccccaaacc | caagaggca | gcaacgaaaa | cctaaaggca | ataaaaactc | 300 |
| cattttagca | actgaacagg | aaataaccta | tgcggaatta | aaccttcaaa | aagcttctca | 360 |
| ggattttcaa | gggaatgaca | aaacctatca | ctgcaaagat | ttaccatcag | ctccagagaa | 420 |
| gctcattgtt | gggatcctgg | gaattatctg | tcttatctta | atggcctctg | tggtaacgat | 480 |

```
agttgttatt ccctcacgtc attgtggcca ttgtcctgag gagtggatta catattccaa    540
cagttgttac tacattggta aggaaagaag aacttgggaa gagagtttgc tggcctgtac    600
ttcgaagaac tccagtctgc tttctataga taatgaagaa gaaatgaaat ttctgtccat    660
catttcacca tcctcatgga ttggtgtgtt tcgtaacagc agtcatcatc catgggtgac    720
aatgaatggt ttggctttca acatgagat aaaagactca gataatgctg aacttaactg    780
tgcagtgcta caagtaaatc gacttaaatc agcccagtgt ggatcttcaa taatatatca    840
ttgtaagcat aagctttaga ggtaaagcgt ttgcatttgc agtgcatcag ataaattgta    900
tatttcttaa aatagaaata tattatgatt gcataaatct taaatgaat tatgttattt    960 gctctaataa gaaaattcta aatcaattat tgaaacagga tacacacaat tactaaagta   1020
cagacatcct agcatttgtg tcgggctcat tttgctcaac atggtatttg tggttttcag   1080
cctttctaaa agttgcatgt tatgtgagtc agcttatagg aagtaccaag aacagtcaaa   1140
cccatggaga cagaaagtag aatagtggtt gccaatgtct gagggaggtt gaaataggag   1200
atgacctcta actgatagaa cgttactttg tgtcgtgatg aaaactttct aaatttcagt   1260
agtggtgatg gttgtaactc tgcgaatata ctaaacatca ttgatttta atcattttaa    1320 gtgcatgaaa tgtatgcttt gtacacgaca cttcaataaa gctatccaga aaaaaaaaaa   1380
aa                                                                  1382
```

<210> SEQ ID NO 211
<211> LENGTH: 1563
<212> TYPE: DNA
<213> ORGANISM: Homo sapiens

<400> SEQUENCE: 211

```
gcatgcccca gaggtacaga tgtatatgtc tcccaggaag tctctgtggg tgaaggactg     60
atctcaagtt gtggctgaca ctagttaaag ccaagttaga gggctgtttc agggtctaca    120
ttgagactac agttgatatg cctacctcct gagacactag tgtgtgagtc tcctcctggg    180
cccctgggca aatggttttg gcagcatgac caaggcctaa atggggctga aggcaagcac    240
aggaggatgg gtccctttc aggtctggag atggaatcac tgttgctata gcaggccttt    300
ttatgagact aacctggcct ctccactaaa ggatgtgtga ctttctgggg acagaagagt    360
acagtccctg acatcacaca ctgcagagat ggataaccaa ggagtaatct actcagacct    420
gaatctgccc ccaaacccaa agaggcagca acgaaaacct aaaggcaata aaagctccat    480
tttagcaact gaacaggaaa taacctatgc ggaattaaac cttcaaaaag cttctcagga    540
ttttcaaggg aatgacaaaa cctatcactg caaagattta ccatcagctc cagagaagct    600
cattgttggg atcctgggaa ttatctgtct tatcttaatg gcctctgtgg taacgatagt    660
tgttattccc tcacgtcatt gtggccattg tcctgaggag tggattacat attccaacag    720
ttgttactac attggtaagg aaagaagaac ttgggaagag agtttgctgg cctgtacttc    780
gaagaactcc agtctgcttt ctatagataa tgaagaagaa atgaaatttc tgtccatcat    840 ttccaccatcc tcatggattg gtgtgtttcg taacagcagt catcatccat gggtgacaat    900
gaatggtttg gctttcaaac atgagataaa agactcagat aatgctgaac ttaactgtgc    960
agtgctacaa gtaaatcgac ttaaatcagc ccagtgtgga tcttcaataa tatatcattg   1020
taagcataag ctttagaggt aaagcgtttg catttgcagt gcatcagata aattgtatat   1080
ttcttaaaat agaaatatat tatgattgca taaatcttaa aatgaattat gttatttgct   1140
```

```
ctaataagaa aattctaaat caattattga aacaggatac acacaattac taaagtacag    1200
acatcctagc atttgtgtcg ggctcatttt gctcaacatg gtatttgtgg ttttcagcct    1260
ttctaaaagt tgcatgttat gtgagtcagc ttataggaag taccaagaac agtcaaaccc    1320
atggagacag aaagtagaat agtggttgcc aatgtctgag ggaggttgaa ataggagatg    1380
acctctaact gatagaacgt tactttgtgt cgtgatgaaa actttctaaa tttcagtagt    1440
ggtgatggtt gtaactctgc gaatatacta aacatcattg atttttaatc attttaagtg    1500
catgaaatgt atgctttgta cacgacactt caataaagct atccagaaaa aaaaaaaaa     1560 aaa                                                                  1563

<210> SEQ ID NO 212
<211> LENGTH: 1617
<212> TYPE: DNA
<213> ORGANISM: Homo sapiens

<400> SEQUENCE: 212
gcatgcccca gaggtacaga tgtatatgtc tcccaggaag tctctgtggg tgaaggactg      60
atctcaagtt gtggctgaca ctagttaaag ccaagttaga gggctgtttc agggtctaca     120
ttgagactac agttgatatg cctacctcct gagacactag tgtgtgagtc tcctcctggg     180
cccctgggca aatggttttg gcagcatgac caaggcctaa atggggctga aggcaagcac     240
aggaggatgg gtccctttc aggtctggag atggaatcac tgttgctata gcaggccttt      300
ttatgagact aacctggcct ctccactaaa ggatgtgtga ctttctgggg acagaagagt     360
acagtccctg acatcacaca ctgcagagat ggataaccaa ggagtaatct actcagacct     420
gaatctgccc ccaaacccaa agaggcagca acgaaaacct aaaggcaata aaagctccat     480
tttagcaact gaacaggaaa taacctatgc ggaattaaac cttcaaaaag cttctcagga     540
ttttcaaggg aatgacaaaa cctatcactg caaagattta ccatcagctc cagagaagct     600
cattgttggg atcctgggaa ttatctgtct tatcttaatg gcctctgtgg taacgatagt     660
tgttattccc tctacattaa tacagaggca caacaattct tccctgaata caagaactca     720
gaaagcacgt cattgtggcc attgtcctga ggagtggatt acatattcca acagttgtta     780
ctacattggt aaggaaagaa gaacttggga agagagtttg ctggcctgta cttcgaagaa     840
ctccagtctg ctttctatag ataatgaaga agaaatgaaa tttctgtcca tcatttcacc     900
atcctcatgg attggtgtgt tcgtaacag cagtcatcat ccatgggtga caatgaatgg      960
tttggctttc aaacatgaga taaaagactc agataatgct gaacttaact gtgcagtgct    1020
acaagtaaat cgacttaaat cagcccagtg tggatcttca ataatatatc attgtaagca    1080
taagctttag aggtaaagcg tttgcatttg cagtgcatca gataaattgt atatttctta    1140
aaatagaaat atattatgat tgcataaatc ttaaaatgaa ttatgttatt tgctctaata    1200
agaaaattct aaatcaatta ttgaaacagg atacacacaa ttactaaagt acagacatcc    1260
tagcatttgt gtcgggctca ttttgctcaa catggtattt gtggttttca gcctttctaa    1320
aagttgcatg ttatgtgagt cagcttatag gaagtaccaa gaacagtcaa acccatggag    1380
acagaaagta gaatagtggt tgccaatgtc tgagggaggt tgaaatagga gatgacctct    1440
aactgataga acgttacttt gtgtcgtgat gaaaactttc taaatttcag tagtggtgat    1500
ggttgtaact ctgcgaatat actaaacatc attgattttt aatcatttta agtgcatgaa    1560
atgtatgctt tgtacacgac acttcaataa agctatccag aaaaaaaaaa aaaaaaa      1617
```